United States Patent
Blake et al.

(10) Patent No.: US 12,187,721 B2
(45) Date of Patent: Jan. 7, 2025

(54) PROTEIN TYROSINE PHOSPHATASE INHIBITORS

(71) Applicant: Array BioPharma Inc., Boulder, CO (US)

(72) Inventors: James Francis Blake, Longmont, CO (US); Mark Laurence Boys, Lyons, CO (US); Mark Joseph Chicarelli, Longmont, CO (US); Adam Wade Cook, Broomfield, CO (US); Mohamed S. A. Elsayed, Boulder, CO (US); Jay Bradford Fell, Longmont, CO (US); John Peter Fischer, Longmont, CO (US); Ronald Jay Hinklin, Longmont, CO (US); Oren Teague Mcnulty, Nederland, CO (US); Macedonio J. Mejia, Denver, CO (US); Martha E. Rodriguez, Lafayette, CO (US); Christina Elizabeth Wong, Boulder, CO (US)

(73) Assignee: Array BioPharma Inc., Boulder, CO (US)

( * ) Notice: Subject to any disclaimer, the term of this patent is extended or adjusted under 35 U.S.C. 154(b) by 906 days.

(21) Appl. No.: 17/285,997

(22) PCT Filed: Oct. 17, 2019

(86) PCT No.: PCT/US2019/056786
§ 371 (c)(1),
(2) Date: Apr. 16, 2021

(87) PCT Pub. No.: WO2020/081848
PCT Pub. Date: Apr. 23, 2020

(65) Prior Publication Data
US 2021/0380582 A1 Dec. 9, 2021

Related U.S. Application Data

(60) Provisional application No. 62/916,119, filed on Oct. 16, 2019, provisional application No. 62/746,952, filed on Oct. 17, 2018.

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC ...... C07D 471/04; C07D 519/00; A61P 35/00
See application file for complete search history.

(56) References Cited

U.S. PATENT DOCUMENTS

| 9,096,590 B2 * | 8/2015 | Ren .......................... A61P 9/10 |
| 2012/0225846 A1 | 9/2012 | Bioenergenix |

FOREIGN PATENT DOCUMENTS

| EA | 201691442 A1 | 12/2016 |
| EP | 1939194 | 7/2008 |
| WO | 2004/052370 | 6/2004 |
| WO | 2004/052371 | 6/2004 |
| WO | 2005/007099 | 1/2005 |
| WO | 2006/039718 | 1/2006 |
| WO | 2006/050501 | 5/2006 |
| WO | 2007/125405 | 11/2007 |
| WO | 2008/003702 | 1/2008 |
| WO | 2008/138878 | 11/2008 |
| WO | 2009/091939 | 7/2009 |
| WO | 2010/129816 | 11/2010 |
| WO | 2011/022439 | 2/2011 |
| WO | 2011/149937 | 12/2011 |
| WO | 2012/148540 | 11/2012 |
| WO | 2013/071264 | 5/2013 |
| WO | 2014/151147 | 9/2014 |
| WO | 2015/107493 | 7/2015 |
| WO | 2015/107494 | 7/2015 |
| WO | 2015/107495 | 7/2015 |
| WO | 2016/049568 | 3/2016 |
| WO | 2016/203404 | 12/2016 |
| WO | 2016/203405 | 12/2016 |
| WO | 2016/203406 | 12/2016 |

(Continued)

OTHER PUBLICATIONS

International Search Report Dated Dec. 17, 2019.
Farmatsevticheskaya Khimiya (Pharmaceutical Chemistry) by V.G. Belikov, Moscow: MEDpress-Inform, 2007, 622 pages altogether, specifically see pp. 27-29.
V. N. Zhulenko and Gorshkov G.I., Farmakologiya (Pharmacology), Moscow: KolosS, 2008, pp. 34-35.
Kharkevich, D.A., Farmakologiya (Pharmacology), 10th Ed., Moscow: GEOTAR-Media, 2010, pp. 73-74.

*Primary Examiner* — Kamal A Saeed
(74) *Attorney, Agent, or Firm* — Beau Burton

(57) ABSTRACT

Compounds of Formula Ia or a stereoisomer, tautomer, prodrug or pharmaceutically acceptable salt thereof are provided, which are useful for the treatment of hyperproliferative diseases. Methods of using compounds of Formula Ia or a stereoisomer, tautomer, prodrug or pharmaceutically acceptable salt thereof, for in vitro, in situ, and in vivo diagnosis, prevention or treatment of such disorders in mammalian cells, or associated pathological conditions are disclosed

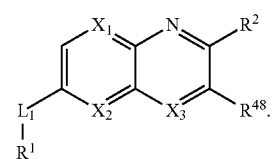

22 Claims, No Drawings

(56) References Cited

FOREIGN PATENT DOCUMENTS

| | | |
|---|---|---|
| WO | 2017/210134 | 12/2017 |
| WO | 2017/211303 | 12/2017 |
| WO | 2017/216706 | 12/2017 |
| WO | 2018/013597 | 1/2018 |
| WO | 2018/057884 | 3/2018 |
| WO | 2018/081091 | 5/2018 |
| WO | 2018/136264 | 7/2018 |
| WO | 2018/136265 | 7/2018 |
| WO | 2018/172984 | 9/2018 |
| WO | 2018/218133 | 11/2018 |
| WO | 2019/051084 | 3/2019 |
| WO | 2019/051469 | 3/2019 |
| WO | 2019/067843 | 4/2019 |
| WO | 2019/075265 | 4/2019 |
| WO | 2019/118909 | 6/2019 |
| WO | 2019/152454 | 8/2019 |
| WO | 2019/182960 | 9/2019 |
| WO | 2019/183364 | 9/2019 |
| WO | 2019/183367 | 9/2019 |
| WO | 2019/233810 | 12/2019 |
| WO | 2020/063760 | 1/2020 |
| WO | 2020/076723 | 4/2020 |
| WO | 2020/201991 | 10/2020 |

OTHER PUBLICATIONS

Russian Office Action of Oct. 6, 2021, for RU Application No. 22021109327. Translation of Office Action included.

* cited by examiner

PROTEIN TYROSINE PHOSPHATASE INHIBITORS

CROSS-REFERENCE TO RELATED APPLICATIONS

This patent application claims the benefit of priority of PCT/US2019/056786 filed Oct. 17, 2019, which claims benefit of U.S. Application Ser. No. 62/916,119, filed Oct. 16, 2019, which also claims the benefit of priority of U.S. Application Ser. No. 62/746,952, file Oct. 17, 2018. The entire content of the applications referenced above are hereby incorporated by reference herein.

BACKGROUND OF THE INVENTION

Field of the Invention

The present invention relates to compounds that inhibit SHP2 and are useful for treating hyperproliferative and neoplastic diseases. The present invention further relates to methods for treating cancer or hyperproliferative diseases with compounds of the present invention.

Description of the State of the Art

SHP2 is a protein tryosine phosphatase (PTP) containing Src Homology 2 (SH2) domains encoded by the PTPN11 gene. SHP2 contributes to multiple cellular functions including proliferation, differentiation, cell cycle maintenance and migration. SHP2 is necessary for full activation of the Ras/ERK1/2 pathway, a key signaling cascade in cancer biology downstream of a wide array of receptor tyrosine kinases and other signal transducers. SHP2 has also been shown to promote PI3K/AKT, JAK/STAT, JNK, and NF-κB signaling, which are also associated with various human cancers. SHP2 is an oncoprotein. See Frankson, Rochelle, el al. "Therapeutic Targeting of Oncogenic Tyrosine Phosphatases." *Cancer Research*. Vol. 77, No. 21 (2017): pp. 5701-5705. Fedele, Carmine, et al. "SHP2 Inhibition Prevents Adaptive Resistance to MEK inhibitors in Multiple Cancer Models." *Cancer Discovery*, Vol. 8, No. 10 (2018): pp. 1237-49. Nichols, Robert J., et al. "Efficacy of SHP2 phosphatase inhibition in cancers with nucleotide-cycling oncogenic RAS, RAS-GTP dependent oncogenic BRAF or NF1 loss." bioRxiv 188730; doi: https://doi.org/10.1101/188730.

Therefore, small-molecular inhibitors of SHP2 would be useful for treating a broad spectrum of cancers, such as, for example, melanoma, juvenile myelomoncytic leukemias, neuroblastoma, Philadelphia chromosome positive chronic myeloid, Philadelphia chromosome positive acute lymphoblastic leukemias, acute myeloid leukemias, myeloproliferative neoplasms (such as Polycythemia Vera, Essential Thrombocythemia and Primary Myelofibrosis), breast cancer, lung cancer, liver cancer, colorectal cancer, esophageal cancer, gastric cancer, squamous-cell carcinoma of the head and neck, glioblastoma, anaplastic large-cell lymphoma, thyroid carcinoma, spitzoid neoplasms, as well as, Neurofibramatosis and Noonan Syndrome.

SHP2 inhibitors are known, see for example, WO 2015/107493; WO 2015/107494; WO 2015/107495; WO 2016/203404; WO 2016/203405; WO 2016/203406; WO 2017/210134; WO 2017/211303; WO 2017/216706; WO 2018/013597; WO 2018/057884; WO 2018/081091; WO 2018/136264; WO 2018/136265; and WO 2018/172984. However, it is well known that there is difficulty in developing a compound into an approved medicine. DiMasi, Joseph A. "Success rates for new drugs entering clinical testing in the United States." *Clinical Pharmacology & Therapeutics*. Vol. 58, no. 1 (1995): pp. 1-14. Scanned, J W, Bosley J. "When Quality Beats Quantity: Decision Theory, Drug Discovery, and the Reproducibility Crisis." PloS ONE 11(2) (2016): e0147215. doi: 10.1371/journal.pone.0147215.

SUMMARY OF THE INVENTION

There is a continuing need for new and novel therapeutic agents that can be used for cancer and hyperproliferative conditions. Design and development of new pharmaceutical compounds is essential.

More specifically, one aspect provides compounds of Formula I:

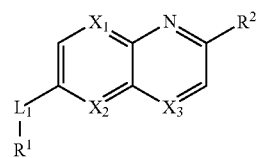

or a stereoisomer, tautomer, or pharmaceutically acceptable salt thereof, wherein $X_1$, $X_2$, $X_3$, $L_1$, $R^1$, and $R^2$ are as defined herein.

Another aspect provides compounds of Formulas II, III, IV, V, or VI, or a stereoisomer, tautomer or pharmaceutically acceptable salt thereof.

Another aspect provides a method for treating a hyperproliferative disorder by administering a therapeutically effective quantity of a compound according to Formula I, II, III, IV, V, or VI, or a stereoisomer, tautomer or pharmaceutically acceptable salt thereof, to a patient in need thereof. The compound can be administered alone or co-administered with at least one other anti-hyperproliferative or chemotherapeutic compound.

Another aspect provides a method of inhibiting SHP2 protein tyrosine phosphatase activity in a cell comprising treating the cell with a compound according to Formula I, II, III, IV, V, or VI, or a stereoisomer, tautomer or pharmaceutically acceptable salt thereof, in an amount effective to attenuate or eliminate SHP2 kinase activity.

Another aspect provides methods of treating or preventing a disease or disorder modulated by SHP2, comprising administering to a mammal in need of such treatment an effective amount of a compound of Formula I, II, III, IV, V, or VI, or a stereoisomer, tautomer or pharmaceutically acceptable salt thereof. Examples of such diseases and disorders include, but are not limited to, hyperproliferative disorders, such as cancer.

Another aspect provides methods of treating or preventing cancer, comprising administering to a mammal in need of such treatment an effective amount of a compound of Formula I, II, III, IV, V, or VI, or a stereoisomer, tautomer or pharmaceutically acceptable salt thereof, alone or in combination with one or more additional compounds having anti-cancer properties.

Another aspect provides a method of treating a hyperproliferative disease in a mammal comprising administering a therapeutically effective amount of a compound of Formula I, II, III, IV, V, or VI, or a stereoisomer, tautomer or pharmaceutically acceptable salt thereof, to the mammal.

Another aspect provides the use of a compound of Formula I, II, III, IV, V, or VI, or a stereoisomer, tautomer or pharmaceutically acceptable salt thereof, in the manufacture of a medicament for the treatment of a hyperproliferative disease.

Another aspect provides a compound of Formula I, II, III, IV, V, or VI, or a stereoisomer, tautomer or pharmaceutically acceptable salt thereof, for use in the treatment of hyperproliferative diseases.

Another aspect provides a pharmaceutical composition comprising a compound of Formula I, II, III, IV, V, or VI, or a stereoisomer, tautomer or pharmaceutically acceptable salt thereof, and a pharmaceutically acceptable carrier, diluent or excipient.

Another aspect provides intermediates for preparing compounds of Formula I, II, III, IV, V, or VI. Certain compounds of the Formulas may be used as intermediates for other compounds of the Formulas.

Another aspect includes processes for preparing, methods of separation, and methods of purification of the compounds described herein.

DETAILED DESCRIPTION OF THE INVENTION

Reference will now be made in detail to certain embodiments, examples of which are illustrated in the accompanying structures and formulas. While enumerated embodiments will be described, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature and similar materials differs from or contradicts this application, including but not limited to defined terms, term usage, described techniques, or the like, this application controls.

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein" refers to the broadest definition for each group as provided in the Detailed Description of the Invention or the broadest claim. In all other embodiments provided below, substituents that can be present in each embodiment, and which are not explicitly defined, retain the broadest definition provided in the Detailed Description of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components. Additionally, the words "include," "including," and "includes" when used in this specification and in the following claims are intended to specify the presence of stated features, integers, components, or steps, but they do not preclude the presence or addition of one or more other features, integers, components, steps, or groups thereof.

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., $R^1$, $R^{4a}$, Ar, $X_1$ or Het) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable that is inherently discrete, the variable can be equal to any integer value of the numerical range, including the end-points of the range. Similarly, for a variable that is inherently continuous, the variable can be equal to any real value of the numerical range, including the end-points of the range. As an example, a variable that is described as having values between 0 and 2, can be 0, 1 or 2 for variables that are inherently discrete, and can be 0.0, 0.1, 0.01, 0.001, or any other real value for variables that are inherently continuous.

Compounds of Formula I exhibit tautomerism. Tautomeric compounds can exist as two or more interconvertible species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates; while in phenols, the enol form predominates. Common prototropic tautomers include keto/enol (—C(=O)—CH$_2$-↔—C(—OH)=CH—), amide/imidic acid (—C(=O)—NH—↔—C(—OH)=N—) and amidine (—C(=NR)—NH—↔—C(—NHR)=N—) tautomers. The latter two are particularly common in heteroaryl and heterocyclic rings, and the present invention encompasses all tautomeric forms of the compounds.

It will be appreciated by the skilled artisan that some of the compounds of Formula I may contain one or more chiral centers and therefore exist in two or more stereoisomeric forms. The racemates of these isomers, the individual isomers and mixtures enriched in one enantiomer, as well as diastereomers when there are two chiral centers, and mixtures partially enriched with specific diastereomers are within the scope of the present invention. The present invention includes all the individual stereoisomers (e.g., enantiomers), racemic mixtures or partially resolved mixtures of the compounds of Formula I and, where appropriate, the individual tautomeric forms thereof.

The compounds of Formula I may contain a basic center and suitable acid addition salts are formed from acids that form non-toxic salts. Examples of salts of inorganic acids include the hydrochloride, hydrobromide, hydroiodide, chloride, bromide, iodide, sulfate, bisulfate, nitrate, phosphate, and hydrogen phosphate. Examples of salts of organic acids include acetate, fumarate, pamoate, aspartate, besylate, carbonate, bicarbonate, camsylate, D and L-lactate, D and L-tartrate, esylate, mesylate, malonate, orotate, gluceptate, methylsulfate, stearate, glucuronate, 2-napsylate, tosylate, hibenzate, nicotinate, isethionate, malate, maleate, citrate, gluconate, succinate, saccharate, benzoate, esylate, and pamoate salts. For a review on suitable salts, see Berge, Stephen M., et al. "Pharmaceutical salts." *J. Pharm. Sci.* Vol. 66, No. 1(1977): 1-19, and Paulekuhn, G. Steffen, et al. "Trends in Active Pharmaceutical Ingredient Salt Selection based on Analysis of the Orange Book Database." *J. Med. Chem.* Vol. 50, No. 26 (2007): 6665-6672.

Technical and scientific terms used herein have the meaning commonly understood by one of skill in the art to which the present invention pertains, unless otherwise defined. Reference is made herein to various methodologies and materials known to those of skill in the art. A standard reference work setting forth the general principles of pharmacology include Hardman, Joel Griffith, el al. *Goodman & Gilman's The Pharmacological Basis of Therapeutics.* New York: McGraw-Hill Professional, 2001. The starting materials and reagents used in preparing these compounds generally are either available from commercial suppliers, such as Sigma-Aldrich (St. Louis, MO), or are prepared by methods known to those skilled in the art following procedures set forth in references. Materials, reagents and the like to which reference are made in the following description and examples are obtainable from commercial sources, unless otherwise noted. General synthetic procedures have been described in treatises, such as Louis F. Fieser and Mary Fieser, *Reagents for Organic Synthesis*, v. 1-23, New York: Wiley 1967-2006 ed. (also available via the Wiley InterScience® website); LaRock, Richard C., *Comprehensive Organic Transformations: A Guide to Functional Group Preparations.* New York: Wiley-VCH, 1999; B. Trost and F Fleming, eds. *Comprehensive Organic Synthesis*, v. 1-9, Oxford: Pergamon 1991; A. R. Katritzky and C. W. Rees, eds. *Comprehensive Heterocyclic Chemistry.* Oxford: Pergamon 1984; A. R. Katritzky and C. W. Rees, eds. *Comprehensive Heterocyclic Chemistry II.* Oxford: Pergamon 1996; and Paquette, Leo A., ed. Organic Reactions, v. 1-40, New York: Wiley & Sons 1991; and will be familiar to those skilled in the art.

The term "alkyl" includes linear or branched-chain radicals of carbon atoms. Some alkyl moieties have been abbreviated, for example, methyl ("Me"), ethyl ("Et"), propyl ("Pr") and butyl ("Bu"), and further abbreviations are used to designate specific isomers of compounds, for example, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or 5-butyl ("s-Bu"), 1,1-dimethylethyl or t-butyl ("t-Bu") and the like. The abbreviations are sometimes used in conjunction with elemental abbreviations and chemical structures, for example, methanol ("MeOH") or ethanol ("EtOH"). In certain embodiments, alkyl is $C_{1-10}$ alkyl. In certain embodiments, alkyl is $C_{1-6}$ alkyl.

The term "Boc" means tert-butyloxycarbonyl. Additional abbreviations used throughout the application may include, for example, benzyl ("Bn"), phenyl ("Ph"), acetate ("Ac") and mesylate ("Ms").

The terms "alkenyl" and "alkynyl" also include linear or branched-chain radicals of carbon atoms.

The terms "heterocycle" and "heterocyclic" include four to seven membered saturated or partially unsaturated rings containing one, two or three heteroatoms selected from the group consisting of O, N, S, S(=O) and S(=O)$_2$. In certain instances, these terms may be specifically further limited, such as, "five to six membered heterocyclic" only including five and six membered rings.

The term "heteroaryl" includes five to six membered aromatic rings containing one, two, three or four heteroatoms selected from the group consisting of O, N and S. In certain instances, these terms may be specifically further limited, such as, five to six membered heteroaryl, wherein the heteroaryl contains one or two nitrogen heteroatoms. As well known to those skilled in the art, heteroaryl rings have less aromatic character than their all-carbon counter parts. Thus, for the purposes of the invention, a heteroaryl group need only have some degree of aromatic character.

A bond drawn into ring system (as opposed to connected at a distinct vertex) indicates that the bond may be attached to any of the suitable ring atoms. A bond with a wavy line on it indicates the point of attachment.

The terms "treat" or "treatment" refer to therapeutic, prophylactic, palliative or preventative measures. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder, as well as those prone to have the condition or disorder or those in which the condition or disorder is to be prevented.

The phrases "therapeutically effective amount" or "effective amount" mean an amount of a compound described herein that, when administered to a mammal in need of such treatment, sufficient to (i) treat or prevent the particular disease, condition, or disorder, (ii) attenuate, ameliorate, or eliminate one or more symptoms of the particular disease, condition, or disorder, or (iii) prevent or delay the onset of one or more symptoms of the particular disease, condition, or disorder described herein. The amount of a compound that will correspond to such an amount will vary depending upon factors such as the particular compound, disease condition and its severity, the identity (e.g., weight) of the mammal in need of treatment, but can nevertheless be routinely determined by one skilled in the art.

The terms "cancer" and "cancerous" refer to or describe the physiological condition in mammals that is typically characterized by abnormal or unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, skin cancer, including melanoma, as well as head and neck cancer.

The phrase "pharmaceutically acceptable" indicates that the substance or composition is compatible chemically and/or toxicologically, with the other ingredients comprising a formulation, and/or the mammal being treated therewith.

The phrase "pharmaceutically acceptable salt," as used herein, refers to pharmaceutically acceptable organic or inorganic salts of a compound described herein.

The compounds described herein also include other salts of such compounds that are not necessarily pharmaceutically acceptable salts, and which may be useful as intermediates for preparing and/or purifying compounds described herein and/or for separating enantiomers of compounds described herein.

The term "mammal" means a warm-blooded animal that has or is at risk of developing a disease described herein and includes, but is not limited to, guinea pigs, dogs, cats, rats, mice, hamsters, and primates, including humans.

SHP2 Inhibitors

Provided herein are compounds, and pharmaceutical formulations thereof, that are potentially useful in the treatment of diseases, conditions and/or disorders modulated by SHP2.

One embodiment provides compounds of Formula Ia:

Ia or a stereoisomer, tautomer, or pharmaceutically acceptable salt thereof, wherein:
  $X_1$ is selected from CH and N;
  $X_2$ is selected from CH and N;
  $X_3$ is selected from CH and N;
  $L_1$ is selected from a direct bond, S, $CH_2$, O or NH;
  $R^1$ is selected from phenyl, heteroaryl, bicyclic aryl, bicyclic heterocyclyl, and bicyclic heteroaryl,
  wherein the phenyl, heteroaryl, bicyclic aryl, bicyclic heterocyclyl and bicyclic heteroaryl are optionally substituted with one or more groups selected from the group consisting of halogen, OH, oxo, cyano, alkyl optionally substituted with halogen, cyano or OH, —O(alkyl) optionally substituted with halogen, cyano or OH, $NHR^a$, and a heterocycle optionally substituted with halogen, cyano, OH or alkyl optionally substituted with OH or oxo;

$R^2$ is:

$X_{11}$ is selected from $CR^{13}R^{14}$, $SiR^{13}R^{14}$, NH and O;
$X_{12}$ is selected from $CHR^{15}$ and NH, wherein one or both of $X_{11}$ and $X_{12}$ must be carbon;
$R^{10}$ is selected from hydrogen and alkyl;
$R^{11}$ is selected from hydrogen, OH and $CH_2NH_2$;
$R^{12}$, $R^{16}$ and $R^{17}$ are hydrogen;
$R^{13}$ is selected from hydrogen, OH, and ($C_0$-$C_3$ alkyl) $NR^bR^c$;
$R^{14}$ is selected from hydrogen, OH, alkyl optionally substituted with halogen, OH, methyl, $OCH_3$ and a heteroaryl;
$R^{15}$ is selected from hydrogen or $NH_2$;
or one of the following groups may join together:
  $R^{10}$ and $R^{11}$ may join together as $CH_2NHCH_2$ to form a fused bicyclic,
  $R^{10}$ and $R^{15}$ may join together as alkyl to form a bridged bi cyclic,
  $R^{11}$ and $R^{12}$ may join together as alkyl substituted with $NH_2$ to form a spirocycle,
  $R^{13}$ and $R^{14}$ may join together as a group selected from cycloalkyl, heterocycle, bicyclic carbocycle, and bicyclic heterocycle, wherein the cycloalkyl, heterocycle, carbocycle and heterocycle are optionally substituted with F, Cl, OH, $OCH_3$, CN, methyl or $NH_2$ to form a spirocycle,
  $R^{10}$ and $R^{16}$ may join together as alkyl, O or NH to form a bridged bicyclic,
  $R^{11}$ and $R^{15}$ may join together as alkyl to form a bridged bicyclic,
  $R^{11}$ and $R^{16}$ may join together as alkyl or O to form a bridged bicyclic,
  $R^{11}$ and $R^{17}$ may join together as alkyl to form a bridged bicyclic, or
  $R^{13}$ and $R^{15}$ may join together as $NHCH_2$, or cycloalkyl wherein the cycloalkyl is substituted with $NH_2$ to form a fused bicyclic;
$R^{48}$ is selected from hydrogen and methyl;
$R^a$ is hydrogen, alkyl optionally substituted with OH, methoxy, halogen or cyano, or cyclopropyl;
$R^b$ and $R^c$ are independently selected from hydrogen, alkyl and a Boc group; and
a, b, c and d are selected from 0 and 1.

One embodiment provides compounds of Formula Ia:

Ia or a stereoisomer, tautomer, or pharmaceutically acceptable salt thereof, wherein:
  $X_1$ is selected from CH and N;

$X_2$ is selected from CH and N;
$X_3$ is selected from CH and N;
$L_1$ is selected from a direct bond, S, $CH_2$, O or NH;
$R^1$ is selected from phenyl, a 5 to 6 membered heteroaryl wherein the heteroaryl contains one to four heteroatoms selected from the group consisting of nitrogen, oxygen and sulfur, a 10 membered bicyclic aryl, a 9-10 membered bicyclic heterocyclyl wherein the heterocyclyl contains one to three heteroatoms selected from the group consisting of nitrogen, oxygen and sulfur, and a 9-10 membered bicyclic heteroaryl wherein the bicyclic heteroaryl contains one to three heteroatoms selected from the group consisting of nitrogen, oxygen and sulfur,
wherein the phenyl, heteroaryl, bicyclic aryl, bicyclic heterocyclyl and bicyclic heteroaryl are optionally substituted with one or more groups selected from the group consisting of halogen, OH, oxo, cyano, $C_1$-$C_3$ alkyl optionally substituted with halogen, cyano or OH, —O($C_1$-$C_3$ alkyl) optionally substituted with halogen, cyano or OH, $NHR^a$, and 3 to 6 membered heterocycle optionally substituted with halogen, cyano, OH or $C_1$-$C_3$ alkyl optionally substituted with OH or oxo, wherein the heterocycle contains one or two heteroatoms selected from nitrogen, oxygen, sulfur and $SO_2$;
$R^2$ is:

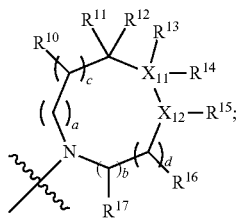

$X_{11}$ is selected from $CR^{13}R^{14}$, $SiR^{13}R^{14}$, NH and O;
$X_{12}$ is selected from $CHR^{15}$ and NH, wherein one or both of $X_{11}$ and $X_{12}$ must be carbon;
$R^{10}$ is selected from hydrogen and $C_1$-$C_3$ alkyl;
$R^{11}$ is selected from hydrogen, OH and $CH_2NH_2$;
$R^{12}$, $R^{16}$ and $R^{17}$ are hydrogen;
$R^{13}$ is selected from hydrogen, OH, and ($C_0$-$C_3$ alkyl) $NR^bR^c$;
$R^{14}$ is selected from hydrogen, OH, $C_1$-$C_3$ alkyl optionally substituted with halogen, OH, methyl, $OCH_3$ and a 5 to 6 membered heteroaryl wherein the heteroaryl contains one to three heteroatoms selected from nitrogen, oxygen and sulfur;
$R^{15}$ is selected from hydrogen or $NH_2$;
or one of the following groups may join together:
  $R^{10}$ and $R^{11}$ may join together as $CH_2NHCH_2$ to form a fused bicyclic,
  $R^{10}$ and $R^{15}$ may join together as $C_1$-$C_4$ alkyl to form a bridged bi cyclic,
  $R^{11}$ and $R^{12}$ may join together as $C_1$-$C_4$ alkyl substituted with $NH_2$ to form a spirocyclic,
  $R^{13}$ and $R^{14}$ may join together as a group selected from $C_3$-$C_6$ cycloalkyl, 4 to 6 membered heterocycle wherein the heterocycle contains one to three heteroatoms selected from the group consisting of nitrogen, oxygen and sulfur, saturated or partially unsaturated 8 to 10 membered bicyclic carbocycle, and a saturated or partially unsaturated 8 to 10 membered bicyclic heterocycle wherein the heterocycle contains one to three heteroatoms selected from the group consisting of nitrogen, oxygen and sulfur, wherein the cycloalkyl, heterocycle, bicyclic carbocycle and bicyclic heterocycle are optionally substituted with F, Cl, OH, $OCH_3$, CN, methyl or $NH_2$ to form a spirocyclic,
  $R^{10}$ and $R^{16}$ may join together as $C_1$-$C_4$ alkyl, O or NH to form a bridged bicyclic,
  $R^{11}$ and $R^{15}$ may join together as $C_1$-$C_4$ alkyl to form a bridged bicyclic,
  $R^{11}$ and $R^{16}$ may join together as $C_1$-$C_4$ alkyl or O to form a bridged bicyclic,
  $R^{11}$ and $R^{17}$ may join together as $C_1$-$C_4$ alkyl to form a bridged bicyclic, or
  $R^{13}$ and $R^{15}$ may join together as $NHCH_2$, or $C_3$-$C_6$ cycloalkyl wherein the cycloalkyl is substituted with $NH_2$ to form a fused bicyclic;
$R^{48}$ is selected from hydrogen and methyl;
$R^a$ is hydrogen, $C_1$-$C_4$ alkyl optionally substituted with OH, methoxy, halogen or cyano, or cyclopropyl;
$R^b$ and $R^c$ are independently selected from hydrogen, $C_1$-$C_3$ alkyl and a Boc group; and
a, b, c and d are selected from 0 and 1.
In certain embodiments:
$X_1$ is CH, $X_2$ is N and $X_3$ is N; or $X_1$ is N, $X_2$ is N and $X_3$ is CH; or $X_1$ is CH, $X_2$ is CH and $X_3$ is N; $L_1$ is selected from a direct bond, S, $CH_2$, O or NH;
$R^1$ is selected from the group consisting of: (a) phenyl optionally substituted with one to three substituents selected from the group consisting of halogen, $C_1$-$C_3$ alkyl optionally substituted with halogen, —O($C_1$-$C_3$ alkyl) optionally substituted with halogen, and cyano; (b) a 6 membered heteroaryl, optionally substituted with one to three groups selected from halogen; $C_1$-$C_3$ alkyl optionally substituted with halogen or OH; methoxy; $NHR^a$; and 3 to 6 membered heterocycle optionally substituted with OH or $C_1$-$C_3$ alkyl optionally substituted with OH or oxo, wherein the heterocycle contains one or two heteroatoms selected from nitrogen, oxygen and $SO_2$; wherein the heteroaryl contains one or two nitrogen heteroatoms; (c) a 10 membered bicyclic aryl; (d) a 10 membered bicyclic heterocyclyl optionally substituted with halogen, OH or oxo, wherein the bicyclic heterocyclyl contains one or two nitrogen heteroatoms; and (e) a 9-10 membered bicyclic heteroaryl optionally substituted with halogen, cyano, amino or $C_1$-$C_3$ alkyl optionally substituted with halogen, wherein the bicyclic heteroaryl contains one to three nitrogen heteroatoms;
$R^2$ is:

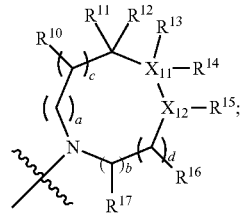

$X_{11}$ is selected from $CR^{13}R^{14}$, $SiR^{13}R^{14}$, NH and O;
$X_{12}$ is selected from $CHR^{15}$ and NH, wherein one or both of $X_{11}$ and $X_{12}$ must be carbon;

$R^{10}$ is selected from hydrogen and methyl;
$R^{11}$ is selected from hydrogen, OH and $CH_2NH_2$;
$R^{12}$, $R^{16}$ and $R^{17}$ are hydrogen;
$R^{13}$ is selected from hydrogen, OH, $CH_2NH_2$, $NH_2$, $NH(CH_3)$, $N(CH_3)_2$, $C(NH_2)(CH_3)_2$ or NHBoc;
$R^{14}$ is selected from hydrogen, OH, methyl, ethyl, propyl, $CF_3$, $CH_2OH$, $CH_2CH_2OH$, $CH_2C(CH_3)_2OH$, $CH_2OCH_3$, $CH_2CH_2OCH_3$ and —$(CH_2)$pyridin-2-yl;
$R^{15}$ is selected from hydrogen or $NH_2$;
or one of the following groups may join together:
 $R^{10}$ and $R^{11}$ may join together as $CH_2NHCH_2$ to form a fused bicyclic,
 $R^{10}$ and $R^{15}$ may join together as ethyl or propyl to form a bridged bicyclic,
 $R^{11}$ and $R^{12}$ may join together as cyclobutane substituted with $NH_2$ to form a spirocyclic,
 $R^{13}$ and $R^{14}$ may join together as a group selected from cyclopentyl, tetrahydrofuran, azetidine, 2,3-dihydro-1H-indene. 6,7-dihydro-5H-cyclopenta[b]pyridine. 2,3-dihydrobenzofuran, or bicyclo[4.2.0]octa-1(6),2,4-triene, optionally substituted with F, Cl, OH, $OCH_3$, CN, methyl or $NH_2$ to form a spirocyclic,
 $R^{10}$ and $R^{16}$ may join together as methyl, ethyl, propyl, O or NH to form a bridged bicyclic,
 $R^{11}$ and $R^{15}$ may join together as methyl or ethyl to form a bridged bicyclic,
 $R^{11}$ and $R^{16}$ may join together as methyl, ethyl, or O to form a bridged bicyclic,
 $R^{11}$ and $R^{17}$ may join together as ethyl to form a bridged bicyclic, or
 $R^{13}$ and $R^{15}$ may join together as $NHCH_2$, or cyclopentyl or cyclohexyl wherein the cyclopentyl or cyclohexyl is substituted with $NH_2$ to form a fused bicyclic;
$R^{48}$ is selected from hydrogen and methyl;
$R^a$ is hydrogen, $C_1$-$C_4$ alkyl optionally substituted with OH, methoxy, halogen or cyano, or cyclopropyl; and
a, b, c and d are selected from 0 and 1.
One embodiment provides compounds of Formula Ia:

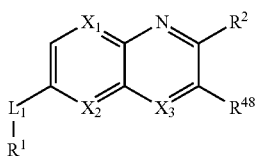

Ia or a stereoisomer, tautomer, or pharmaceutically acceptable salt thereof, wherein:
 $X_1$ is selected from CH and N;
 $X_2$ is selected from CH and N;
 $X_3$ is selected from CH and N;
 $L_1$ is selected from a direct bond, S, $CH_2$, O and NH;
 $R^1$ is selected from phenyl, a 5 to 6 membered heteroaryl wherein the heteroaryl contains one to four heteroatoms selected from the group consisting of nitrogen, oxygen and sulfur, a 10 membered bicyclic aryl, a 9-10 membered bicyclic heterocyclyl wherein the heterocyclyl contains one to three heteroatoms selected from the group consisting of nitrogen, oxygen and sulfur, and a 9-10 membered bicyclic heteroaryl wherein the bicyclic heteroaryl contains one to three heteroatoms selected from the group consisting of nitrogen, oxygen and sulfur,
 wherein the phenyl, heteroaryl, bicyclic aryl, bicyclic heterocyclyl and bicyclic heteroaryl are optionally substituted with one or more groups selected from the group consisting of halogen, OH, oxo, cyano, $C_1$-$C_3$ alkyl optionally substituted with halogen, cyano or OH, —$O(C_1$-$C_3$ alkyl) optionally substituted with halogen, cyano or OH, $NHR^a$, and 3 to 6 membered heterocycle optionally substituted with halogen, cyano, OH or $C_1$-$C_3$ alkyl optionally substituted with OH or oxo, wherein the heterocycle contains one or two heteroatoms selected from nitrogen, oxygen, sulfur and $SO_2$;
$R^2$ is selected from the group consisting of:

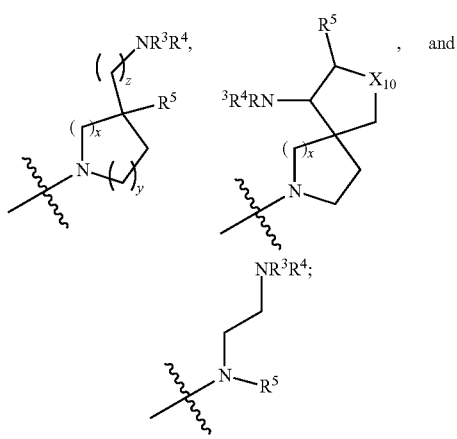

$R^3$ and $R^4$ are independently selected from hydrogen and methyl;
$R^5$ is selected from the group consisting of hydrogen, methyl, OH and $CH_2OH$;
$R^{48}$ is selected from hydrogen and methyl;
$R^a$ is hydrogen, $C_1$-$C_4$ alkyl optionally substituted with OH, methoxy, halogen or cyano, or cyclopropyl;
$X_{10}$ is CH or O;
x is 1 or 2;
y is 1 or 2; and
z is 0 or 1.
In certain embodiments:
$X_1$ is CH, $X_2$ is N and $X_3$ is N; or $X_1$ is N, $X_2$ is N and $X_3$ is CH; or $X_1$ is CH, $X_2$ is CH and $X_3$ is N;
$L_1$ is selected from a direct bond, S, $CH_2$, O or NH;
$R^1$ is selected from the group consisting of: (a) phenyl optionally substituted with one to three substituents selected from the group consisting of halogen, $C_1$-$C_3$ alkyl optionally substituted with halogen, —$O(C_1$-$C_3$ alkyl) optionally substituted with halogen, and cyano; (b) a 6 membered heteroaryl, optionally substituted with one to three groups selected from halogen; $C_1$-$C_3$ alkyl optionally substituted with halogen or OH; methoxy; $NHR^a$; and 3 to 6 membered heterocycle optionally substituted with OH or $C_1$-$C_3$ alkyl optionally substituted with OH or oxo, wherein the heterocycle contains one or two heteroatoms selected from nitrogen, oxygen and $SO_2$; wherein the heteroaryl contains one or two nitrogen heteroatoms; (c) a 10 membered bicyclic aryl; (d) a 10 membered bicyclic heterocyclyl optionally substituted with halogen, OH or oxo, wherein the bicyclic heterocyclyl contains one or two nitrogen heteroatoms; and (e) a 9-10 membered bicyclic heteroaryl optionally substituted with halogen, cyano, amino or $C_1$-$C_3$ alkyl optionally substituted with halogen, wherein the bicyclic heteroaryl contains one to three nitrogen heteroatoms;

$R^2$ is selected from the group consisting of:

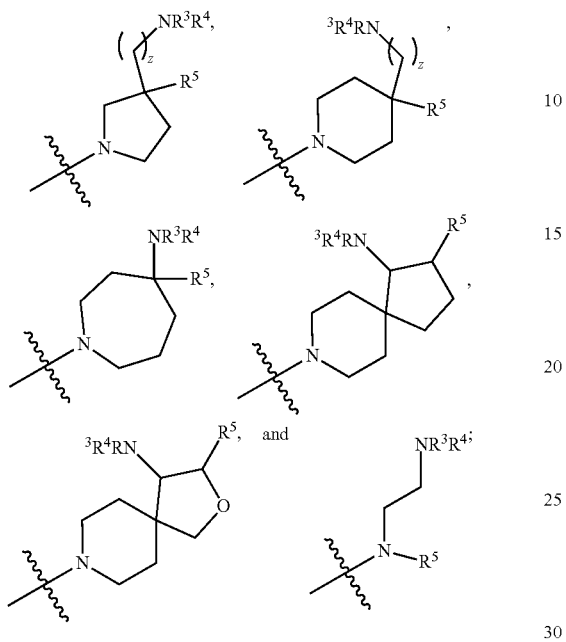

$R^3$ and $R^4$ are independently selected from hydrogen and methyl;
$R^5$ is selected from the group consisting of hydrogen, methyl, OH and $CH_2OH$;
$R^a$ is hydrogen, $C_1$-$C_4$ alkyl optionally substituted with OH, methoxy, halogen or cyano, or cyclopropyl;
z is 0 or 1.

One embodiment provides compounds of Formula Ia:

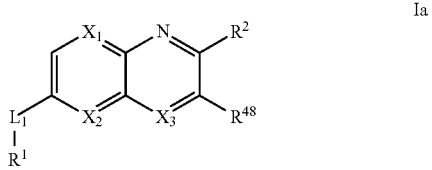

Ia or a stereoisomer, tautomer, or pharmaceutically acceptable salt thereof, wherein:
$X_1$ is selected from CH and N;
$X_2$ is selected from CH and N;
$X_3$ is selected from CH and N;
$L_1$ is selected from a direct bond, S, $CH_2$, O and NH;
$R^1$ is selected from phenyl, a 5 to 6 membered heteroaryl wherein the heteroaryl contains
one to four heteroatoms selected from the group consisting of nitrogen, oxygen and sulfur, a 10 membered bicyclic aryl, a 9-10 membered bicyclic heterocyclyl wherein the heterocyclyl contains
one to three heteroatoms selected from the group consisting of nitrogen, oxygen and sulfur, and a 9-10 membered bicyclic heteroaryl wherein the bicyclic heteroaryl contains one to three heteroatoms selected from the group consisting of nitrogen, oxygen and sulfur, wherein the phenyl, heteroaryl, bicyclic aryl, bicyclic heterocyclyl and bicyclic heteroaryl
are optionally substituted with one or more groups selected from the group consisting of halogen, OH, cyano, $C_1$-$C_3$ alkyl optionally substituted with halogen, cyano or OH, —O($C_1$-$C_3$ alkyl) optionally substituted with halogen, cyano or OH, $NHR^a$, and 3 to 6 membered heterocycle optionally substituted with halogen, cyano, OH or $C_1$-$C_3$ alkyl optionally substituted with OH or oxo, wherein the heterocycle contains one or two heteroatoms selected from nitrogen, oxygen, sulfur and $SO_2$;

$R^2$ is selected from the group consisting of:

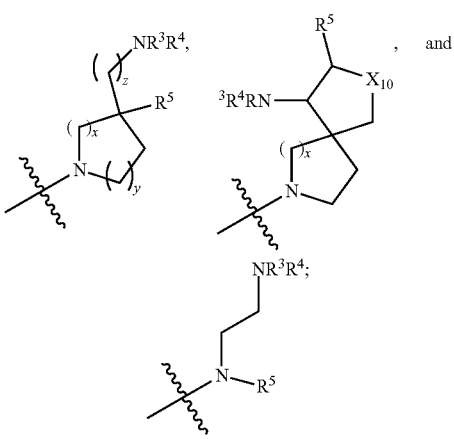

$R^3$ and $R^4$ are independently selected from hydrogen and methyl;
$R^5$ is selected from the group consisting of hydrogen, methyl, OH and $CH_2OH$;
$R^{48}$ is selected from hydrogen and methyl;
$R^a$ is hydrogen, $C_1$-$C_4$ alkyl optionally substituted with OH, methoxy, halogen or cyano, or cyclopropyl;
$X_{10}$ is CH or O;
x is 1 or 2;
y is 1 or 2; and
z is 0 or 1.

One embodiment provides compounds of Formula I:

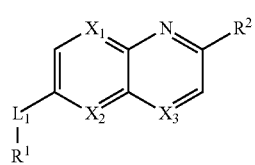

I or a stereoisomer, tautomer, or pharmaceutically acceptable salt thereof, wherein:
$X_1$ is selected from CH and N;
$X_2$ is selected from CH and N;
$X_3$ is selected from CH and N;
$L_1$ is selected from a direct bond, S, $CH_2$, O or NH;
$R^1$ is selected from phenyl, a 5 to 6 membered heteroaryl wherein the heteroaryl contains one to four heteroatoms selected from the group consisting of nitrogen, oxygen and sulfur, a 10 membered bicyclic aryl, and a 9-10 membered bicyclic heteroaryl wherein the bicyclic heteroaryl contains one to three heteroatoms selected from the group consisting of nitrogen, oxygen and sulfur, wherein the phenyl, heteroaryl, bicyclic aryl and bicyclic heteroaryl are optionally substituted with one or more groups selected from the group consisting of halogen, cyano, $C_1$-$C_3$ alkyl optionally substituted with halogen, cyano or OH, —O($C_1$-$C_3$ alkyl) optionally substituted with halogen, cyano or OH, NHR$^a$, and 3 to 6 membered heterocycle optionally substituted with halogen, cyano or OH, wherein the heterocycle contains one or two heteroatoms selected from nitrogen, oxygen and sulfur;

$R^2$ is selected from the group consisting of:

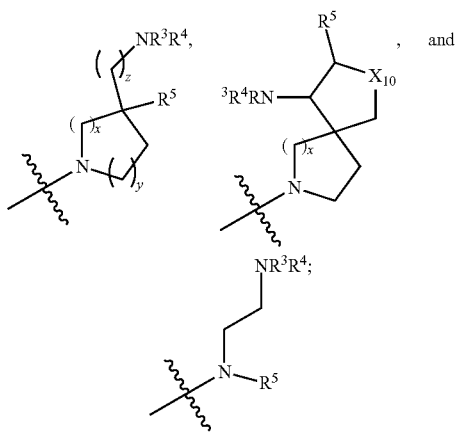

$R^3$ and $R^4$ are independently selected from hydrogen and methyl;

$R^5$ is selected from the group consisting of hydrogen, methyl, OH and $CH_2OH$;

$R^a$ is hydrogen or $C_1$-$C_3$ alkyl optionally substituted with OH, methoxy, halogen or cyano;

$X_{10}$ is CH or O;

x is 1 or 2;

y is 1 or 2; and z is 0 or 1.

In certain embodiments:

$X_1$ is CH, $X_2$ is N and $X_3$ is N; or $X_1$ is N, $X_2$ is N and $X_3$ is CH; or $X_1$ is CH, $X_2$ is CH and $X_3$ is N;

$L_1$ is selected from a direct bond, S, $CH_2$, O or NH;

$R^1$ is selected from the group consisting of: (a) phenyl optionally substituted with one to three substituents selected from the group consisting of halogen, $C_1$-$C_3$ alkyl optionally substituted with halogen, —O($C_1$-$C_3$ alkyl) optionally substituted with halogen, and cyano; (b) a 6 membered heteroaryl, optionally substituted with one or two groups selected from halogen, methoxy, NHR$^a$, and 3 to 6 membered heterocycle optionally substituted with OH, wherein the heterocycle contains one nitrogen heteroatom, wherein the heteroaryl contains one nitrogen heteroatom; (c) a 10 membered bicyclic aryl; and (d) a 9-10 membered bicyclic heteroaryl optionally substituted with $C_1$-$C_3$ alkyl, wherein the bicyclic heteroaryl contains one to three nitrogen heteroatoms;

$R^2$ is selected from the group consisting of:

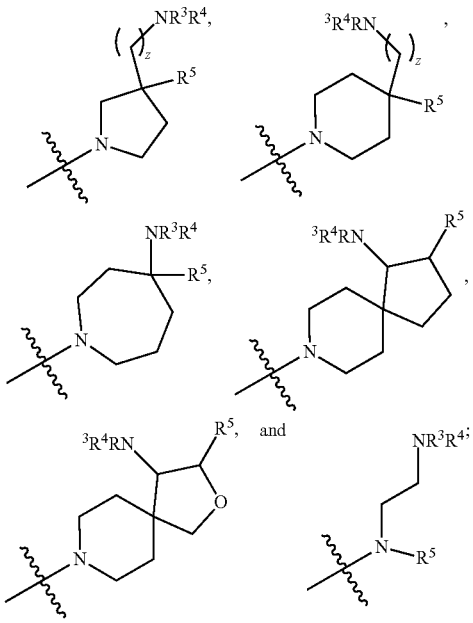

$R^3$ and $R^4$ are independently selected from hydrogen and methyl;

$R^5$ is selected from the group consisting of hydrogen, methyl, OH and $CH_2OH$;

$R^a$ is hydrogen or $C_1$-$C_3$ alkyl optionally substituted with OH, methoxy, halogen or cyano;

z is 0 or 1.

In another embodiment, compounds of Formula I or a stereoisomer or pharmaceutically acceptable salt thereof are provided.

In another embodiment, compounds of Formula I or a tautomer or pharmaceutically acceptable salt thereof are provided.

In another embodiment, compounds of Formula I or a stereoisomer or tautomer thereof are provided.

In another embodiment, compounds of Formula I or a stereoisomer thereof are provided.

In another embodiment, compounds of Formula I or a tautomer thereof are provided.

In another embodiment, compounds of Formula I or a pharmaceutically acceptable salt thereof are provided.

In certain embodiments, $X_1$ is selected from CH and N; and $X_2$ is selected from CH and N; and $X_3$ is selected from CH and N, wherein only one or two of $X_1$, $X_2$ and $X_3$ may be N.

In certain embodiments, $X_1$ is selected from CH and N; and $X_2$ is selected from CH and N; and $X_3$ is selected from CH and N, wherein only one of $X_1$, $X_2$ and $X_3$ may be N.

In certain embodiments, $X_1$ is CH, $X_2$ is N and $X_3$ is N.

In certain embodiments, compounds of the invention have the Formula IIa:

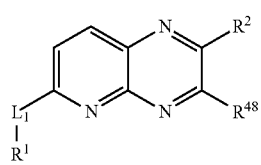

IIa or a stereoisomer, tautomer or pharmaceutically acceptable salt thereof, wherein $L_1$, $R^1$, $R^2$, and $R^{48}$ are as defined herein.

In certain embodiments, $X_1$ is CH, $X_2$ is N and $X_3$ is N. In certain embodiments, compounds of the invention have the Formula II:

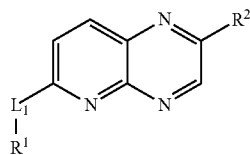

II or a stereoisomer, tautomer or pharmaceutically acceptable salt thereof, wherein $L_1$, $R^1$, and $R^2$ are as defined herein.

In certain embodiments, $X_1$ is N, $X_2$ is N and $X_3$ is CH. In certain embodiments, compounds of the invention have the Formula IIIa:

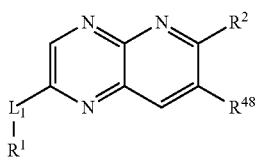

IIIa or a stereoisomer, tautomer or pharmaceutically acceptable salt thereof, wherein $L_1$, $R^1$, $R^2$, and $R^{48}$ are as defined herein.

In certain embodiments, $X_1$ is N, $X_2$ is N and $X_3$ is CH. In certain embodiments, compounds of the invention have the Formula III:

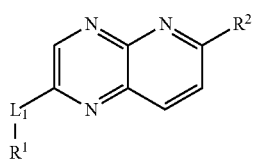

III or a stereoisomer, tautomer or pharmaceutically acceptable salt thereof, wherein $L_1$, $R^1$, and $R^2$ are as defined herein.

In certain embodiments, $X_1$ is CH, $X_2$ is CH and $X_3$ is N. In certain embodiments, compounds of the invention have the Formula IVa:

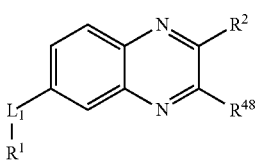

IVa or a stereoisomer, tautomer or pharmaceutically acceptable salt thereof, wherein $L_1$, $R^1$, $R^2$, and $R^{48}$ are as defined herein.

In certain embodiments, $X_1$ is CH, $X_2$ is CH and $X_3$ is N. In certain embodiments, compounds of the invention have the Formula IV:

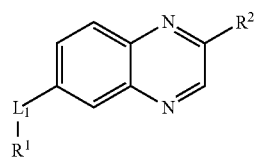

IV or a stereoisomer, tautomer or pharmaceutically acceptable salt thereof, wherein $L_1$, $R^1$, and $R^2$ are as defined herein.

In certain embodiments, $L_1$ is selected from a direct bond, S, $CH_2$, O or NH. In certain embodiments, $L_1$ is selected from a direct bond and S. In certain embodiments, $L_1$ is selected from S, $CH_2$, O or NH. In certain embodiments, $L_1$ is selected from a direct bond, S, O or NH. In certain embodiments, $L_1$ is selected from a S, O or NH. In certain embodiments, $L_1$ is selected from a direct bond and S. In certain embodiments, $L_1$ is a direct bond. In certain embodiments, $L_1$ is S. In certain embodiments, $L_1$ is $CH_2$. In certain embodiments, $L_1$ is O. In certain embodiments, $L_1$ is NH.

In certain embodiments, compounds of the invention have the Formula Va:

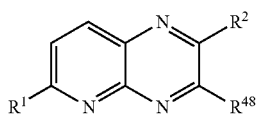

Va or a stereoisomer, tautomer or pharmaceutically acceptable salt thereof, wherein $R^1$ and $R^2$ are as defined herein.

In certain embodiments, compounds of the invention have the Formula V:

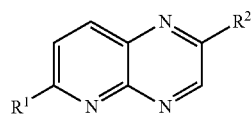

V or a stereoisomer, tautomer or pharmaceutically acceptable salt thereof, wherein $R^1$ and $R^2$ are as defined herein.

In certain embodiments, compounds of the invention have the Formula VIa:

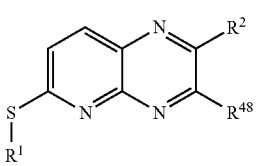

VIa or a stereoisomer, tautomer or pharmaceutically acceptable salt thereof, wherein $R^1$ and $R^2$ are as defined herein.

In certain embodiments, compounds of the invention have the Formula VI:

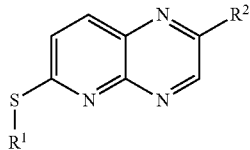

VI or a stereoisomer, tautomer or pharmaceutically acceptable salt thereof, wherein $R^1$ and $R^2$ are as defined herein.

In certain embodiments, $R^1$ is selected from phenyl, a 5 to 6 membered heteroaryl wherein the heteroaryl contains one to four heteroatoms selected from the group consisting of nitrogen, oxygen and sulfur, a 10 membered bicyclic aryl, a 9-10 membered bicyclic heterocyclyl wherein the heterocyclyl contains one to three heteroatoms selected from the group consisting of nitrogen, oxygen and sulfur, and a 9-10 membered bicyclic heteroaryl wherein the bicyclic heteroaryl contains one to three heteroatoms selected from the group consisting of nitrogen, oxygen and sulfur, wherein the phenyl, heteroaryl, bicyclic aryl, bicyclic heterocyclyl and bicyclic heteroaryl are optionally substituted with one to three groups selected from the group consisting of halogen; oxo; cyano; $C_1$-$C_3$ alkyl optionally substituted with halogen, cyano or OH; —O($C_1$-$C_3$ alkyl) optionally substituted with halogen, cyano or OH; $NHR^a$; and 3 to 6 membered heterocycle optionally substituted with halogen, cyano, OH or $C_1$-$C_3$ alkyl optionally substituted with OH or oxo, wherein the heterocycle contains one or two heteroatoms selected from nitrogen, oxygen, sulfur and $SO_2$. In certain embodiments, $R^1$ is selected from phenyl, a 5 to 6 membered heteroaryl wherein the heteroaryl contains one to four heteroatoms selected from the group consisting of nitrogen, oxygen and sulfur, a 10 membered bicyclic aryl, a 9-10 membered bicyclic heterocyclyl wherein the heterocyclyl contains one to three heteroatoms selected from the group consisting of nitrogen, oxygen and sulfur, and a 9-10 membered bicyclic heteroaryl wherein the bicyclic heteroaryl contains one to three heteroatoms selected from the group consisting of nitrogen, oxygen and sulfur, wherein the phenyl, heteroaryl, bicyclic aryl, bicyclic heterocyclyl and bicyclic heteroaryl are optionally substituted with one to three groups selected from the group consisting of halogen; cyano; $C_1$-$C_3$ alkyl optionally substituted with halogen, cyano or OH; —O($C_1$-$C_3$ alkyl) optionally substituted with halogen, cyano or OH; $NHR^a$; and 3 to 6 membered heterocycle optionally substituted with halogen, cyano, OH or $C_1$-$C_3$ alkyl optionally substituted with OH or oxo, wherein the heterocycle contains one or two heteroatoms selected from nitrogen, oxygen, sulfur and $SO_2$. In certain embodiments, $R^1$ is selected from the group consisting of: (a) phenyl optionally substituted with one to three substituents selected from the group consisting of halogen, $C_1$-$C_3$ alkyl optionally substituted with halogen, —O($C_1$-$C_3$ alkyl) optionally substituted with halogen, and cyano; (b) a 5 to 6 membered heteroaryl optionally substituted with one to three selected from halogen; $C_1$-$C_3$ alkyl optionally substituted with halogen or OH; methoxy; $NHR^a$; and 3 to 6 membered heterocycle optionally substituted with OH or $C_1$-$C_3$ alkyl optionally substituted with OH or oxo, wherein the heterocycle contains one or two heteroatoms selected from the group consisting of nitrogen, oxygen, sulfur and $SO_2$; wherein the heteroaryl contains one, two, three of four heteroatoms selected from the group consisting of nitrogen, oxygen and sulfur; (c) a 10 membered bicyclic aryl optionally substituted with halogen or methyl; (d) a 9-10 membered bicyclic heterocyclyl optionally substituted with one to three groups selected from halogen, oxo, $C_1$-$C_3$ alkyl optionally substituted with halogen, —O($C_1$-$C_3$ alkyl) optionally substituted with halogen, or cyano, wherein the bicyclic heterocyclyl contains one to three nitrogen, sulfur or oxygen heteroatoms; and (e) a 9-10 membered bicyclic heteroaryl optionally substituted with one to three groups selected from halogen, $C_1$-$C_3$ alkyl optionally substituted with halogen, —O($C_1$-$C_3$ alkyl) optionally substituted with halogen, or cyano, wherein the bicyclic heteroaryl contains one to three nitrogen, sulfur or oxygen heteroatoms. In certain embodiments, $R^1$ is selected from the group consisting of: (a) phenyl optionally substituted with one to three substituents selected from the group consisting of halogen, $C_1$-$C_3$ alkyl optionally substituted with halogen, —O($C_1$-$C_3$ alkyl) optionally substituted with halogen, and cyano; (b) a 6 membered heteroaryl, optionally substituted with one to three groups selected from halogen; $C_1$-$C_3$ alkyl optionally substituted with halogen or OH; methoxy; $NHR^a$; and 3 to 6 membered heterocycle optionally substituted with OH or $C_1$-$C_3$ alkyl optionally substituted with OH or oxo, wherein the heterocycle contains one or two heteroatoms selected from nitrogen, oxygen and $SO_2$; wherein the heteroaryl contains one or two nitrogen heteroatoms; (c) a 10 membered bicyclic aryl; (d) a 9-10 membered bicyclic heterocyclyl optionally substituted with halogen or oxo, wherein the bicyclic heterocyclyl contains one or two nitrogen heteroatoms; and (e) a 9-10 membered bicyclic heteroaryl optionally substituted with halogen, cyano or $C_1$-$C_3$ alkyl optionally substituted with halogen, wherein the bicyclic heteroaryl contains one to three nitrogen heteroatoms. In certain embodiments, $R^1$ is selected from the group consisting of: (a) phenyl optionally substituted with one to three substituents selected from the group consisting of halogen, $C_1$-$C_3$ alkyl optionally substituted with halogen, —O($C_1$-$C_3$ alkyl) optionally substituted with halogen, and cyano; (b) a 6 membered heteroaryl, optionally substituted with one to three groups selected from halogen; $C_1$-$C_3$ alkyl optionally substituted with halogen or OH; methoxy; $NHR^a$; and 3 to 6 membered heterocycle optionally substituted with OH or $C_1$-$C_3$ alkyl optionally substituted with OH or oxo, wherein the heterocycle contains one or two heteroatoms selected from nitrogen, oxygen and $SO_2$; wherein the heteroaryl contains one or two nitrogen heteroatoms; (c) a 10 membered bicyclic aryl; (d) a 9-10 membered bicyclic heterocyclyl, wherein the bicyclic heterocyclyl contains one or two nitrogen heteroatoms; and (e) a 9-10 membered bicyclic heteroaryl optionally substituted with halogen, cyano or $C_1$-$C_3$ alkyl optionally substituted with halogen, wherein the bicyclic heteroaryl contains one to three nitrogen heteroatoms. In certain embodiments, $R^1$ is selected from the group consisting of phenyl, 2,3-dichlorophenyl, 3-chlorophenyl, 4-fluorophenyl, 3-chloro-2-trifluoromethylphenyl, 2-chloro-3-methoxyphenyl, 3-chloro-2-fluorophenyl, 2-chloro-6-fluoro-3-methoxyphenyl, 2,3-dichloro-4-methoxyphenyl, 2-chloro-3-cyanophenyl, 2-chloro-3-fluorophenyl, 2-amino-3-chloropyridin-4-yl, 3-chloro-2-(pyrrolidine-1-yl)pyridine-4-yl, 3-chloro-2-methoxypyridin-4-yl, 3-chloro-2-(methylamino)pyridin-4-yl), 3-chloro-2-(3-hydroxypyrrolidin-1-yl)pyridin-4-yl, 3-chloro-2-((2-hydroxyethyl)amino) pyridin-4-yl, 3-chloro-2-methylpyridin-4-yl, 6-amino-2,3-dichloropyridin-4-yl, 3-chloro-2-(2-(hydroxymethyl) pyrrolidin-1-yl)pyridin-4-yl, 2-amino-3-methylpyridin-4-yl, 3-chloro-2-(1,1-dioxidothiomorpholino)pyridin-4-yl, 3-chloro-2-(4-hydroxypiperidin-1-yl)pyridin-4-yl, 3-chloro-2-morpholinopyridin-4-yl, 2-(4-acetylpiperazin-1-yl)-3-chloropyridin-4-yl, 3-chloro-2-((S)-3-(hydroxymethyl)pyrrolidin-1-yl)pyridin-4-yl, 3-chloro-2-((S)-3-hydroxypyrrolidin-1-yl)pyridin-4-yl, 3-chloro-2-(3-hydroxypyrrolidin-1-yl)pyridin-4-yl, 3-chloro-2-(hydroxymethyl)pyridin-4-yl, 3-chloro-2-methylpyridin-4-yl, 2-aminopyridin-3-yl, 6-chloro-2-methylpyridin-3-yl, 6-amino-2-chloropyridin-3-yl, 2-chloro-6-methylpyridin-3-yl, 3-chloro-2-((R)-3-(hydroxymethyl)pyrrolidin-1-yl)pyridin-4-yl, 2,3-dimethylpyridin-4-yl, 2-amino-3-fluoropyridin-4-yl, 6-amino-2-(trifluoromethyl)pyridin-3-yl, 2-amino-5-chloropyridin-4-yl, 6-amino-4,5-dichloropyridin-3-yl, 6-amino-3-chloro-2-methoxypyridin-4-yl, 2-amino-3-methoxypyridin-4-yl, 6-amino-5-chloropyrimidin-4-yl, 2-(trifluoromethyl)pyridin-3-yl, 3-chloro-2-((2-methoxyethyl)amino)pyridin-4-yl, 3-chloro-2-(cyclopropylamino)pyridin-4-yl, 3-fluoropyridin-4-yl, 3-chloropyridin-4-yl, 3-(trifluoromethyl)pyridin-4-yl, 3-chloro-2-((2-cyano-2-methylpropyl)amino)pyridin-4-yl, 3-chloro-2-((3-methoxypropyl)amino)pyridin-4-yl, 2-amino-3-(trifluoromethyl)pyridin-4-yl, 2-(trifluoromethyl)pyridin-4-yl, 3,4-dihydroquinolin-1(2H)-yl, 3,4-dihydroquinoxalin-1(2H)-yl, 2,3-dihydro-1H-pyrrolo[2,3-b]pyridin-4-yl, 3,4-dihydro-1,5-naphthyridin-1(2H)-yl, 3,3-difluoro-2-oxo-2,3-dihydro-1H-pyrrolo[2,3-b]pyridin-4-yl, 7-hydroxy-6,7-dihydro-5H-cyclopenta[b]pyridin-4-yl, naphthalen-1-yl, 1-methyl-1H-indazol-7-yl, pyrazolo[1,5-a]pyridine-4-yl, pyrazolo[1,5-a]pyrazin-4-yl, isoquinolin-8-yl, 3H-imidazo[4,5-b]pyridin-7-yl, 6-chloroimidazo[1,2-a]pyridin-3-yl, 6-cyanoimidazo[1,2-a]pyridin-3-yl, 1H-pyrazolo[3,4-b]pyridin-4-yl, 1,8-naphthyridin-4-yl, 1H-pyrrolo[2,3-b]pyridin-4-yl, 1-methyl-1H-pyrrolo[2,3-b]pyridin-4-yl, 5-chloro-1H-pyrrolo[2,3-b]pyridin-4-yl, 5-(trifluoromethyl)-1H-pyrrolo[2,3-b]pyridin-4-yl, 3-methyl-1H-pyrrolo[2,3-b]pyridin-4-yl, 6-amino-1H-pyrrolo[2,3-b]pyridin-4-yl and 5-fluoro-1H-pyrrolo[2,3-b]pyridin-4-yl.

In certain embodiments, $R^1$ is selected from phenyl, a 5 to 6 membered heteroaryl wherein the heteroaryl contains one to four heteroatoms selected from the group consisting of nitrogen, oxygen and sulfur, a 10 membered bicyclic aryl, and a 9-10 membered bicyclic heteroaryl wherein the bicyclic heteroaryl contains one to three heteroatoms selected from the group consisting of nitrogen, oxygen and sulfur, wherein the phenyl, heteroaryl, bicyclic aryl and bicyclic heteroaryl are optionally substituted with one to three groups selected from the group consisting of halogen, cyano, $C_1$-$C_3$ alkyl optionally substituted with halogen, cyano or OH, —O($C_1$-$C_3$ alkyl) optionally substituted with halogen, cyano or OH, $NHR^a$, and 3 to 6 membered heterocycle optionally substituted with halogen, cyano or OH, wherein the heterocycle contains one or two heteroatoms selected from nitrogen, oxygen and sulfur. In certain embodiments, $R^1$ is selected from the group consisting of: (a) phenyl optionally substituted with one to three substituents selected from the group consisting of halogen, $C_1$-$C_3$ alkyl optionally substituted with halogen, —O($C_1$-$C_3$ alkyl) optionally substituted with halogen, and cyano; (b) a 5 to 6 membered heteroaryl optionally substituted with one or two groups selected from halogen, methoxy, $NHR^a$, and 3 to 6 membered heterocycle optionally substituted with OH, wherein the heterocycle contains one or two heteroatoms selected from the group consisting of nitrogen, oxygen and sulfur, wherein the heteroaryl contains one, two, three of four heteroatoms selected from the group consisting of nitrogen, oxygen and sulfur; (c) a 10 membered bicyclic aryl optionally substituted with halogen or methyl; and (d) a 9-10 membered bicyclic heteroaryl optionally substituted with one to three groups selected from halogen, $C_1$-$C_3$ alkyl optionally substituted with halogen, —O($C_1$-$C_3$ alkyl) optionally substituted with halogen, or cyano, wherein the bicyclic heteroaryl contains one to three nitrogen, sulfur or oxygen heteroatoms. In certain embodiments, $R^1$ is selected from the group consisting of: (a) phenyl optionally substituted with one to three substituents selected from the group consisting of halogen, $C_1$-$C_3$ alkyl optionally substituted with halogen, —O($C_1$-$C_3$ alkyl) optionally substituted with halogen, and cyano; (b) a 6 membered heteroaryl, optionally substituted with one or two groups selected from halogen, methoxy, $NHR^a$, and 3 to 6 membered heterocycle optionally substituted with OH, wherein the heterocycle contains one nitrogen heteroatom, wherein the heteroaryl contains one nitrogen heteroatom; (c) a 10 membered bicyclic aryl; and (d) a 9-10 membered bicyclic heteroaryl optionally substituted with $C_1$-$C_3$ alkyl, wherein the bicyclic heteroaryl contains one to three nitrogen heteroatoms. In certain embodiments, $R^1$ is selected from the group consisting of 2,3-dichlorophenyl, 3-chlorophenyl, 3-chloro-2-trifluoromethylphenyl, 2-chloro-3-methoxyphenyl, 3-chloro-2-fluorophenyl, 2-chloro-6-fluoro-3-methoxyphenyl, 2,3-dichloro-4-methoxyphenyl, 2-chloro-3-cyanophenyl, 2-chloro-3-fluorophenyl, 2-amino-3-chloropyridin-4-yl, 3-chloro-2-(pyrrolidine-1-yl)pyridine-4-yl, 3-chloro-2-methoxypyridin-4-yl, 3-chloro-2-(methylamino)pyridine-4-yl), 3-chloro-2-(3-hydroxypyrrolidin-1-yl)pyridin-4-yl, 3-chloro-2-((2-hydroxyethyl)amino)pyridin-4-yl, naphthalen-1-yl, 1-methyl-1H-indazol-7-yl, pyrazolo[1,5-a]pyridine-4-yl, pyrazolo[1,5-a]pyrazin-4-yl and isoquinolin-8-yl.

In certain embodiments, $R^1$ is phenyl optionally substituted with one or more groups selected from the group consisting of halogen, cyano, $C_1$-$C_3$ alkyl optionally substituted with halogen, cyano or OH, —O($C_1$-$C_3$ alkyl) optionally substituted with halogen, cyano or OH, $NHR^a$, and 3 to 6 membered heterocycle optionally substituted with halogen, cyano or OH, wherein the heterocycle contains one or two heteroatoms selected from nitrogen, oxygen and sulfur. In certain embodiments, $R^1$ is phenyl optionally substituted with one to three groups selected from the group consisting of halogen, cyano, $C_1$-$C_3$ alkyl optionally substituted with halogen, cyano or OH, —O($C_1$-$C_3$ alkyl) optionally substituted with halogen, cyano or OH, $NHR^a$, and 3 to 6 membered heterocycle optionally substituted with halogen, cyano or OH, wherein the heterocycle contains one or two heteroatoms selected from nitrogen, oxygen and sulfur. In certain embodiments, $R^1$ is phenyl optionally substituted with one to three substituents selected from the group consisting of halogen, $C_1$-$C_3$ alkyl optionally substituted with halogen, —O($C_1$-$C_3$ alkyl) optionally substituted with halogen, and cyano. In certain embodiments, $R^1$ is phenyl optionally substituted with one to three substituents selected from the group consisting of halogen, trifluoromethyl, methoxy and cyano. In certain embodiments, $R^1$ is selected from the group consisting of phenyl, 2,3-dichlorophenyl, 3-chlorophenyl, 4-fluorophenyl, 3-chloro-2-trifluoromethylphenyl, 2-chloro-3-methoxyphenyl, 3-chloro-2-fluorophenyl, 2-chloro-6-fluoro-3-methoxyphenyl, 2,3-dichloro-4-methoxyphenyl, 2-chloro-3-cyanophenyl and 2-chloro-3-fluorophenyl.

In certain embodiments, $R^1$ is phenyl optionally substituted with one or more groups selected from the group consisting of halogen, cyano, $C_1$-$C_3$ alkyl optionally substituted with halogen, cyano or OH, —O($C_1$-$C_3$ alkyl) optionally substituted with halogen, cyano or OH, NHR$^a$, and 3 to 6 membered heterocycle optionally substituted with halogen, cyano or OH,
wherein the heterocycle contains one or two heteroatoms selected from nitrogen, oxygen and sulfur. In certain embodiments, R$^1$ is phenyl optionally substituted with one to three groups selected from the group consisting of halogen, cyano, C$_1$-C$_3$ alkyl optionally substituted with halogen, cyano or OH, —O(C$_1$-C$_3$ alkyl) optionally substituted with halogen, cyano or OH, NHR$^a$, and 3 to 6 membered heterocycle optionally substituted with halogen, cyano or OH, wherein the heterocycle contains one or two heteroatoms selected from nitrogen, oxygen and sulfur. In certain embodiments, R$^1$ is phenyl optionally substituted with one to three substituents selected from the group consisting of halogen, C$_1$-C$_3$ alkyl optionally substituted with halogen, —O(C$_1$-C$_3$ alkyl) optionally substituted with halogen, and cyano. In certain embodiments, R$^1$ is phenyl optionally substituted with one to three substituents selected from the group consisting of halogen, trifluoromethyl, methoxy and cyano. In certain embodiments, R$^1$ is selected from the group consisting of 2,3-dichlorophenyl, 3-chlorophenyl, 3-chloro-2-trifluoromethylphenyl, 2-chloro-3-methoxyphenyl, 3-chloro-2-fluorophenyl, 2-chloro-6-fluoro-3-methoxyphenyl, 2,3-dichloro-4-methoxyphenyl, 2-chloro-3-cyanophenyl and 2-chloro-3-fluorophenyl.

In certain embodiments, R$^1$ is a 5 to 6 membered heteroaryl optionally substituted with one or more groups selected from halogen; cyano; C$_1$-C$_3$ alkyl optionally substituted with halogen, cyano or OH; —O(C$_1$-C$_3$ alkyl) optionally substituted with halogen, cyano or OH; NHR$^a$; and 3 to 6 membered heterocycle optionally substituted with halogen, cyano, OH or C$_1$-C$_3$ alkyl optionally substituted with OH or oxo, wherein the heterocycle contains one or two heteroatoms selected from nitrogen, oxygen, sulfur and SO$_2$; wherein the heteroaryl contains one, two, three or four heteroatoms selected from the group consisting of nitrogen, oxygen and sulfur. In certain embodiments, R$^1$ is a 5 to 6 membered heteroaryl optionally substituted with one to three groups selected from halogen; cyano; C$_1$-C$_3$ alkyl optionally substituted with halogen, cyano or OH; —O(C$_1$-C$_3$ alkyl) optionally substituted with halogen, cyano or OH; NHR$^a$, and 3 to 6 membered heterocycle optionally substituted with halogen, cyano, OH or C$_1$-C$_3$ alkyl optionally substituted with OH or oxo, wherein the heterocycle contains one or two heteroatoms selected from nitrogen, oxygen, sulfur and SO$_2$; wherein the heteroaryl contains one, two, three or four heteroatoms selected from the group consisting of nitrogen, oxygen and sulfur. In certain embodiments, R$^1$ is a 5 to 6 membered heteroaryl optionally substituted with one to three selected from halogen; C$_1$-C$_3$ alkyl optionally substituted with halogen or OH; methoxy; NHR$^a$; and 3 to 6 membered heterocycle optionally substituted with OH or C$_1$-C$_3$ alkyl optionally substituted with OH or oxo, wherein the heterocycle contains one or two heteroatoms selected from the group consisting of nitrogen, oxygen, sulfur and SO$_2$; wherein the heteroaryl contains one, two, three of four heteroatoms selected from the group consisting of nitrogen, oxygen and sulfur. In certain embodiments, R$^1$ is a 5 to 6 membered heteroaryl optionally substituted with one to three selected from halogen; C$_1$-C$_3$ alkyl optionally substituted with halogen or OH; methoxy; NHR$^a$; and 3 to 6 membered heterocycle optionally substituted with OH or C$_1$-C$_3$ alkyl optionally substituted with OH or oxo, wherein the heterocycle contains one or two heteroatoms selected from nitrogen, oxygen and SO$_2$; wherein the heteroaryl contains one or two nitrogen heteroatoms. In certain embodiments, R$^1$ is 6 membered heteroaryl, optionally substituted with one to three groups selected from halogen; C$_1$-C$_3$ alkyl optionally substituted with halogen or OH; methoxy; NHR$^a$; and 3 to 6 membered heterocycle optionally substituted with OH or C$_1$-C$_3$ alkyl optionally substituted with OH or oxo, wherein the heterocycle contains one or two heteroatoms selected from the group consisting of nitrogen, oxygen, sulfur and SO$_2$; wherein the heteroaryl contains one, two, three of four heteroatoms selected from the group consisting of nitrogen, oxygen and sulfur. In certain embodiments, R$^1$ is 6 membered heteroaryl, optionally substituted with one to three groups selected from halogen; C$_1$-C$_3$ alkyl optionally substituted with halogen or OH; methoxy; NHR$^a$; and 3 to 6 membered heterocycle optionally substituted with OH or C$_1$-C$_3$ alkyl optionally substituted with OH or oxo, wherein the heterocycle contains one or two heteroatoms selected from the group consisting of nitrogen, oxygen, sulfur and SO$_2$; wherein the heteroaryl contains one or two nitrogen heteroatoms. In certain embodiments, R$^1$ is 6 membered heteroaryl, optionally substituted with one to three groups selected from halogen; C$_1$-C$_3$ alkyl optionally substituted with halogen or OH; methoxy; NHR$^a$; and 3 to 6 membered heterocycle optionally substituted with OH or C$_1$-C$_3$ alkyl optionally substituted with OH or oxo, wherein the heterocycle contains one or two heteroatoms selected from nitrogen, oxygen and SO$_2$; wherein the heteroaryl contains one or two nitrogen heteroatoms. In certain embodiments, R$^1$ is 6 membered heteroaryl, optionally substituted with one to three groups selected from halogen; C$_1$-C$_3$ alkyl optionally substituted with halogen or OH; methoxy; NHR$^a$; and 5 or 6 membered heterocycle optionally substituted with OH or C$_1$-C$_3$ alkyl optionally substituted with OH or oxo, wherein the heterocycle contains one or two heteroatoms selected from nitrogen, oxygen and SO$_2$; wherein the heteroaryl contains one or two nitrogen heteroatoms. In certain embodiments, R$^1$ is pyridinyl or pyrimidinyl optionally substituted with one to three groups selected from halogen; C$_1$-C$_3$ alkyl optionally substituted with halogen or OH; methoxy; NHR$^a$; and 3 to 6 membered heterocycle optionally substituted with OH or C$_1$-C$_3$ alkyl optionally substituted with OH or oxo, wherein the heterocycle contains one or two heteroatoms selected from the group consisting of nitrogen, oxygen, sulfur and SO$_2$. In certain embodiments, R$^1$ is pyridinyl or pyrimidinyl optionally substituted with one to three groups selected from halogen; C$_1$-C$_3$ alkyl optionally substituted with halogen or OH; methoxy; NHR$^a$; and 3 to 6 membered heterocycle optionally substituted with OH or C$_1$-C$_3$ alkyl optionally substituted with OH or oxo, wherein the heterocycle contains one or two heteroatoms selected from nitrogen, oxygen and SO$_2$. In certain embodiments, R$^1$ is pyridinyl or pyrimidinyl optionally substituted with one to three groups selected from halogen; C$_1$-C$_3$ alkyl optionally substituted with halogen or OH; methoxy; NHR$^a$; and 5 or 6 membered heterocycle optionally substituted with OH or C$_1$-C$_3$ alkyl optionally substituted with OH or oxo, wherein the heterocycle contains one or two heteroatoms selected from nitrogen, oxygen and SO$_2$. In certain embodiments, R$^1$ is pyridinyl or pyrimidinyl optionally substituted with one to three groups selected from halogen; C$_1$-C$_3$ alkyl optionally substituted with halogen or OH; methoxy; NHR$^a$; and 5 or 6 membered heterocycle optionally substituted with OH, CH$_2$OH or C(=O)CH$_3$, wherein the heterocycle contains one or two heteroatoms selected from nitrogen, oxygen and SO$_2$. In certain embodiments, R$^1$ is pyridinyl or pyrimidinyl optionally substituted with one to three groups selected from halogen; C$_1$-C$_3$ alkyl optionally substituted with halogen or OH; methoxy; NHR$^a$; and a 5 to 6 membered heterocycle optionally substituted with OH or $C_1$-$C_3$ alkyl optionally substituted with OH or oxo, wherein the heterocycle contains one or two heteroatoms selected from nitrogen, oxygen and $SO_2$. In certain embodiments, $R^1$ is selected from the group consisting of 2-amino-3-chloropyridin-4-yl, 3-chloro-2-(pyrrolidine-1-yl)pyridine-4-yl, 3-chloro-2-methoxypyridin-4-yl, 3-chloro-2-(methylamino)pyridine-4-yl), 3-chloro-2-(3-hydroxypyrrolidin-1-yl)pyridin-4-yl, 3-chloro-2-((2-hydroxyethyl)amino)pyridin-4-yl, 3-chloro-2-methylpyridin-4-yl, 6-amino-2,3-dichloropyridin-4-yl, 3-chloro-2-(2-(hydroxymethyl)pyrrolidin-1-yl)pyridin-4-yl, 2-amino-3-methylpyridin-4-yl, 3-chloro-2-(1,1-dioxidothiomorpholino)pyridin-4-yl, 3-chloro-2-(4-hydroxypiperidin-1-yl)pyridin-4-yl, 3-chloro-2-morpholinopyridin-4-yl, 2-(4-acetylpiperazin-1-yl)-3-chloropyridin-4-yl, 3-chloro-2-((S)-3-(hydroxymethyl)pyrrolidin-1-yl)pyridin-4-yl, 3-chloro-2-((S)-3-hydroxypyrrolidin-1-yl)pyridin-4-yl, 3-chloro-2-(3-hydroxypyrrolidin-1-yl)pyridin-4-yl, 3-chloro-2-(hydroxymethyl)pyridin-4-yl, 3-chloro-2-methylpyridin-4-yl, 2-aminopyridin-3-yl, 6-chloro-2-methylpyridin-3-yl, 6-amino-2-chloropyridin-3-yl, 2-chloro-6-methylpyridin-3-yl, 3-chloro-2-((R)-3-(hydroxymethyl)pyrrolidin-1-yl)pyridin-4-yl, 2,3-dimethylpyridin-4-yl, 2-amino-3-fluoropyridin-4-yl, 6-amino-2-(trifluoromethyl)pyridin-3-yl, 2-amino-5-chloropyridin-4-yl, 6-amino-4,5-dichloropyridin-3-yl, 6-amino-3-chloro-2-methoxypyridin-4-yl, 2-amino-3-methoxypyridin-4-yl, 6-amino-5-chloropyrimidin-4-yl, 2-(trifluoromethyl)pyridin-3-yl, 3-chloro-2-((2-methoxyethyl)amino)pyridin-4-yl, 3-chloro-2-(cyclopropylamino)pyridin-4-yl, 3-fluoropyridin-4-yl, 3-chloropyridin-4-yl, 3-(trifluoromethyl)pyridin-4-yl, 3-chloro-2-((2-cyano-2-methylpropyl)amino)pyridin-4-yl, 3-chloro-2-((3-methoxypropyl)amino)pyridin-4-yl, 2-amino-3-(trifluoromethyl)pyridin-4-yl and 2-(trifluoromethyl)pyridin-4-yl.

In certain embodiments, $R^1$ is a 5 to 6 membered heteroaryl optionally substituted with one or more groups selected from halogen, cyano, $C_1$-$C_3$ alkyl optionally substituted with halogen, cyano or OH, —O($C_1$-$C_3$ alkyl) optionally substituted with halogen, cyano or OH, NHR$^a$, and 3 to 6 membered heterocycle optionally substituted with halogen, cyano or OH, wherein the heterocycle contains one or two heteroatoms selected from nitrogen, oxygen and sulfur, wherein the heteroaryl contains one, two, three or four heteroatoms selected from the group consisting of nitrogen, oxygen and sulfur. In certain embodiments, $R^1$ is a 5 to 6 membered heteroaryl optionally substituted with one or two groups selected from halogen, cyano, $C_1$-$C_3$ alkyl optionally substituted with halogen, cyano or OH, —O($C_1$-$C_3$ alkyl) optionally substituted with halogen, cyano or OH, NHR$^a$, and 3 to 6 membered heterocycle optionally substituted with halogen, cyano or OH, wherein the heterocycle contains one or two heteroatoms selected from nitrogen, oxygen and sulfur, wherein the heteroaryl contains one, two, three or four heteroatoms selected from the group consisting of nitrogen, oxygen and sulfur. In certain embodiments, $R^1$ is a 5 to 6 membered heteroaryl optionally substituted with one or two groups selected from halogen, methoxy, NHR$^a$, and 3 to 6 membered heterocycle optionally substituted with OH, wherein the heterocycle contains one or two heteroatoms selected from the group consisting of nitrogen, oxygen and sulfur, wherein the heteroaryl contains one, two, three of four heteroatoms selected from the group consisting of nitrogen, oxygen and sulfur. In certain embodiments, $R^1$ is a 5 to 6 membered heteroaryl optionally substituted with one or two groups selected from halogen, methoxy, NHR$^a$, and 3 to 6 membered heterocycle optionally substituted with OH, wherein the heterocycle contains one nitrogen heteroatom, wherein the heteroaryl contains one nitrogen heteroatom. In certain embodiments, $R^1$ is 6 membered heteroaryl, optionally substituted with one or two groups selected from halogen, methoxy, NHR$^a$, and 3 to 6 membered heterocycle optionally substituted with OH, wherein the heterocycle contains one or two heteroatoms selected from the group consisting of nitrogen, oxygen and sulfur, wherein the heteroaryl contains one, two, three or four heteroatoms selected from the group consisting of nitrogen, oxygen and sulfur. In certain embodiments, $R^1$ is 6 membered heteroaryl, optionally substituted with one or two groups selected from halogen, methoxy, NHR$^a$, and 3 to 6 membered heterocycle optionally substituted with OH, wherein the heterocycle contains one or two heteroatoms selected from the group consisting of nitrogen, oxygen and sulfur, wherein the heteroaryl contains one nitrogen heteroatom. In certain embodiments, $R^1$ is 6 membered heteroaryl, optionally substituted with one or two groups selected from halogen, methoxy, NHR$^a$, and 3 to 6 membered heterocycle optionally substituted with OH, wherein the heterocycle contains one nitrogen heteroatom, wherein the heteroaryl contains one nitrogen heteroatom. In certain embodiments, $R^1$ is 6 membered heteroaryl, optionally substituted with one or two groups selected from halogen, methoxy, NHR$^a$, and 5 membered heterocycle optionally substituted with OH, wherein the heterocycle contains one nitrogen heteroatom, wherein the heteroaryl contains one nitrogen heteroatom. In certain embodiments, $R^1$ is pyridinyl optionally substituted with one or two groups selected from halogen, methoxy, NHR$^a$, and 3 to 6 membered heterocycle optionally substituted with OH, wherein the heterocycle contains one or two heteroatoms selected from the group consisting of nitrogen, oxygen and sulfur. In certain embodiments, $R^1$ is pyridinyl optionally substituted with one or two groups selected from halogen, methoxy, NHR$^a$, and 3 to 6 membered heterocycle optionally substituted with OH, wherein the heterocycle contains one nitrogen heteroatom. In certain embodiments, $R^1$ is pyridinyl optionally substituted with one or two groups selected from halogen, methoxy, NHR$^a$, and 5 membered heterocycle optionally substituted with OH, wherein the heterocycle contains one nitrogen heteroatom. In certain embodiments, $R^1$ is pyridinyl optionally substituted with one or two groups selected from halogen, methoxy, NHR$^a$, and pyrrolidinyl optionally substituted with OH. In certain embodiments, $R^1$ is selected from the group consisting of 2-amino-3-chloropyridin-4-yl, 3-chloro-2-(pyrrolidine-1-yl)pyridine-4-yl, 3-chloro-2-methoxypyridin-4-yl, 3-chloro-2-(methylamino)pyridine-4-yl), 3-chloro-2-(3-hydroxypyrrolidin-1-yl)pyridin-4-yl, and 3-chloro-2-((2-hydroxyethyl)amino)pyridin-4-yl.

In certain embodiments, $R^1$ is a 10 membered bicyclic aryl optionally substituted with one or more groups selected from halogen, cyano, $C_1$-$C_3$ alkyl optionally substituted with halogen, cyano or OH, —O($C_1$-$C_3$ alkyl) optionally substituted with halogen, cyano or OH, NHR$^a$, and 3 to 6 membered heterocycle optionally substituted with halogen, cyano or OH, wherein the heterocycle contains one or two heteroatoms selected from nitrogen, oxygen and sulfur. In certain embodiments, $R^1$ is a 10 membered bicyclic aryl optionally substituted with one to three groups selected from halogen, cyano, $C_1$-$C_3$ alkyl optionally substituted with halogen, cyano or OH, —O($C_1$-$C_3$ alkyl) optionally substituted with halogen, cyano or OH, NHR$^a$, and 3 to 6 membered heterocycle optionally substituted with halogen, cyano or OH, wherein the heterocycle contains one or two heteroatoms selected from nitrogen, oxygen and sulfur. In certain embodiments, $R^1$ is a 10 membered bicyclic aryl optionally substituted with halogen or methyl. In certain embodiments, $R^1$ is a 10 membered bicyclic aryl. In certain embodiments, $R^1$ is naphthalen-1-yl.

In certain embodiments, $R^1$ is a 9-10 membered bicyclic heterocyclyl optionally substituted with one or more groups selected from halogen, OH, oxo, cyano, $C_1$-$C_3$ alkyl optionally substituted with halogen, cyano or OH, —O($C_1$-$C_3$ alkyl) optionally substituted with halogen, cyano or OH, $NHR^a$, and 3 to 6 membered heterocycle optionally substituted with halogen, cyano or OH, wherein the heterocycle contains one or two heteroatoms selected from nitrogen, oxygen and sulfur, wherein the bicyclic heterocyclyl contains one to three nitrogen, sulfur or oxygen heteroatoms. In certain embodiments, $R^1$ is a 9-10 membered bicyclic heterocyclyl optionally substituted with one to three groups selected from halogen, OH, oxo, cyano, $C_1$-$C_3$ alkyl optionally substituted with halogen, cyano or OH, —O($C_1$-$C_3$ alkyl) optionally substituted with halogen, cyano or OH, $NHR^a$, and 3 to 6 membered heterocycle optionally substituted with halogen, cyano or OH, wherein the heterocycle contains one or two heteroatoms selected from nitrogen, oxygen and sulfur, wherein the bicyclic heterocyclyl contains one to three nitrogen, sulfur or oxygen heteroatoms. In certain embodiments, $R^1$ is a 9-10 membered bicyclic heterocyclyl optionally substituted with one or more groups selected from halogen, OH, oxo, cyano, $C_1$-$C_3$ alkyl optionally substituted with halogen, cyano or OH, —O($C_1$-$C_3$ alkyl) optionally substituted with halogen, cyano or OH, $NHR^a$, and 3 to 6 membered heterocycle optionally substituted with halogen, cyano or OH, wherein the heterocycle contains one or two heteroatoms selected from nitrogen, oxygen and sulfur, wherein the bicyclic heterocyclyl contains one or two nitrogen heteroatoms. In certain embodiments, $R^1$ is a 9-10 membered bicyclic heterocyclyl optionally substituted with one to three groups selected from halogen, OH and oxo, wherein the bicyclic heterocyclyl contains one or two nitrogen heteroatoms. In certain embodiments, $R^1$ is selected from the group consisting of 3,4-dihydroquinolin-1(2H)-yl, 3,4-dihydroquinoxalin-1(2H)-yl, 2,3-dihydro-1H-pyrrolo[2,3-b]pyridin-4-yl and 3,4-dihydro-1,5-naphthyridin-1(2H)-yl, 3,3-difluoro-2-oxo-2,3-dihydro-1H-pyrrolo[2,3-b]pyridin-4-yl and 7-hydroxy-6,7-dihydro-5H-cyclopenta[b]pyridin-4-yl.

In certain embodiments, $R^1$ is a 9-10 membered bicyclic heteroaryl optionally substituted with one or more groups selected from halogen, cyano, $C_1$-$C_3$ alkyl optionally substituted with halogen, cyano or OH, —O($C_1$-$C_3$ alkyl) optionally substituted with halogen, cyano or OH, $NHR^a$, and 3 to 6 membered heterocycle optionally substituted with halogen, cyano or OH, wherein the heterocycle contains one or two heteroatoms selected from nitrogen, oxygen and sulfur, wherein the bicyclic heteroaryl contains one to three nitrogen, sulfur or oxygen heteroatoms. In certain embodiments, $R^1$ is a 9-10 membered bicyclic heteroaryl optionally substituted with one to three groups selected from halogen, cyano, $C_1$-$C_3$ alkyl optionally substituted with halogen, cyano or OH, —O($C_1$-$C_3$ alkyl) optionally substituted with halogen, cyano or OH, $NHR^a$, and 3 to 6 membered heterocycle optionally substituted with halogen, cyano or OH, wherein the heterocycle contains one or two heteroatoms selected from nitrogen, oxygen and sulfur, wherein the bicyclic heteroaryl contains one to three nitrogen, sulfur or oxygen heteroatoms. In certain embodiments, $R^1$ is a 9-10 membered bicyclic heteroaryl optionally substituted with: halogen; $C_1$-$C_3$ alkyl optionally substituted with halogen; —O($C_1$-$C_3$ alkyl) optionally substituted with halogen; cyano; or $NHR^a$; wherein the bicyclic heteroaryl contains one to three nitrogen, sulfur or oxygen heteroatoms. In certain embodiments, $R^1$ is a 9-10 membered bicyclic heteroaryl optionally substituted with one to three groups selected from: halogen; $C_1$-$C_3$ alkyl optionally substituted with halogen; —O($C_1$-$C_3$ alkyl) optionally substituted with halogen; cyano; or $NHR^a$; wherein the bicyclic heteroaryl contains one to three nitrogen, sulfur or oxygen heteroatoms. In certain embodiments, $R^1$ is a 9-10 membered bicyclic heteroaryl optionally substituted with: halogen; $C_1$-$C_3$ alkyl optionally substituted with halogen; —O($C_1$-$C_3$ alkyl) optionally substituted with halogen; cyano; or $NHR^a$; wherein the bicyclic heteroaryl contains one to three nitrogen heteroatoms. In certain embodiments, $R^1$ is a 9-10 membered bicyclic heteroaryl optionally substituted with halogen, cyano, $C_1$-$C_3$ alkyl optionally substituted with halogen, or $NHR^a$, wherein the bicyclic heteroaryl contains one to three nitrogen, sulfur or oxygen heteroatoms. In certain embodiments, $R^1$ is a 9-10 membered bicyclic heteroaryl optionally substituted with halogen, cyano, $C_1$-$C_3$ alkyl optionally substituted with halogen, or $NHR^a$, wherein the bicyclic heteroaryl contains one to three nitrogen heteroatoms. In certain embodiments, $R^1$ is a 9-10 membered bicyclic heteroaryl optionally substituted with methyl, trifluoromethyl, cyano, halogen or amino, wherein the bicyclic heteroaryl contains one to three nitrogen heteroatoms. In certain embodiments, $R^1$ is a 9-10 membered bicyclic heteroaryl optionally substituted with one to three methyl, methoxy, trifluoromethyl, cyano, halogen or amino groups, wherein the bicyclic heteroaryl contains one to three nitrogen heteroatoms. In certain embodiments, $R^1$ is a 9-10 membered bicyclic heteroaryl optionally substituted with one to three methyl, trifluoromethyl, cyano, halogen or amino groups, wherein the bicyclic heteroaryl contains one to three nitrogen heteroatoms. In certain embodiments, $R^1$ is a 9-10 membered bicyclic heteroaryl optionally substituted with methyl, trifluoromethyl, cyano, halogen or amino, wherein the bicyclic heteroaryl contains one to three nitrogen heteroatoms. In certain embodiments, $R^1$ is selected from the group consisting of 1-methyl-1H-indazol-7-yl, pyrazolo[1,5-a]pyridine-4-yl, pyrazolo[1,5-a]pyrazin-4-yl, isoquinolin-8-yl, 3H-imidazo[4,5-b]pyridin-7-yl, 6-chloroimidazo[1,2-a]pyridin-3-yl, 6-cyanoimidazo[1,2-a]pyridin-3-yl, 1H-pyrazolo[3,4-b]pyridin-4-yl, 1,8-naphthyridin-4-yl, 1H-pyrrolo[2,3-b]pyridin-4-yl, 1-methyl-1H-pyrrolo[2,3-b]pyridin-4-yl, 5-chloro-1H-pyrrolo[2,3-b]pyridin-4-yl, 5-(trifluoromethyl)-1H-pyrrolo[2,3-b]pyridin-4-yl, 3-methyl-1H-pyrrolo[2,3-b]pyridin-4-yl, 6-amino-1H-pyrrolo[2,3-b]pyridin-4-yl and 5-fluoro-1H-pyrrolo[2,3-b]pyridin-4-yl.

In certain embodiments, $R^1$ is a 9-10 membered bicyclic heteroaryl optionally substituted with one or more groups selected from halogen, cyano, $C_1$-$C_3$ alkyl optionally substituted with halogen, cyano or OH, —O($C_1$-$C_3$ alkyl) optionally substituted with halogen, cyano or OH, $NHR^a$, and 3 to 6 membered heterocycle optionally substituted with halogen, cyano or OH, wherein the heterocycle contains one or two heteroatoms selected from nitrogen, oxygen and sulfur, wherein the heteroaryl contains one to three nitrogen, sulfur or oxygen heteroatoms. In certain embodiments, $R^1$ is a 9-10 membered bi cyclic heteroaryl optionally substituted with one to three groups selected from halogen, cyano, $C_1$-$C_3$ alkyl optionally substituted with halogen, cyano or OH, —O(C$_1$-C$_3$ alkyl) optionally substituted with halogen, cyano or OH, NHR$^a$, and 3 to 6 membered heterocycle optionally substituted with halogen, cyano or OH, wherein the heterocycle contains one or two heteroatoms selected from nitrogen, oxygen and sulfur, wherein the bicyclic heteroaryl contains one to three nitrogen, sulfur or oxygen heteroatoms. In certain embodiments, R$^1$ is a 9-10 membered bicyclic heteroaryl optionally substituted with halogen, C$_1$-C$_3$ alkyl optionally substituted with halogen, —O(C$_1$-C$_3$ alkyl) optionally substituted with halogen, or cyano, wherein the bicyclic heteroaryl contains one to three nitrogen, sulfur or oxygen heteroatoms. In certain embodiments, R$^1$ is a 9-10 membered bicyclic heteroaryl optionally substituted with one to three groups selected from halogen, C$_1$-C$_3$ alkyl optionally substituted with halogen, —O(C$_1$-C$_3$ alkyl) optionally substituted with halogen, or cyano, wherein the bicyclic heteroaryl contains one to three nitrogen, sulfur or oxygen heteroatoms. In certain embodiments, R$^1$ is a 9-10 membered bicyclic heteroaryl optionally substituted with halogen, C$_1$-C$_3$ alkyl optionally substituted with halogen, —O(C$_1$-C$_3$ alkyl) optionally substituted with halogen, or cyano, wherein the bicyclic heteroaryl contains one to three nitrogen heteroatoms. In certain embodiments, R$^1$ is a 9-10 membered bicyclic heteroaryl optionally substituted with C$_1$-C$_3$ alkyl or halogen, wherein the bicyclic heteroaryl contains one to three nitrogen, sulfur or oxygen heteroatoms. In certain embodiments, R$^1$ is a 9-10 membered bicyclic heteroaryl optionally substituted with C$_1$-C$_3$ alkyl or halogen, wherein the bicyclic heteroaryl contains one to three nitrogen heteroatoms. In certain embodiments, R$^1$ is a 9-10 membered bicyclic heteroaryl optionally substituted with methyl or halogen, wherein the bicyclic heteroaryl contains one to three nitrogen heteroatoms. In certain embodiments, R$^1$ is a 9-10 membered bicyclic heteroaryl optionally substituted with one to three methyl, methoxy, trifluoromethyl or halogen groups, wherein the bicyclic heteroaryl contains one to three nitrogen heteroatoms. In certain embodiments, R$^1$ is a 9-10 membered bicyclic heteroaryl optionally substituted with one to three methyl or halogen groups, wherein the bicyclic heteroaryl contains one to three nitrogen heteroatoms. In certain embodiments, R$^1$ is a 9-10 membered bicyclic heteroaryl optionally substituted with methyl, wherein the bicyclic heteroaryl contains one to three nitrogen heteroatoms. In certain embodiments, R$^1$ is selected from the group consisting of 1-methyl-1H-indazol-7-yl, pyrazolo[1,5-a]pyridine-4-yl, pyrazolo[1,5-a]pyrazin-4-yl and isoquinolin-8-yl.

In certain embodiments, R$^a$ is hydrogen; C$_1$-C$_4$ alkyl optionally substituted with OH, methoxy, halogen or cyano; or cyclopropyl. In certain embodiments, R$^a$ is hydrogen, C$_1$-C$_4$ alkyl optionally substituted with OH, methoxy or cyano, or cyclopropyl. In certain embodiments, R$^a$ is hydrogen, methyl, 2-hydroxyethyl, 2-methoxyethyl, cyclopropylamino or 2-cyano-2-methylpropyl.

In certain embodiments, R$^a$ is hydrogen or C$_1$-C$_3$ alkyl optionally substituted with OH, methoxy, halogen or cyano. In certain embodiments, R$^a$ is hydrogen or C$_1$-C$_3$ alkyl optionally substituted with OH. In certain embodiments, R$^a$ is hydrogen or C$_1$-C$_3$ alkyl optionally substituted with OH. In certain embodiments, R$^a$ is hydrogen, methyl or 2-hydroxyethyl.

In certain embodiments, R$^2$ is selected from the group consisting of:

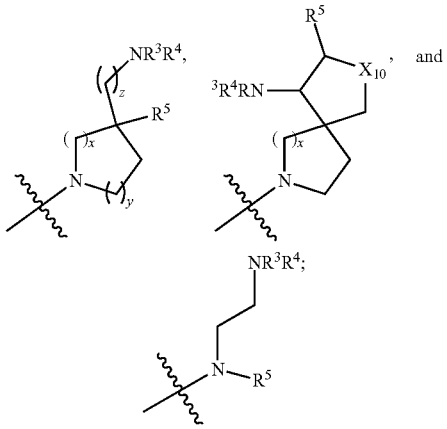

wherein R$^3$ and R$^4$ are selected from hydrogen and methyl; R$^5$ is selected from the group consisting of hydrogen, methyl, OH and CH$_2$OH; x is 1 or 2; y is 1 or 2; and z is 0 or 1. In certain embodiments, R$^2$ is selected from the group consisting of:

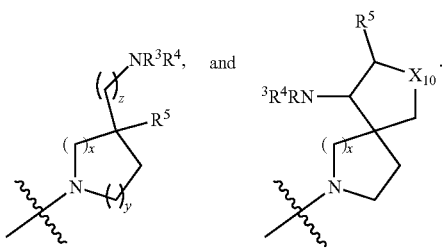

In certain embodiments, x is 1 or 2. When x is 1, R$^2$ has the structure:

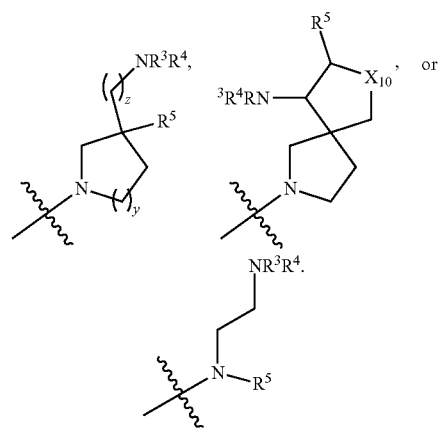

When x is 2, $R^2$ has the structure:
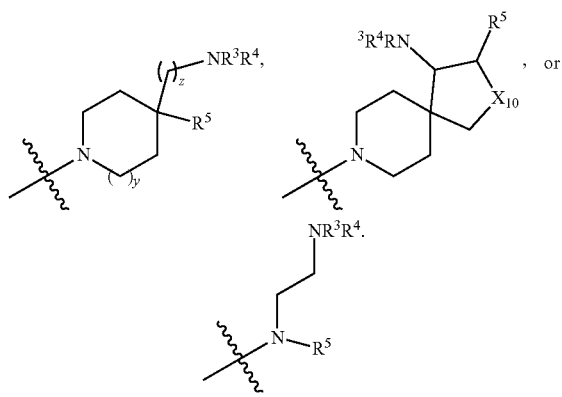
In certain embodiments, y is 1 or 2. When y is 1, $R^2$ has the structure:
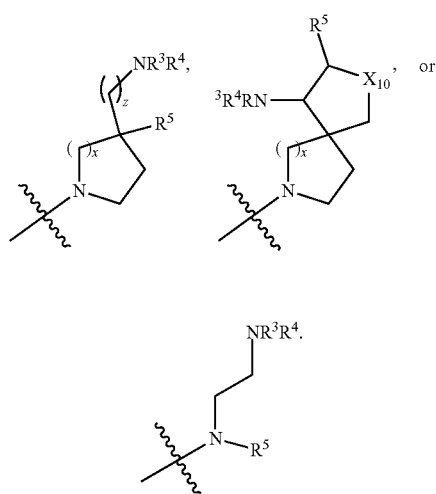
When y is 2, $R^2$ has the structure:
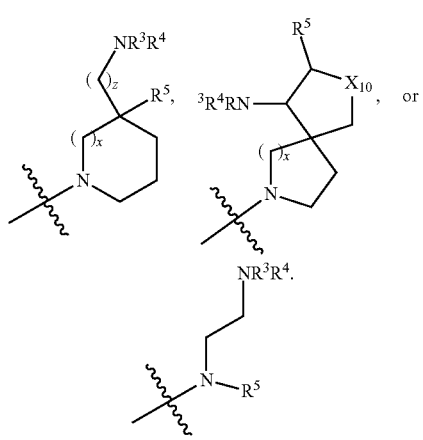
In certain embodiments, x is 1 and y is 1. When x is 1 and y is 1, $R^2$ has the structure:
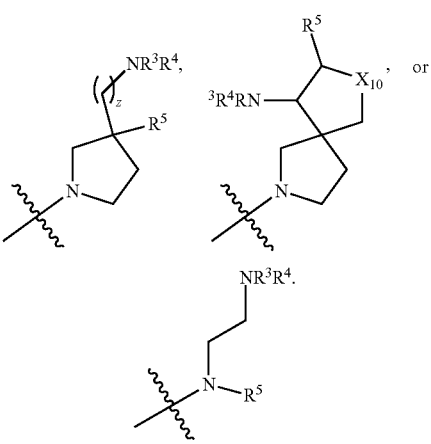
In certain embodiments, x is 2 and y is 1. When x is 2 and y is 1, $R^2$ has the structure:
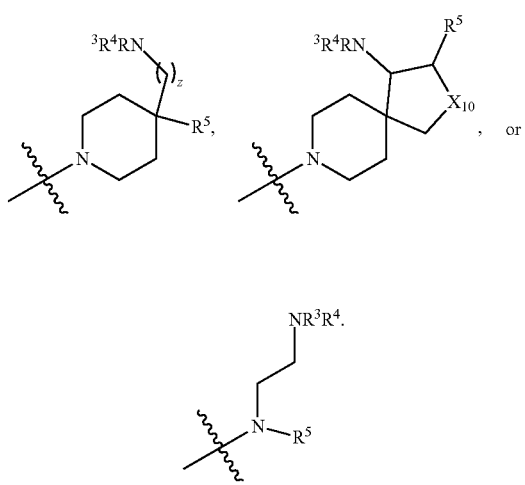
In certain embodiments, x is 2 and y is 2. When x is 2 and y is 2, $R^2$ has the structure:
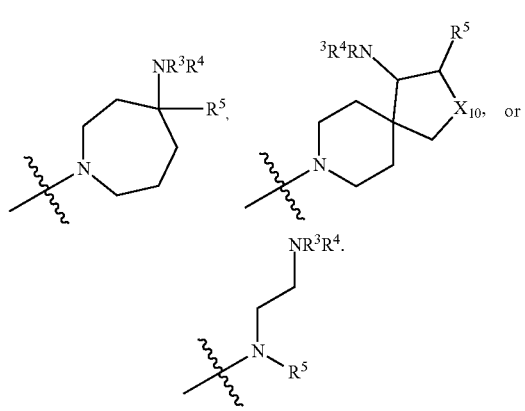

In certain embodiments, $R^2$ is selected from the group consisting of:
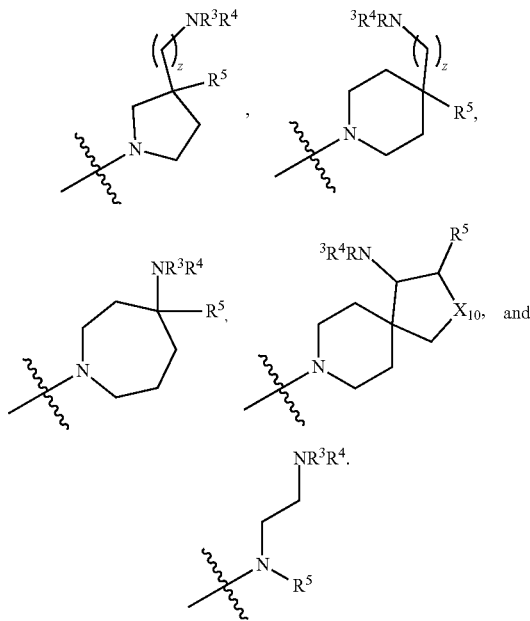
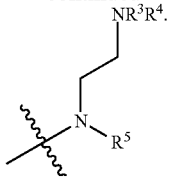
When $X_{10}$ is O, $R^2$ has the structure:
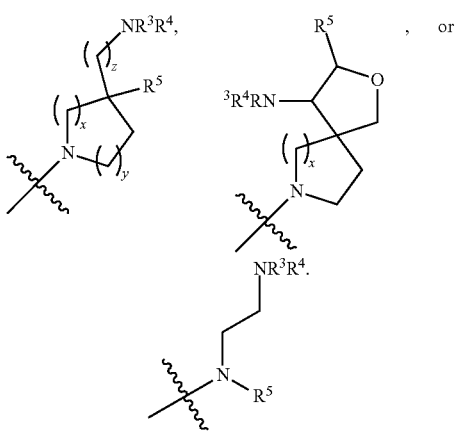
In certain embodiments, $R^2$ is selected from the group consisting of:
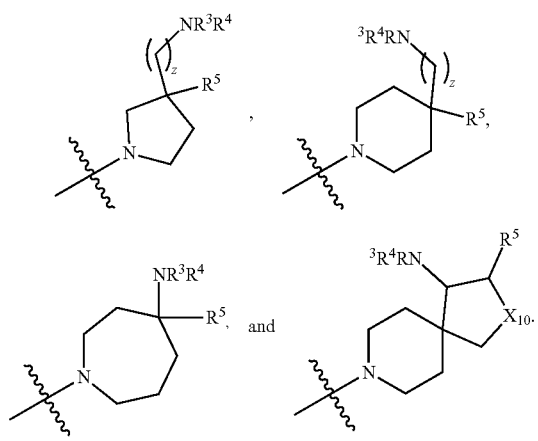
In certain embodiments, $R^2$ is selected from the group consisting of:
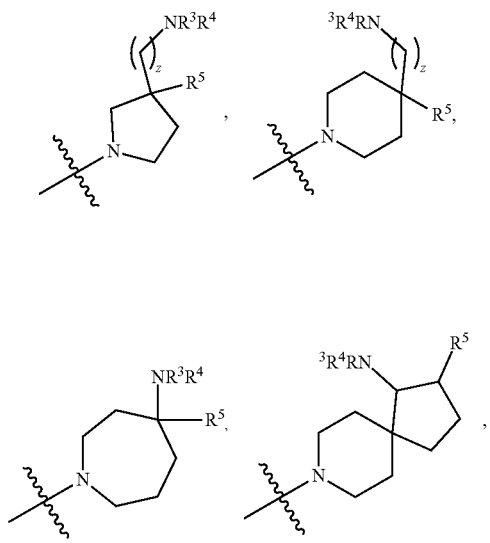
In certain embodiments, $X_{10}$ is CH or O. When $X_{10}$ is CH, $R^2$ has the structure:
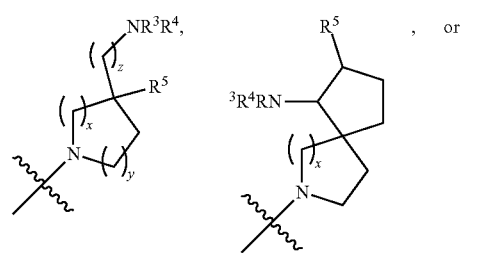
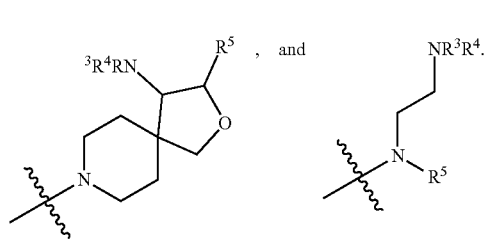

In certain embodiments, $R^2$ is selected from the group consisting of:
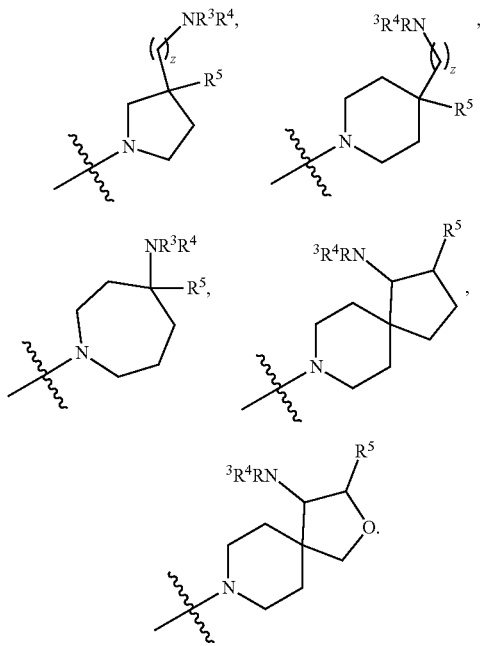
In certain embodiments, z is 0, 1 or 2. When z is 0, $R^2$ has the structure:
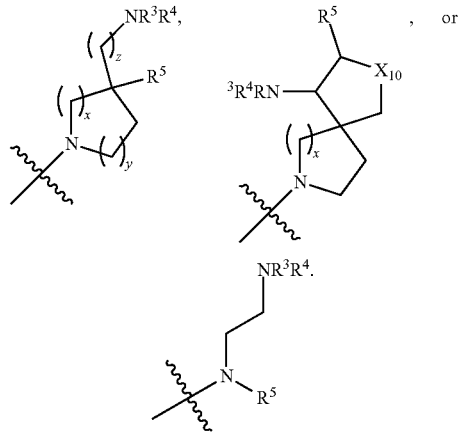
When z is 1, $R^2$ has the structure:
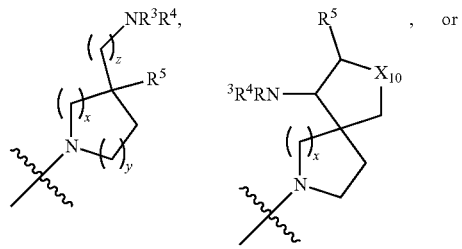
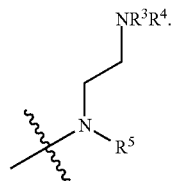
In certain embodiments, $R^2$ is selected from the group consisting of:
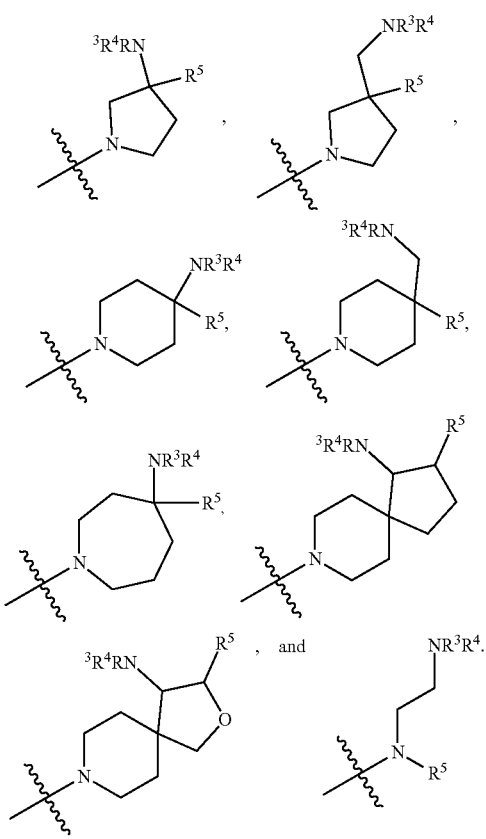
In certain embodiments, $R^2$ is selected from the group consisting of:
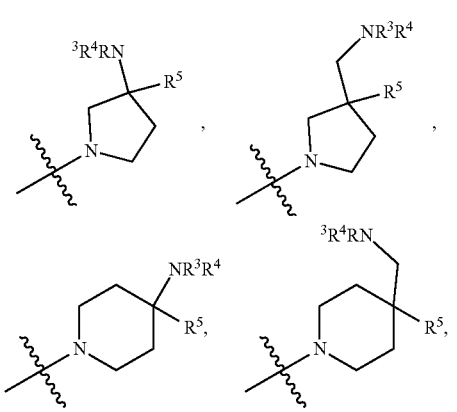

-continued
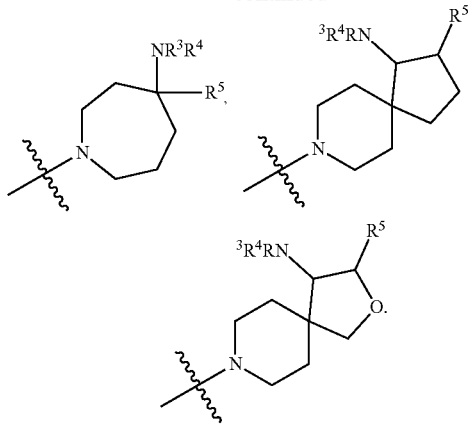
In certain embodiments, $R^2$ is:
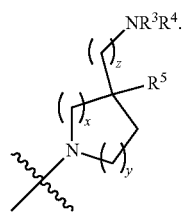
In certain embodiments, $R^2$ is:
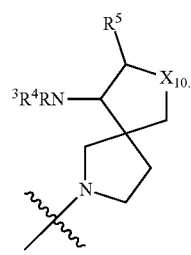
In certain embodiments, $R^2$ is:
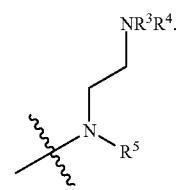
In certain embodiments, $R^2$ is:
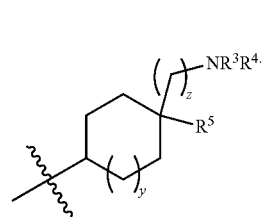
In certain embodiments, $R^2$ is:
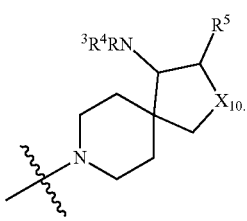
In certain embodiments, $R^2$ is:
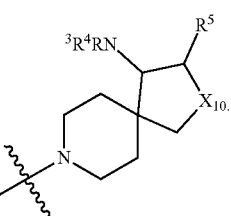
In certain embodiments, $R^2$ is:
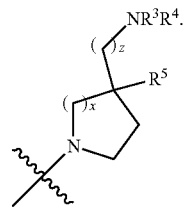
In certain embodiments, $R^2$ is:
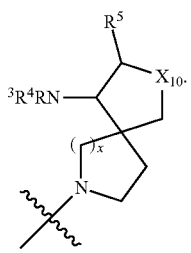
In certain embodiments, $R^2$ is:
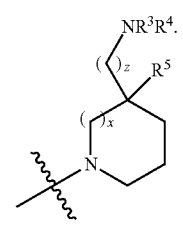
In certain embodiments, $R^2$ is:
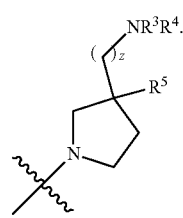

In certain embodiments, $R^2$ is:
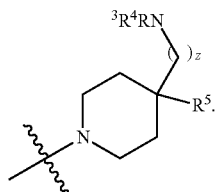
In certain embodiments, $R^2$ is:
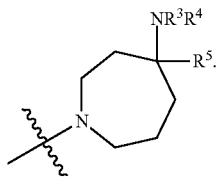
In certain embodiments, $R^2$ is:
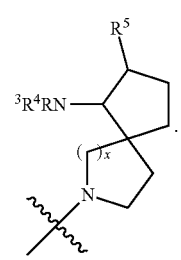
In certain embodiments, $R^2$ is:
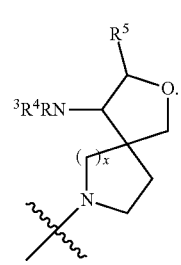
In certain embodiments, $R^2$ is:
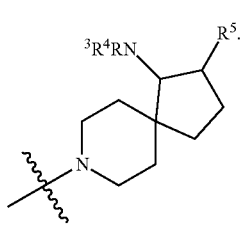
In certain embodiments, $R^2$ is:
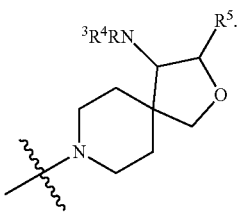
In certain embodiments, $R^2$ is:
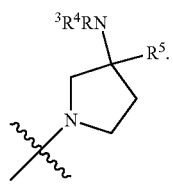
In certain embodiments, $R^2$ is:
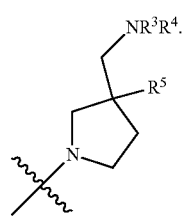
In certain embodiments, $R^2$ is:
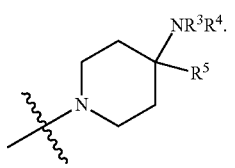
In certain embodiments, $R^2$ is:
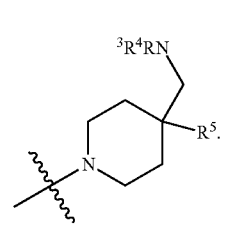

In certain embodiments, $R^2$ is:

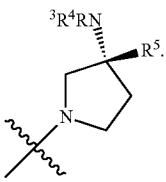

In certain embodiments, $R^2$ is:

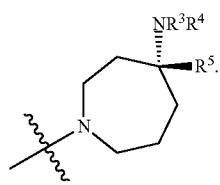

In certain embodiments, $R^2$ is:

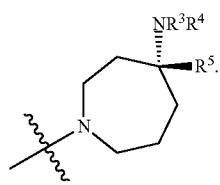

In certain embodiments, $R^2$ is:

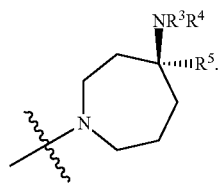

In certain embodiments, $R^2$ is:

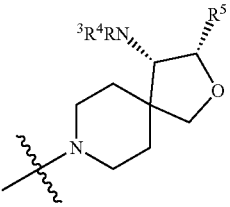

In certain embodiments, $R^3$ and $R^4$ are independently selected from hydrogen and methyl. In certain embodiments, $R^3$ and $R^4$ are hydrogen. In certain embodiments, $R^3$ and $R^4$ are methyl. In certain embodiments, $R^3$ is hydrogen and $R^4$ is methyl.

In certain embodiments, $R^5$ is selected from the group consisting of hydrogen, methyl, OH and $CH_2OH$. In certain embodiments, $R^5$ is hydrogen. In certain embodiments, $R^5$ is methyl. In certain embodiments, $R^5$ is OH. In certain embodiments, $R^5$ is $CH_2OH$.

In certain embodiments, $R^2$ is:

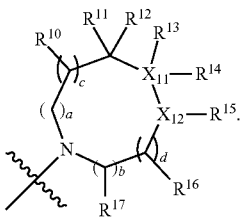

In certain embodiments, $R^2$ is selected from the group consisting of:

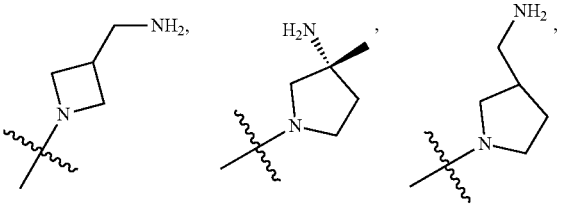

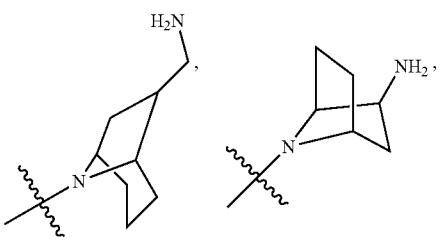

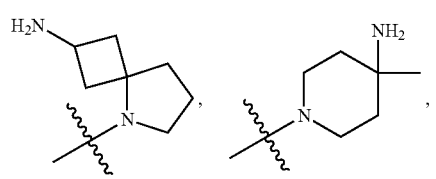

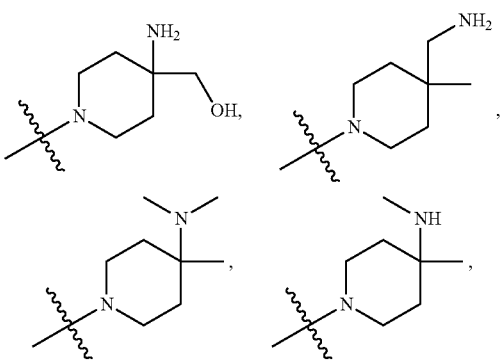

-continued
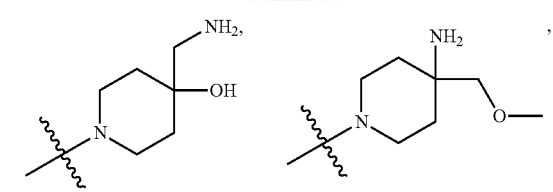
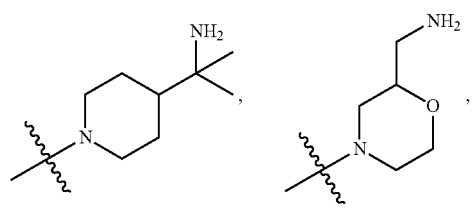
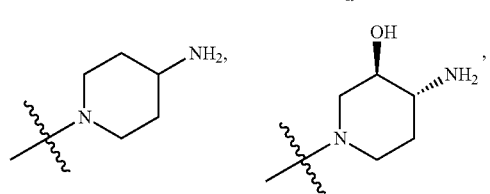
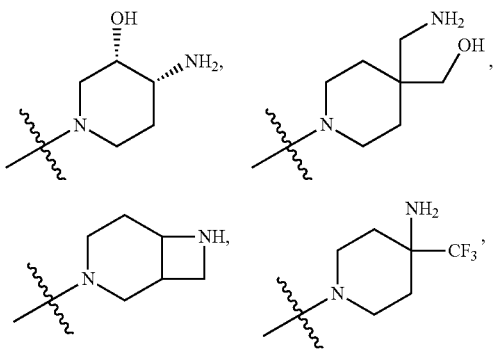
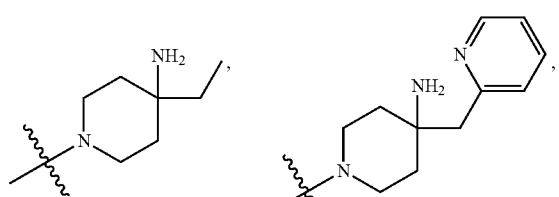
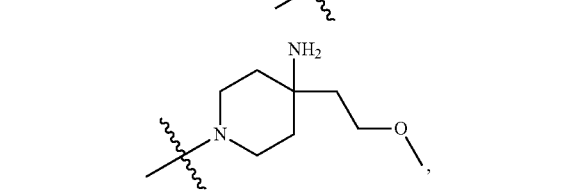
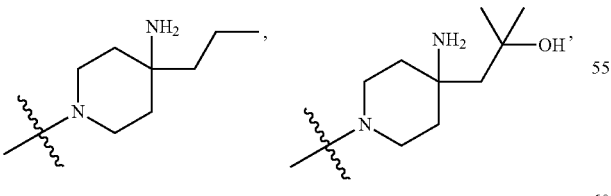
-continued
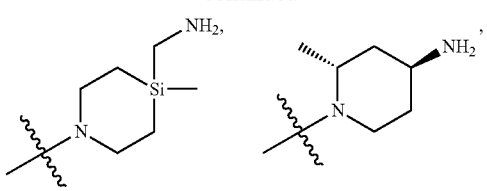
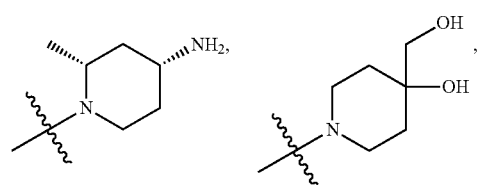
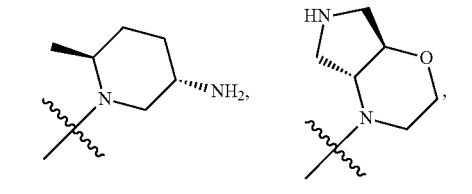
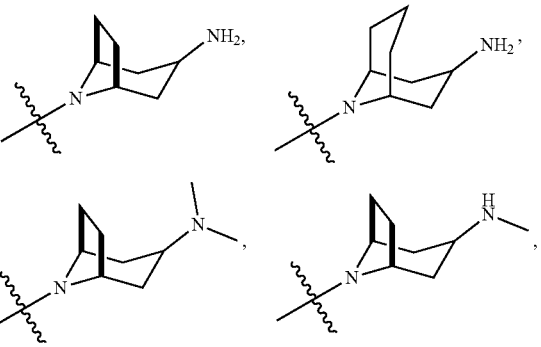
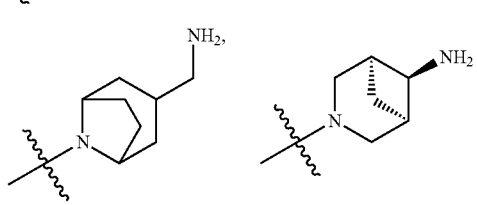
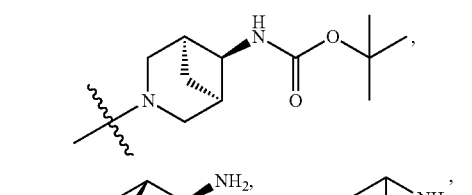
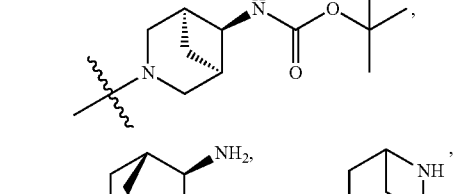

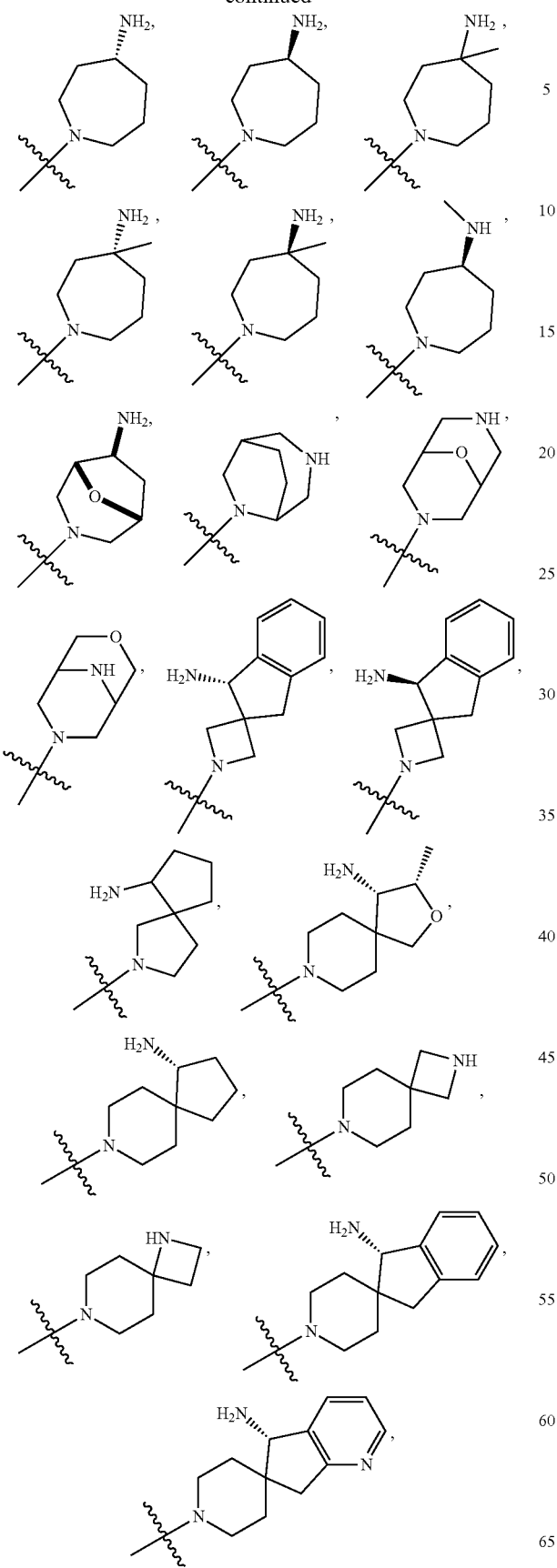
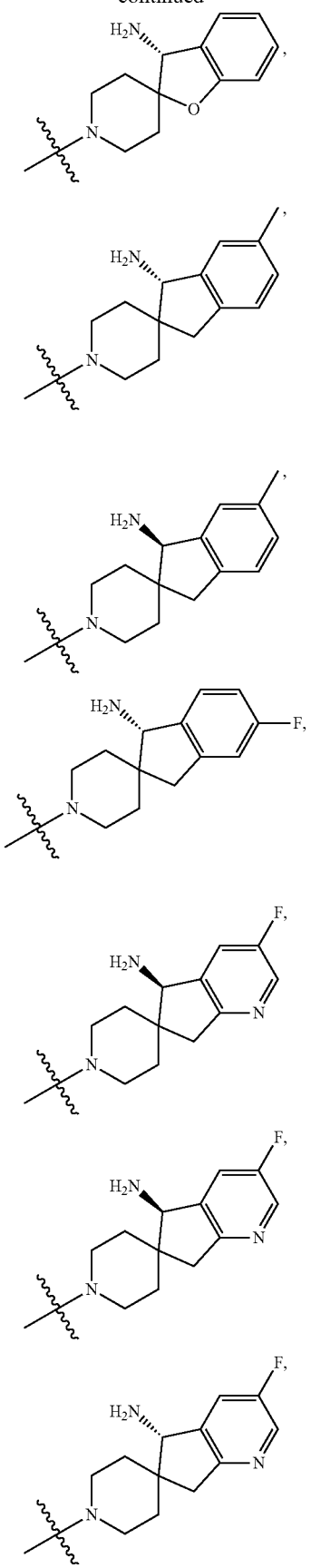

47
-continued
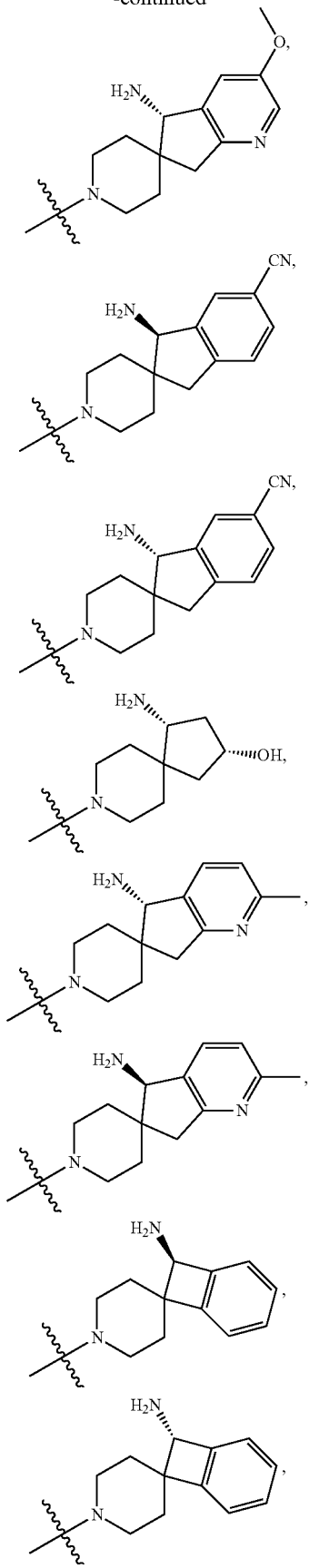
48
-continued
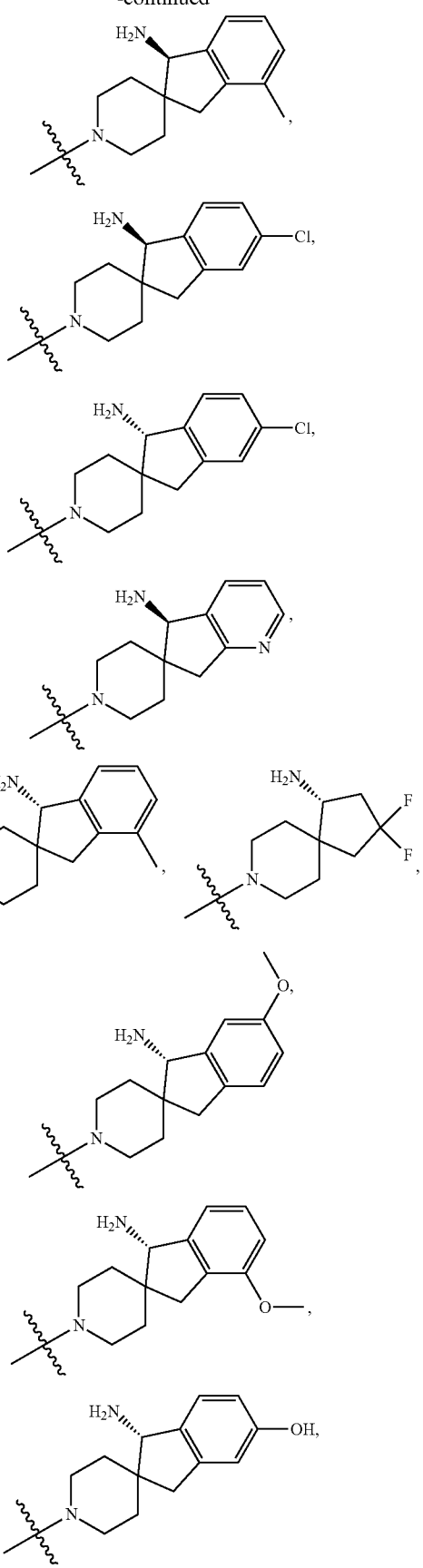

-continued

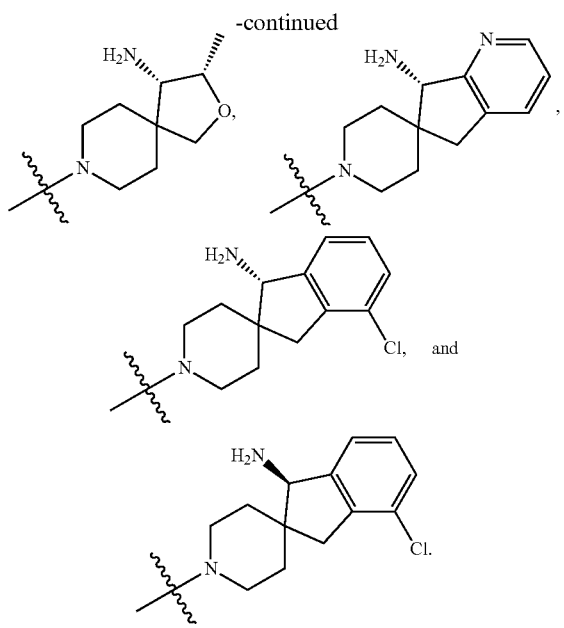

In certain embodiments, $X_{11}$ is selected from $CR^{13}R^{14}$, $SiR^{13}R^{14}$, NH and O. In certain embodiments, $X_{11}$ is selected from $CR^{13}R^{14}$, NH and O. In certain embodiments, $X_{11}$ is selected from $CR^{13}R^{14}$ and $SiR^{13}R^{14}$. In certain embodiments, $X_{11}$ is selected from NH and O. In certain embodiments, $X_{11}$ is $CR^{13}R^{14}$. In certain embodiments, $X_{11}$ is $SiR^{13}R^{14}$. In certain embodiments, $X_{11}$ is NH. In certain embodiments, $X_{11}$ is O.

In certain embodiments, $X_{12}$ is selected from $CHR^{15}$ and NH. In certain embodiments, $X_{12}$ is $CHR^{15}$. In certain embodiments, $X_{12}$ is NH.

In certain embodiments, $X_{11}$ is selected from $CR^{13}R^{14}$, $SiR^{13}R^{14}$, NH and O; and $X_{12}$ is selected from $CHR^{15}$ and NH, wherein one or both of $X_{11}$ and $X_{12}$ must be carbon. In certain embodiments, $X_{11}$ is $CR^{13}R^{14}$; and $X_{12}$ is selected from $CHR^{15}$ and NH, or $X_{11}$ is selected from $CR^{13}R^{14}$, $SiR^{13}R^{14}$, NH and O; and $X_{12}$ is $CHR^{15}$. In certain embodiments, $X_{11}$ is $CR^{13}R^{14}$; and $X_{12}$ is selected from $CHR^{15}$ and NH. In certain embodiments, $X_{11}$ is selected from $CR^{13}R^{14}$, $SiR^{13}R^{14}$, NH and O; and $X_{12}$ is $CHR^{15}$. In certain embodiments, $X_{11}$ is $CR^{13}R^{14}$; and $X_{12}$ is $CHR^{15}$. In certain embodiments, $X_{11}$ is $CR^{13}R^{14}$; and $X_{12}$ is NH. In certain embodiments, $X_{11}$ is $SiR^{13}R^{14}$; and $X_{12}$ is $CHR^{15}$. In certain embodiments, $X_{11}$ is NH; and $X_{12}$ is $CHR^{15}$. In certain embodiments, $X_{11}$ is O; and $X_{12}$ is $CHR^{15}$.

In certain embodiments, $R^{10}$ is selected from hydrogen and alkyl. In certain embodiments, $R^{10}$ is selected from hydrogen and $C_1$-$C_3$ alkyl. In certain embodiments, $R^{10}$ is selected from hydrogen and methyl. In certain embodiments, $R^{10}$ is hydrogen. In certain embodiments, $R^{10}$ is methyl.

In certain embodiments, $R^{11}$ is selected from hydrogen, OH and $CH_2NH_2$. In certain embodiments, $R^{11}$ is selected from hydrogen, OH and $CH_2NH_2$. In certain embodiments, $R^{11}$ is hydrogen. In certain embodiments, $R^{11}$ is OH. In certain embodiments, $R^{11}$ is $CH_2NH_2$.

In certain embodiments, $R^{12}$, $R^{16}$ and $R^{17}$ are hydrogen.

In certain embodiments, $R^{13}$ is selected from hydrogen, OH, and $(C_0$-$C_3$ alkyl)$NR^bR^c$. In certain embodiments, $R^{13}$ is selected from hydrogen, OH, $CH_2NH_2$, $NH_2$, $NH(CH_3)$, $N(CH_3)_2$, $C(NH_2)(CH_3)_2$ or NHBOC. In certain embodiments, $R^{13}$ is hydrogen. In certain embodiments, $R^{13}$ is OH. In certain embodiments, $R^{13}$ is $(C_0$-$C_3$ alkyl)$NR^bR^c$. In certain embodiments, $R^{13}$ is $CH_2NH_2$. In certain embodiments, $R^{13}$ is $NH_2$. In certain embodiments, $R^{13}$ is $NH(CH_3)$. In certain embodiments, $R^{13}$ is $N(CH_3)_2$. In certain embodiments, $R^{13}$ is $C(NH_2)(CH_3)_2$. In certain embodiments, $R^{13}$ is NHBoc.

In certain embodiments, $R^b$ and $R^c$ are independently selected from hydrogen, alkyl and a Boc group. In certain embodiments, $R^b$ and $R^c$ are independently selected from hydrogen, $C_1$-$C_3$ alkyl and a Boc group. In certain embodiments, $R^b$ and $R^c$ are independently selected from hydrogen, methyl and a Boc group. In certain embodiments, $R^b$ is selected from hydrogen, methyl and a Boc group, and $R^c$ is hydrogen or methyl. In certain embodiments, $R^b$ is selected from hydrogen, methyl and a Boc group, and $R^c$ is hydrogen. In certain embodiments, $R^b$ and $R^c$ are independently selected from hydrogen and methyl. In certain embodiments, $R^b$ is methyl and $R^c$ is hydrogen. In certain embodiments, $R^b$ and $R^c$ are hydrogen. In certain embodiments, $R^b$ is a Boc group, $R^c$ is hydrogen.

In certain embodiments, $R^{14}$ is selected from hydrogen, OH, alkyl optionally substituted with halogen, OH, methyl, $OCH_3$ and a heteroaryl. In certain embodiments, $R^{14}$ is selected from hydrogen, OH, $C_1$-$C_3$ alkyl optionally substituted with halogen, OH, methyl, $OCH_3$ and a 5 to 6 membered heteroaryl wherein the heteroaryl contains one to three heteroatoms selected from nitrogen, oxygen and sulfur. In certain embodiments, $R^{14}$ is selected from hydrogen, OH, $C_1$-$C_3$ alkyl optionally substituted with halogen, OH, methyl, $OCH_3$ and a 6 membered heteroaryl wherein the heteroaryl contains one nitrogen heteroatom. In certain embodiments, $R^{14}$ is selected from hydrogen, OH, methyl, ethyl, propyl, $CF_3$, $CH_2OH$, $CH_2CH_2OH$, $CH_2C(CH_3)_2OH$, $CH_2OCH_3$, $CH_2CH_2OCH_3$ and —$(CH_2)$pyridin-2-yl.

In certain embodiments, $R^{15}$ is selected from hydrogen or $NH_2$. In certain embodiments, $R^{15}$ is hydrogen. In certain embodiments, $R^{15}$ is $NH_2$.

In certain embodiments, two R groups in $R^2$ may join together to form a bridged, spirocyclic or fused bicycle. Only one set of two R groups within $R^2$ may join together to form the bridged, spirocyclic or fused bicyclic, selected from: $R^{10}$ and $R^{11}$ may join together to form a fused bicyclic, $R^{10}$ and $R^{15}$ may join together to form a bridged bicyclic, $R^{11}$ and $R^{12}$ may join together to form a spirocyclic, $R^{13}$ and $R^{14}$ may join together to form a spirocyclic, $R^{10}$ and $R^{16}$ may join together to form a bridged bicyclic, $R^{11}$ and $R^{15}$ may join together to form a bridged bicyclic, $R^{11}$ and $R^{16}$ may join together to form a bridged bicyclic, $R^{11}$ and $R^{17}$ may join together to form a bridged bicyclic, or $R^{13}$ and $R^{15}$ may join together to form a fused bicyclic.

In certain embodiments, $R^{10}$ and $R^{11}$ may join together as $CH_2NHCH_2$ to form a fused bicyclic.

In certain embodiments, $R^{10}$ and $R^{15}$ may join together as alkyl to form a bridged bicyclic. In certain embodiments, $R^{10}$ and $R^{15}$ may join together as $C_1$-$C_4$ alkyl to form a bridged bicyclic. In certain embodiments, $R^{10}$ and $R^{15}$ may join together as ethyl or propyl to form a bridged bicyclic. In certain embodiments, $R^{10}$ and $R^{15}$ may join together as ethyl to form a bridged bicyclic. In certain embodiments, $R^{10}$ and $R^{15}$ may join together as propyl to form a bridged bicyclic.

In certain embodiments, $R^{11}$ and $R^{12}$ may join together as alkyl substituted with $NH_2$ to form a spirocycle. In certain embodiments, $R^{11}$ and $R^{12}$ may join together as $C_1$-$C_4$ alkyl substituted with $NH_2$ to form a spirocycle. In certain embodiments, $R^{11}$ and $R^{12}$ may join together as cyclobutane substituted with $NH_2$ to form a spirocycle.

In certain embodiments, $R^{13}$ and $R^{14}$ may join together as a group selected from cycloalkyl, heterocycle, bicyclic carbocycle, and bicyclic heterocycle, wherein the cycloalkyl, heterocycle, carbocycle and heterocycle are optionally substituted with F, Cl, OH, $OCH_3$, CN, methyl or $NH_2$, to form a spirocycle. In certain embodiments, $R^{13}$ and $R^{14}$ may join together as a group selected from $C_3$-$C_6$ cycloalkyl, 4 to 6 membered heterocycle wherein the heterocycle contains one to three heteroatoms selected from the group consisting of nitrogen, oxygen and sulfur, saturated or partially unsaturated 8 to 10 membered bicyclic carbocycle, and a saturated or partially unsaturated 8 to 10 membered bicyclic heterocycle wherein the heterocycle contains one to three heteroatoms selected from the group consisting of nitrogen, oxygen and sulfur, wherein the cycloalkyl, heterocycle, bicyclic carbocycle and bicyclic heterocycle are optionally substituted with F, Cl, OH, $OCH_3$, CN, methyl or $NH_2$, to form a spirocycle. In certain embodiments, $R^{13}$ and $R^{14}$ may join together as a group selected from $C_3$-$C_6$ cycloalkyl, 4 to 6 membered heterocycle wherein the heterocycle contains one to three heteroatoms selected from the group consisting of nitrogen and oxygen, saturated or partially unsaturated 8 to 10 membered bicyclic carbocycle, and a saturated or partially unsaturated 8 to 10 membered bicyclic heterocycle wherein the heterocycle contains one to three heteroatoms selected from the group consisting of nitrogen and oxygen, wherein the cycloalkyl, heterocycle, bicyclic carbocycle and bicyclic heterocycle are optionally substituted with F, Cl, OH, $OCH_3$, CN, methyl or $NH_2$, to form a spirocycle. In certain embodiments, $R^{13}$ and $R^{14}$ may join together as a group selected from $C_3$-$C_6$ cycloalkyl, 4 to 6 membered heterocycle wherein the heterocycle contains one heteroatom selected from the group consisting of nitrogen and oxygen, saturated or partially unsaturated 8 to 10 membered bicyclic carbocycle, and a saturated or partially unsaturated 8 to 10 membered bicyclic heterocycle wherein the heterocycle contains one heteroatom selected from the group consisting of nitrogen and oxygen, wherein the cycloalkyl, heterocycle, bicyclic carbocycle and bicyclic heterocycle are optionally substituted with F, Cl, OH, $OCH_3$, CN, methyl or $NH_2$, to form a spirocycle. In certain embodiments, $R^{13}$ and $R^{14}$ may join together as a group selected from cyclopentyl, tetrahydrofuran, azetidine, 2,3-dihydro-1H-indene. 6,7-dihydro-5H-cyclopenta[b]pyridine. 2,3-dihydrobenzofuran, or bicyclo[4.2.0]octa-1(6),2,4-triene, optionally substituted with F, Cl, OH, $OCH_3$, CN, methyl or $NH_2$, to form a spirocycle.

In certain embodiments, $R^{10}$ and $R^{16}$ may join together as alkyl, O or NH to form a bridged bicyclic. In certain embodiments, $R^{10}$ and $R^{16}$ may join together as $C_1$-$C_4$ alkyl, O or NH to form a bridged bicyclic. In certain embodiments, $R^{10}$ and $R^{16}$ may join together as $C_1$-$C_3$ alkyl, O or NH to form a bridged bicyclic. In certain embodiments, $R^{10}$ and $R^{16}$ may join together as $C_1$-$C_3$ alkyl to form a bridged bicyclic. In certain embodiments, $R^{10}$ and $R^{16}$ may join together as O to form a bridged bicyclic. In certain embodiments, $R^{10}$ and $R^{16}$ may join together as NH to form a bridged bicyclic. In certain embodiments, $R^{10}$ and $R^{16}$ may join together as methyl, ethyl, propyl, O or NH, to form a bridged bicyclic. In certain embodiments, $R^{10}$ and $R^{16}$ may join together as methyl, ethyl, or propyl to form a bridged bicyclic.

In certain embodiments, $R^{11}$ and $R^{15}$ may join together as alkyl to form a bridged bicyclic. In certain embodiments, $R^{11}$ and $R^{15}$ may join together as $C_1$-$C_4$ alkyl to form a bridged bicyclic. In certain embodiments, $R^{11}$ and $R^{15}$ may join together as $C_1$-$C_3$ alkyl to form a bridged bicyclic. In certain embodiments, $R^{11}$ and $R^{15}$ may join together as methyl or ethyl to form a bridged bicyclic.

In certain embodiments, $R^{11}$ and $R^{16}$ may join together as alkyl or O to form a bridged bicyclic. In certain embodiments, $R^{11}$ and $R^{16}$ may join together as $C_1$-$C_4$ alkyl or O to form a bridged bicyclic. In certain embodiments, $R^{11}$ and $R^{16}$ may join together as $C_1$-$C_3$ alkyl or O to form a bridged bicyclic. In certain embodiments, $R^{11}$ and $R^{16}$ may join together as $C_1$-$C_3$ alkyl to form a bridged bicyclic. In certain embodiments, $R^{11}$ and $R^{16}$ may join together as methyl, ethyl, or O, to form a bridged bicyclic. In certain embodiments, $R^{11}$ and $R^{16}$ may join together as methyl or ethyl to form a bridged bicyclic. In certain embodiments, $R^{11}$ and $R^{16}$ may join together as O to form a bridged bicyclic.

In certain embodiments, $R^{11}$ and $R^{17}$ may join together as alkyl to form a bridged bicyclic. In certain embodiments, $R^{11}$ and $R^{17}$ may join together as $C_1$-$C_4$ alkyl to form a bridged bicyclic. In certain embodiments, $R^{11}$ and $R^{17}$ may join together as $C_1$-$C_3$ alkyl to form a bridged bicyclic. In certain embodiments, $R^{11}$ and $R^{17}$ may join together as ethyl to form a bridged bicyclic.

In certain embodiments, $R^{13}$ and $R^{15}$ may join together as $NHCH_2$, or cycloalkyl substituted with $NH_2$ to form a fused bicyclic. In certain embodiments, $R^{13}$ and $R^{15}$ may join together as $NHCH_2$, or $C_3$-$C_6$ cycloalkyl substituted with $NH_2$ to form a fused bicyclic. In certain embodiments, $R^{13}$ and $R^{15}$ may join together as $NHCH_2$, or cyclopentyl or cyclohexyl wherein the cyclopentyl or cyclohexyl are substituted with $NH_2$ to form a fused bicyclic. In certain embodiments, $R^{13}$ and $R^{15}$ may join together as $NHCH_2$ to form a fused bicyclic. In certain embodiments, $R^{13}$ and $R^{15}$ may join together as cyclopentyl or cyclohexyl wherein the cyclopentyl or cyclohexyl are substituted with $NH_2$ to form a fused bicyclic.

In certain embodiments, a, b, c and d are selected from 0 and 1.

In certain embodiments, a, b, c, and d are 1, wherein $R^2$ is:

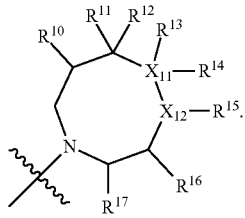

In certain embodiments, a is 0, and b, c, and d are 1, wherein $R^2$ is:

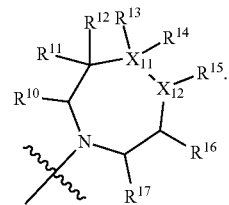

In certain embodiments, a and b are 0 and c and d are 1, wherein $R^2$ is:

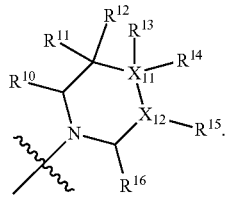

In certain embodiments, a, b and c are 0 and d is 1, wherein $R^2$ is:

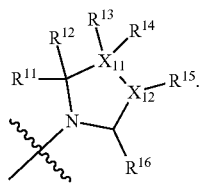

In certain embodiments, a, b and d are 0 and c is 1, wherein $R^2$ is:

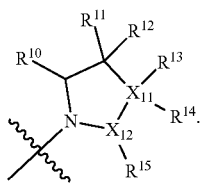

In certain embodiments, a, b, c and d are 0, wherein $R^2$ is:

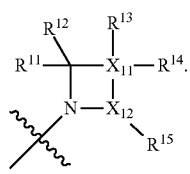

In certain embodiments, $R^{48}$ is selected from hydrogen and methyl. In certain embodiments, $R^{48}$ is hydrogen. In certain embodiments, $R^{48}$ is methyl.

In certain embodiments, a compound of Examples 1 to 221 are provided. In certain embodiments, a compound of Examples 1-6, 8-20, 22-46, 48, 49, and 51-221 are provided. In certain embodiments, a compound of Examples 1-4, 6, 8-20, 22-33, 35-45, 48, 49 and 51-221 are provided. In certain embodiments, a compound of Examples 1, 2, 4, 6, 8, 9, 12-18, 20, 22, 24-33, 35, 36, 38-45, 48, 49 and 51-221 are provided.

In certain embodiments, a compound of Examples 1 to 51. In certain embodiments, a compound of Examples 1-6, 8-20, 22-46, 48, 49 and 51. In certain embodiments, a compound of Examples 1-4, 6, 8-20, 22-33, 35-45, 48, 49 and 51. In certain embodiments, a compound of Examples 1, 2, 4, 6, 8, 9, 12-18, 20, 22, 24-33, 35, 36, 38-45, 48, 49 and 51.

In certain embodiments, a compound of Formula I, Ia, II, IIa, III, IIIa, IV, IVa, V, Va, VI or VIa is provided. In certain embodiments, a compound of Formula I, Ia, II, IIa, III, IIIa, IV, IVa, V, Va, VI or VIa is provided, with the proviso that the compound is not Example 7, 21, 47 or 50. In certain embodiments, a compound of Formula I, Ia, II, IIa, III, IIIa, IV, IVa, V, Va, VI or VIa is provided, with the proviso that the compound is not Example 5, 7, 21, 34, 46, 47 or 50. In certain embodiments, a compound of Formula I, Ia, II, IIa, III, IIIa, IV, IVa, V, Va, VI or VIa is provided, with the proviso that the compound is not Example 3, 5, 7, 10, 11, 19, 21, 23, 34, 37, 46, 47 or 50.

In certain embodiments, a compound of Formula I, II, III, IV, V, or VI is provided. In certain embodiments, a compound of Formula I, II, III, IV, V, or VI is provided, with the proviso that the compound is not Example 7, 21, 47 or 50. In certain embodiments, a compound of Formula I, II, III, IV, V, or VI is provided, with the proviso that the compound is not Example 5, 7, 21, 34, 46, 47 or 50. In certain embodiments, a compound of Formula I, II, III, IV, V, or VI is provided, with the proviso that the compound is not Example 3, 5, 7, 10, 11, 19, 21, 23, 34, 37, 46, 47 or 50.

It will be appreciated that certain compounds described herein may contain asymmetric or chiral centers, and therefore exist in different stereoisomeric forms. It is intended that all stereoisomeric forms of the compounds described herein, including but not limited to, diastereomers, enantiomers and atropisomers, as well as mixtures thereof such as racemic mixtures, form part of the present compounds.

In the structures shown herein, where the stereochemistry of any particular chiral atom is not specified, then all stereoisomers are contemplated and included as the compounds described herein. Where stereochemistry is specified by a solid wedge or dashed line representing a particular configuration, then that stereoisomer is so specified and defined.

It will also be appreciated that certain compounds of Formula I may be used as intermediates for further compounds of Formula I.

It will be further appreciated that the compounds described herein may exist in unsolvated, as well as solvated forms with pharmaceutically acceptable solvents, such as water, ethanol, and the like, and it is intended that the compounds embrace both solvated and unsolvated forms.

Synthesis of Compounds

Compounds described herein may be synthesized by synthetic routes that include processes analogous to those well-known in the chemical arts, particularly in light of the description contained herein. The starting materials are generally available from commercial sources such as Sigma-Aldrich (St. Louis, MO), Alfa Aesar (Ward Hill, MA), or TCI (Portland, OR), or are readily prepared using methods well known to those skilled in the art (e.g., prepared by methods generally described in Louis F. Fieser and Mary Fieser, *Reagents for Organic Synthesis*, v. 1-23, New York: Wiley 1967-2006 ed. (also available via the Wiley InterScience® website), or *Beilsteins Handbuch der organischen Chemie*. 4, Aufl. ed. Springer-Verlag, Berlin, including supplements (also available via the Beilstein online database)).

For illustrative purposes, Schemes 1-3 show general methods for preparing the compounds described herein, as well as key intermediates. For a more detailed description of the individual reaction steps, see the Examples section below. Those skilled in the art will appreciate that other synthetic routes may be used to synthesize the compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

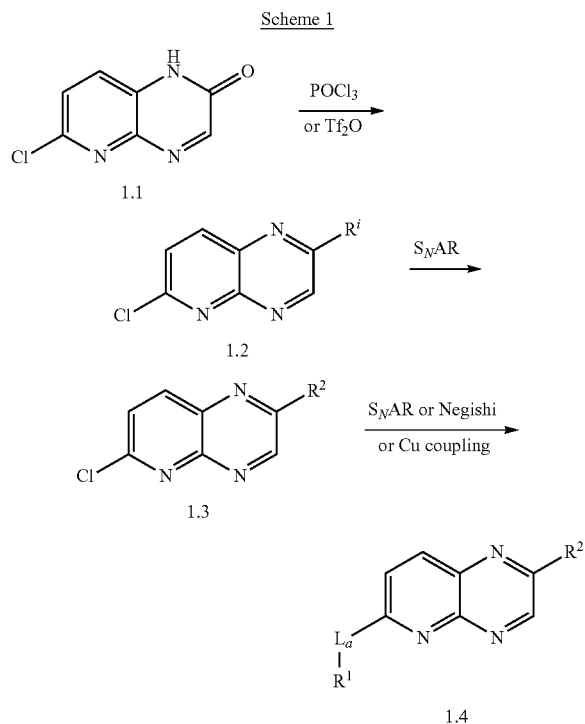

Scheme 1

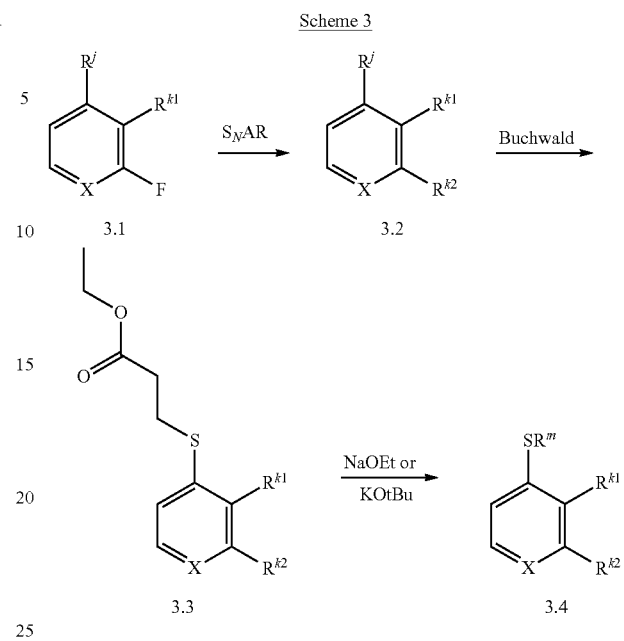

Scheme 3

Scheme 1 shows a general scheme for the synthesis of compound 1.4. 6-Chloropyrido[2,3-b]pyrazin-2(1H)-one 1.1 may be reacted with $POCl_3$ or triflic anhydride ("$Tf_2O$") to give pyridopyrazine 1.2, where $R^i$ is Cl or triflate ("OTf"). Pyridopyrazine 1.2 may be subjected to a $S_NAR$ reaction to provide pyridopyrazine 1.3, where $R^2$ is defined herein. A further $S_NAR$ reaction of pyridopyrazine 1.3 gives pyridopyrazine 1.4, where $L_a$ is S, CH, O or NH, and $R^1$ is as defined herein. Alternatively a Negisi or copper coupling may be used to also provide pyridopyrazine 1.4.

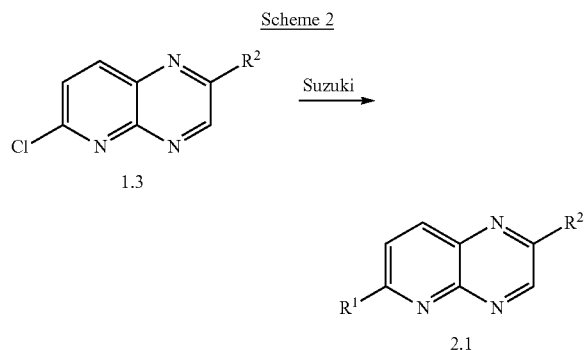

Scheme 2 shows a general scheme for preparing pyridopyrazine 2.1, wherein $R^1$ and $R^2$ are as defined herein. Pyridopyrazine 1.3 may be subjected to a Suzuki reaction to provide pyridopyrazine 2.1.

Scheme 3 shows a general scheme for preparing compound 3.4, wherein $R^j$ is I, Br or Cl, $R^{k1}$ is selected from halogen and methyl; $R^{k2}$ is selected from cyano, —O($C_1$-$C_3$ alkyl) optionally substituted with halogen, cyano or OH, NHR$^a$, and 3 to 6 membered heterocycle optionally substituted with halogen, cyano or OH, wherein the heterocycle is nitrogen linked and contains one or two nitrogen heteroatoms; and $R^m$ is hydrogen, Na or K. Compound 3.1, where X is C or N, may be subjected to a $S_NAR$ reaction to provide compound 3.2. Compound 3.2 may be subjected to a Buchwald cross coupling to provide compound 3.3. Compound 3.3 is reacted with sodium ethoxide to provide compound 3.4.

Methods of Separation

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. *Stereochemistry of Organic Compounds*. New York: John Wiley & Sons, Inc., 1994; Lochmuller, C. E L, el al. "Chromatographic resolution of enantiomers: Selective review." *J. Chromatogr*. Vol. 113, No. 3 (1975): pp. 283-302). Racemic mixtures of chiral compounds described herein may be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., ed. *Drug Stereochemistry: Analytical Methods and Pharmacology*. New York: Marcel Dekker, Inc., 1993.

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid, can result in formation of the diastereomeric salts.

Alternatively, by method (2), the substrate to be resolved is reacted with one enantiomer of a chiral compound to form a diastereomeric pair (Eliel, E. and Wilen, S. *Stereochemistry of Organic Compounds*. New York: John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III, Peyton. "Resolution of (±)-5-Bromonomicotine. Synthesis of (R)- and (S)-Nornicotine of High Enantiomeric Purity." *J. Org. Chem*. Vol. 47, No. 21(1982): pp. 4165-4167), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111).

By method (3), a racemic mixture of two enantiomers can be separated by chromatography using a chiral stationary phase (Lough, W. J., ed. *Chiral Liquid Chromatography*. New York: Chapman and Hall, 1989; Okamoto, Yoshio, et al. "Optical resolution of dihydropyridine enantiomers by high-performance liquid chromatography using phenylcarbamates of polysaccharides as a chiral stationary phase." *J. of Chromatogr*. Vol. 513 (1990): pp. 375-378). Enriched or purified enantiomers can be distinguished by methods used to distinguish other chiral molecules with asymmetric carbon atoms, such as optical rotation and circular dichroism.

Biological Evaluation

Determination of the activity of SHP2 activity of a compound of Formula I is possible by a number of direct and indirect detection methods. Certain exemplary compounds described herein were assayed for their SHP2 inhibition assay (Biological Example 1). A cell-based assay (Biological Example 2) was used to determine the effect of SHP2 inhibitors on down-stream signaling by assaying ERK1/2 phosphorylation.

Administration and Pharmaceutical Formulations

The compounds described herein may be administered by any convenient route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal.

The compounds may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents. If parenteral administration is desired, the compositions will be sterile and in a solution or suspension form suitable for injection or infusion.

A typical formulation is prepared by mixing a compound described herein and a carrier, diluent or excipient. Suitable carriers, diluents and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound described herein or pharmaceutical composition thereof) or aid in the manufacturing of the pharmaceutical product (i.e., medicament).

One embodiment includes a pharmaceutical composition comprising a compound of Formula I, II, III, IV, V, or VI, or a stereoisomer, tautomer or pharmaceutically acceptable salt thereof. A further embodiment provides a pharmaceutical composition comprising a compound of Formula I, II, III, IV, V, or VI, or a stereoisomer, tautomer or pharmaceutically acceptable salt thereof, together with a pharmaceutically acceptable carrier, diluent or excipient.

Methods of Treatment with Compounds of the Invention

Also provided are methods of treating or preventing a disease or condition by administering one or more compounds described herein, or a stereoisomer, tautomer or pharmaceutically acceptable salt thereof. In one embodiment, a method of treating a hyperproliferative disease in a mammal comprising administering a therapeutically effective amount of the compound of Formula I, II, III, IV, V, or VI, or a stereoisomer, tautomer or pharmaceutically acceptable salt thereof, to the mammal is provided.

Another embodiment provides a method of treating or preventing cancer in a mammal in need of such treatment, wherein the method comprises administering to said mammal a therapeutically effective amount of a compound of Formula I, II, III, IV, V, or VI, or a stereoisomer, tautomer or pharmaceutically acceptable salt thereof.

Another embodiment provides a method of treating or preventing pain in a mammal in need of such treatment, wherein the method comprises administering to said mammal a therapeutically effective amount of a compound of Formula I, II, III, IV, V, or VI, or a stereoisomer, tautomer or pharmaceutically acceptable salt thereof.

Another embodiment provides a method of treating or preventing an inflammatory disorder in a mammal in need of such treatment, wherein the method comprises administering to said mammal a therapeutically effective amount of a compound of Formula I, II, III, IV, V, or VI, or a stereoisomer, tautomer or pharmaceutically acceptable salt thereof.

Another embodiment provides a method of inhibiting SHP2 protein tyrosine phosphatase activity in a cell comprising treating the cell with a compound according to Formula I, II, III, IV, V, or VI, or a stereoisomer, tautomer or pharmaceutically acceptable salt thereof.

Another embodiment provides a method of inhibiting SHP2 protein tyrosine phosphatase activity in a cell comprising treating the cell with a compound according to Formula I, II, III, IV, V, or VI, or a stereoisomer, tautomer or pharmaceutically acceptable salt thereof, in an amount effective to attenuate or eliminate SHP2 kinase activity.

Another embodiment provides a method of inhibiting SHP2 protein tyrosine phosphatase activity in a patient in need thereof comprising the step of administering to said patient a compound according to Formula I, II, III, IV, V, or VI, or a stereoisomer, tautomer or pharmaceutically acceptable salt thereof.

Another embodiment provides a method of treating or ameliorating the severity of a hyperproliferative disorder in a patient in need thereof comprising administering to said patient a compound according to Formula I, II, III, IV, V, or VI, or a stereoisomer, tautomer or pharmaceutically acceptable salt thereof.

Another embodiment provides a method of treating or ameliorating the severity of a hyperproliferative disorder in a patient in need thereof comprising co-administering to said patient a compound according to Formula I, II, III, IV, V, or VI, or a stereoisomer, tautomer or pharmaceutically acceptable salt thereof, with at least one other chemotherapeutic agent used to treat or ameliorate the hyperproliferative disorder.

Another embodiment provides a method of treating or ameliorating the severity of pain in a patient in need thereof comprising administering to said patient a compound according to Formula I, II, III, IV, V, or VI, or a stereoisomer, tautomer or pharmaceutically acceptable salt thereof.

Another embodiment provides a method of treating or ameliorating the severity of an inflammatory disorder in a patient in need thereof comprising administering to said patient a compound according to Formula I, II, III, IV, V, or VI, or a stereoisomer, tautomer or pharmaceutically acceptable salt thereof.

In another embodiment, a method of treating or preventing a disease or disorder modulated by SHP2, comprising administering to a mammal in need of such treatment an effective amount of a compound of Formula I, II, III, IV, V, or VI, or a stereoisomer, tautomer or pharmaceutically acceptable salt thereof. Examples of such diseases and disorders include, but are not limited to, hyperproliferative diseases, such as cancer, and pain or inflammatory diseases.

Another embodiment provides the use of a compound of Formula I, II, III, IV, V, or VI, or a stereoisomer, tautomer or pharmaceutically acceptable salt thereof, in the manufacture of a medicament for the treatment of a hyperproliferative disease. Another embodiment provides the use of a compound of Formula I, II, III, IV, V, or VI, or a stereoisomer, tautomer or pharmaceutically acceptable salt thereof, in the manufacture of a medicament for the treatment of cancer.

Another embodiment provides the use of a compound of Formula I, II, III, IV, V, or VI, or a stereoisomer, tautomer or pharmaceutically acceptable salt thereof, in the manufacture of a medicament for the treatment of pain.

Another embodiment provides the use of a compound of Formula I, II, III, IV, V, or VI, or a stereoisomer, tautomer or pharmaceutically acceptable salt thereof, in the manufacture of a medicament for the treatment of an inflammatory disease.

Another embodiment provides the use of a compound of Formula I, II, III, IV, V, or VI, or a stereoisomer, tautomer or pharmaceutically acceptable salt thereof, for use in the treatment of hyperproliferative diseases. Another embodiment provides the use of a compound of Formula I, II, III, IV, V, or VI, or a stereoisomer, tautomer or pharmaceutically acceptable salt thereof, for use in the treatment of cancer.

Another embodiment provides the use of a compound of Formula I, II, III, IV, V, or VI, or a stereoisomer, tautomer or pharmaceutically acceptable salt thereof, for use in the treatment of pain.

Another embodiment provides the use of a compound of Formula I, II, III, IV, V, or VI, or a stereoisomer, tautomer or pharmaceutically acceptable salt thereof, for use in the treatment of inflammatory diseases.

In certain embodiments, the hyperproliferative disease is cancer. In certain embodiments, the cancer may be selected from melanoma, juvenile myelomoncytic leukemias, neuroblastoma, Philadelphia chromosome positive chronic myeloid, Philadelphia chromosome positive acute lymphoblastic leukemias, acute myeloid leukemias, myeloproliferative neoplasms (such as Polycythemia Vera, Essential Thrombocythemia and Primary Myelofibrosis), breast cancer, lung cancer, liver cancer, colorectal cancer, esophageal cancer, gastric cancer, squamous-cell carcinoma of the head and neck, glioblastoma, anaplastic large-cell lymphoma, thyroid carcinoma, and spitzoid neoplasms. In certain embodiments, the cancer is melanoma. In certain embodiments, the cancer is juvenile myelomoncytic leukemias. In certain embodiments, the cancer is neuroblastoma. In certain embodiments, the cancer is Philadelphia chromosome positive chronic myeloid. In certain embodiments, the cancer is Philadelphia chromosome positive acute lymphoblastic leukemias. In certain embodiments, the cancer is acute myeloid leukemias. In certain embodiments, the cancer is myeloproliferative neoplasms, such as Polycythemia Vera, Essential Thrombocythemia and Primary Myelofibrosis. In certain embodiments, the cancer is selected from the group consisting of Polycythemia Vera, Essential Thrombocythemia and Primary Myelofibrosis. In certain embodiments, the cancer is Polycythemia Vera. In certain embodiments, the cancer is Essential Thrombocythemia. In certain embodiments, the cancer is Primary Myelofibrosis. In certain embodiments, the cancer is breast cancer. In certain embodiments, the cancer is lung cancer. In certain embodiments, the cancer is liver cancer. In certain embodiments, the cancer is colorectal cancer. In certain embodiments, the cancer is esophageal cancer. In certain embodiments, the cancer is gastric cancer. In certain embodiments, the cancer is squamous-cell carcinoma of the head and neck. In certain embodiments, the cancer is glioblastoma. In certain embodiments, the cancer is anaplastic large-cell lymphoma. In certain embodiments, the cancer is thyroid carcinoma. In certain embodiments, the cancer is spitzoid neoplasms.

In certain embodiments, the cancer is selected from the group consisting of NSCLC, a colon cancer, an esophageal cancer, a rectal cancer, JMML, breast cancer, melanoma, and a pancreatic cancer.

In certain embodiments, the disease or disorder may be selected from Neurofibramatosis and Noonan Syndrome. In certain embodiments, the disease or disorder is Neurofibramatosis. In certain embodiments, the disease or disorder is Noonan Syndrome.

In certain embodiments, the disease or disorder is Schwannomatosis.

In certain embodiments, the disease or disorder comprising a cell containing a mutation encoding the $KRAS^{G12C}$ variant. See WO 2019/051084.

In certain embodiments, the hyperproliferative disease is a disease or disorder comprising a cell with a mutation encoding an NF1 loss of function ("$NF1^{LOF}$") variant. In certain embodiments, the NF1 mutation is a loss of function mutation. In certain embodiments, the disease or disorder is a tumor comprising cells with an NF1 loss of function mutation. In certain embodiments, the tumor is an NSCLC or melanoma tumor. In certain embodiments, the disease is selected from neurofibromatosis type I, neurofibromatosis type II, schwannomatosis, and Watson syndrome.

In certain embodiments, the disease or disorder associated with a RAS pathway mutation in a cell of the subject that renders the cell at least partially dependent on signaling flux through SHP2. In certain embodiments, the RAS pathway mutation is a RAS mutation selected from a KRAS mutation, an NRAS mutation, a SOS mutation, a BRAF Class III mutation, a Class I MEK1 mutation, a Class II MEK1 mutation, and an FI mutation. In certain embodiments, the KRAS mutation is selected from a $KRAS^{G12A}$ mutation, a $KRAS^{G12C}$ mutation, a $KRAS^{G12D}$ mutation, a $KRAS^{G12F}$ mutation, a $KRAS^{G12I}$ mutation, a $KRAS^{G12L}$ mutation, a $KRAS^{G12R}$ mutation, a $KRAS^{G12S}$ mutation, a $KRAS^{G12V}$ mutation, and a $KRAS^{G12Y}$ mutation. In certain embodiments, the KRAS mutation is a $KRAS^{G12A}$ mutation. In certain embodiments, the KRAS mutation is a $KRAS^{G12C}$ mutation. In certain embodiments, the KRAS mutation is a $KRAS^{G12D}$ mutation. In certain embodiments, the KRAS mutation is a $KRAS^{G12F}$ mutation. In certain embodiments, the KRAS mutation is a $KRAS^{G12I}$ mutation. In certain embodiments, the KRAS mutation is a $KRAS^{G12L}$ mutation. In certain embodiments, the KRAS mutation is a $KRAS^{G12R}$ mutation. In certain embodiments, the KRAS mutation is a $KRAS^{G12S}$ mutation. In certain embodiments, the KRAS mutation is a $KRAS^{G12V}$ mutation. In certain embodiments, the KRAS mutation is a $KRAS^{G12Y}$ mutation. In certain embodiments, the BRAF Class III mutation is selected from one or more of the following amino acid substitutions in human BRAF: D287H; P367R; V459L; G466V; G466E; G466A; S467L; G469E; N581S; N581I; D594N; D594G; D594A; D594H; F595L; G596D; G596R and A762E. In certain embodiments, the Class I MEK1 mutation is selected from one or more of the following amino acid substitutions in human MEK1: D67N; P124L; P124S; and L177V. In certain embodiments, the Class II MEK1 mutation is selected from one or more of the following amino acid substitutions in human MEK1: AE51-Q58; AF53-Q58; E203K; L177M; C121S; F53L; K57E; Q56P; and K57N.

Combination Therapy

The compounds described herein and stereoisomers, tautomers and pharmaceutically acceptable salts thereof may be employed alone or in combination with other therapeutic agents for treatment. The compounds described herein may be used in combination with one or more additional drugs, for example an anti-hyperproliferative (or anti-cancer) agent that works through action on a different target protein. The second compound of the pharmaceutical combination formulation or dosing regimen preferably has complementary activities to the compound described herein, such that they do not adversely affect each other. Such molecules are suitably present in combination in amounts that are effective for the purpose intended. The compounds may be administered together in a unitary pharmaceutical composition or separately and, when administered separately this may occur simultaneously or sequentially in any order. Such sequential administration may be close in time or remote in time.

In certain embodiments, the compound of Formula I is administered in combination with an inhibitor of the RAS pathway. In certain embodiments, the inhibitor of the RAS pathway is a MEK inhibitor or ERK inhibitor. In certain embodiments, the inhibitor of the Ras pathway is selected from one or more of trametinib, binimetinib, selumetinib, cobimetinib, LErafAON (NeoPharm), ISIS 5132; vemurafenib, pimasertib, TAK733, R04987655 (CH4987655); CI-1040; PD-0325901; CH5126766; MAP855; AZD6244; Refametinib (RDEA 119/BAY 86-9766); GDC-0973/XL581; AZD8330 (ARRY-424704/ARRY-704); R05126766; ARS-853; LY3214996; BVD523; GSK1 120212; Ulixertinib, and Abemaciclib.

EXAMPLES

For illustrative purposes, the following Examples are included. However, it is to be understood that these Examples do not limit the invention and are only meant to suggest a method of practicing the invention. Persons skilled in the art will recognize that the chemical reactions described may be readily adapted to prepare a number of other compounds described herein, and alternative methods for preparing the compounds are deemed to be within the scope of this invention. For example, the synthesis of non-exemplified compounds may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds described herein.

In the Examples described below, unless otherwise indicated all temperatures are set forth in degrees Celsius. Reagents were purchased from commercial suppliers such as Sigma-Aldrich, Alfa Aesar, or TCI, and were used without further purification unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel column or on a silica SepPak cartridge (Waters) (unless otherwise stated). $^1$H NMR spectra were recorded on a Varian instrument operating at 400 MHz. $^1$H-NMR spectra were obtained as CDCl$_3$, CD$_3$OD, D$_2$O, (CD$_3$)$_2$SO, (CD$_3$)$_2$CO, C$_6$D$_6$, CD$_3$CN solutions (reported in ppm), using tetramethylsilane (0.00 ppm) or residual solvent (CDCl$_3$: 7.26 ppm; CD$_3$OD: 3.31 ppm; D$_2$O: 4.79 ppm; (CD$_3$)$_2$SO: 2.50 ppm; (CD$_3$)$_2$CO: 2.05 ppm; C$_6$D$_6$: 7.16 ppm; CD$_3$CN: 1.94 ppm) as the reference standard. When peak multiplicities are reported, the following abbreviations are used: s (singlet), d (doublet), t (triplet), q (quartet), m (multiplet), br (broadened), dd (doublet of doublets), dt (doublet of triplets). Coupling constants, when given, are reported in Hertz (Hz).

Biological Example 1

SHP2 Enzymatic Assay

A fluorescence intensity kinetic assay was configured for full-length SHP2 that monitors the amount of 6,8-difluoro-7-hydroxy-4-methylcoumarin ("DiFMU") formed upon hydrolysis of 6,8-difluoro-4-methylumbelliferyl phosphate ("DiFMUP") by SHP2. Assay mixtures consisted of 25 mM K$^+$HEPES, pH 7.4, 0.01% Triton X-100, 1 mM DTT, 50 mM KCl, 100 µg/mL bovine γ-globulin, 50 µM DiFMUP, 1 µM SHP2 activating peptide (LN(pY)IDLDLV(dPEG8)LST(pY)ASINFQK-amide), 1 nM full-length SHP2 (His6-tagged SHP2(2-527), recombinantly expressed in *E. coli* and purified in-house) and 2% dimethylsulfoxide ("DMSO") (from compound). Compounds were typically diluted in DMSO across a 10-point dosing range created using a 3-fold serial dilution protocol at a top dose of 20 µM. The assay was run in 384-well, polystyrene, low-volume, non-treated, black microtiter plates (Costar 4511) in a final volume of 20 µL. Low control wells lacked enzyme. The assays were initiated by the addition of a mixture of SHP2 and the activating peptide, and following a 15 second mix on an orbital shaker, were read in kinetic mode for 15 minutes (30 seconds/cycle) at ambient temperature on a PerkinElmer EnVision microplate reader (λEx=355 nm, λEm=460 nm). Initial velocities (slopes of the tangents at t=0) were estimated from exponential fits to the slightly nonlinear progress curves and then were converted to percent of control ("POC") using the following equation:

$$POC = \frac{Sample - \overline{X}_{min}}{\overline{X}_{max} - \overline{X}_{min}} \times 100$$

Where: $\overline{X}_{max}$ Average Uninhibited Controls
$\overline{X}_{min}$ Average Background A 4-parameter logistic model was the fit to the POC data for each compound. From that fit, the IC$_{50}$ was estimated and is defined as the concentration of compound at which the curve crosses 50 POC.

Table 1 contains representative data for Examples disclosed herein. The reported IC$_{50}$ in Table 1 may be from a single assay or the mean of multiple assays. Examples 1-51 were tested in the above assay and were found to have an IC$_{50}$ of less than 10 µM. Examples 1-51 were tested in the above assay and were found to have an IC$_{50}$ of less than 9.5 µM. Examples 1-6, 8-20, 22-46, 48, 49 and 51 were tested in the above assay and were found to have an IC$_{50}$ of less than 5 µM. Examples 1-4, 6, 8-20, 22-33, 35-45, 48, 49 and 51 were tested in the above assay and were found to have an IC$_{50}$ of 2.5 µM or less. Examples 1, 2, 4, 6, 8, 9, 12-18, 20, 22, 24-33, 35, 36, 38-45, 48, 49 and 51 were tested in the above assay and were found to have an IC$_{50}$ of 1 µM or less.

Table 1 contains Examples tested in the above assay:

TABLE 1

| Example # | Biological Example 1 IC$_{50}$ (nM) |
|---|---|
| Example 1 | 33 |
| Example 2 | 93 |
| Example 3 | 1800 |
| Example 4 | 64 |
| Example 5 | 4000 |
| Example 6 | 58 |
| Example 7 | 9500 |
| Example 8 | 59 |
| Example 9 | 62 |
| Example 10 | 2000 |
| Example 11 | 2300 |
| Example 12 | 61 |
| Example 13 | 84 |
| Example 14 | 100 |
| Example 15 | 340 |
| Example 16 | 290 |
| Example 17 | 870 |
| Example 18 | 570 |
| Example 19 | 1700 |
| Example 20 | 360 |
| Example 21 | 5700 |
| Example 22 | 700 |
| Example 23 | 2500 |
| Example 24 | 200 |
| Example 25 | 100 |
| Example 26 | 920 |
| Example 27 | 500 |
| Example 28 | 830 |
| Example 29 | 320 |
| Example 30 | 420 |
| Example 31 | 100 |
| Example 32 | 420 |
| Example 33 | 100 |
| Example 34 | 2600 |
| Example 35 | 270 |
| Example 36 | 400 |
| Example 37 | 1100 |
| Example 38 | 290 |
| Example 39 | 320 |
| Example 40 | 440 |
| Example 41 | 56 |
| Example 42 | 95 |
| Example 43 | 100 |
| Example 44 | 120 |
| Example 45 | 92 |
| Example 46 | 2900 |
| Example 47 | 6000 |
| Example 48 | 460 |
| Example 49 | 63 |
| Example 50 | 9000 |
| Example 51 | 65 |
| Example 52 | 70 |
| Example 53 | 123 |
| Example 54 | 60 |
| Example 55 | 121 |
| Example 56 | 42 |
| Example 57 | 49 |
| Example 58 | 153 |
| Example 59 | 405 |
| Example 60 | 245 |
| Example 61 | 1570 |
| Example 62 | 165 |
| Example 63 | 280 |
| Example 64 | 730 |
| Example 65 | 5764 |
| Example 66 | 2752 |
| Example 67 | 42 |
| Example 68 | 69 |
| Example 69 | 79 |
| Example 70 | 5966 |
| Example 71 | 120 |
| Example 72 | 149 |
| Example 73 | 35 |

TABLE 1-continued

| Example # | Biological Example 1 IC$_{50}$ (nM) |
|---|---|
| Example 74 | 42 |
| Example 75 | 30 |
| Example 76 | 28 |
| Example 77 | 344 |
| Example 78 | 331 |
| Example 79 | 425 |
| Example 80 | 743 |
| Example 81 | 72 |
| Example 82 | 65 |
| Example 83 | 173 |
| Example 84 | 102 |
| Example 85 | 481 |
| Example 86 | 53 |
| Example 87 | 126 |
| Example 88 | 105 |
| Example 89 | 79 |
| Example 90 | 183 |
| Example 91 | 106 |
| Example 92 | 66 |
| Example 93 | 49 |
| Example 94 | 49 |
| Example 95 | 4721 |
| Example 96 | 503 |
| Example 97 | 176 |
| Example 98 | 169 |
| Example 99 | 157 |
| Example 100 | 121 |
| Example 101 | 56 |
| Example 102 | 44 |
| Example 103 | 79 |
| Example 104 | 3346 |
| Example 105 | 82 |
| Example 106 | 101 |
| Example 107 | 120 |
| Example 108 | 84 |
| Example 109 | 27 |
| Example 110 | 44 |
| Example 111 | 34 |
| Example 112 | 33 |
| Example 113 | 53 |
| Example 114 | 40 |
| Example 115 | 60 |
| Example 116 | 36 |
| Example 117 | 50 |
| Example 118 | 45 |
| Example 119 | 39 |
| Example 120 | 633 |
| Example 121 | 99 |
| Example 122 | 64 |
| Example 123 | 21 |
| Example 124 | 52 |
| Example 125 | 38 |
| Example 126 | 30 |
| Example 127 | 82 |
| Example 128 | 100 |
| Example 129 | 34 |
| Example 130 | 96 |
| Example 131 | 419 |
| Example 132 | 31 |
| Example 133 | 92 |
| Example 134 | 238 |
| Example 135 | 4025 |
| Example 136 | 160 |
| Example 137 | 64 |
| Example 138 | 574 |
| Example 139 | 93 |
| Example 140 | 75 |
| Example 141 | 74 |
| Example 142 | 26 |
| Example 143 | 1756 |
| Example 144 | 89 |
| Example 145 | 27 |
| Example 146 | 89 |
| Example 147 | 50 |
| Example 148 | 93 |
| Example 149 | 98 |
| Example 150 | 50 |
| Example 151 | 76 |
| Example 152 | 30 |
| Example 153 | 164 |
| Example 154 | 1211 |
| Example 155 | 45 |
| Example 156 | 32 |
| Example 157 | 282 |
| Example 158 | 106 |
| Example 159 | 50 |
| Example 160 | 60 |
| Example 161 | 45 |
| Example 162 | 39 |
| Example 163 | 52 |
| Example 164 | 203 |
| Example 165 | 15953 |
| Example 166 | 3992 |
| Example 167 | 50 |
| Example 168 | 54 |
| Example 169 | 35 |
| Example 170 | 62 |
| Example 171 | 56 |
| Example 172 | 112 |
| Example 173 | 237 |
| Example 174 | 335 |
| Example 175 | 1226 |
| Example 176 | 109 |
| Example 177 | 220 |
| Example 178 | 57 |
| Example 179 | 80 |
| Example 180 | 274 |
| Example 181 | 75 |
| Example 182 | 80 |
| Example 183 | 268 |
| Example 184 | 413 |
| Example 185 | 408 |
| Example 186 | 2311 |
| Example 187 | 261 |
| Example 188 | 151 |
| Example 189 | 59 |
| Example 190 | 3646 |
| Example 191 | 134 |
| Example 192 | 45 |
| Example 193 | 138 |
| Example 194 | 238 |
| Example 195 | 506 |
| Example 196 | 563 |
| Example 197 | 1507 |
| Example 198 | 3986 |
| Example 199 | 344 |
| Example 200 | 48 |
| Example 201 | 130 |
| Example 202 | 132 |
| Example 203 | 142 |
| Example 204 | 47 |
| Example 205 | 114 |
| Example 206 | 2027 |
| Example 207 | 730 |
| Example 208 | 67 |
| Example 209 | 40 |
| Example 210 | 63 |
| Example 211 | 54 |
| Example 212 | 197 |
| Example 213 | 112 |
| Example 214 | 304 |
| Example 215 | 780 |
| Example 216 | 3085 |
| Example 217 | 845 |
| Example 218 | 47 |
| Example 219 | 4194 |
| Example 220 | 96 |
| Example 221 | 183 |

Biological Example 2

Cellular Phospho-p44/42 MAPK (Erk 1/2) (Thr202/Tyr204) Assay

Inhibition of ERK1/2 (Thr202/Tyr204) phosphorylation was determined by the following cellular assay, which comprises incubating cells with a compound for 1 hour and quantifying pERK signal by In-Cell Western on fixed cells and normalizing to GAPDH signal. KYSE520 cells were obtained from DSMZ and grown in RPMI supplemented with 10% fetal bovine serum, pennicillin/streptomycin, 2 mM L-alanyl-L-glutamine dipeptide in 0.85% NaCl (Glutamax™), non-essential amino acids, and sodium pyruvate. Cells were plated in 96-well plates at 30,000 cells/well and allowed to attach overnight at 37° C./5% $CO_2$. Cells were treated with compounds prepared as a 10-point, 1:3 dilution series (range: 20 µM-1 nM), with a final DMSO concentration of 0.5%. After 1 hour incubation, cells were fixed in 3.7% formaldehyde in Dulbecco's phosphate-buffered saline ("dPBS") at room temperature for 20 minutes. Cells were then washed with dPBS and permeabilized in 100% MeOH at room temperature for 10 minutes. Following permeabilization, cells were washed in dPBS and incubated in LI-COR Blocking Buffer (LI-COR Biosciences, Cat #927-40000) for 1 hour or longer. Plates were then incubated with an antibody specific for the MEK-dependent ERK1/2 phosphorylation sites, threonine 202 and tyrosine 204 (Cell Signaling Technologies; Cat #9101), downstream of SHP2 in the MAP kinase signal transduction pathway, as well as GAPDH (Millipore; Cat #MAB374). pErk1/2 (Thr202/Tyr204) antibody was diluted in LI-COR blocking buffer containing 0.05% polysorbate-20 (Tween-20) at 1:250; GAPDH was diluted at 1:2,500. The plates were incubated overnight at 4° C. After washing with PBS/0.05% Tween-20, the cells were incubated with fluorescently-labeled secondary antibodies (Anti-rabbit-Alexa Flour680, Invitrogen Cat #A21109; Anti-mouse-IRDye800CW, Li-cor Bioscieces Cat #926-32210, both at 1:1000 dilution) for 1 hour. Cells were then washed, as above, and analyzed for fluorescence at both 680 nm and 800 nm wavelengths using the Aerius Infrared Imaging System (LI-COR Biosciences, Model 9250). Phosphorylated Erk1/2 (Thr202/Tyr204) signal was normalized to GAPDH signal for each well. $IC_{50}$ values were calculated from the normalized values using a 4-parameter fit in BioAssay software. Table 2 contains representative data for Examples disclosed herein. The reported $IC_{50}$ in Table 2 may be from a single assay or the mean of multiple assays.

Table 2 contains selected Examples tested in the above assay:

TABLE 2

| Example # | Biological Example 2 $IC_{50}$ (nM) |
| --- | --- |
| Example 1 | 59 |
| Example 4 | 550 |
| Example 13 | 79 |
| Example 25 | 650 |
| Example 33 | 80 |
| Example 41 | 110 |
| Example 57 | 91 |
| Example 67 | 48 |
| Example 71 | 176 |
| Example 76 | 8 |
| Example 78 | 87 |
| Example 91 | 317 |

TABLE 2-continued

| Example # | Biological Example 2 $IC_{50}$ (nM) |
| --- | --- |
| Example 108 | 11 |
| Example 117 | 6 |
| Example 125 | 5 |
| Example 134 | 810 |
| Example 142 | 4 |
| Example 163 | 30 |
| Example 178 | 17 |
| Example 185 | 166 |
| Example 189 | 98 |
| Example 200 | 122 |
| Example 210 | 16 |
| Example 218 | 67 |

Intermediate Example A

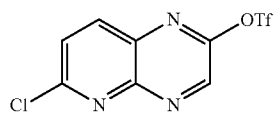 [SMILES: O=S(=O)(Oc1cnc2nc(Cl)ccc2n1)C(F)(F)F]

6-chloropyrido[2,3-b]pyrazin-2-yl trifluoromethanesulfonate

N-Ethyl-N-isopropylpropan-2-amine (3.0 mL, 16 mmol) was added to a slurry of 6-chloropyrido[2,3-b]pyrazin-2(1H)-one (2.0 g, 11 mmol) in dichloromethane ("DCM") (110 mL, 11 mmol) cooled to 0° C., followed by $Tf_2O$ (2.1 mL, 13 mmol). The reaction was held at 0° C. for 30 minutes. The reaction was concentrated and directly chromatographed using 5-50% ethyal acetate ("EtOAc")/hexanes to give 6-chloropyrido[2,3-b]pyrazin-2-yl trifluoromethanesulfonate (2.6 g, 8.2 mmol, 75% yield). $^1H$ NMR (400 MHz, ($CDCl_3$) δ 8.98 (s, 1H), 8.38 (d, 1H, J=8.6 Hz), 7.84 (d, 1H, J=8.6 Hz).

Intermediate Example B

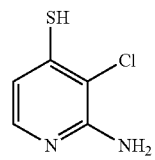

2-amino-3-chloropyridine-4-thiol

Step A: 3-Mercaptopropionic acid 2-ethylhexyl ester (2.3 mL, 22 mmol) and Hunig's base (6.9 mL, 39 mmol) were added to a mixture of 3-chloro-4-iodopyridin-2-amine (5.0 g, 20 mmol), $Pd(OAc)_2$ (0.22 g, 0.98 mmol) and xantphos (1.1 g, 2.0 mmol) in dioxane (65 mL, 20 mmol) under Ar gas. The reaction was heated to 100° C. under argon for 18 hours. The reaction was diluted in EtOAc and filtered through diatomaceous silica (Celite®). The filtrate was concentrated to provide methyl 3-((2-amino-3-chloropyridin-4-yl)thio)propanoate (4.3 g, 17 mmol, 88% yield).

Step B: NaOEt (7.1 mL, 19 mmol) was added to methyl 3-((2-amino-3-chloropyridin-4-yl)thio)propanoate (4.3 g, 17 mmol) in tetrahydrofuran ("THF") (87 mL, 17 mmol) and was stirred under N$_2$ for 1 hour at room temperature. DCM (20 mL) was added, and this mixture was stirred for 5 minutes. The reaction was concentrated, and the solid was titrated with DCM, filtered, and dried. The solids were brought up in water (slurry), and 1N HCl was added to bring the pH to about 6. The solids were filtered and washed with water to provide 2-amino-3-chloropyridine-4-thiol (1.4 g, 9.0 mmol, 52% yield). $^1$H NMR (400 MHz, (CD$_3$)$_2$SO) δ 11.4 (br, 1H), 7.06 (d, 1H, J=6.8 Hz), 6.70 (br, 2H), 6.65 (d, 1H, J=7.0 Hz); m/z (esi/APCI) M+1=161.0.

Intermediate Example C

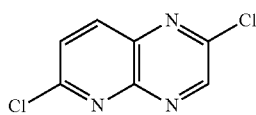 [SMILES: Clc1cnc2nc(Cl)ccc2n1]

2,6-dichloropyrido[2,3-b]pyrazine

6-Chloropyrido[2,3-b]pyrazin-2(1H)-one (0.95 g, 5.2 mmol) was placed in toluene (5 mL). POCl$_3$ (5.3 mL, 57 mmol) was added, and the reaction was refluxed for 22 hours. The reaction was cooled to 0° C., and water was added followed by saturated bicarbonate. The mixture was extracted with DCM (3×50 mL), the organics were combined, dried, filtered and concentrated to provide 2,6-dichloropyrido[2,3-b]pyrazine (0.90 g, 4.5 mmol, 86% yield). The intermediate was used as is.

Intermediate Example D

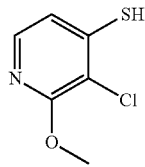

3-chloro-2-methoxypyridine-4-thiol

3-Chloro-2-methoxypyridine-4-thiol was prepared according to Intermediate Example B, substituting 3-chloro-4-iodo-2-methoxypyridine for 3-chloro-4-iodopyridin-2-amine in Step A. m/z (esi/APCI) M+1=176.0.

Intermediate Example E

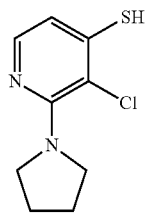

3-chloro-2-(pyrrolidin-1-yl)pyridine-4-thiol

Step A: 3-Chloro-2-fluoro-4-iodopyridine (4.0 g, 16 mmol) and pyrrolidine (3.9 mL, 46 mmol) were placed in DMSO (20 mL) and heated to 70° C. for 30 minutes. Water was added, and the mixture was extracted with ether. The ether layers were washed with water, dried, filtered and concentrated to provide 3-chloro-4-iodo-2-(pyrrolidin-1-yl) pyridine (4.5 g, 14 mmol, 93% yield).
Step B: 3-Chloro-2-(pyrrolidin-1-yl)pyridine-4-thiol was prepared according to Intermediate Example B, substituting 3-chloro-4-iodo-2-(pyrrolidin-1-yl)pyridine for 3-chloro-4-iodopyridin-2-amine in Step A. $^1$H NMR (400 MHz, (CD$_3$)$_2$SO) δ 11.28 (br, 1H), 7.06 (br, 1H), 6.82 (d, 1H, 6.7 Hz), 3.56 (m, 4H), 1.88 (m, 4H); m/z (esi/APCI) M+1=215.0.

Intermediate Example F

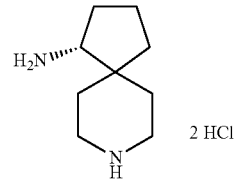 [SMILES: N[C@@H]1CCCC12CCNCC2]

(R)-8-azaspiro[4.5]decan-1-amine dihydrochloride

Step A: Tetraethoxytitanium (5.0 g, 22 mmol) and (R)-2-methylpropane-2-sulfinamide (1.4 g, 12 mmol) were added to a solution of 8-boc-1-oxo-8-aza-spiro[4.5]decane (1.4 g, 5.5 mmol) in THF (37 mL, 5.5 mmol). The reaction was heated to 65° C. overnight. The solution was cooled to 0° C., and MeOH (20 mL) was added followed by dropwise addition of LiBH$_4$ (5.5 mL, 11 mmol). The reaction was stirred at 0° C. for 1 hour. The reaction was next poured into NH$_4$Cl, and the slurry filtered through Celite®. The Celite® was washed with EtOAc. The mixture was separated, and the aqueous layer extracted with EtOAc. The combined organics were washed with brine, dried over Na$_2$SO$_4$ and concentrated in vacuo. The material was chromatographed using a 10-70% EtOAc/hexanes gradient to give tert-butyl (R)-1-(((R)-tert-butylsulfinyl)amino)-8-azaspiro[4.5]decane-8-carboxylate (0.7 g, 2.0 mmol, 35% yield).
Step B: tert-Butyl (R)-1-(((R)-tert-butylsulfinyl)amino)-8-azaspiro[4.5]decane-8-carboxylate (1.6 g, 4.3 mmol) was placed in MeOH (10 mL) and treated with HCl (11 mL, 43 mmol). The reaction was stirred for 1 hour at room temperature. The reaction was concentrated, and the resulting solid was tritrated with methyl tert-butyl ether ("MTBE") (30 mL) and filtered to provide (R)-8-azaspiro[4.5]decan-1-amine dihydrochloride (0.88 g, 3.9 mmol, 89% yield), m/z (esi/APCI) M+1=155.2.

Intermediate Example G

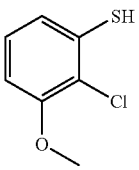

2-chloro-3-methoxybenzenethiol

2-Chloro-3-methoxybenzenethiol was prepared according to Intermediate Example B, substituting 1-bromo-2-chloro-3-methoxybenzene for 3-chloro-4-iodopyridin-2-amine in Step A. m/z (esi/APCI) M+1=175.0.

Intermediate Example H

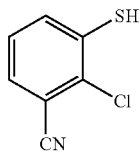

2-chloro-3-mercaptobenzonitrile

2-Chloro-3-mercaptobenzonitrile was prepared according to Intermediate Example B, substituting 3-bromo-2-chlorobenzonitrile for 3-chloro-4-iodopyridin-2-amine in Step A. m/z (esi/APCI) M+1=170.0.

Intermediate Example I

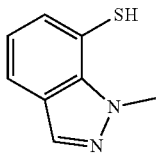

1-methyl-1H-indazole-7-thiol

1-Methyl-1H-indazole-7-thiol was prepared according to Intermediate Example B, substituting 7-bromo-1-methyl-1H-indazole for 3-chloro-4-iodopyridin-2-amine in Step A. m/z (esi/APCI) M+1=165.1.

Intermediate Example J

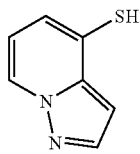

pyrazolo[1,5-a]pyridine-4-thiol

Pyrazolo[1,5-a]pyridine-4-thiol was prepared according to Intermediate Example B, substituting 4-bromo-pyrazolo(1,5-a)pyridine for 3-chloro-4-iodopyridin-2-amine in Step A. m/z (esi/APCI) M+1=151.1.

Intermediate Example K

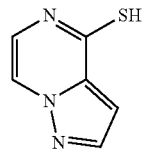

Pyrazolo[1,5-a]pyrazine-4-thiol

Pyrazolo[1,5-a]pyrazine-4-thiol was prepared according to Intermediate Example B, substituting 4-chloropyrazolo[1,5-a]pyrazine for 3-chloro-4-iodopyridin-2-amine in Step A. m/z (esi/APCI) M+1=152.1.

Intermediate Example L

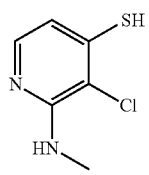

3-chloro-2-(methylamino)pyridine-4-thiol

3-Chloro-2-(methylamino)pyridine-4-thiol was Prepared according to Intermediate Example E, substituting methylamine for pyrolidine in Step A. m/z (esi/APCI) M+1=175.0.

Intermediate Example M

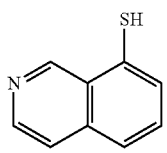 [SMILES: Sc1cccc2ccncc12]

Isoquinoline-8-thiol was prepared according to Intermediate Example B, substituting 8-bromoisoquinoline for 3-chloro-4-iodopyridin-2-amine in Step A. m/z (esi/APCI) M+1=321.1.

Intermediate Example N

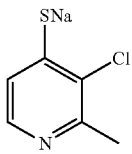

Sodium 3-chloro-2-methylpyridine-4-thiolate

Step A: 3-Mercaptopropionic acid 2-ethylhexyl ester (0.47 mL, 4.3 mmol) and Hunig's base (1.4 mL, 7.9 mmol) were added to a mixture of 3-chloro-4-iodo-2-methylpyridine (1.0 g, 3.945 mmol), Pd(OAc)$_2$ (0.044 g, 0.20 mmol) and xantphos (0.230 g, 0.40 mmol) in dioxane (13 mL, 4.0 mmol) under Ar gas. The reaction was heated to 100° C. under Argon for 18 hours. The reaction was diluted in EtOAc (60 mL) and filtered through Celite®. The filtrate was concentrated, and the resulting residue was purified by silica gel (5-60% EtOAc in hexanes) to provide methyl 3-((3-chloro-2-methylpyridin-4-yl)thio)propanoate (962 mg, 3.9 mmol, 99% yield).

Step B: NaOEt (1.6 mL, 4.3 mmol) was added to methyl 3-((3-chloro-2-methylpyridin-4-yl)thio)propanoate (962 mg, 3.9 mmol) in THF (20 mL, 3.9 mmol) and was stirred under N$_2$ for 1 hour at room temperature. The reaction mixture was poured onto ether, and solids were filtered and washed with ether to provide sodium 3-chloro-2-methylpyridine-4-thiolate (701 mg, 3.9 mmol, 99% yield).

Intermediate Example O

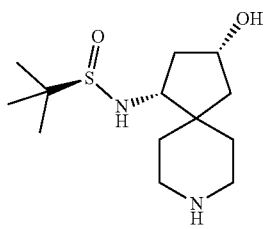 [SMILES: CC(C)(C)[S@@](=O)N[C@@H]1C[C@H](O)CC12CCNCC2]

(R)—N-((1R,3R)-3-hydroxy-8-azaspiro[4.5]decan-1-yl)-2-methylpropane-2-sulfinamide Step A: A mixture of tert-butyl 4-formylpiperidine-1-carboxylate (30 g, 140.84 mmol), lithium tert-butoxide (13.4 g, 169 mmol) and allyl bromide (10.2 mL, 161.96 mmol) in DMF (288 mL) was stirred for 15 minutes at 0° C. The mixture was poured into a separating funnel containing saturated aqueous NH$_4$Cl:H$_2$O (1:1, 160 mL), and it was extracted with EtOAc (5×60 mL). The combined organic phases were dried over Na$_2$SO$_4$, filtered, and concentrated under reduced pressure. The obtained residue was purified by flash chromatography (gradient: 0-10% EtOAc/Hexane) to get tert-butyl 4-formyl-4-(prop-2-en-1-yl)piperidine-1-carboxylate (24 g, 67%) as a colorless oil. LCMS: 254.1 (M$^+$H).

Step B: Vinyl magnesium bromide (1M in THF, 102 mL, 102.92 mmol) was added to a stirred solution of tert-butyl 4-formyl-4-(prop-2-en-1-yl)piperidine-1-carboxylate (21 g, 83.00 mmol) in THF (260 mL) at −78° C. under N$_2$ atmosphere. The resulting solution was gradually warmed to room temperature within 1 hour. The mixture was poured into a separation funnel containing saturated aqueous solution of NH$_4$Cl (60 mL) and extracted with EtOAc (3×100 mL). The combined organic phases were dried over Na$_2$SO$_4$, filtered, dried under reduced pressure to get the desired crude product tert-butyl 4-(1-hydroxyprop-2-en-1-yl)-4-(prop-2-en-1-yl)piperidine-1-carboxylate (21 g) as an oil. This compound was used for next step without any further purification. LCMS: 282.4 (M$^+$H).

Step C: Dess-Martin periodinane (54 g, 128.11 mmol) was added to a stirred solution of tert-butyl 4-(1-hydroxyprop-2-en-1-yl)-4-(prop-2-en-1-yl)piperidine-1-carboxylate (18 g, 64.05 mmol) in DCM (240 mL) and was stirred for 1 hour at room temperature under nitrogen atmosphere. The mixture was filtered through a pad of Celite®, the filtrate was poured into a separation funnel containing saturated NaHCO$_3$ solution, and was extracted with DCM. The combined organic phases were dried over Na$_2$SO$_4$, filtered and concentrated under reduced pressure to provide a yellow semi-solid (20 g). This semi-solid was suspended in hexane (100 mL) and sonicated for 5 minutes. The white suspension was filtered through a pad of Celite®, and the volatiles were removed under reduced pressure to get crude yellow oil. The obtained residue was combined with the crude product of another batch (batch size: 3 g of tert-butyl 4-(1-hydroxyprop-2-en-1-yl)-4-(prop-2-en-1-yl)piperidine-1-carboxy late) and purified by flash chromatography (gradient: 0-10% EtOAc/hexane) to get tert-butyl 4-(prop-2-en-1-yl)-4-(prop-2-enoyl)piperidine-1-carboxy late (15 g, 65%, 2 steps) as an oil. LCMS: 280.1 (M$^+$H).

Step D: Grubbs II (1.3 g, 1.61 mmol) was added to a stirred solution of tert-butyl 4-(prop-2-en-1-yl)-4-(prop-2-enoyl)piperidine-1-carboxylate (15 g, 53.76 mmol) in toluene (degassed, 540 mL), and the resulting mixture was stirred for 45 minutes at 85° C. The solvent was concentrated, and the resulting residue (17.9 g) was purified by silica column chromatography (gradient: 0-50% EtOAc/hexane) to get tert-butyl 1-oxo-8-azaspiro[4.5]dec-2-ene-8-carboxylate (10 g, 74%) as a solid. LCMS: 252.0 (M$^+$H).

Step E: A mixture of CuCl (532 mg, 5.37 mmol), (S)-Tol-BINAP (3.6 g, 5.37 mmol) and sodium tert-butoxide (517 mg, 5.37 mmol) in THF (45 mL) was stirred for 30 minutes at room temperature. Bis(pinacolato)diboron (11.8 g, 46.61 mmol) in THF (15 mL) was added, and the reaction mixture was allowed to stir at room temperature for 10 minutes. A solution of tert-butyl 1-oxo-8-azaspiro[4.5]dec-2-ene-8-carboxylate (9 g, 35.85 mmol) in THF (36 mL) was added, followed by MeOH (2.7 mL). The resulting mixture was stirred for 16 hours at room temperature. Water (110 mL) was added, followed by sodium perborate (17.9 g, 179.28 mmol), and the resulting mixture was vigorously stirred for 10 minutes at 0° C. The resulting green suspension was filtered through a pad of Celite®, poured into a separation funnel containing saturated NaHCO$_3$ solution, and extracted with EtOAc (3×50 mL). The combined organic phases were dried, filtered and concentrated under reduced pressure. The obtained residue was purified by silica column chromatography (gradient: 0-60% EtOAc/hexane) to get the desired product tert-butyl (3R)-3-hydroxy-1-oxo-8-azaspiro[4.5]decane-8-carboxylate (5.1 g, 53%) as a solid.

Step F: tert-Butyldimethylsilyl chloride (1.9 g, 13.0 mmol) was added to the stirred solution of imidazole (817 mg, 12.0 mmol) in dry DMF (27 mL) at 0° C. and stirred for 15 minutes at room temperature. tert-Butyl (3R)-3-hydroxy-1-oxo-8-azaspiro[4.5]decane-8-carboxylate (2.7 g, 10.0 mmol) was added to the reaction mixture and allowed to stir at room temperature for 4 hours. The reaction mixture was diluted by addition of cold water and extracted with EtOAc (2×30 mL). The combined organic layer was then dried over sodium sulfate and concentrated under reduced pressure. The resulting residue was purified by flash chromatography (gradient: 0-30% EtOAc/hexane) to get tert-butyl (3R)-3-[(tert-butyldimethylsilyl)oxy]-1-oxo-8-azaspiro[4.5]decane-8-carboxylate (3.1 g, 81%) as a solid. LCMS: 384.3 (M$^+$H).

Step G: A solution of tert-butyl (3R)-3-[(tert-butyldimethylsilyl)oxy]-1-oxo-8-azaspiro[4.5]decane-8-carboxylate (7.4 g, 27.3 mmol), titanium (IV) ethoxide (22.8 mL, 109.2 mmol), and (R)-(+)-2-methyl-2-propanesulfinamide (6.6 g, 54.6 mmol) in THF (80 mL) was stirred for 4 hours at 65° C. Water was added to the reaction mixture, stirred for 15 minutes, and filtered through a pad of Celite®. The filtrate was washed with EtOAc (2×60 mL), dried, and concentrated to get the crude product. The obtained residue was purified by flash chromatography (gradient: 0-40% EtOAc/hexane) to get tert-butyl(1E,3R)-3-[(tert-butyldimethylsilyl)oxy]-1-{[(R)-2-methylpropane-2-sulfinyl]imino}-8 azaspiro[4.5]decane-8-carboxylate (3.5 g, 53%). LCMS: 487.6 (M+H).

Step H: A solution of tert-butyl(1E,3R)-3-[(tert-butyldimethylsilyl)oxy]-1-{[(R)-2-methylpropane-2-sulfinyl]imino}-8 azaspiro[4.5]decane-8-carboxylate (745 mg, 1.53 mmol) in THF (7 mL) was cooled to −78° C. followed by addition of MeOH (0.07 mL). Lithium borohydride (84 mg, 3.83 mmol) was added, and the resulting reaction mixture was stirred for 3 hours at −78° C. At completion saturated aqueous solution of $NH_4Cl$ (10 mL) was slowly added to quench the excess of borohydride, and the reaction mixture was diluted with EtOAc (20 mL). The resulting mixture was vigorously stirred for 15 minutes at room temperature and then extracted with EtOAc (2×20 mL). The reaction mixture was concentrated to get the crude product tert-butyl (1R,3R)-3-[(tert-butyldimethylsilyl)oxy]-1-{[(R)-2-methylpropane-2-sulfinyl]amino}-8-azaspiro [4.5]decane-8-carboxylate (745 mg) as colorless sticky mass, proceeded to the next step without any purification. LCMS: 489.4 ($M^+H$).

Step I: TBAF solution (1.0M in THF, 2.3 mL, 2.29 mmol) was added to a stirred solution of tert-butyl (1R,3R)-3-[(tert-butyldimethylsilyl)oxy]-1-{[(R)-2-methylpropane-2-sulfinyl]amino}-8-azaspiro [4.5]decane-8-carboxylate (745 mg, 1.52 mmol) in THF (7 mL) at room temperature and allowed to stir for 2 hours at the same temperature. At completion, the reaction mixture was treated with saturated $NaHCO_3$ solution and extracted with EtOAc (2×20 mL). The combined organic phases was washed with brine, dried over $Na_2SO_4$, filtered and concentrated. The resulting residue was purified by flash chromatography (gradient: 0-10% MeOH/DCM) to get tert-butyl (1R,3R)-3-hydroxy-1-{[(R)-2-methylpropane-2-sulfinyl]amino}-8-azaspiro[4.5]decane-8-carboxylate (315 mg, 55%, 2 steps) as a solid.

Step J: tert-Butyl (1R,3R)-3-hydroxy-1-{[(R)-2-methylpropane-2-sulfinyl]amino}-8-azaspiro[4.5]decane-8-carboxylate (200 mg, 0.53 mmol) was added to a solution of TFA/DCM (2 mL, 1:10) at 0° C. and stirred for 2 hours at room temperature. After completion, the reaction mixture was concentrated. The obtained residue was dissolved in MeOH (0.5 mL), and solid $NaHCO_3$ was added to the reaction mixture. The resulting reaction mixture was stirred for 15 minutes at room temperature, filtered, and the filtrate was concentrated under reduced pressure. The obtained residue was triturated with a mixture of 10% MeOH in DCM, and the solid residue was filtered off. The filtrate was concentrated to get the crude product as light brown sticky solid. It was purified by column chromatography using neutral alumina as stationary phase and 0-15% MeOH in DCM as mobile phase to get (R)—N-[(1R,3R)-3-hydroxy-8-azaspiro[4.5]decan-1-yl]-2-methylpropane-2-sulfinamide (79.2 mg, 32%) as a solid.

Intermediate Example P

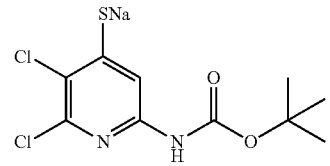

Sodium 6-((tert-butoxycarbonyl)amino)-2,3-dichloropyridine-4-thiolate

Step A: LiHMDS (1M in THF; 26 mL, 26.99 mmol) was added drop wise to a stirred solution of 5,6-dichloropyridin-2-amine (2.0 g, 12.27 mmol) in THF (64 mL) at 0° C., and the reaction mixture was stirred for 15 minutes at the same temperature. $Boc_2O$ (3.1 mL, 13.49 mmol) was added and stirred for 15 minutes at this temperature. The reaction mixture was allowed to warm to room temperature and stirred for another 30 minutes. After completion (monitored by TLC), the reaction mixture was quenched with ice-cooled water (20 mL) and extracted with ethyl acetate (3×30 mL). The combined organics were washed with brine, dried over anhydrous $Na_2SO_4$, filtered, and the filtrate was removed under reduced pressure to get crude, which was purified by silica gel combiflash chromatography using 5% ethyl acetate in hexane as an eluant to afford tert-butyl (5,6-dichloropyridin-2-yl)carbamate (2.8 g, 86%) as a solid. LCMS: 207 ($M^+H$-56).

Step B: n-BuLi (1.9M in THF; 4 mL, 7.63 mmol) was added to a stirred solution of diisopropylamine (1.1 mL, 7.63 mmol) in THF (8 mL) at −78° C. and stirred for 1 hour. Then a solution of tert-butyl (5,6-dichloropyridin-2-yl)carbamate (1.0 g, 3.82 mmol) in THF (6 mL) was added at same temperature and stirred at −78° C. for another 2 hours. A solution of iodine (1.2 g, 4.58 mmol) in THF (6 mL) was added at −78° C. and stirred for a further 30 minutes. After completion (monitored by TLC), the reaction mixture was diluted with saturated ammonium chloride solution (10 mL), and the reaction mixture was extracted with ethyl acetate (2×20 mL). The organic part was dried over anhydrous $Na_2SO_4$, filtered and concentrated under reduced pressure to get crude product, which was purified by silica gel combiflash chromatography using 3-5% ethyl acetate in hexane as an eluant to afford tert-butyl (5,6-dichloro-4-iodopyridin-2-yl)carbamate (0.85 g, 57%) as a solid. LCMS: 332.8 ($M^+H$-56).

Step C: DIPEA (9.0 mL, 51.54 mmol) was added to a stirred solution of tert-butyl (5,6-dichloro-4-iodopyridin-2-yl)carbamate (10.0 g, 25.77 mmol) and 3-mercapto-propionic acid methyl ester (3.2 mL, 28.35 mmol) in dioxane (150 mL) and degassed with argon for 15 minutes. Xantphos (0.75 g, 1.28 mmol) and $Pd(OAc)_2$ (0.35 g, 1.54 mmol) were added and degassed for another 10 minutes with argon. The reaction mixture was stirred in preheated oil bath at 100° C. for 4 hours. After completion (monitored by TLC), the reaction mixture was filtered through Ccelite® pad and washed with ethyl acetate (2×80 mL). Solvent was evaporated and crude was purified through flash silica gel column chromatography using 20% ethyl acetate in hexane as an eluant to afford methyl 3-((6-((tert-butoxycarbonyl)amino)-2,3-dichloropyridin-4-yl)thio)propanoate (8.1 g, 82%). LCMS: 381.0 ($M^+H$).

Step D: NaOEt (21% wt. in EtOH; 4.7 mL, 14.47 mmol) was added to a stirred solution of methyl 3-((6-(tert-butoxycarbonyl)amino)-2,3-dichloropyridin-4-yl)thio)propanoate (5.0 g, 13.16 mmol) in THF (50 mL) at 0° C. and stirred for 40 minutes at the same temperature. After completion (monitored by TLC), the reaction mixture was concentrated and crude was triturated with DCM (20 mL), diethyl ether (20 mL) and pentane (40 mL) at 0° C., and the solid was filtered and dried in vacuum to afford desired sodium 6-((tert-butoxycarbonyl)amino)-2,3-dichloropyridine-4-thiolate (3.98 g, 94%) as a solid. UPLC: 293.0 (M+H).

Intermediate Example Q

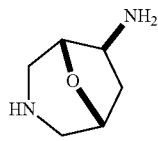

(1R*,5R*,6S*)-8-oxa-3-azabicyclo[3.2.1]octan-6-amine

Step A: Rel-(1<S*,5R*,6R*)-3-(tert-butoxycarbonyl)-8-oxa-3-azabicyclo[3.2.1]octane-6-carboxylic acid (365 mg, 1.42 mmol) was diluted with tert-butanol (7 mL), followed by the addition of triethylamine (395 µL, 2.84 mmol) and dropwise addition of diphenylphosphoryl azide (336 µL, 1.56 mmol). After stirring for 30 minutes, the reaction was heated to 93° C. and stirred for 12 hours. The reaction was allowed to cool and diluted with DCM and 10% sodium carbonate. The layers were separated, and the DCM was dried over MgSO$_4$, filtered and concentrated. The material was purified on silica gel eluting with 10-100% ethyl acetate/hexanes to afford tert-butyl (1S*,5S*,6R*)-6-((tert-butoxycarbonyl)amino)-8-oxa-3-azabicyclo[3.2.1]octane-3-carboxylate (144 mg, 0.44 mmol, 31% yield).

Step B: tert-Butyl (1S*,5S*,6R*)-6-((tert-butoxycarbonyl)amino)-8-oxa-3-azabicyclo[3.2.1]octane-3-carboxylate (146 mg, 0.45 mmol) was diluted with DCM (2 mL), followed by the addition of TFA (2 mL). After stirring for 3 hours, the reaction was concentrated to afford (1R*,5R*,6S*)-8-oxa-3-azabicyclo[3.2.1]octan-6-amine (57 mg, 0.45 mmol, 100% yield).

Intermediate Example R

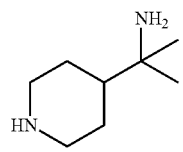

2-(piperidin-4-yl)propan-2-amine tert-Butyl 4-(2-aminopropan-2-yl)piperidine-1-carboxylate (260 mg, 1.07 mmol) was diluted with DCM (3 mL), followed by the addition of TFA (3 mL). After stirring for 2 hours, the reaction was concentrated to afford 2-(piperidin-4-yl)propan-2-amine (140 mg, 0.98 mmol, 92% yield).

Intermediate Example S

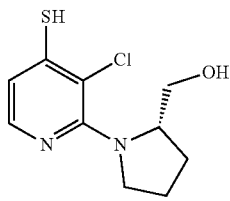 [SMILES: OC[C@@H]1CCCN1c1nccc(S)c1Cl]

(S)-(1-(3-chloro-4-mercaptopyridin-2-yl)pyrrolidin-2-yl)methanol

Step A: (A)-Pyrrolidin-2-yl methanol 1 (0.79 g, 7.8 mmol) was added to a solution of 3-chloro-2-fluoro-4-iodopyridine (1.0 g, 3.9 mmol) in DMSO (4 mL), and the reaction heated to 80° C. for 4 hours. The reaction was poured into water and extracted with MTBE. The organics were washed with water, brine, dried over MgSO$_4$ and concentrated in vacuo to give CY)-(1-(3-chloro-4-iodopyridin-2-yl)pyrrolidin-2-yl)methanol (1.2 g, 91% yield). m/z (esi/APCI) M+1=339.0.

Step B: Xantphos (0.21 g, 0.35 mmol), potassium ethanethioate (0.40 g, 3.5 mmol) and Pd$_2$(dba)$_3$ (0.19 g, 0.21 mmol) were added to a solution of (S)-(1-(3-chloro-4-iodopyridin-2-yl)pyrrolidin-2-yl)methanol (1.2 g, 3.5 mmol) in dioxanes (15 mL). The reaction was sparged with argon for 10 minutes and heated to 80° C. for 2 hours. The reaction was filtered through GF/F paper and concentrated in vacuo. The residue was chromatographed using 0-100% EtOAc/DCM as eluent to give (S)—S-(3-chloro-2-(2-(hydroxymethyl)pyrrolidin-1-yl)pyridin-4-yl) ethanethioate (0.90 g, 89% yield), m/z (esi/APCI) M+1=287.1.

Step C: Ammonium hydroxide (0.70 mL, 13 mmol) was added to a solution of (S)—S-(3-chloro-2-(2-(hydroxymethyl)pyrrolidin-1-yl)pyridin-4-yl) ethanethioate (0.90 g, 3.1 mmol) in THF (15 mL), and the reaction stirred at room temperature for 2 hours. The reaction was concentrated in vacuo, and water was added to the residue. The water was acidified to about pH 5 using 1N HCl. The aqueous layer was extracted with EtOAc. The organics were separated, washed with brine, dried over MgSO$_4$ and concentrated in vacuo to give (S)-(1-(3-chloro-4-mercaptopyridin-2-yl)pyrrolidin-2-yl)methanol (0.44 g, 57%). m/z (esi/APCI) M+1=245.1.

Intermediate Example T

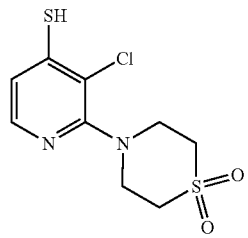 [SMILES: O=S1(=O)CCN(c2nccc(S)c2Cl)CC1]

4-(3-chloro-4-mercaptopyridin-2-yl)thiomorpholine 1,1-dioxide 4-(3-Chloro-4-mercaptopyridin-2-yl)thiomorpholine 1,1-dioxide was prepared according to Intermediate Example S, substituting thiomorpholine 1,1 dioxide for (S)-pyrrolidin-2-ylmethanol in Step A.

Intermediate Example U

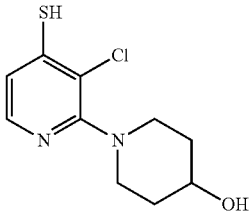 [SMILES: OC1CCN(c2nccc(S)c2Cl)CC1]

1-(3-chloro-4-mercaptopyridin-2-yl)piperidin-4-ol

Step A: Piperidin-4-ol (0.39 g, 3.9 mmol) was added to a solution of 3-chloro-2-fluoro-4-iodopyridine (0.50 g, 1.9 mmol) in DMSO (2 mL), and the reaction was heated to 80° C. overnight. The reaction was poured into water and extracted with EtOAc. The organics were washed with water (3 X), brine, dried over MgSO$_4$ and concentrated in vacuo to give 1-(3-chloro-4-iodopyridin-2-yl)piperidin-4-ol. m/z (esi/APCI) M$^+$1=339.0.

Step B: Xantphos (0.062 g, 0.11 mmol), Hunig's Base (0.37 mL, 2.1 mmol), 2-ethylhexyl 3-mercaptopropanoate (0.23 g, 1.1 mmol), and Pd$_2$(dba)$_3$ (0.058 g, 0.064 mmol) were added to a solution of 1-(3-chloro-4-iodopyridin-2-yl)piperidin-4-ol (0.36 g, 1.1 mmol) in dioxanes (2 mL). The reaction was sparged with argon for 10 minutes and heated to 100° C. for 2 hours. The reaction was cooled, filtered through GF/F paper and concentrated in vacuo. THF (5 mL) and sodium ethanolate (0.34 g, 1.1 mmol) were added to the residue, and the reaction was stirred at room temperature for 1 hour. The reaction was diluted with DCM, stirred 10 minutes and concentrated in vacuo. The material was taken up in water, made basic with NaOH, and the aqueous layer washed with EtOAc. The layers were separated. The aqueous layer was acidified with 1M HCl and extracted twice with EtOAc. The combined organics were washed with brine, dried over MgSO$_4$ and concentrated in vacuo to give 1-(3-chloro-4-mercaptopyridin-2-yl)piperidin-4-ol (0.10 g, 38%). m/z (esi/APCI) M$^+$1=245.1.

Intermediate Example V

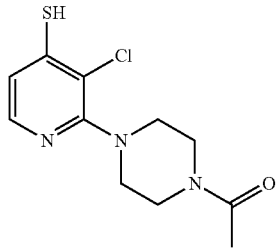 [SMILES: CC(=O)N1CCN(c2nccc(S)c2Cl)CC1]

1-(4-(3-chloro-4-mercaptopyridin-2-yl)piperazin-1-yl)ethan-1-one 1-(4-(3-Chloro-4-mercaptopyridin-2-yl)piperazin-1-yl)ethan-1-one was prepared according to Intermediate Example U, substituting 1-(piperazin-1-yl)ethan-1-one for piperidin-4-ol in Step A.

Intermediate Example W

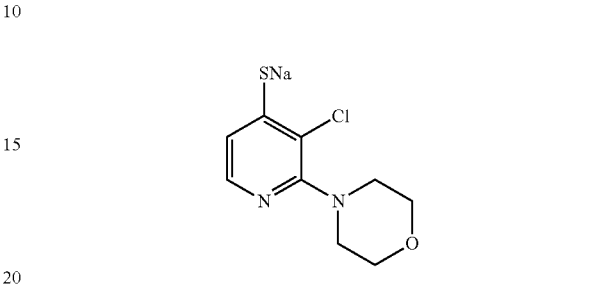

Sodium 3-chloro-2-morpholinopyridine-4-thiolate

Step A: Morpholine (0.34 g, 3.9 mmol) was added to a solution of 3-chloro-2-fluoro-4-iodopyridine (0.50 g, 1.9 mmol) in DMSO (2 mL), and the reaction was heated to 80° C. overnight. The reaction was poured into water and extracted with EtOAc. The layers were separated. The organics were washed with water (3 X), brine, dried over MgSO$_4$ and concentrated in vacuo to give 1-(3-chloro-4-iodopyridin-2-yl)piperidin-4-ol (0.5 g, 79%). m/z (esi/APCI) M$^+$1=325.0.

Step B: Xantphos (0.089 g, 0.15 mmol), Hunig's Base (0.54 mL, 3.1 mmol), 2-ethylhexyl 3-mercaptopropanoate (0.34 g, 1.5 mmol), and Pd$_2$(dba)$_3$ (0.085 g, 0.092 mmol) were added to a solution of 4-(3-chloro-4-iodopyridin-2-yl)morpholine (0.50 g, 1.5 mmol) in dioxanes (2 mL). The reaction was sparged with argon for 10 minutes and heated to 100° C. for 2 hours. The reaction was cooled, filtered through GF/F paper and concentrated in vacuo. THF (5 mL) and sodium ethanolate (0.50 g, 1.5 mmol) were added to the residue, and the reaction was stirred at room temperature for 1 hour. The reaction was next diluted with DCM, stirred 10 minutes and concentrated in vacuo. The residue was partitioned again in DCM. The slurry that formed was filtered, and the solid washed with DCM to give crude sodium 3-chloro-2-morpholinopyridine-4-thiolate. m/z (esi/APCI) M$^+$1=231.1.

Intermediate Example X

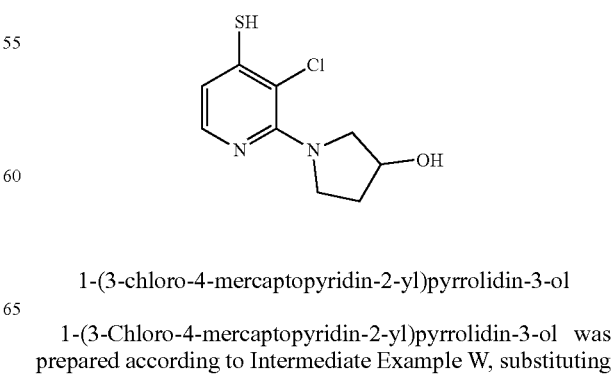

1-(3-chloro-4-mercaptopyridin-2-yl)pyrrolidin-3-ol 1-(3-Chloro-4-mercaptopyridin-2-yl)pyrrolidin-3-ol was prepared according to Intermediate Example W, substituting 3-pyrrolidinol (0.32 mL, 3.9 mmol) for morpholine in Step A. m/z (esi/APCI) M+1=231.1.

Intermediate Example Y

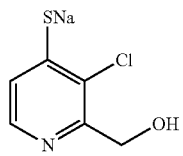

Sodium 3-chloro-2-(hydroxymethyl)pyridine-4-thiolate

Step A: Xantphos (0.13 g, 0.22 mmol), Pd$_2$(dba)$_3$ (0.12 g, 0.13 mmol), N-ethyl-A-isopropylpropan-2-amine (0.79 mL, 4.4 mmol) and 2-ethylhexyl 3-mercaptopropanoate (0.48 g, 2.2 mmol) were added to a solution of (3,4-dichloropyridin-2-yl)methanol (0.39 g, 2.2 mmol) in dioxanes (4 mL). The reaction was sparged with argon for 10 minutes and heated to 100° C. overnight. The reaction was cooled, filtered through GF/F paper and concentrated in vacuo. The residue was chromatographed using 20-80% EtOAc/Hexanes as eluent to give 2-ethylhexyl 3-((3-chloro-2-(hydroxymethyl)pyridin-4-yl)thio)propanoate (0.43 g, 1.2 mmol, 55% yield), m/z (esi/APCI) M+1=360.2.

Step B: Sodium ethanolate (0.426 g, 1.31 mmol) was added to a solution of 2-ethylhexyl 3-((3-chloro-2-(hydroxymethyl)pyridin-4-yl)thio)propanoate (0.43 g, 1.19 mmol) in THF (10 mL), and the reaction was stirred at room temperature for 1 hour. The reaction was concentrated, and the solids slurried in MTBE and filtered. The solids were further washed with MTBE to give sodium 3-chloro-2-(hydroxymethyl)pyridine-4-thiolate (0.158 g, 66.9% yield), m/z (esi/APCI) M+1=176.1.

Intermediate Example Z

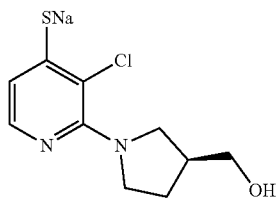

Sodium (M-3-chloro-2-(3-(hydroxymethyl)pyrrolidin-1-yl)pyridine-4-thiolate

Step A: (S)-Pyrrolidin-3-yl methanol (0.39 g, 3.9 mmol) was added to a solution of 3-chloro-2-fluoro-4-iodopyridine (0.50 g, 1.9 mmol) in DMSO (2 mL), and the reaction was heated to 80° C. overnight. The reaction was poured into water and extracted with MTBE. The organics were washed with water, brine, dried over MgSO$_4$ and concentrated in vacuo to give (S)-(1-(3-chloro-4-iodopyridin-2-yl)pyrrolidin-3-yl)methanol (0.51 g, 78% yield), in z (esi/APCI) M+1=339.0.

Step B: Xantphos (0.087 g, 0.15 mmol), Pd$_2$(dba)$_3$ (0.083 g, 0.090 mmol), and 2-ethylhexyl 3-mercaptopropanoate (0.33 g, 1.5 mmol) were added to a solution of (S)-(1-(3-chloro-4-iodopyridin-2-yl)pyrrolidin-3-yl)methanol (0.51 g, 1.5 mmol) in dioxanes (4 mL). The reaction was sparged with argon for 10 minutes and heated to 100° C. for 2 hours. The reaction was cooled, filtered through GF/F paper and concentrated in vacuo. The residue was chromatographed using 20-80% EtOAc/Hexanes as eluent to give 2-ethylhexyl 3-((3-chloro-2-((5')-3-(hydroxymethyl)pyrrolidin-1-yl)pyridin-4-yl)thio)propanoate (0.52 g, 80% yield). m/z (esi/APCI) M+1=429.2.

Step C: Sodium ethanolate (0.39 g, 1.2 mmol) was added to a solution of 2-ethylhexyl 3-((3-chloro-2-((S)-3-(hydroxymethyl)pyrrolidin-1-yl)pyridin-4-yl)thio)propanoate (0.52 g, 1.2 mmol) in THF (10 mL), and the reaction was stirred at room temperature for 1 hour. The reaction was filtered, and the solids were washed with MTBE to give sodium (S)-3-chloro-2-(3-(hydroxymethyl)pyrrolidin-1-yl)pyridine-4-thiolate (0.10 g, 34% yield), m/z (esi/APCI) M+1=245.1.

Intermediate Example AB

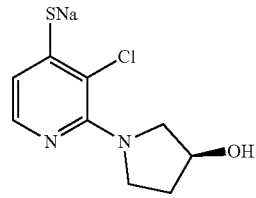

Sodium (M-3-chloro-2-(3-hydroxypyrrolidin-1-yl)pyridine-4-thiolate

Sodium (S)-3-chloro-2-(3-hydroxypyrrolidin-1-yl)pyridine-4-thiolate was prepared according to Intermediate Example Z, substituting (S)-(–)-3-hydroxypyrrolidine for (S)-pyrrolidin-3-ylmethanol in Step A. m/z (esi/APCI) M+1=231.1.

Intermediate Example AC

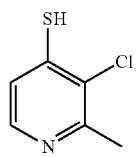

3-chloro-2-methylpyridine-4-thiol

3-Chloro-2-methylpyridine-4-thiol was prepared according to Intermediate Example B, substituting 3,4-dichloro-2-methylpyridine for 3-chloro-4-iodopyridin-2-amine in Step A. m/z (esi/APCI) M+1=159.6.

Intermediate Example AD

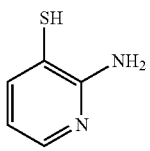

2-aminopyridine-3-thiol

2-Aminopyridine-3-thiol was prepared according to Intermediate Example B, substituting 3-bromo-2-pyridinamine for 3-chloro-4-iodopyridin-2-amine in Step A. m/z (esi/APCI) $M^+1=127.1$.

Intermediate Example AE

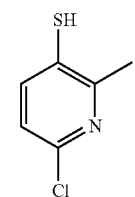

6-chloro-2-methylpyridine-3-thiol

6-Chloro-2-methylpyridine-3-thiol was prepared according to Intermediate Example B, substituting 3-bromo-6-chloro-2-methylpyridine for 3-chloro-4-iodopyridin-2-amine in Step A. m/z (esi/APCI) $M^+1=160.1$.

Intermediate Example AF

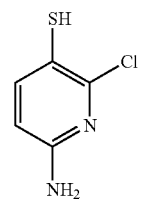

6-amino-2-chloropyridine-3-thiol

6-Amino-2-chloropyridine-3-thiol was prepared according to Intermediate Example B, substituting 2-amino-5-bromo-6-chloropyridine for 3-chloro-4-iodopyridin-2-amine in Step A. m/z (esi/APCI) $M^+1=161.1$.

Intermediate Example AG

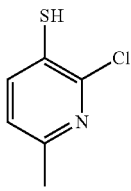

2-chloro-6-methylpyridine-3-thiol

2-Chloro-6-methylpyridine-3-thiol was prepared according to Intermediate Example B, substituting 3-bromo-2-chloro-6-methylpyridine for 3-chloro-4-iodopyridin-2-amine in Step A. m/z (esi/APCI) $M^+1=160.1$.

Intermediate Example AH

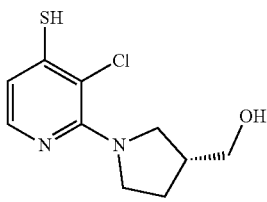 [SMILES: OC[C@@H]1CCN(c2nccc(S)c2Cl)C1]

(R)-(1-(3-chloro-4-mercaptopyridin-2-yl)pyrrolidin-3-yl)methanol (R)-(1-(3-Chloro-4-mercaptopyridin-2-yl)pyrrolidin-3-yl)methanol was prepared according to Intermediate Example E, substituting (R)-3-pyrrolidin-3-yl-methanol for pyrrolidine in Step A. m/z (esi/APCI) $M^+1=245.1$.

Intermediate Example AI

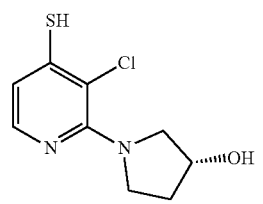 [SMILES: O[C@@H]1CCN(c2nccc(S)c2Cl)C1]

(R)-1-(3-chloro-4-mercaptopyridin-2-yl)pyrrolidin-3-ol (R)-(1-(3-Chloro-4-mercaptopyridin-2-yl)pyrrolidin-3-yl)methanol was prepared according to Intermediate Example E, substituting (R)-(+)-3-pyrrolidinol for pyrrolidine in Step A. m/z (esi/APCI) $M^+1=231.1$.

Intermediate Example AJ

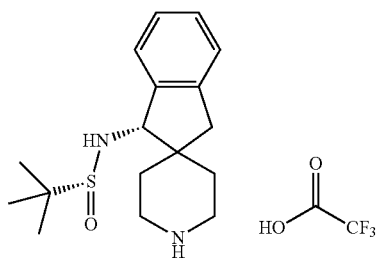 [SMILES: CC(C)(C)[S@@](=O)N[C@@H]1c2ccccc2CC12CCNCC2 ; O=C(O)C(F)(F)F]

(R)—N—(((S)-1,3-dihydrospiro[indene-2,4'-piperidin]-1'-yl)-2-methylpropane-2-sulfinamide 2,2,2-trifluoroacetate Step A: tert-Butyl 1-oxo-1,3-dihydrospiro[indene-2,4'-piperidine]-1'-carboxylate (1.0 g, 3.32 mmol) and (R)-2-methylpropane-2-sulfinamide (1.21 g, 10.0 mmol) were placed in THF (10 mL). Ti(OEt)$_4$ (4.87 mL, 23.23 mmol) was added, and the reaction was heated to 65° C. for 2 days. The reaction was cooled, and EtOAc was added, followed by water. The solids were filtered off, and the layers were separated. The organic layer was dried, filtered and concentrated to provide crude material that was used in the next step.

Step B: tert-Butyl (R,E)-1-((tert-butylsulfinyl)imino)-1,3-dihydrospiro[indene-2,4'-piperidine]-1'-carboxylate (1.32 g, 3.26 mmol) was placed in THF (15 mL) and cooled to –45° C. NaBH$_4$ (0.19 g, 4.89 mmol) was added, and the reaction was allowed to slowly warm to room temperature and was stirred for 18 hours. Water was added, and the mixture was extracted with DCM (3×25 mL). The extracts were combined and concentrated, and the resulting residue was purified by silica gel (0-5% MeOH in DCM with 2% NH$_4$OH). The first eluting peak was collected to provide tert-butyl (S)-1-(((R)-tert-butylsulfinyl)amino)-1,3-dihydrospiro[indene-2,4'-piperidine]-1'-carboxylate (500 mg, 1.23 mmol, 38% yield).

Step C: tert-Butyl (S)-1-(((R)-tert-butylsulfinyl)amino)-1,3-dihydrospiro[indene-2,4'-piperidine]-1'-carboxylate (500 mg, 1.23 mmol) was placed in DCM (1 mL) and cooled to 0° C. TFA (1 mL) was added, and the reaction was stirred for 45 minutes. The reaction was concentrated, and the material was used as is. m/z (esi/APCI) M$^+$1=307.1.

Intermediate Example AK

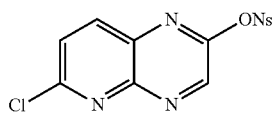

6-chloropyrido[2,3-b]pyrazin-2-yl 4-nitrobenzenesulfonate

6-Chloropyrido[2,3-b]pyrazin-2-ol (20 g, 110 mmol) was partially dissolved in DMF (200 mL), and triethylamine (18.4 mL, 132 mmol) was added. 4-Nitrobenzenesulfonyl chloride (24.4 g, 110 mmol) was then added. After 20 minutes, the reaction was poured into water (1.5 L), stirred vigorously for 15 minutes, filtered and dried in a vacuum oven to afford 6-chloropyrido[2,3-b]pyrazin-2-yl 4-nitrobenzenesulfonate (37.4 g, 102 mmol, 93% yield) as a solid. Mass spectrum: m/z=367.0 (M$^+$H).

Intermediate Example AL

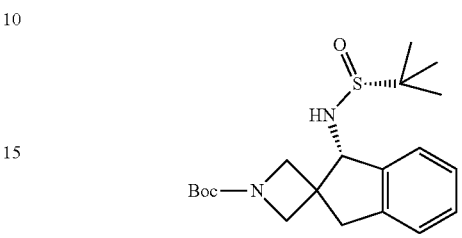

tert-butyl (R)-1'-(((R)-tert-butylsulfinyl)amino)-1',3'-dihydrospiro[azetidine-3,2'-indene]-1-carboxylate Step A: tert-Butyl 3-cyanoazetidine-1-carboxylate (1 g, 5.49 mmol) was dissolved in THF (15 mL) and cooled to –78° C. N-Lithiohexamethyldisilazane (6.86 mL, 6.86 mmol) was added to the solution dropwise. A solution of 1-(bromomethyl)-2-iodobenzene (1.79 g, 6.04 mmol) in THF (2 mL) was added to the mixture via syringe under nitrogen. After 3 hours, the reaction was quenched with sat NH$_4$Cl and extracted with EtOAc (2×15 mL). The combined organic layers were washed with brine, dried, and evaporated. The resulting residue was purified using 80 g silica gel column and EtOAc/hexanes 10-70% as solvent system yielding tert-butyl 3-cyano-3-(2-iodobenzyl)azetidine-1-carboxylate (1.7 g, 4.27 mmol, 78% yield) as an oil. m/z (esi/APCI) M$^+$1=399.1.

Step B: tert-Butyl 3-cyano-3-(2-iodobenzyl)azetidine-1-carboxylate (1.6 g, 4.0 mmol) was dissolved in THF (40 mL), and the solution was cooled to –78° C. n-Butyl lithium (1.9 mL, 4.8 mmol) solution in hexane was added to the reaction under nitrogen dropwise over 10 minutes. The reaction was kept at –78° C. for 2 hours, was brought to room temperature and quenched with sat NH$_4$Cl solution. The product was extracted with EtOAc, and the organic layer was dried and evaporated. The resulting residue was purified using 40 g silica gel column (EtOAc/hexanes 10-60%) yielded tert-butyl 1'-oxo-1',3'-dihydrospiro[azetidine-3,2'-indene]-1-carboxylate (0.73 g, 2.7 mmol, 66% yield) as a solid, m/z (esi/APCI) M$^+$1=274.1.

Step C tert-Butyl 1'-oxo-1',3'-dihydrospiro[azetidine-3,2'-indene]-1-carboxylate (0.72 g, 2.63 mmol) was suspended in tetraethoxytitanium (2.50 mL, 18.4 mmol), and (R)-2-methylpropane-2-sulfinamide (0.958 g, 7.90 mmol) was added to the mixture. The reaction was heated up in an oil bath to 90° C. for 18 hours. The reaction mixture was cooled down to room temperature and diluted with EtOAc (20 mL). Brine (50 mL) was added to the mixture, and the reaction was stirred vigorously for 10 minutes. The solid formed was filtered through a pad of Celite®, and the organic layer was separated. The aqueous layer was extracted once with EtOAc (30 mL). The combined organic layers were washed with brine, dried and evaporated to give a residue. The resulting residue was purified using a 40 g silica gel column (EtOAc/hexanes 20-80%) yielded tert-butyl (R,E)-1'-(tert-butylsulfinyl)imino)-1',3'-dihydrospiro[azetidine-3,2'-indene]-1-carboxylate (0.82 g, 2.18 mmol, 83% yield) as a solid. m/z (esi/APCI) M+1=377.2.

Step D: tert-Butyl (R,E)-1'-((tert-butylsulfinyl)imino)-1',3'-dihydrospiro[azetidine-3,2'-indene]-1-carboxylate (0.10 g, 0.27 mmol) was dissolved in THF (3 mL) and was cooled down to −78° C. NaBH$_4$ (0.030 g, 0.80 mmol) was added portion wise to the mixture, and the reaction was warmed up to room temperature over 3 hours. The reaction was quenched with saturated NH$_4$Cl and extracted with EtOAc (2×10 mL). The combined organic layers were washed with brine, dried and evaporated. The resulting residue was purified using 12 g silica gel column (EtOAc/hexanes mixture 10-80%) collecting the 1$^{st}$ peak to provide tert-butyl (R)-1'-(((R)-tert-butylsulfinyl)amino)-1',3'-dihydrospiro[azetidine-3,2'-indene]-1-carboxylate (0.032 g, 0.085 mmol, 32% yield), and the 2$^{nd}$ peak to give tert-butyl (S)-1'-(((R)-tert-butylsulfinyl)amino)-1',3'-dihydrospiro[azetidine-3,2'-indene]-1-carboxylate (0.025 g, 0.066 mmol, 25% yield), m/z (esi/APCI) M+1=379.2.

Intermediate Example AM

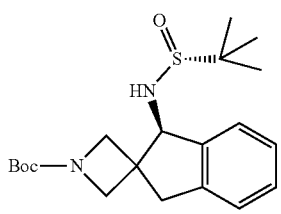 [SMILES: CC(C)(C)OC(=O)N1CC2(Cc3ccccc3[C@@H]2N[S@](=O)C(C)(C)C)C1]

tert-butyl (S)-1'-(((R)-tert-butylsulfinyl)amino)-1',3'-dihydrospiro[azetidine-3,2'-indene]-1-carboxylate This compound was prepared using similar procedures to that described under Intermediate Example AL, collecting the second eluting peak in Step D. m/z (esi/APCI) M+1=379.2.

Intermediate Example AN

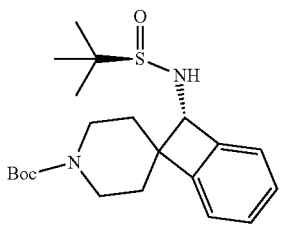 [SMILES: CC(C)(C)OC(=O)N1CCC2(CC1)c1ccccc1[C@H]2N[S@](=O)C(C)(C)C]

tert-butyl (S)-8-(((R)-tert-butylsulfinyl)amino)spiro[bicyclo[4.2.0]octane-7,4'-piperidine]-1,3,5-triene-1'-carboxylate Step A: 2-(2-iodophenyl)acetonitrile (1.3 mL, 10 mmol) was dissolved in DMF (20 mL), and the solution was cooled to 0° C. NaH (1.0 g, 26 mmol) 60% suspension in mineral oil was added to the solution in portions, and the mixture was heated at 60° C. for 1.5 hours. tert-Butyl bis(2-chloroethyl)carbamate (3.0 g, 12 mmol) was added to the reaction, and the mixture was stirred at 60° C. for 2 hours. The reaction was cooled down to room temperature, brine (25 mL) was added, and the mixture was extracted with EtOAc (3×100 mL). The combined organic layers were washed with brine, dried and evaporated to give a residue, which was purified with flash chromatography (EtOAc/hex 5-70%). The second eluting peak was collected to provide tert-butyl 4-(2-iodophenyl)-4-cyanopiperidine-1-carboxylate (1.8 g, 4.9 mmol, 48% yield) as an oil. m/z (esi/APCI) M+1=413.

Step B: Diisobutylaluminium hydride ("DIBAL-H"; 2.4 mL, 2.4 mmol) 1M solution in DCM was added to a −78° C. cold solution of tert-butyl 4-cyano-4-(2-iodophenyl)piperidine-1-carboxylate (0.9 g, 2.2 mmol). The reaction was stirred at −78° C., then warmed to room temperature and stirred overnight. Additional DIBAL-H was added, and the reaction was stirred for 2 hours. The reaction was quenched with 2M HCl solution, and the mixture was extracted with EtOAc (3×15 mL). The organic layers were combined, washed with saturated NaHCO$_3$ solution, dried and evaporated to give a residue which was purified using 40 g silica gel column (EtOAc/hexanes 5-60%) to provide tert-butyl 4-formyl-4-(2-iodophenyl)piperidine-1-carboxylate (0.35 g, 0.84 mmol, 39% yield) m/z (esi/APCI) M+1=416.0.

Step C: tert-butyl 4-formyl-4-(2-iodophenyl)piperidine-1-carboxylate (0.088 g, 0.21 mmol) was dissolved in THF (3 mL), and (R)-2-methylpropane-2-sulfinamide (0.027 g, 0.22 mmol) and tetraethoxytitanium (0.058 mL, 0.42 mmol) were added to the mixture. The reaction was stirred at 60° C. for overnight. Brine (10 mL) was added, and the mixture was stirred vigorously for 5 minutes. EtOAc (10 mL) was added to the mixture, and the precipitate formed was removed by filtration. The organic layer was separated, and the aqueous layer was extracted with EtOAc (10 mL). The combined organic layers were dried and evaporated. The resulting residue was purified using silica gel column (12 gm) (EtOAc/hexanes 0-60%) yielded tert-buty 1 (R,Z)-4-(((tert-butylsulfinyl)imino)methyl)-4-(2-iodophenyl)piperidine-1-carboxylate (0.067 g, 0.13 mmol, 61.0% yield) as an oil. m/z (esi/APCI) M+1=519.1.

Step D: tert-Butyl (R,Z)-4-(((tert-butylsulfinyl)imino)methyl)-4-(2-iodophenyl)piperidine-1-carboxylate (0.067 g, 0.13 mmol) was dissolved in THF (2 mL) and cooled to −78° C. sec-Butyl lithium (0.18 mL, 0.26 mmol) 1.4 M solution in cyclohexane was added to the solution via syringe. The mixture was stirred at −78° C. for 2 hours and was quenched with saturated NH$_4$Cl. The mixture was extracted with EtOAc (2×5 mL), and the combined organic layers were washed with brine, dried and evaporated. The resulting residue was purified using 12 g silica gel column (EtOAc/hexanes 10-70%) collecting the 1$^{st}$ peak yielded tert-butyl (S)-8-(((R)-tert-butylsulfinyl)amino)spiro[bicyclo[4.2.0]octane-7,4'-piperidine]-1,3,5-triene-1'-carboxylate (0.021 g, 71%) as a solid, m/z (esi/APCI) M+1=393.1.

Intermediate Example AO

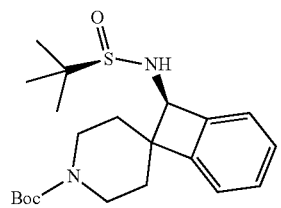 [SMILES: CC(C)(C)OC(=O)N1CCC2(CC1)c1ccccc1[C@@H]2N[S@](=O)C(C)(C)C]

tert-butyl (R)-8-(((R)-tert-butylsulfinyl)amino)spiro[bicyclo[4.2.0]octane-7,4'-piperidine]-1,3,5-triene-1'-carboxylate tert-Butyl (R)-8-(((R)-tert-butylsulfinyl)amino)spiro[bicyclo[4.2.0]octane-7,4'-piperidine]-1,3,5-triene-1'-carboxylate was prepared following Intermediate Example AN collecting the $2^{nd}$ peak from step D. m/z (esi/APCI) M$^+$1=393.1.

Intermediate Example AP

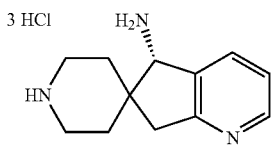

(S)-5,7-dihydrospiro[cyclopenta[b]pyridine-6,4'-piperidin]-5-amine Tri-HCl Salt

Step A: 2-Chloropyridine (458 mL, 4.84 mmol) was dissolved in dry THF (15 mL), and the solution was cooled down to −70° C. in IPA/dry ice bath. Lithium diisopropylamide ("LDA"; 2.75 mL, 5.50 mmol) was added dropwise to the mixture, and the reaction was warmed to −60° C. and stirred at that temperature for 1.5 hours. tert-Butyl 4-formyl-4-methylpiperidine-1-carboxylate (1 g, 4.40 mmol) in THF (3 mL) was added to the mixture and stirred at −60° C. for 1 hour. The reaction was quenched with water and partitioned between EtOAc and water. The organic layer was separated, dried, and concentrated. The resulting residue was purified using 40 g silica gel column (EtOAc/hexanes 10-80%) yielded tert-butyl 4-((2-chloropyridin-3-yl)(hydroxy)methyl)-4-methylpiperidine-1-carboxylate (1.06 g, 3.11 mmol, 71% yield).

Step B tert-Butyl 4-((2-chloropyridin-3-yl)(hydroxy)methyl)-4-methylpiperidine-1-carboxylate (1.06 g, 3.11 mmol) was dissolved in DCM (8 mL), and DMP (2.64 g, 6.22 mmol) was added to the solution. The mixture was stirred at room temperature for 1 hour and was quenched with 10% sodium bisulfite solution. The organic layer was separated and washed with saturated sodium bicarbonate solution and brine, dried and evaporated. The resulting residue was purified using silica gel flash chromatography (EtOAc/hexanes 10-100%) provided tert-butyl 4-(2-chloronicotinoyl)-4-methylpiperidine-1-carboxylate (0.31 g, 0.92 mmol, 29% yield) as an oil.

Step C: tert-Butyl 4-(2-chloronicotinoyl)-4-methylpiperidine-1-carboxylate (8.13 g, 24.0 mmol) was dissolved in mesitylene (70 mL) in a pressure tube. Tricyclohexylphosphoniumtetrafluoroborate (0.884 g, 2.40 mmol), diacetoxypalladium (0.269 g, 1.20 mmol), pivalic acid (0.735 g, 7.20 mmol) and cesium carbonate (15.6 g, 48.0 mmol) were added to the reaction mixture. Nitrogen gas was bubbled for 5 minutes in the reaction mixture, and the tube was sealed and heated at 140° C. for 72 hours. The reaction was cooled to room temperature and diluted with EtOAc (50 mL). The mixture was filtered using a pad of Celite® and was washed with EtOAc several times. The filtrate was evaporated under vacuum to give a residue. The residue was purified using 330 g silica column (EtOAc/hex 20-80%) to give tert-butyl 5-oxo-5,7-dihydrospiro[cyclopenta[b]pyridine-6,4'-piperidine]-1'-carboylate (2.23 g, 7.37 mmol, 31% yield) as a solid, m/z (esi/APCI) M$^+$1=303.1.

Step D: tert-Butyl 5-oxo-5,7-dihydrospiro[cyclopenta[b]pyridine-6,4'-piperidine]-1'-carboxylate (2.23 g, 7.375 mmol) was suspended in tetraethoxytitanium (6.98 mL, 51.62 mmol), and (R)-2-methylpropane-2-sulfinamide (2.68 g, 22.12 mmol) was added to the mixture. The reaction was heated to 90° C. and stirred for 18 hours. The reaction was cooled to room temperature, and EtOAc (250 mL) was added, followed by brine (200 mL). The mixture was stirred vigorously for 10 minutes, and then it was filtered to remove the precipitate formed. EtOAc layer was separated and washed with brine twice, dried and evaporated. The resulting residue was purified using 120 g silica gel column (EtOAc/Hexanes 10-100%). Collection of the second eluting peak provided tert-butyl (R,Z)-5-((tert-butylsulfinyl)imino)-5,7-dihydrospiro[cyclopenta[b]pyridine-6,4'-piperidine]-1'-carboxylate (2.8 g, 6.90 mmol, 94% yield) as a solid, m/z (esi/APCI) M$^+$1=406.2.

Step E: tert-Butyl (R,Z)-5-((tert-butylsulfinyl)imino)-5,7-dihydrospiro[cyclopenta[Z]pyridine-6,4'-piperidine]-1'-carboxylate (0.15 g, 0.37 mmol) was dissolved in THF (2 mL) in a vial. The solution was cooled to −78° C., and LiBH$_4$ (0.28 mL, 0.55 mmol) 2M in THF was added in one portion. The reaction was kept at −78° C. for 1 hour. The reaction was slowly warmed room temperature and was stirred for 18 hours. The reaction was quenched with saturated NH$_4$Cl followed by extraction with EtOAc (3×10 mL). The combined organic layers were washed with brine, dried and evaporated. The resulting residue was purified using column chromatography using 24 gm silica column (EtOAc/Hexanes 10-80%) gave tert-butyl (5)-5-(((R)-tert-butylsulfinyl)amino)-5,7-dihydrospiro[cyclopenta[b]pyridine-6,4'-piperidine]-1'-carboxylate (0.11 g, 0.27 mmol, 73% yield) as a solid, m/z (esi/APCI) M$^+$1=408.2.

Step F: tert-Butyl (5)-5-(((R)-tert-butylsulfinyl)amino)-5,7-dihydrospiro[cyclopenta[b]pyridine-6,4'-piperidine]-1'-carboxylate (3.45 g, 8.46 mmol) was dissolved in DCM (10 mL), and to that solution (4 mL) of 4M HCl solution in dioxane was added. The reaction mixture was stirred at room temperature overnight. Ether (100 mL) was added to the mixture, and the precipitate formed was filtered to give (S)-5,7-dihydrospiro[cyclopenta[b]pyridine-6,4'-piperidin]-5-amine (1.62 g, 7.97 mmol, 94% yield) as a solid as the tri-HCl salt, m/z (esi/APCI) M$^+$1=204.1.

Intermediate Example AQ

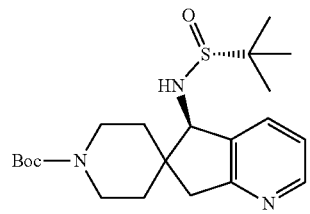 [SMILES: CC(C)(C)OC(=O)N1CCC2(CC1)Cc1ncccc1[C@@H]2N[S@](=O)C(C)(C)C]

tert-butyl (R)-5-(((R)-tert-butylsulfinyl)amino)-5,7-dihydrospiro[cyclopenta[b]pyridine-6,4'-piperidine]-1'-carboxylate tert-Butyl (R)-5-(((R)-tert-butylsulfinyl)amino)-5,7-dihydrospiro[cyclopenta[b]pyridine-6,4'-piperidine]-1'-carboxy- Intermediate Example AR

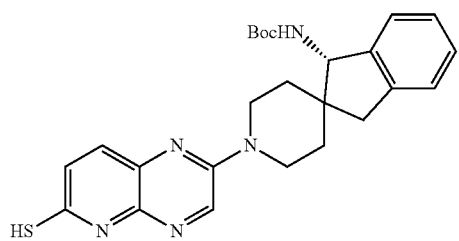 [SMILES: CC(C)(C)OC(=O)N[C@@H]1c2ccccc2CC12CCN(c1cnc3nc(S)ccc3n1)CC2]

tert-butyl (S)-(1'-(6-mercaptopyrido[2,3-b]pyrazin-2-yl)-1,3-dihydrospiro[indene-2,4'-piperidin]-1-yl)carbamate Step A: (S)-1,3-Dihydrospiro[indene-2,4'-piperidin]-1-amine dihydrochloride (3 g, 10.9 mmol) was suspended in 1,4-dioxane (36.3 mL, 10.9 mmol), and triethylamine (4.56 mL, 32.7 mmol) was added to the mixture. After 20 minutes of stirring at room temperature, 6-chloropyrido[2,3-b]pyrazin-2-yl trifluoromethanesulfonate (3.42 g, 10.9 mmol) was added, and the mixture was stirred at room temperature for 2 hours. Methyl 3-mercaptopropanoate (1.31 g, 10.9 mmol), Pd(OAc)$_2$ (0.245 g, 1.09 mmol) and xantphos (1.26 g, 2.18 mmol) were added to the reaction and nitrogen was bubbled in the reaction mixture for 2 minutes. The reaction was heated to 90° C. overnight, and it was cooled down to room temperature, mixed with EtOAc (30 mL) and filtered. The filtrate was evaporated, and the residue was purified with silica gel column (80 g) (MeOH/DCM 2-20%) to provide methyl (S)-3-((2-(1-amino-1,3-dihydrospiro[indene-2,4'-piperidin]-1'-yl)pyrido[2,3-b]pyrazin-6-yl)thio)propanoate (1.6 g, 3.56 mmol, 33% yield) as a solid, m/z (esi/APCI) M$^+$1=450.2.

Step B: Methyl (S)-3-((2-(1-amino-1,3-dihydrospiro[indene-2,4'-piperidin]-1'-yl)pyrido[2,3-b]pyrazin-6-yl)thio)propanoate (1.6 g, 3.6 mmol) was dissolved in DCM (25 mL). Triethylamine ("TEA"; 0.99 mL, 7.1 mmol), 4-dimethylaminopyridine ("DMAP"; 0.043 g, 0.36 mmol) and BOC-anhydride (0.91 mL, 3.9 mmol) were added to the mixture and were stirred at room temperature overnight. The reaction was quenched with water (30 mL) and was extracted with DCM (30 mL). The combined organic layers were dried and evaporated. The resulting residue was purified using silica gel column (80 g) (EtOAc/hexanes 10-80%) yielded methyl (S)-3-((2-(1-((tert-butoxycarbonyl)amino)-1,3-dihydrospiro[indene-2,4'-piperidin]-1'-yl)pyrido[2,3-b]pyrazin-6-yl)thio)propanoate (0.48 g, 0.87 mmol, 25% yield) as a solid, m/z (esi/APCI) M$^+$1=550.2.

Step C: Methyl (S)-3-((2-(1-((tert-butoxycarbonyl)amino)-1,3-dihydrospiro[indene-2,4'-piperidin]-1'-yl)pyrido[2,3-b]pyrazin-6-yl)thio)propanoate (0.48 g, 0.87 mmol) was dissolved in THF (10 mL), and sodium ethanolate (0.65 mL, 1.75 mmol) 21% solution in ethanol was added to the solution slowly. The reaction was stirred at room temperature for 1 hour and was quenched with saturated NH$_4$Cl (10 mL). The aqueous layer was extracted with EtOAc (2×15 mL), and the combined organic layers were washed brine, dried and evaporated. The resulting residue was purified using (40 g) silica gel column (EtOAc/hexanes 10-100%) yielded tert-butyl (S)-(1'-(6-mercaptopyrido[2,3-b]pyrazin-2-yl)-1,3-dihydrospiro[indene-2,4'-piperidin]-1-yl)carbamate (0.321 g, 0.69 mmol, 79% yield) as a solid, m/z (esi/APCI) M$^+$1=464.2.

Intermediate Example AS

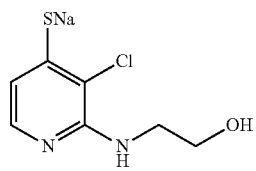

Sodium 3-chloro-2-((2-hydroxyethyl)amino)pyridine-4-thiolate

Step A: To a stirred solution of 3-chloro-2-fluoro-4-iodopyridine (1.0 g, 3.89 mmol) in DMSO (5 mL) was added 2-aminoethan-1-ol (0.47 mL, 7.78 mmol) and stirred at 70° C. for 16 hours. The reaction mixture was diluted with water and extracted with ethyl acetate. The organic part was dried (Na$_2$SO$_4$), concentrated, and the resulting residue was purified by silica gel column chromatography (40% EtOAc-Hex) to afford 2-((3-chloro-4-iodopyridin-2-yl)amino)ethan-1-ol (820 mg, 70% yield) as a solid, m/z (esi) M+1=298.8.

Step B: To a stirred solution of 2-((3-chloro-4-iodopyridin-2-yl)amino)ethan-1-ol (500 mg, 1.67 mmol) and methyl 3-mercaptopropanoate (0.2 mL, 1.84 mmol) in dioxane (5 mL) were added DIPEA (0.6 mL, 3.35 mmol) and degassed with argon for 10 minutes. Xantphos (48 mg, 0.08 mmol) and Pd(OAc)$_2$ (23 mg, 0.10 mmol) were added and degassed for another 10 minutes. The reaction mixture was stirred in pre-heated oil bath in sealed tube at 100° C. for 4 hours. The reaction mixture was filtered through Celite® pad and washed with ethyl acetate. Solvent was evaporated, and the crude material was purified by silica gel column chromatography (60% EtOAc/hexane) to afford methyl 3-((3-chloro-2-((2-hydroxyethyl)amino)pyridin-4-yl)thio)propanoate (460 mg, 94% yield) as a solid, m/z (esi) M+1=290.9.

Step C: To a stirred solution of 3-((3-chloro-2-((2-hydroxyethyl)amino)pyridin-4-yl)thio)propanoate (500 mg, 1.72 mmol) in THF (10 mL) was added NaOEt (21% wt. in EtOH) (1.5 mL, 2.06 mmol) at 0° C. and stirred for 30 minutes at 0° C. The reaction mixture was concentrated and crude was triturated with DCM and solid precipitate was filtered to afford sodium 3-chloro-2-((2-hydroxyethyl)amino)pyridine-4-thiolate (350 mg, 90% yield) as a solid. m/z (esi) M+1=205.1.

Intermediate Example AT

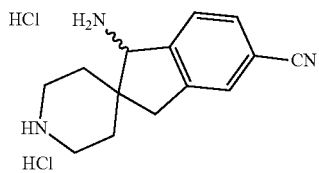 [SMILES: Cl ; N#Cc1ccc2c(c1)CC1(CCNCC1)C2N ; Cl]

1-amino-1,3-dihydrospiro[indene-2,4'-piperidine]-5-carbonitrile dihydrochloride Step A: To a stirred solution of 5-chloro-2,3-dihydro-1H-inden-1-one (5.0 g, 30.12 mmol) in DMF (50 mL) was added NaH (60% wt in paraffin) (3.61 g, 90.36 mmol) at 0° C. and stirred at room temperature for 30 minutes. N-Benzyl-2-chloro-N-(2-chloroethyl)ethan-1-amine (8.89 g, 33.13 mmol) was added portion wise at 0° C. and stirred at room temperature for another 5 hours. The reaction mixture was quenched with ice water and extracted with ethyl acetate. The organic part was dried (Na₂SO₄), filtered, concentrated and crude was purified by silica gel column chromatography (25% EtOAc-hexane) to afford 1'-benzyl-5-chlorospiro[indene-2,4'-piperidin]-1(3H)-one (2 g, 20% yield) as a liquid, m/z (esi) M+1=325.9.

Step B: To a stirred solution of r-benzyl-5-chlorospiro[indene-2,4'-piperidin]-1(3H)-one (2.0 g, 6.15 mmol) in DCE (20 mL) was added 1-chloroethyl chloroformate (3.49 g, 24.61 mmol) at 0° C. and stirred for 10 minutes. The reaction mixture was stirred at 80° C. for 16 hours. Then the reaction mixture was concentrated, and the crude material was dissolved in MeOH (20 mL) and again stirred at 80° C. for 1 hour. The reaction mixture was concentrated to afford 5-chlorospiro[indene-2,4'-piperidin]-1(3H)-one hydrochloride (1.45 g, crude) as a gummy liquid, which was used for the next step without further purification, m/z (esi) M+1=236.1.

Step C: To a stirred solution of 5-chlorospiro[indene-2,4'-piperidin]-1(3H)-one hydrochloride (1.45 g, 6.17 mmol) in DCM (15 mL) was added triethylamine (3.43 mL, 24.68 mmol) and Boc anhydride (2.12 mL, 9.25 mmol) at 0° C., and the reaction mixture was stirred at room temperature for 16 hours. The reaction mixture was concentrated and purified by silica gel column chromatography (30% EtOAc-hexane) to afford tert-butyl 5-chloro-1-oxo-1,3-dihydrospiro[indene-2,4'-piperidine]-1'-carboxylate (400 mg, 19% yield, 2 steps) as a solid. m/z (esi) M+1=336.3.

Step D: To a stirred solution of tert-butyl 5-chloro-1-oxo-1,3-dihydrospiro[indene-2,4'-piperidine]-1'-carboxylate (1.4 g, 4.14 mmol) in DMF (10 mL) were added Zn(CN)₂ (982.0 mg, 8.35 mmol) and zinc powder (55.0 mg, 0.83 mmol) and stirred for 10 minutes. The reaction mixture was degassed with argon, then trixiephos (383.0 mg, 0.41 mmol) followed by Pd(OAc)₂ (232.0 mg, 0.41 mmol) were added. The reaction mixture was stirred at 120° C. for 16 hours. The reaction mixture was diluted with water and extracted with ethyl acetate. The organic part was dried (Na₂SO₄), filtered and concentrated, and the crude material was purified by silica gel column chromatography (30% EtOAc-hexane) to afford tot-butyl 5-cyano-1-oxo-1,3-dihydrospiro [indene-2,4'-piperidine]-1'-carboxylate (250 mg, 18% yield) as a sticky solid, m/z (esi) M+1=326.3.

Step E: To a stirred solution of tert-butyl 5-cyano-1-oxo-1,3-dihydrospiro[indene-2,4'-piperidine]-1'-carboxylate (500 mg, 1.53 mmol) in titanium (IV) ethoxide (1.62 mL, 7.66 mmol) was added (R)-2-methylpropane-2-sulfinamide (204.5 mg, 1.68 mmol) and stirred at 90° C. for 1 hour. The reaction mixture was poured onto EtOAc and brine, stirred for 15 minutes. Solid precipitated was filtered off. The organic layer was washed with brine, dried (Na₂SO₄) and concentrated to afford tert-butyl 1-(((R)-tert-butylsulfinyl)amino)-5-cyano-1,3-dihydrospiro[indene-2,4'-piperidine]-1'-carboxylate (600 mg, crude) as a gummy liquid, which was used for the next step without further purification, m/z (esi) M+1=430.3.

Step F: To a stirred solution of tert-butyl 1-(((R)-tert-butylsulfinyl)amino)-5-cyano-1,3-dihydrospiro[indene-2,4'-piperidine]-1'-carboxylate (600.0 mg, 1.39 mmol) in MeOH (10 mL) was added NaBH₄ (105.8 mg, 2.79 mmol) at −10° C. and stirred at room temperature for 2 hours. The reaction mixture was concentrated, diluted with ethyl acetate and washed with water. The organic layer was dried (Na₂SO₄), filtered, concentrated and purified by silica gel column chromatography (40% EtOAc-hexane) to afford tert-butyl 1-(((R)-tert-butylsulfinyl)amino)-5-cyano-1,3-dihydrospiro [indene-2,4'-piperidine]-1'-carboxylate (430 mg, 71% yield) as a solid, m/z (esi) M+1=432.1.

Step G: To a stirred solution of tert-butyl 1-(((R)-tert-butylsulfinyl) amino)-5-cyano-1,3-dihydrospiro[indene-2,4'-piperidine]-1'-carboxylate (430.0 mg, 0.99 mmol) in MeOH (3 mL) at 0° C. was added 4M HCl in dioxane (3 mL) and stirred at 0° C. for 2 hours. The reaction mixture was concentrated, and crude was triturated with diethyl ether to afford 3-amino-1,3-dihydrospiro[indene-2,4'-piperidine]-6-carbonitrile dihydrochloride (250 mg, 84% yield) as a solid, m/z (esi) M+1=228.4.

Intermediate Example AU

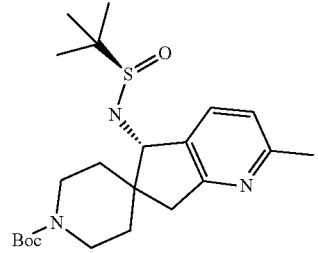 [SMILES: Cc1ccc2c(n1)CC1(CCN(C(=O)OC(C)(C)C)CC1)[C@@H]2N[S@](=O)C(C)(C)C]

tert-butyl (S)-5-(((R)-tert-butylsulfinyl)amino)-2-methyl-5,7-dihydrospiro[cyclopenta[b]pyridine-6,4'-piperidine]-1'-carboxylate Step A: A mixture of cyclopentane-1,3-dione (20.0 g, 204.08 mmol), but-3-en-2-one (26.78 mL, 306.12 mmol), molecular sieves 4A (100 g) and NH₄OAc (31.42 g, 408.16 mmol) in toluene (800 mL) was stirred at reflux for 24 hours. After completion, the reaction mixture was filtered through a bed of Celite®, concentrated and the resulting residue was purified by silica gel column chromatography (50% EtOAc/hexane) to afford 2-methyl-6,7-dihydro-5H-cyclopenta[b]pyridin-5-one (6.0 g, 20% yield) as a liquid, m/z (esi) M+1=148.3.

Step B: To a stirred solution of 2-methyl-6,7-dihydro-5H-cyclopenta[b]pyridin-5-one (5.0 g, 34.01 mmol) in DMF (60 mL) was added NaH (60 wt % in paraffin) (4.0 g, 102.04 mmol) at 0° C. and stirred for 30 min at room temperature. N-Benzyl-2-chloro-A-(2-chloroethyl)ethan-1-amine hydrochloride (7.31 g, 27.21 mmol) was added portion wise at 0° C. and stirred for another 16 hours at room temperature. The reaction mixture was quenched with ice water and extracted with ethyl acetate. The organic part was dried (Na₂SO₄), filtered, concentrated, and the crude material was purified by silica gel (0-15% MeOH in DCM) to afford 1'-benzyl-2-methylspiro[cyclopenta[Z)]pyridine-6,4'-piperidine]-5(7H)-one (1.2 g, 11% yield) as a liquid, m/z (esi) M+1=306.9.

Step C: To a stirred solution of 1'-benzyl-2-methylspiro[cyclopenta[Z)]pyridine-6,4'-piperidin]-5(7H)-one (400.0 mg, 1.31 mmol) in ethanol (15 mL) were added ammonium formate (247.14 mg, 3.92 mmol) followed by Pd/C (200 mg), and the reaction mixture was purged with argon for 10 minutes. Then the reaction mixture was refluxed at 80° C. for 16 hours. The reaction mixture was concentrated to afford 2-methylspiro[cyclopenta[b]pyridine-6,4'-piperidin]-5(7H)-one. which was used for next step without further purification, m/z (esi) M+1=217.2.

Step D: To a stirred solution of 2-methylspiro[cyclopenta[b]pyridine-6,4'-piperidin]-5(7H)-one (280.0 mg, 1.29 mmol) in DCM (10 mL) was added triethylamine (0.72 mL, 5.18 mmol) at 0° C., followed by Boc anhydride (0.45 mL, 1.94 mmol), and the reaction mixture was stirred at room temperature for 1 hour. The reaction mixture was concentrated and purified by silica gel column chromatography (30% EtOAc/hexane) to afford tert-butyl 2-methyl-5-oxo-5,7-dihydrospiro[cyclopenta[Z)]pyridine-6,4'-piperidine]-1'-carboxylate (200 mg, 48% yield, 2 steps) as a solid, m/z (esi) M+1=317.2.

Step E: tert-Butyl 2-methyl-5-oxo-5,7-dihydrospiro[cyclopenta[b]pyridine-6,4'-piperidine]-1'-carboxylate (400 mg, 1.26 mmol) and (R)-2-methylpropane-2-sulfinamide (460.21 mg, 3.80 mmol) were added to titanium (IV) ethoxide (866.20 mg, 3.79 mmol) at 90° C. and stirred at 90° C. for 5 hours. The reaction mixture was poured onto ethyl acetate and brine. After stirring for 15 minutes, the precipitated solid was filtered off, and the liquid part was separated. The organic layer was washed with brine, dried (Na$_2$SO$_4$), filtered and concentrated under reduced pressure. The resulting residue was purified by silica gel column chromatography to afford the tert-butyl (R,E)-1-((tert-butylsulfinyl)imino)-5-methyl-1,3-dihydrospiro[indene-2,4'-piperidine]-1'-carboxylate (410 mg, 77% yield) as a gummy liquid. m/z (esi) M+1=420.2.

Step F: To solution of tert-butyl (R,E)-1-((tert-butylsulfinyl)imino)-5-methyl-1,3-dihydrospiro[indene-2,4'-piperidine]-1'-carboxylate (410 mg, 0.98 mmol) in MeOH (10 mL) at 0° C. was added NaBH$_4$ (185 mg, 4.89 mmol) and stirred at the room temperature for 4 hours. The reaction mixture was quenched with the ice water and extracted with EtOAc. The combined organic layer was dried (Na$_2$SO$_4$), filtered and concentrated under reduced pressure. The resulting residue was purified by silica gel column chromatography (1% MeOH-DCM) and then with preparative HPLC (Chiralpak IG (21.0×250 mm), 5p n-Hexane/EtOH/IPA: 80/20/0.1, 21.0 mL/min, 20 min, 276 nm, MeOH) to afford tert-butyl (R)-5-(((R)-tert-butylsulfinyl)amino)-2-methyl-5,7-dihydrospiro[cyclopenta[b]pyridine-6,4'-piperidine]-1'-carboxylate (40 mg, 10% yield), m/z (esi) M+1=422.4.

Intermediate Example AV

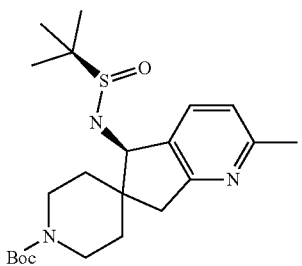

tert-butyl (R)-5-(((R)-tert-butylsulfinyl)amino)-2-methyl-5,7-dihydrospiro[cyclopenta[b]pyridine-6,4'-piperidine]-1'-carboxylate tert-Butyl (R)-5-(((R)-tert-butylsulfinyl)amino)-2-methyl-5,7-dihydrospiro[cyclopenta[b]pyridine-6,4'-piperidine]-1'-carboxylate was prepared according to Intermediate Example AU, collecting the second peak in Step F. m/z (esi) M+1=422.5.

Intermediate Example AW

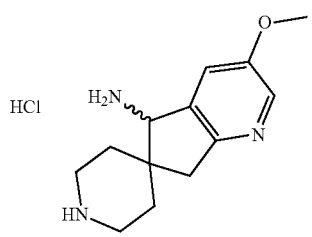 [SMILES: Cl ; COc1cnc2c(c1)C(N)C1(CCNCC1)C2]

3-methoxy-5,7-dihydrospiro[cyclopenta[b]pyridine-6,4'-piperidin]-5-amine hydrochloride Step A: To a stirred solution of 5-bromo-6-chloropyridin-3-ol (5.0 g, 24.16 mmol) and K$_2$CO$_3$ (5.0 g, 36.25 mmol) in ACN (30 mL) was added MeI (1.65 mL, 26.58 mmol) and the mixture was stirred at room temperature for 16 hours. The reaction mixture was extracted with EtOAc. The organic phase was dried (over Na$_2$SO$_4$), filtered and concentrated under reduced pressure. The residue was purified by silica gel column chromatography using EtOAc/hex solution (0-10% EtOAc/hexane) to afford 3-bromo-2-chloro-5-methoxypyridine (3.48 g, 65% yield) as a solid, m/z (esi) M+1=223.9.

Step B: To a stirred solution of tert-butyl 4-formyl-4-methylpiperidine-1-carboxylate (3.89 g, 17.12 mmol) in THF (55 mL) was added iPrMgBr (19.76 mL, 1.3M in THF, 25.68 mmol) dropwise at 0° C. and stirred at room temperature for 2 hours. 3-Bromo-2-chloro-5-methoxypyridine (5.68 g, 25.68 mmol) in THF (10 mL) was added dropwise at 0° C. and stirred at room temperature for 30 minutes. The reaction mixture was quenched with saturated NH$_4$Cl solution and extracted with EtOAc. Organic part was dried (over Na$_2$SO$_4$), filtered, concentrated and was purified by silica gel column chromatography (15-20% EtOAc/hexane) to afford tert-butyl 4-((2-chloro-5-methoxypyridin-3-yl)(hydroxy)methyl)-4-methylpiperidine-1-carboxylate (2.157 g, 83% yield) as a sticky solid, m/z (esi) M+1=371.4.

Step C: To a stirred solution of tert-butyl 4-((2-chloro-5-methoxypyridin-3-yl)(hydroxy)methyl)-4-methylpiperidine-1-carboxylate (1.1 g, 2.97 mmol) in DCM (16 mL) was added Dess-Martin periodinane (1.89 g, 4.45 mmol) at 0° C. and stirred at room temperature for 3 hours under nitrogen atmosphere. The reaction mixture was quenched with saturated sodium thiosulphate solution and extracted with DCM. The organic phase was washed with 1N NaOH solution, concentrated and was purified by silica gel column chromatography (15-20% EtOAc/hexane) to afford tert-butyl 4-(2-chloro-5-methoxynicotinoyl)-4-methylpiperidine-1-carboxylate (860 mg, 78% yield) as an oil. m/z (esi) M+1=369.1.

Step D: To a flame-dried sealed tube under argon was added tricyclohexylphosphonium tetrafluoroborate (145 mg, 0.39 mmol), Palladium(II) acetate (44 mg, 0.19 mmol), pivalic acid (121 mg, 1.18 mmol), cesium carbonate (1.54 g, 4.72 mmol) and tert-butyl 4-(2-chloro-5-methoxynicotinoyl)-4-methylpiperidine-1-carboxylate (1.45 g, 3.94 mmol) in mesitylene (20 mL). The mixture was degassed with argon for 10 minutes and heated at 140° C. for 48 hours. The reaction mixture was cooled to room temperature and was filtered through Celite® bed and washed with EtOAc. The organic phase was washed with brine, dried over Na$_2$SO$_4$, filtered and concentrated. The residue was purified by silica gel column chromatography (0-10% EtOAc/hexane) to get tert-butyl 3-methoxy-5-oxo-5,7-dihydrospiro[cyclopenta[b]pyridine-6,4'-piperidine]-1'-carboxylate (0.84 g, 64% yield) as a solid, m/z (esi) M+1=333.2.

Step E: To a stirred solution of tert-butyl 3-methoxy-5-oxo-5,7-dihydrospiro[cyclopenta[Z)]pyridine-6,4'-piperidine]-1'-carboxylate (575 mg, 1.73 mmol) in titanium(IV) ethoxide (2.2 mL, 10.38 mmol), was added (R)-(+)-2-methyl-2-propanesulfinamide (629 mg, 5.19 mmol) and was stirred at 110° C. for 4 hours. The reaction mixture was allowed to cool to room temperature, and the reaction mixture was diluted with EtOAc and water. The resulting mixture was vigorously stirred for 15 minutes at room temperature and then filtered through a pad of Celite®. The filtrate was extracted with EtOAc, washed with brine, dried over Na$_2$SO$_4$ and filtered. The organic phase was concentrated and the resulting residue was purified by silica gel column chromatography (40-50% EtOAc/hexane) to provide tert-butyl (R,Z)-5-((tert-butylsulfinyl)imino)-3-methoxy-5,7-dihydrospiro[cyclopenta[b]pyridine-6,4'-piperidine]-1'-carboxylate as a semisolid (0.64 g, 84% yield), m/z (esi) M+1=437.2.

Step F: To a stirred solution of tert-butyl (R,Z)-5-((tert-butylsulfinyl)imino)-3-methoxy-5,7-dihydrospiro[cyclopenta[b]pyridine-6,4'-piperidine]-1'-carboxylate (590 mg, 1.35 mmol) in MeOH (10 mL), was added sodium borohydride (256 mg, 6.77 mmol) at 0° C. and was stirred for 3 hours. After completion of reaction, the reaction mixture was allowed to increase the temperature to room temperature. Saturated aqueous NH$_4$Cl solution was slowly added to quench the reaction, MeOH was evaporated, and the reaction mixture was extracted with EtOAc. The organic phase was washed with brine, dried over Na$_2$SO$_4$, filtered and concentrated. The resulting residue was purified by silica gel column chromatography (0-4% MeOH/DCM) to get tert-butyl 5-(((R)-tert-butylsulfinyl)amino)-3-methoxy-5,7-dihydrospiro[cyclopenta[b]pyridine-6,4'-piperidine]-1'-carboxylate (0.58 g, 97% yield) as a solid, m/z (esi) M+1=437.9.

Step G: To a stirred solution of tert-butyl 5-(((R)-tert-butylsulfinyl)amino)-3-methoxy-5,7-dihydrospiro[cyclopenta[b]pyridine-6,4'-piperidine]-1'-carboxylate (600 mg, 1.37 mmol) in MeOH (12 mL) was added dioxane-HCl (4M; 12 mL) at 0° C. and was stirred for 2 hours. The reaction mixture was concentrated, and the crude material was triturated with diethyl ether to afford 3-methoxy-5,7-dihydrospiro[cyclopenta[b]pyridine-6,4'-piperidin]-5-amine hydrochloride (418 mg, 99% yield) as a solid. The crude used in next step without purification, m/z (esi) M+1=234.3.

Intermediate Example AX

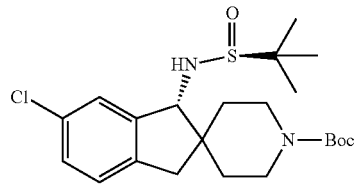 [SMILES: CC(C)(C)OC(=O)N1CCC2(CC1)Cc1ccc(Cl)cc1[C@@H]2N[S@@](=O)C(C)(C)C]

tert-butyl (R)-1-(((S)-tert-butylsulfinyl)amino)-6-chloro-1,3-dihydrospiro[indene-2,4'-piperidine]-1'-carboxylate Step A: To a stirred solution of 6-chloro-2,3-dihydro-1H-inden-1-one (2.0 g, 12.05 mmol) in DMF (40 mL) was added NaH (60% in mineral oil) (1.45 g, 36.14 mmol) at 0° C., and the mixture was stirred for 30 minutes at 0-5° C. N-benzyl-2-chloro-N-(2-chloroethyl)ethan-1-amine hydrochloride (3.06 g, 13.25 mmol) was added portion wise, and the mixture was stirred at 60° C. for 16 hours. The reaction was quenched with brine solution and was extracted with EtOAc. The combined organic layers were washed with brine, dried over anhydrous Na$_2$SO$_4$, filtered, and concentrated under reduced pressure to get crude, which was purified by silica gel (EtOAc/hexane) solution to get 1'-benzyl-6-chlorospiro[indene-2,4'-piperidin]-1(3H)-one (1.55 g, 40% yield) as an oil. m/z (esi) M+1: 325.9.

Step B: To a stirred solution of r-benzyl-6-chlorospiro[indene-2,4'-piperidin]-1(3H)-one (1.55 g, 4.78 mmol) in dichloroethane ("DCE"; 24 mL) was added 1-chloroethyl chloroformate (1.55 mL, 14.34 mmol) and was refluxed for 1 hour. Then DCE was evaporated under reduced pressure, and MeOH (24 mL) was added and refluxed for 1 hour. MeOH was evaporated to dryness to get 6-chlorospiro[indene-2,4'-piperidin]-1(3H)-one (1.13 g, crude) as a solid, m/z (esi) M+1: 236.2.

Step C: To a stirred solution of 6-chlorospiro[indene-2,4'-piperidin]-1(3H)-one (1.13 g, 4.79 mmol) in DCM (20 mL), was added TEA (2.66 mL, 19.16 mmol) followed by boc-anhydride (1.65 mL, 7.19 mmol) at 0° C. and was stirred at room temperature for 1 hour. The reaction was evaporated to dryness and was purified by silica gel column chromatography (15-20% EtOAc/hexane) to afford tert-butyl 6-chloro-1-oxo-1,3-dihydrospiro[indene-2,4'-piperidine]-1'-carboxylate (1.3 g, 81%, 2 steps yield) as a solid, m/z (esi) M+1: 336.3.

Step D: A solution of tert-butyl 6-chloro-1-oxo-1,3-dihydrospiro[indene-2,4'-piperidine]-1'-carboxylate (800 mg, 2.38 mmol), titanium(IV) ethoxide (1.99 mL, 9.5 mmol), and (R)-(+)-2-methylpropane-2-sulfinamide (577.5 mg, 4.76 mmol) in THF (15 mL) was stirred at 90° C. for 12 hours. The reaction was cooled to room temperature and quenched with water. The compound was extracted with EtOAc. The combined organic phases were washed with brine, dried over anhydrous Na$_2$SO$_4$, filtered, and concentrated under reduced pressure to get crude, which was purified by silica gel column chromatography (20-25% EtOAc/hexane) to get tert-butyl (R,E)-1-((tert-butylsulfinyl)imino)-6-chloro-1,3-dihydrospiro[indene-2,4'-piperidine]-1'-carboxylate (861 mg, 94% yield) as a solid, m/z (esi) M+1: 438.8.

Step E: To a stirred solution of tert-butyl (R,E)-1-((tert-butylsulfinyl)imino)-6-chloro-1,3-dihydrospiro[indene-2,4'- piperidine]-1'-carboxylate (1 g, 2.28 mmol) in MeOH (20 mL) was added sodium borohydride (43 mg, 11.42 mmol) at 0° C. and was stirred at 25° C. for 3 hours. Saturated aqueous NH₄Cl solution was slowly added to quench the excess of borohydride, and the reaction mixture was diluted with EtOAc. The resulting mixture was vigorously stirred for 15 minutes at room temperature and then extracted with EtOAc. The combined organic parts were washed with brine, dried over anhydrous Na₂SO₄, filtered, and concentrated under reduced pressure to get the crude, which was purified by normal preparative HPLC purification (Chiralpak IC (20.0×250 mm), 5µ, hexane/EtOH/iPrNH₂ 80/20/0.1, 1.0 mL/min) collecting peak 1 to provide tert-butyl (R)-1-(((S)-tert-butylsulfinyl)amino)-6-chloro-1,3-dihydrospiro[indene-2,4'-piperidine]-1'-carboxylate 528 mg, 51% yield), m/z (esi) M+1: 441.2.

Intermediate Example AY

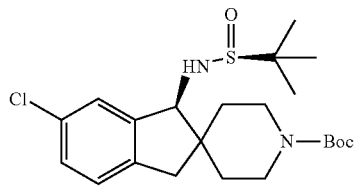 [SMILES: CC(C)(C)OC(=O)N1CCC2(CC1)Cc1ccc(Cl)cc1[C@H]2N[S@@](=O)C(C)(C)C]

tert-butyl (S)-1-(((S)-tert-butylsulfinyl)amino)-6-chloro-1,3-dihydrospiro[indene-2,4'-piperidine]-1'-carboxylate Was prepared according to Intermediate Example AX, collecting peak 2 in Step E to provide tert-butyl (S)-1-(((S)-tert-butylsulfinyl)amino)-6-chloro-1,3-dihydrospiro[indene-2,4'-piperidine]-1'-carboxylate. m/z (esi) M+1: 441.2.

Intermediate Example AZ

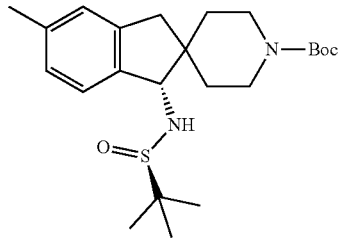 [SMILES: Cc1ccc2c(c1)CC1(CCN(C(=O)OC(C)(C)C)CC1)[C@@H]2N[S@](=O)C(C)(C)C]

tert-butyl (S)-1-(((S)-1-(((R)-tert-butylsulfinyl)amino)-5-methyl-1,3-dihydrospiro[indene-2,4'-piperidine]-1'-carboxylate Step A: To a stirred solution of 5-methyl-2, 3-dihydro-1H-inden-1-one (4.0 g, 27.39 mmol) in DMF (80 mL) was added NaH (60% dispersion in mineral oil, 1.97 g, 82.19 mmol) portion wise at 0° C. The mixture was stirred at 0° C. for 30 minutes. N-Benzyl-2-chloro-N-(2-chloroethyl)ethan-1-amine hydrocloride (8.09 g, 30.13 mmol) was added portion wise to the reaction mixture and was stirred at room temperature for 16 hours. The reaction was diluted with brine and extracted with EtOAc. Organic parts were combined and washed with brine, dried over anhydrous Na₂SO₄, filtered, and concentrated under reduced pressure. The residue was purified by silica gel column chromatography (25% EtOAc/hexane) to afford 1'-benzyl-5-methylspiro[indene-2,4'-piperidin]-1(3H)-one (4.0 g, 48% yield) as a solid, m/z (esi) M+1=305.6.

Step B: To a stirred solution of r-benzyl-5-methylspiro[indene-2,4'-piperidin]-1(3H)-one (5.0 g, 16.37 mmol) in DCE (100 mL) was added chloroethyl chloroformate (6.97 g, 49.11 mmol) at 0° C. and stirred for 10 minutes. The reaction mixture was stirred at 80° C. for 1 hour. The reaction mixture was concentrated to dryness, and MeOH (100 mL) was added and was stirred at 75° C. for 1 hour. The reaction mixture was concentrated under reduced pressure to afford 5-methylspiro[indene-2,4'-piperidin]-1(3H)-one (3.5 g, crude) as a liquid, which was used for the next step without further purification, m/z (esi) M+1=215.9.

Step C: To a stirred solution of 5-methylspiro[indene-2,4'-piperidin]-1(3H)-one (3.5 g, 16.27 mmol) in DCM (35 mL) was added triethyl amine (9.07 mL, 65.11 mmol) at 0° C. Boc anhydride (5.61 mL, 24.42 mmol) was added at 0° C., and the reaction mixture was stirred at room temperature for 16 hours. The reaction mixture was concentrated under reduced pressure and purified by silica gel column chromatography (10% EtOAc/hexane) to afford tert-butyl 5-methyl-1-oxo-1,3-dihydrospiro[indene-2,4'-piperidine]-1'-carboxylate (520 mg, 68% yield, 2 steps) as a solid, m/z (esi) M+1=316.2.

Step D: tert-Butyl 5-methyl-1-oxo-1,3-dihydrospiro[indene-2,4'-piperidine]-1'-carboxylate (1.9 gm, 6.03 mmol) and (R)-(+)-2-methylpropane-2-sulfinamide (2.19 g, 18.09 mmol) were added into warm (100° C.) titanium (IV) ethoxide (4.12 g, 18.09 mmol) and stirred at 100° C. for 19 hours. The reaction mixture was poured into EtOAc and brine, and the mixture was stirred for 15 minutes. Solids were filtered off, and the liquid part was separated. The organic layer was washed with brine, dried over anhydrous Na₂SO₄, and concentrated under reduced pressure. The resulting residue was purified by silica gel column chromatography (1% MeOH/DCM) to afford the tert-butyl (R,E)-1-((tert-butyl-sulfinyl)imino)-5-methyl-1,3-dihydrospiro[indene-2,4'-piperidine]-1'-carboxylate (1.25 g, 49% yield) as a solid, m/z (esi) M+1=418.9.

Step E: To a solution at 0° C. of tert-butyl (R,E)-1-((tert-butylsulfinyl)imino)-5-methyl-1,3-dihydro-spiro[indene-2,4'-piperidine]-1'-carboxylate (1.3 g, 3.10 mmol) in MeOH (30 mL) was added sodium borohydride (470 mg, 12.42 mmol) and was stirred at room temperature for 4 hours. The reaction mixture was quenched with the ice water and extracted with EtOAc. The combined organic layers were dried over anhydrous Na₂SO₄, filtered, and concentrated under reduced pressure. The resulting residue was purified by silica gel column chromatography (30% EtOAc/hexane) to afford tert-butyl (S)-1-(((R)-tert-butylsulfinyl)amino)-5-methyl-1,3-dihydrospiro[indene-2,4'-piperidine]-1'-carboxylate (310 mg, 24% yield) (m/z (esi) M−1=419.3).

Intermediate Example BA

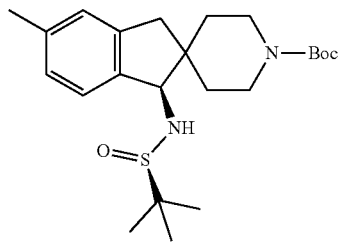 [SMILES: Cc1ccc2c(c1)CC1(CCN(C(=O)OC(C)(C)C)CC1)[C@H]2N[S@](=O)C(C)(C)C]

tert-butyl (R)-1-(((R)-tert-butylsulfinyl)amino)-5-methyl-1,3-dihydrospiro[indene-2,4'-piperidine]-1'-carboxylate Tert-butyl (R)-1-(((R)-tert-butylsulfinyl)amino)-5-methyl-1,3-dihydrospiro[indene-2,4'-piperidine]-1'-carboxylate was prepared according to Intermediate Example AZ collecting the second peak in Step E. (m/z (esi) M−1=419.3).

Intermediate Example BC

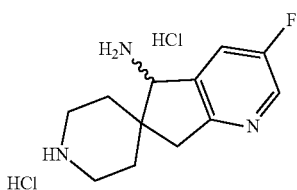 [SMILES: NC1c2cc(F)cnc2CC12CCNCC2 ; Cl ; Cl]

3-fluoro-5,7-dihydrospiro[cyclopenta[b]pyridine-6,4'-piperidin]-5-amine dihydrochloride Step A: To a stirred solution of 3-bromo-2-chloro-5-fluoropyridine (5.0 g, 22.02 mmol) in THF (100 mL) was added isopropylmagnesium chloride (1.5 M in THF) (15 mL) drop wise at 0° C. and stirred at RT for 2 h. Tert-butyl 4-formyl-4-methylpiperidine-1-carboxylate (9.2 mL, 44.05 mmol) in THF (50 mL) was added drop wise at 0° C. and stirred at RT for 30 min. The reaction was quenched with sat ammonium chloride solution and extracted with EtOAc. The organic part was dried, filtered, concentrated and was purified by column chromatography to afford desired tert-butyl 4-((2-chloro-5-fluoropyridin-3-yl)(hydroxy)methyl)-4-methylpiperidine-1-carboxylate (7.0 g, 89% yield) as light yellow sticky solid, m/z (esi) M+1=359.3.

Step B: To a stirred solution of tert-butyl 4-((2-chloro-5-fluoropyridin-3-yl)(hydroxy)methyl)-4-methylpiperidine-1-carboxylate (2.7 g, 6.14 mmol) in DCM (25 mL) was added DMP (4.7 g, 11.31 mmol) at 0° C. and stirred at RT for 3 h. The reaction mixture was quenched with sodium thiosulphate (30 mL) and extracted with DCM. The organic part was washed with 2M NaOH solution, dried (Na$_2$SO$_4$), filtered and concentrated. The resulting residue was purified by silica gel flash chromatography (20% EtOAc-hexane) to afford tert-butyl 4-(2-chloro-5-fluoronicotinoyl)-4-methylpiperidine-1-carboxylate (1.8 g, 67% yield) as brown solid, m/z (esi) M+1=357.2.

Step C: To a stirred solution of tert-butyl 4-(2-chloro-5-fluoronicotinoyl)-4-methylpiperidine-1-carboxylate (2 g, 5.61 mmol) in 1,3,5 mesitylene (10 mL) were added PCy$_3$H.BF$_4$ (210 mg, 0.56 mmol), $^t$BuCOOH (172 mg, 1.68 mmol) and Cs$_2$CO$_3$ (2.2 g, 6.74 mmol) at RT and degassed with N$_2$ balloon for 5 min. Pd(OAc)$_2$ (70 mg, 0.28 mmol) was added to the reaction mixture and again degassed with N$_2$ balloon. The reaction mixture was stirred at 140° C. for 72 h. The reaction was cooled and was purified by silica gel flash chromatography (50% EtOAc/hexane) to afford tert-butyl 3-fluoro-5-oxo-5,7-dihydrospiro[cyclopenta[b]pyridine-6,4'-piperidine]-1'-carboxylate (1 g, 56% yield) as brown solid, m/z (esi) M+1=321.2.

Step D: To a stirred solution of tert-butyl 3-fluoro-5-oxo-5,7-dihydrospiro[cyclopenta[b]pyridine-6,4'-piperidine]-1'-carboxylate (1 g, 3.12 mmol) in Ti(OEt)$_4$ (2.5 mL, 9.37 mmol) was added R-(+)-2-methyl-2-propanesulfinamide (0.8 g, 6.25 mmol) at RT and reaction mixture was stirred at 100° C. for 16 h. The reaction mixture was quenched with water and added an excess of ethyl acetate. The solution was filtrated via sintered funnel and organic layer was separated. The organic layer was dried (Na$_2$SO$_4$), filtered, concentrated and was purified by silica gel flash chromatography (20% EtOAc/hexane) to afford tert-butyl (R,Z)-5-((tert-butylsulfinyl)imino)-3-fluoro-5,7-dihydrospiro [cyclopenta[b]pyridine-6,4'-piperidine]-1'-carboxylate (1 g, 76% yield) as a yellow solid, m/z (esi) M+1=424.0.

Step E: To a stirred solution of tert-butyl (R,Z)-5-((tert-butylsulfinyl)imino)-3-fluoro-5,7-dihydrospiro[cyclopenta[b]pyridine-6,4'-piperidine]-1'-carboxylate (1.1 g, 2.6 mmol) in methanol (50 mL) was added NaBH$_4$ (400 mg, 10.4 mmol) at 0° C. and stirred for 10 min. The reaction mixture warmed to RT and stirred for 3 h. The reaction mixture was quenched with ice, evaporated and extracted with EtOAc. The organic layer was concentrated and purified by silica gel flash chromatography (30% EtOAc/hexane) to afford tert-butyl 5-(((R)-tert-butylsulfinyl)amino)-3-fluoro-5,7-dihydrospiro [cyclopenta[b]pyridine-6,4'-piperidine]-1'-carboxylate (800 mg, 72% yield) of off white solid, in z (esi) M+1=426.1.

Step F: To a stirred solution of tert-butyl 5-(((R)-tert-butylsulfinyl)amino)-3-fluoro-5,7-dihydrospiro [cyclopenta[b]pyridine-6,4'-piperidine]-1'-carboxylate (700 mg, 1.6 mmol) in MeOH (4 mL) was added HCl (4M in 1,4-dioxane) (5 mL) at 0° C. and stirred for 1.5 h. The reaction mixture was concentrated to afford 3-fluoro-5,7-dihydrospiro[cyclopenta[b]pyridine-6,4'-piperidin]-5-amine dihydrochloride (480 mg, 99% yield) as white solid, m/z (esi) M+1=222.1.

Intermediate Example BD

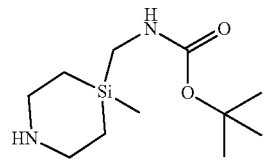 [SMILES: CC(C)(C)OC(=O)NC[Si]1(C)CCNCC1]

tert-butyl ((4-methyl-1,4-azasilinan-4-yl)methyl)carbamate

Step A: In a 500 mL two neck flask, containing a solution of vinyl magnesium bromide (1.0M in THF)(107 mL, 107 mmol) in THF (50 mL) at 0° C., dichloro(chloromethyl)(methyl)silane (5 g, 30.58 mmol) was slowly added and the reaction mixture was stirred at rt for 16 hr. After the completion of reaction, the reaction mixture was slowly quenched with an excess amount of saturated aqueous ammonium chloride solution and was stirred at room temperature for 30 min. The reaction mixture was extracted with ethyl acetate (2×200 mL) and the combined organic layer was dried over anhydrous sodium sulfate, filtered and concentrated under reduced pressure to get (chloromethyl)(methyl)divinylsilane (2.6 g crude) as a light yellow oil. The crude was used in next step without further purification.

Step B: A suspension of (chloromethyl)(methyl)divinylsilane (2) (2.5 g, 17.48 mmol), potassium phthalimide (3.5 g, 19.2 mol) and potassium iodide (0.29 g, 1.74 mmol) in DMF (15 mL) was heated at 80° C. for 16 hr under $N_2$ atmosphere. The reaction mixture was slowly quenched with water and extracted with ethyl acetate (2×100 mL), washed with brine (100 mL) and the combined organic layer was dried over anhydrous sodium sulfate, filtered and concentrated under reduced pressure to get the crude, which was purified by normal silica column chromatography (eluted at 5-8% ethyl acetate in hexane) to afford 2-((methyldivinylsilyl) methyl) isoindoline-1, 3-dione as light yellow oil (2.0 g, 25%; 2 steps).

Step C: A solution of 9-BBN (0.5M in THF) (54.6 mL, 27.3 mmol) and 2-((methyldivinylsilyl) methyl) isoindoline-1,3-dione (2 g, 7.81 mmol) in THF (1 mL) was stirred for 16 h at room temperature. The reaction mixture was subsequently treated with $H_2O$ (2 mL) and then with an aqueous solution of NaOH (3M) (6 mL) at rt. An aqueous solution of $H_2O_2$ (30%) (6 mL) was added drop wise within 15 min at 0° C., and the solution was stirred at rt for 4 h. The reaction mixture was cooled to rt, water was added, organic layer was separated, and the aqueous layer was washed with DCM. The organic layer was then dried over anhydrous sodium sulfate and evaporated under reduced pressure. The resulting residue was purified by normal silica column chromatography (eluted at 75-80% ethyl acetate in hexane) to afford 2-((bis(2-hydroxyethyl)(methyl)silyl) methyl)isoindoline-1, 3-dione as white solid (240 mg, 11%).

Step D: Methanesulfonyl chloride (0.4 mL, 5.98 mmol) and TEA (1.37 mL, 9.52 mmol) were added sequentially in single portion at –20° C. to a stirred solution of 2-((bis(2-hydroxyethyl)(methyl)silyl)methyl)isoindoline-1,3-dione (800 mg, 2.72 mmol) in DCM (500 mL) and the mixture was stirred at –20° C. for 3 h. Allylamine (excess) was added in a single portion at –20° C. to the mixture and was then warmed to 20° C. and stirred at 20° C. for 16 h. The solvent and excess allylamine were removed from the reaction mixture under reduced pressure, followed by sequential addition of ethyl acetate and saturated $NaHCO_3$ solution at 20° C. The organic layer was separated, the aqueous layer was extracted with ethyl acetate and the combined organic extracts were dried over anhydrous sodium sulfate and evaporated under reduced pressure to get crude which was purified by normal silica column chromatography (eluted at 5% methanol in DCM) to afford 2-((1-allyl-4-methyl-1,4-azasilinan-4-yl)methyl)isoindoline-1,3-dione as light yellow oil (122 mg, 14% in 2 steps).

Step E: A mixture of 2-((1-allyl-4-methyl-1,4-azasilinan-4-yl)methyl)isoindoline-1,3-dione (450 mg, 1.43 mmol) and methyl hydrazine (40% aq. soln.)(0.12 mL, 2.15 mmol) in EtOH-THF (10 mL) was refluxed for 2 hr. Ethyl acetate was evaporated in vacuum, DCM was added to the reaction mixture and filtered. The solid part was removed by filtration and the filtrate was evaporated under reduced pressure to get (1-allyl-4-methyl-1, 4-azasilinan-4-yl) methanamine (7) (255 mg, crude) as a light yellow oil. The crude was used in next step without further purification.

Step F: Tert-butyl ((1-allyl-4-methyl-1,4-azasilinan-4-yl) methyl)carbamate

To a stirred solution of (1-allyl-4-methyl-1,4-azasilinan-4-yl)methanamine (7) (170 mg, 0.92 mmol) in DCM (10 mL) was added Boc anhydride (0.33 mL, 1.38 mmol) and the reaction mixture was stirred at rt for 4 hr. After the completion of starting material, water was added and the aqueous layer was extracted with ethyl acetate (2×50 mL). The organic layers were dried over anhydrous sodium sulfate, filtered and evaporated under reduced pressure to get crude which was purified by normal silica column chromatography (eluted at 2% methanol in DCM) to afford tert-butyl ((1-allyl-4-methyl-1,4-azasilinan-4-yl)methyl)carbamate as light yellow oil (130 mg, 2 steps, 32%).

Step G: To a solution of tert-butyl ((1-allyl-4-methyl-1, 4-azasilinan-4-yl)methyl)carbamate (165 mg, 0.64 mmol) in DCM (10 mL), 1,3-dimethylbarbituric acid (198.3 mg, 0.70 mmol) was added followed by the addition of $(PPh_3)_4Pd$ (73.1 mg, 0.06 mmol). The reaction mixture was then purged with $N_2$ and heated in an oil bath at 40° C. for 3 hr. After the completion of reaction, the reaction mixture was evaporated under reduced pressure to get crude, which was purified by amine silica column chromatography (eluted at 3% methanol in DCM) to afford tert-butyl ((4-methyl-1, 4-azasilinan-4-yl) methyl)carbamate (91 mg, 60%) as light yellow solid.

Intermediate Example BE

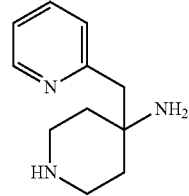 [SMILES: NC1(Cc2ccccn2)CCNCC1]

4-(pyridin-2-ylmethyl)piperidin-4-amine 4-(pyridin-2-ylmethyl)piperidin-4-amine was prepared according to Intermediate Example R, substituting tert-Butyl 4-(2-aminopropan-2-yl)piperidine-1-carboxylate for tert-butyl 4-amino-4-(pyridin-2-ylmethyl)piperidine-1-carboxylate in Step A. m/z (esi/APCI) M+1=192.2.

Intermediate Example BF

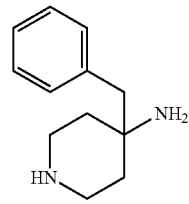 [SMILES: NC1(Cc2ccccc2)CCNCC1]

4-benzylpiperidin-4-amine 4-benzylpiperidin-4-amine was prepared according to Intermediate Example R, substituting tert-Butyl 4-(2-aminopropan-2-yl)piperidine-1-carboxylate for tert-butyl 4-amino-4-benzylpiperidine-1-carboxylate in Step A. m/z (esi/APCI) M⁺1=191.1.

Intermediate Example BG

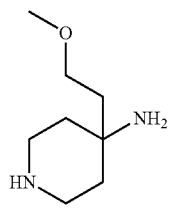

4-(2-methoxyethyl)piperidin-4-amine 4-(2-methoxyethyl)piperidin-4-amine was prepared according to Intermediate Example R, substituting tert-Butyl 4-(2-aminopropan-2-yl)piperidine-1-carboxylate for tert-butyl 4-amino-4-(2-methoxyethyl)piperidine-1-carboxylate in Step A. m/z (esi/APCI) M⁺1=159.2.

Intermediate Example BH

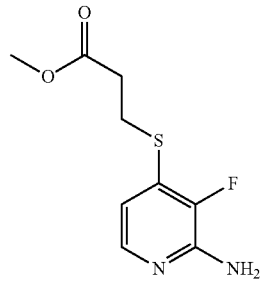

methyl 3-((2-amino-3-fluoropyridin-4-yl)thio)propanoate

2-Amino-3-fluoro-4-iodopyridine (1.1 g, 4.4 mmol) was dissolved in 1,4-dioxane (10 mL, 4.4 mmol). 4,5-Bis(diphenylphosphino)-9,9-dimethylxanthene (0.26 g, 0.45 mmol), and methyl 3-((2-amino-3-fluoropyridin-4-yl)thio)propanoate (0.95 g, 4.1 mmol) were added to the reaction solution. The reaction was placed under nitrogen. N,N-diisopropylethylamine (1.5 mL, 8.9 mmol) was added and the resulting solution was stirred at 100° C. The crude material was purified by silica gel (EtOAc:hexane 0-100%) to provide methyl 3-((2-amino-3-fluoropyridin-4-yl)thio)propanoate (0.95 g, 92% yield), m/z (esi/APCI) M⁺1=231.1.

Intermediate Example BI

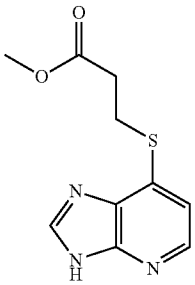 [SMILES: COC(=O)CCSc1ccnc2[nH]cnc12]

methyl 3-((3H-imidazo[4,5-b]pyridin-7-yl)thio)propanoate

Methyl 3-((3H-imidazo[4,5-b]pyridin-7-yl)thio)propanoate was prepared according to Intermediate Example BH, substituting 2-amino-3-fluoro-4-iodopyridine for 7-bromo-3H-imidazo[4,5-b]pyridine in Step A. m/z (esi/APCI) M+1=238.1.

Intermediate Example B J

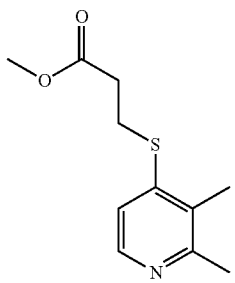

methyl 3-((2,3-dimethylpyridin-4-yl)thio)propanoate

Methyl 3-((2,3-dimethylpyridin-4-yl)thio)propanoate was prepared according to Intermediate Example BH, substituting 2-amino-3-fluoro-4-iodopyridine for 4-bromo-2,3-dimethylpyridine in Step A. m/z (esi/APCI) M⁺1=226.1.

Intermediate Example BK

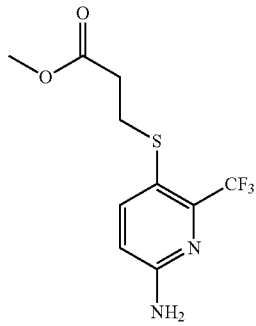 [SMILES: COC(=O)CCSc1ccc(N)nc1C(F)(F)F]

methyl 3-((6-amino-2-(trifluoromethyl)pyridin-3-yl)thio)propanoate

Methyl 3-((6-amino-2-(trifluoromethyl)pyridin-3-yl)thio)propanoate was prepared according to Intermediate Example BH, substituting 2-amino-3-fluoro-4-iodopyridine for 5-bromo-6-trifluoromethylpyridin-2-ylamine in Step A. m/z (esi/APCI) M$^+$1=281.

Intermediate Example BL

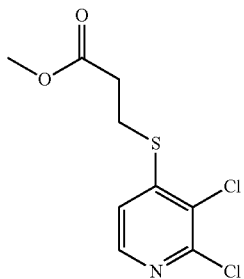

methyl 3-((2,3-dichloropyridin-4-yl)thio)propanoate

Methyl 3-((2,3-dichloropyridin-4-yl)thio)propanoate was prepared according to Intermediate Example BH, substituting 2-amino-3-fluoro-4-iodopyridine for 2,3-dichloro-4-iodopyridine in Step A. m/z (esi/APCI) M+1=281.

Intermediate Example BM

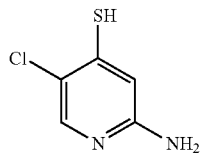

2-amino-5-chloropyridine-4-thiol 2-amino-5-chloropyridine-4-thiol was prepared according to Intermediate Example B, substituting 3-chloro-4-iodopyridin-2-amine for 4-bromo-5-chloropyridin-2-amine in Step A. m/z (esi/APCI) M$^+$1=161.

Intermediate Example BN

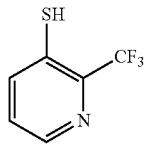

2-(trifluoromethyl)pyridine-3-thiol

Step A: To a solution of 3-bromo-2-(trifluoromethyl)pyridine (0.25 g, 1.11 mmol), Pd(OAc)$_2$ (0.012 g, 0.055 mmol) and Xantphos (0.064 g, 0.11 mmol) in dioxane (3.69 mL, 1.11 mmol) under Ar gas was added 3-Mercaptopropionic acid 2-ethylhexyl ester (0.13 mL, 1.22 mmol) and Hunig's base (0.39 mL, 2.21 mmol). The reaction was further sparged with argon for 10 minutes and then heated to 100° C. overnight. The reaction was cooled, filtered through celite and concentrated in vacuo. The crude methyl 3-((2-(trifluoromethyl)pyridin-3-yl)thio)propanoate (0.29 g, 1.11 mmol, 99% yield) was used without purification, m/z (esi/APCI) M$^+$1=266.1.

Step B: A 21% w/w solution of NaOEt (0.46 mL, 1.22 mmol) in THF was added to a solution of methyl 3-((2-(trifluoromethyl)pyridin-3-yl)thio)propanoate (0.29 g, 1.11 mmol) in THF (5.54 mL, 1.11 mmol) and this was stirred under nitrogen for 1 hour at room temp. DCM (20 mL) was added and this was stirred for 5 minutes and then water (25 mL) was added. The water phase was brought to ~ pH 6 with 1N HCl and the phases were separated. The water phase was extracted with DCM (3×15 mL). The pooled organic phase was washed with brine (25 mL), dried over Na2SO4, filtered and concentrated in vacuo to provide crude 2-(trifluoromethyl)pyridine-3-thiol (0.043 g, 0.24 mmol, 22% yield), m/z (esi/APCI) M$^+$1=180.

Intermediate Example BO

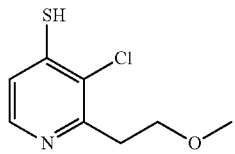

3-chloro-2-(2-methoxyethyl)pyridine-4-thiol

Step A: A mixture of 3-chloro-2-fluoro-4-iodopyridine (0.26 g, 1.01 mmol) and 2-methoxyethan-1-amine (0.11 mL, 2.02 mmol) in DMSO (2.02 mL, 1.01 mmol) was heated to 70° C. and stirred for 16 hours. Added the mixture to water (20 mL) and then extracted the organics from the water phase with EtOAc (3×15 mL). The organic phases were pooled and washed with brine (25 mL), dried over Na2SO4, filtered and concentrated in vacuo. The resultant crude 3-chloro-4-iodo-N-(2-methoxyethyl)pyridin-2-amine (0.31 g, 0.98 mmol, 97% yield) which was used as is in next step, m/z (esi/APCI) M$^+$1=313.

Step B: To a mixture of 3-chloro-4-iodo-N-(2-methoxyethyl)pyridin-2-amine (0.31 g, 0.98 mmol), Pd(OAc)$_2$ (0.011 g, 0.049 mmol) and Xantphos (0.057 g, 0.098 mmol) in dioxane (3.26 mL, 0.98 mmol) under Ar gas was added 3-Mercaptopropionic acid 2-ethylhexyl ester (0.12 mL, 1.08 mmol) and Hunig's base (0.34 mL, 1.96 mmol). The reaction was further sparged with argon for 10 minutes and then heated to 100° C. overnight. The mixture was cooled, filtered through celite and concentrated in vacuo. The crude methyl 3-((3-chloro-2-((2-methoxyethyl)amino)pyridin-4-yl)thio)propanoate (0.30 g, 0.98 mmol, 99% yield) was used without purification, m/z (esi/APCI) M$^+$1=305.1.

Step C: A 21% w/w solution of NaOEt (0.40 mL, 1.08 mmol) in THF was added to methyl 3-((3-chloro-2-((2-methoxyethyl)amino)pyridin-4-yl)thio)propanoate (0.30 g, 0.98 mmol) in THF (4.89 mL, 0.98 mmol) and this was stirred under nitrogen for 1 hour at room temp. DCM (20 mL) was added and was stirred for 5 minutes and water (25 mL) was added. The water phase was brought to ~ pH 6 with 1N HCl and the phases were separated. The water phase was extracted with DCM (3×15 mL). The pooled organic phase was washed with brine (25 mL), dried over Na2SO4, filtered and concentrated in vacuo to provide crude 3-chloro-2-((2-methoxyethyl)amino)pyridine-4-thiol (0.11 g, 0.49 mmol, 50% yield), m/z (esi/APCI) M$^+$1=219.1.

Intermediate Example BP

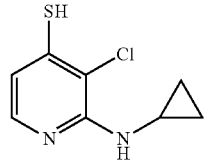 [SMILES: Sc1ccnc(NC2CC2)c1Cl]

3-chloro-2-(cyclopropylamino)pyridine-4-thiol 3-chloro-2-(cyclopropylamino)pyridine-4-thiol was prepared according to Intermediate Example BO, substituting 4-bromo-3-chloro-2-fluoro-pyridine and cyclopropanamine for 3-chloro-2-fluoro-4-iodopyridine and 2-methoxyethan-1-amine respectively in Step A. m/z (esi/APCI) M$^+$1=201.1.

Intermediate Example BQ

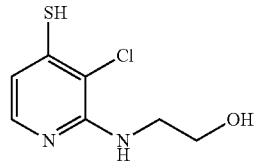 [SMILES: OCCNc1nccc(S)c1Cl]

2-((3-chloro-4-mercaptopyridin-2-yl)amino)ethan-1-ol 2-((3-chloro-4-mercaptopyridin-2-yl)amino)ethan-1-ol was prepared according to Intermediate Example BO, substituting 2-((tert-butyldimethylsilyl)oxy)ethan-1-amine for 2-methoxyethan-1-amine in Step A. m/z (esi/APCI) M$^+$1=205.1.

Intermediate Example BR

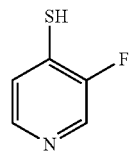

3-fluoropyridine-4-thiol 3-fluoropyridine-4-thiol was prepared according to Intermediate Example BN, substituting 4-bromo-3-fluoropyridine for 3-chloro-2-fluoro-4-iodopyridine in Step A and in Step B, the material was purified by flash chromatography with a 0 to 50% EtOAc in hexanes gradient, m/z (esi/APCI) M$^+$1=130.1.

Intermediate Example BS

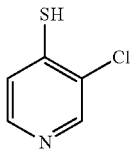

3-chloropyridine-4-thiol 3-chloropyridine-4-thiol was prepared according to Intermediate Example BN, substituting 3-chloro-4-iodopyridine for 3-chloro-2-fluoro-4-iodopyridine in Step A. m/z (esi/APCI) M$^+$1=146.1.

Intermediate Example BT

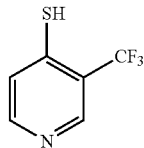 [SMILES: FC(F)(F)c1cnccc1S]

3-(trifluoromethyl)pyridine-4-thiol 3-(trifluoromethyl)pyridine-4-thiol was prepared according to Intermediate Example BN, substituting 4-bromo-3-(trifluoromethyl)pyridine hydrobromide for 3-chloro-2-fluoro-4-iodopyridine in Step A. m/z (esi/APCI) M$^+$1=180.

Intermediate Example BU

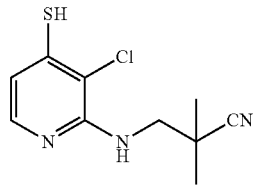

3-((3-chloro-4-mercaptopyridin-2-yl)amino)-2,2-dimethylpropanenitrile 3-((3-chloro-4-mercaptopyridin-2-yl)amino)-2,2-dimethylpropanenitrile was prepared according to Intermediate Example BO, substituting 3-amino-2,2-dimethylpropanenitrile for 2-methoxyethan-1-amine in Step A. Also in Step A, the product crashed out of water and was filtered instead of performing an aqueous workup. In Step C, the product was purified by flash chromatography with a 10 to 100% EtOAc in hexanes gradient. m/z (esi/APCI) M$^+$1=242.1.

Intermediate Example BV

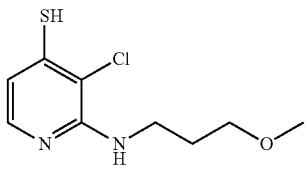

3-chloro-2-((3-methoxypropyl)amino)pyridine-4-thiol 3-chloro-2-((3-methoxypropyl)amino)pyridine-4-thiol was prepared according to Intermediate Example BO, substituting 3-methoxypropan-1-amine for 2-methoxyethan-1-amine in Step A and in Step C, the product was purified by flash chromatography with a 1 to 15% MeOH in DCM gradient, m/z (esi/APCI) M$^+$1=233.1.

Intermediate Example BW

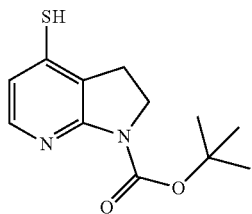 [SMILES: CC(C)(C)OC(=O)N1CCc2c(S)ccnc21]

tert-butyl 4-mercapto-2,3-dihydro-1H-pyrrolo[2,3-b]pyridine-1-carboxylate tert-butyl 4-mercapto-2,3-dihydro-1H-pyrrolo[2,3-b]pyridine-1-carboxylate was prepared according to Intermediate Example BN, substituting 4-bromo-2,3-dihydro-pyrrolo[2,3-b]pyridine-1-carboxylic acid tert-butyl ester for 3-chloro-2-fluoro-4-iodopyridine in Step A. m/z (esi/APCI) M$^+$1=253.1.

Intermediate Example BX

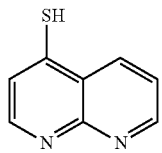 [SMILES: Sc1ccnc2ncccc12]

1,8-naphthyridine-4-thiol 1,8-naphthyridine-4-thiol was prepared according to Intermediate Example BN, substituting 4-bromo-[1,8]naphthyridine for 3-chloro-2-fluoro-4-iodopyridine in Step A. m/z (esi/APCI) M$^+$1=163.

Intermediate Example BY

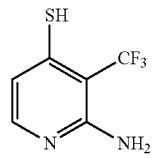

2-amino-3-(trifluoromethyl)pyridine-4-thiol 2-amino-3-(trifluoromethyl)pyridine-4-thiol was prepared according to Intermediate Example BN, substituting 4-iodo-3-(trifluoromethyl)-2-pyridinamine for 3-chloro-2-fluoro-4-iodopyridine in Step A. m/z (esi/APCI) M$^+$1=195.

Intermediate Example BZ

1H-pyrrolo[2,3-b]pyridine-4-thiol 1H-pyrrolo[2,3-b]pyridine-4-thiol was prepared according to Intermediate Example BN, substituting 4-iodo-1H-pyrrolo[2,3-b]pyridine for 3-chloro-2-fluoro-4-iodopyridine in Step A. m/z (esi/APCI) M$^+$1=151.

Intermediate Example CA

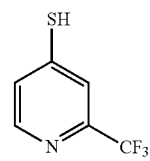 [SMILES: FC(F)(F)c1cc(S)ccn1]

2-(trifluoromethyl)pyridine-4-thiol 2-(trifluoromethyl)pyridine-4-thiol was prepared according to Intermediate Example BN, substituting 4-bromo-2-trifluoromethylpyridine for 3-chloro-2-fluoro-4-iodopyridine in Step A. m/z (esi/APCI) M$^+$1=180.

Intermediate Example CB

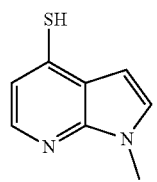

1-methyl-1H-pyrrolo[2,3-b]pyridine-4-thiol 1-methyl-1H-pyrrolo[2,3-b]pyridine-4-thiol was prepared according to Intermediate Example BN, substituting 4-iodo-1-methyl-1H-pyrrolo[2,3-b]pyridine for 3-chloro-2-fluoro-4-iodopyridine in Step A. m/z (esi/APCI) $M^+1=165$.

Intermediate Example CD

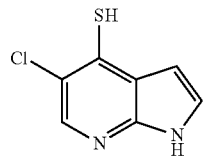 [SMILES: Sc1c(Cl)cnc2[nH]ccc12]

5-chloro-1H-pyrrolo[2,3-b]pyridine-4-thiol 5-chloro-1H-pyrrolo[2,3-b]pyridine-4-thiol was prepared according to Intermediate Example AL, substituting 5-chloro-4-iodo-1H-pyrrolo[2,3-b]pyridine for 3-chloro-2-fluoro-4-iodopyridine in Step A. Also in Step A, the product was purified by flash chromatography with a 10 to 100% EtOAc in hexane gradient and in Step B, the product was purified by flash chromatography with a 1 to 20% MeOH in DCM with a 2% NH$_4$OH modifier gradient, m/z (esi/APCI) $M^+1=185$.

Intermediate Example CE

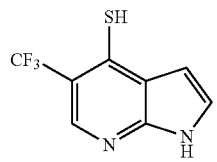 [SMILES: FC(F)(F)c1cnc2[nH]ccc2c1S]

5-(trifluoromethyl)-1H-pyrrolo[2,3-b]pyridine-4-thiol 5-(trifluoromethyl)-1H-pyrrolo[2,3-b]pyridine-4-thiol was prepared according to Intermediate Example BN, substituting 4-chloro-5-(trifluoromethyl)-1H-pyrrolo[2,3-b]pyridine for 3-chloro-2-fluoro-4-iodopyridine in Step A. Also in Step A, the product was purified by flash chromatography with a 10 to 100% EtOAc in hexane gradient and in Step B, the product was purified by flash chromatography with a 1 to 20% MeOH in DCM with a 2% NH$_4$OH modifier gradient, m/z (esi/APCI) $M^+1=219$.

Intermediate Example CF

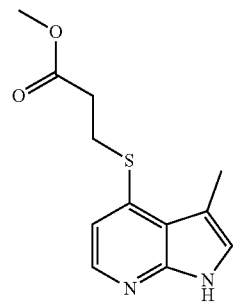 [SMILES: COC(=O)CCSc1ccnc2[nH]cc(C)c12]

methyl 3-((3-methyl-1H-pyrrolo[2,3-b]pyridin-4-yl)thio)propanoate

To a mixture of 4-chloro-3-methyl-1H-pyrrolo[2,3-b]pyridine (0.20 g, 1.20 mmol), Pd(OAc)$_2$ (0.013 g, 0.060 mmol) and Xantphos (0.069 g, 0.12 mmol) in dioxane (3.0 mL, 1.200 mmol) under Ar gas was added methyl 3-mercaptopropanoate (0.15 mL, 1.32 mmol) and Hunig's base (0.42 mL, 2.4 mmol). The reaction was heated to 150° C. under argon in a microwave reactor for 2 hours. 3-mercaptopropanoate (0.15 mL, 1.32 mmol) was added and heated to 200° C. in the microwave reactor for 2 hours. The reaction mixture was cooled and diluted with EtOAc (25 mL) and filtered through celite. The filtrate was concentrated and the resulting residue was purified by flash chromatography with a 0 to 10% MeOH in EtOAc gradient. The material was subjected to a DCM trituration to afford methyl 3-((3-methyl-1H-pyrrolo[2,3-b]pyridin-4-yl)thio)propanoate (0.042 g, 0.17 mmol, 14% yield), m/z (esi/APCI) $M^+1=251.1$.

Intermediate Example CG

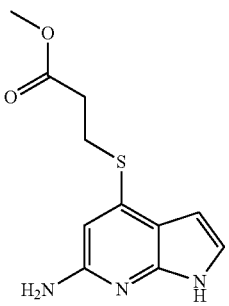 [SMILES: COC(=O)CCSc1cc(N)nc2[nH]ccc12]

methyl 3-((6-amino-1H-pyrrolo[2,3-b]pyridin-4-yl)thio)propanoate

To a mixture of 4-bromo-1H-pyrrolo[2,3-b]pyridin-6-amine (0.25 g, 1.18 mmol), Pd(OAc)$_2$ (0.013 g, 0.059 mmol) and Xantphos (0.068 g, 0.12 mmol) in dioxane (2.95 mL, 1.18 mmol) under Ar gas was added 3-mercaptopropionic acid 2-ethylhexyl ester (0.14 mL, 1.30 mmol) and Hunig's base (0.41 mL, 2.36 mmol). The reaction was heated to 150° C. under argon in a microwave reactor for 2 hours. The reaction mixture was cooled, diluted with EtOAc (25 mL)

and filtered through celite. The filtrate was concentrated and the resulting residue was purified by flash chromatography with a 0 to 20% MeOH in EtOAc gradient to afford methyl 3-((6-amino-1H-pyrrolo[2,3-b]pyridin-4-yl)thio)propanoate (0.11 g, 0.42 mmol, 35% yield), m/z (esi/APCI) M$^+$1=252.1.

Intermediate Example CH

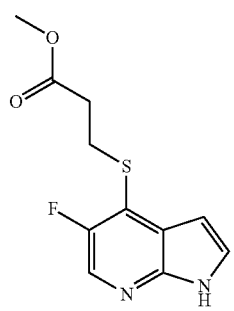 [SMILES: COC(=O)CCSc1c(F)cnc2[nH]ccc12]

methyl 3-((5-fluoro-1H-pyrrolo[2,3-b]pyridin-4-yl)thio)propanoate

To a mixture of 5-fluoro-4-iodo-1H-pyrrolo[2,3-b]pyridine (0.25 g, 0.95 mmol), Pd(OAc)$_2$ (0.011 g, 0.048 mmol) and Xantphos (0.055 g, 0.095 mmol) in dioxane (3.18 mL, 0.95 mmol) under Ar gas was added 3-mercaptopropionic acid 2-ethylhexyl ester (0.11 mL, 1.05 mmol) and Hunig's base (0.33 mL, 1.91 mmol). The mixture was heated to 100° C. under argon for 18 hours. The reaction mixture was cooled, diluted with EtOAc (25 mL) and filtered through celite. The filtrate was concentrated and the resulting residue was purified by flash chromatography with a 0 to 20% MeOH in EtOAc gradient to afford methyl 3-((5-fluoro-1H-pyrrolo[2,3-b]pyridin-4-yl)thio)propanoate (0.12 g, 0.47 mmol, 49% yield), m/z (esi/APCI) M$^+$1=255.1.

Intermediate Example CI

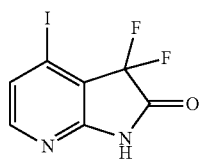 [SMILES: O=C1Nc2nccc(I)c2C1(F)F]

3,3-difluoro-4-iodo-1,3-dihydro-2H-pyrrolo[2,3-b]pyridin-2-one

To a solution of 2-amino-4-iodopyridine (2.50 g, 11.36 mmol), Ethyl bromodifluoroacetate (3.64 mL, 28.41 mmol), and Bis(cyclopentadienyl)iron (0.22 g, 1.14 mmol) in DMSO (21.85 mL, 11.36 mmol) was added a 35% aqueous solution of hydrogen peroxide (2.52 mL, 85.22 mmol) at −5° C. while stirring. The reaction was slowly warmed to rt and was stirred for 22 hours. The mixture was poured into water (100 mL) and the organics were extracted from the water phase (3×50 mL). Once pooled, the organic layers were washed with water (50 mL) and brine (3×50 mL). The organic layer was dried over Na2SO4, filtered and concentrated in vacuo. The brown residue was purified by flash chromatography using a 10 to 100% EtOAc in hexanes gradient to obtain 3,3-difluoro-4-iodo-1,3-dihydro-2H-pyrrolo[2,3-b]pyridin-2-one (0.93 g, 3.13 mmol, 27% yield), m/z (esi/APCI) M$^+$1=296.9.

Intermediate Example CJ

Sodium 2-(trifluoromethyl)pyridine-3-thiolate

Step A. Sodium ethoxide (0.32 mL, 0.85 mmol) was added to methyl 3-((2-(trifluoromethyl)pyridin-3-yl)thio)propanoate (255 mg, 0.77 mmol)(Intermediate Example AL Step A) in THF (3.8 mL) and this mixture was stirred under N2 for 2 hours at room temperature. The mixture was evaporated in vac to give crude sodium 2-(trifluoromethyl)pyridine-3-thiolate (258 mg, 0.898 mmol, 117% yield) which was used as is.

Intermediate Example CK

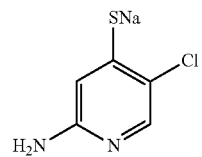

Sodium 2-amino-5-chloropyridine-4-thiolate

Step A: 2-ethylhexyl 3-((2-amino-5-chloropyridin-4-yl)thio)propanoate was prepared according to Intermediate Example N, Step A using 4-bromo-5-chloropyridin-2-amine in place of 3-chloro-4-iodo-2-methylpyridine. m/z (esi/APCI) M+1=345.2.

Step B: To a solution of 2-ethylhexyl 3-((2-amino-5-chloropyridin-4-yl)thio)propanoate (0.58 g, 1.7 mmol) in THF (10 mL) was added sodium ethanolate (0.54 g, 1.7 mmol) and the reaction stirred at room temperature for 1 hr. The reaction was concentrated in vacuo and the solids triturated with 15% MeOH/MTBE (20 mL), filtered and dried in vacuo to give sodium 2-amino-5-chloropyridine-4-thiolate. m/z (esi/APCI) M+1=161.1.

Intermediate Example CL

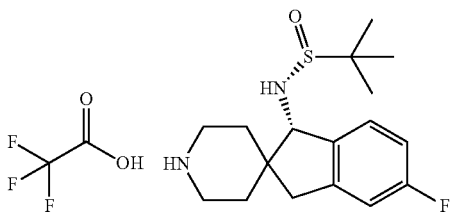

(R)—N—((S)-5-fluoro-1,3-dihydrospiro[indene-2,4'-piperidin]-1-yl)-2-methylpropane-2-sulfinamide 2,2,2-trifluoroacetate (R)—N—((S)-5-fluoro-1,3-dihydrospiro[indene-2,4'-piperidin]-1-yl)-2-methylpropane-2-sulfinamide 2,2,2-trifluoroacetate was made according to Intermediate Example AJ while starting the Step B reaction temperature at −78° C. m/z (esi/APCI) M+1=325.9.

Intermediate Example CM

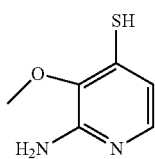

2-amino-3-methoxypyridine-4-thiol 2-amino-3-methoxypyridine-4-thiol was prepared according to Intermediate Example B, substituting 4-bromo-3-methoxypyridin-2-amine for 3-chloro-4-iodopyridin-2-amine in Step A. m/z (esi/APCI) M+1=157.2.

Intermediate Example CN

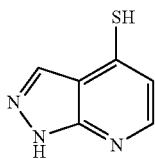

1H-pyrazolo[3,4-b]pyridine-4-thiol 1H-pyrazolo[3,4-b] pyridine-4-thiol was prepared according to Intermediate Example B, substituting 4-iodo-1H-pyrazolo[3,4-b] pyridine for 3-chloro-4-iodopyridin-2-amine in Step A. m/z (esi/APCI) M+1=152.2.

Intermediate Example CO

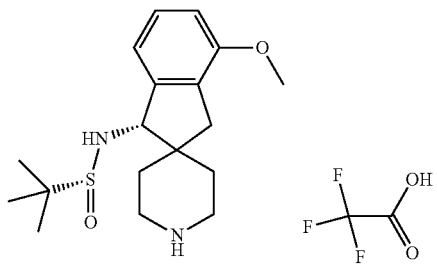 [SMILES: COc1cccc2c1CC1(CCNCC1)[C@@H]2N[S@](=O)C(C)(C)C ; O=C(O)C(F)(F)F]

(R)—N—((S)-4-methoxy-1,3-dihydrospiro[indene-2,4'-piperidin]-1-yl)-2-methylpropane-2-sulfinamide 2,2,2-trifluoroacetate Step A: To solution of 4-methoxy-2,3-dihydro-1H-inden-1-one (1 g, 6.16 mmol) in DMF (12.3 mL) under Argon was added sodium hydride, 60% dispersion in mineral oil (0.74 g, 18.5 mmol) in portions. The mixture was stirred at room temperature for 10 minutes. N-benzyl-2-chloro-N-(2-chloroethyl) ethan-1-amine (1.57 g, 6.78 mmol) was added dropwise and the mixture was stirred overnight at room temperature. The reaction was partitioned between EtOAc and water. The combined organics were washed with brine, dried over sodium sulfate, and concentrated in vacuo. The concentrate was purified by silica gel chromatography (0-100% EtOAc/hexanes) to give r-benzyl-4-methoxyspiro[indene-2,4'-piperidin]-1(3H)-one (1.51 g, 76% yield).

Step B: A solution of r-benzyl-4-methoxyspiro[indene-2,4'-piperidin]-1(3H)-one (1.51 g, 4.70 mmol) and di-tert-butyl dicarbonate (1.13 g, 5.18 mmol) in EtOH (23.5 mL) and THF (23.5 mL) was purged with nitrogen for 5 minutes. To this solution was added palladium (1.25 g, 1.18 mmol) (Degussa Type, 10 wt % palladium, 50% H$_2$O), and was immediately capped and purged with nitrogen for an additional 5 minutes. The solution was stirred under H2 introduced via vacuum followed by balloon pressure. The mixture was stirred at ambient temperature for 2 hours. The mixture was diluted with MeOH and filtered through packed celite. The filtrate was concentrated in vacuo to provide crude tert-butyl 4-methoxy-1-oxo-1,3-dihydrospiro[indene-2,4'-piperidine]-1'-carboxylate (0.86 g, 55% yield).

Step C: To a solution of tert-butyl 4-methoxy-1-oxo-1,3-dihydrospiro[indene-2,4'-piperidine]-1'-carboxylate (856 mg, 2.58 mmol) in THF (1.29 mL) was added (R)-(+)-2-Methyl-2-propanesulfinamide (939 mg, 7.75 mmol) and tetraethoxytitanium (4.12 g, 18.1 mmol) and the reaction stirred for 50 hours at 90° C. EtOAc was added followed by water. The solids were filtered off and the layers were separated. The organic layer was dried, filtered and concentrated to provide crude material that was purified by normal phase (0-100%, EtOAc/hexanes) to give tert-butyl (R,Z)-1-((tert-butylsulfinyl)imino)-4-methoxy-1,3-dihydrospiro[indene-2,4'-piperidine]-1'-carboxylate (0.79 g, 70% yield).

Step D: tert-butyl (R,Z)-1-((tert-butylsulfinyl)imino)-4-methoxy-1,3-dihydrospiro[indene-2,4'-piperidine]-1'-carboxylate (0.79 g, 1.8 mmol) was placed in THF (15 mL) and cooled to 0° C. NaBH$_4$ (0.1 g, 2.7 mmol) was added and the reaction was slowly warmed to room temperature and stirred for 18 hours. Water was added and the mixture was extracted with DCM. The extracts were combined, concentrated and the residue was purified by normal phase chromatography (0-5% MeOH in DCM with 2% NH$_4$OH). The first eluting peak was collected to provide tert-butyl (S)-1-(((R)-tert-butylsulfinyl)amino)-4-methoxy-1,3-dihydrospiro[indene-2,4'-piperidine]-1'-carboxylate (0.12 g, 15% yield).

Step E: To a solution of tert-butyl (S)-1-(((R)-tert-butylsulfinyl)amino)-4-methoxy-1,3-dihydrospiro[indene-2,4'-piperidine]-1'-carboxylate (12 mg, 0.28 mmol) in DCM (550 μL) was added TFA (106 μL, 1.37 mmol) and the reaction was stirred at room temperature for 1 hour. The reaction was concentrated in vacuo and taken forward as crude (R)—N—((S)-4-methoxy-1,3-dihydrospiro[indene-2,4'-piperidin]-1-yl)-2-methylpropane-2-sulfinamide2,2,2-trifluoroacetate (124 mg, 100% yield), m/z (esi/APCI) M$^+$1=337.2.

Intermediate Example CP

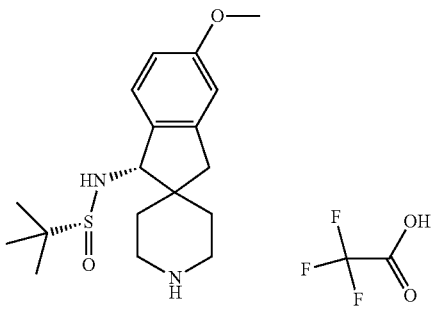 [SMILES: COc1ccc2c(c1)CC1(CCNCC1)[C@@H]2N[S@](=O)C(C)(C)C ; O=C(O)C(F)(F)F]

(R)—N—((S)-5-methoxy-1,3-dihydrospiro[indene-2,4'-piperidin]-1-yl)-2-methylpropane-2-sulfinamide 2,2,2-trifluoroacetate (R)—N—((S)-5-methoxy-1,3-dihydrospiro[indene-2,4'-piperidin]-1-yl)-2-methylpropane-2-sulfinamide 2,2,2-trifluoroacetate was prepared according to Intermediate Example CO, substituting 6-methoxy-1-indanone for 4-methoxy-2,3-dihydro-1H-inden-1-one in Step A. m/z (esi/APCI) M+1=337.2.

Intermediate Example CQ

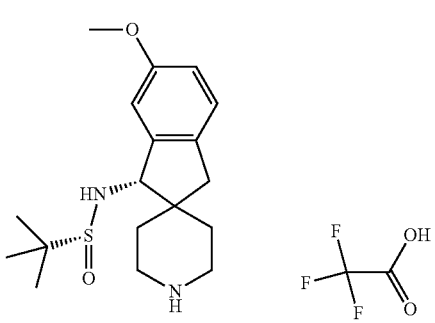 [SMILES: COc1ccc2c(c1)[C@@H](N[S@](=O)C(C)(C)C)C1(CCNCC1)C2 ; O=C(O)C(F)(F)F]

(R)—N—((S)-5-methyoxy-1,3-dihydrospiro[indene-2,4'-piperidin]-1-yl)-2-methylpropane-2-sulfinamide 2,2,2-trifluoroacetate (R)—N—((S)-5-methoxy-1,3-dihydrospiro[indene-2,4'-piperidin]-1-yl)-2-methylpropane-2-sulfinamide 2,2,2-trifluoroacetate was prepared according to Intermediate Example CO, substituting 5-methoxy-1-indanone for 4-methoxy-2,3-dihydro-1H-inden-1-one in Step A. m/z (esi/APCI) M+1=337.2.

Intermediate Example CR

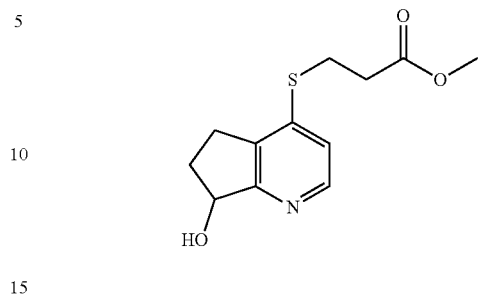

Methyl 3-((7-hydroxy-6,7-dihydro-5H-cyclopenta[b]pyridin-4-yl)thio)propanoate 4-chloro-6,7-dihydro-5H-cyclopenta[b]pyridin-7-ol (500 mg, 2.94 mmol), Xantphos (85.3 mg, 0.15 mmol) and N-ethyl-N-isopropylpropan-2-amine (1.02 mL, 5.90 mmol) were dissolved in dioxane (10 mL) in a sealed tube and nitrogen bubbled through for 3 min. Pd$_2$(dba)$_3$ (67.5 mg, 0.073 mmol) was added, followed by methyl 3-mercaptopropanoate (359 µL, 3.24 mmol). The reaction was sealed and heated at 130° C. overnight. The reaction was cooled, filtered through celite, washed with EtOAc, concentrated and purified over silica gel (0-10% MeOH in EtOAc) to afford methyl 3-((7-hydroxy-6,7-dihydro-5H-cyclopenta[b]pyridin-4-yl)thio)propanoate (515 mg, 2.03 mmol, 69% yield) as a tan solid. Mass spectrum: m/z=254.1 (M$^+$H).

Intermediate Example CS

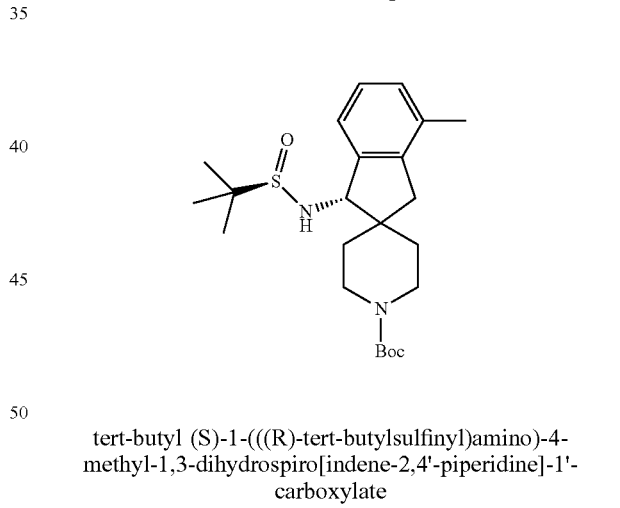

tert-butyl (S)-1-(((R)-tert-butylsulfinyl)amino)-4-methyl-1,3-dihydrospiro[indene-2,4'-piperidine]-1'-carboxylate Step A: To a stirred solution of 4-methyl-2,3-dihydro-1H-inden-1-one (2 g, 13.69 mmol) in DMF (25 mL), was added NaH (60%, 0.98 g, 15.06 mmol) at 0° C. and stirred for 30 min at above temperature. N-benzyl-2-chloro-N-(2-chloroethyl)ethan-1-amine hydrochloride salt was added and was stirred for 18 h at RT. The reaction was quenched with aqueous saturated NH$_4$Cl solution and extracted with ethyl acetate. The combined organic layer was washed with water, brine, dried over anhydrous sodium sulfate, filtered and concentrated. The resulting residue was purified by Combi-Flash column (eluted at 25% ethyl acetate in hexane) to afford r-benzyl-4-methylspiro[indene-2,4'-piperidin]-1(3H)-one (1.5 g, 39%) as yellow solid, m/z (esi) M+1=305.8.

Step B: To a stirred solution of r-benzyl-4-methylspiro[indene-2,4'-piperidin]-1(3H)-one (1.5 g, 4.91 mmol) in DCE (10 mL), was added 1-chloroethyl chloroformate (1.59 mL, 14.73 mmol) and refluxed for 1 h. The volatiles were concentrated under reduced pressure to get crude brown oil. To the crude residue methanol was added and refluxed for another 1 h. The reaction was concentrated under reduced pressure to get 4-methylspiro[indene-2,4'-piperidin]-1(3H)-one as a crude, which was used in next step without further purification, m/z (esi) M+1=215.7.

Step C: To a stirred solution of 4-methylspiro[indene-2,4'-piperidin]-1(3H)-one (1 g, crude) in DCM (15 mL), was added TEA (3.23 mL, 23.22 mmol) followed by addition of boc-anhydride (2.13 mL, 9.28 mmol) and was stirred for 18 h at RT. The reaction was concentrated under reduced pressure to get crude which was purified by Combi-Flash column (eluted at 10-15% ethyl acetate in hexane) to afford tert-butyl 4-methyl-1-oxo-1,3-dihydrospiro[indene-2,4'-piperidine]-1'-carboxylate (1.5 g, 66%, 2 steps) as sticky liquid.

Step D: To tert-butyl 4-methyl-1-oxo-1,3-dihydrospiro[indene-2,4'-piperidine]-1'-carboxylate (1 g, 3.17 mmol) was added Ti(OEt)$_4$ (8.77 mL, 41.84 mmol) and heated to 90° C. At above temperature (R)-2-Methyl propane-2-sulfinamide (1.1 g, 9.51 mmol) was added and the heating was continued at 90° C. for 24 h. The reaction was poured into ethyl acetate (50 mL) and to it aqueous saturated brine solution (50 mL) was added. The precipitated solid was filtered and the filtrate was washed with water, brine, dried over anhydrous sodium sulfate, filtered and concentrated to get a crude which was purified by Combi-Flash column (eluted at 20% ethyl acetate in hexane) to afford tert-butyl (R,Z)-1-((tert-butylsulfinyl)imino)-4-methyl-1,3-dihydrospiro[indene-2,4'-piperidine]-1'-carboxylate (800 mg, 60%) as white solid, m/z (esi) M+1=418.8.

Step E: To a stirred solution of tert-butyl (R,Z)-1-((tert-butylsulfinyl)imino)-4-methyl-1,3-dihydrospiro[indene-2,4'-piperidine]-1'-carboxylate (1.1 g, 2.62 mmol) in methanol (60 mL), was added sodium borohydride (600 mg, 15.76 mmol) at RT and stirred for 4 h. The reaction was quenched with saturated NH$_4$Cl solution and extracted with ethyl acetate. The combined organic part was washed with water, brine, dried over anhydrous sodium sulfate, filtered and concentrated to get a crude which was purified by Combi-Flash column (eluted at 25% ethyl acetate in hexane) to afford tert-butyl (S)-1-(((R)-tert-butylsulfinyl)amino)-4-methyl-1,3-dihydrospiro[indene-2,4'-piperidine]-1'-carboxylate (440 mg, 40%) (m/z (esi) M+1=421.4) (m/z (esi) M+1=421.4) as off white solid.

Intermediate Example CT

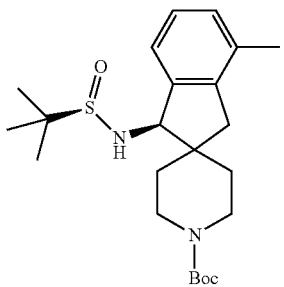 [SMILES: Cc1cccc2c1CC1(CCN(C(=O)OC(C)(C)C)CC1)[C@H]2N[S@](=O)C(C)(C)C]

tert-butyl (R)-1-(((R)-tert-butylsulfinyl)amino)-4-methyl-1,3-dihydrospiro[indene-2,4'-piperidine]-1'-carboxylate tert-butyl (R)-1-(((R)-tert-butylsulfinyl)amino)-4-methyl-1,3-dihydrospiro[indene-2,4'-piperidine]-1'-carboxylate, was prepared according to Intermediate Example CS, collecting the second peak, (m/z (esi) M+1=421.4) as off white solid.

Example 1

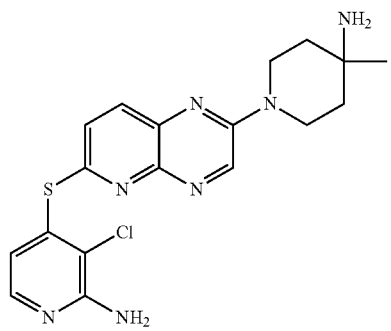 [SMILES: CC1(N)CCN(c2cnc3nc(Sc4ccnc(N)c4Cl)ccc3n2)CC1]

4-((2-(4-amino-4-methylpiperidin-1-yl)pyrido[2,3-b]pyrazin-6-yl)thio)-3-chloropyridin-2-amine Step A: N-Ethyl-N-isopropylpropan-2-amine (0.25 mL, 1.4 mmol) was added to a solution of 6-chloropyrido[2,3-b]pyrazin-2-yl trifluoromethanesulfonate (0.40 g, 1.3 mmol) in dimethylacetamide ("DMA") cooled to 0° C., followed by %/7-butyl (4-methylpiperidin-4-yl)carbamate (0.30 g, 1.4 mmol). The reaction was stirred at 0° C. for 1 hour. The reaction was poured onto water and extracted twice with MTBE. The combined organics were washed with water, brine, dried over MgSO$_4$, filtered and concentrated in vacuo. The material was purified by silica gel chromatography (10-100% EtOAc in hexanes) to give tot-butyl (1-(6-chloropyrido[2,3%]pyrazin-2-yl)-4-methylpiperidin-4-yl)carbamate (0.46 g, 1.3 mmol, 98% yield).

Step B: tot-Butyl (1-(6-chloropyrido[2,3-b]pyrazin-2-yl)-4-methylpiperidin-4-yl)carbamate (0.18 g, 0.46 mmol), potassium phosphate (0.30 g, 1.4 mmol), tetramethylethylenediamine ("TMEDA") (0.042 mL, 0.28 mmol), 2-amino-3-chloropyridine-4-thiol (0.22 g, 1.4 mmol) and copper(I) iodide (0.026 g, 0.14 mmol) were placed in dioxane (1.9 mL, 0.47 mmol). The mixture was degassed with Ar, sealed, and heated to 100° C. for 18 hours. The reaction was cooled to room temperature, and water was added. The mixture was worked up with DCM and water. The organics were washed with brine and dried with Na$_2$SO$_4$. This solution was concentrated and purified by silica gel (DCM:MeOH (1-10%) to give boc protected product. This material was stirred with trifluoroacetic acid ("TFA"):DCM (1:1 10 mL) for 1 hour at room temperature. The mixture was concentrated and purified reverse phase chromatography (5-95% ACN:water (1% TFA)) to provide product. This material was brought up in 10% MeOH in DCM and saturated NaHCO$_3$. The organics were washed with brine, dried with Na$_2$SO$_4$, filtered and concentrated to give 4-((2-(4-amino-4-methylpiperidin-1-yl)pyrido[2,3-b]pyrazin-6-yl)thio)-3-chloropyridin-2-amine (0.084 g, 0.21 mmol, 45% yield). $^1$H NMR (400 MHz, (CDCl$_3$) δ 8.74 (s, 1H), 7.90 (d, 1H, J=8.6 Hz), 7.86 (d, 1H, 5.3 Hz) 7.49 (d, 1H, J=8.6 Hz), 6.68 (d, 1H, J=5.3 Hz), 4.92 (br, 2H), 3.97 (m, 2H), 3.78 (m, 2H), 1.68 (m, 2H), 1.58 (m, 2H); m/z (esi/APCI) M+1=402.1.

Example 2

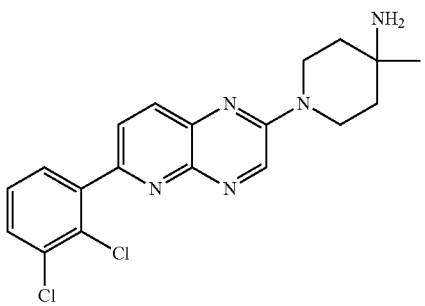 [SMILES: CC1(N)CCN(c2cnc3nc(-c4cccc(Cl)c4Cl)ccc3n2)CC1]

1-(6-(2,3-dichlorophenyl)pyrido[2,3-b]pyrazin-2-yl)-4-methylpiperidin-4-amine

Step A: %/7-Butyl (1-(6-chloropyrido[2,3-b]pyrazin-2-yl)-4-methylpiperidin-4-yl)carbamate (0.20 g, 0.53 mmol) (Example 1, Step A), (2,3-dichlorophenyl)boronic acid (0.20 g, 1.1 mmol), and K$_2$CO$_3$ (0.29 g, 2.1 mmol) were placed in ACN (2 mL), and the mixture was degassed with N$_2$. Dichloro[1,1'-bis(diphenylphosphino)ferrocene]palladium (II) dichloromethane adduct (0.84 g, 0.11 mmol) was added, and the reaction was degassed and heated to 90° C. for 18 hours. Water was added, and the reaction was extracted with DCM. The extracts were combined, concentrated, and purified by silica gel (0-5% MeOH in DCM) to provide %/7-butyl (1-(6-(2,3-dichlorophenyl)pyrido[2,3-b]pyrazin-2-yl)-4-methylpiperidin-4-yl)carbamate (0.22 g, 0.45 mmol, 85% yield).

Step B: tert-Butyl (1-(6-(2,3-dichlorophenyl)pyrido[2,3-b]pyrazin-2-yl)-4-methylpiperidin-4-yl)carbamate (0.22 g, 0.45 mmol) was dissolved in DCM (10 mL), treated with TFA (1 mL), and stirred at room temperature for two hours. The reaction was concentrated and purified by reverse phase chromatography (5-95% acetonitrile ("ACN") in water with 0.1% TFA). Fractions containing the second eluting peak were combined, and the ACN was evaporated off. Saturated bicarbonate was added, and the mixture was extracted with DCM. The extracts were combined, dried, filtered, and concentrated to provide 1-(6-(2,3-dichlorophenyl)pyrido[2,3%]pyrazin-2-yl)-4-methylpiperidin-4-amine (0.063 g, 0.16 mmol, 36% yield). $^1$H NMR (400 MHz, (CD$_3$)$_2$SO) δ 9.02 (s, 1H), 8.05 (d, 1H, J=8.6 Hz), 7.82 (d, 1H, 8.6 Hz) 7.75 (dd, 1H, J=8.0, 1.8 Hz), 7.60 (dd, 1H, J=8.0, 1.8 Hz), 7.50 (m, 1H), 4.01 (m, 2H), 3.75 (m, 2H), 1.50 (m, 4H) 1.11 (s, 3H); m/z (esi/APCI) M+1=390.1.

Example 3

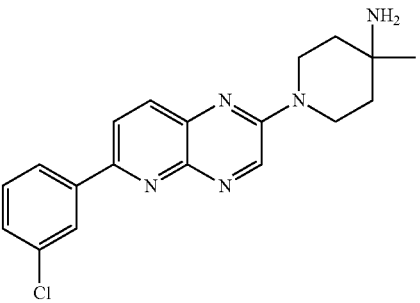 [SMILES: CC1(N)CCN(c2cnc3nc(-c4cccc(Cl)c4)ccc3n2)CC1]

1-(6-(3-chlorophenyl)pyrido[2,3-b]pyrazin-2-yl)-4-methylpiperidin-4-amine 1-(6-(3-Chlorophenyl)pyrido[2,3-b]pyrazin-2-yl)-4-methylpiperidin-4-amine was prepared according to Example 2, Steps A-B, collecting the first eluting peak in Step B provided title compound, m/z (esi/APCI) M+1=390.1.

Example 4

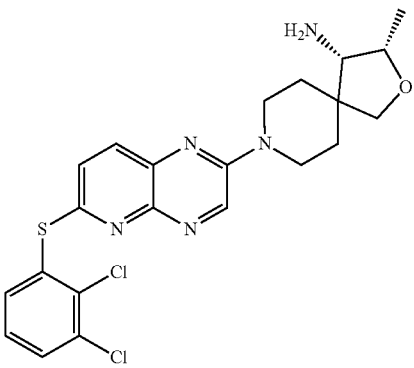 [SMILES: C[C@@H]1OCC2(CCN(c3cnc4nc(Sc5cccc(Cl)c5Cl)ccc4n3)CC2)[C@@H]1N]

(3S,4S)-8-(6-((2,3-dichlorophenyl)thio)pyrido[2,3-b]pyrazin-2-yl)-3-methyl-2-oxa-8-azaspiro[4.5]decan-4-amine Step A: 2,6-Dichloropyrido[2,3-b]pyrazine (0.13 g, 0.63 mmol), (3S,4S)-3-methyl-2-oxa-8-azaspiro[4.5]decan-4-amine dihydrochloride (0.15 g, 0.63 mmol), and Hunig's Base (0.55 mL, 3.1 mmol) were placed in DMF (5 mL), and the mixture was stirred for one hour at 0° C. Water was added, and the mixture was extracted with EtOAc and washed with water. The extracts were combined, concentrated, and purified by silica gel (0-10% MeOH in DCM with 0.25% NH$_4$OH) to provide (3S,4S)-8-(6-chloropyrido[2,3-b]pyrazin-2-yl)-3-methyl-2-oxa-8-azaspiro[4.5]decan-4-amine (0.13 g, 0.40 mmol, 64% yield) as a 4:1 mixture of regioisomers.

Step B: (3S,4S)-8-(6-Chloropyrido[2,3-b]pyrazin-2-yl)-3-methyl-2-oxa-8-azaspiro[4.5]decan-4-amine (50 mg, 0.15 mmol), potassium phosphate (95 mg, 0.5 mmol), TMEDA (14 mL, 0.090 mmol), 2,3-dichlorobenzenethiol (81 mg, 0.45 mmol) and copper(I) iodide (8.6 mg, 0.045 mmol) were placed in dioxane (1.5 mL). The mixture was degassed with Ar, sealed, and heated to 100° C. for 18 hours. The reaction was cooled to room temperature, and water was added. The mixture was extracted with DCM (3×15 mL), and the extracts were combined and concentrated. The resulting residue was purified by silica gel (0-5% MeOH in DCM with 0.25% NH$_4$OH) to provide a mixture of regioisomers. The regioisomers were separated by SFC (Chiral Tech. AS-H column, 1 cm×250 mm, 5 u, 19 mL/minute, 3100 psi, isocratic 25% (80:20:01) MeOH:isopropyl alcohol ("IPA"): diethylamine ("DEA")). Collecting the second eluting peak provided (3S,4S)-8-(6-((2,3-dichlorophenyl)thio)pyrido[2,3-b]pyrazin-2-yl)-3-methyl-2-oxa-8-azaspiro[4.5]decan-4-amine (30 mg, 0.062 mmol, 42% yield). $^1$H NMR (400 MHz, (CD$_3$)$_2$SO) δ 8.90 (s, 1H), 7.92 (d, 1H, J=8.6 Hz), 7.75 (dd, 1H, J=8.0, 1.4 Hz), 7.67 (dd, 1H, J=7.8, 1.4 Hz), 7.41 (m, 2H), 4.10 (m, 3H), 3.73 (d, 1H, J=8.6 Hz), 3.53 (d, 1H, J=8.6 Hz) 3.45 (m, 2H), 3.03 (m, 1H), 1.80-1.48 (m, 4H), 1.10 (d, 3H, J=6.5 Hz); m/z (esi/APCI) M+1=476.1.

Example 5

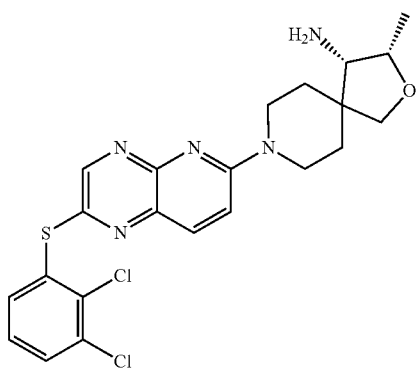 [SMILES: C[C@@H]1OCC2(CCN(c3ccc4nc(Sc5cccc(Cl)c5Cl)cnc4n3)CC2)[C@@H]1N]

(3S,4S)-8-(2-((2,3-dichlorophenyl)thio)pyrido[2,3-b]
pyrazin-6-yl)-3-methyl-2-oxa-8-azaspiro[4.5]decan-
4-amine (3S,4S)-8-(2-((2,3-Dichlorophenyl)thio)pyrido[2,3-b]
pyrazin-6-yl)-3-methyl-2-oxa-8-azaspiro[4.5]decan-4-amine was prepared in Example 4, collecting the first eluting peak in Step B provided the title compound, m/z (esi/APCI) M+1=476.1.

Example 6

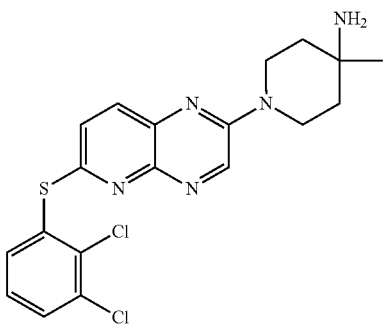

1-(6-((2,3-dichlorophenyl)thio)pyrido[2,3-b]pyrazin-
2-yl)-4-methylpiperidin-4-amine Step A: 2,6-Dichloropyrido[2,3-b]pyrazine (0.59 g, 3.0 mmol), tert-butyl 4-methylpiperidin-4-ylcarbamate (1.1 g, 5.3 mmol), and Hunig's Base (0.26 mL, 1.5 mmol) were placed in DMF (5 mL), and the mixture was stirred for one hour at room temperature. Water was added, and the mixture was brought up in water, extracted with EtOAc, and washed with water. The extracts were combined, concentrated, and purified by silica gel (0-55% EtOAc in hexanes) collecting the second eluting peak to provide tert-butyl (1-(6-chloro-pyrido[2,3-b]pyrazin-2-yl)-4-methylpiperidin-4-yl)carbamate (0.70 g, 1.9 mmol, 63% yield).

Step B: tert-Butyl (1-(6-chloropyrido[2,3-b]pyrazin-2-yl)-4-methylpiperidin-4-yl)carbamate potassium phosphate (0.25 g, 1.2 mmol), TMEDA (0.036 mL, 0.24 mmol), 2,3-dichlorobenzenethiol (0.21 g, 1.2 mmol) and copper(I) iodide (0.022 g, 0.12 mmol) were placed in dioxane (1.5 mL), and the mixture was degassed with Ar sealed and heated to 100° C. for 18 hours. The reaction was cooled to room temperature, and water was added. The mixture was extracted with DCM (3×15 mL), and the extracts were combined and concentrated. The resulting residue was purified by silica gel (0-50% EtOAc in hexanes) to provide tert-butyl (1-(6-((2,3-dichlorophenyl)thio)pyrido[2,3-b]pyrazin-2-yl)-4-methylpiperidin-4-yl)carbamate (0.20 g, 0.38 mmol, 32% yield).

Step C: tert-Butyl (1-(6-((2,3-dichlorophenyl)thio)pyrido[2,3-b]pyrazin-2-yl)-4-methylpiperidin-4-yl)carbamate (0.2 g, 0.38 mmol) was dissolved in DCM (10 mL), treated with TFA (1 mL), and stirred at room temperature for one hour. The reaction mixture was concentrated down. Saturated bicarbonate was added, and the mixture was extracted with 10% MeOH in DCM. The extracts were combined, dried, filtered, and concentrated to provide 1-(6-((2,3-dichlorophenyl)thio)pyrido[2,3-b]pyrazin-2-yl)-4-methylpiperidin-4-amine (0.14 g, 0.32 mmol, 85% yield). $^1$H (400 MHz, (CD$_3$)$_2$SO) δ 8.68 (s, 1H), 7.83 (d, 1H, J=8.6 Hz), 7.62 (dd, 1H, J=7.8, 1.6 Hz), 7.50 (dd, 1H, J=8.0, 1.4 Hz), 7.25 (m, 2H), 7.22 (d, 1H, J=1.8 Hz), 3.92 (m, 2H), 3.76 (m, 2H), 1.68 (m, 2H), 1.58 (m, 2H), 1.22 (s, 3H); m/z (esi/APCI) M+1=420.0.

Example 7

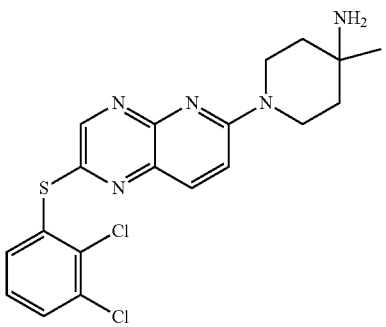 [SMILES: CC1(N)CCN(c2ccc3nc(Sc4cccc(Cl)c4Cl)cnc3n2)CC1]

1-(2-((2,3-dichlorophenyl)thio)pyrido[2,3-b]pyrazin-
6-yl)-4-methylpiperidin-4-amine 1-(2-((2,3-Dichlorophenyl)thio)pyrido[2,3-b]pyrazin-6-yl)-4-methylpiperidin-4-amine was prepared in Example 6, collecting the first eluting peak, tert-butyl (1-(2-chloropyrido[2,3-b]pyrazin-6-yl)-4-methylpiperidin-4-yl)carbamate, in Step A. m/z (esi/APCI) M+1=420.0.

Example 8

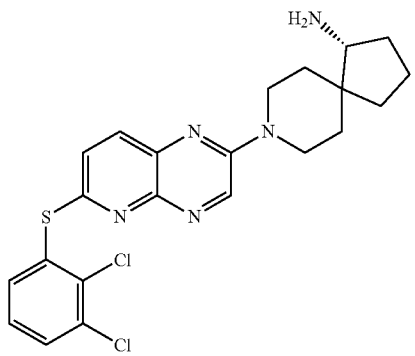 [SMILES: N[C@@H]1CCCC12CCN(c1cnc3nc(Sc4cccc(Cl)c4Cl)ccc3n1)CC2]

(R)-8-(6-((2,3-dichlorophenyl)thio)pyrido[2,3-b]pyrazin-2-yl)-8-azaspiro[4.5]decan-1-amine N-Ethyl-N-isopropylpropan-2-amine (0.14 mL, 0.80 mmol) was added to a solution of 6-chloropyrido[2,3-b]pyrazin-2-yl trifluoromethanesulfonate (50 mg, 0.16 mmol) in dioxane cooled to 0° C., followed by (R)-8-azaspiro[4.5]decan-1-amine dihydrochloride (36 mg, 0.16 mmol). The reaction was stirred at room temperature for 3 hours, then for 2 hours at 60° C. 2,3-Dichlorothiophenol (57 mg, 0.32 mmol) was added, and the reaction was heated to 100° C. for 18 hours. The reaction was concentrated and purified by silica gel (0-15% MeOH in DCM with 0.1% NH$_4$OH) to yield (R)-8-(6-((2,3-dichlorophenyl)thio)pyrido[2,3-b]pyrazin-2-yl)-8-azaspiro[4.5]decan-1-amine (47 mg, 0.10 mmol, 64% yield). $^1$H (400 MHz, (CD$_3$)$_2$SO) δ 8.62 (s, 1H), 7.71 (d, 1H, J=8.6 Hz), 7.52 (dd, 1H, J=7.8, 1.6 Hz), 7.49 (dd, 1H, J=8.0, 1.4 Hz), 7.22 (m, 2H), 7.18 (d, 1H, J=8.8 Hz), 4.35 (m, 2H), 3.65 (m, 1H), 3.29-2.99 (m, 4H), 2.10 (m, 1H) 1.90 (m, 1H), 1.82-1.50 (m, 6H); m/z (esi/APCI) M+1=460.1.

Example 9

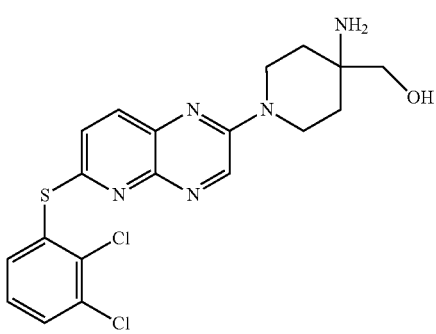 [SMILES: NC1(CO)CCN(c2cnc3nc(Sc4cccc(Cl)c4Cl)ccc3n2)CC1]

(4-amino-1-(6-((2,3-dichlorophenyl)thio)pyrido[2,3-b]pyrazin-2-yl)piperidin-4-yl)methanol Step A: N-Ethyl-N-isopropylpropan-2-amine (0.43 mL, 2.4 mmol) was added to a solution of 6-chloropyrido[2,3-b]pyrazin-2-yl trifluoromethanesulfonate (0.15 g, 0.48 mmol) in DMA (2 mL), followed by (4-aminopiperidin-4-yl)methanol dihydrochloride (0.11 g, 0.53 mmol). The reaction was stirred at room temperature for 2 hours. The reaction was poured into water and extracted twice with MTBE. The combined organics were washed with water, brine, dried over MgSO$_4$ and concentrated in vacuo. The material was chromatographed (0-15% MeOH in DCM with 0.1% NH$_4$OH) as eluent to give (4-amino-1-(6-chloropyrido[2,3-b]pyrazin-2-yl)piperidin-4-yl)methanol (0.024 g, 0.082 mmol, 17% yield).

Step B: (4-Amino-1-(6-chloropyrido[2,3-b]pyrazin-2-yl)piperidin-4-yl)methanol (0.024 g, 0.082 mmol), Hunig's base (0.043 mL, 0.25 mmol), and 2,3-dichlorobenzenethiol (0.029 g, 0.16 mmol) were placed in dioxane (1 mL), and the mixture was heated to 100° C. for 2 hours. The reaction was concentrated and purified by silica gel (5-20% MeOH in DCM with 1% NH$_4$OH) to provide (4-amino-1-(6-((2,3-dichlorophenyl)thio)pyrido[2,3-b]pyrazin-2-yl)piperidin-4-yl)methanol (0.023 g, 0.053 mmol, 66% yield). $^1$H (400 MHz, (CD$_3$)$_2$SO) δ 8.87 (s, 1H), 7.90 (d, 1H, J=8.6 Hz), 7.74 (dd, 1H, J=8.2, 1.6 Hz), 7.65 (dd, 1H, J=7.8, 1.6 Hz), 7.43 (m, 1H), 7.37 (d, 1H, J=8.6 Hz), 4.67 (br, 1H), 4.16 (m, 2H), 3.54 (m, 2H), 3.16 (m, 3H), 1.55 (m, 2H), 1.35 (m, 2H); m/z (esi/APCI) M+1=436.0.

Example 10

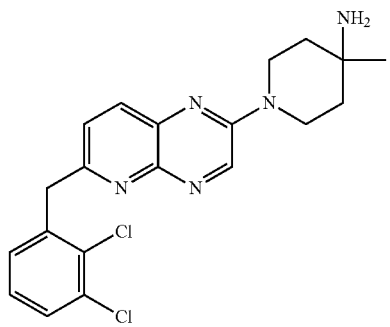

1-(6-(2,3-dichlorobenzyl)pyrido[2,3-b]pyrazin-2-yl)-4-methylpiperidin-4-amine tert-Butyl (1-(6-chloropyrido[2,3-b]pyrazin-2-yl)-4-methylpiperidin-4-yl)carbamate (75 mg, 0.20 mmol; Example 1, Step A), (2,3-dichlorobenzyl)zinc(II) chloride (1.0 mL, 0.50 mmol) and Pd(Ph$_3$P)$_4$ (23 mg, 0.02 mmol) were placed in THF (1 mL), and the mixture was degassed with N$_2$. The reaction was heated to 60° C. for 3 hours. The reaction was cooled, and TFA (1 mL) was added. The reaction was stirred at room temperature for 30 minutes. The reaction was concentrated and purified by reverse phase chromatography (5-95% ACN:water with 0.1% TFA). The product was brought up in 10% MeOH in DCM, and saturated bicarbonate was added. The layers were separated, and the aqueous was extracted with 10% MeOH in DCM (3×10 mL), organics were combined, dried with sodium sulfate and filtered to provide 1-(6-(2,3-dichlorobenzyl)pyrido[2,3-b]pyrazin-2-yl)-4-methylpiperidin-4-amine (8.9 mg, 0.02 mmol, 11% yield). $^1$H NMR (400 MHz, CDCl$_3$) δ 8.74 (s, 1H), 7.88 (d, 1H, J=8.4 Hz), 7.35 (m, 1H) 7.28 (m, 1H), 7.16 (t, 1H, J=7.8 Hz), 7.49 (s, 1H), 3.92 (m, 2H), 3.78 (m, 2H), 1.68 (m, 2H) 1.58 (m, 2H), 1.25 (s, 3H); m/z (esi/APCI) M+1=402.1.

Example 11

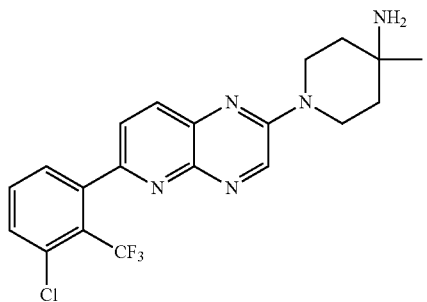

1-(6-(3-chloro-2-(trifluoromethyl)phenyl)pyrido[2,3-b]pyrazin-2-yl)-4-methylpiperidin-4-amine Step A: N-Ethyl-N-isopropylpropan-2-amine (0.054 g, 0.41 mmol) was added to a solution of 6-chloropyrido[2,3-b]pyrazin-2-yl trifluoromethanesulfonate (0.13 g, 0.41 mmol) in DMA cooled to 0° C., followed by tert-butyl (4-methylpiperidin-4-yl)carbamate (0.089 g, 0.41 mmol). The reaction was stirred at 0° C. for 1 hour. The reaction was poured into water and extracted twice with MTBE. The combined organics were washed with water, brine, dried over MgSO₄ and concentrated in vacuo. The material was chromatographed using 10-100% EtOAc/hexanes as eluent to give tert-butyl (1-(6-chloropyrido[2,3-b]pyrazin-2-yl)-4-methylpiperidin-4-yl)carbamate (0.16 g, 0.42 mmol, 100% yield). ¹H NMR (400 MHz, CDCl₃) δ 8.73 (s, 1H), 7.92 (d, 1H, J=8.6 Hz), 7.57 (d, 1H, J=8.6 Hz), 4.43 (s, 1H), 4.10 (dt, 2H, J=18.4, 4.3 Hz), 3.55-3.48 (m, 2H), 2.20 (br d, 2H, J=13.3 Hz), 1.72-1.65 (M, 2H), 1.44 (s, 9H), 1.41 (s, 3H); m/z (esi/APCI) M+1=378.2.

Step B: 2,2,2-Trifluoroacetic acid (1 mL) was added to a solution of tert-butyl (1-(6-chloropyrido[2,3-b]pyrazin-2-yl)-4-methylpiperidin-4-yl)carbamate (0.16 g, 0.42 mmol) in DCM (1 mL), and the reaction was stirred at room temperature for 1 hour. The reaction was concentrated in vacuo, and the residue partitioned between EtOAc and basic water. The layers were separated. The organics were washed with brine, dried over MgSO₄ and concentrated in vacuo to give 1-(6-chloropyrido[2,3-b]pyrazin-2-yl)-4-methylpiperidin-4-amine (0.072 g, 0.26 mmol, 61% yield).

Step C: Potassium carbonate (0.12 mL, 0.26 mmol), 3-chloro-2-(trifluoromethyl)phenylboronic acid (0.057 g, 0.25 mmol) and Pd(Ph₃P)₄ (0.015 g, 0.013 mmol) were added to a solution of 1-(6-chloropyrido[2,3-b]pyrazin-2-yl)-4-methylpiperidin-4-amine (0.035 g, 0.13 mmol) in dioxanes (2 mL) in a microwave vial. The slurry was sparged with Ar for 10 minutes, capped and heated to 100° C. for 1 hour. The reaction was concentrated and chromatographed eluting with EtOAc followed by 0-10% MeOH/DCM with 0.2% NH₄OH as additive to give 1-(6-(3-chloro-2-(trifluoromethyl)phenyl)pyrido[2,3-b]pyrazin-2-yl)-4-methylpiperidin-4-amine (0.011 g, 20% yield). ¹H NMR (400 MHz, CDCl₃) δ 8.80 (s, 1H), 8.00 (d, 1H, J=8.2 Hz), 7.59-7.56 (m, 1H), 7.50 (s, 1H), 7.49-7.43 (m, 2H), 4.02- 3.96 (m, 2H), 3.84-3.76 (m, 2H), 1.73-1.66 (m, 2H), 1.61-1.55 (m, 2H), 1.23 (s, 3H); m/z (esi/APCI) M+1=422.2.

Example 12

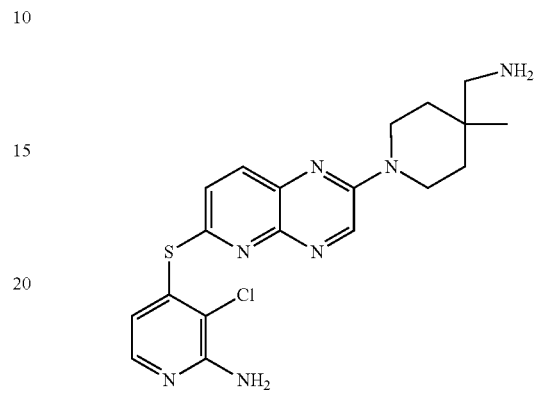

4-((2-(4-(aminomethyl)-4-methylpiperidin-1-yl) pyrido[2,3-b]pyrazin-6-yl)thio)-3-chloropyridin-2-amine Step A: N-Ethyl-N-isopropylpropan-2-amine (0.40 mL, 2.2 mmol) was added to a solution of 6-chloropyrido[2,3-b]pyrazin-2-yl trifluoromethanesulfonate (0.20 g, 0.64 mmol) in dioxanes cooled to 0° C., followed by tert-butyl ((4-methylpiperidin-4-yl)methyl)carbamate (0.15 g, 0.64 mmol). The reaction was stirred at 0° C. for 1 hour. 2-Amino-3-chloropyridine-4-thiol (0.20 g, 1.3 mmol) was added to the reaction, and the reaction was heated to 100° C. for 4 hours. The reaction was concentrated in vacuo, and the material chromatographed using 10-100% EtOAc/hexanes as eluent to give tert-butyl ((1-(6-((2-amino-3-chloropyridin-4-yl)thio)pyrido[2,3-b]pyrazin-2-yl)-4-methylpiperidin-4-yl)methyl)carbamate (0.11 g, 33% yield), m/z (esi/APCI) M+1=516.2.

Step B: TFA (1 mL) was added to a solution of tert-butyl ((1-(6-((2-amino-3-chloropyridin-4-yl)thio)pyrido[2,3-b]pyrazin-2-yl)-4-methylpiperidin-4-yl)methyl)carbamate (0.11 g, 0.21 mmol) in DCM (1 mL), and the reaction was stirred at room temperature for 1 hour. The reaction was concentrated in vacuo, and the material was partitioned between EtOAc and 1N NaOH. The layers were separated. The organics were washed with brine, dried over MgSO₄ and concentrated in vacuo. The material was chromatographed using 0-10% MeOH/DCM with 0.2% NH₄OH to give 4-((2-(4-(aminomethyl)-4-methylpiperidin-1-yl)pyrido[2,3-b]pyrazin-6-yl)thio)-3-chloropyridin-2-amine (0.053 g, 0.13 mmol, 60% yield). ¹H NMR (400 MHz, CDCl₃) δ 8.73 (s, 1H), 7.90 (d, 1H, J=8.6 Hz), 7.83 (d, 1H, J=5.0 Hz), 7.50 (d, 1H, J=8.6 Hz), 6.67 (d, 1H, J=5.0 Hz), 4.92 (s, 2H), 4.11 (dt, 2H, J=13.3, 4.7 Hz), 3.57-3.50 (m, 2H), 2.60 (s, 2H), 1.64-1.47 (m, 4H), 1.05 (s, 3H); m/z (esi/APCI) M+1=416.1.

Example 13

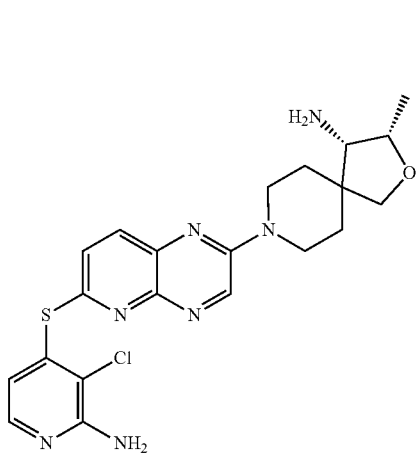 [SMILES: C[C@@H]1OCC2(CCN(c3cnc4nc(Sc5ccnc(N)c5Cl)ccc4n3)CC2)[C@@H]1N]

(3S,4S)-8-(6-((2-amino-3-chloropyridin-4-yl)thio)
pyrido[2,3-b]pyrazin-2-yl)-3-methyl-2-oxa-8-
azaspiro[4,5]decan-4-amine Step A: N-Ethyl-N-isopropylpropan-2-amine (0.94 mL, 5.2 mmol) was added to a solution of 6-chloropyrido[2,3-b]pyrazin-2-yl trifluoromethanesulfonate (0.47 g, 1.5 mmol) in DMA cooled to 0° C., followed by (3S,4S)-3-methyl-2-oxa-8-azaspiro[4.5]decan-4-amine dihydrochloride (0.36 g, 1.5 mmol). The reaction was stirred at 0° C. for 1 hour. The reaction was poured into water and extracted three times with DCM. The combined organics were washed with water, brine, dried over MgSO$_4$ and concentrated in vacuo. The material was chromatographed eluting with 0-10% MeOH/DCM with 0.2% NH$_4$OH as additive to give (3S,4S)-8-(6-chloropyrido[2,3-b]pyrazin-2-yl)-3-methyl-2-oxa-8-azaspiro[4.5]decan-4-amine (0.42 g, 84% yield), m/z (esi/APCI) M+1=334.2.

Step B: N-Ethyl-N-isopropylpropan-2-amine (0.097 mL, 0.54 mmol) and 2-amino-3-chloropyridine-4-thiol (0.087 g, 0.54 mmol) were added to a solution of (3S,4S)-8-(6-chloropyrido[2,3%]pyrazin-2-yl)-3-methyl-2-oxa-8-azaspiro[4.5]decan-4-amine (0.090 g, 0.27 mmol) in dioxanes, and the reaction was stirred at 100° C. for 2 hours. The reaction was concentrated in vacuo, and the residue chromatographed eluting with 0-10% MeOH/DCM with 0.2% NH$_4$OH as additive to give (3S,4S)-8-(6-((2-amino-3-chloropyridin-4-yl)thio)pyrido[2,3%]pyrazin-2-yl)-3-methyl-2-oxa-8-azaspiro[4.5]decan-4-amine (0.059 g, 0.13 mmol, 48% yield). $^1$H (400 MHz, CDCl$_3$) δ 8.73 (s, 1H), 7.90 (d, 1H, J=8.6 Hz), 7.84 (d, 1H, J=5.5 Hz), 7.49 (d, 1H, J=8.6 Hz), 6.69 (d, 1H, J=5.0 Hz), 4.95 (s, 2H), 4.22-4.16 (m, 1H), 4.14-4.04 (m, 2H), 3.83 (d, 1H, J=8.6 Hz), 3.70 (d, 1H, J=8.9 Hz), 3.65-3.59 (m, 1H), 3.55-3.48 (m, 1H), 3.05 (d, 1H, J=4.7 Hz), 1.96-1.89 (m, 1H), 1.83-1.69 (m, 3H), 1.24 (d, 3H, J=6.2 Hz); m/z (esi/APCI) M+1=458.1.

Example 14

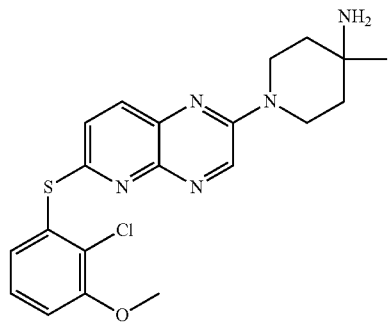

1-(6-((2-chloro-3-methoxyphenyl)thio)pyrido[2,3-b]
pyrazin-2-yl)-4-methylpiperidin-4-amine Step A: N-Ethyl-N-isopropylpropan-2-amine (0.25 mL, 1.4 mmol) was added to a solution of 6-chloropyrido[2,3-b]pyrazin-2-yl trifluoromethanesulfonate (0.40 g, 1.3 mmol) in DMA cooled to 0° C., followed by tert-butyl (4-methylpiperidin-4-yl)carbamate (0.30 g, 1.4 mmol). The reaction was stirred at 0° C. for 1 hour. The reaction was poured onto water and extracted twice with MTBE. The combined organics were washed with water, brine, dried over MgSO$_4$, filtered and concentrated in vacuo. The material was purified by silica gel chromatography (10-100% EtOAc in hexanes) to give tert-butyl (1-(6-chloropyrido[2,3-b]pyrazin-2-yl)-4-methylpiperidin-4-yl)carbamate (0.46 g, 1.3 mmol, 98% yield).

Step B: Hunig's base (38 µL, 0.21 mmol) and 2-chloro-3-methoxybenzenethiol (37 mg, 0.21 mmol) were added to a solution of tert-butyl (1-(6-chloropyrido[2,3-b]pyrazin-2-yl)-4-methylpiperidin-4-yl)carbamate (40 mg, 0.11 mmol) in dioxane (1.1 mL, 0.11 mmol). The reaction was stirred at 100° C. for 2 hours. The reaction was concentrated in vacuo and purified by silica gel chromatography (0%-10% DCM:MeOH). The desired fractions were combined and concentrated in vacuo. The concentrate was suspended in DCM, and TFA (81 µL, 1.06 mmol) was added. The mixture was stirred at room temperature for 1 hour. The reaction was concentrated in vacuo and partitioned between DCM and 1M NaOH, and the layers were separated. The combined organics were washed with brine, dried over Na$_2$SO$_4$ and concentrated in vacuo. The residue was purified by normal phase chromatography using 0%-10% DCM:MeOH (2% NH$_4$OH) as eluent. Fractions containing product were combined and concentrated in vacuo to give 1-(6-((2-chloro-3-methoxyphenyl)thio)pyrido[2,3%]pyrazin-2-yl)-4-methylpiperidin-4-amine (13 mg, 0.032 mmol, 30% yield). $^1$H NMR (400 MHz, CDCl$_3$) δ 8.67 (s, 1H), 7.78 (d, 1H, J=9.6 Hz), 7.34-7.32 (m, 1H), 7.15 (d, 1H, J=8.7 Hz), 7.00 (d, 1H, J=8.2 Hz), 3.94 (s, 3H), 3.92-3.87 (m, 2H), 3.80-3.73 (m, 2H), 1.70-1.65 (m, 2H), 1.62-1.58 (m, 2H), 1.24 (s, 3H); m/z (esi/APCI) M+1=416.1.

Example 15

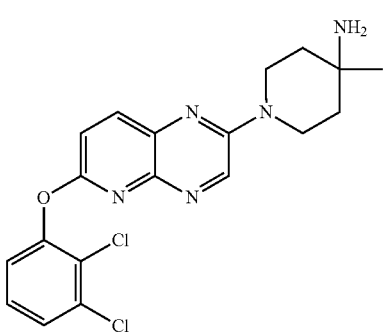

1-(6-(2,3-dichlorophenoxy)pyrido[2,3-b]pyrazin-2-yl)-4-methylpiperidin-4-amine

Step A: N-Ethyl-N-isopropylpropan-2-amine (0.25 mL, 1.4 mmol) was added to a solution of 6-chloropyrido[2,3-b]pyrazin-2-yl trifluoromethanesulfonate (0.40 g, 1.3 mmol) in DMA cooled to 0° C., followed by tert-butyl (4-methylpiperidin-4-yl)carbamate (0.30 g, 1.4 mmol). The reaction was stirred at 0° C. for 1 hour. The reaction was poured onto water and extracted twice with MTBE. The combined organics were washed with water, brine, dried over MgSO$_4$, filtered and concentrated in vacuo. The material was purified by silica gel chromatography (10-100% EtOAc in hexanes) to give tert-butyl (1-(6-chloropyrido[2,3-b]pyrazin-2-yl)-4-methylpiperidin-4-yl)carbamate (0.46 g, 1.3 mmol, 98% yield).

Step B: N-Ethyl-N-isopropylpropan-2-amine (38 µL, 0.21 mmol), cesium carbonate (69 mg, 0.21 mmol) and 2,3-dichlorophenol (35 mg, 0.21 mmol) were added to a solution of tert-butyl (1-(6-chloropyrido[2,3%]pyrazin-2-yl)-4-methylpiperidin-4-yl)carbamate (40 mg, 0.11 mmol) in 1,4-dioxane (1.06 mL, 0.11 mmol). The reaction was microwaved at 150° C. for 3 hours. The reaction was partitioned between water and EtOAc. The combined organics were washed with brine, dried over Na$_2$SO$_4$ and concentrated in vacuo. The concentrate was purified by prep HPLC (Gilson, 5-95% ACN/0.1% TFA in water/0.1% TFA). Fractions containing product were combined and partitioned between DCM and 1M NaOH, and the layers were separated. The combined organics were washed with brine, dried over Na$_2$SO$_4$ and concentrated in vacuo to give 1-(6-(2,3-dichlorophenoxy)pyrido[2,3-b]pyrazin-2-yl)-4-methylpiperidin-4-amine (9 mg, 0.022 mmol, 21% yield). $^1$H NMR (400 MHz, CDCl$_3$) δ 8.57 (s, 1H), 8.04 (d, 1H, J=8.8 Hz), 7.37-7.31 (m, 2H), 7.26-7.22 (m, 2H), 3.90-3.83 (m, 2H), 3.77-3.69 (m, 2H), 1.71-1.64 (m, 2H), 1.59-1.53 (m, 2H), 1.22 (s, 3H); m/z (esi/APCI) M+1=404.1.

Example 16

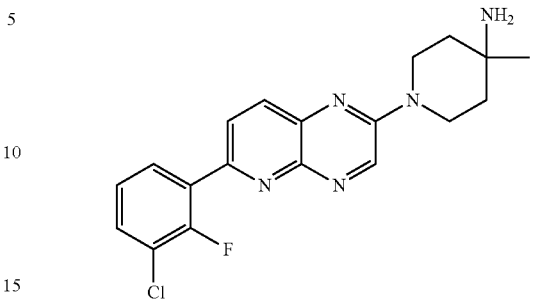

1-(6-(3-chloro-2-fluorophenyl)pyrido[2,3-b]pyrazin-2-yl)-4-methylpiperidin-4-amine Step A: N-Ethyl-N-isopropylpropan-2-amine (0.25 mL, 1.4 mmol) was added to a solution of 6-chloropyrido[2,3-b]pyrazin-2-yl trifluoromethanesulfonate (0.40 g, 1.3 mmol) in DMA cooled to 0° C., followed by tert-butyl (4-methylpiperidin-4-yl)carbamate (0.30 g, 1.4 mmol). The reaction was stirred at 0° C. for 1 hour. The reaction was poured onto water and extracted twice with MTBE. The combined organics were washed with water, brine, dried over MgSO$_4$, filtered and concentrated in vacuo. The material was purified by silica gel chromatography (10-100% EtOAc in hexanes) to give tert-butyl (1-(6-chloropyrido[2,3-b]pyrazin-2-yl)-4-methylpiperidin-4-yl)carbamate (0.46 g, 1.3 mmol, 98% yield).

Step B: K$_2$CO$_3$ (0.24 mL, 0.48 mmol) was added to a solution of tert-butyl (4-(6-bromopyrido[2,3%]pyrazin-2-yl)-1-methylcyclohexyl)carbamate (40 mg, 0.095 mmol) and 3-chloro-2-fluorophenylboronic acid (33 mg, 0.19 mmol) in dioxane (0.95 µL, 0.095 mmol). The reaction was degassed with Ar for 10 minutes, followed by addition of Pd(Ph$_3$P)$_4$ (11.0 mg, 0.0095 mmol). The reaction was heated to 90° C. for 2 hours. The reaction was partitioned between EtOAc and water, and the layers were separated. The organics were washed with brine, dried over Na$_2$SO$_4$ and concentrated in vacuo. The concentrate was purified by normal phase chromatography eluting with a 0%-100% DCM:EtOAc gradient to give tert-butyl (1-(6-(3-chloro-2-fluorophenyl)pyrido[2,3-b]pyrazin-2-yl)-4-methylpiperidin-4-yl)carbamate (44 mg, 0.092 mmol, 97% yield).

Step C: tert-Butyl (1-(6-(3-chloro-2-fluorophenyl)pyrido[2,3%]pyrazin-2-yl)-4-methylpiperidin-4-yl)carbamate (44 mg, 0.092 mmol) was dissolved in dichloromethane (0.92 mL, 0.092 mmol) and treated with 2,2,2-trifluoroacetic acid (0.11 mL, 1.4 mmol). The reaction was stirred at room temperature for 1 hour. The reaction was concentrated in vacuo, and the residue was partitioned between DCM and 1M NaOH. The layers were separated. The combined organics were washed with brine, dried over Na$_2$SO$_4$ and concentrated in vacuo. The concentrate was chromatographed eluting with a 0%-15% DCM:MeOH (2% NH$_4$OH) gradient to give 1-(6-(3-chloro-2-fluorophenyl)pyrido[2,3%]pyrazin-2-yl)-4-methylpiperidin-4-amine (28 mg, 0.074 mmol, 80% yield). $^1$H NMR (400 MHz, CDCl$_3$) δ 8.80 (s, 1H), 8.15 (t, 1H, J=7.2 Hz), 8.06-8.00 (m, 2H), 7.47 (t, 1H, J=7.0 Hz), 7.24 (t, 1H, J=8.0 Hz), 4.04-3.96 (m, 2H), 3.86-3.77 (m, 2H), 1.75-1.67 (m, 2H), 1.63-1.57 (m, 2H), 1.24 (s, 3H); m/z (esi/APCI) M+1=372.2.

Example 17

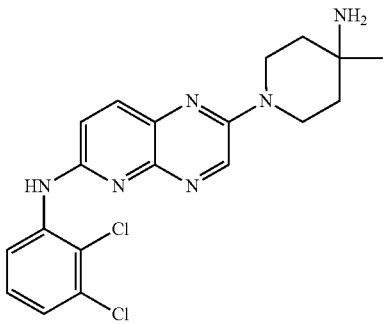

2-(4-amino-4-methylpiperidin-1-yl)-N-(2,3-dichlorophenyl)pyrido[2,3-b]pyrazin-6-amine Step A: N-Ethyl-N-isopropylpropan-2-amine (0.25 mL, 1.4 mmol) was added to a solution of 6-chloropyrido[2,3-b]pyrazin-2-yl trifluoromethanesulfonate (0.40 g, 1.3 mmol) in DMA cooled to 0° C., followed by tert-butyl (4-methylpiperidin-4-yl)carbamate (0.30 g, 1.4 mmol). The reaction was stirred at 0° C. for 1 hour. The reaction was poured onto water and extracted twice with MTBE. The combined organics were washed with water, brine, dried over MgSO$_4$, filtered and concentrated in vacuo. The material was purified by silica gel chromatography (10-100% EtOAc in hexanes) to give tert-butyl (1-(6-chloropyrido[2,3-b]pyrazin-2-yl)-4-methylpiperidin-4-yl)carbamate (0.46 g, 1.3 mmol, 98% yield).

Step B: Hunig's base (37 μL, 0.21 mmol), 2,3-dichloroaniline (34 mg, 0.21 mmol), rac-2,2-bis(Diphenylphosphino)-1,1'-binaphthyl (13 mg, 0.021 mmol), and tris(dibenzylideneacetone)dipalladium (0) (19 mg, 0.021 mmol) were added to a solution of tert-butyl (1-(6-chloropyrido[2,3-b]pyrazin-2-yl)-4-methyl piperidin-4-yl)carbamate (40 mg, 0.11 mmol) in dioxane (1.1 mL, 0.11 mmol) was added under Argon. The reaction was stirred at 100° C. for 2 hours in the microwave. The reaction was partitioned between water and EtOAc. The combined organics were washed with brine, dried over Na$_2$SO$_4$ and concentrated in vacuo. The concentrate was chromatographed using 0%-50% DCM: EtOAc as eluent. This was combined, concentrated and dissolved in DCM and treated with TFA (82 μL, 1.1 mmol). The reaction was stirred at room temperature for 1 hour. The reaction was concentrated in vacuo. The residue was partitioned between EtOAc and 1M NaOH, and the layers were separated. The combined organics were washed with brine, dried over Na$_2$SO$_4$ and concentrated in vacuo. The concentrate was chromatographed eluting with a 0%-15% DCM:MeOH (2% NH$_4$OH) gradient to give 2-(4-amino-4-methylpiperidin-1-yl)-N-(2,3-dichlorophenyl)pyrido[2,3-b]pyrazin-6-amine (1.1 mg, 0.0027 mmol, 3% yield). $^1$H NMR (400 MHz, CDCl$_3$) δ 8.76 (dd, 1H, J=8.4, 1.5 Hz), 8.63 (s, 1H), 7.90 (d, 1H, J=8.9 Hz), 7.28 (s, 1H), 7.12 (dd, 2H, J=8.1, 1.5 Hz), 3.89-3.81 (m, 2H), 3.78-3.70 (m, 2H), 1.75-1.67 (m, 2H), 1.62-1.56 (m, 2H), 1.23 (s, 3H); m/z (esi/APCI) M+1=403.1.

Example 18

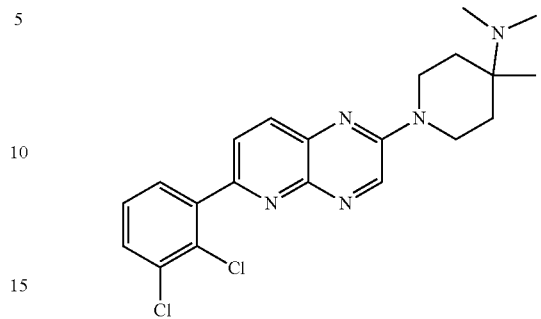

1-(6-(2,3-dichlorophenyl)pyrido[2,3-b]pyrazin-2-yl)-N,N,4-trimethylpiperidin-4-amine Formaldehyde (0.64 g, 8 mmol) was added to a solution of tert-butyl (1-(6-(2,3-dichlorophenyl)pyrido[2,3-b]pyrazin-2-yl)-4-methylpiperidin-4-yl)(methyl)carbamate (0.20 g, 0.39 mmol) in formic acid (3.6 g, 80 mmol). The reaction was heated to 65° C. for 2 hours sealed in a microwave vessel (conventional heating). The reaction was then heated to 80° C. for 28 hours. The reaction was concentrated in vacuo and dissolved into water, and the water basified with 1N NaOH. The aqueous layer was extracted twice with EtOAc. The combined organics were washed with brine, dried over MgSO$_4$ and concentrated in vacuo. The material was chromatographed using 0-10% MeOH/DCM with 0.2% NH$_4$OH to give 1-(6-(2,3-dichlorophenyl)pyrido[2,3-b]pyrazin-2-yl)-N,N,4-trimethylpiperidin-4-amine (0.033 g, 20% yield). $^1$H (400 MHz, CDCl$_3$) δ 8.79 (s, 1H), 8.02 (d, 1H, J=8.6 Hz), 7.84 (d, 1H, J=8.6 Hz), 7.68-7.66 (m, 1H), 7.54-7.51 (m, 1H), 7.31 (t, 1H, J=7.8 Hz), 3.94-3.88 (m, 2H), 3.83-3.75 (m, 2H), 2.25 (s, 6H), 1.99-1.91 (m, 2H), 1.61-1.54 (m, 2H), 0.98 (s, 3H); m/z (esi/APCI) M+1=416.1.

Example 19

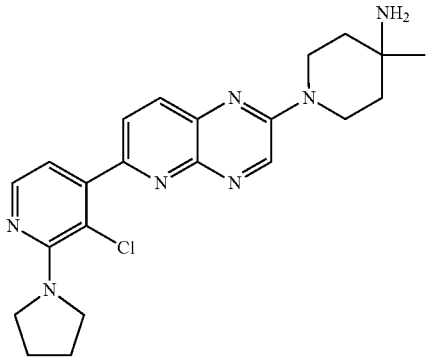 [SMILES: CC1(N)CCN(c2cnc3nc(-c4ccnc(N5CCCC5)c4Cl)ccc3n2)CC1]

1-(6-(3-chloro-2-(pyrrolidin-1-yl)pyridin-4-yl)pyrido[2,3-b]pyrazin-2-yl)-4-methylpiperidin-4-amine Step A: K$_2$CO$_3$ (1.6 mL, 3.2 mmol) and (3-chloro-2-fluoropyridin-4-yl)boronic acid (0.46 g, 2.6 mmol) was added to a slurry of tert-butyl (1-(6-chloropyrido[2,3-b]pyrazin-2-yl)-4-methylpiperidin-4-yl)carbamate (0.40 g, 1.1 mmol) in dioxanes (2 mL). The reaction was sparged with Ar for 15 minutes, followed by addition of Pd(Ph₃P)₄ (0.12 g, 0.11 mmol). The reaction was heated to 80° C. for 2 hours. The reaction was concentrated in vacuo, and the material was chromatographed using 10-100% EtOAc/hexanes as eluent to give tert-butyl (1-(6-(3-chloro-2-fluoropyridin-4-yl)pyrido[2,3-b]pyrazin-2-yl)-4-methylpiperidin-4-yl)carbamate (0.23 g, 46% yield), m/z (esi/APCI) M+1=473.2.

Step B: Pyrrolidine (0.015 g, 0.21 mmol) and N-ethyl-N-isopropylpropan-2-amine (0.014 g, 0.11 mmol) were added to a solution of tert-butyl (1-(6-(3-chloro-2-fluoropyridin-4-yl)pyrido[2,3-b]pyrazin-2-yl)-4-methylpiperidin-4-yl)carbamate (0.025 g, 0.053 mmol) in dioxanes (0.5 mL). The reaction was sealed in a microwave vial and heated to 130° C. for 2 hours in a microwave. The reaction was concentrated in vacuo, and the material purified by column chromatography using 10-100% EtOAc/hexanes as eluent to give tert-butyl (1-(6-(3-chloro-2-(pyrrolidin-1-yl)pyridin-4-yl)pyrido[2,3-b]pyrazin-2-yl)-4-methylpiperidin-4-yl)carbamate (0.028 g, 0.053 mmol, 100% yield), m/z (esi/APCI) M+1=524.2.

Step C: TFA (1 mL) was added to a solution of tert-butyl (1-(6-(3-chloro-2-(pyrrolidin-1-yl)pyridin-4-yl)pyrido[2,3-b]pyrazin-2-yl)-4-methylpiperidin-4-yl)carbamate (0.028 g, 0.053 mmol) in DCM (1 mL). The reaction was stirred at room temperature for 1 hour. The reaction was concentrated in vacuo, and the material partitioned between EtOAc and 1N NaOH. The layers were separated. The organics were washed with brine, dried over MgSO₄ and concentrated in vacuo to give 1-(6-(3-chloro-2-(pyrrolidin-1-yl)pyridin-4-yl)pyrido[2,3-b]pyrazin-2-yl)-4-methylpiperidin-4-amine (0.0087 g, 0.021 mmol, 38% yield). ¹H (400 MHz, CDCl₃) δ 8.80 (s, 1H), 8.14 (d, 1H, J=5.0 Hz), 8.02 (d, 1H, J=8.6 Hz), 7.80 (d, 1H, J=8.6 Hz), 6.98 (d, 1H, J=5.0 Hz), 4.02-3.97 (m, 2H), 3.84-3.77 (m, 2H), 3.72-3.68 (m, 4H), 1.97-1.93 (m, 4H), 1.73-1.66 (m, 2H), 1.61-1.56 (m, 2H), 1.23 (s, 3H). m/z (esi/APCI) M+1=424.2.

The following compounds in Table 3 were prepared according to the above procedures using appropriate starting materials and intermediates.

TABLE 3

| Ex. # | Structure | Name | Prep | MS |
|---|---|---|---|---|
| 20 | 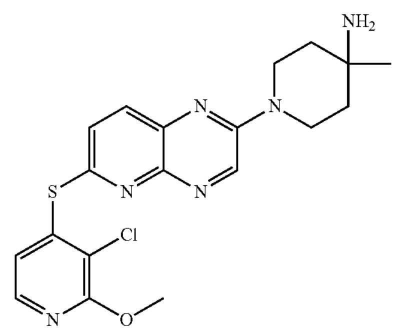 [SMILES: COc1nccc(Sc2ccc3nc(N4CCC(C)(N)CC4)cnc3n2)c1Cl] | 1-(6-((3-chloro-2-methoxypyridin-4-yl)thio)pyrido[2,3-b]pyrazin-2-yl)-4-methylpiperidin-4-amine | Ex. 1 | 390.1 |
| 21 | 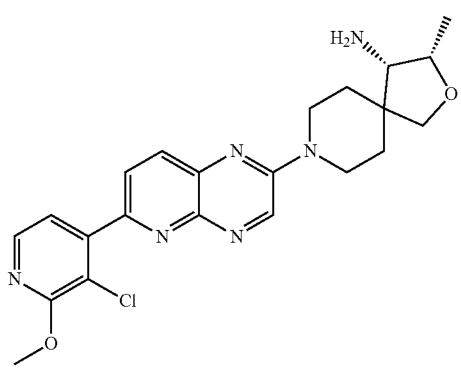 [SMILES: COc1nccc(-c2ccc3nc(N4CCC5(CC4)CO[C@@H](C)[C@H]5N)cnc3n2)c1Cl] | (3S,4S)-8-(6-(3-chloro-2-methoxypyridin-4-yl)pyrido[2,3-b]pyrazin-2-yl)-3-methyl-2-oxa-8-azaspiro[4.5]decan-4-amine | Ex. 2 | 441.1 |
| 22 | 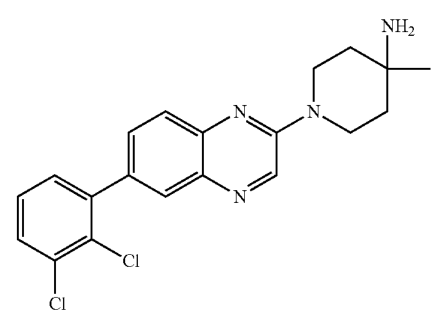 [SMILES: CC1(N)CCN(c2cnc3cc(-c4cccc(Cl)c4Cl)ccc3n2)CC1] | 1-(6-(2,3-dichlorophenyl)quinoxalin-2-yl)-4-methylpiperidin-4-amine | Ex. 2 | 387.1 |

TABLE 3-continued

| Ex. # | Structure | Name | Prep | MS |
|---|---|---|---|---|
| 23 | 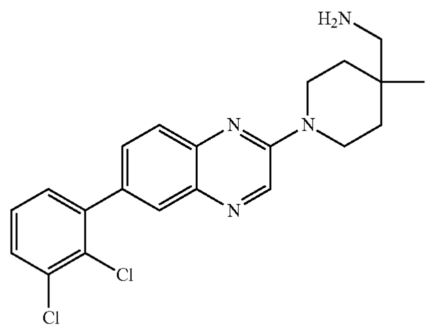 [SMILES: CC1(CN)CCN(c2cnc3cc(-c4cccc(Cl)c4Cl)ccc3n2)CC1] | (1-(6-(2,3-dichlorophenyl)quinoxalin-2-yl)-4-methylpiperidin-4-yl)methanamine | Ex. 2 | 401.1 |
| 24 | 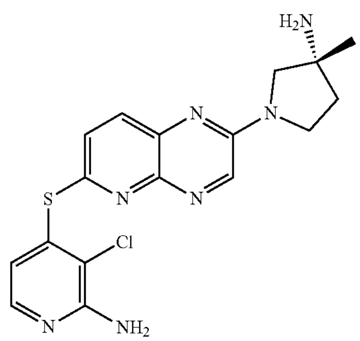 [SMILES: C[C@@]1(N)CCN(c2cnc3nc(Sc4ccnc(N)c4Cl)ccc3n2)C1] | (R)-4-((2-(3-amino-3-methylpyrrolidin-1-yl)pyrido[2,3-b]pyrazin-6-yl)thio)-3-chloropyridin-2-amine | Ex. 1 | 388.1 |
| 25 | 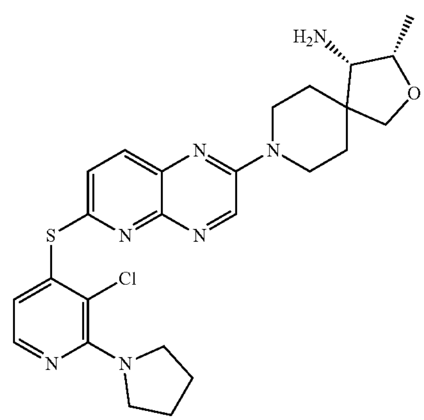 [SMILES: C[C@@H]1OCC2(CCN(c3cnc4nc(Sc5ccnc(N6CCCC6)c5Cl)ccc4n3)CC2)[C@@H]1N] | (3S,4S)-8-(6-((3-chloro-2-(pyrrolidin-1-yl)pyridin-4-yl)thio)pyrido[2,3-b]pyrazin-2-yl)-3-methyl-2-oxa-8-azaspiro[4.5]decan-4-amine | Ex. 11 | 402.1 |
| 26 | 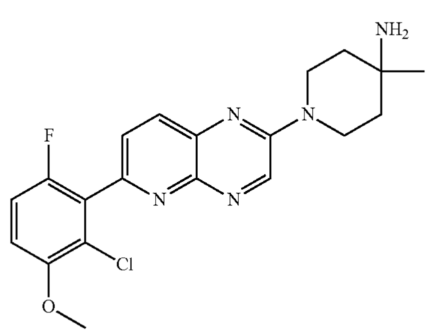 [SMILES: COc1ccc(F)c(-c2ccc3nc(N4CCC(C)(N)CC4)cnc3n2)c1Cl] | 1-(6-(2-chloro-6-fluoro-3-methoxyphenyl)pyrido[2,3-b]pyrazin-2-yl)-4-methylpiperidin-4-amine | Ex. 11 | 402.1 |

TABLE 3-continued

| Ex. # | Structure | Name | Prep | MS |
|---|---|---|---|---|
| 27 | 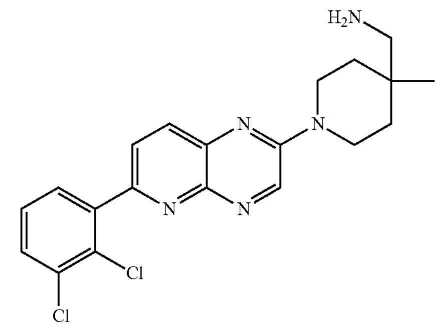 [SMILES: CC1(CN)CCN(c2cnc3nc(-c4cccc(Cl)c4Cl)ccc3n2)CC1] | (1-(6-(2,3-dichlorophenyl)pyrido[2,3-b]pyrazin-2-yl)-4-methylpiperidin-4-yl)methanamine | Ex. 2 | 402.1 |
| 28 | 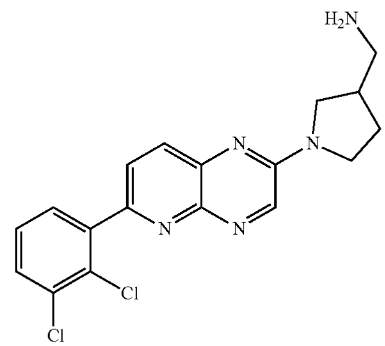 [SMILES: NCC1CCN(c2cnc3nc(-c4cccc(Cl)c4Cl)ccc3n2)C1] | (1-(6-(2,3-dichlorophenyl)pyrido[2,3-b]pyrazin-2-yl)pyrrolidin-3-yl)methanamine | Ex. 2 | 374.1 |
| 29 | 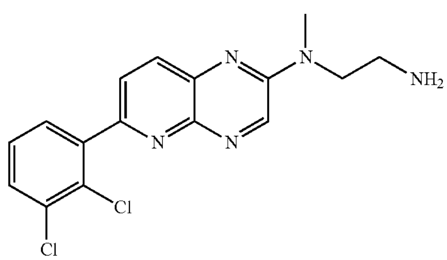 [SMILES: CN(CCN)c1cnc2nc(-c3cccc(Cl)c3Cl)ccc2n1] | N1-(6-(2,3-dichlorophenyl)pyrido[2,3-b]pyrazin-2-yl)-N1-methylethane-1,2-diamine | Ex. 2 | 348.0 |
| 30 | 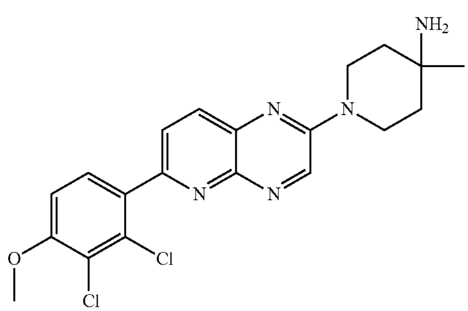 [SMILES: COc1ccc(-c2ccc3nc(N4CCC(C)(N)CC4)cnc3n2)c(Cl)c1Cl] | 1-(6-(2,3-dichloro-4-methoxyphenyl)pyrido[2,3-b]pyrazin-2-yl)-4-methylpiperidin-4-amine | Ex. 2 | 418.1 |
| 31 | 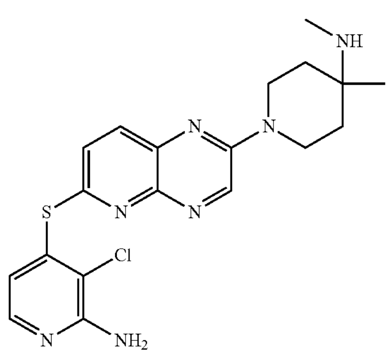 [SMILES: CNC1(C)CCN(c2cnc3nc(Sc4ccnc(N)c4Cl)ccc3n2)CC1] | 3-chloro-4-((2-(4-methyl-4-(methylamino)piperidin-1-yl)pyrido[2,3-b]pyrazin-6-yl)thio)pyridin-2-amine | Ex. 12 | 416.2 |

TABLE 3-continued

| Ex. # | Structure | Name | Prep | MS |
|---|---|---|---|---|
| 32 | 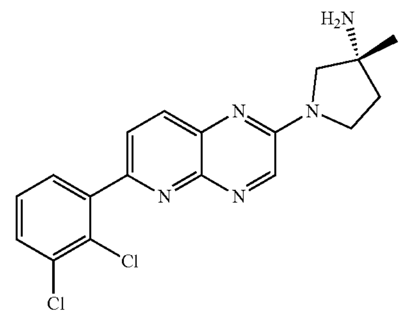 [SMILES: C[C@@]1(N)CCN(c2cnc3nc(-c4cccc(Cl)c4Cl)ccc3n2)C1] | (R)-1-(6-(2,3-dichlorophenyl)pyrido[2,3-b]pyrazin-2-yl)-3-methylpyrrolidin-3-amine | Ex. 2 | 374.1 |
| 33 | 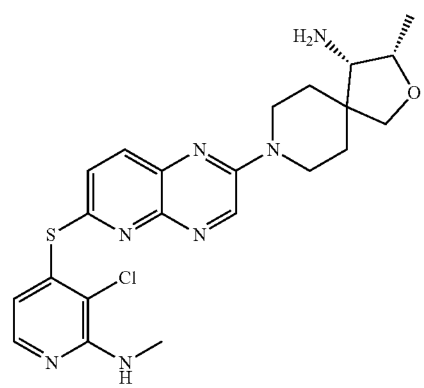 [SMILES: CNc1nccc(Sc2ccc3nc(N4CCC5(CC4)CO[C@@H](C)[C@H]5N)cnc3n2)c1Cl] | (3S,4S)-8-(6-((3-chloro-2-(methylamino)pyridin-4-yl)thio)pyrido[2,3-b]pyrazin-2-yl)-3-methyl-2-oxa-8-azaspiro[4.5]decan-4-amine | Ex. 9 | 472.2 |
| 34 | 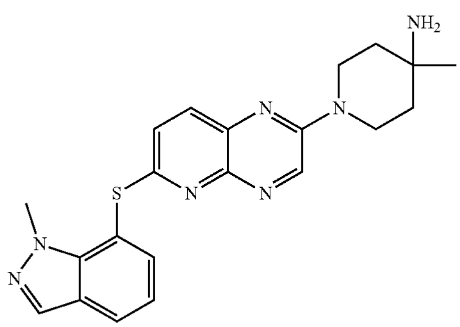 [SMILES: Cn1ncc2cccc(Sc3ccc4nc(N5CCC(C)(N)CC5)cnc4n3)c21] | 4-methyl-1-(6-((1-methyl-1H-indazol-7-yl)thio)pyrido[2,3-b]pyrazin-2-yl)piperidin-4-amine | Ex. 14 | 406.2 |
| 35 | 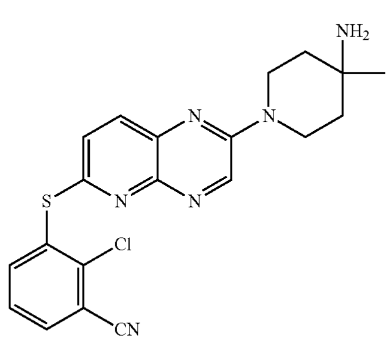 [SMILES: CC1(N)CCN(c2cnc3nc(Sc4cccc(C#N)c4Cl)ccc3n2)CC1] | 3-((2-(4-amino-4-methylpiperidin-1-yl)pyrido[2,3-b]pyrazin-6-yl)thio)-2-chlorobenzonitrile | Ex. 14 | 411.1 |

TABLE 3-continued

| Ex. # | Structure | Name | Prep | MS |
|---|---|---|---|---|
| 36 | 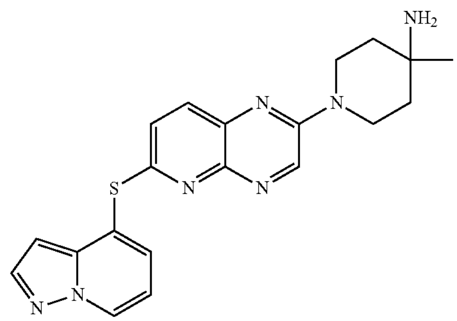 [SMILES: CC1(N)CCN(c2cnc3nc(Sc4cccn5nccc45)ccc3n2)CC1] | 4-methyl-1-(6-(pyrazolo[1,5-a]pyridin-4-ylthio)pyrido[2,3-b]pyrazin-2-yl)piperidin-4-amine | Ex. 14 | 392.2 |
| 37 | 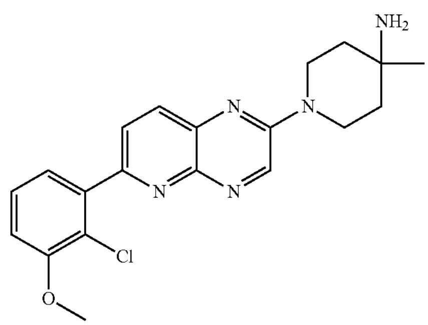 [SMILES: COc1cccc(-c2ccc3nc(N4CCC(C)(N)CC4)cnc3n2)c1Cl] | 1-(6-(2-chloro-3-methoxyphenyl)pyrido[2,3-b]pyrazin-2-yl)-4-methylpiperidin-4-amine | Ex. 16 | 384.2 |
| 38 | 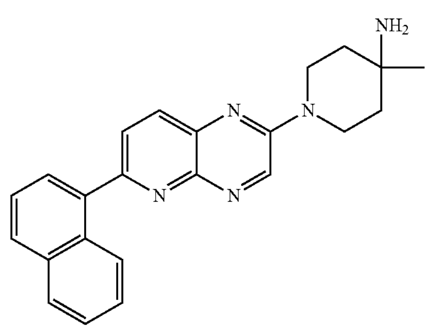 [SMILES: CC1(N)CCN(c2cnc3nc(-c4cccc5ccccc45)ccc3n2)CC1] | 4-methyl-1-(6-(naphthalen-1-yl)pyrido[2,3-b]pyrazin-2-yl)piperidin-4-amine | Ex. 16 | 370.2 |
| 39 | 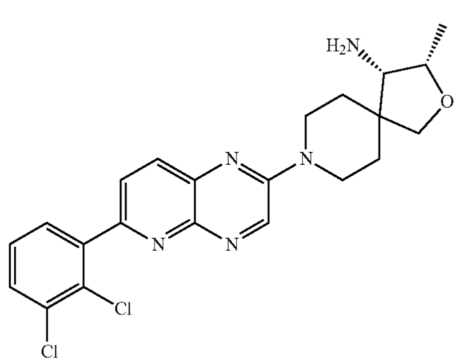 [SMILES: C[C@@H]1OCC2(CCN(c3cnc4nc(-c5cccc(Cl)c5Cl)ccc4n3)CC2)[C@@H]1N] | (3S,4S)-8-(6-(2,3-dichlorophenyl)pyrido[2,3-b]pyrazin-2-yl)-3-methyl-2-oxa-8-azaspiro[4.5]decan-4-amine | Ex. 16 | 444.2 |

TABLE 3-continued

| Ex. # | Structure | Name | Prep | MS |
|---|---|---|---|---|
| 40 | 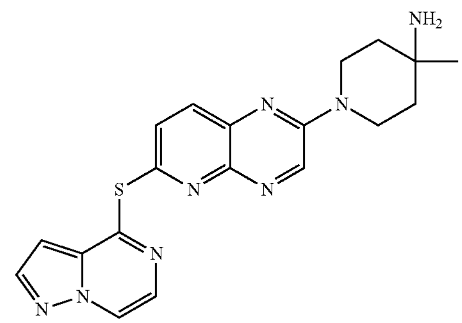 [SMILES: CC1(N)CCN(c2cnc3nc(Sc4nccn5nccc45)ccc3n2)CC1] | 4-methyl-1-(6-(pyrazolo[1,5-a]pyrazin-4-ylthio)pyrido[2,3-b]pyrazin-2-yl)piperidin-4-amine | Ex. 17 | 393.2 |
| 41 | 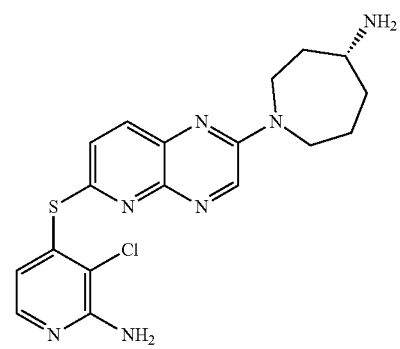 [SMILES: Nc1nccc(Sc2ccc3nc(N4CCC[C@@H](N)CC4)cnc3n2)c1Cl] | (R)-1-(6-((2-amino-3-chloropyridin-4-yl)thio)pyrido[2,3-b]pyrazin-2-yl)azepan-4-amine | Ex. 12 | 402.2 |
| 42 | 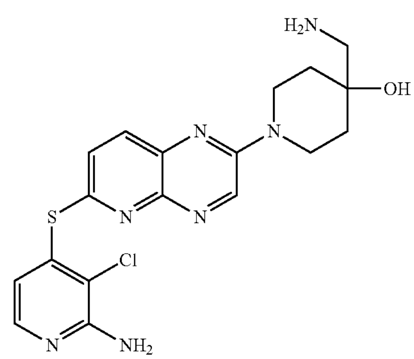 [SMILES: NCC1(O)CCN(c2cnc3nc(Sc4ccnc(N)c4Cl)ccc3n2)CC1] | 1-(6-((2-amino-3-chloropyridin-4-yl)thio)pyrido[2,3-b]pyrazin-2-yl)-4-(aminomethyl)piperidin-4-ol | Ex. 8 | 418.1 |
| 43 | 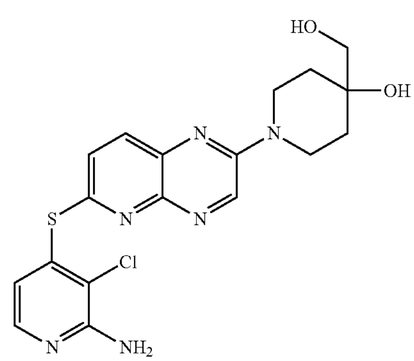 [SMILES: Nc1nccc(Sc2ccc3nc(N4CCC(O)(CO)CC4)cnc3n2)c1Cl] | (4-amino-1-(6-((2-amino-3-chloropyridin-4-yl)thio)pyrido[2,3-b]pyrazin-2-yl)piperidin-4-yl)methanol | Ex. 8 | 418.1 |

TABLE 3-continued

| Ex. # | Structure | Name | Prep | MS |
|---|---|---|---|---|
| 44 | 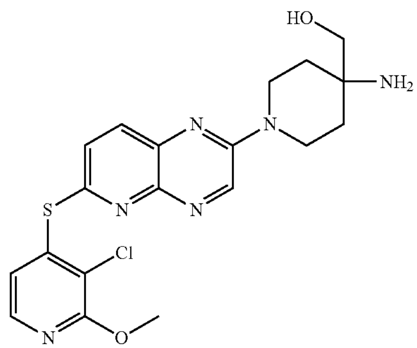 [SMILES: COc1nccc(Sc2ccc3nc(N4CCC(N)(CO)CC4)cnc3n2)c1Cl] | (4-amino-1-(6-((3-chloro-2-methoxypyridin-4-yl)thio)pyrido[2,3-b]pyrazin-2-yl)piperidin-4-yl)methanol | Ex. 8 | 433.1 |
| 45 | 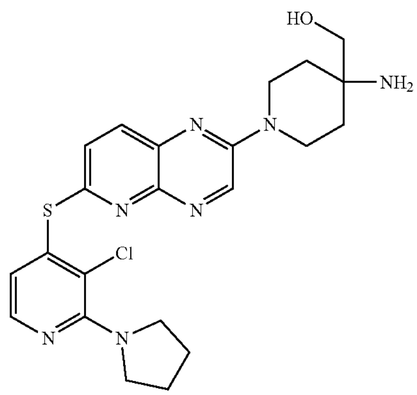 [SMILES: NC1(CO)CCN(c2cnc3nc(Sc4ccnc(N5CCCC5)c4Cl)ccc3n2)CC1] | (4-amino-1-(6-((3-chloro-2-(pyrrolidin-1-yl)pyridin-4-yl)thio)pyrido[2,3-b]pyrazin-2-yl)piperidin-4-yl)methanol | Ex. 8 | 472.1 |
| 46 | 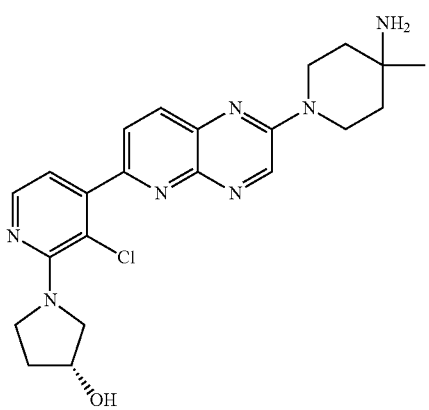 [SMILES: CC1(N)CCN(c2cnc3nc(-c4ccnc(N5CC[C@@H](O)C5)c4Cl)ccc3n2)CC1] | (R)-1-(4-(2-(4-amino-4-methylpiperidin-1-yl)pyrido[2,3-b]pyrazin-6-yl)-3-chloropyridin-2-yl)pyrrolidin-3-ol | Ex. 19 | 440.2 |
| 47 | 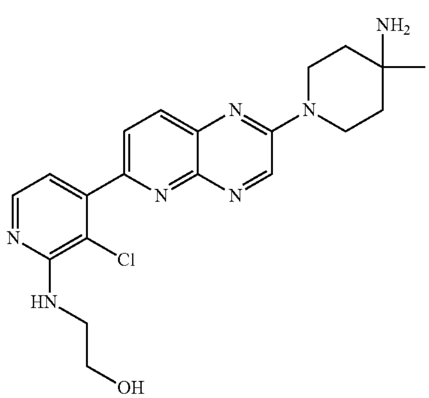 [SMILES: CC1(N)CCN(c2cnc3nc(-c4ccnc(NCCO)c4Cl)ccc3n2)CC1] | 2-((4-(2-(4-amino-4-methylpiperidin-1-yl)pyrido[2,3-b]pyrazin-6-yl)-3-chloropyridin-2-yl)amino)ethan-1-ol | Ex. 19 | 414.2 |

TABLE 3-continued

| Ex. # | Structure | Name | Prep | MS |
|---|---|---|---|---|
| 48 | 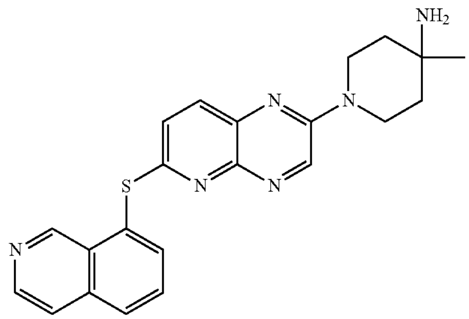 [SMILES: CC1(N)CCN(c2cnc3nc(Sc4cccc5ccncc45)ccc3n2)CC1] | 1-(6-(isoquinolin-8-ylthio)pyrido[2,3-b]pyrazin-2-yl)-4-methylpiperidin-4-amine | Ex. 14 | 403.2 |
| 49 | 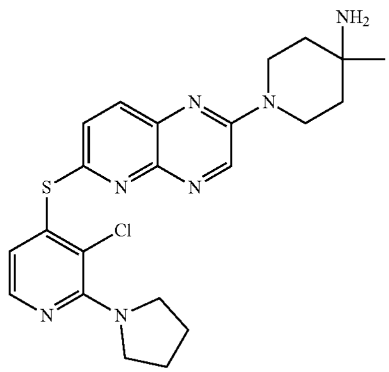 [SMILES: CC1(N)CCN(c2cnc3nc(Sc4ccnc(N5CCCC5)c4Cl)ccc3n2)CC1] | 1-(6-((3-chloro-2-(pyrrolidin-1-yl)pyridin-4-yl)thio)pyrido[2,3-b]pyrazin-2-yl)-4-methylpiperidin-4-amine | Ex. 14 | 456.1 |
| 50 | 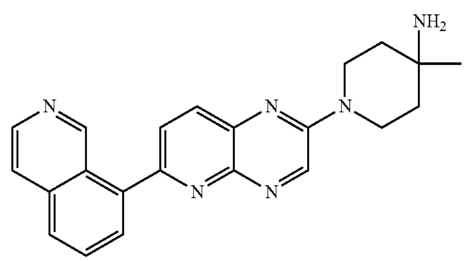 [SMILES: CC1(N)CCN(c2cnc3nc(-c4cccc5ccncc45)ccc3n2)CC1] | 1-(6-(isoquinolin-8-yl)pyrido[2,3-b]pyrazin-2-yl)-4-methylpiperidin-4-amine | Ex. 16 | 371.2 |
| 51 | 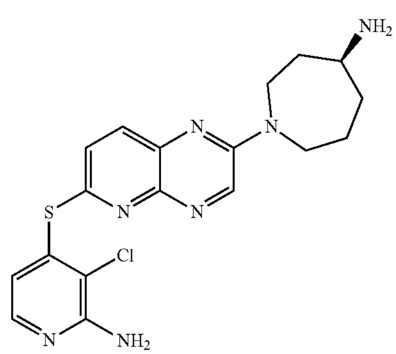 [SMILES: Nc1nccc(Sc2ccc3nc(N4CCC[C@H](N)CC4)cnc3n2)c1Cl] | (S)-1-(6-((2-amino-3-chloropyridin-4-yl)thio)pyrido[2,3-b]pyrazin-2-yl)azepan-4-amine | Ex. 12 | 402.1 |
| 52 | 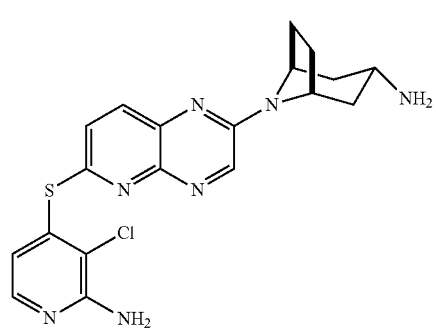 [SMILES: Nc1nccc(Sc2ccc3nc(N4[C@H]5CC[C@H]4CC(N)C5)cnc3n2)c1Cl] | (1R,3s,5S)-8-(6-((2-amino-3-chloropyridin-4-yl)thio)pyrido[2,3-b]pyrazin-2-yl)-8-azabicyclo[3.2.1]octan-3-amine | Ex. 12 | 414.1 |

TABLE 3-continued

| Ex. # | Structure | Name | Prep | MS |
|---|---|---|---|---|
| 53 | 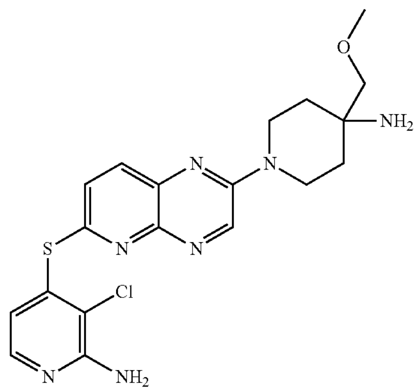 [SMILES: COCC1(N)CCN(c2cnc3nc(Sc4ccnc(N)c4Cl)ccc3n2)CC1] | 4-((2-(4-amino-4-(methoxymethyl)piperidin-1-yl)pyrido[2,3-b]pyrazin-6-yl)thio)-3-chloropyridin-2-amine | Ex. 8 | 432.1 |
| 54 | 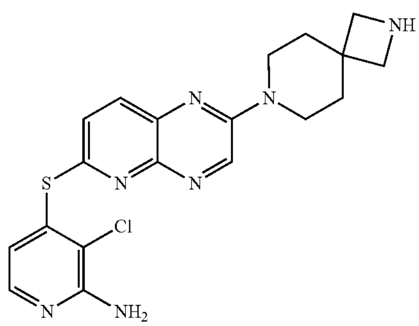 [SMILES: Nc1nccc(Sc2ccc3nc(N4CCC5(CC4)CNC5)cnc3n2)c1Cl] | 4-((2-(2,7-diazaspiro[3.5]nonan-7-yl)pyrido[2,3-b]pyrazin-6-yl)thio)-3-chloropyridin-2-amine | Ex. 12 | 414.1 |
| 55 | 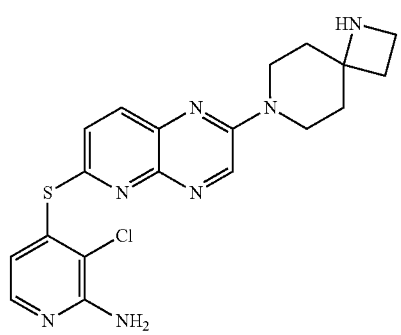 [SMILES: Nc1nccc(Sc2ccc3nc(N4CCC5(CCN5)CC4)cnc3n2)c1Cl] | 4-((2-(1,7-diazaspiro[3.5]nonan-7-yl)pyrido[2,3-b]pyrazin-6-yl)thio)-3-chloropyridin-2-amine | Ex. 12 | 414.0 |
| 56 | 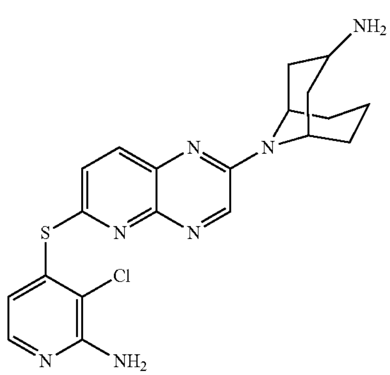 [SMILES: Nc1nccc(Sc2ccc3nc(N4C5CCCC4CC(N)C5)cnc3n2)c1Cl] | (1R,5S)-9-(6-((2-amino-3-chloropyridin-4-yl)thio)pyrido[2,3-b]pyrazin-2-yl)-9-azabicyclo[3.3.1]nonan-3-amine | Ex. 12 | 428.1 |

TABLE 3-continued

| Ex. # | Structure | Name | Prep | MS |
|---|---|---|---|---|
| 57 | 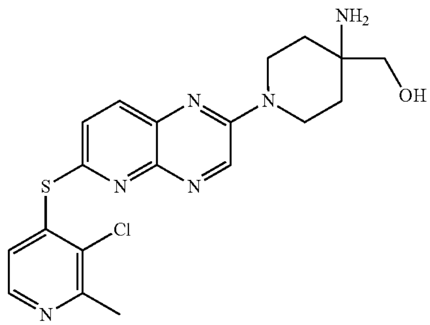 [SMILES: Cc1nccc(Sc2ccc3nc(N4CCC(N)(CO)CC4)cnc3n2)c1Cl] | (4-amino-1-(6-((3-chloro-2-methylpyridin-4-yl)thio)pyrido[2,3-b]pyrazin-2-yl)piperidin-4-yl)methanol | Ex. 12 | 417.1 |
| 58 | 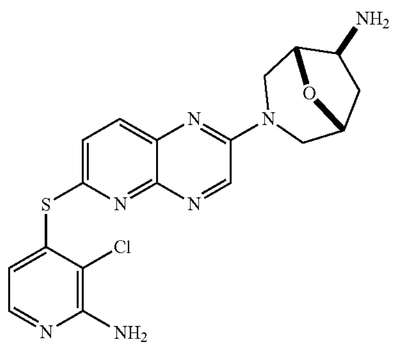 [SMILES: Nc1nccc(Sc2ccc3nc(N4C[C@H]5C[C@H](N)[C@@H](C4)O5)cnc3n2)c1Cl] | (1R,5R,6S)-3-(6-((2-amino-3-chloropyridin-4-yl)thio)pyrido[2,3-b]pyrazin-2-yl)-8-oxa-3-azabicyclo[3.2.1]octan-6-amine | Ex. 13 | 416.2 |
| 59 | 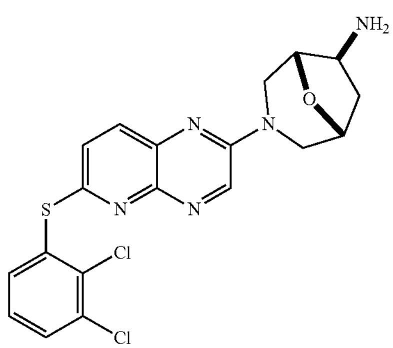 [SMILES: N[C@H]1C[C@@H]2CN(c3cnc4nc(Sc5cccc(Cl)c5Cl)ccc4n3)C[C@H]1O2] | (1R,5R,6S)-3-(6-((2,3-dichlorophenyl)thio)pyrido[2,3-b]pyrazin-2-yl)-8-oxa-3-azabicyclo[3.2.1]octan-6-amine | Ex. 13 | 434.1 |
| 60 | 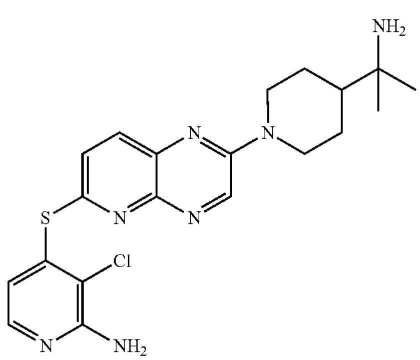 [SMILES: CC(C)(N)C1CCN(c2cnc3nc(Sc4ccnc(N)c4Cl)ccc3n2)CC1] | 4-((2-(4-(2-aminopropan-2-yl)piperidin-1-yl)pyrido[2,3-b]pyrazin-6-yl)thio)-3-chloropyridin-2-amine | Ex. 13 | 430.2 |

TABLE 3-continued
| Ex. # | Structure | Name | Prep | MS |
|---|---|---|---|---|
| 61 | 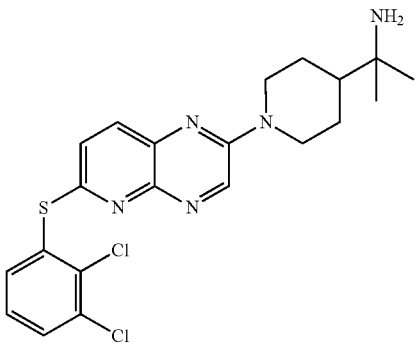 [SMILES: CC(C)(N)C1CCN(c2cnc3nc(Sc4cccc(Cl)c4Cl)ccc3n2)CC1] | 2-(1-(6-((2,3-dichlorophenyl)thio)pyrido[2,3-b]pyrazin-2-yl)piperidin-4-yl)propan-2-amine | Ex. 13 | 448.2 |
| 62 | 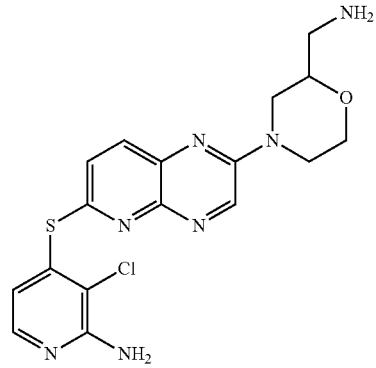 [SMILES: NCC1CN(c2cnc3nc(Sc4ccnc(N)c4Cl)ccc3n2)CCO1] | 4-((2-(2-(aminomethyl)morpholino)pyrido[2,3-b]pyrazin-6-yl)thio)-3-chloropyridin-2-amine | Ex. 14 | 404.1 |
| 63 | 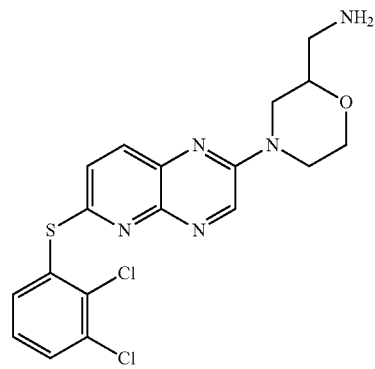 [SMILES: NCC1CN(c2cnc3nc(Sc4cccc(Cl)c4Cl)ccc3n2)CCO1] | (4-(6-((2,3-dichlorophenyl)thio)pyrido[2,3-b]pyrazin-2-yl)morpholin-2-yl)methanamine | Ex. 14 | 422.1 |
| 64 | 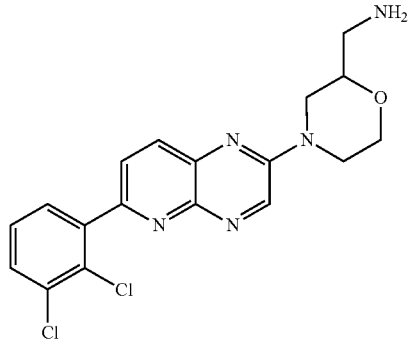 [SMILES: NCC1CN(c2cnc3nc(-c4cccc(Cl)c4Cl)ccc3n2)CCO1] | (4-(6-(2,3-dichlorophenyl)pyrido[2,3-b]pyrazin-2-yl)morpholin-2-yl)methanamine | Ex. 16 | 390.1 |

TABLE 3-continued

| Ex. # | Structure | Name | Prep | MS |
|---|---|---|---|---|
| 65 | 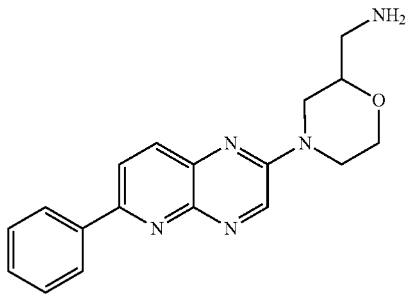 [SMILES: NCC1CN(c2cnc3nc(-c4ccccc4)ccc3n2)CCO1] | (4-(6-phenylpyrido[2,3-b]pyrazin-2-yl)morpholin-2-yl)methanamine | Ex. 16 | 322.2 |
| 66 | 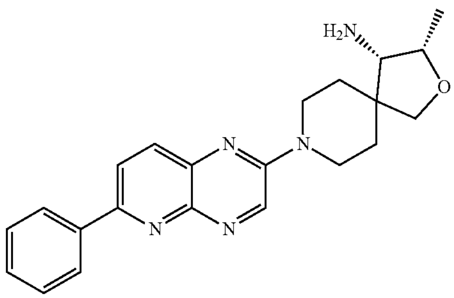 [SMILES: C[C@@H]1OCC2(CCN(c3cnc4nc(-c5ccccc5)ccc4n3)CC2)[C@@H]1N] | (3S,4S)-3-methyl-8-(6-phenylpyrido[2,3-b]pyrazin-2-yl)-2-oxa-8-azaspiro[4.5]decan-4-amine | Ex. 2 | 376.2 |

Example 67

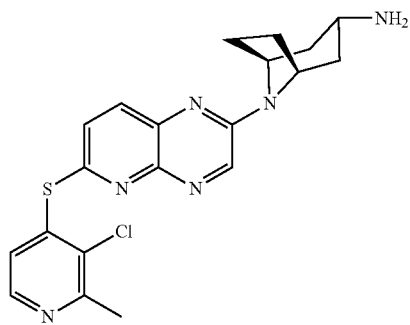 [SMILES: Cc1nccc(Sc2ccc3nc(N4[C@H]5CC[C@H]4CC(N)C5)cnc3n2)c1Cl]

(1R,3s,5S)-8-(6-((3-chloro-2-methylpyridin-4-yl)thio)pyrido[2,3-b]pyrazin-2-yl)-8-azabicyclo[3.2.1]octan-3-amine dihydrochloride N-Ethyl-N-isopropylpropan-2-amine (240 μL, 1.36 mmol) was added to a solution of 6-chloropyrido[2,3-b]pyrazin-2-yl trifluoromethanesulfonate (85 mg, 0.27 mmol) in dioxane (2 mL), followed by exo-3-(Boc-amino)-8-azabicyclo[3.2.1]octane (67.5 mg, 0.30 mmol), and the reaction was stirred at room temperature for 3 hours. Sodium 3-chloro-2-methylpyridine-4-thiolate (98.4 mg, 0.54 mmol) was added, and the reaction was heated to 75° C. for 18 hours. The reaction was concentrated and purified by silica gel (0-12% MeOH in DCM) to provide Boc product. The material was brought up in DCM (2 mL), and 4N HCl (1 mL) was added. The reaction was stirred for 4 hours. The reaction was concentrated to provide (1R,3s,5S)-8-(6-((3-chloro-2-methylpyridin-4-yl)thio)pyrido[2,3-Z]pyrazin-2-yl)-8-azabicyclo[3.2.1]octan-3-amine dihydrochloride (84 mg, 0.17 mmol, 64% yield). $^1$H NMR (400 MHz, $(CD_3)_2$SO) δ 8.95 (s, 1H), 8.34 (d, 1H, J=5.6 Hz), 8.13 (d, 1H, J=8.5 Hz), 7.90 (br s, 3H), 7.79 (d, 1H, J=8.5 Hz), 7.25 (d, 1H, J=5.6 Hz), 4.93 (s, 2H), 3.66 (m, 1H), 3.52-3.45 (m, 2H), 2.65 (s, 3H), 2.08 (m, 2H); m/z (esi/APCI) M+1=413.1.

Example 68

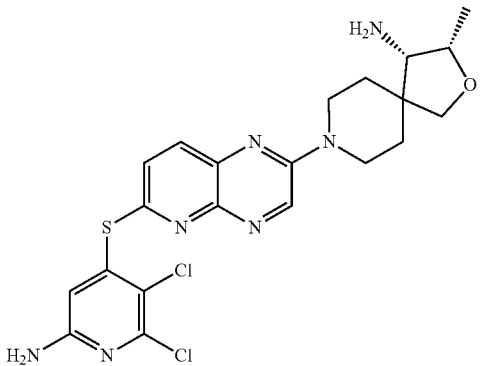 [SMILES: C[C@@H]1OCC2(CCN(c3cnc4nc(Sc5cc(N)nc(Cl)c5Cl)ccc4n3)CC2)[C@@H]1N]

(3S,4S)-8-(6-((6-amino-2,3-dichloropyridin-4-yl)thio)pyrido[2,3-b]pyrazin-2-yl)-3-methyl-2-oxa-8-azaspiro[4.5]decan-4-amine (3S,4S)-8-(6-Chloropyrido[2,3-b]pyrazin-2-yl)-3-methyl-2-oxa-8-azaspiro[4.5]decan-4-amine (50 mg, 0.15 mmol), tert-butyl (5,6-dichloro-4-mercaptopyridin-2-yl)carbamate (66 mg, 0.23 mmol) and Hunig's base (65 μL, 0.37 mmol) were placed in dioxane (1 mL) and heated to 70° C. for 18 hours. The reaction was concentrated down and purified by silica gel (0-15% MeOH in DCM with 2% NH$_4$OH) to provide Boc product. The material was brought up in DCM (5 mL), and TFA was added. The reaction was stirred for 5 hours. The reaction was concentrated and purified by reverse phase chromatography (5-95% ACN:water with 0.1% TFA). The material was brought up in 10% MeOH in DCM, and saturated sodium bicarbonate was added. The mixture was extracted with 10% MeOH in DCM (3×10 mL). The extracts were combined, dried with sodium sulfate, filtered and concentrated to provide (3%45')-8-(6-((6-amino-2,3-dichloropyridin-4-yl)thio)pyrido[2,3-b]pyrazin-2-yl)-3-methyl-2-oxa-8-azaspiro[4.5]decan-4-amine (32 mg, 0.06 mmol, 43% yield). $^1$H NMR (400 MHz, (CD$_3$)$_2$SO) δ 9.03 (s, 1H), 8.03 (d, 1H, J=8.5 Hz), 7.72 (d, 1H, J=8.5 Hz), 6.55 (s, 2H), 6.16 (s, 1H), 4.08 (m, 3H), 3.70 (d, 1H, J=8.5 Hz), 3.67-3.54 (m, 2H), 3.50 (d, 1H, J=8.5 Hz), 2.92 (d, 1H, J=5.1 Hz), 1.80 (m, 1H), 1.68 (m, 1H), 1.60-1.50 (m, 2H), 1.36 (m, 2H), 1.09 (d, 3H, J=6.3 Hz); m/z (esi/APCI) M+1=492.1.

Example 69

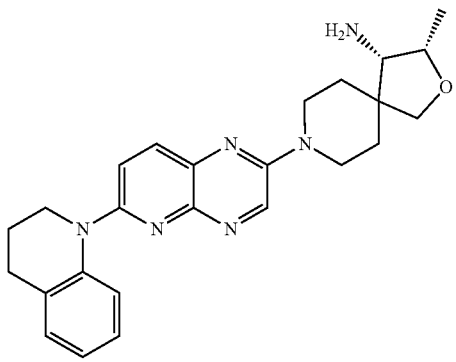 [SMILES: C[C@@H]1OCC2(CCN(c3cnc4nc(N5CCCc6ccccc65)ccc4n3)CC2)[C@@H]1N]

(3S,4S)-8-(6-(3,4-dihydroquinolin-1(2H)-yl)pyrido[2,3-b]pyrazin-2-yl)-3-methyl-2-oxa-8-azaspiro[4,5]decan-4-amine Step A: N-Ethyl-N-isopropylpropan-2-amine (0.94 mL, 5.2 mmol) was added to a solution of 6-chloropyrido[2,3-b]pyrazin-2-yl trifluoromethanesulfonate (0.47 g, 1.5 mmol) in DMA cooled to 0° C., followed by (3S,4S)-3-methyl-2-oxa-8-azaspiro[4.5]decan-4-amine dihydrochloride (0.36 g, 1.5 mmol). The reaction was stirred at 0° C. for 1 hour. The reaction was poured into water and extracted three times with DCM. The combined organics were washed with water, brine, dried over MgSO$_4$ and concentrated in vacuo. The material was chromatographed eluting with 0-10% MeOH/DCM with 0.2% NH$_4$OH as additive to give (3S,4S)-8-(6-chloropyrido[2,3-b]pyrazin-2-yl)-3-methyl-2-oxa-8-azaspiro[4.5]decan-4-amine (0.42 g, 84% yield), m/z (esi/APCI) M$^+$1=334.2.

Step B: Tripotassium phosphate (19 mg, 0.09 mmol) and bis(tri-t-butylphosphine)palladium (0) (1.15 mg, 0.0022 mmol) were added to a solution of (3S,4S)-8-(6-chloro-pyrido[2,3-b]pyrazin-2-yl)-3-methyl-2-oxa-8-azaspiro[4.5]decan-4-amine (15 mg, 0.045 mmol) and 1,2,3,4-tetrahydroquinoline (11 μL, 0.09 mmol) in DMA (449 μL, 0.045 mmol). This mixture was purged with nitrogen and heated to 100° C. for 20 hours. The reaction was poured onto water and extracted three times with EtOAc. The combined organics were washed with water, brine, dried over Na$_2$SO$_4$, filtered and concentrated in vacuo. The resultant residue was chromatographed eluting with 0-15% MeOH/DCM with 0.2% NH$_4$OH as additive to give ((3S,4S)-8-(6-(3,4-dihydroquinolin-1(2H)-yl)pyrido[2,3-b]pyrazin-2-yl)-3-methyl-2-oxa-8-azaspiro[4.5]decan-4-amine (0.0029 g, 0.0067 mmol, 15% yield). $^1$H (500 MHz, CDCl$_3$) δ 8.59 (s, 1H), 7.71 (d, 1H, J=9.3 Hz), 7.55 (d, 1H, J=9.3 Hz), 7.30 (d, 1H, J=8.1 Hz), 7.18 (d, 1H, J=7.6 Hz), 7.13 (t, 1H, J=7.8 Hz), 6.99 (t, 1H, J=7.3 Hz), 4.25-4.19 (m, 1H), 4.14 (t, 2H, J=6.3 Hz), 4.06-3.96 (m, 2H), 3.84 (d, 1H, J=8.8 Hz), 3.72 (d, 1H, J=8.8 Hz), 3.53-3.44 (m, 1H), 3.42-3.35 (m, 1H), 3.03 (d, 1H, J=3.7 Hz), 2.77 (t, 2H, J=6.3 Hz), 2.06-2.00 (m, 2H), 1.98-1.90 (m, 1H), 1.85-1.70 (m, 3H), 1.26 (d, 3H, J=6.2 Hz); m/z (esi/APCI) M+1=431.3.

Example 70

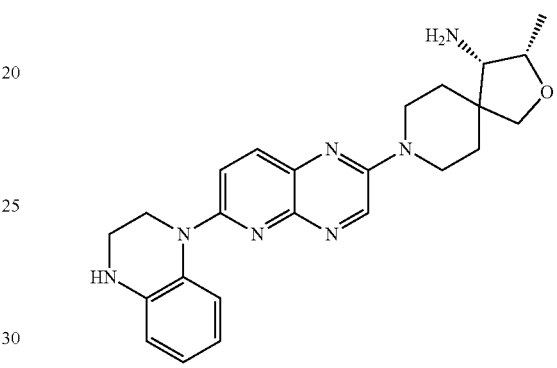

(3S,4S)-8-(6-(3,4-dihydroquinoxalin-1(2H)-yl)pyrido[2,3-b]pyrazin-2-yl)-3-methyl-2-oxa-8-azaspiro[4.5]decan-4-amine Step A: N-Ethyl-N-isopropylpropan-2-amine (0.94 mL, 5.2 mmol) was added to a solution of 6-chloropyrido[2,3-b]pyrazin-2-yl trifluoromethanesulfonate (0.47 g, 1.5 mmol) in DMA cooled to 0° C., followed by (3S,4S)-3-methyl-2-oxa-8-azaspiro[4.5]decan-4-amine dihydrochloride (0.36 g, 1.5 mmol). The reaction was stirred at 0° C. for 1 hour. The reaction was poured into water and extracted three times with DCM. The combined organics were washed with water, brine, dried over MgSO$_4$ and concentrated in vacuo. The material was chromatographed eluting with 0-10% MeOH/DCM with 0.2% NH$_4$OH as additive to give (3S,4S)-8-(6-chloropyrido[2,3-b]pyrazin-2-yl)-3-methyl-2-oxa-8-azaspiro[4.5]decan-4-amine (0.42 g, 84% yield), m/z (esi/APCI) M$^+$1=334.2.

Tripotassium phosphate (32 mg, 0.15 mmol) and bis(tri-t-butylphosphine)palladium (0) (1.9 mg, 0.0037 mmol) were added to a solution of (3S,4S)-8-(6-chloropyrido[2,3-b]pyrazin-2-yl)-3-methyl-2-oxa-8-azaspiro[4.5]decan-4-amine (25 mg, 0.075 mmol) and 3,4-dihydro-2H-quinoxaline-1-carboxylic acid tert-butyl ester (35 mg, 0.15 mmol) in DMA (749 μL, 0.075 mmol). This mixture was purged with nitrogen and heated to 100° C. for 20 hours. The reaction was poured onto water and extracted three times with EtOAc. The combined organics were washed with water, brine, dried over Na$_2$SO$_4$, filtered and concentrated in vacuo. The resultant residue was resuspended in DCM and treated with TFA. This was stirred for 1 hour at room temperature and then concentrated in vacuo. The residue was purified by HPLC eluting with a 5-60% ACN in water gradient with 0.1% TFA as additive. The product fractions were free-based with concentrated NaHCO₃, and the organics were extracted with DCM, washed with brine, dried over Na₂SO₄ and concentrated in vacuo to yield (3S,4S)-8-(6-(3,4-dihydroquinoxalin-1(2H)-yl)pyrido[2,3-b]pyrazin-2-yl)-3-methyl-2-oxa-8-azaspiro[4.5]decan-4-amine (0.011 g, 0.025 mmol, 33% yield). ¹H (500 MHz, CDCl₃) δ 8.59 (s, 1H), 7.74 (d, 1H, J=9.0 Hz), 7.60 (d, 1H, J=9.0 Hz), 7.23 (d, 1H, J=8.3 Hz), 6.94 (t, 1H, J=8.1 Hz), 6.69-6.64 (m, 2H), 4.29 (t, 2H, J=5.1 Hz), 4.25-4.19 (m, 1H), 4.08-3.96 (m, 2H), 3.86 (d, 1H, J=9.0 Hz), 3.73 (d, 1H, J=9.0 Hz), 3.49 (t, 2H, J=5.1 Hz), 3.48-3.42 (m, 1H), 3.42-3.33 (m, 1H), 3.05 (d, 1H, J=3.7 Hz), 1.98-1.90 (m, 1H), 1.87-1.72 (m, 3H), 1.29 (d, 3H, J=6.1 Hz); m/z (esi/APCI) M⁺1=432.3.

Example 71

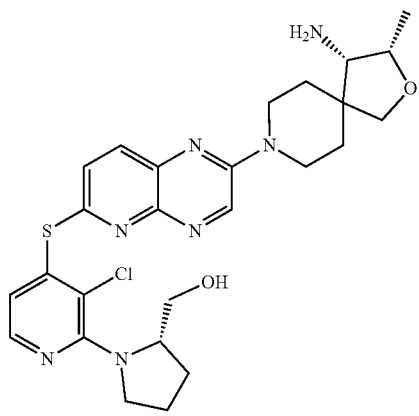 [SMILES: C[C@@H]1OCC2(CCN(c3cnc4nc(Sc5ccnc(N6CCC[C@H]6CO)c5Cl)ccc4n3)CC2)[C@@H]1N]

((S)-1-(4-((2-((3S,4S)-4-amino-3-methyl-2-oxa-8-azaspiro[4.5]decan-8-yl)pyrido[2,3-b]pyrazin-6-yl)thio)-3-chloropyridin-2-yl)pyrrolidin-2-yl)methanol (S)-(1-(3-Chloro-4-mercaptopyridin-2-yl)pyrrolidin-2-yl)methanol (0.11 g, 0.45 mmol) and N-ethyl-N-isopropylpropan-2-amine (0.081 mL, 0.45 mmol) were added to a solution of (3S,4S)-8-(6-chloropyrido[2,3-b]pyrazin-2-yl)-3-methyl-2-oxa-8-azaspiro[4.5]decan-4-amine (0.050 g, 0.15 mmol) in dioxanes (2 mL) in a microwave vessel, and the reaction was heated in the microwave to 120° C. for 2 hours. The reaction was concentrated in vacuo, and the reaction chromatographed using 0-10% MeOH/DCM with 0.2% NH₄OH as additive to give 90% pure product. The material was further purified by reverse preparative HPLC using 5-95% ACN/water with 0.1% TFA as modifier. Fractions containing product were diluted with NaOH, and the aqueous layer was extracted with EtOAc. The layers were separated. The organics were washed with brine, dried over MgSO₄ and concentrated in vacuo to give ((S)-1-(4-((2-((3S,4S)-4-amino-3-methyl-2-oxa-8-azaspiro[4.5]decan-8-yl)pyrido[2,3-b]pyrazin-6-yl)thio)-3-chloropyridin-2-yl)pyrrolidin-2-yl)methanol (0.010 g, 12% yield). ¹H NMR (500 MHz, (CDCl₃)) δ 8.75 (s, 1H), 7.94 (d, J=8.2 Hz, 1H), 7.84 (d, J=5.3 Hz, 1H), 7.56 (d, J=8.3 Hz, 1H), 6.73 (d, J=5.3 Hz, 1H), 4.54-4.49 (m, 1H), 4.24-4.29 (m, 1H), 4.16-4.07 (m, 1H), 4.02-3.96 (m, 1H), 3.85 (d, J=8.7 Hz, 1H), 3.80 (dd, J=2.4, 11.2 Hz, 1H), 3.72 (d, J=8.7 Hz, 1H), 3.68-3.63 (m, 2H), 3.59-3.52 (m, 2H), 3.03 (d, J=4.4 Hz, 1H), 2.15-2.10 (m, 1H), 2.00-1.93 (m, 2H), 1.86-1.72 (m, 5H), 1.30-1.26 (m, 4H); m/z (esi/APCI) M⁺1=542.2.

Example 72

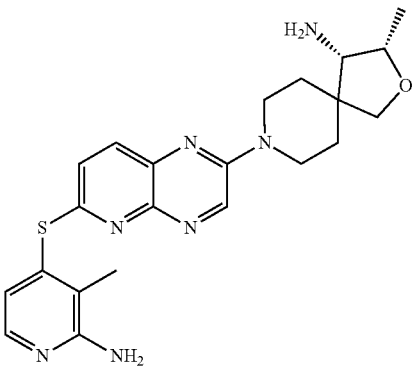 [SMILES: Cc1c(Sc2ccc3nc(N4CCC5(CC4)CO[C@@H](C)[C@H]5N)cnc3n2)ccnc1N]

(3S,4S)-8-(6-((2-amino-3-methylpyridin-4-yl)thio)pyrido[2,3-b]pyrazin-2-yl)-3-methyl-2-oxa-8-azaspiro[4,5]decan-4-amine (3S,4S)-8-(6-((2-Amino-3-methylpyridin-4-yl)thio)pyrido[2,3-b]pyrazin-2-yl)-3-methyl-2-oxa-8-azaspiro[4.5]decan-4-amine was prepared according to Example 71, substituting 2-amino-3-methylpyridine-4-thiol for (5')-(1-(3-chloro-4-mercaptopyridin-2-yl)pyrrolidin-2-yl)methanol, while also adding DMA (0.5 mL) to the reaction, m/z (esi/APCI) M⁺1=438.2.

Example 73

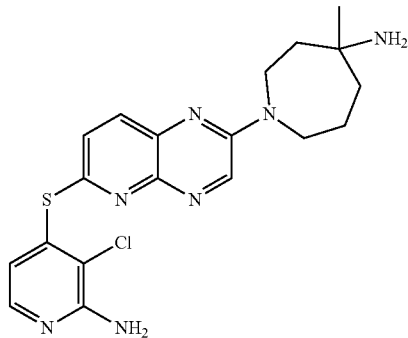 [SMILES: CC1(N)CCCN(c2cnc3nc(Sc4ccnc(N)c4Cl)ccc3n2)CC1]

1-(6-((2-amino-3-chloropyridin-4-yl)thio)pyrido[2,3-b]pyrazin-2-yl)-4-methylazepan-4-amine Step A: TFA (1 mL) was added to a solution of tert-butyl 4-amino-4-methylazepane-1-carboxylate (0.17 g, 0.75 mmol) in DCM (1 mL), and the reaction was stirred at room temperature for 1 hour. The reaction was concentrated in vacuo and taken up in DCM (5 mL). Hunig's base (0.78 mL, 4.5 mmol) and 6-chloropyrido[2,3-b]pyrazin-2-yl trifluoromethanesulfonate (0.23 g, 0.75 mmol) were added, and the reaction was stirred at 0° C. for 1 hour. The reaction was concentrated in vacuo, and the residue chromatographed using 0-10% MeOH/DCM with 0.2% NH₄OH as eluent to give 1-(6-chloropyrido[2,3-b]pyrazin-2-yl)-4-methylazepan-4-amine (0.22 g, 100% yield), m/z (esi/APCI) M⁺1=292.2.

Step B: 2-Amino-3-chloropyridine-4-thiol (0.36 g, 2.3 mmol) and N-ethyl-N-isopropylpropan-2-amine (0.29 g, 2.3 mmol) were added to a solution of 1-(6-chloropyrido[2,3-b]pyrazin-2-yl)-4-methylazepan-4-amine (0.22 g, 0.75 mmol) in dioxanes (10 mL) with DMA (2 mL), and the reaction was stirred for 18 hours at 80° C. The reaction was concentrated in vacuo, and the material was chromatographed twice using 0-10% MeOH/DCM to give 1-(6-((2-amino-3-chloropyridin-4-yl)thio)pyrido[2,3-b]pyrazin-2-yl)-4-methylazepan-4-amine (0.17 g, 55% yield). $^1$H NMR (500 MHz, (CDCl$_3$)) δ 8.66 (s, 1H), 7.94 (d, J=8.2 Hz, 1H), 7.84 (d, J=5.3 Hz, 1H), 7.52 (d, J=8.7 Hz, 1H), 6.66 (d, J=5.3 Hz, 1H), 4.94 (br s, 2H), 3.92-3.86 (m, 2H), 3.85-3.77 (m, 2H), 2.18-2.10 (m, 1H), 1.92-1.77 (m, 3H), 1.66-1.55 (m, 2H), 1.21 (s, 3H); m/z (esi/APCI) M$^+$1=416.2.

Example 74

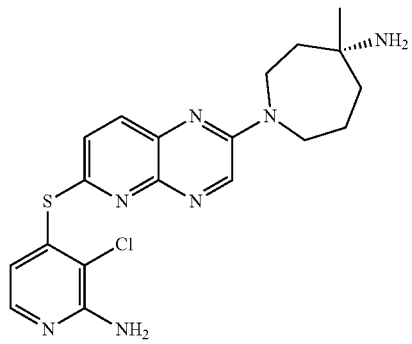

(R)-1-(6-((2-amino-3-chloropyridin-4-yl)thio)pyrido[2,3-b]pyrazin-2-yl)-4-methylazepan-4-amine 1-(6-((2-Amino-3-chloropyridin-4-yl)thio)pyrido[2,3-b]pyrazin-2-yl)-4-methylazepan-4-amine (0.17 g, 0.42 mmol) enantiomers were separated by chiral SFC using 0.5 mL methanol loading at 10 mg/mL using an AD-H column (2×15 cm) using 45% (2:1) EtOH/ACN with 0.2% DEA/CO$_2$ at 100 bar of pressure with a flow rate 55 mL/minute monitoring at 220 nM wavelength. Peak 1 isolate. $^1$H NMR (500 MHz, (CDCl$_3$)) δ 8.66 (s, 1H), 7.94 (d, J=8.2 Hz, 1H), 7.84 (d, J=5.3 Hz, 1H), 7.52 (d, J=8.3 Hz, 1H), 6.66 (d, J=5.3 Hz, 1H), 4.94 (br s, 2H), 3.92-3.86 (m, 2H), 3.85-3.77 (m, 2H), 2.17-2.10 (m, 1H), 1.93-1.77 (m, 3H), 1.66-1.55 (m, 2H), 1.21 (s, 3H); m/z (esi/APCI) M$^+$1=416.2.

Example 75

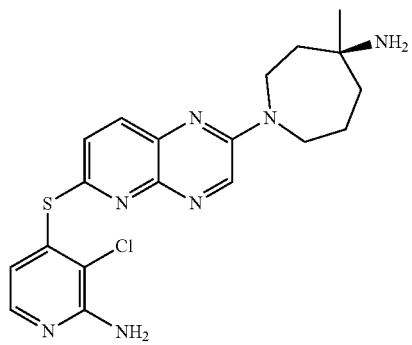 [SMILES: C[C@]1(N)CCCN(c2cnc3nc(Sc4ccnc(N)c4Cl)ccc3n2)CC1]

(S)-1-(6-((2-amino-3-chloropyridin-4-yl)thio)pyrido[2,3-b]pyrazin-2-yl)-4-methylazepan-4-amine 1-(6-((2-Amino-3-chloropyridin-4-yl)thio)pyrido[2,3-b]pyrazin-2-yl)-4-methylazepan-4-amine (0.17 g, 0.42 mmol) enantiomers were separated by chiral SFC using 0.5 mL methanol loading at 10 mg/mL using an AD-H column (2×15 cm) using 45% (2:1) EtOH/ACN with 0.2% DEA/CO$_2$ at 100 bar of pressure with a flow rate 55 mL/minute monitoring at 220 nM wavelength. Peak 2 isolate. $^1$H NMR (500 MHz, (CDCl$_3$)) δ 8.66 (s, 1H), 7.94 (d, J=8.2 Hz, 1H), 7.84 (d, J=5.3 Hz, 1H), 7.52 (d, J=8.7 Hz, 1H), 6.66 (d, J=5.3 Hz, 1H), 4.94 (br s, 2H), 3.96-3.86 (m, 2H), 3.84-3.77 (m, 2H), 2.20-2.09 (m, 1H), 1.96-1.77 (m, 3H), 1.69-1.55 (m, 2H), 1.20 (s, 3H); m/z (esi/APCI) M$^+$1=416.2.

Example 76

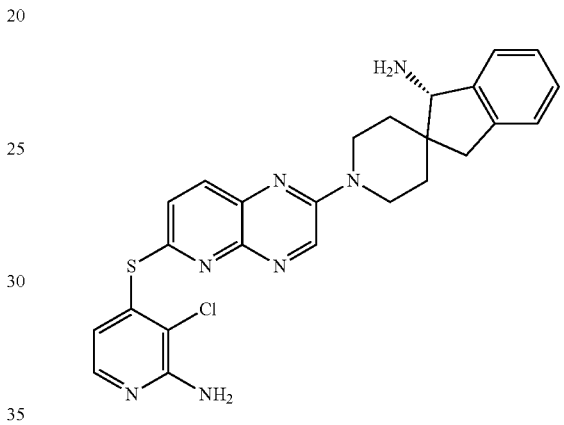

(S)-1'-(6-((2-amino-3-chloropyridin-4-yl)thio)pyrido[2,3-b]pyrazin-2-yl)-1,3-dihydrospiro[indene-2,4'-piperidin]-1-amine N-Ethyl-N-isopropylpropan-2-amine (147 μL, 0.82 mmol) was added to a solution of 6-chloropyrido[2,3-b]pyrazin-2-yl 4-nitrobenzenesulfonate (75 mg, 0.20 mmol) in dioxane (4 mL) cooled to 0° C., followed by (R)—N—((S)-1,3-dihydrospiro[indene-2,4'-piperidin]-1-yl)-2-methylpropane-2-sulfinamide compound with 2,2,2-trifluoroacetaldehyde (1:1) (207 mg, 0.51 mmol). The reaction was stirred at 60° C. for 20 hours. Sodium 2-amino-3-chloropyridine-4-thiolate (75 mg, 0.41 mmol) was added, and the reaction was heated to 80° C. for 4 hours. The reaction was concentrated and purified by silica gel (0-12% MeOH in DCM with 2% NH$_4$OH). The material was brought up in 10% MeOH in DCM (2 mL), and 4N HCl in dioxane (1 mL) was added. The reaction was stirred for 1 hour. The reaction was concentrated and purified by reverse phase chromatography (0-50% ACN:water with 0.1% TFA). The fractions were combined, and saturated bicarbonate was added. The mixture was extracted with 10% MeOH in DCM (3×10 mL). The extracts were combined, dried, filtered and concentrated to provide (5)-1'-(6-((2-amino-3-chloropyridin-4-yl)thio)pyrido[2,3-b]pyrazin-2-yl)-1,3-dihydrospiro[indene-2,4'-piperidin]-1-amine (9.9 mg, 0.020 mmol, 10% yield). $^1$H NMR (500 MHz, (CDCl$_3$) δ 8.76 (s, 1H), 7.91 (d, J=8.6 Hz, 1H), 7.84 (d, J=5.3 Hz, 1H), 7.50 (d, J=8.6 Hz, 1H), 7.33 (m, 1H), 7.24 (m, 3H) 6.69 (d, J=5.3 Hz, 1H), 4.93 (br s, 2H), 4.44 (m, 2H), 4.01 (s, 1H), 3.38 (m, 2H), 3.13 (d, J=15.7 Hz, 1H), 2.77 (d, J=15.7 Hz, 1H), 1.97-1.78 (m, 2H), 1.69 (m, 1H), 1.45 (m, 1H); m/z (esi/APCI) M$^+$1=490.1.

Example 77

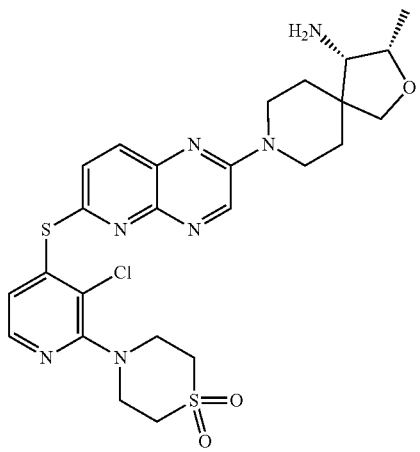 [SMILES: C[C@@H]1OCC2(CCN(c3cnc4nc(Sc5ccnc(N6CCS(=O)(=O)CC6)c5Cl)ccc4n3)CC2)[C@@H]1N]

4-(4-((2-((3S,4S)-4-amino-3-methyl-2-oxa-8-azaspiro[4.5]decan-8-yl)pyrido[2,3-b]pyrazin-6-yl)thio)-3-chloropyridin-2-yl)thiomorpholine 1,1-dioxide 4-(4-((2-((3S,4S)-4-Amino-3-methyl-2-oxa-8-azaspiro[4.5]decan-8-yl)pyrido[2,3-b]pyrazin-6-yl)thio)-3-chloropyridin-2-yl)thiomorpholine 1,1-di oxide was prepared according to Example 13, substituting 4-(3-chloro-4-mercaptopyridin-2-yl)thiomorpholine 1,1-dioxide for 2-amino-3-chloropyridine-4-thiol in Step B. m/z (esi/APCI) M$^+$1=576.2.

Example 78

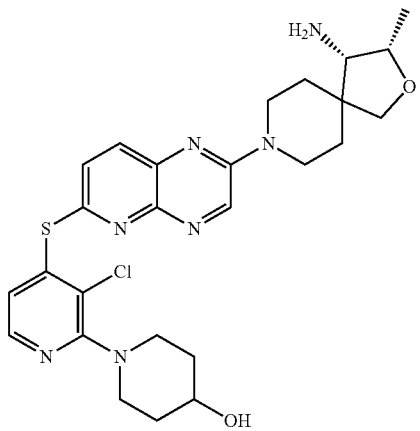 [SMILES: C[C@@H]1OCC2(CCN(c3cnc4nc(Sc5ccnc(N6CCC(O)CC6)c5Cl)ccc4n3)CC2)[C@@H]1N]

1-(4-((2-((3S,4S)-4-amino-3-methyl-2-oxa-8-azaspiro[4.5]decan-8-yl)pyrido[2,3-b]pyrazin-6-yl)thio)-3-chloropyridin-2-yl)piperidin-4-ol 1-(4-((2-((3S,4S)-4-Amino-3-methyl-2-oxa-8-azaspiro[4.5]decan-8-yl)pyrido[2,3-b]pyrazin-6-yl)thio)-3-chloropyridin-2-yl)piperidin-4-ol was prepared according to Example 13, substituting 1-(3-chloro-4-mercaptopyridin-2-yl)piperidin-4-ol for 2-amino-3-chloropyridine-4-thiol in Step B. m/z (esi/APCI) M$^+$1=542.2.

Example 79

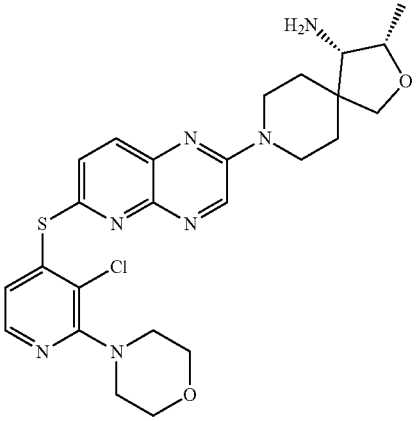 [SMILES: C[C@@H]1OCC2(CCN(c3cnc4nc(Sc5ccnc(N6CCOCC6)c5Cl)ccc4n3)CC2)[C@@H]1N]

(3S,4S)-8-(6-((3-chloro-2-morpholinopyridin-4-yl)thio)pyrido[2,3-b]pyrazin-2-yl)-3-methyl-2-oxa-8-azaspiro[4.5]decan-4-amine (3S,4S)-8-(6-((3-Chloro-2-morpholinopyridin-4-yl)thio)pyrido[2,3-b]pyrazin-2-yl)-3-methyl-2-oxa-8-azaspiro[4.5]decan-4-amine was prepared according to Example 13, substituting 3-chloro-2-morpholinopyridine-4-thiol for 2-amino-3-chloropyridine-4-thiol in Step B. m/z (esi/APCI) M$^+$1=528.2.

Example 80

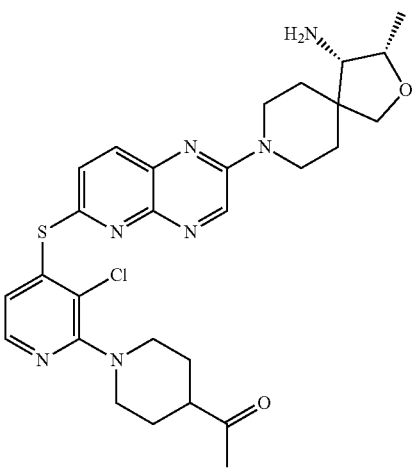 [SMILES: CC(=O)C1CCN(c2nccc(Sc3ccc4nc(N5CCC6(CC5)CO[C@@H](C)[C@H]6N)cnc4n3)c2Cl)CC1]

1-(4-(4-((2-((3S,4S)-4-amino-3-methyl-2-oxa-8-azaspiro[4.5]decan-8-yl)pyrido[2,3-b]pyrazin-6-yl)thio)-3-chloropyridin-2-yl)piperazin-1-yl)ethan-1-one 1-(4-(4-((2-((3S,4S)-4-Amino-3-methyl-2-oxa-8-azaspiro[4.5]decan-8-yl)pyrido[2,3-b]pyrazin-6-yl)thio)-3- chloropyridin-2-yl)piperazin-1-yl)ethan-1-one was prepared according to Example 13, substituting 1-(4-(3-chloro-4-mercaptopyridin-2-yl)piperazin-1-yl)ethan-1-one for 2-amino-3-chloropyridine-4-thiol in Step B. m/z (esi/APCI) M+1=569.2.

Example 81

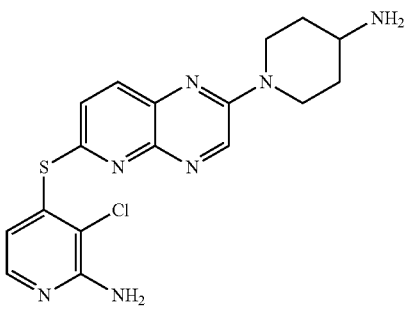 [SMILES: Nc1nccc(Sc2ccc3nc(N4CCC(N)CC4)cnc3n2)c1Cl]

4-((2-(4-aminopiperidin-1-yl)pyrido[2,3-b]pyrazin-6-yl)thio)-3-chloropyridin-2-amine 4-((2-(4-Aminopiperidin-1-yl)pyrido[2,3-b]pyrazin-6-yl)thio)-3-chloropyridin-2-amine was prepared according to Example 12, substituting tert-butyl piperidin-4-ylcarbamate for tert-butyl ((4-methylpiperidin-4-yl)methyl)carbamate in Step A. m/z (esi/APCI) M+1=388.2.

Example 82

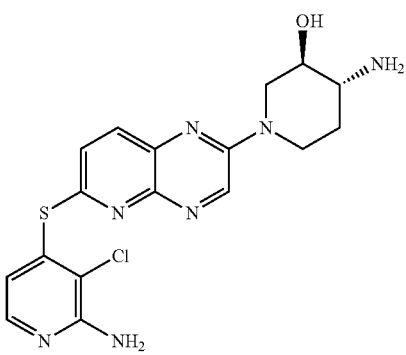 [SMILES: Nc1nccc(Sc2ccc3nc(N4CC[C@@H](N)[C@H](O)C4)cnc3n2)c1Cl]

(3R,4R)-4-amino-1-(6-((2-amino-3-chloropyridin-4-yl)thio)pyrido[2,3-b]pyrazin-2-yl)piperidin-3-ol (3R,4R)-4-Amino-1-(6-((2-amino-3-chloropyridin-4-yl)thio)pyrido[2,3-b]pyrazin-2-yl)piperidin-3-ol was prepared according to Example 12, substituting tert-butyl ((3R,4R)-3-hydroxypiperidin-4-yl)carbamate for tert-butyl ((4-methylpiperidin-4-yl)methyl)carbamate in Step A. m/z (esi/APCI) M+1=404.1.

Example 83

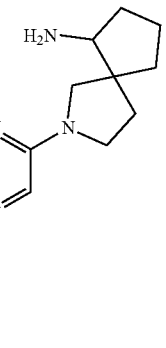

2-(6-((2-amino-3-chloropyridin-4-yl)thio)pyrido[2,3-b]pyrazin-2-yl)-2-azaspiro[4.4]nonan-6-amine 2-(6-((2-Amino-3-chloropyridin-4-yl)thio)pyrido[2,3-b]pyrazin-2-yl)-2-azaspiro[4.4]nonan-6-amine was prepared according to Example 12, substituting tert-butyl N-{2-azaspiro[4.4]nonan-6-yl}carbamate for tert-butyl ((4-methylpiperidin-4-yl)methyl)carbamate in Step A. m/z (esi/APCI) M+1=428.1.

Example 84

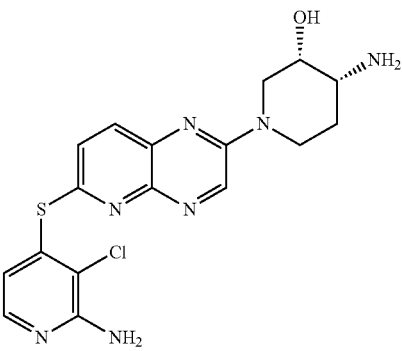 [SMILES: Nc1nccc(Sc2ccc3nc(N4CC[C@@H](N)[C@@H](O)C4)cnc3n2)c1Cl]

(3S,4R)-4-amino-1-(6-((2-amino-3-chloropyridin-4-yl)thio)pyrido[2,3-b]pyrazin-2-yl)piperidin-3-ol (3S,4R)-4-Amino-1-(6-((2-amino-3-chloropyridin-4-yl)thio)pyrido[2,3-b]pyrazin-2-yl)piperidin-3-ol was prepared according to Example 12, substituting tert-butyl ((3S,4R)-3-hydroxypiperidin-4-yl)carbamate for tert-butyl ((4-methylpiperidin-4-yl)methyl)carbamate in Step A. m/z (esi/APCI) M+1=404.1.

Example 85

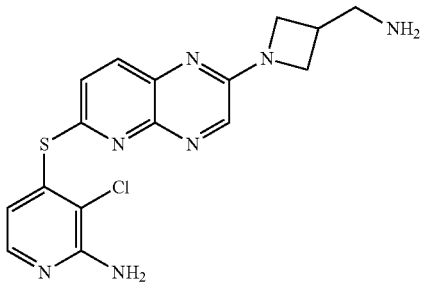 [SMILES: NCC1CN(c2cnc3nc(Sc4ccnc(N)c4Cl)ccc3n2)C1]

4-((2-(3-(aminomethyl)azetidin-1-yl)pyrido[2,3-b]pyrazin-6-yl)thio)-3-chloropyridin-2-amine 4-((2-(3-(Aminomethyl)azetidin-1-yl)pyrido[2,3-b]pyrazin-6-yl)thio)-3-chloropyridin-2-amine was prepared according to Example 12, substituting tert-butyl (azetidin-3-ylmethyl)carbamate for tert-butyl ((4-methylpiperidin-4-yl)methyl)carbamate in Step A. m/z (esi/APCI) M+1=374.1.

Example 86

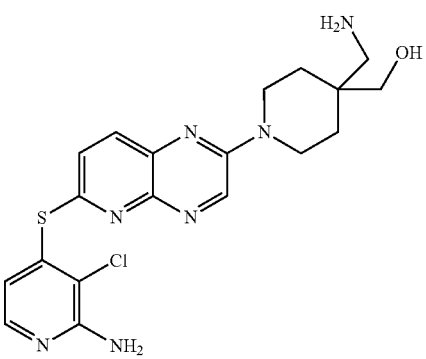 [SMILES: NCC1(CO)CCN(c2cnc3nc(Sc4ccnc(N)c4Cl)ccc3n2)CC1]

(1-(6-((2-amino-3-chloropyridin-4-yl)thio)pyrido[2,3-b]pyrazin-2-yl)-4-(aminomethyl)piperidin-4-yl)methanol Step A: tert-Butyl ([4-(hydroxymethyl)-4-piperidinyl]methyl)carbamate (0.19 g, 0.77 mmol) and Hunig's base (0.40 mL, 2.3 mmol) were added to a solution of 6-chloropyrido[2,3-b]pyrazin-2-yl trifluoromethanesulfonate (0.24 g, 0.77 mmol) in DMA cooled to 0° C., and the reaction was stirred while warming to room temperature over 2 hours. The reaction was poured into water and extracted into EtOAc, and the layers were separated. The organics were washed with water, brine, dried over MgSO$_4$ and concentrated in vacuo. The residue was chromatographed using 0-100% EtOAc/DCM as eluent to give a solid. The solid was taken up in dioxanes (10 mL) and DMA (2 mL), followed by addition of 2-amino-3-chloropyridine-4-thiol (0.37 g, 2.3 mmol) and Hunig's base (0.40 mL, 2.3 mmol). The reaction was heated to 100° C. for 16 hours. The reaction was poured into water, and the aqueous layer was extracted into EtOAc. The layers were separated. The organics were washed with water, brine, dried over MgSO$_4$ and concentrated in vacuo. The material was chromatographed using 50-100% EtOAc/DCM as eluent to give tert-butyl ((1-(6-((2-amino-3-chloropyridin-4-yl)thio)pyrido[2,3-b]pyrazin-2-yl)-4-(hydroxymethyl)piperidin-4-yl)methyl)carbamate (0.18 g, 44% yield).

Step B: TFA (1 mL) was added to a solution of tert-butyl ((1-(6-((2-amino-3-chloropyridin-4-yl)thio)pyrido[2,3-b]pyrazin-2-yl)-4-(hydroxymethyl)piperidin-4-yl)methyl)carbamate (0.18 g, 0.34 mmol) in DCM (2 mL), and the reaction was stirred at room temperature for 1 hour. The reaction was concentrated in vacuo, and the residue was partitioned between EtOAc and 1N NaOH. The layers were separated. The organics were washed with brine, dried over MgSO$_4$ and concentrated in vacuo. The material was purified by chromatography using 0-10% MeOH/DCM with 0.2% NH$_4$OH as eluent to give (1-(6-((2-amino-3-chloropyridin-4-yl)thio)pyrido[2,3-b]pyrazin-2-yl)-4-(aminomethyl)piperidin-4-yl)methanol (0.062 g, 42% yield), m/z (esi/APCI) M+1=432.1; $^1$H NMR (500 MHz, (CD$_3$)$_2$SO) δ 8.95 (s, 1H), 7.97 (d, J=8.3 Hz, 1H), 7.78 (d, J=4.8 Hz, 1H), 7.59 (d, J=8.3 Hz, 1H), 6.49 (br s, 2H), 6.40 (d, J=5.3 Hz, 1H), 3.80 (br s, 4H), 3.40 (br s, 2H), 2.60 (br s, 2H), 1.49 (br s, 4H).

Example 87

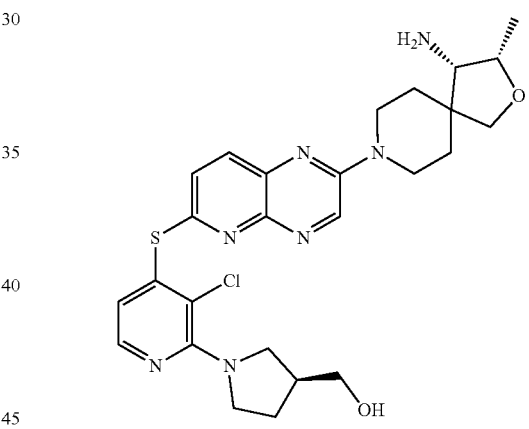

((S)-1-(4-((2-((3S,4S)-4-amino-3-methyl-2-oxa-8-azaspiro[4.5]decan-8-yl)pyrido[2,3-b]pyrazin-6-yl)thio)-3-chloropyridin-2-yl)pyrrolidin-3-yl)methanol Water (0.1 mL) and sodium (S)-3-chloro-2-(3-(hydroxymethyl)pyrrolidin-1-yl)pyridine-4-thiolate (0.11 g, 0.40 mmol) were added to a solution of (3S'4S')-8-(6-chloropyrido[2,3-b]pyrazin-2-yl)-3-methyl-2-oxa-8-azaspiro[4.5]decan-4-amine (0.045 g, 0.14 mmol) in dioxanes (2 mL), and the reaction was heated to 90° C. for 1 hour. Hunig's base (0.024 mL, 0.14 mmol), water (0.1 mL) and DMA (200 uL) were added to the reaction, and the reaction was heated to 90° C. for 18 hours. The reaction was cooled and concentrated in vacuo, and the residue was chromatographed using 0-8% MeOH/DCM with 0.2% NH$_4$OH to give ((S)-1-(4-((2-((3S,4S)-4-amino-3-methyl-2-oxa-8-azaspiro[4.5]decan-8-yl)pyrido[2,3-b]pyrazin-6-yl)thio)-3-chloropyridin-2-yl)pyrrolidin-3-yl)methanol (0.018 g, 25% yield), in z (esi/APCI) M+1=542.2. $^1$H NMR (500 MHz, (CDCl$_3$)) δ 8.74 (s, 1H), 7.91 (m, 2H), 7.52 (d, J=8.3

Hz, 1H), 6.70 (d, J=5.3 Hz, 1H), 4.24-4.19 (m, 1H), 4.15-4.07 (m, 2H), 3.84 (d, J=8.7 Hz, 1H), 3.76-3.69 (m, 6H), 3.68-3.59 (m, 3H), 3.56-3.51 (m, 1H), 3.03 (d, J=4.8 Hz, 1H), 2.50 (quintet, J=6.8 Hz, 1H), 2.09 (hextet, J=5.8 Hz, 1H), 1.97-1.92 (m, 1H), 1.82-1.71 (m, 3H), 1.26 (d, J=6.3 Hz, 3H).

Example 88

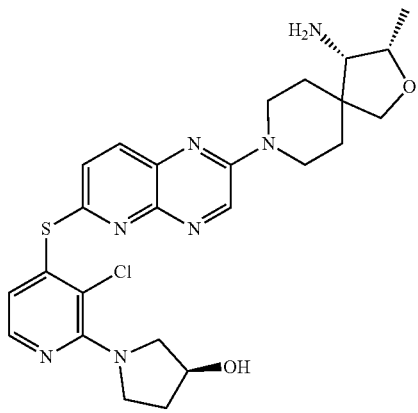 [SMILES: C[C@@H]1OCC2(CCN(c3cnc4nc(Sc5ccnc(N6CC[C@H](O)C6)c5Cl)ccc4n3)CC2)[C@@H]1N]

(S)-1-(4-((2-((3S,4S)-4-amino-3-methyl-2-oxa-8-azaspiro[4.5]decan-8-yl)pyrido[2,3-b]pyrazin-6-yl)thio)-3-chloropyridin-2-yl)pyrrolidin-3-ol (S)-1-(4-((2-((3S,4S)-4-Amino-3-methyl-2-oxa-8-azaspiro[4.5]decan-8-yl)pyrido[2,3-b]pyrazin-6-yl)thio)-3-chloropyridin-2-yl)pyrrolidin-3-ol was prepared according to Example 87, substituting sodium (S)-3-chloro-2-(3-hydroxypyrrolidin-1-yl)pyridine-4-thiolate for sodium (5)-3-chloro-2-(3-(hydroxymethyl)pyrrolidin-1-yl)pyridine-4-thiolate. m/z (esi/APCI) M$^+$1=528.2.

Example 89

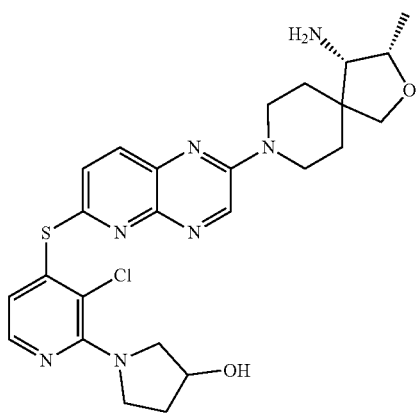 [SMILES: C[C@@H]1OCC2(CCN(c3cnc4nc(Sc5ccnc(N6CCC(O)C6)c5Cl)ccc4n3)CC2)[C@@H]1N]

1-(4-((2-((3S,4S)-4-amino-3-methyl-2-oxa-8-azaspiro[4.5]decan-8-yl)pyrido[2,3-b]pyrazin-6-yl)thio)-3-chloropyridin-2-yl)pyrrolidin-3-ol 1-(4-((2-((3S,4S)-4-amino-3-methyl-2-oxa-8-azaspiro[4.5]decan-8-yl)pyrido[2,3-b]pyrazin-6-yl)thio)-3-chloropyridin-2-yl)pyrrolidin-3-ol was prepared according to Example 87, substituting sodium 3-chloro-2-(3-hydroxypyrrolidin-1-yl)pyridine-4-thiolate for sodium (5')-3-chloro-2-(3-(hydroxymethyl)pyrrolidin-1-yl)pyridine-4-thiolate. m/z (esi/APCI) M$^+$1=528.2.

Example 90

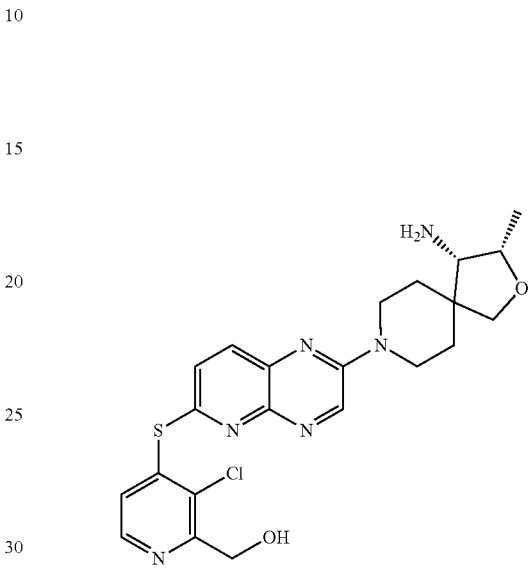

(4-((2-((3S,4S)-4-amino-3-methyl-2-oxa-8-azaspiro[4.5]decan-8-yl)pyrido[2,3-b]pyrazin-6-yl)thio)-3-chloropyridin-2-yl)methanol Sodium 3-chloro-2-(hydroxymethyl)pyridine-4-thiolate (0.15 g, 0.75 mmol) and Hunig's Base (0.079 mL, 0.45 mmol) were added to a solution of (3S,4S)-8-(6-chloropyrido[2,3-b]pyrazin-2-yl)-3-methyl-2-oxa-8-azaspiro[4.5]decan-4-amine (0.050 g, 0.15 mmol) in DMA (2 mL) in a microwave vessel, and the reaction was heated to 150° C. for 2 hours. The reaction was poured into basic water, and the aqueous layer was extracted with EtOAc. The layers were separated. The organics were washed with water, brine, dried over MgSO$_4$ and concentrated in vacuo. The material was chromatographed using 0-10% MeOH/DCM with 0.2% NH$_4$OH as modifier to give (4-((2-((3S,4S)-4-amino-3-methyl-2-oxa-8-azaspiro[4.5]decan-8-yl)pyrido[2,3-b]pyrazin-6-yl)thio)-3-chloropyridin-2-yl)methanol (0.011 g, 16% yield), m/z (esi/APCI) M$^+$1=473.2. $^1$H NMR (500 MHz, (CDCl$_3$)) δ 8.76 (s, 1H), 8.31 (d, J=4.8 Hz, 1H), 7.97 (d, J=8.7 Hz, 1H), 7.58 (d, J=8.3 Hz, 1H), 7.36 (d, J=5.3 Hz, 1H), 4.81 (s, 2H), 4.23-4.19 (m, 1H), 4.17-4.08 (m, 2H), 3.85 (d, J=8.7 Hz, 1H), 3.72 (d, J=8.7 Hz, 1H), 3.68-3.64 (m, 1H), 3.59-3.53 (m, 1H), 3.02 (d, J=4.8 Hz, 1H), 1.95-1.93 (m, 1H), 1.85-1.72 (m, 3H), 1.25 (d, J=6.3 Hz, 3H).

Example 91

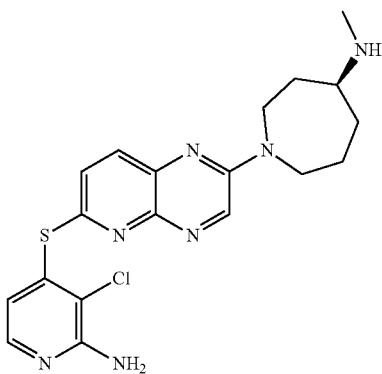 [SMILES: CN[C@H]1CCCN(c2cnc3nc(Sc4ccnc(N)c4Cl)ccc3n2)CC1]

(S)-1-(6-((2-amino-3-chloropyridin-4-yl)thio)pyrido[2,3-b]pyrazin-2-yl)-N-methylazepan-4-amine Step A: N-Ethyl-N-isopropylpropan-2-amine (0.33 g, 2.6 mmol) and (S)-tert-butyl azepan-4-ylcarbamate (0.27 g, 1.3 mmol) were added to a solution of 6-chloropyrido[2,3-b]pyrazin-2-yl trifluoromethanesulfonate (0.40 g, 1.3 mmol) in dioxanes (15 mL) cooled to 0° C., and the reaction was stirred for 2 hours while warming to room temperature. The reaction was concentrated in vacuo, and the material was chromatographed using 0-100% EtOAc/DCM as eluent to give tert-butyl (S)-(1-(6-chloropyrido[2,3-b]pyrazin-2-yl)azepan-4-yl)carbamate (0.47 g, 1.2 mmol, 98% yield).

Step B: Sodium hydride (0.11 g, 2.8 mmol) was added to a solution of tert-butyl (S)-(1-(6-chloropyrido[2,3-b]pyrazin-2-yl)azepan-4-yl)carbamate (0.35 g, 0.926 mmol) in DMA cooled to 0° C., followed by addition of iodomethane (0.40 ml, 6.5 mmol). The reaction was stirred at 0° C. for 7 hours. The reaction was poured into water, and the aqueous layer was extracted with MTBE. The layers were separated. The organics were washed with water, brine, dried over $MgSO_4$ and concentrated in vacuo. The material was chromatographed using 0-100% EtOAc/DCM as eluent to give tert-butyl (S)-(1-(6-chloropyrido[2,3-b]pyrazin-2-yl)azepan-4-yl)(methyl)carbamate (0.20 g, 55% yield), m/z (esi/APCI) $M^+1=392.2$.

Step C: N-Ethyl-N-isopropylpropan-2-amine (0.20 g, 1.5 mmol) and 2-amino-3-chloropyridine-4-thiol (0.25 g, 1.5 mmol) were added to a solution of tert-butyl (S)-(1-(6-chloropyrido[2,3-b]pyrazin-2-yl)azepan-4-yl)(methyl)carbamate (0.20 g, 0.51 mmol) in dioxanes (15 mL) and DMA (2 mL), and the reaction was heated to 90° C. for 7 hours. The reaction was cooled, and the dioxanes were removed in vacuo. The material was partitioned between EtOAc and water, and the layers were separated. The organics were washed with brine, dried over $MgSO_4$ and concentrated in vacuo. The residue was chromatographed using 0-100% EtOAc/DCM as eluent to give tert-butyl (S)-(1-(6-((2-amino-3-chloropyridin-4-yl)thio)pyrido[2,3-b]pyrazin-2-yl)azepan-4-yl)(methyl)carbamate (0.24 g, 91% yield), m/z (esi/APCI) $M^+1=516.2$.

Step D: TFA (1 mL) was added to a solution of tert-butyl (S)-(1-(6-((2-amino-3-chloropyridin-4-yl)thio)pyrido[2,3-b]pyrazin-2-yl)azepan-4-yl)(methyl)carbamate (0.26 g, 0.50 mmol) in DCM (1 mL), and the reaction was stirred at room temperature for 1 hour. The reaction was concentrated in vacuo, and the residue partitioned between EtOAc and 1N NaOH. The layers were separated. The organics were washed with brine, dried over $MgSO_4$ and concentrated in vacuo. The material was purified by column chromatography using 0-10% MeOH/DCM with 0.2% $NH_4OH$ as eluent to give (S)-1-(6-((2-amino-3-chloropyridin-4-yl)thio)pyrido[2,3-b]pyrazin-2-yl)-N-methylazepan-4-amine (0.064 g, 31% yield), m/z (esi/APCI) $M^+1=416.2$; $^1H$ NMR (500 MHz, ($CDCl_3$)) δ 8.65 (s, 1H), 7.93 (d, J=8.7 Hz, 1H), 7.84 (d, J=5.3 Hz, 1H), 7.52 (d, J=8.3 Hz, 1H), 6.66 (d, J=5.3 Hz, 1H), 4.94 (br s, 2H), 3.98-3.92 (m, 2H), 3.83-3.73 (m, 2H), 2.68-2.63 (m, 1H), 2.45 (s, 3H), 2.22-2.17 (m, 1H), 2.13-2.07 (m, 1H), 1.92-1.88 (m 1H), 1.85-1.81 (m, 1H), 1.77-1.71 (m, 1H), 1.58-1.52 (m, 1H).

Example 92

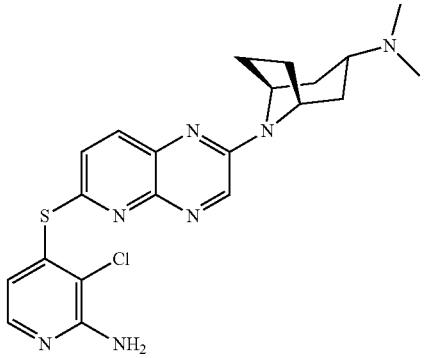 [SMILES: CN(C)C1C[C@@H]2CC[C@@H](C1)N2c1cnc2nc(Sc3ccnc(N)c3Cl)ccc2n1]

(1R,3s,5S)-8-(6-((2-amino-3-chloropyridin-4-yl)thio)pyrido[2,3-b]pyrazin-2-yl)-N,N-dimethyl-8-azabicyclo[3.2.1]octan-3-amine Step A: Hunig's Base (668 µL, 3.83 mmol) and exo-3-(Boc-amino)-8-azabicyclo[3.2.1]octane (289 mg, 1.28 mmol) were added to a solution of 6-chloropyrido[2,3-b]pyrazin-2-yl trifluoromethanesulfonate (400 mg, 1.28 mmol) in dioxanes cooled to 0° C. The reaction was gradually warmed to room temperature and stirred overnight. The reaction was concentrated in vacuo, and the material was chromatographed using 10-80% EtOAc/Hexanes as eluent to give tert-butyl ((1R,3s,5S)-8-(6-chloropyrido[2,3-b]pyrazin-2-yl)-8-azabicyclo[3.2.1]octan-3-yl)carbamate (482 mg, 1.24 mmol, 97% yield).

Step B: tert-Butyl ((1R,3s,5S)-8-(6-chloropyrido[2,3-b]pyrazin-2-yl)-8-azabicyclo[3.2.1]octan-3-yl)carbamate (50 mg, 0.1282 mmol) was dissolved in formic acid (72.57 µL, 1.92 mmol) and treated with formaldehyde (1441 µL, 19.24 mmol). The reaction mixture was stirred at 65° C. for 2 hours. The reaction was cooled to room temperature and partitioned between 1M NaOH and DCM. The combined organics were dried over $Na_2SO_4$, concentrated in vacuo and chromatographed eluting with a 0%-10% DCM:MeOH gradient. All fractions containing clean product were combined and concentrated in vacuo to give (1R,3s,5S)-8-(6-chloropyrido[2,3-b]pyrazin-2-yl)-N,N-dimethyl-8-azabicyclo[3.2.1]octan-3-amine (33 mg, 0.10 mmol, 81% yield).

Step C: Hunig's base (54 µL, 0.31 mmol) and 2-amino-3-chloropyridine-4-thiol (20 mg, 0.12 mmol) were added to a solution of (1R,3s,5S)-8-(6-chloropyrido[2,3-b]pyrazin-2-yl)-N,N-dimethyl-8-azabicyclo[3.2.1]octan-3-amine (33 mg, 0.10 mmol) in dioxane (1038 µL, 0.10 mmol), and the reaction was stirred at 100° C. overnight. The reaction was next concentrated in vacuo and chromatographed using a 0-15% DCM:MeOH (2% $NH_4OH$) gradient to give (1R,3s,5S)-8-(6-((2-amino-3-chloropyridin-4-yl)thio)pyrido[2,3-b]pyrazin-2-yl)-N,N-dimethyl-8-azabicyclo[3.2.1]octan-3-amine (4.7 mg, 0.011 mmol, 10% yield). $^1$H NMR (500 MHz, (CDCl$_3$)) δ 8.62 (s, 1H), 7.94 (d, 1H, J=8.6 Hz), 7.85 (d, 1H, J=5.3 Hz), 7.52 (d, 1H, J=8.5 Hz), 6.68 (d, 1H, J=5.3 Hz), 4.96 (s, 2H), 4.85 (s, 2H), 2.79-2.72 (m, 1H), 2.21 (s, 6H), 2.18-2.14 (m, 2H), 1.91 (d, 4H, J=7.3 Hz), 1.80-1.73 (m, 2H); m/z (esi/APCI) M$^+$1=442.2.

Example 93

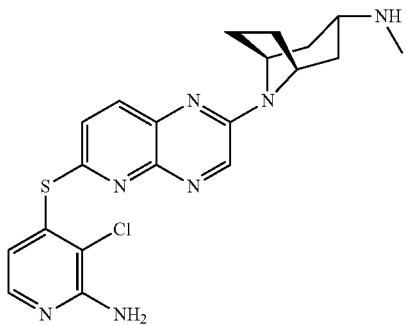 [SMILES: CNC1C[C@@H]2CC[C@@H](C1)N2c1cnc2nc(Sc3ccnc(N)c3Cl)ccc2n1]

(1S,3s,5S)-8-(6-((2-amino-3-chloropyridin-4-yl)thio)pyrido[2,3-b]pyrazin-2-yl)-N-methyl-8-azabicyclo[3.2.1]octan-3-amine Step A: Hunig's base (668 µL, 3.83 mmol) and exo-3-(Boc-amino)-8-azabicyclo[3.2.1]octane (289 mg, 1.28 mmol) were added to a solution of 6-chloropyrido[2,3-b]pyrazin-2-yl trifluoromethanesulfonate (400 mg, 1.28 mmol) in dioxanes cooled to 0° C. The reaction was gradually warmed to room temperature and stirred overnight. The reaction was concentrated in vacuo, and the material was chromatographed using 10-80% EtOAc/Hexanes as eluent to give tert-butyl ((1R,3s,5S)-8-(6-chloropyrido[2,3-b]pyrazin-2-yl)-8-azabicyclo[3.2.1]octan-3-yl)carbamate (482 mg, 1.24 mmol, 97% yield).

Step B: tert-Butyl ((1R,3s,5S)-8-(6-chloropyrido[2,3-b]pyrazin-2-yl)-8-azabicyclo[3.2.1]octan-3-yl)carbamate (200 mg, 0.51 mmol) was dissolved in DMA (5130 µL, 0.51 mmol) under nitrogen and cooled to 0° C. Sodium hydride, 60% dispersion in mineral oil (61.6 mg, 1.54 mmol) neat as a solid was added, and the reaction was stirred at 0° C. for 15 minutes under nitrogen. Iodomethane (397 µL, 6.16 mmol) was subsequently added dropwise, and the reaction was stirred at 0° C. for 1 hour. The reaction was slowly added to water and partitioned with EtOAc. The combined organics were washed with brine, dried over $Na_2SO_4$, and concentrated in vacuo. The concentrate was chromatographed eluting with a 0-50% DCM:EtOAc gradient to give tert-butyl ((1R,3s,5S)-8-(6-chloropyrido[2,3-b]pyrazin-2-yl)-8-azabicyclo[3.2.1]octan-3-yl)(methyl)carbamate (178 mg, 0.44 mmol, 86% yield).

Step C: Hunig's base (231 µL, 1.32 mmol) and 2-amino-3-chloropyridine-4-thiol (84.9 mg, 0.53 mmol) were added to a solution of tert-butyl ((1R,3s,5,S)-8-(6-chloropyrido[2,3-b]pyrazin-2-yl)-8-azabicyclo[3.2.1]octan-3-yl)(methyl)carbamate (178 mg, 0.44 mmol) in dioxane (4407 µL, 0.44 mmol), and the reaction was stirred at 100° C. for 1 hour. Cesium carbonate (144 mg, 0.44 mmol) was added, and the reaction was stirred overnight at 100° C. The reaction was cooled to room temperature and partitioned between water and EtOAc. The combined organics were washed with brine, dried over $Na_2SO_4$ and concentrated in vacuo. The concentrate was chromatographed using a 10-80% Hexane:EtOAc gradient to give tert-butyl ((1R,3s,5,S)-8-(6-((2-amino-3-chloropyridin-4-yl)thio)pyrido[2,3-b]pyrazin-2-yl)-8-azabicyclo[3.2.1]octan-3-yl)(methyl)carbamate (83 mg, 0.16 mmol, 36% yield).

Step D: tert-Butyl ((1R,3s,5S)-8-(6-((2-amino-3-chloropyridin-4-yl)thio)pyrido[2,3-b]pyrazin-2-yl)-8-azabicyclo[3.2.1]octan-3-yl)(methyl)carbamate (83 mg, 0.16 mmol) was dissolved in dichloromethane (1572 µL, 0.16 mmol) and treated with TFA (60.5 µL, 0.79 mmol). The reaction was stirred at room temperature for 30 minutes. The reaction was concentrated in vacuo and partitioned between DCM and 1M NaOH. The combined organics were washed with brine, dried over $Na_2SO_4$ and concentrated in vacuo. The concentrate was chromatographed eluting with a 0-10% DCM:MeOH (2% $NH_4OH$) gradient to give (1R,3s,5,S)-8-(6-((2-amino-3-chloropyridin-4-yl)thio)pyrido[2,3-b]pyrazin-2-yl)-N-methyl-8-azabicyclo[3.2.1]octan-3-amine (31.6 mg, 0.074 mmol, 47% yield). $^1$H NMR (500 MHz, (CDCl$_3$)) δ 8.62 (s, 1H), 7.93 (d, 1H, J=8.6 Hz), 7.85 (d, 1H, J=5.3 Hz), 7.52 (d, 1H, J=8.6 Hz), 6.68 (d, 1H, J=5.3 Hz), 4.95 (s, 2H), 4.85 (s, 2H), 3.12-3.05 (m, 1H), 2.41 (s, 3H), 2.21-2.15 (m, 2H), 2.09-2.03 (m, 2H), 1.93 (d, 2H, J=10.6 Hz); m/z (esi/APCI) M$^+$1=428.2.

The following compounds in Table 4 were prepared according to the above procedures using appropriate starting materials and intermediates.

TABLE 4

| Ex. # | Structure | Name | Prep | MS |
|---|---|---|---|---|
| 94 | 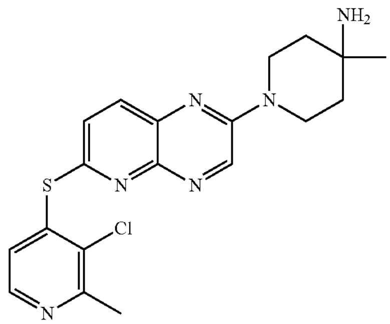 [SMILES: Cc1nccc(Sc2ccc3nc(N4CCC(C)(N)CC4)cnc3n2)c1Cl] | 1-(6-((3-chloro-2-methylpyridin-4-yl)thio)pyrido[2,3-b]pyrazin-2-yl)-4-methylpiperidin-4-amine | Ex. 14 | 401.1 |
| 95 | 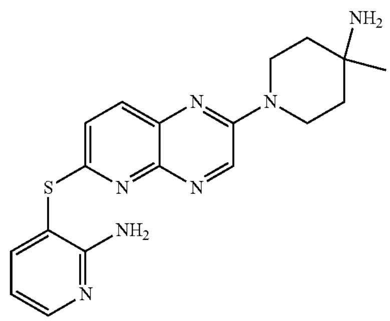 [SMILES: CC1(N)CCN(c2cnc3nc(Sc4cccnc4N)ccc3n2)CC1] | 3-((2-(4-amino-4-methylpiperidin-1-yl)pyrido[2,3-b]pyrazin-6-yl)thio)pyridin-2-amine | Ex. 14 | 368.2 |
| 96 | 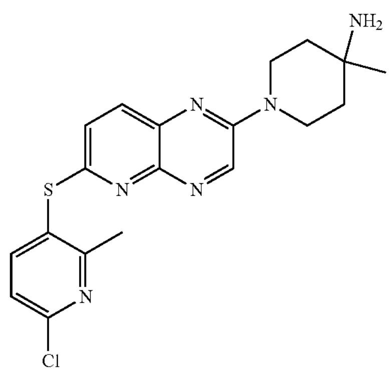 [SMILES: Cc1nc(Cl)ccc1Sc1ccc2nc(N3CCC(C)(N)CC3)cnc2n1] | 1-(6-((6-chloro-2-methylpyridin-3-yl)thio)pyrido[2,3-b]pyrazin-2-yl)-4-methylpiperidin-4-amine | Ex. 14 | 401.2 |
| 97 | 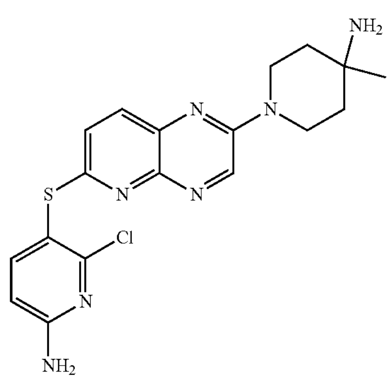 [SMILES: CC1(N)CCN(c2cnc3nc(Sc4ccc(N)nc4Cl)ccc3n2)CC1] | 5-((2-(4-amino-4-methylpiperidin-1-yl)pyrido[2,3-b]pyrazin-6-yl)thio)-6-chloropyridin-2-amine | Ex. 14 | 402.1 |

TABLE 4-continued

| Ex. # | Structure | Name | Prep | MS |
|---|---|---|---|---|
| 98 | 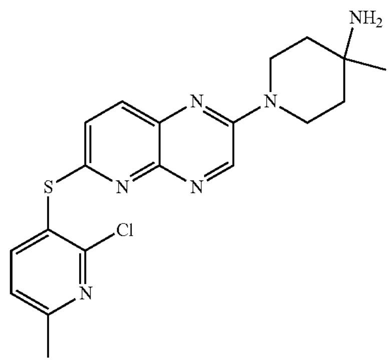 [SMILES: Cc1ccc(Sc2ccc3nc(N4CCC(C)(N)CC4)cnc3n2)c(Cl)n1] | 1-(6-((2-chloro-6-methylpyridin-3-yl)thio)pyrido[2,3-b]pyrazin-2-yl)-4-methylpiperidin-4-amine | Ex. 14 | 401.1 |
| 99 | 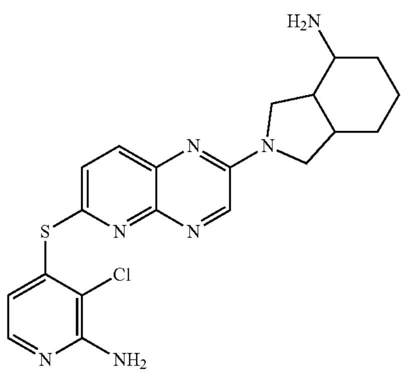 [SMILES: Nc1nccc(Sc2ccc3nc(N4CC5CCCC(N)C5C4)cnc3n2)c1Cl] | 2-(6-((2-amino-3-chloropyridin-4-yl)thio)pyrido[2,3-b]pyrazin-2-yl)octahydro-1H-isoindol-4-amine | Ex. 12 | 428.1 |
| 100 | 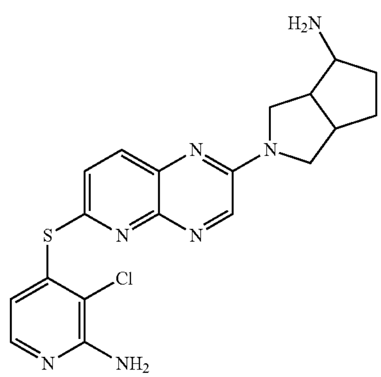 [SMILES: Nc1nccc(Sc2ccc3nc(N4CC5CCC(N)C5C4)cnc3n2)c1Cl] | 2-(6-((2-amino-3-chloropyridin-4-yl)thio)pyrido[2,3-b]pyrazin-2-yl)octahydrocyclopenta[c]pyrrol-4-amine | Ex. 12 | 414.2 |
| 101 | 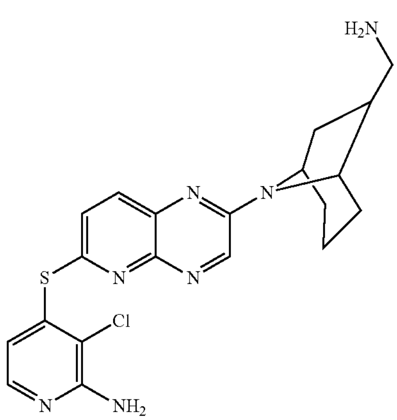 [SMILES: NCC1CC2CCCC1N2c1cnc2nc(Sc3ccnc(N)c3Cl)ccc2n1] | 4-((2-(3-(aminomethyl)-9-azabicyclo[3.3.1]nonan-9-yl)pyrido[2,3-b]pyrazin-6-yl)thio)-3-chloropyridin-2-amine | Ex. 12 | 442.2 |

TABLE 4-continued

| Ex. # | Structure | Name | Prep | MS |
|---|---|---|---|---|
| 102 | 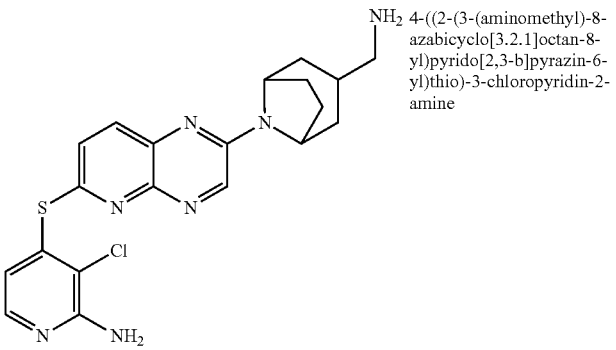 | 4-((2-(3-(aminomethyl)-8-azabicyclo[3.2.1]octan-8-yl)pyrido[2,3-b]pyrazin-6-yl)thio)-3-chloropyridin-2-amine | Ex. 12 | 428.2 |
| 103 | 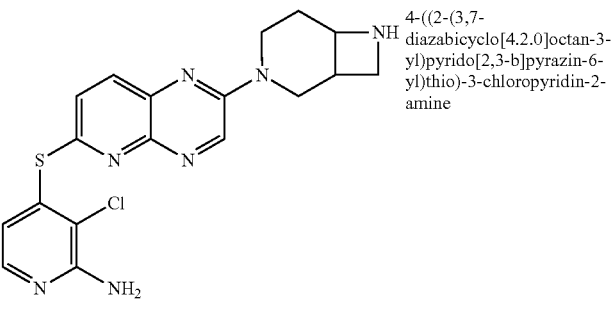 | 4-((2-(3,7-diazabicyclo[4.2.0]octan-3-yl)pyrido[2,3-b]pyrazin-6-yl)thio)-3-chloropyridin-2-amine | Ex. 12 | 400.1 |
| 104 | 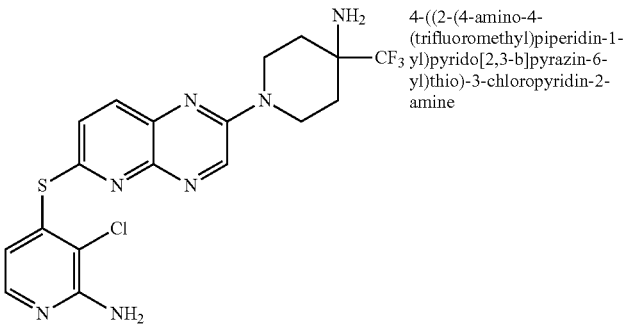 | 4-((2-(4-amino-4-(trifluoromethyl)piperidin-1-yl)pyrido[2,3-b]pyrazin-6-yl)thio)-3-chloropyridin-2-amine | Ex. 12 | 456.1 |
| 105 | 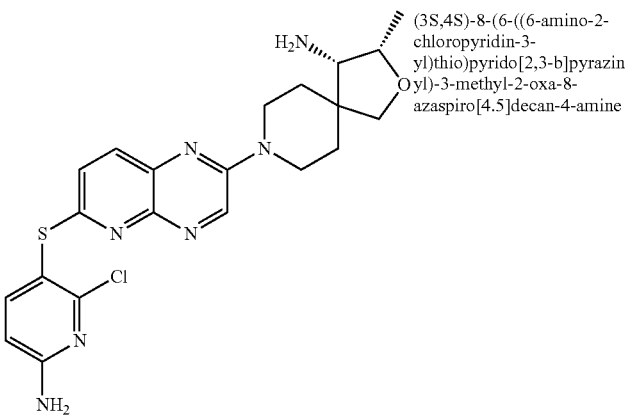 | (3S,4S)-8-(6-((6-amino-2-chloropyridin-3-yl)thio)pyrido[2,3-b]pyrazin-2-yl)-3-methyl-2-oxa-8-azaspiro[4.5]decan-4-amine | Ex. 4 | 458.2 |

TABLE 4-continued

| Ex. # | Structure | Name | Prep | MS |
|---|---|---|---|---|
| 106 | 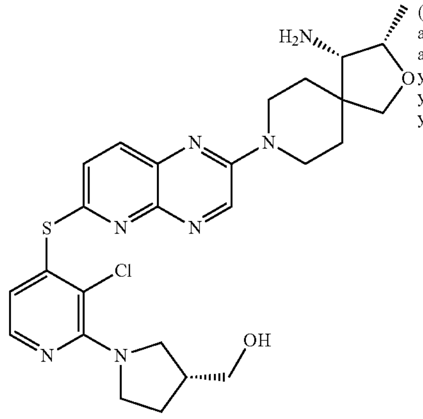 | ((R)-1-(4-((2-((3S,4S)-4-amino-3-methyl-2-oxa-8-azaspiro[4.5]decan-8-yl)pyrido[2,3-b]pyrazin-6-yl)thio)-3-chloropyridin-2-yl)pyrrolidin-3-yl)methanol | Ex. 4 | 542.2 |
| 107 | 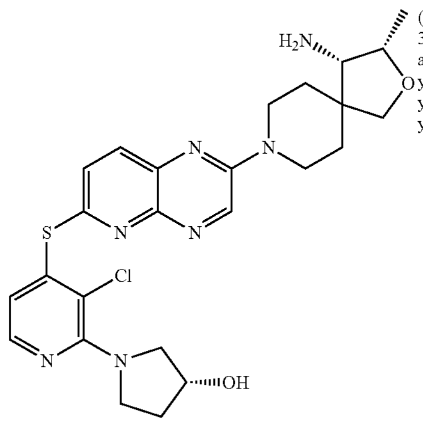 | (R)-1-(4-((2-((3S,4S)-4-amino-3-methyl-2-oxa-8-azaspiro[4.5]decan-8-yl)pyrido[2,3-b]pyrazin-6-yl)thio)-3-chloropyridin-2-yl)pyrrolidin-3-ol | Ex. 4 | 528.2 |

Example 108

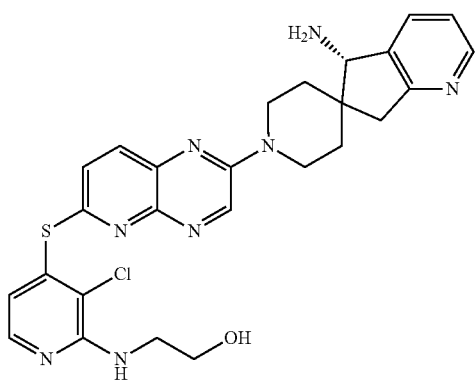

(S)-2-((4-((2-(5-amino-5,7-dihydrospiro[cyclopenta[b]pyridine-6,4'-piperidin]-1'-yl)pyrido[2,3-b]pyrazin-6-yl)thio)-3-chloropyridin-2-yl)amino)ethan-1-ol Step A: To a stirred solution of 6-chloropyrido[2,3-b]pyrazin-2-yl trifluoromethanesulfonate (60 mg, 0.20 mmol) in dioxane (2 mL) was added triethylamine (0.03 mL, 0.72 mmol) at 0° C. and stirred for 5 min. (S)-5,7-dihydrospiro[cyclopenta[b]pyridine-6,4'-piperidin]-5-amine (54 mg, 0.19 mmol) in dioxane (1 mL) was added drop wise and stirred at 0° C. for 1 h. The reaction mixture was diluted with water and extracted with ethyl acetate. The organic part was dried, concentrated and crude was purified by silica gel column chromatography (1% MeOH-DCM) to afford (S)-1'-(6-chloropyrido[2,3-b]pyrazin-2-yl)-5,7-dihydrospiro[cyclopenta[b]pyridine-6,4'-piperidin]-5-amine (70 mg, 94% yield) as yellow solid.

Step B: To a stirred solution of (S)-1'-(6-chloropyrido[2,3-b]pyrazin-2-yl)-5,7-dihydrospiro [cyclopenta[b]pyridine-6,4'-piperidin]-5-amine (60 mg, 0.16 mmol) in dioxane (3 mL) was added sodium 3-chloro-2-((2-hydroxyethyl)amino)pyridine-4-thiolate (100 mg, 0.18 mmol) and stirred at 120° C. for 16 h. After completion the reaction mixture was concentrated and purified by silica gel column chromatography (10% MeOH/DCM) to afford (S)-2-((4-((2-(5-amino-5,7-dihydrospiro [cyclopenta[b]pyridine-6,4'-piperidin]-1'-yl)pyrido[2,3-b]pyrazin-6-yl)thio)-3-chloro-pyridin-2-yl)amino)ethan-1-ol (18 mg, 21% yield) as yellow solid. $^1$H NMR (400 MHz, DMSO-$d_6$) δ 9.02 (s, 1H), 8.35 (d, J=5.1 Hz, 1H), 8.00 (d, J=8.5 Hz, 1H), 7.88 (d, J=5.4 Hz, 1H), 7.69 (d, j=7.6 Hz, 1H), 7.59 (d, j=8.7 Hz, 1H), 7.24-7.15 (m, 1H), 6.52 (t, J=5.6 Hz, 1H), 6.45 (d, J=5.2 Hz, 1H), 4.75 (s, 1H), 4.49 (d, j=13.5 Hz, 2H), 3.98 (s, 1H), 3.58-3.51 (m, 2H), 3.50-3.41 (m, 2H), 3.17 (d, j=16.2 Hz, 1H), 2.83 (d, J=16.4 Hz, 1H), 1.93-1.70 (m, 2H), 1.61 (d, j=12.8 Hz, 1H), 1.25 (d, j=10.9 Hz, 2H). m/z (esi) M+1=535.5.

Example 109

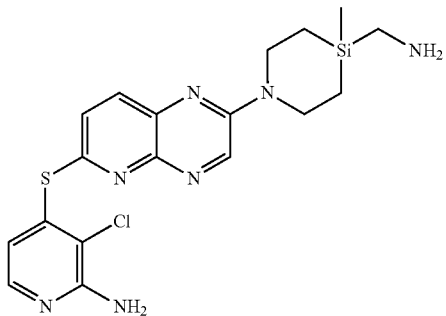 [SMILES: C[Si]1(CN)CCN(c2cnc3nc(Sc4ccnc(N)c4Cl)ccc3n2)CC1]

4-((2-(4-(Aminomethyl)-4-methyl-1,4-azasilinan-1-yl)pyrido[2,3-b]pyrazin-6-yl)thio)-3-chloropyridin-2-amine Step A: To a stirred solution of 6-chloropyrido[2,3-b]pyrazin-2-yl trifluoromethanesulfonate (50 mg, 0.17 mmol) in dioxane (4 mL) was added triethyl amine (0.06 mL, 0.42 mmol) at 0° C. and stirred for 5 min. Tert-butyl ((4-methyl-1,4-azasilinan-4-yl)methyl)carbamate (41 mg, 0.16 mmol) in dioxane (1 mL) was added drop wise and stirred for 1 h at 0° C. After completion, the reaction mixture was diluted with water and extracted with ethyl acetate. The organic part was dried, concentrated and the crude material was purified by silica gel column chromatography (1% MeOH-DCM) to afford tert-butyl ((1-(6-chloropyrido[2,3-b]pyrazin-2-yl)-4-methyl-1,4-azasilinan-4-yl)methyl)carbamate (60 mg, 87% yield) as off white solid, m/z (esi) M+1=408.3.

Step B: To a stirred solution of tert-butyl ((1-(6-chloropyrido[2,3-b]pyrazin-2-yl)-4-methyl-1,4-azasilinan-4-yl)methyl)carbamate (50 mg, 0.12 mmol) in dioxane (5 mL) was added sodium 2-amino-3-chloropyridine-4-thiolate (45 mg, 0.24 mmol) and stirred at 120° C. for 16 h. The reaction mixture was concentrated and the crude material was purified by silica gel column chromatography (3% MeOH-DCM) to afford tert-butyl ((1-(6-((2-amino-3-chloropyridin-4-yl)thio)pyrido[2,3-b]pyrazin-2-yl)-4-methyl-1,4-azasilinan-4-yl)methyl)carbamate (70 mg, impure) as yellow solid, m/z (esi) M+1=531.8.

Step C: To a stirred solution of tert-butyl ((1-(6-((2-amino-3-chloropyridin-4-yl)thio)pyrido[2,3-b]pyrazin-2-yl)-4-methyl-1,4-azasilinan-4-yl)methyl)carbamate (70 mg, 0.13 mmol) in DCM (2 mL) was added 4M HCl in dioxane (2 mL) at 0° C. and stirred for 2 h at room temperature. The reaction mixture was concentrated, and the crude material was diluted with sat. sodium bicarbonate solution and extracted with 15% MeOH/DCM. The organic part was dried and concentrated and the resulting residue was purified by reverse phase Prep HPLC (20-65% ACN:water (20 mM $NH_4CO_3$)) to afford 4-((2-(4-(aminomethyl)-4-methyl-1,4-azasilinan-1-yl)pyrido[2,3-b]pyrazin-6-yl)thio)-3-chloropyridin-2-amine (10 mg, 17% yield, 2 steps) as yellow solid. $^1$H NMR (400 MHz, MeOH-$d_4$) δ 8.81 (s, 1H), 8.02 (d, J=8.4 Hz, 1H), 7.72 (d, J=5.1 Hz, 1H), 7.63 (d, j=8.3 Hz, 1H), 6.48 (d, j=5.3 Hz, 1H), 4.28-3.94 (m, 5H), 2.35 (s, 2H), 1.35-1.25 (m, 1H), 1.21-1.05 (m, 2H), 1.05-0.92 (m, 3H), 0.25 (s, 3H). m/z (esi) M+1=432.4.

Example 110

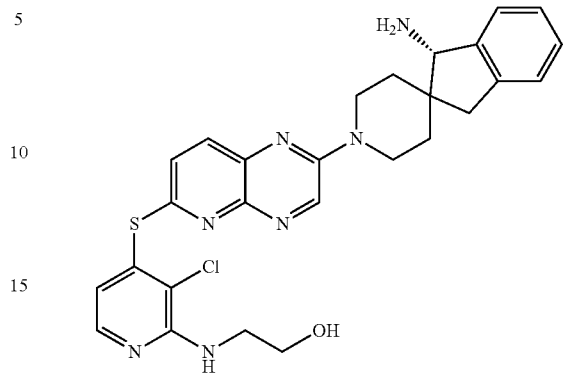

(S)-2-((4-((2-(1-amino-1,3-dihydrospiro[indene-2,4'-piperidin]-1'-yl)pyrido[2,3-b]pyrazin-6-yl)thio)-3-chloropyridin-2-yl)amino)ethan-1-ol Step A: To a stirred solution of 6-chloropyrido[2,3-b]pyrazin-2-yl trifluoromethanesulfonate (100 mg, 0.32 mmol) in dioxane (4 mL) was added triethyl amine (0.06 mL, 0.39 mmol) at 0° C. and stirred for 5 min. (S)—N—((S)-1,3-dihydrospiro[indene-2,4'-piperidin]-1-yl)-2-methylpropane-2-sulfinamide (97 mg, 0.19 mmol) in dioxane (1 mL) was added drop wise stirred for 1 h at 0° C. The reaction mixture was diluted with water and extracted with ethyl acetate. The organic part was dried ($Na_2SO_4$), concentrated and crude was purified by silica gel column chromatography (1% MeOH-DCM) to afford (S)—N—((S)-1'-(6-chloropyrido[2,3-b]pyrazin-2-yl)-1,3-dihydrospiro[indene-2,4'-piperidin]-1-yl)-2-methylpropane-2-sulfinamide (120 mg, 78% yield) as off white solid, in z (esi) M+1=470.1.

Step B: To a stirred solution of (S)—N—((S)-1'-(6-chloropyrido[2,3-b]pyrazin-2-yl)-1,3-dihydrospiro [indene-2,4'-piperidin]-1-yl)-2-methylpropane-2-sulfinamide (50 mg, 0.11 mmol) in dioxane (2 mL) was added sodium 3-chloro-2-((2-hydroxyethyl)amino)pyridine-4-thiolate (65 mg, 0.32 mmol) and stirred at 120° C. for 16 h. The reaction mixture was concentrated and crude was purified by silica gel column chromatography (3% MeOH-DCM) to afford (S)—N—((S)-1'-(6-((3-chloro-2-((2-hydroxyethyl)amino)pyridin-4-yl)thio)pyrido[2,3-b]pyrazin-2-yl)-1,3-dihydrospiro [indene-2,4'-piperidin]-1-yl)-2-methylpropane-2-sulfinamide (50 mg, 73% yield) as yellow solid, m/z (esi) M+1=638.3.

Step C: To a stirred solution of (S)—N—((S)-1'-(6-((3-chloro-2-((2-hydroxyethyl)amino)pyridin-4-yl)thio)pyrido [2,3-b]pyrazin-2-yl)-1,3-dihydrospiro [indene-2,4'-piperidin]-1-yl)-2-methylpropane-2-sulfinamide (100 mg, 0.16 mmmol) in DCM (5 mL) was added 4M HCl in dioxane (2 mL) at ice cold condition and stirred for 2 h at room temperature. The reaction mixture was concentrated, diluted with sat. sodium bicarbonate solution and extracted with 15% MeOH in DCM. The organic part was dried ($Na_2SO_4$), filtered, concentrated and crude was purified by silica gel column chromatography (10% MeOH-DCM) to afford (S)-2-((4-((2-(1-amino-1,3-dihydrospiro [indene-2,4'-piperidin]-1'-yl)pyrido[2,3-b]pyrazin-6-yl)thio)-3-chloropyridin-2-yl)amino)ethan-1-ol (30 mg, 36% yield) as yellow solid. $^1$H NMR (400 MHz, DMSO-$d_6$) δ 9.01 (s, 1H), 7.99 (d, J=8.6 Hz, 1H), 7.88 (d, J=5.3 Hz, 1H), 7.59 (d, J=8.5 Hz, 1H), 7.35-7.28 (m, 1H), 7.25-7.12 (m, 3H), 6.53 (t, J=5.5 Hz, 1H), 6.45 (d, 0.7=5.3 Hz, 1H), 4.75 (t, j=5.5 Hz, 1H), 4.47 (dd, j=9.4, 13.6 Hz, 2H), 3.88 (s, 1H), 3.54 (t, j=5.7 Hz, 2H), 3.46 (q, j=6.0 Hz, 2H), 3.12 (d, j=15.7 Hz, 1H), 2.68 (d, J=15.3 Hz, 1H), 1.93-1.78 (m, 1H), 1.77-1.65 (m, 1H), 1.58 (d, j=13.4 Hz, 1H), 1.26-1.14 (m, 2H). m/z (esi) M+1=534.4.

Example 111

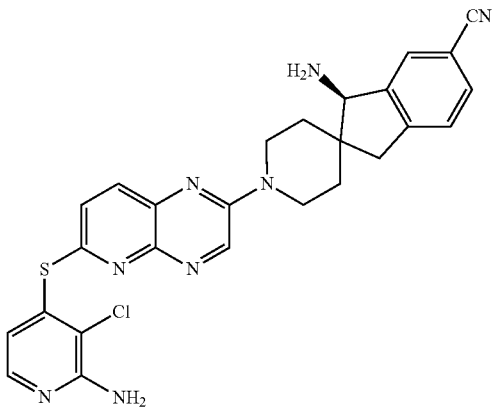 [SMILES: N#Cc1ccc2c(c1)[C@H](N)C1(CCN(c3cnc4nc(Sc5ccnc(N)c5Cl)ccc4n3)CC1)C2]

(R)-1-amino-1'-(6-((2-amino-3-chloropyridin-4-yl)thio)pyrido[2,3-b]pyrazin-2-yl)-1,3-dihydrospiro[indene-2,4'-piperidine]-6-carbonitrile Step A: To a stirred solution of 6-chloropyrido[2,3-b]pyrazin-2-yl trifluoromethanesulfonate (100 mg, 0.33 mmol) in dioxane (2 mL) was added triethylamine (0.11 mL, 0.84 mmol) at 0° C. and stirred for 5 min. 3-Amino-1,3-dihydrospiro[indene-2,4'-piperidine]-6-carbonitrile dihydrochloride in dioxane (1 mL) was added drop wise at 0° C. and stirred for 1 h. The reaction mixture was diluted with water and extracted with ethyl acetate. The organic part was dried (Na₂SO₄), filtered, concentrated and purified by silica gel column chromatography (2% MeOH-DCM) to afford (3S)-3-amino-1'-{6-chloropyrido[2,3-b]pyrazin-2-yl}-1,3-dihydrospiro[indene-2,4'-piperidine]-6-carbonitrile (120 mg, 91% yield) as yellow solid, m/z (esi) M+1=391.1.

Step B: To a stirred solution of (3S)-3-amino-1'-{6-chloropyrido[2,3-b]pyrazin-2-yl}-1,3-dihydrospiro[indene-2,4'-piperidine]-6-carbonitrile (120 mg, 0.3 mmol) in dioxane (5 mL) was added sodium 2-amino-3-chloropyridine-4-thiolate (112 mg, 0.61 mmol) and stirred at 120° C. for 16 h. The reaction mixture was concentrated, purified by silica gel column chromatography (5% MeOH-DCM) to afford racemic product which was subjected to chiral separation (chiralpak IC (250×21 mm) 5μ, Flow:25 g/min, Mobile Phase: 40% CO₂+60% (0.5% Isopropylamine in methanol), ABPR:120 bar, temperature:35° C.) to afford (R)-1-amino-r-(6-((2-amino-3-chloropyridin-4-yl)thio)pyrido [2,3-b]pyrazin-2-yl)-1,3-dihydrospiro[indene-2,4'-piperidine]-6-carbonitrile (13623-89-CM-A3-8-p2) (20 mg, 13% yield). ¹H NMR (400 MHz, DMSO-d₆) δ 9.01 (s, 1H), 7.99 (d, J=8.6 Hz, 1H), 7.79 (d, J=5.3 Hz, 1H), 7.70-7.57 (m, 3H), 7.49 (d, J=7.8 Hz, 1H), 6.49-6.39 (m, 3H), 4.49 (t, J=15.4 Hz, 2H), 3.91 (s, 1H), 3.31-3.11 (m, 3H), 2.71 (d, J=15.9 Hz, 1H), 1.85 (t, J=10.9 Hz, 1H), 1.75-1.57 (m, 2H), 1.09 (d, J=13.5 Hz, 1H), m/z (esi) M+1=515.1.

Example 112

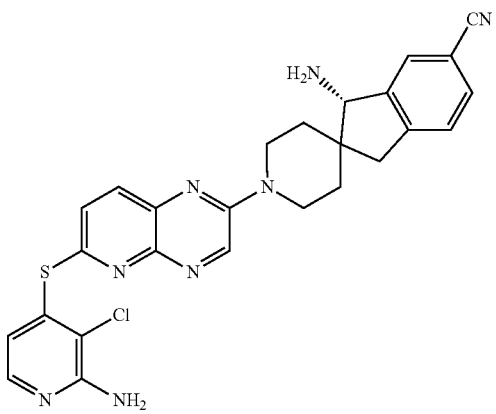 [SMILES: N#Cc1ccc2c(c1)[C@@H](N)C1(CCN(c3cnc4nc(Sc5ccnc(N)c5Cl)ccc4n3)CC1)C2]

(S)-1-amino-1'-(6-((2-amino-3-chloropyridin-4-yl)thio)pyrido[2,3-b]pyrazin-2-yl)-1,3-dihydro spiro[indene-2,4'-piperidine]-6-carbonitrile Was prepared according to Example 111 collecting the first eluting peak in Step B (10 mg, 6% yield). ¹H NMR (400 MHz, DMSO-d₆) δ 9.01 (s, 1H), 7.99 (d, J=8.5 Hz, 1H), 7.79 (d, J=5.3 Hz, 1H), 7.67 (d, J=6.7 Hz, 2H), 7.60 (d, J=8.5 Hz, 1H), 7.49 (d, J=7.8 Hz, 1H), 6.53-6.38 (m, 3H), 4.49 (t, J=15.0 Hz, 2H), 3.92 (s, 1H), 3.19 (d, J=16.0 Hz, 1H), 2.76-2.63 (m, 1H), 1.92-1.78 (m, 1H), 1.77-1.54 (m, 2H), 1.15-1.06 (m, 1H). m/z (esi) M+1=515.1.

Example 113

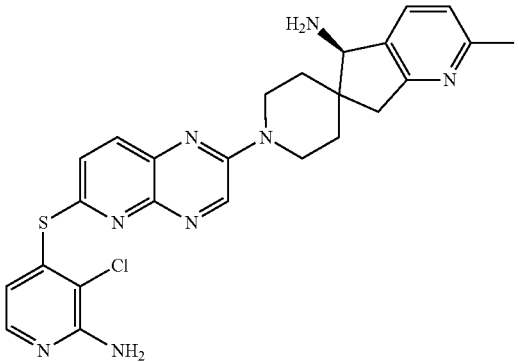 [SMILES: Cc1ccc2c(n1)CC1(CCN(c3cnc4nc(Sc5ccnc(N)c5Cl)ccc4n3)CC1)[C@H]2N]

(R)-1'-(6-((2-amino-3-chloropyridin-4-yl)thio)pyrido[2,3-b]pyrazin-2-yl)-2-methyl-5,7-dihydrospiro[cyclopenta[b]pyridine-6,4'-piperidin]-5-amine Step A: To a stirred solution of tert-butyl (R)-5-(((R)-tert-butylsulfinyl)amino)-2-methyl-5,7-dihydrospiro[cyclopenta[b]pyridine-6,4'-piperidine]-1'-carboxylate [indene-2,4'-piperidin-1-yl)-2-methylpropane-2-sulfinamide (160 mg, 0.38 mmol) in DCM (2 mL) was added 4M HCl in dioxane (2 mL) at 0° C. and stirred for 2 h at room temperature. The reaction mixture was concentrated to afford (R)-2-methyl-5,7-dihydrospiro[cyclopenta[b]pyridine-6,4'-piperidin]-5-amine dihydrochloride (75 mg, 67% yield) as white solid, m/z (esi) M+1=218.1.

Step B: To a stirred solution of 6-chloropyrido[2,3-b]pyrazin-2-yl trifluoromethanesulfonate (60 mg, 0.19 mmol) in dioxane (2 mL) was added triethylamine (0.1 mL, 0.78 mmol) at 0° C. and stirred for 5 min. (R)-2-Methyl-5,7-dihydrospiro[cyclopenta[b]pyridine-6,4'-piperidin]-5-amine dihydrochloride (43 mg, 0.19 mmol) in dioxane (1 mL) was added drop wise and stirred for 1 h at 0° C. The reaction mixture was diluted with water and extracted with ethyl acetate. The organic part was dried (Na2SO4), filtered, concentrated and purified by silica gel column chromatography (1% MeOH/DCM) to afford (R)-1'-(6-chloropyrido[2,3-b]pyrazin-2-yl)-2-methyl-5,7-dihydrospiro[cyclopenta[b]pyridine-6,4'-pipe-ridin]-5-amine (35 mg, 47% yield) as off white solid, m/z (esi) M+1=381.1.

Step C: To a stirred solution of (R)-1'-(6-chloropyrido[2,3-b]pyrazin-2-yl)-2-methyl-5,7-dihydrospiro[cyclopenta[b]pyridine-6,4'-piperidin]-5-amine (60 mg, 0.15 mmol) in dioxane (3 mL) was added sodium 2-amino-3-chloropyridine-4-thiolate (87 mg, 0.47 mmol) and stirred at 120° C. for 16 h. The reaction mixture was concentrated and crude material was purified by silica gel column chromatography (10% MeOH-DCM) to afford (R)-1'-(6-((2-amino-3-chloro-pyridin-4-yl)thio)pyrido[2,3-b]pyrazin-2-yl)-2-methyl-5,7-dihydrospiro [cyclopenta [b] pyridine-6,4'-piperidin]-5-amine (15 mg, 19% yield) as yellow solid, m/z (esi) M+1=505.4.

Example 114

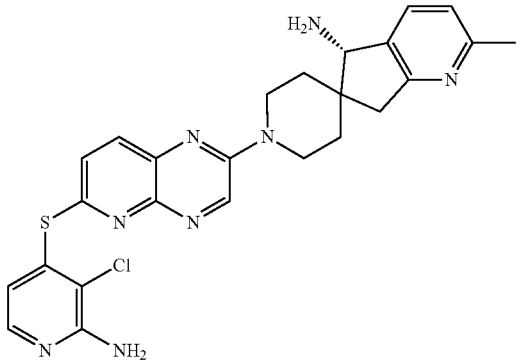 [SMILES: Cc1ccc2c(n1)CC1(CCN(c3cnc4nc(Sc5ccnc(N)c5Cl)ccc4n3)CC1)[C@@H]2N]

(S)-1'-(6-((2-amino-3-chloropyridin-4-yl)thio)pyrido[2,3-b]pyrazin-2-yl)-2-methyl-5,7-dihydrospiro[cyclopenta[b]pyridine-6,4'-piperidin]-5-amine Step A: To a stirred solution of tert-butyl (S)-5-(((R)-tert-butylsulfinyl)amino)-2-methyl-5,7-dihydrospiro[cyclopenta[b]pyridine-6,4'-piperidine]-1'-carboxylate [indene-2,4'-piperidin]-1-yl)-2-methylpropane-2-sulfinamide (100 mg, 0.16 mmol) in DCM (5 mL) was added 4M HCl in dioxane (2 mL) at 0° C. and stirred for 2 h at room temperature. The reaction mixture was concentrated to afford (S)-2-methyl-5,7-dihydrospiro[cyclopenta [b] pyridine-6,4'-piperidin]-5-amine dihydrochloride (50 mg, 72% yield) as white solid, m/z (esi) M+1=218.2.

Step B: To a stirred solution of 6-chloropyrido[2,3-b]pyrazin-2-yl trifluoromethanesulfonate (60 mg, 0.19 mmol) in dioxane (2 mL) was added triethylamine (0.1 mL, 0.78 mmol) at 0° C. and stirred for 5 min. (S)-2-Methyl-5,7-dihydrospiro[cyclopenta[b]pyridine-6,4'-piperidin]-5-amine dihydrochloride (43 mg, 0.19 mmol) in dioxane (1 mL) was added drop wise and stirred for 1 h at 0° C. The reaction mixture was diluted with water and extracted with ethyl acetate. The organic part was dried (Na2SO4), filtered, concentrated and purified by silica gel column chromatography (1% MeOH/DCM) to afford (S)-1'-(6-chloropyrido[2,3-b]pyrazin-2-yl)-2-methyl-5,7-dihydrospiro[cyclopenta[b]pyridine-6,4'-piperi-din]-5-amine (35 mg, 47% yield) as off white solid, m/z (esi) M+1=381.0.

Step C: To a stirred solution of (S)-1'-(6-chloropyrido[2,3-b]pyrazin-2-yl)-2-methyl-5,7-dihydrospiro[cyclopenta[b]pyridine-6,4'-piperidin]-5-amine (60 mg, 0.15 mmol) in dioxane (3 mL) was added sodium 2-amino-3-chloropyridine-4-thiolate (87 mg, 0.47 mmol) and stirred at 120° C. for 16 h. The reaction mixture was concentrated and purified by silica gel column chromatography (10% MeOH-DCM) to afford (S)-1'-(6-((2-amino-3-chloropyridin-4-yl)thio)pyrido[2,3-b]pyrazin-2-yl)-2-methyl-5,7-dihydrospiro [cyclopenta [b] pyridine-6,4'-piperidin]-5-amine (15 mg, 19% yield) as yellow solid, m/z (esi) M+1=505.4.

Example 115

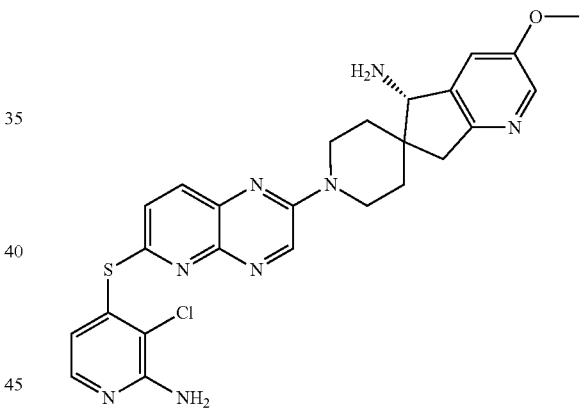

(S)-1'-(6-((2-amino-3-chloropyridin-4-yl)thio)pyrido[2,3-b]pyrazin-2-yl)-3-methoxy-5,7-dihydrospiro[cyclopenta[b]pyridine-6,4'-piperidin]-5-amine Step A: To a stirred solution of 3-methoxy-5,7-dihydrospiro[cyclopenta[b]pyridine-6,4'-piperidin]-5-amine hydrochloride (97.45 mg, 0.32 mmol) in 1,4 dioxane (5 mL) TEA (0.22 mL, 1.59 mmol) was added at RT and stirred for 20 min and then 6-chloropyrido[2,3-b]pyrazin-2-yl trifluoromethane sulfonate (100 mg, 0.32 mmol) was added and stirred for 1 h at RT. The reaction was concentrated and the resulting residue was purified by silica gel column chromatography (7-14% MeOH/DCM) to get 1'-(6-chloropyrido[2,3-b]pyrazin-2-yl)-3-methoxy-5,7-dihydrospiro [cyclopenta [b] pyridine-6,4'-piperidin]-5-amine (75 mg, 59% yield) as light yellow solid, m/z (esi) M+1=397.3

Step B: To a stirred solution of 1'-(6-chloropyrido[2,3-b]pyrazin-2-yl)-3-methoxy-5,7-dihydrospiro[cyclopenta[b]pyridine-6,4'-piperidin]-5-amine (130 mg, 0.32 mmol) in 1,4 dioxane (4 mL) sodium 2-amino-3-chloropyridine-4-thiolate (56.13 mg, 0.32 mmol) was added and heated to 120° C. for 16 h. The reaction was cooled and was purified by silica gel column chromatography (7-14% MeOH/DCM) to get 98 mg of the mixture of isomers. These isomers were separated by chiral prep HPLC (Chiralpak IG 21.0×250 mm/5μ, DCM/EtOH/iPrNH$_2$ 60/40/0.1, 9.0 mL/min) to get (S)-1'-(6-((2-amino-3-chloropyridin-4-yl)thio)pyrido[2,3-b]pyrazin-2-yl)-3-methoxy-5,7-dihydrospiro[cyclopenta[b]pyridine-6,4'-piperidin]-5-amine (9.2 mg, 5% yield) as light yellow sticky solid. $^1$H NMR (400 MHz, Methanol-d$_4$) δ 8.87 (s, 1H), 8.06-7.97 (m, 2H), 7.73 (d, J=5.4 Hz, 1H), 7.62 (d, J=8.6 Hz, 1H), 7.44 (d, J=2.7 Hz, 1H), 6.51 (d, J=5.4 Hz, 1H), 4.61-4.52 (m, 2H), 4.02 (s, 1H), 3.87 (s, 3H), 3.47-3.37 (m, 2H), 3.18 (d, J=16.1 Hz, 1H), 2.87 (d, J=16.1 Hz, 1H), 1.99-1.80 (m, 2H), 1.70 (d, J=13.4 Hz, 1H), 1.47 (d, J=13.8 Hz, 1H). m/z (esi) M+1=521.2.

Example 116

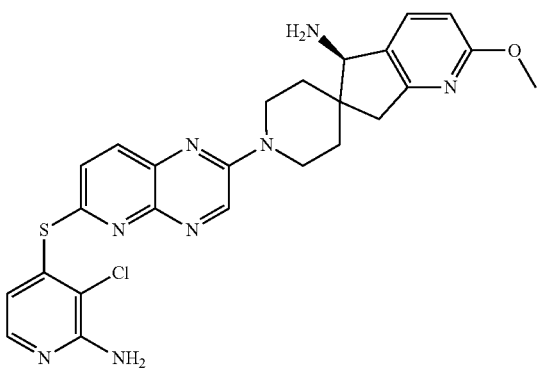 [SMILES: COc1ccc2c(n1)CC1(CCN(c3cnc4nc(Sc5ccnc(N)c5Cl)ccc4n3)CC1)[C@H]2N]

(R)-1'-(6-((2-amino-3-chloropyridin-4-yl)thio)pyrido [2,3-b]pyrazin-2-yl)-2-methoxy-5,7-dihydrospiro [cyclopenta[b]pyridine-6,4'-piperidin]-5-amine (R)-1'-(6-((2-amino-3-chloropyridin-4-yl)thio)pyrido[2,3-b]pyrazin-2-yl)-3-methoxy-5,7-dihydrospiro[cyclopenta[b]pyridine-6,4'-piperidin]-5-amine was prepared according to Example 115, collecting Peak 2 in Step D. $^1$H NMR (400 MHz, Methanol-d$_4$) δ 8.87 (s, 1H), 8.06-7.97 (m, 2H), 7.73 (d, J=5.4 Hz, 1H), 7.62 (d, J=8.6 Hz, 1H), 7.44 (d, J=2.7 Hz, 1H), 6.51 (d, J=5.4 Hz, 1H), 4.61-4.52 (m, 2H), 4.02 (s, 1H), 3.87 (s, 3H), 3.47-3.37 (m, 2H), 3.18 (d, J=16.1 Hz, 1H), 2.87 (d, J=16.1 Hz, 1H), 1.99-1.80 (m, 2H), 1.70 (d, J=13.4 Hz, 1H), 1.47 (d, J=13.8 Hz, 1H) m/z (esi) M+1=521.2.

Example 117

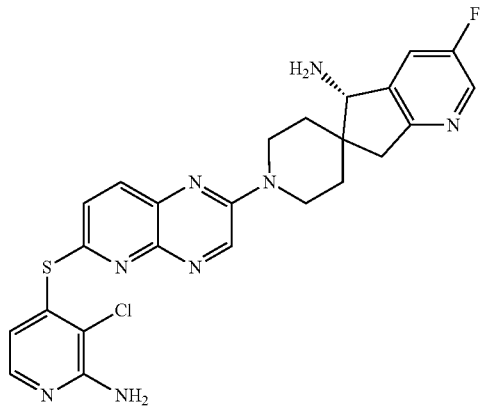 [SMILES: Nc1nccc(Sc2ccc3nc(N4CCC5(CC4)Cc4ncc(F)cc4[C@H]5N)cnc3n2)c1Cl]

(S)-1'-(6-((2-amino-3-chloropyridin-4-yl)thio)pyrido [2,3-b]pyrazin-2-yl)-3-fluoro-5,7-dihydrospiro[cyclopenta[b]pyridine-6,4'-piperidin]-5-amine Step A: To a stirred solution of 3-fluoro-5,7-dihydrospiro [cyclopenta[b]pyridine-6,4' piperidin]-5-amine dihydrochloride (480 mg, 1.63 mmol) and 6-chloropyrido[2,3-b] pyrazin-2-yl trifluoromethane-sulfonate (490 mg, 1.63 mmol) in 1,4-dioxane (1 mL) was added TEA (1.1 mL, 8.19 mmol) at 0° C. and stirred at RT for 1 h. The reaction mixture was quenched with water (15 mL), extracted with EtOAc, dried (Na$_2$SO$_4$), filtered and concentrated. The resulting residue was purified by silica gel flash chromatography (1-3% MeOH-DCM) to afford T-(6-chloropyrido[2,3-b] pyrazin-2-yl)-3-fluoro-5,7-dihydrospiro[cyclopenta[b]pyridine-6,4'-piperidin]-5-amine (400 mg, 63% yield) product as yellow solid, m/z (esi) M+1=385.2.

Step B: To a stirred solution of 1'-{6-chloropyrido[2,3-b] pyrazin-2-yl}-6-fluoro-1,3-dihydrospiro[cyclopenta[b]pyridine-2,4'-piperidine]-1-amine (200 mg, 0.51 mmol) in 1,4-dioxane (10 mL) was added sodium 2-amino-3-chloropyridine-4-thiol (300 mg, 1.56 mmol) and stirred at 120° C. for 16 h. The reaction mixture was concentrated and purified by silica gel flash chromatography (10% MeOH-DCM) to afford 200 mg of 1'-{6-[(2-amino-3-chloropyridin-4-yl)sulfanyl]pyrido[2,3-b] pyrazin-2-yl}-6-fluoro-1,3-dihydrospiro [cyclopenta[b]pyridine-2,4'-pipe-ridine]-1-amine as yellow solid. Isomers were separated by chiral prep HPLC (Chiralpak IG (21.0×250 mm/5μ, Mobile phase: n-Hexane/EtOH/DCM/IPamine: 40/30/30/0.1, 21.0 mL/min, 20 min, 250 nm) to afford (S)-1'-(6-((2-amino-3-chloropyridin-4-yl)thio) pyrido[2,3-b]pyrazin-2-yl)-3-fluoro-5,7-dihydrospiro[cyclopenta[b] pyridine-6,4'-piperidin]-5-amine (40.46 mg, 15% yield). $^1$H NMR (400 MHz, DMSO-d$_6$) δ 9.02 (s, 1H), 8.33 (s, 1H), 8.00 (d, J=8.5 Hz, 1H), 7.80 (d, J=5.3 Hz, 1H), 7.64-7.53 (m, 2H), 6.49-6.40 (m, 3H), 4.50 (d, J=13.6 Hz, 2H), 4.02 (s, 1H), 3.42-3.34 (m, 1H), 3.15 (d, J=16.3 Hz, 1H), 2.82 (d, J=16.3 Hz, 1H), 1.89-1.70 (m, 2H), 1.63 (d, J=13.3 Hz, 1H), 1.25 (brs, 1H). m/Z (esi) (M+1+2)=511.4.

Example 118

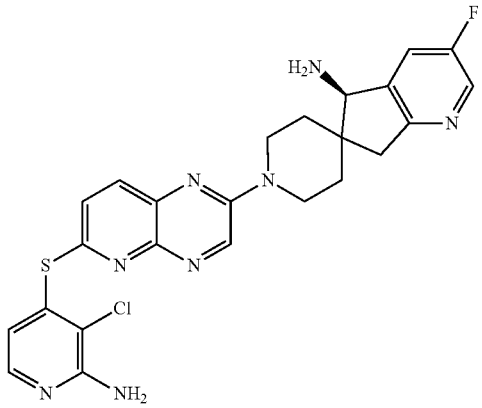 [SMILES: Nc1nccc(Sc2ccc3nc(N4CCC5(CC4)Cc4ncc(F)cc4[C@@H]5N)cnc3n2)c1Cl]

(R)-1'-(6-((2-amino-3-chloropyridin-4-yl)thio)pyrido[2,3-b]pyrazin-2-yl)-3-fluoro-5,7-dihydrospiro[cyclopenta[b]pyridine-6,4'-piperidin]-5-amine (R)-1'-(6-((2-amino-3-chloropyridin-4-yl)thio)pyrido[2,3-b]pyrazin-2-yl)-3-fluoro-5,7-dihydrospiro[cyclopenta[b]pyridine-6,4'-piperidin]-5-amine was prepared according to Example 117, collecting the second eluting peak in Step B. $^1$H NMR (400 MHz, DMSO-$d_6$) δ 9.01 (s, 1H), 8.35 (s, 1H), 8.00 (d, J=8.6 Hz, 1H), 7.80 (d, J=5.2 Hz, 1H), 7.61 (d, J=8.7 Hz, 2H), 6.49-6.40 (m, 3H), 4.50 (d, J=13.5 Hz, 2H), 4.07 (s, 1H), 3.42-3.34 (m, 1H), 3.17 (d, J=16.3 Hz, 1H), 2.85 (d, J=16.3 Hz, 1H), 2.40-1.98 (m, 1H), 1.93-1.70 (m, 2H), 1.63 (d, J=13.3 Hz, 1H), 1.36-1.18 (m, 2H), 1.17 (d, j=6.5 Hz, 1H). m/Z (esi) (M+1+2)=511.4.

Example 119

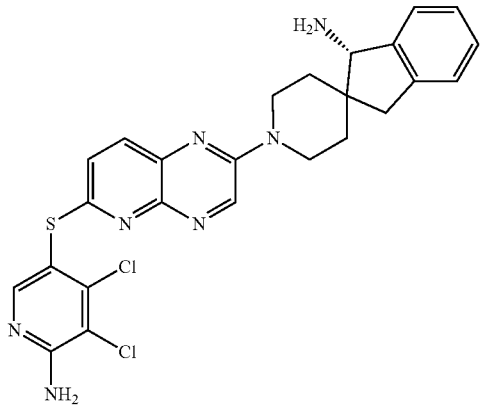 [SMILES: Nc1ncc(Sc2ccc3nc(N4CCC5(CC4)Cc4ccccc4[C@H]5N)cnc3n2)c(Cl)c1Cl]

(S)-1'-(6-((6-amino-4,5-dichloropyridin-3-yl)thio)pyrido[2,3-b]pyrazin-2-yl)-1,3-dihydrospiro[indene-2,4'-piperidin]-1-amine Step A: To a stirred solution of 6-chloropyrido[2,3-b]pyrazin-2-yl trifluoromethanesulfonate (60 mg, 0.19 mmol) in dioxane (2 mL) was added triethylamine (0.06 mL, 0.49 mmol) at 0° C. and stirred at 0° C. for 5 min. (S)-1,3-dihydrospiro[indene-2,4'-piperidin]-1-amine dihydrochloride (54 mg, 0.19 mmol) in dioxane (1 mL) was added drop wise at 0° C. and stirred for 1 h at room temperature. The reaction mixture was diluted with water and extracted with EtOAc. Organic part was dried (Na$_2$SO$_4$), filtered, concentrated and purified by silica gel column chromatography (1% MeOH-DCM) to afford (S)-1'-(6-chloropyrido[2,3-b]pyrazin-2-yl)-1,3-dihydrospiro[indene-2,4'-piperidin]-1-amine (65 mg, 90% yield) as off white solid, m/z (esi) M+1=366.0.

Step B: To a stirred solution of (S)-1'-(6-chloropyrido[2,3-b]pyrazin-2-yl)-1,3-dihydrospiro[indene-2,4'-piperidin]-1-amine (60 mg, 0.16 mmol) in dioxane (2.5 mL) was added sodium 6-amino-4,5-dichloropyridine-3-thiolate (42 mg, 0.18 mmol) and stirred at 120° C. for 1 h. The reaction mixture was concentrated and brought up in DMF (1 mL), filtered and purified by reverse phase prep HPLC (5-60% ACN:Water (20 mM NH$_4$CO$_3$)) to afford (S)-1'-(6-((6-amino-4,5-dichloropyridin-3-yl)thio)pyrido[2,3-b]pyrazin-2-yl)-1,3-dihydrospiro[indene-2,4'-piperidin]-1-amine (18 mg, 21% yield) as yellow solid. $^1$H NMR (400 MHz, DMSO-$d_6$) δ 8.88 (s, 1H), 8.23 (s, 1H), 7.88 (d, J=8.7 Hz, 1H), 7.33-7.11 (m, 7H), 4.40 (t, J=13.4 Hz, 2H), 3.84 (s, 1H), 3.29-3.20 (m, 1H), 3.09 (d, J=15.6 Hz, 1H), 2.65 (d, J=15.8 Hz, 1H), 1.87-1.75 (m, 1H), 1.70 (t, J=12.4 Hz, 1H), 1.55 (d, J=13.4 Hz, 1H), 1.14 (d, J=13.5 Hz, 1H); m/z (esi) M+1=524.4.

Example 120

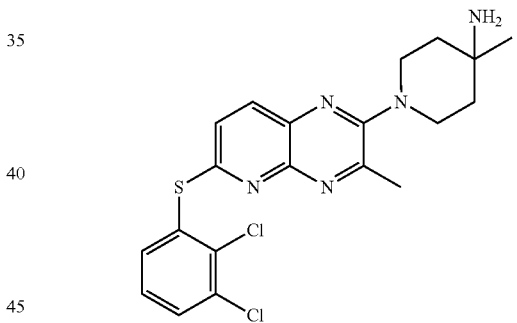

1-(6-((2,3-dichlorophenyl)thio)-3-methylpyrido[2,3-b]pyrazin-2-yl)-4-methylpiperidin-4-amine Step A: A mixture of 6-chloropyridine-2,3-diamine (1.00 g, 7.0 mmol), methyl 2-oxopropanoate (0.96 mL, 10.45 mmol) and Hunig's base (2.41 mL, 13.93 mmol) in DMF (23.22 mL, 7.0 mmol) was stirred at room temp for 4 days. This was then concentrated down and taken up in DCM. Hexanes was added and this was filtered to give 6-chloro-3-methylpyrido[2,3-b]pyrazin-2(1H)-one (0.73 g, 3.71 mmol, 53% yield).

Step B: Hunig's base (0.15 mL, 0.86 mmol) was added to 6-chloro-3-methylpyrido[2,3-b]pyrazin-2(1H)-one (0.11 g, 0.57 mmol) and Tf$_2$O (0.11 mL, 0.63 mmol) in DCM (2.86 mL, 0.57 mmol) at 0° C. This was allowed to warm to room temp slowly overnight. The mixture was concentrated and purified on a column using EtOAc:hex (10-90%) to give 6-chloro-3-methylpyrido[2,3-b]pyrazin-2-yl trifluoromethanesulfonate (0.100 g, 0.31 mmol, 53% yield).

Step C: A mixture of 6-chloro-3-methylpyrido[2,3-b]pyrazin-2-yl trifluoromethanesulfonate (0.10 g, 0.31 mmol), tert-butyl (4-methylpiperidin-4-yl)carbamate (0.065 g, 0.31 mmol) and Hunig's base (0.11 mL, 0.61 mmol) in dioxane (0.76 mL, 0.31 mmol) was heated to 90° C. for 20 min. The reaction was concentrated down and loaded onto a column and purified using EtOAc:hex: (10-90%) to give tert-butyl (1-(6-chloro-3-methylpyrido[2,3-b]pyrazin-2-yl)-4-methylpiperidin-4-yl)carbamate (0.10 g, 0.26 mmol, 84% yield).

Step D: tert-butyl (1-(6-chloro-3-methylpyrido[2,3-b]pyrazin-2-yl)-4-methylpiperidin-4-yl)carbamate (0.050 g, 0.13 mmol), potassium phosphate (0.081 g, 0.38 mmol), TMEDA (0.012 mL, 0.077 mmol), 2,3-dichlorobenzenethiol (0.069 g, 0.38 mmol) and copper(I) iodide (0.0073 g, 0.038 mmol) were placed in dioxane (0.64 mL, 0.13 mmol) and was degassed with Ar sealed and heated to 100° C. for 18 hr. The reaction was cooled to rt and water was added. The mixture was loaded onto a column and purified using EtOAc:hex (10-90%). Fractions were concentrated down and stirred with TFA:DCM (1:14 mL) for 1 hour at room temp. The mixture was concentrated and purified on prep HPLC using ACN:Water (1% TFA) 5-95% to give product. This was worked up with DCM and sat. NaHCO3. The organics were washed with brine and dried with Na2SO4. This was concentrated to give 1-(6-((2,3-dichlorophenyl)thio)-3-methylpyrido[2,3-b]pyrazin-2-yl)-4-methylpiperidin-4-amine (0.028 g, 0.065 mmol, 51% yield). $^1$H NMR (400 MHz, CDCl$_3$) δ, 7.94 (d, 1H, J=8.6 Hz), 7.65 (dd, 1H, J=7.8, 1.6 Hz), 7.52 (dd, 1H, 0.7=8.2, 1.6 Hz), 7.24 (t, 1H, 0.7=7.8 Hz), 7.20 (d, 1H, J=8.6 Hz), 3.46-3.33 (m, 4H), 2.71 (s, 3H), 1.81-1.74 (m, 2H), 1.69-1.60 (m, 2H), 1.25 (s, 3H). m/z (esi) M+1=534.1.

Example 121

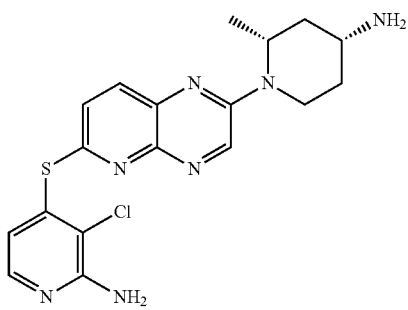 [SMILES: C[C@@H]1C[C@H](N)CCN1c1cnc2nc(Sc3ccnc(N)c3Cl)ccc2n1]

4-((2-((2R,4R)-4-amino-2-methylpiperidin-1-yl)pyrido[2,3-h]pyrazin-6-yl)thio)-3-chloropyridin-2-amine Step A: To a solution of 6-chloropyrido[2,3-b]pyrazin-2-yl 4-nitrobenzenesulfonate (75 mg, 0.20 mmol) in dioxane (2 mL) was added N-ethyl-N-isopropylpropan-2-amine (184 μL, 1.0 mmol) followed by tert-butyl ((2R,4R)-2-methylpiperidin-4-yl)carbamate (48 mg, 0.22 mmol) and the reaction stirred at rt for 18 hr. The reaction was concentrated and purified by silica gel (0-12% MeOH in DCM) to provide ((2R,4R)-1-(6-chloropyrido[2,3-b]pyrazin-2-yl)-2-methylpiperidin-4-yl)carbamate (72 mg, 0.19 mmol, 93% yield).

Step B: tert-butyl ((2R,4R)-1-(6-chloropyrido[2,3-b]pyrazin-2-yl)-2-methylpiperidin-4-yl)carbamate (72 mg, 0.19 mmol), N-ethyl-N-isopropylpropan-2-amine (66 μL, 0.38 mmol) and sodium 2-amino-3-chloropyridine-4-thiolate (69.6 mg, 0.38 mmol) were placed in dioxane (2 mL) and heated to 80 C for 18 hr. The reaction was cooled and concentrated and the resulting residue was purified by silica gel (0-15% MeOH in DCM with 0.2% NH$_4$OH) to provide hoc material. The material was brought up in 10% MeOH in DCM (3 mL) and 4 N HCl in dioxane (2 mL) was added and the reaction was stirred for 18 hr. The material was concentrated and purified by reverse phase chromatography (0-50% ACN:water with 0.1% TFA). The material was brought up in 10% MeOH in DCM and saturated bicarbonate was added and the layers were separated. The organic layer was dried, filtered and concentrated to provide 4-((2-((2R,4R)-4-amino-2-methylpiperidin-1-yl)pyrido[2,3-b]pyrazin-6-yl)thio)-3-chloropyridin-2-amine (19.9 mg, 0.050 mmol, 26.0% yield). $^1$H NMR (400 MHz, DMSO-d$_6$) δ 8.86 (s, 1H), 7.95 (d, 1H, J=8.6 Hz), 7.76 (d, 1H, J=5.3 Hz), 7.57 (d, 1H, J=5.3 Hz), 6.43 (s, 2H), 6.37 (d, 1H, J=5.3 Hz), 4.65 (m, 1H), 4.29 (m, 1H), 3.49 (m, 1H), 3.15 (m, 1H), 1.91-1.77 (m, 3H), 1.61-1.46 (m, 2H), 1.37 (d, 3H, J=6.7 Hz). m/Z (esi) (M+1)=402.1.

Example 122

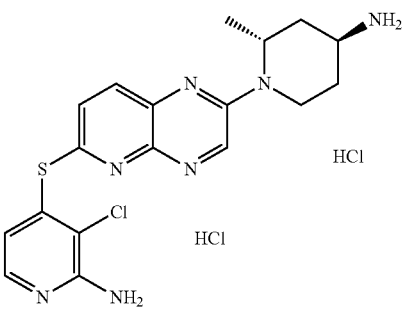 [SMILES: C[C@@H]1C[C@@H](N)CCN1c1cnc2nc(Sc3ccnc(N)c3Cl)ccc2n1 ; Cl ; Cl]

4-((2-((2R,4S)-4-amino-2-methylpiperidin-1-yl)pyrido[2,3-b]pyrazin-6-yl)thio)-3-chloropyridin-2-amine dihydrochloride To a solution of 6-chloropyrido[2,3-b]pyrazin-2-yl 4-nitrobenzenesulfonate (75 mg, 0.21 mmol) in dioxane (2 mL) was added N-ethyl-N-isopropylpropan-2-amine (184 μL, 1.02 mmol) and tert-butyl ((2R,4S)-2-methylpiperidin-4-yl)carbamate (48 mg, 0.23 mmol) and the reaction stirred at rt for 3 hr. sodium 2-amino-3-chloropyridine-4-thiolate (112 mg, 0.61 mmol) was added and the reaction was heated to 75° C. for 18 hr. The reaction was concentrated and purified by silica gel (0-12% MeOH in DCM) to provide hoc product. The material was brought up in DCM (2 mL) and 4 N HCl (1 mL) was added and the reaction was stirred for 4 hr. The reaction was concentrated to provide 4-((2-((2R,4S)-4-amino-2-methylpiperidin-1-yl)pyrido[2,3-b]pyrazin-6-yl)thio)-3-chloropyridin-2-amine dihydrochloride (47.1 mg, 0.12 mmol, 57% yield). $^1$H NMR (400 MHz, DMSO-d$_6$) δ 9.02 (s, 1H), 8.21 (bs, 3H), 8.07 (d, 1H, J=6.5 Hz), 5.13 (m, 1H), 4.62 (m, 1H), 3.25-3.15 (m, 1H), 2.10 (m, 1H), 1.98 (m, 1H), 1.81-1.70 (m, 1H), 1.61-1.50 (m, 1H), 1.24 (d, 3H, J=6.8 Hz). m/Z (esi) (M+1)=402.1.

Example 123

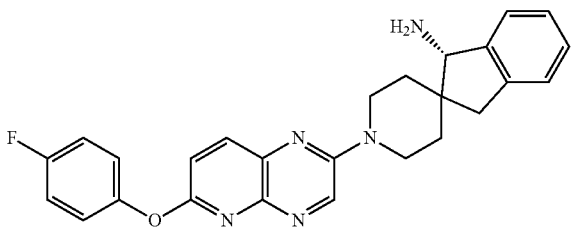 [SMILES: N[C@@H]1c2ccccc2CC12CCN(c1cnc3nc(Oc4ccc(F)cc4)ccc3n1)CC2]

(S)-1'-(6-(4-fluorophenoxy)pyrido[2,3-b]pyrazin-2-yl)-1,3-dihydrospiro[indene-2,4'-piperidin]-1-amine Step A. (S)-1'-(6-chloropyrido[2,3-b]pyrazin-2-yl)-1,3-dihydrospiro[indene-2,4'-piperidin]-1-amine (1.9 g, 5.19 mmol) was suspended in DCM (25.97 mL). Triethylamine (0.9 mL, 6.23 mmol) was added, followed by di-tert-butyl-dicarbonate (1.36 g, 6.23 mmol). The mixture was stirred at room temperature for 18 h. The reaction was partitioned between DCM and water, organics filtered through IPS paper and concentrated to afford tert-butyl (S)-(1'-(6-chloropyrido[2,3-b]pyrazin-2-yl)-1,3-dihydrospiro[indene-2,4'-piperidin]-1-yl)carbamate (2.26 g, 4.86 mmol, 94% yield). LCMS (MM-ES+APCI, Pos): m/z 466.3 (M+H).

Step B. 4-Fluorophenol (14 mg, 0.13 mmol) was added to a solution of potassium tert-butoxide (14 mg, 0.13 mmol) in THF (179 μL) at room temperature. After 30 min, tert-butyl (S)-(r-(6-chloropyrido[2,3-b]pyrazin-2-yl)-1,3-dihydrospiro[indene-2,4'-piperidin]-1-yl)carbamate (50 mg, 0.11 mmol) was added and the mixture was stirred at 65° C. for 18 h. 4-Fluorophenol (14 mg, 0.13 mmol) and potassium tert-butoxide (14 mg, 0.13 mmol) were added and stirring continued at 65° C. for 18 h. The mixture was cooled to at room temperature, diluted with EA/brine, combined extracts filtered through IPS paper, evaporated in vac and purified by silica gel chromatography (0-40% acetone/DCM) to give tert-butyl (S)-(r-(6-(4-fluorophenoxy)pyrido[2,3-b]pyrazin-2-yl)-1,3-dihydrospiro[indene-2,4'-piperidin]-1-yl)carbamate (33 mg, 0.061 mmol, 57% yield). LCMS (MM-ES+APCI, Pos): m/z 542.3 (M+H).

Step C. A mixture of tert-butyl (S)-(1'-(6-(4-fluorophenoxy)pyrido[2,3-b]pyrazin-2-yl)-1,3-dihydrospiro[indene-2,4'-piperidin]-1-yl)carbamate (56 mg, 0.10 mmol) in DCM (0.5 mL) was purged with N2 and treated with 4 N HCl in dioxane (0.2 mL) via syringe at room temperature, stirring was continued at room temperature for 18 h. The mixture was quenched with satd aq NaHC03, aq extracted with DCM, combined extracts filtered through IPS paper, evaporated in vac and purified by silica gel chromatography (0-7% MeOH/DCM with 2% NH4OH) to give (S)-1'-(6-(4-fluorophenoxy)pyrido[2,3-b]pyrazin-2-yl)-1,3-dihydrospiro[indene-2,4'-piperidin]-1-amine (19 mg, 0.043 mmol, 42% yield). LCMS (MM-ES+APCI, Pos): m/z 442.2 (M+H). $^1$H NMR (400 MHz, MeOD) δ 8.64 (s, 1H), 8.05 (d, J=8.99 Hz, 1H), 7.35-7.12 (m, 9H), 4.39 (d, J=8.99 Hz, 2H), 3.93 (s, 1H), 3.32 (dd, J=26.07, 8.47, 2H), 3.15 (d, J=15.83 Hz, 1H), 2.79 (d, J=15.83 Hz, 1H), 1.83 (dt, 0.7=39.1, 12.37 Hz, 2H), 1.61 (d, J=13.39 Hz, 1H), 1.42 (d, j=13.39 Hz, 1H).

Example 124

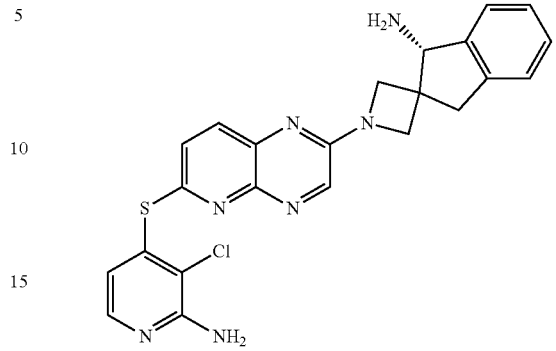

(R)-1-(6-((2-amino-3-chloropyridin-4-yl)thio)pyrido[2,3-b]pyrazin-2-yl)-1',3'-dihydrospiro[azetidine-3,2'-inden]-1'-amine Step A: tert-butyl (R)-1'-(((R)-tert-butylsulfinyl)amino)-1',3'-dihydrospiro[azetidine-3,2'-indene]-1-carboxylate (0.1 g, 0.3 mmol) was dissolved in DCM (1 mL) and TFA (0.3 mL) was added to the mixture. The reaction was stirred at RT for 2 h and the solvents were evaporated to give a residue which was used in the next step without further purification.

Step B: (R)—N—((R)-1',3'-dihydrospiro[azetidine-3,2'-inden]-1'-yl)-2-methylpropane-2-sulfinamide (0.07 g, 0.25 mmol) was dissolved in dioxane (2 mL). Triethylamine (0.13 g, 1.3 mmol) and 6-chloropyrido[2,3-b]pyrazin-2-yl 4-nitrobenzenesulfonate (0.10 g, 0.28 mmol) were added to the mixture. The reaction was heated to 60° C. and stirred for 18 hr. The reaction was quenched with water (15 mL), was extracted with DCM (3×10 mL) and the combined organic layers were washed with brine, dried and evaporated. The resulting residue was purified using 12 g silica gel column (DCM-MeOH 1-20%) provided (R)—N—((R)-1-(6-chloropyrido[2,3-b]pyrazin-2-yl)-1',3'-dihydrospiro[azetidine-3,2'-inden]-1'-yl)-2-methylpropane-2-sulfinamide (0.057 g, 0.13 mmol, 51% yield) as yellow solid, m/z (esi/APCI) M$^+$1=442.1.

Step C: (R)—N—((R)-1-(6-chloropyrido[2,3-b]pyrazin-2-yl)-1',3'-dihydrospiro[azetidine-3,2'-inden]-1'-yl)-2-methylpropane-2-sulfinamide (0.037 g, 0.084 mmol) was dissolved in dioxane (4 mL). Triethylamine (0.025 g, 0.25 mmol) and sodium 2-amino-3-chloropyridine-4-thiolate (0.018 g, 0.10 mmol) were added to the mixture. The reaction was heated to 95° C. and stirred at for 18 hr. The reaction was quenched with water and extracted with DCM (3×10 mL). The combined organic layers were washed with brine, dried and evaporated. The resulting residue was purified by silica gel (DCM/MeOH mixture 2-20%) to provide (R)—N—((R)-1-(6-((2-amino-3-chloropyridin-4-yl)thio)pyrido[2,3-b]pyrazin-2-yl)-1',3'-dihydrospiro[azetidine-3,2'-inden]-1'-yl)-2-methylpropane-2-sulfinamide (0.04 g, 0.071 mmol, 57% yield) as yellow solid, m/z (esi/APCI) M$^+$1=566.2.

Step D: (R)—N—((R)-1-(6-((2-amino-3-chloropyridin-4-yl)thio)pyrido[2,3-b]pyrazin-2-yl)-1',3'-dihydrospiro[azetidine-3,2'-inden]-1'-yl)-2-methylpropane-2-sulfinamide (0.062 g, 0.11 mmol) was dissolved in DCM (3 mL) and HCl (0.27 mL, 1.1 mmol) 4 M solution in dioxane was added dropwise to the mixture. After 30 min, ether (10 mL) was added to the mixture and the yellow solid was filtered off to give (R)-1-(6-((2-amino-3-chloropyridin-4-yl)thio)pyrido[2,3-b]pyrazin-2-yl)-1',3'-dihydrospiro[azetidine-3,2'-inden]-1'-amine (0.041 g, 0.089 mmol, 81% yield) as HCl salt. $^1$H NMR (400 MHz, dmso) δ 8.62 (s, 2H), 8.55 (s, 1H), 8.05 (d, J=8.6 Hz, 1H), 7.80 (d, J=5.5 Hz, 1H), 7.66 (d, J=8.6 Hz, 1H), 7.55 (d, J=7.2 Hz, 1H), 7.39-7.30 (m, 2H), 6.46 (d, J=5.5 Hz, 1H), 4.86 (s, 1H), 4.59 (d, J=10.2 Hz, 1H), 4.40 (d, J=9.0 Hz, 1H), 4.19 (s, 2H), 3.61-3.51 (m, 2H). m/z (esi/APCI) M$^+$1=462.1.

Example 125

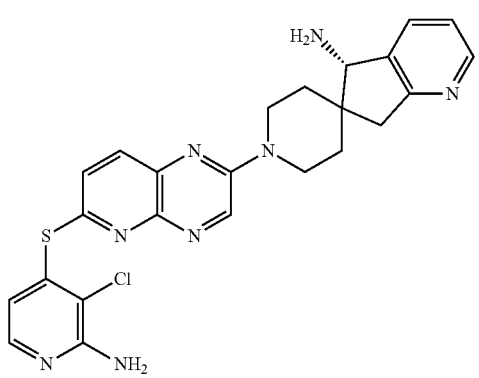 [SMILES: Nc1nccc(Sc2ccc3nc(N4CCC5(CC4)Cc4ncccc4[C@H]5N)cnc3n2)c1Cl]

(S)-1'-(6-((2-amino-3-chloropyridin-4-yl)thio)pyrido[2,3-b]pyrazin-2-yl)-5,7-dihydrospiro[cyclopenta[b]pyridine-6,4'-piperidin]-5-amine Step A: (S)-5,7-dihydrospiro[cyclopenta[b]pyridine-6,4'-piperidin]-5-amine HCl salt (1.52 g, 7.48 mmol) was suspended in dioxane (20 mL). Trimethylamine (4.54 g, 44.9 mmol) was added and was stirred for 30 min at RT. 6-chloropyrido[2,3-b]pyrazin-2-yl trifluoromethanesulfonate (2.35 g, 7.48 mmol) was added to the reaction and the mixture was stirred at RT for 2 h. The reaction was quenched with water (50 mL) and the mixture was extracted with a mixture of DCM and IPA (3×20 mL). The combined organic layers were washed with brine, dried and evaporated. The residue was purified with silica gel column chromatography (120 g) (MeOH/DCM 1-20%) to give (S)-1'-(6-chloropyrido[2,3-b]pyrazin-2-yl)-5,7-dihydrospiro[cyclopenta[6]pyridine-6,4'-piperidin]-5-amine (2.58 g, 7.03 mmol, 94% yield) as yellow solid, m/z (esi/APCI) M$^+$1=467.1.

Step B: (S)-1'-(6-chloropyrido[2,3-b]pyrazin-2-yl)-5,7-dihydrospiro[cyclopenta[6]pyridine-6,4'-piperidin]-5-amine (2.58 g, 7.03 mmol) was dissolved in dioxane (25 mL) and sodium 2-amino-3-chloropyridine-4-thiolate (1.41 g, 7.74 mmol) was added to the solution. The reaction was heated to 90° C. for 18 h. Excess thiolate (0.3 g) was added to the mixture and the reaction was stirred at 90° C. for 2 h. The reaction was quenched with water (50 mL) and the mixture was extracted with a mixture of DCM and IPA (3×30 mL). The combined organic layers were washed with brine, dried and evaporated to give an orange residue which was purified with silica gel column (220 g) (MeOH/DCM 1-20%) to give (S)-1'-(6-((2-amino-3-chloropyridin-4-yl)thio)pyrido[2,3-b]pyrazin-2-yl)-5,7-dihydrospiro[cyclopenta[6]pyridine-6,4'-piperidin]-5-amine (2.45 g, 4.99 mmol, 71% yield) as yellow solid. $^1$H NMR (400 MHz, CDCl$_3$) δ 8.77 (s, 1H), 8.44 (s, 1H), 7.92 (d, J=8.5 Hz, 1H), 7.84 (d, J=3.7 Hz, 1H), 7.65 (d, J=7.3 Hz, 1H), 7.50 (d, J=8.5 Hz, 1H), 7.16 (s, 1H), 6.69 (d, J=3.7 Hz, 1H), 5.31 (s, 2H), 5.00 (s, 2H), 4.51 (m, 2H), 4.05 (s, 1H), 3.36 (q, J=12.1 Hz, 2H), 3.25 (d, J=16.4 Hz, 1H), 2.92 (d, J=16.4 Hz, 1H), 1.93 (dd, J=23.7, 11.3 Hz, 1H), 1.82 (dd, J=24.9, 12.5 Hz, 1H), 1.76-1.67 (m, 2H), 1.43 (d, j=13.1 Hz, 1H). m/z (esi/APCI) M$^+$1=491.1.

Example 126

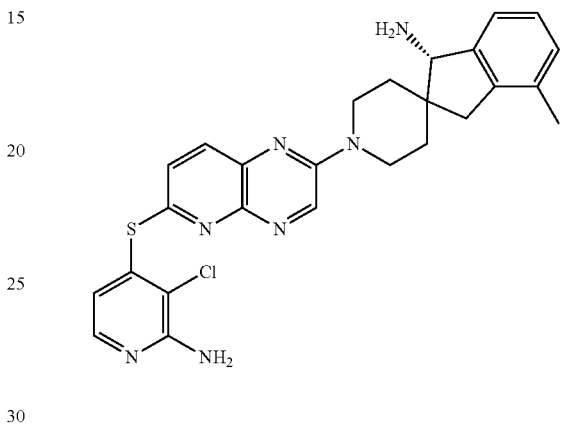

(S)-1'-(6-((2-amino-3-chloropyridin-4-yl)thio)pyrido[2,3-b]pyrazin-2-yl)-4-methyl-1,3-dihydrospiro[indene-2,4'-piperidin]-1-amine tert-butyl (S)-1-(((R)-tert-butylsulfinyl)amino)-4-methyl-1,3-dihydrospiro[indene-2,4'-piperidine]-1'-carboxylate (50 mg, 0.12 mmol) was dissolved in DCM (3 mL) and 4 M HCl in dioxane (1 mL) was added to the solution. The mixture was stirred for 1 h at RT and Et$_2$O (10 mL) was added. The white solid formed was filtered, dried and then suspended in dioxane (3 mL) and triethylamine (31 mg, 0.31 mmol) was added to the mixture. The mixture was stirred at RT for 30 min. 6-chloropyrido[2,3-b]pyrazin-2-yl trifluoromethanesulfonate (33 mg, 0.10 mmol) was added and the reaction was heated to 50° C. and stirred for 1 h. Sodium 2-amino-3-chloropyridine-4-thiolate (19 mg, 0.10 mmol) was added and the reaction was heated to 90° C. for 18 hr. The reaction was cooled to RT then it was quenched with water (10 mL) and the mixture was extracted with DCM/IPA mixture (3×10 mL). The combined organic layers were washed with brine (1×10 mL), dried and evaporated. The resulting residue was purified using 12 g silica gel column (MeOH/DCM 1-15% yielded (S)-1'-(6-((2-amino-3-chloropyridin-4-yl)thio)pyrido[2,3-b]pyrazin-2-yl)-4-methyl-1,3-dihydrospiro[indene-2,4'-piperidin]-1-amine (21 mg, 0.042 mmol, 40% yield). $^1$H NMR (400 MHz, CDCl$_3$) δ 8.77 (s, 1H), 7.92 (d, J=8.3 Hz, 1H), 7.84 (s, 1H), 7.51 (d, J=8.9 Hz, 1H), 7.17 (s, 2H), 7.07 (s, 1H), 6.69 (s, 1H), 4.94 (s, 2H), 4.42 (s, 2H), 4.02 (s, 1H), 3.42 (s, 2H), 3.05 (d, J=16.3 Hz, 1H), 2.68 (d, J=15.4 Hz, 1H), 2.29 (s, 3H), 1.89 (dt, j=23.8, 12.0 Hz, 2H), 1.69 (d, j=12.7 Hz, 1H). m/z (esi/APCI) M$^+$1=504.1.

Example 127

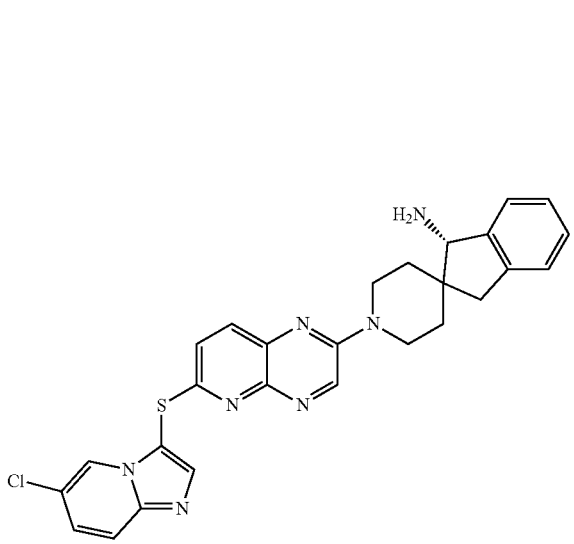 [SMILES: N[C@@H]1c2ccccc2CC12CCN(c1cnc3nc(Sc4cnc5ccc(Cl)cn45)ccc3n1)CC2]

(S)-1'-(6-(((6-chloroimidazo[1,2-a]pyridin-3-yl)thio)
pyrido[2,3-b]pyrazin-2-yl)-1,3-dihydrospiro[indene-
2,4'-piperidin]-1-amine tert-butyl (S)-(1'-(6-mercaptopyrido[2,3-b]pyrazin-2-yl)-1,3-dihydrospiro[indene-2,4'-piperidin]-1-yl)carbamate (30 mg, 0.065 mmol) was dissolved in DCM (2 mL) and NCS (13 mg, 0.097 mmol) was added to the solution under nitrogen. After 20 min of stirring 6-chloroimidazo[1,2-a] pyridine (9.9 mg, 0.065 mmol) was added and the reaction was stirred for 20 min. The reaction was heated to 50° C. for 1.5 h and was quenched with sat NaHCO₃ solution and the organic layer was evaporated to give a yellow residue which was dissolved in DCM (2 mL). TFA (0.1 mL) was added to the mixture and was stirred at rt for 1.5 h. The reaction was evaporated, and the residue was neutralized with sat NaHCO₃ and the water layer was extracted with DCM (2×10 mL). The combined organic layers were washed with brine, dried and evaporated to give a yellow residue which was purified with 12 g silica gel column (MeOH/DCM 1-20%) to give (5)-1'-(6-(((6-chloroimidazo[1,2-a]pyridin-3-yl)thio) pyrido[2,3-b]pyrazin-2-yl)-1,3-dihydrospiro[indene-2,4'-piperidin]-1-amine (4 mg, 0.0078 mmol, 12% yield) as yellow solid. $^1$H NMR (400 MHz, cdcl₃) δ 8.69 (s, 1H), 8.34 (dd, J=2.0, 0.8 Hz, 1H), 8.05 (s, 1H), 7.77 (d, J=8.7 Hz, 1H), 7.68 (dd, J=9.5, 0.8 Hz, 1H), 7.35-7.28 (m, 2H), 7.24-7.19 (m, 2H), 6.92 (d, J=8.7 Hz, 1H), 4.37 (t, J=11.8 Hz, 2H), 3.99 (s, 1H), 3.34 (ddd, J=25.4, 13.6, 3.2 Hz, 2H), 3.10 (d, J=15.6 Hz, 1H), 2.75 (d, J=15.4 Hz, 1H), 1.95-1.75 (m, 2H), 1.66 (d, J=13.4 Hz, 1H), 1.42 (d, J=14.9 Hz, 1H). m/z (esi/APCI) M⁺1=515.2.

Example 128

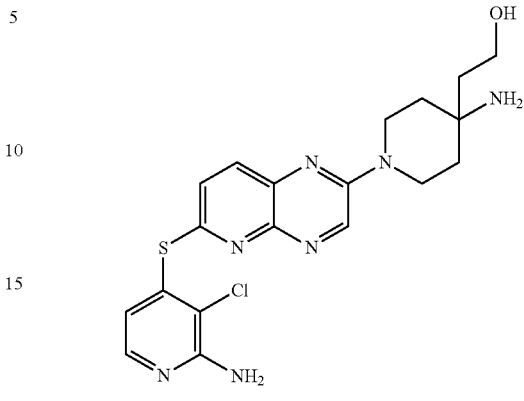

2-(4-amino-1-(6-((2-amino-3-chloropyridin-4-yl)
thio)pyrido[2,3-b]pyrazin-2-yl)piperidin-4-yl)ethan-
1-ol Step A: tert-butyl 4-amino-4-(2-methoxy-2-oxoethyl)piperidine-1-carboxylate (3.0 g, 11 mmol) was dissolved in tetrahydrofuran (30 mL, 11 mmol) in a 100 mL reaction flask charged with a stir bar. The solution was cooled to 0° C. and placed under nitrogen. Lithium aluminum hydride (19 mL, 19 mmol) (1M in THF, anhydrous) was added dropwise over 20 minutes via addition funnel. The reaction was stirred from 0° C. to RT for 1 hour. The reaction was cooled to 0° C. and quenched with water (0.72 µL) followed by 15% NaOH (0.72 µL) then water (2.1 mL). The mixture was stirred at RT for 30 minutes. The crude solution was filtered through celite. The solids were washed with EtOAc and the filtrate was condensed to afford tert-butyl 4-amino-4-(2-hydroxyethyl)piperidine-1-carboxylate (1.8 g, 66% yield), m/z (esi/APCI) M+1=245.2.

Step B: tert-butyl 4-amino-4-(2-hydroxyethyl)piperidine-1-carboxylate (0.25 g, 1.0 mmol) was dissolved in dichloromethane (10 mL, 1.0 mmol), tert-butyldimethylchlorosilane (0.16 g, 1.1 mmol) was added and the solution was stirred at RT for 1 hour. The crude material was condensed, and loaded onto a 24 g silica gel column and isolated over a gradient of 0-5% MeOH:DCM to provide tert-butyl 4-amino-4-(2-((tert-butyldimethylsilyl)oxy)ethyl)piperidine-1-carboxylate (0.26 g, 0.72 mmol, 72% yield), in z (esi/APCI) M+1=359.3.

Step C: tert-butyl 4-amino-4-(2-((tert-butyldimethylsilyl)oxy)ethyl)piperidine-1-carboxylate (0.13 g, 0.37 mmol) was dissolved in dichloromethane (3.7 mL, 0.37 mmol). Trifluoroacetic acid (0.28 mL, 3.7 mmol) was added and the resulting solution was stirred at RT. Upon completion, the reaction was condensed to afford a yellow oil. 4-(2-((tert-butyldimethylsilyl)oxy)ethyl)piperidin-4-amine (0.094 g, 99% yield), m/z (esi/APCI) M+1=259.2.

Step D: 6-chloropyrido[2,3-b]pyrazin-2-yl 4-nitrobenzenesulfonate (0.23 g, 0.63 mmol) and 4-(2-((tert-butyldimethylsilyl)oxy)ethyl)piperidin-4-amine (0.20 g, 0.76 mmol) were dissolved in 1,4-dioxane (3.2 mL, 0.63 mmol). Triethylamine (0.35 mL, 2.5 mmol) was added and the solution was stirred at RT. Upon completion, the reaction was condensed and loaded onto a 40 g silica gel column and was purified over a gradient of 0-10% MeOH:EtOAc to provide 4-(2-((tert-butyldimethylsilyl)oxy)ethyl)-1-(6-chloropyrido

[2,3-b]pyrazin-2-yl)piperidin-4-amine as a yellow solid (0.073 g, 27% yield), m/z (esi/APCI) M+1=422.2.

Step E: 4-(2-((tert-butyldimethylsilyl)oxy)ethyl)-1-(6-chloropyrido[2,3-b]pyrazin-2-yl)piperidin-4-amine (0.073 g, 0.17 mmol) was dissolved in 1,4-dioxane (0.85 mL, 0.17 mmol). Sodium 2-amino-3-chloropyridine-4-thiolate (0.037 g, 0.21 mmol) and triethylamine (0.095 mL, 0.68 mmol), were added and the reaction was stirred at 80° C. for 96 hours. The reaction was condensed and loaded onto a 40 g silica gel column. The desired product was isolated over a gradient of 0-10% MeOH:DCM to provide 4-((2-(4-amino-4-(2-((tert-butyldimethylsilyl)oxy)ethyl)piperidin-1-yl)pyrido[2,3-b]pyrazin-6-yl)thio)-3-chloropyridin-2-amine (0.018 g, 0.032 mmol, 19% yield), m/z (esi/APCI) M+1=546.2.

Step F: To a solution of 4-((2-(4-amino-4-(2-((tert-butyldimethylsilyl)oxy)ethyl)piperi din-1-yl)pyrido[2,3-b]pyrazin-6-yl)thio)-3-chloropyridin-2-amine (0.018 g, 0.032 mmol) in tetrahydrofuran (0.32 mL, 0.032 mmol) was added tetrabutylammonium fluoride (0.011 mL, 0.038 mmol) at RT. The reaction was stirred at RT for 5 hours. The crude reaction was dissolved in 40% Water:60% MeCN+2% TFA and isolated via reverse phase chromatography over a gradient of 5-95% MeCN:H2O+0.1% TFA. Fractions were concentrated down, and saturated sodium bicarbonate was added and the mixture was extracted with EtOAc. The extracts were combined, dried, filtered and concentrated to provide 2-(4-amino-1-(6-((2-amino-3-chloropyridin-4-yl)thio)pyrido[2,3-b]pyrazin-2-yl)piperidin-4-yl)ethan-1-ol (7.2 mg, 0.017 mmol, 52% yield). ¹H NMR (400 MHz, (CD₃)₂SO) δ 8.97 (bs, 1H), 7.98 (d, 1H, J=8.4 Hz), 7.78 (d, 1H, J=5.2), 7.57 (d, 1H, J=8.4), 6.44 (s, 2H), 6.42 (d, 1H, J=5.2 Hz), 3.8 (bs, 4H), 3.61 (t, 2H, J=6.4 Hz), 1.97 (s, 1H), 1.88 (s, 1H), 1.71 (m, 5H), 1.62 (m, 2H); m/z (esi/APCI) M+1=432.1.

Example 129

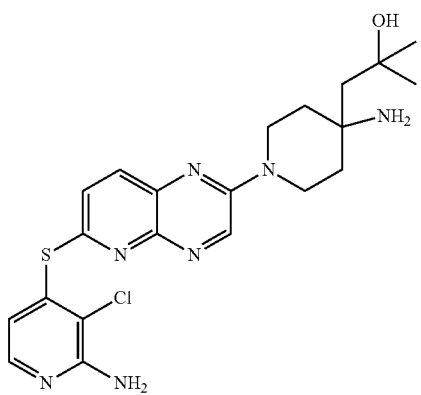 [SMILES: CC(C)(O)CC1(N)CCN(c2cnc3nc(Sc4ccnc(N)c4Cl)ccc3n2)CC1]

1-(4-amino-1-(6-((2-amino-3-chloropyridin-4-yl)thio)pyrido[2,3-b]pyrazin-2-yl)piperidin-4-yl)-2-methylpropan-2-ol Step A: tert-butyl 4-amino-4-(2-methoxy-2-oxoethyl)piperidine-1-carboxylate (0.66 g, 2.4 mmol) was dissolved in anhydrous tetrahydrofuran (10 mL, 2.4 mmol). The solution was cooled to 0° C. Methylmagnesium bromide (8.7 mL, 12 mmol) (1.4M in THF) was added to the cooled solution dropwise. The reaction was warmed to RT and stirred for 2 hours. The reaction was cooled to 0° C., quenched with saturated NH4Cl (5.0 mL), diluted with EtOAc and filtered, tert-butyl 4-amino-4-(2-methoxyethyl)piperidine-1-carboxylate (0.66 g, 99% yield), m/z (esi/APCI) M+1=273.2.

Step B: tert-butyl 4-amino-4-(2-methoxyethyl)piperidine-1-carboxylate (0.33 g, 1.2 mmol) was dissolved in dichloromethane (6.06 mL, 1.2 mmol). 2,2,2-trifluoroacetic acid (0.93 mL, 12 mmol) was added to reaction solution at RT. The reaction was stirred at RT for 1 hour. The reaction was condensed to provide. 1-(4-aminopiperidin-4-yl)-2-methylpropan-2-ol (0.21 g, 99% yield), which was used as is. m/z (esi/APCI) M+1=173.2.

Step C: 6-chloropyrido[2,3-b]pyrazin-2-yl 4-nitrobenzenesulfonate (0.25 g, 0.68 mmol) and 1-(4-aminopiperidin-4-yl)-2-methylpropan-2-ol (0.14 g, 0.82 mmol) were dissolved in 1,4-dioxane (3.4 mL, 0.68 mmol), triethylamine (0.38 mL, 2.7 mmol) was added and the solution was stirred at RT for 1 hour. The reaction was condensed in vacuo and loaded onto a 40 g silica column and purified over a gradient of 0-5% MeOH:DCM. 1-(4-amino-1-(6-chloropyrido[2,3-b]pyrazin-2-yl)piperidin-4-yl)-2-methylpropan-2-ol (0.051 g, 0.15 mmol, 22% yield), m/z (esi/APCI) M+1=336.1.

Step D: 1-(4-amino-1-(6-chloropyrido[2,3-b]pyrazin-2-yl)piperidin-4-yl)-2-methylpropan-2-ol (0.051 g, 0.15 mmol) and sodium 2-amino-3-chloropyridine-4-thiolate (0.034 g, 0.19 mmol) in 1,4-dioxane (0.76 mL, 0.15 mmol). Triethylamine (0.085 mL, 0.61 mmol) was added and the resulting solution was stirred at 80° C. for 48 hours. The reaction was condensed and loaded onto a 40 g silica gel column and isolated over a gradient of 0-20% MeOH:DCM+NH4OH to provide 1-(4-amino-1-(6-((2-amino-3-chloropyridin-4-yl)thio)pyrido[2,3-b]pyrazin-2-yl)piperidin-4-yl)-2-methylpropan-2-ol (1.0 mg, 1.0% yield). ¹H NMR (400 MHz, (CD₃)₂SO) δ 8.96 (bs, 1H), 7.96 (d, 2H, J=8.6 Hz), 7.77 (d, 2H, J=5.2), 7.58 (d, 2H, J=8.6), 6.44 (s, 2H), 6.39 (d, 2H, J=5.2 Hz), 4.1 (d, 2H, J=12.5), 3.61 (m, 4H), 1.6 (m, 2H), 1.5 (s, 1H), 1.15 (m, 6H); m/z (esi/APCI) M+1=460.1.

Example 130

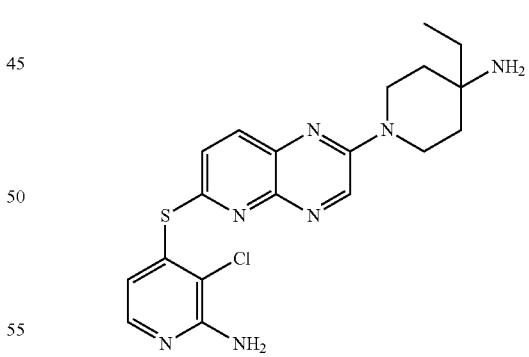

4-((2-(4-amino-4-ethylpiperidin-1-yl)pyrido[2,3-b]pyrazin-6-yl)thio)-3-chloropyridin-2-amine Step A: 6-chloropyrido[2,3-b]pyrazin-2-yl 4-nitrobenzenesulfonate (0.20 g, 0.55 mmol) was dissolved in 1,4-dioxane (2.7 mL, 0.55 mmol). Tert-butyl (4-ethylpiperidin-4-yl)carbamate (0.15 g, 0.65 mmol) and triethylamine (0.30 mL, 2.2 mmol) were added and the reaction was stirred at RT for 6 hours. The crude reaction was condensed and loaded onto a 24 g silica column and purified over a gradient of 10:90 EtOAc:hexane to provide tert-butyl (1-(6-chloropyrido[2,3-b]pyrazin-2-yl)-4-ethylpiperidin-4-yl)carbamate (0.091 g, 0.23 mmol, 42% yield), m/z (esi/APCI) M+1=336.1.

Step B: tert-butyl (1-(6-chloropyrido[2,3-b]pyrazin-2-yl)-4-ethylpiperidin-4-yl)carbamate (0.091 g, 0.23 mmol) was dissolved in 1,4-dioxane (1.2 mL, 0.23 mmol), sodium 2-amino-3-chloropyridine-4-thiolate (0.051 g, 0.28 mmol) was added to the solution followed by triethylamine (0.13 mL, 0.93 mmol). The reaction was stirred at 80° C. overnight. The reaction was condensed and loaded onto a 40 g silica column and purified over a gradient of 0-5% MeOH:DCM. The material was resuspended in DCM and 4 M HCl in dioxane (1.0 mL) was added at RT and stirred for 3 hr. The reaction was concentrated and saturated sodium bicarbonate was added and the mixture was extracted with EtOAc. The extracts were combined, dried, filtered and concentrated to provide 4-((2-(4-amino-4-ethylpiperidin-1-yl)pyrido[2,3-b]pyrazin-6-yl)thio)-3-chloropyridin-2-amine (0.011 g, 0.026 mmol, 11% yield). $^1$H NMR (400 MHz, (CD$_3$)$_2$SO) δ 8.95 (bs, 1H), 7.96 (d, 1H, J=8.6 Hz), 7.77 (d, 2H, J=5.0), 7.58 (d, 2H, 8.6), 6.43 (s, 1H), 6.39 (s, 1H), 4.1 (4, 2H, J=5.4 Hz), 3.60 (d, 1H, J=13.69 Hz), 3.55 (m, 2H), 1.42 (m, 2H), 1.27 (m, 4H), 1.62 (t, 3H, J=7.62 Hz); m/z (esi/APCI) M+1=416.1.

Example 131

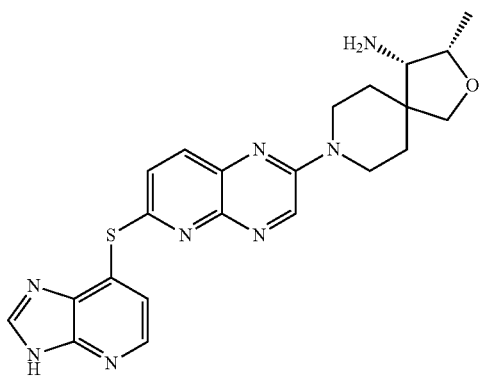 [SMILES: C[C@@H]1OCC2(CCN(c3cnc4nc(Sc5ccnc6[nH]cnc56)ccc4n3)CC2)[C@@H]1N]

(3S,4S)-8-(6-(((3H-imidazo[4,5-b]pyridin-7-yl)thio) pyrido[2,3-b]pyrazin-2-yl)-3-methyl-2-oxa-8-azaspiro[4.5]decan-4-amine (3S,4S)-8-(6-chloropyrido[2,3-b]pyrazin-2-yl)-3-methyl-2-oxa-8-azaspiro[4.5]decan-4-amine (Example 13, Step A) (0.051 g, 0.15 mmol) and methyl 3-((3H-imidazo[4,5-b]pyridin-7-yl)thio)propanoate (0.044 g, 0.18 mmol) were dissolved in N,N-dimethylacetamide (0.77 mL, 0.15 mmol). Potassium tert-butoxide (0.15 mL, 0.15 mmol) 1 M solution was added to the mixture. The resulting solution was stirred overnight at 100° C. The crude reaction was condensed and loaded onto a 40 g silica gel column. Desired product was isolated over a gradient of 0-20% MeOH:DCM with 0.2% NH4OH to provide (3S,4S)-8-(6-(((3H-imidazo[4,5-b]pyridin-7-yl)thio)pyrido[2,3-b]pyrazin-2-yl)-3-methyl-2-oxa-8-azaspiro[4.5]decan-4-amine (0.016 g, 0.035 mmol, 23% yield). $^1$H NMR (400 MHz, (CD$_3$)$_2$SO) δ 8.93 (bs, 1H), 8.4 (s, 1H), 7.89 (d, 1H, J=8.6 Hz), 4.05 (m, 4H), 3.68 (d, 2H, J=8.6 Hz), 3.53 (m, 4H), 1.7 (m, 1H), 1.66 (m, 1H), 1.51 (m, 3H), 1.2 (s, 3H), 1.06 (d, 4H, J=6.4 Hz); m/z (esi/APCI) M$^+$1=430.1.

Example 132

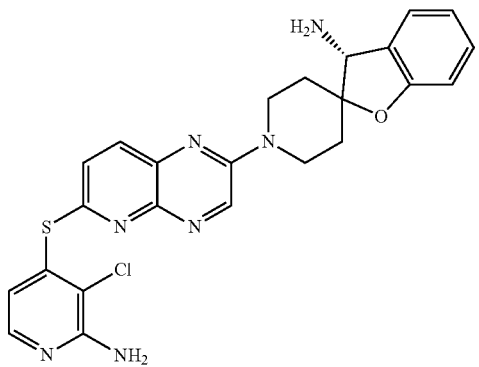

1R)-1'-(6-((2-amino-3-chloropyridin-4-yl)thio) pyrido[2,3-b]pyrazin-2-yl)-3H-spiro[benzofuran-2, 4'-piperidin]-3-amine Step A: (R)—N—((R)-1'-(6-chloropyrido[2,3-b]pyrazin-2-yl)-3H-spiro[benzofuran-2,4'-piperidin]-3-yl)-2-methyl-propane-2-sulfinamide (0.060 g, 0.13 mmol) and 670 mg of sodium 2-amino-3-chloropyridine-4-thiolate (0.046 g, 0.25 mmol) were diluted in N,N-dimethylacetamide (0.64 mL, 0.13 mmol). Triethylamine (0.071 mL, 0.51 mmol) was added and the reaction was stirred for 48 hours at 100° C. The crude material was loaded onto a 40 g silica gel column and isolated over a gradient of 50-100% EtOAc:hexane to provide (R)—N—((R)-1'-(6-((2-amino-3-chloropyridin-4-yl)thio)pyrido[2,3-b]pyrazin-2-yl)-3H-spiro[benzofuran-2,4'-piperidin]-3-yl)-2-methylpropane-2-sulfinamide (0.048 g, 0.081 mmol, 64% yield), m/z (esi/APCI) M$^+$1=596.2.

Step B: (R)—N—((R)-1'-(6-((2-amino-3-chloropyridin-4-yl)thio)pyrido[2,3-b]pyrazin-2-yl)-3H-spiro[benzofuran-2,4'-piperidin]-3-yl)-2-methylpropane-2-sulfinamide (0.048 g, 0.081 mmol) was constituted in 1,4-dioxane (0.81 mL, 0.081 mmol), hydrochloric acid Soln 4.0 M in 1,4-dioxane (0.16 mL, 0.65 mmol) was added and the reaction was stirred at RT for 15 minutes. The reaction was quenched with sat. Na2SO4 (3.0 mL). The mixture was extracted EtOAc. Extracts were combined and concentrated and the resulting residue was loaded onto a 12 g silica gel column and isolated over a gradient of 0-10% MeOH:EtOAc to provide (R)-1'-(6-((2-amino-3-chloropyridin-4-yl)thio)pyrido[2,3-b]pyrazin-2-yl)-3H-spiro[benzofuran-2,4'-piperidin]-3-amine (0.030 g, 0.060 mmol, 74% yield). $^1$H NMR (400 MHz, (CD$_3$)$_2$SO) δ 9.06 (bs, 1H), 8.09 (d, 1H), 7.80 (d, 1H), 7.63 (d, 1H), 7.36 (d, 1H), 7.17 (m, 1H), 6.90 (m, 1H), 6.82 (d, 1H), 6.46 (m, 2H), 4.51 (m, 2H), 4.18 (s, 1H), 3.51 (m, 2H), 1.99 (s, 2H), 1.84 (m, 3H), 1.17 (m, 2H); m/z (esi/APCI) M$^+$1=492.1.

Example 133

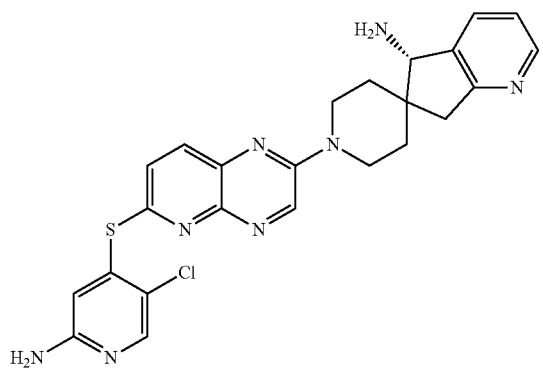 [SMILES: Nc1cc(Sc2ccc3nc(N4CCC5(CC4)Cc4ncccc4[C@H]5N)cnc3n2)c(Cl)cn1]

(S)-1'-(6-((2-amino-5-chloropyridin-4-yl)thio)pyrido[2,3-b]pyrazin-2-yl)-5,7-dihydrospiro[cyclopenta[b]pyridine-6,4'-piperidin]-5-amine Step A: (S)-5,7-dihydrospiro[cyclopenta[b]pyridine-6,4'-piperidin]-5-amine dihydrochloride (9.4 mL, 1.9 mmol) and 6-chloropyrido[2,3-b]pyrazin-2-yl trifluoromethanesulfonate (0.59 g, 1.9 mmol) were constituted in 1,4-dioxane (0.17 g, 1.9 mmol). Triethylamine (1.3 mL, 9.4 mmol) was added and the resulting solution was stirred at 50° C. for two hours. The crude reaction was then condensed and loaded onto a 80 g silica gel cartridge and isolated over a gradient of 1-10% MeOH:DCM to provide (S)-1'-(6-chloropyrido[2,3-b]pyrazin-2-yl)-5,7-dihydrospiro[cyclopenta[b]pyridine-6,4'-piperidin]-5-amine (0.14 g, 20% yield), m/z (esi/APCI) M+1=367.1.

Step B: sodium 2-amino-5-chloropyridine-4-thiolate (0.039 g, 0.21 mmol) and (S)-1'-(6-chloropyrido[2,3-b]pyrazin-2-yl)-5,7-dihydrospiro[cyclopenta[b]pyridine-6,4'-piperidin]-5-amine (0.050 g, 0.14 mmol) were dissolved in 1,4-dioxane (0.68 mL, 0.14 mmol). Triethylamine (0.038 mL, 0.27 mmol) was added and the resulting solution was stirred at 80° C. for 18 hr. The crude reaction was loaded onto a 40 g silica gel column and isolated over a gradient of 0-10% MeOH:EtOAc+NH4OH to provide (S)-1'-(6-((2-amino-5-chloropyridin-4-yl)thio)pyrido[2,3-b]pyrazin-2-yl)-5,7-dihydrospiro[cyclopenta[b]pyridine-6,4'-piperidin]-5-amine (0.013 g, 0.024 mmol, 1% yield). $^1$H NMR (400 MHz, (CD$_3$)$_2$SO) δ 9.07 (s, 1H), 8.62 (bs, 2H), 8.617 (d, 1H), 8.02 (m, 2H), 7.6 (d, 1H), 6.65 (bs, 5H), 6.2 (bs, 1H), 4.53 (m, 4H), 3.14 (d, 2H), 1.85 (m, 2H), 1.62 (m, 2H); m/z (esi/APCI) M+1=491.1.

Example 134

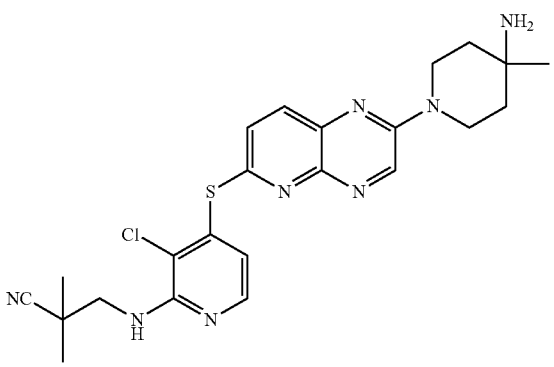 [SMILES: CC(C)(C#N)CNc1nccc(Sc2ccc3nc(N4CCC(C)(N)CC4)cnc3n2)c1Cl]

3-((4-((2-(4-amino-4-methylpiperidin-1-yl)pyrido[2,3-b]pyrazin-6-yl)thio)-3-chloropyridin-2-yl)amino)-2,2-dimethylpropanenitrile Step A: N-Ethyl-N-isopropylpropan-2-amine (0.25 mL, 1.4 mmol) was added to a solution of 6-chloropyrido[2,3-b]pyrazin-2-yl trifluoromethanesulfonate (0.40 g, 1.3 mmol) in DMA cooled to 0° C., followed by tert-butyl (4-methylpiperidin-4-yl)carbamate (0.30 g, 1.4 mmol). The reaction was stirred at 0° C. for 1 hour. The reaction was poured onto water and extracted twice with MTBE. The combined organics were washed with water, brine, dried over MgSO$_4$, filtered and concentrated in vacuo. The material was purified by silica gel chromatography (10-100% EtOAc in hexanes) to give tert-butyl (1-(6-chloropyrido[2,3-b]pyrazin-2-yl)-4-methylpiperidin-4-yl)carbamate (0.46 g, 1.3 mmol, 98% yield).

Step B: tert-butyl (1-(6-chloropyrido[2,3-b]pyrazin-2-yl)-4-methylpiperidin-4-yl)carbamate (25 mg, 0.066 mmol), Hunig's base (35 μL, 0.20 mmol), and 3-((3-chloro-4-mercaptopyridin-2-yl)amino)-2,2-dimethylpropanenitrile (48 mg, 0.20 mmol) were placed in 1,4-dioxane (662 μL, 0.066 mmol). The reaction was stirred at 100° C. for 18 hours. The mixture was concentrated in vacuo and then resuspended in DCM (5 mL). TFA (5 mL) was added and the solution was stirred at room temperature for 2 hrs. This was then was concentrated in vacuo and purified by preparatory HPLC (5 to 95% ACN in water with a 0.1% TFA modifier). Fractions containing product were combined and partitioned between DCM and 1M NaOH, and the layers were separated. The combined organics were washed with brine, dried over Na$_2$SO$_4$, filtered and concentrated in vacuo to give 3-((4-((2-(4-amino-4-methylpiperidin-1-yl)pyrido[2,3-b]pyrazin-6-yl)thio)-3-chloropyridin-2-yl)amino)-2,2-dimethylpropanenitrile (0.013 g, 0.027 mmol, 40% yield) as a yellow solid. $^1$H NMR (400 MHz, CDCl$_3$) δ 8.74 (s, 1H), 7.90 (d, 1H, J=8.6 Hz), 7.85 (d, 1H, J=5.3 Hz), 7.50 (d, 1H, J=8.6 Hz), 6.64 (d, 1H, 5.5 Hz), 5.41 (m, 1H), 3.95 (m, 2H), 3.81 (m, 2H), 3.75 (d, 2H, J=6.7 Hz), 1.74-1.66 (m, 2H), 1.64-1.56 (m, 2H), 1.40 (s, 6H), 1.24 (s, 3H). m/z (esi/APCI) M+1=483.2.

Example 135

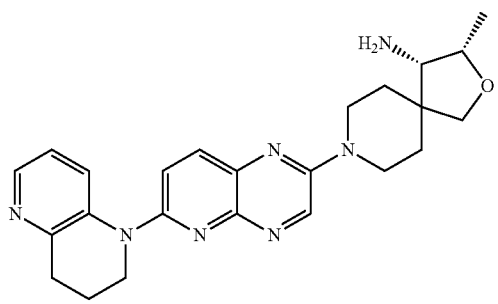 [SMILES: C[C@@H]1OCC2(CCN(c3cnc4nc(N5CCCc6ncccc65)ccc4n3)CC2)[C@@H]1N]

(3S,4S)-8-(6-(3,4-dihydro-1,5-naphthyridin-1(2H)-yl)pyrido[2,3-b]pyrazin-2-yl)-3-methyl-2-oxa-8-azaspiro[4.5]decan-4-amine (3S,4S)-8-(6-(3,4-dihydro-1,5-naphthyridin-1(2H)-yl)pyrido[2,3-b]pyrazin-2-yl)-3-methyl-2-oxa-8-azaspiro[4.5]decan-4-amine was prepared according to Example 69, substituting 1,2,3,4-Tetrahydro-[1,5]naphthyridine for 1,2,3,4-tetrahydroquinoline in Step B. m/z (esi/APCI) M$^+$1=432.3.

Example 136

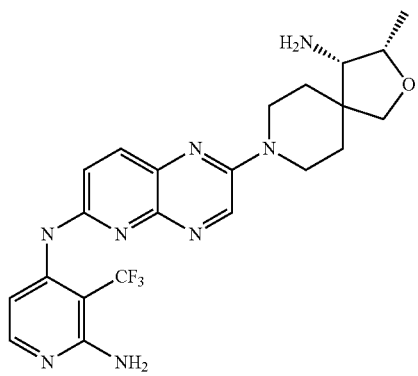 [SMILES: C[C@@H]1OCC2(CCN(c3cnc4nc(Nc5ccnc(N)c5C(F)(F)F)ccc4n3)CC2)[C@@H]1N]

(3S,4S)-8-(6-((2-amino-3-(trifluoromethyl)pyridin-4-yl)thio)pyrido[2,3-b]pyrazin-2-yl)-3-methyl-2-oxa-8-azaspiro[4.5]decan-4-amine (3S,4S)-8-(6-((2-amino-3-(trifluoromethyl)pyridin-4-yl)thio)pyrido[2,3-b]pyrazin-2-yl)-3-methyl-2-oxa-8-azaspiro[4.5]decan-4-amine was prepared according to Example 13, substituting 2-amino-3-(trifluoromethyl)pyridine-4-thiol for 2-amino-3-chloropyridine-4-thiol in Step B. In addition, the final product in Step B was purified by HPLC (5 to 95% ACN in water with a 0.1% TFA modifier), m/z (esi/APCI) M$^+$1=492.2.

Example 137

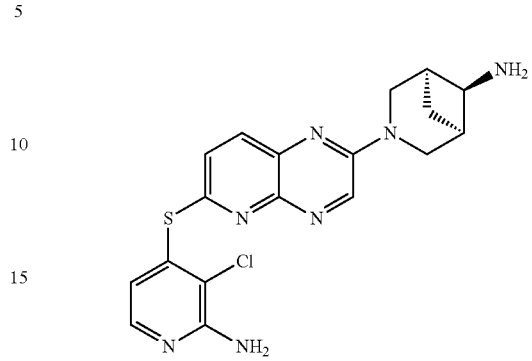

((1R,5S,6r)-3-(6-((2-amino-3-chloropyridin-4-yl)thio)pyrido[2,3-b]pyrazin-2-yl)-3-azabicyclo[3.1.1]heptan-6-amine Step A: To a solution of endo-6-(boc-amino)-3-azabicyclo[3.1.1]heptane (0.17 g, 0.82 mmol) and 6-chloropyrido[2,3-b]pyrazin-2-yl 4-nitrobenzenesulfonate (0.25 g, 0.68 mmol) in 1,4-dioxane (3.41 mL, 0.68 mmol) was added triethylamine (0.38 mL, 2.73 mmol) and this was stirred at rt for 72 hours. The mixture was filtered through celite, concentrated in vacuo and used as is in the next step. Assumed quantitative yield of tert-butyl ((1R,5S,6r)-3-(6-chloropyrido[2,3-b]pyrazin-2-yl)-3-azabicyclo[3.1.1]heptan-6-yl)carbamate (0.26 g, 0.68 mmol, 99% yield), m/z (esi/APCI) M$^+$1=492.2.

Step B: 2-amino-3-chloropyridine-4-thiol (0.041 g, 0.26 mmol), Hunig's base (0.148 mL, 0.85 mmol), and tert-butyl ((1R,5S,6r)-3-(6-chloropyrido[2,3-b]pyrazin-2-yl)-3-azabicyclo[3.1.1]heptan-6-yl)carbamate (0.064 g, 0.17 mmol) were placed in 1,4-dioxane (1.14 mL, 0.17 mmol) and was heated to 100° C. for 18 hours. The reaction was cooled, DCM (25 mL) was added and was filtered over celite. The solids were washed with DCM (25 mL) and then 3:1 DCM:IPA (25 mL) and then the filtrate was concentrated in vacuo. This material was purified by flash chromatography using a 0 to 15% MeOH in EtOH gradient. The resulting solid was resuspended in DCM (5 mL) and TFA (5 mL). This mixture was stirred for 1 hour at rt and was concentrated in vacuo. The resulting residue was free-based with sat. NaHC03 (15 mL) and extracted with 3:1 DCM:IPA (2×25 mL). The organics were pooled and washed with brine (15 mL), dried with Na2SO4, filtered and concentrated in vacuo. The resulting residue was purified via flash chromatography using a 0 to 15% MeOH in DCM with a 1% NH4OH modifier, to provide (1R,5S,6r)-3-(6-((2-amino-3-chloropyridin-4-yl)thio)pyrido[2,3-b]pyrazin-2-yl)-3-azabicyclo[3.1.1]heptan-6-amine (0.026 g, 0.064 mmol, 38% yield). $^1$H NMR (400 MHz, DMSO-4) δ 8.77 (s, 1H), 8.03 (d, 1H, J=8.4 Hz), 7.76 (d, 1H, J=5.3 Hz), 7.60 (d, 1H, J=8.6 Hz), 6.63 (bs, 2H), 6.36 (d, 1H, J=5.3 Hz), 3.91-3.70 (m, 4H), 3.31 (m, 1H), 2.50 (m, 1H), 2.13 (bs, 1H), 1.73 (m, 1H), 1.32 (d, 1H, J=9.6 Hz), m/z (esi/APCI) M+1=400.1.

Example 138

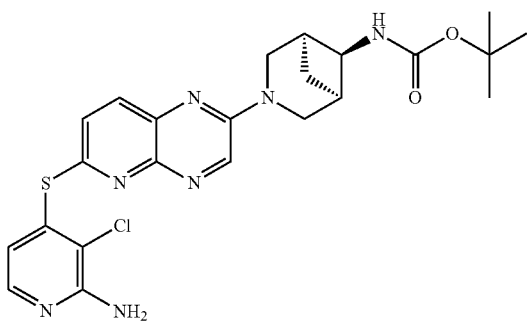 [SMILES: CC(C)(C)OC(=O)N[C@H]1[C@@H]2C[C@H]1CN(c1cnc3nc(Sc4ccnc(N)c4Cl)ccc3n1)C2]

(tert-butyl ((1R,5S,6r)-3-(6-((2-amino-3-chloropyridin-4-yl)thio)pyrido[2,3-b]pyrazin-2-yl)-3-azabicyclo[3.1.1]heptan-6-yl)carbamate tert-butyl ((1R,5S,6r)-3-(6-((2-amino-3-chloropyridin-4-yl)thio)pyrido[2,3-b]pyrazin-2-yl)-3-azabicyclo[3.1.1]heptan-6-yl)carbamate was prepared according to Example 121, except that the deprotection in Step B with TFA was not performed. m/z (esi/APCI) M+1=500.2.

Example 139

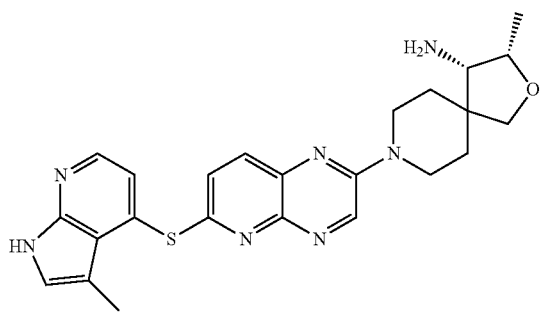 [SMILES: Cc1c[nH]c2nccc(Sc3ccc4nc(N5CCC6(CC5)CO[C@@H](C)[C@H]6N)cnc4n3)c12]

(3S,4S)-3-methyl-8-(6-((3-methyl-1H-pyrrolo[2,3-b]pyridin-4-yl)thio)pyrido[2,3-b]pyrazin-2-yl)-2-oxa-8-azaspiro[4.5]decan-4-amine Step A: N-Ethyl-N-isopropylpropan-2-amine (0.94 mL, 5.2 mmol) was added to a solution of 6-chloropyrido[2,3-b]pyrazin-2-yl trifluoromethanesulfonate (0.47 g, 1.5 mmol) in DMA cooled to 0° C., followed by (3S,4S)-3-methyl-2-oxa-8-azaspiro[4.5]decan-4-amine dihydrochloride (0.36 g, 1.5 mmol). The reaction was stirred at 0° C. for 1 hour and was poured into water and extracted three times with DCM. The combined organics were washed with water, brine, dried over MgSO₄ and concentrated in vacuo. The material was chromatographed eluting with 0-10% MeOH/DCM with 0.2% NH₄OH as additive to give (3S,4S)-8-(6-chloropyrido[2,3-b]pyrazin-2-yl)-3-methyl-2-oxa-8-azaspiro[4.5]decan-4-amine (0.42 g, 84% yield). m/z (esi/APCI) M+1=334.2.

Step B: Methyl 3-((3-methyl-1H-pyrrolo[2,3-b]pyridin-4-yl)thio)propanoate (0.042 g, 0.17 mmol), (3S,4S)-8-(6-chloropyrido[2,3-b]pyrazin-2-yl)-3-methyl-2-oxa-8-azaspiro[4.5]decan-4-amine (0.030 g, 0.09 mmol), and potassium tert-butoxide (0.18 mL, 0.18 mmol) were dissolved in NMP (0.90 mL, 0.090 mmol) and was heated to 100° C. for 18 hours. The reaction was cooled, DCM (25 mL) was added and was filtered over celite. The solids were washed with DCM (25 mL) and 3:1 DCM:IPA (25 mL) and the filtrate was concentrated in vacuo. This material was purified by flash chromatography using a 0 to 20% MeOH in DCM (with a 2% NH4OH modifier) gradient to obtain (3S,4S)-3-methyl-8-(6-((3-methyl-1H-pyrrolo[2,3-b]pyridin-4-yl)thio)pyrido[2,3-b]pyrazin-2-yl)-2-oxa-8-azaspiro[4.5]decan-4-amine (0.016 g, 0.033 mmol, 37% yield). ¹H NMR (400 MHz, DMSO-d₆) δ 11.60 (s, 1H), 8.90 (s, 1H), 8.15 (d, 1H, J=8.6 Hz), 7.26 (m, 1H), 7.22 (d, 1H, J=8.6 Hz), 7.11 (d, 1H, J=8.6), 4.07-3.95 (m, 3H), 3.66 (d, 1H, J=8.4 Hz), 3.60-3.48 (m, 2H), 3.46 (d, 1H, J=8.6 Hz), 2.88 (d, 1H, J=5.3 Hz), 2.23 (s, 3H), 1.76 (m, 1H), 1.64 (m, 1H), 1.52 (m, 2H), 1.06 (d, 3H, J=6.5 Hz). m/z (esi/APCI) M+1=462.2.

Example 140

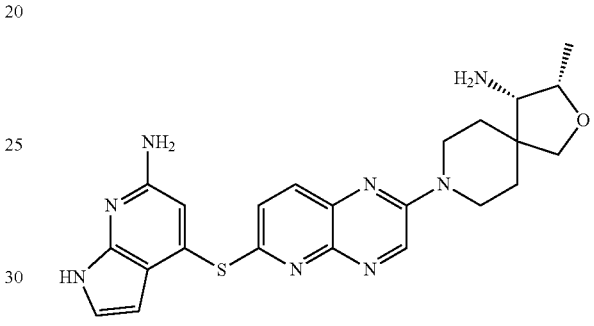

(3S,4S)-8-(6-(((6-amino-1H-pyrrolo[2,3-b]pyridin-4-yl)thio)pyrido[2,3-b]pyrazin-2-yl)-3-methyl-2-oxa-8-azaspiro[4.5]decan-4-amine (3S,4S)-8-(6-(((6-amino-1H-pyrrolo[2,3-b]pyridin-4-yl)thio)pyrido[2,3-b]pyrazin-2-yl)-3-methyl-2-oxa-8-azaspiro[4.5]decan-4-amine was prepared according to Example 139, substituting methyl 3-((6-amino-1H-pyrrolo[2,3-b]pyridin-4-yl)thio)propanoate for methyl 3-((3-methyl-1H-pyrrolo[2,3-b]pyridin-4-yl)thio)propanoate in Step A. m/z (esi/APCI) M+1=463.2.

Example 141

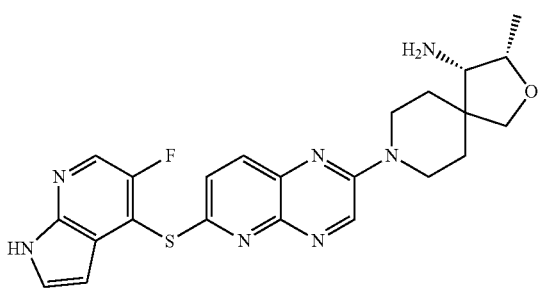 [SMILES: C[C@@H]1OCC2(CCN(c3cnc4nc(Sc5c(F)cnc6[nH]ccc56)ccc4n3)CC2)[C@@H]1N]

(3S,4S)-8-(6-(((5-fluoro-1H-pyrrolo[2,3-b]pyridin-4-yl)thio)pyrido[2,3-b]pyrazin-2-yl)-3-methyl-2-oxa-8-azaspiro[4.5]decan-4-amine Step A: N-Ethyl-N-isopropylpropan-2-amine (0.94 mL, 5.2 mmol) was added to a solution of 6-chloropyrido[2,3- b]pyrazin-2-yl trifluoromethanesulfonate (0.47 g, 1.5 mmol) in DMA cooled to 0° C., followed by (3S,4S)-3-methyl-2-oxa-8-azaspiro[4.5]decan-4-amine dihydrochloride (0.36 g, 1.5 mmol). The reaction was stirred at 0° C. for 1 hour and was poured into water and extracted three times with DCM. The combined organics were washed with water, brine, dried over MgSO$_4$, filtered and concentrated in vacuo. The material was chromatographed eluting with 0-10% MeOH/DCM with 0.2% NH$_4$OH as additive to give (3S,4S)-8-(6-chloropyrido[2,3-b]pyrazin-2-yl)-3-methyl-2-oxa-8-azaspiro[4.5]decan-4-amine (0.42 g, 84% yield), m/z (esi/APCI) M+1=334.2.

Step B: Methyl 3-((5-fluoro-1H-pyrrolo[2,3-b]pyridin-4-yl)thio)propanoate (0.066 g, 0.26 mmol), (3S,4S)-8-(6-chloropyrido[2,3-b]pyrazin-2-yl)-3-methyl-2-oxa-8-azaspiro[4.5]decan-4-amine (0.029 g, 0.087 mmol), and potassium tert-butoxide (0.27 mL, 0.27 mmol) were placed in NMP (0.87 mL, 0.087 mmol) and was heated to 100° C. for 18 hours. The reaction was heated to 150° C. for 2 hours in a microwave reactor. The reaction mixture was cooled to room temperature, DCM (25 mL) was added and was filtered over celite. The solids were washed with DCM (25 mL) and then 3:1 DCM:IPA (25 mL) and the filtrate was concentrated in vacuo. This material was purified by preparatory HPLC using a 5 to 95% ACN in water (with a 0.1% TFA modifier) gradient. The resulting fractions were then free-based with sat. NaHCO3 (15 mL) and extracted with 3:1 DCM:IPA (2×25 mL). The organics were pooled and washed with brine (15 mL), dried over Na2SO4, filtered and concentrated in vacuo to obtain (3S,4S)-8-(6-((5-fluoro-1H-pyrrolo[2,3-b]pyridin-4-yl)thio)pyrido[2,3-b]pyrazin-2-yl)-3-methyl-2-oxa-8-azaspiro[4.5]decan-4-amine (0.0024 g, 0.0052 mmol, 5.9% yield). $^1$H NMR (400 MHz, DMSO-d$_6$) δ 12.08 (s, 1H), 8.87 (s, 1H), 8.34 (d, 1H, J=1.8 Hz), 7.86 (d, 1H, J=8.6 Hz), 7.61 (m, 1H), 7.31 (d, 1H, J=8.6), 6.26 (m, 1H), 4.09-3.94 (m, 3H), 3.66 (d, 1H, J=8.6 Hz), 3.47 (d, 1H, J=8.4 Hz), 2.89 (d, 1H, J=5.3 Hz), 1.80-1.42 (m, 5H), 1.06 (d, 3H, J=6.5 Hz), m/z (esi/APCI) M+1=466.2.

Example 142

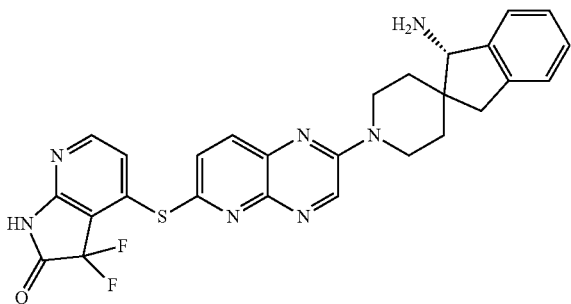 [SMILES: N[C@@H]1c2ccccc2CC12CCN(c1cnc3nc(Sc4ccnc5c4C(F)(F)C(=O)N5)ccc3n1)CC2]

(S)-4-((2-(1-amino-1,3-dihydrospiro[indene-2,4'-piperidin]-1'-yl)pyrido[2,3-b]pyrazin-6-yl)thio)-3,3-difluoro-1,3-dihydro-2H-pyrrolo[2,3-b]pyridin-2-one Step A: (R)—N—((S)-1,3-dihydrospiro[indene-2,4'-piperidin]-1'-yl)-2-methylpropane-2-sulfinamide (2.00 g, 6.53 mmol) was suspended in 1,4-dioxane (22 mL, 6.53 mmol) and triethylamine (2.73 mL, 19.6 mmol) was added to the mixture. After 20 min of stirring at RT, 6-chloropyrido[2,3-b]pyrazin-2-yl trifluoromethanesulfonate (2.05 g, 6.53 mmol) was added and the mixture was stirred at RT for 2 h. Methyl 3-mercaptopropanoate (0.54 mL, 6.53 mmol), palladium (II) acetate (0.15 g, 0.65 mmol) and Xanthphos (0.76 g, 1.3 mmol) were added to the reaction and nitrogen was bubbled in the reaction mixture for 2 min. The reaction was heated up to 90° C. overnight and was cooled down to RT, mixed with EtOAc (30 mL) and filtered. The filtrate was evaporated and the residue was purified by flash chromatography, eluting with a 2 to 20% MeOH in DCM gradient to give methyl 3-((2-((S)-1-(((R)-tert-butylsulfinyl)amino)-1,3-dihydrospiro[indene-2,4'-piperidin]-1'-yl)pyrido[2,3-b]pyrazin-6-yl)thio)propanoate (1.6 g, 2.89 mmol, 44.3% yield), m/z (esi/APCI) M+1=554.2.

Step B: Methyl 3-((2-((S)-1-(((R)-tert-butylsulfinyl)amino)-1,3-dihydrospiro[indene-2,4'-piperidin]-1'-yl)pyrido[2,3-b]pyrazin-6-yl)thio)propanoate (1.3 g, 2.35 mmol) was dissolved in THF (10 mL) and then a 21% solution of sodium ethanolate (1.75 mL, 4.70 mmol) in ethanol was added slowly. The reaction was stirred at RT for 1 h and the reaction was quenched with sat NH4Cl (10 mL). The aqueous layer was extracted with EtOAc (2×15 mL) and the combined organic layers were washed brine, dried and evaporated in vacuo. The product was purified using flash chromatography, eluting with a 10 to 100% EtOAc in hexanes gradient, which yielded (R)—N—((S)-1'-(6-mercaptopyrido[2,3-b]pyrazin-2-yl)-1,3-dihydrospiro[indene-2,4'-piperidin]-1-yl)-2-methylpropane-2-sulfinamide (0.32 g, 0.69 mmol, 29% yield), m/z (esi/APCI) M+1=468.2.

Step C: A solution of 3,3-difluoro-4-iodo-1,3-dihydro-2H-pyrrolo[2,3-b]pyridin-2-one (0.026 g, 0.087 mmol), (R)—N—((S)-1'-(6-mercaptopyrido[2,3-b]pyrazin-2-yl)-1,3-dihydrospiro[indene-2,4'-piperidin]-1-yl)-2-methylpropane-2-sulfinamide (0.037 g, 0.079 mmol), tris(dibenzylideneacetone)dipalladium (0) (0.0036 g, 0.0040 mmol) and 4,5-Bis(diphenylphosphino)-9,9-dimethylxanthene (0.0046 g, 0.0079 mmol) in 1,4-dioxane (0.79 mL, 0.079 mmol) was heated to 100° C. for 16 hours. The reaction was quenched with EtOAc (25 mL) and water (25 mL), filtered over GF/F paper, and then the biphasic mixture was separated. The organic phase was washed with brine (25 mL), dried over Na2SO4, filtered and concentrated in vacuo. The resulting residue was resuspended in dioxane (5 mL) and subjected to 4M HCl in dioxane (5 mL) while stirring at rt for 15 minutes. The mixture was concentrated in vacuo and then resuspended in 25 mL of a mixture of 3:1 DCM:IPA. Added 25 mL of sat. NaHC03 and let stir for 5 minutes. Separated the layers and then extracted organics from the aqueous layer with DCM:IPA (2×15 mL). Pooled the organic layers and washed with brine (25 mL), dried over Na2SO4, filtered and concentrated in vacuo. This was purified using flash chromatography, eluting with a 0 to 20% MeOH in EtOAc gradient (with a 2% NH4OH additive) to yield (S)-4-((2-(1-amino-1,3-dihydrospiro[indene-2,4'-piperidin]-1'-yl)pyrido[2,3-b]pyrazin-6-yl)thio)-3,3-difluoro-1,3-dihydro-2H-pyrrolo[2,3-b]pyridin-2-one (0.0081 g, 0.015 mmol, 19% yield). $^1$H NMR (400 MHz, DMSO-d$_6$) δ 9.03 (s, 1H), 8.14 (d, 1H, J=5.9 Hz), 8.02 (d, 1H, J=8.6 Hz), 7.74 (d, 1H, J=8.6), 7.34-7.15 (m, 5H), 6.89 (d, 1H, J=5.9 Hz), 6.65 (bs, 4H), 4.48 (m, 2H), 3.90 (s, 1H), 3.35 (m, 1H), 3.11 (d, 1H, J=15.7 Hz), 2.70 (d, 1H, J=15.5 Hz), 1.81 (m, 1H), 1.58 (m, 1H), 1.20 (m, 1H). m/z (esi/APCI) M+1=532.2.

Example 143

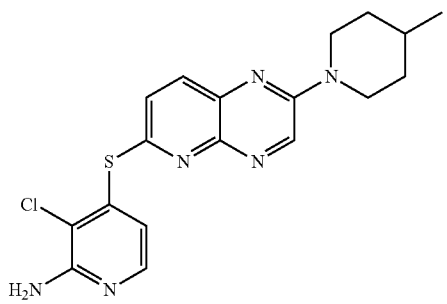 [SMILES: CC1CCN(c2cnc3nc(Sc4ccnc(N)c4Cl)ccc3n2)CC1]

3-chloro-4-((2-(4-methylpiperidin-1-yl)pyrido[2,3-b]pyrazin-6-yl)thio)pyridin-2-amine To a solution of 6-chloropyrido[2,3-b]pyrazin-2-yl trifluoromethanesulfonate (0.18 g, 0.57 mmol) in DMA (1 mL) was added 4-methylpiperidine (0.057 g, 0.57 mmol) and Hunig's Base (0.60 mL, 3.4 mmol) and the reaction stirred at 0° C. for 1 hr. To the reaction was added 2-amino-3-chloropyridine-4-thiol (0.092 g, 0.57 mmol) and the reaction heated to 120° C. in the microwave for 2 hrs. The reaction was cooled and poured into water and the water layer extracted with EtOAc and the layers separated. The organics were washed with water, brine, dried over $MgSO_4$, filtered and concentrated in vacuo. The material was chromatographed using 0-100% EtOAc/DCM as eluent to give 3-chloro-4-((2-(4-methylpiperidin-1-yl)pyrido[2,3-b]pyrazin-6-yl)thio)pyridin-2-amine (0.023 g, 10% yield).m/z (esi/APCI) M+1=387.1; $^1$H NMR (400 MHz, $CDCl_3$) δ 8.73 (s, 1H), 7.91 (d, J=8.5 Hz, 1H), 7.82 (d, J=5.3 Hz, 1H), 7.50 (d, J=8.6 Hz, 1H), 6.66 (d, J=5.3 Hz, 1H), 4.94 (s, 2H), 4.58 (d, J=11.8 Hz, 2H), 3.05 (t, J=12.9 Hz, 2H), 1.83 (d, J=12.8 Hz, 2H), 1.78-1.69 (m, 1H), 1.32-1.21 (m, 2H), 1.0 (d, J=5.5 Hz, 3H).

Example 144

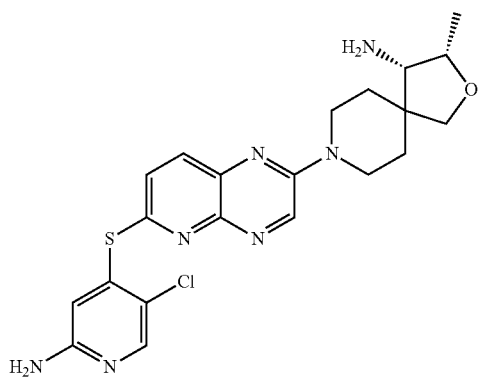 [SMILES: C[C@@H]1OCC2(CCN(c3cnc4nc(Sc5cc(N)ncc5Cl)ccc4n3)CC2)[C@@H]1N]

(3S,4S)-8-(6-((2-amino-5-chloropyridin-4-yl)thio)pyrido[2,3-b]pyrazin-2-yl)-3-methyl-2-oxa-8-azaspiro[4,5]decan-4-amine (3S,4S)-8-(6-((2-amino-5-chloropyridin-4-yl)thio)pyrido[2,3-b]pyrazin-2-yl)-3-methyl-2-oxa-8-azaspiro[4.5]decan-4-amine was made according to example 71 substituting DMA for dioxane as solvent and increasing the reaction temperature to 150° C. m/z (esi/APCI) M+1=558.2.

Example 145

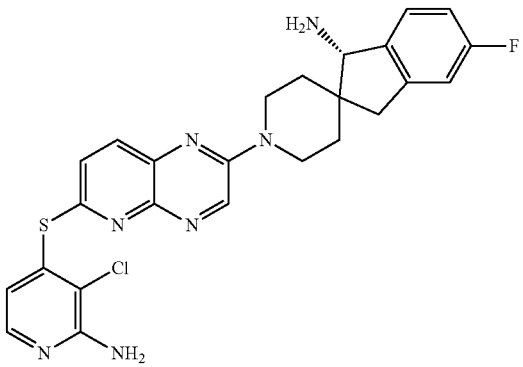 [SMILES: Nc1nccc(Sc2ccc3nc(N4CCC5(CC4)Cc4cc(F)ccc4[C@H]5N)cnc3n2)c1Cl]

(S)-1'-(6-((2-amino-3-chloropyridin-4-yl)thio)pyrido[2,3-b]pyrazin-2-yl)-5-fluoro-1,3-dihydrospiro[indene-2,4'-piperidin]-1-amine Step A: To a solution of N—((S)-5-fluoro-1,3-dihydrospiro[indene-2,4'-piperidin]-1-yl)-2-methylpropane-2-sulfinamide 2,2,2-trifluoroacetate (0.30 g, 0.68 mmol) in DCM at room temperature was added N-ethyl-N-isopropylpropan-2-amine (0.44 g, 3.4 mmol) and 6-chloropyrido[2,3-b]pyrazin-2-yl trifluoromethanesulfonate (0.21 g, 0.68 mmol) and the reaction stirred at room temperature for 1 hr. The reaction mixture was washed with brine, dried over $MgSO_4$, filtered and concentrated in vacuo. The material was chromatographed using 0-100% EtOAc/hexanes as eluent to give (R)—N—((S)-1'-(6-chloropyrido[2,3-b]pyrazin-2-yl)-5-fluoro-1,3-dihydrospiro[indene-2,4'-piperidin]-1-yl)-2-methylpropane-2-sulfinamide (0.34 g, 102%). m/z (esi/APCI) M+1=488.2.

Step B: To a solution of N-ethyl-N-isopropylpropan-2-amine (0.27 g, 2.1 mmol) and sodium 2-amino-3-chloropyridine-4-thiolate (0.38 g, 2.1 mmol) in 2:1 dioxane/DMA was added (R)—N—((S)-1'-(6-chloropyrido[2,3-b]pyrazin-2-yl)-5-fluoro-1,3-dihydrospiro[indene-2,4'-piperidin]-1-yl)-2-methylpropane-2-sulfinamide (0.34 g, 0.70 mmol) and the reaction heated overnight at 75° C. followed by heating the reaction to 140° C. for 45 minutes in the microwave. The reaction was poured into water and extracted into EtOAc and the layers separated. The organics were washed with brine, dried over $MgSO_4$ and concentrated in vacuo. The material was purified by chromatography using 0-10% MeOH/DCM as eluent to give (R)—N—((S)-1'-(6-((2-amino-3-chloropyridin-4-yl)thio)pyrido[2,3-b]pyrazin-2-yl)-5-fluoro-1,3-dihydrospiro[indene-2,4'-piperidin]-1-yl)-2-methylpropane-2-sulfinamide (0.015 g, 4% yield), m/z (esi/APCI) M+1=612.2.

Step C: To a solution of (R)—N—((S)-1'-(6-((2-amino-3-chloropyridin-4-yl)thio)pyrido[2,3-b]pyrazin-2-yl)-5-fluoro-1,3-dihydrospiro[indene-2,4'-piperidin]-1-yl)-2-methylpropane-2-sulfinamide (0.015 g, 0.025 mmol) in 5 mL of methanol was added 2 mL of 4M HCl in dioxane and the reaction stirred at rt for 1 hr. The reaction was concentrated in vacuo and the material taken up in 20% MeOH/DCM with 0.4M $NH_4OH$ and concentrated. The residue was chromatographed using 0-10% MeOH/DCM with 2% $NH_4OH$ modifier to give (S)-1'-(6-((2-amino-3-chloropyridin-4-yl)thio)pyrido[2,3-b]pyrazin-2-yl)-5-fluoro-1,3- dihydrospiro[indene-2,4'-piperidin]-1-amine (0.0023 g, 18% yield), m/z (esi/APCI) M+1=508.1. ¹H NMR (400 MHz, (CDCl₃) δ 8.75 (s, 1H), 7.97 (d, J=8.5 Hz, 1H), 7.84 (d, J=5.3 Hz, 1H), 7.49 (d, J=8.6 Hz, 1H), 7.26 (m, 1H), 6.95-6.90 (m, 2H), 6.69 (d, J=5.3 Hz, 1H), 4.94 (s, 3H), 4.45-4.38 (m, 2H), 3.96 (s, 1H), 3.38 (m, 4H), 3.10 (d, J=16.4 Hz, 1H), 2.75 (d, J=15.8 Hz, 1H), 1.92-1.79 (m, 2H), 1.68 (m, 1H), 1.44 (m, 1H).

Example 146

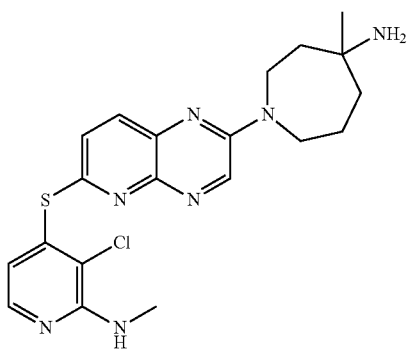 [SMILES: CNc1nccc(Sc2ccc3nc(N4CCCC(C)(N)CC4)cnc3n2)c1Cl]

1-(6-((3-chloro-2-(methylamino)pyridin-4-yl)thio)pyrido[2,3-b]pyrazin-2-yl)-4-methylazepan-4-amine 1-(6-((3-chloro-2-(methylamino)pyridin-4-yl)thio)pyrido[2,3-b]pyrazin-2-yl)-4-methylazepan-4-amine was made according to example 73 substituting 3-chloro-2-(methylamino)pyridine-4-thiol for 2-amino-3-chloropyridine-4-thiol in Step 2 while heating the reaction to 150° C. in a microwave for 2 hrs. m/z (esi/APCI) M+1=430.2. ¹H NMR (400 MHz, (CDCl₃) δ 8.43 (s, 1H), 7.91 (d, J=5.5 Hz, 1H), 7.89 (d, J=8.7 Hz, 1H), 7.45 (d, J=8.6 Hz, 1H), 6.56 (d, J=5.3 Hz, 1H), 5.13-5.1 (m, 1H), 3.91-3.73 (m, 4H), 3.05 (d, J=4.9 Hz, 3H), 2.17-2.05 (m, 1H), 1.90-1.75 (m, 4H), 1.67-1.52 (m, 3H), 1.26-1.23 (m, 1H), 1.18 (s, 3H).

Example 147

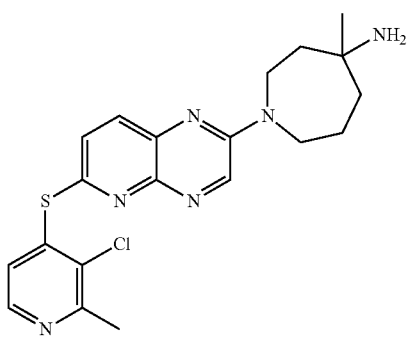 [SMILES: Cc1nccc(Sc2ccc3nc(N4CCCC(C)(N)CC4)cnc3n2)c1Cl]

1-(6-((3-chloro-2-methylpyridin-4-yl)thio)pyrido[2,3-b]pyrazin-2-yl)-4-methylazepan-4-amine 1-(6-((3-chloro-2-methylpyridin-4-yl)thio)pyrido[2,3-b]pyrazin-2-yl)-4-methylazepan-4-amine was made according to example 73 substituting 3-chloro-2-methylpyridine-4-thiol for 2-amino-3-chloropyridine-4-thiol in step 2 while heating the reaction to 100° C. in a microwave for 6 hrs. m/z (esi/APCI) M+1=415.2. ¹H NMR (400 MHz, (CDCl₃) δ 8.65 (s, 1H), 8.18 (d, J=5.3 Hz, 1H), 7.95 (d, J=8.5 Hz, 1H), 7.55 (d, J=8.5 Hz, 1H), 7.13 (d, J=5.8 Hz, 1H), 3.92-3.75 (m, 4H), 2.66 (s, 3H), 2.17-2.08 (m, 1H), 1.91-1.77 (m, 4H), 1.66-1.51 (m, 3H), 1.26 (m, 1H), 1.19 (s, 3 h).

Example 148

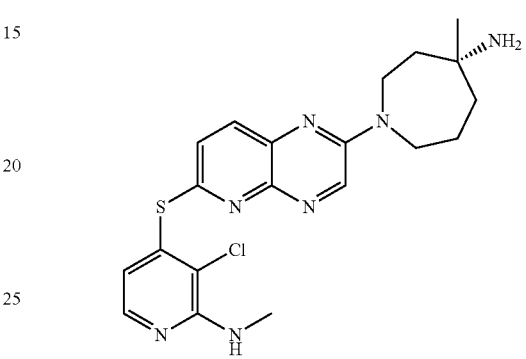

(R)-1-(6-((3-chloro-2-(methylamino)pyridin-4-yl)thio)pyrido[2,3-b]pyrazin-2-yl)-4-methylazepan-4-amine 1-(6-((3-chloro-2-(methylamino)pyridin-4-yl)thio)pyrido[2,3-b]pyrazin-2-yl)-4-methylazepan-4-amine enantiomers were separated by chiral SFC using 2 mL methanol loading at 4 mg/mL on an IG (2×15 cm) column eluting with 50% isopropanol with 0.2% DEA/CO₂ at 100 bar of pressure with a flow rate of 50 mL/minute monitoring at 220 nM wavelength. Peak 1 isolate, m/z (esi/APCI) M+1=430.2. ¹H NMR (400 MHz, (CDCl₃) δ 8.62 (s, 1H), 7.91 (d, J=5.1 Hz, 1H), 7.89 (d, J=8.6 Hz, 1H), 7.45 (d, J=8.8 Hz, 1H), 6.55 (d, J=5.3 Hz, 1H), 5.15-5.09 (m, 1H), 3.89-3.74 (m, 4H), 3.05 (d, J=4.9 Hz, 3H), 2.16-2.05 (m, 1H), 1.91-1.73 (m, 4H), 1.65-1.51 (m, 3H), 1.30-1.21 (m, 1H), 1.18 (s, 3H).

Example 149

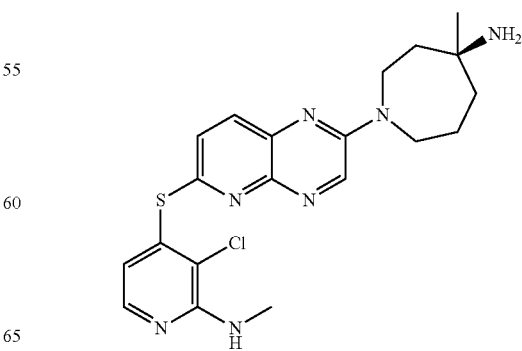

221

(S)-1-(6-((3-chloro-2-(methylamino)pyridin-4-yl)
thio)pyrido[2,3-b]pyrazin-2-yl)-4-methylazepan-4-
amine 1-(6-((3-chloro-2-(methylamino)pyridin-4-yl)thio)pyrido
[2,3-b]pyrazin-2-yl)-4-methylazepan-4-amine enantiomers
were separated by chiral SFC using 2 mL methanol loading
at 4 mg/mL using an IG (2×15 cm) column eluting with 50%
isopropanol with 0.2% DEA/CO$_2$ at 100 bar of pressure with
a flow rate 50 mL/minute monitoring at 220 nM wavelength.
Peak 2 isolate, m/z (esi/APCI) M+1=430.2. $^1$H NMR (400
MHz, (CDCl$_3$) δ 8.62 (s, 1H), 7.91 (d, J=5.1 Hz, 1H), 7.89
(d, J=8.6 Hz, 1H), 7.45 (d, J=8.9 Hz, 1H), 6.55 (d, J=5.4 Hz,
1H), 5.15-5.09 (m, 1H), 3.89-3.74 (m, 4H), 3.05 (d, J=4.9
Hz, 3H), 2.16-2.05 (m, 1H), 1.92-1.6z3 (m, 4H), 1.65-1.51
(m, 3H), 1.30-1.21 (m, 1H), 1.18 (s, 3H).

Example 150

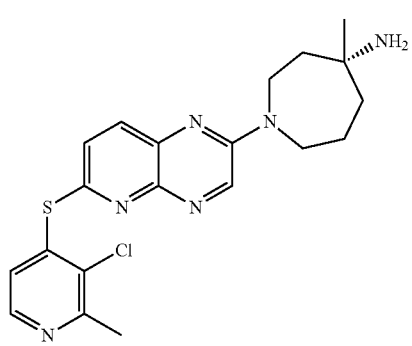 [SMILES: Cc1nccc(Sc2ccc3nc(N4CCC[C@@](C)(N)CC4)cnc3n2)c1Cl]

(R)-1-(6-((3-chloro-2-methylpyridin-4-yl)thio)pyrido
[2,3-b]pyrazin-2-yl)-4-methylazepan-4-amine 1-(6-((3-chloro-2-methylpyridin-4-yl)thio)pyrido[2,3-b]
pyrazin-2-yl)-4-methylazepan-4-amine enantiomers were
separated by chiral SFC using 1.5 mL methanol loading at
6 mg/mL using an AD-H (2×15 cm) column eluting with
40% methanol with 0.1% DEA/CO$_2$ at 100 bar of pressure
with a flow rate of 70 mL/minute monitoring at 220 nM
wavelength. Peak 1 isolate, m/z (esi/APCI) M+1=415.1. $^1$H
NMR (500 MHz, (CDCl$_3$) 8.65 (s, 1H), 8.18 (d, J=6.2 Hz,
1H), 7.95 (d, J=8.5 Hz, 1H), 7.55 (d, J=8.5 Hz, 1H), 7.13 (d,
J=5.8 Hz, 1H), 3.92-3.75 (m, 4H), 2.64 (s, 3H), 2.15-2.05
(m, 1H), 1.91-1.76 (m, 4H), 1.66-1.55 (m, 3H), 1.26 (m,
1H), 1.19 (s, 3 h).

Example 151

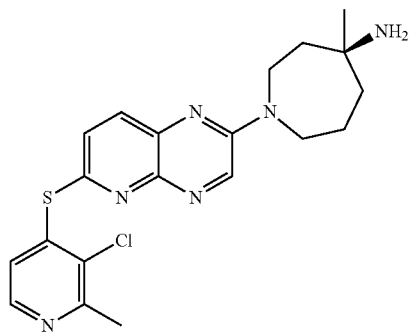 [SMILES: Cc1nccc(Sc2ccc3nc(N4CCC[C@](C)(N)CC4)cnc3n2)c1Cl]

222

(S)-1-(6-((3-chloro-2-methylpyridin-4-yl)thio)pyrido
[2,3-b]pyrazin-2-yl)-4-methylazepan-4-amine 1-(6-((3-chloro-2-methylpyridin-4-yl)thio)pyrido[2,3-b]
pyrazin-2-yl)-4-methylazepan-4-amine enantiomers were
separated by chiral SFC using 1.5 mL methanol loading at
6 mg/mL using an AD-H (2×15 cm) column eluting with
40% methanol with 0.1% DEA/CO$_2$ at 100 bar of pressure
with a flow rate of 70 mL/minute monitoring at 220 nM
wavelength. Peak 2 isolate, m/z (esi/APCI) M+1=415.2. $^1$H
NMR (500 MHz, (CDCl$_3$) 8.64 (s, 1H), 8.18 (d, J=5.4 Hz,
1H), 7.94 (d, J=8.5 Hz, 1H), 7.54 (d, J=8.6 Hz, 1H), 7.13 (d,
J=5.5 Hz, 1H), 3.90-3.74 (m, 4H), 2.66 (s, 3H), 2.17-2.08
(m, 1H), 1.91-1.77 (m, 4H), 1.66-1.51 (m, 3H), 1.26 (m,
1H), 1.19 (s, 3 h).

Example 152

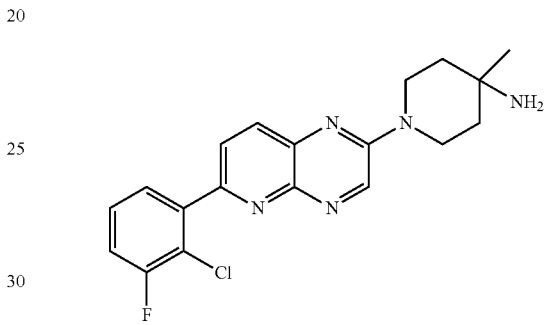

1-(6-(2-chloro-3-fluorophenyl) pyrido[2,3-b]
pyrazin-2-yl)-4-methylpiperidin-4-amine Step A: To a solution of tert-butyl (4-(6-bromopyrido[2,
3-b]pyrazin-2-yl)-1-methylcyclohexyl)carbamate (40 mg,
0.1 mmol) and 2-chloro-3-fluorophenylboronic acid (33 mg,
0.19 mmol) in dioxane (900 μL) was added K$_2$CO$_3$ (2M, 240
μL, 0.47 mmol) and the reaction degassed with Argon for 10
minutes. Palladium tetrakis (11 mg, 0.01 mmol) was added
and the reaction was heated to 90° C. for 2 hours. The
reaction was cooled to room temperature, partitioned
between EtOAc and water and the layers separated. The
organics were washed with brine, dried over sodium sulfate,
filtered and concentrated in vacuo. The concentrate was
purified by normal phase chromatography (0-100% EtOAc/
DCM) provide tert-butyl (1-(6-(2-chloro-3-fluorophenyl)
pyrido[2,3-b] pyrazin-2-yl)-4-methylpiperidin-4-yl) car-
bamate (30 mg, 67% yield).

Step B: tert-butyl (1-(6-(2-chloro-3-fluorophenyl) pyrido
[2,3-b] pyrazin-2-yl)-4-methylpiperidin-4-yl) carbamate (30
mg, 0.063 mmol) was dissolved in dichloromethane (600
μL) and treated with 2,2,2-trifluoroacetic acid (73 μL, 0.95
mmol). The reaction stirred at room temperature for 1 hour.
The reaction was concentrated in vacuo and the residue was
partitioned between EtOAc and 1M NaOH. The combined
organics were washed with brine, dried over sodium sulfate,
filtered and concentrated in vacuo. The concentrate was
chromatographed (0-15% DCM/MeOH with 2% NH$_4$OH)
to provide 1-(6-(2-chloro-3-fluorophenyl)pyrido[2,3-b]
pyrazin-2-yl)-4-methylpiperidin-4-amine (13.1 mg, 55%
yield). $^1$H NMR (400 MHz, (CDCl$_3$) δ 8.81 (s, 1H), 8.04 (d,
1H, J=8.6 Hz) 7.89 (d, 1H, 8.6 Hz) 7.61 (d, 1H, J=7.4 Hz),
7.38-7.32 (m, 1H), 7.24-7.19 (m, 1H), 4.04-3.97 (m, 2H), 3.86-3.78 (m, 2H), 1.75-1.67 (m, 2H), 1.63-1.56 (m, 2H), 1.24 (s, 1H); m/z (esi/APCI) M+1=372.2.

Example 153

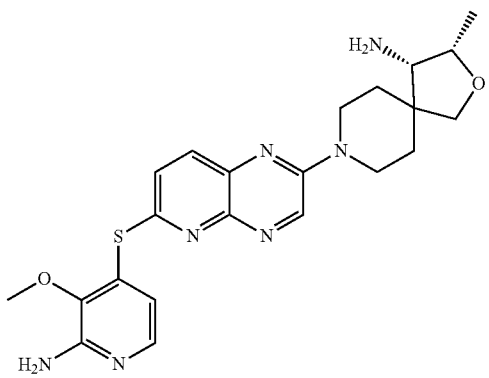 [SMILES: COc1c(Sc2ccc3nc(N4CCC5(CC4)CO[C@@H](C)[C@H]5N)cnc3n2)ccnc1N]

(3S,4S)-8-(6-((2-amino-3-methoxypyridin-4-yl)thio) pyrido[2,3-b]pyrazin-2-yl)-3-methyl-2-oxa-8-azaspiro [4.5] decan-4-amine To a solution of (3S,4S)-8-(6-chloropyrido[2,3-b]pyrazin-2-yl)-3-methyl-2-oxa-8-azaspiro[4.5]decan-4-amine (30 mg, 0.09 mmol) in dioxane (0.9 mL) in a microwave tube was added Hunig's base (63 µL, 0.36 mmol), cesium carbonate (117 mg, 0.36 mmol) and 2-amino-3-methoxypyridine-4-thiol (14 mg, 0.09 mmol) and the reaction was stirred at 150° C. for 4 hours. The reaction was concentrated in vacuo and chromatographed (0-100% EtOAc/hexanes to give (3S,4S)-8-(6-((2-amino-3-methoxypyridin-4-yl)thio)pyrido[2,3-b]pyrazin-2-yl)-3-methyl-2-oxa-8-azaspiro[4.5]decan-4-amine (4 mg, 10% yield). $^1$H NMR (400 MHz, (CDCl$_3$) δ 8.72 (s, 1H), 7.86 (d, 1H, J=8.6 Hz), 7.75 (d, 1H, 5.4 Hz), 7.41 (d, 1H, J=8.6 Hz), 6.73 (d, 1H, J=5.4 Hz), 4.76 (s, 1H), 4.22-4.03 (m, 4H), 3.86 (s, 3H), 3.83 (d, 1H, J=8.9 Hz), 3.72-3.69 (m, 1H), 3.65-3.57 (m, 1H), 3.55-3.47 (m, 1H), 3.01 (d, 1H, J=4.6 Hz), 1.96-1.89 (m, 1H), 1.81-1.69 (m, 3H), 1.24 (d, 3H, J=6.4 Hz); m/z (esi/APCI) M+1=454.2.

Example 154

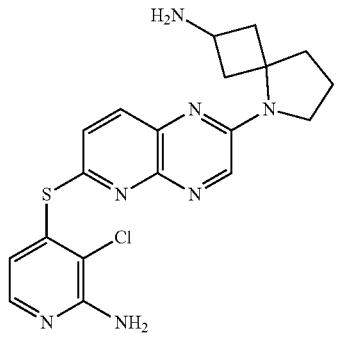 [SMILES: Nc1nccc(Sc2ccc3nc(N4CCCC45CC(N)C5)cnc3n2)c1Cl]

5-(6-((2-amino-3-chloropyridin-4-yl)thio)pyrido[2,3-b]pyrazin-2-yl)-5-azaspiro[3.4]octan-2-amine Step A: To a solution of 6-chloropyrido[2,3-b]pyrazin-2-yl 4-nitrobenzenesulfonate (350 mg, 0.95 mmol) in dioxane (6.3 mL) was added 2-(boc-amino)-5-aza-spiro[3.4]octane (216 mg, 0.95 mmol) and Hunig's base (493 mg, 3.82 mmol). The reaction mixture was stirred at 80° C. for 18 hr. To the reaction mixture was added 2-amino-3-chloropyridine-4-thiol (153 mg, 0.95 mmol) and the reaction heated to 100° C. for 7 hours followed by 72 hours at room temperature. The reaction was microwaved at 150° C. for 8 hours and concentrated in vacuo. The concentrate was chromatographed (10-80% EtOAc/hex) to give tert-butyl (5-(6-((2-amino-3-chloropyridin-4-yl)thio)pyrido[2,3-b]pyrazin-2-yl)-5-azaspiro[3.4]octan-2-yl)carbamate (218 mg, 44% yield).

Step B: tert-butyl (5-(6-((2-amino-3-chloropyridin-4-yl)thio)pyrido[2,3-b]pyrazin-2-yl)-5-azaspiro[3.4]octan-2-yl)carbamate (218 mg, 0.42 mmol) was dissolved in dichloromethane (4.2 mL) and treated with TFA (160 µL, 2.12 mmol). The reaction was stirred at room temperature for 30 minutes, concentrated in vacuo and partitioned between DCM and 1M NaOH. The combined organics were washed with brine, dried over sodium sulfate, filtered and concentrated in vacuo. The concentrate was chromatographed (0-10% MeOH/DCM with 2% NH$_4$OH) to give 5-(6-((2-amino-3-chloropyridin-4-yl)thio)pyrido[2,3-b]pyrazin-2-yl)-5-azaspiro[3.4]octan-2-amine (136 mg, 78% yield). $^1$H NMR (400 MHz, (CDCl$_3$) δ 8.50 (s, 1H), 7.92 (d, 1H, J=8.6 Hz), 7.82 (d, 1H, J=5.4), 7.51 (d, 1H, J=8.5 Hz), 6.65 (d, 1H, J=5.4 Hz), 4.93 (s, 1H), 4.19-4.12 (m, 1H), 3.65 (t, 2H, J=6.7 Hz), 3.57 (t, 2H, J=111 Hz), 3.48 (s, 2H), 2.29 (t, 2H, J=6.9 Hz), 2.01-1.94 (m, 2H), 1.79-1.74 (m, 2H), 1.39 (s, 2H); m/z (esi/APCI) M+1=414.2.

Example 155

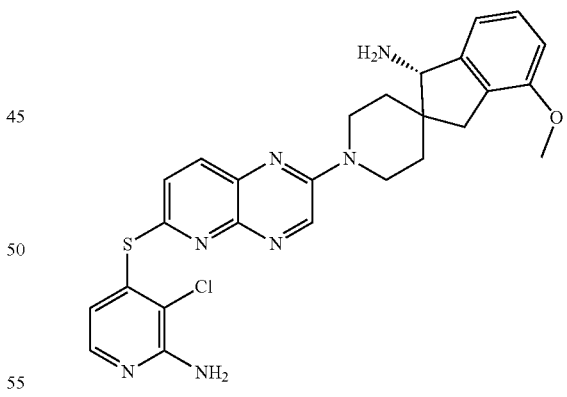

6-((2-amino-3-chloropyridin-4-yl)thio)-N-(3-(aminomethyl)tetrahydrofuran-3-yl)pyrido[2,3-b]pyrazin-2-amine Step A: To a solution of 6-chloropyrido[2,3-b]pyrazin-2-yl trifluoromethanesulfonate (86.3 mg, 0.28 mmol) in DCM (2.7 mL) was added N-ethyl-N-isopropylpropan-2-amine (240 µL, 1.38 mmol) and 6-chloropyrido[2,3-b]pyrazin-2-yl trifluoromethanesulfonate (86 mg, 0.28 mmol) and stirred at room temperature for 2 hours. The reaction mixture was washed with brine, dried over sodium sulfate, filtered and concentrated in vacuo. The material was chromatographed (0-100% EtOAc/hex to give (R)—N—((S)-1'-(6-chloro-pyrido[2,3-b]pyrazin-2-yl)-4-methoxy-1,3-dihydrospiro[indene-2,4'-piperidin]-1-yl)-2-methylpropane-2-sulfinamide (133 mg, 97% yield).

Step B: To a solution of (R)—N—((S)-1'-(6-chloropyrido[2,3-b]pyrazin-2-yl)-4-methoxy-1,3-dihydrospiro[indene-2,4'-piperidin]-1-yl)-2-methylpropane-2-sulfinamide (133 mg, 0.27 mmol) and sodium 2-amino-3-chloropyridine-4-thiolate (146 mg, 0.8 mmol) in 2:1 dioxanes/DMA was added N-ethyl-N-isopropylpropan-2-amine (139 µL, 0.8 mmol) and the reaction heated 140° C. in the microwave for 6 hours followed by 1 hour at 150° C. The reaction was partitioned between water and EtOAc and the layers separated. The organics were washed with brine, dried over sodium sulfate, filtered and concentrated in vacuo. The material was taken forward as crude (R)—N—((S)-1'-(6-((2-amino-3-chloro-pyridin-4-yl)thio)pyrido[2,3-b]pyrazin-2-yl)-4-methoxy-1,3-dihydrospiro[indene-2,4'-piperidin]-1-yl)-2-methylpropane-2-sulfinamide (146 mg, 88% yield).

Step C: (R)—N—((S)-1'-(6-((2-amino-3-chloropyridin-4-yl)thio)pyrido[2,3-b]pyrazin-2-yl)-4-methoxy-1,3-dihydrospiro[indene-2,4'-piperidin]-1-yl)-2-methylpropane-2-sulfinamide (146 mg, 0.23 mmol) was dissolved in MeOH (2.3 mL) and treated with HCl (4.0 M in 1,4-dioxane) (175 µL, 0.7 mmol). The reaction was stirred at room temperature for 1 hour. The reaction was concentrated in vacuo and purified by prep HPLC (Gilson, 5-95% ACN/water with 0.1% TFA). Fractions containing clean desired product were combined and partitioned between DCM and 1M NaOH. The combined organics were washed with brine, dried over sodium sulfate, filtered and concentrated in vacuo to give (S)-1'-(6-((2-amino-3-chloropyridin-4-yl)thio)pyrido[2,3-b]pyrazin-2-yl)-4-methoxy-1,3-dihydrospiro[indene-2,4'-piperidin]-1-amine (9.8 mg, 8.0% yield). $^1$H NMR (400 MHz, (DMSO) δ 9.01 (s, 1H), 7.99 (d, 1H, J=7.7 Hz), 7.79 (d, 1H, J=4.2 Hz), 7.59 (d, 1H, J=8.1 Hz), 7.17 (t, 1H, J=7.4 Hz), 6.91 (d, 1H, J=7.1 Hz), 6.79 (d, 1H, J=7.8 Hz), 6.46 (s, 2H), 6.42 (d, 1H, J=4.8 Hz), 4.46 (d, 2H, J=10.6 Hz), 3.83 (s, 1H), 3.77 (s, 3H), 3.57 (s, 3H), 3.37 (d, 1H, J=11.9 Hz), 3.03 (d, 1H, J=15.1 Hz), 2.56 (s, 1H), 1.84-1.69 (m, 2H), 1.56 (d, 1H, J=13.3 Hz), 1.23 (s, 1H); m/z (esi/APCI) M+1=520.2.

Example 156

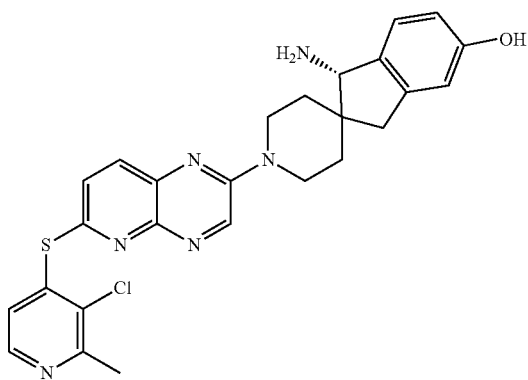 [SMILES: Cc1nccc(Sc2ccc3nc(N4CCC5(CC4)Cc4cc(O)ccc4[C@H]5N)cnc3n2)c1Cl]

(S)-1-amino-1'-(6-((3-chloro-2-methylpyridin-4-yl)thio)pyrido[2,3-b]pyrazin-2-yl)-1,3-dihydrospiro[indene-2,4'-piperidin]-5-ol Step A: To a solution of (R)—N—((S)-5-methoxy-1,3-dihydrospiro[indene-2,4'-piperidin]-1-yl)-2-methylpropane-2-sulfinamide 2,2,2-trifluoroacetate (250 mg, 0.56 mmol) in DCM (5.5 mL) was added N-ethyl-N-isopropylpropan-2-amine (485 µL, 2.77 mmol) and 6-chloropyrido[2,3-b]pyrazin-2-yl trifluoromethanesulfonate (174 mg, 0.555 mmol) and stirred at room temperature for 2 hours. The reaction mixture was washed with brine, dried over sodium sulfate, filtered and concentrated in vacuo. The material was chromatographed (0-100% EtOAc/hex) to give (R)—N—((S)-1'-(6-chloropyrido[2,3-b]pyrazin-2-yl)-5-methoxy-1,3-dihydrospiro[indene-2,4'-piperidin]-1-yl)-2-methylpropane-2-sulfinamide (92 mg, 33% yield).

Step B: To a solution of (R)—N—((S)-1'-(6-chloropyrido[2,3-b]pyrazin-2-yl)-5-methoxy-1,3-dihydrospiro[indene-2,4'-piperidin]-1-yl)-2-methylpropane-2-sulfinamide (50 mg, 0.1 mmol) and sodium 3-chloro-2-methylpyridine-4-thiolate (54.5 mg, 0.3 mmol) in 2:1 dioxanes/DMA was added N-ethyl-N-isopropylpropan-2-amine (52 µL, 0.3 mmol) and the reaction was microwaved at 150° C. for 1 hour. The reaction was poured into water and extracted into EtOAc and the layers separated. The organics were next washed with brine, dried over sodium sulfate, filtered and concentrated in vacuo. The material was taken forward as crude (R)—N—((S)-1'-(6-((3-chloro-2-methylpyridin-4-yl)thio)pyrido[2,3-b]pyrazin-2-yl)-5-methoxy-1,3-dihydrospiro[indene-2,4'-piperidin]-1-yl)-2-methylpropane-2-sulfinamide (52 mg, 85% yield).

Step C: (R)—N—((S)-1'-(6-((3-chloro-2-methylpyridin-4-yl)thio)pyrido[2,3-b]pyrazin-2-yl)-5-methoxy-1,3-dihydrospiro[indene-2,4'-piperidin]-1-yl)-2-methylpropane-2-sulfinamide (52.9 mg, 0.09 mmol) was dissolved in MeOH (900 µl) and treated with Hydrochloric Acid Solution (4.0 M in 1,4-dioxane) (21 µL, 0.09 mmol). The reaction was stirred at room temperature for 1 hour, was concentrated in vacuo and taken forward as crude (S)-1'-(6-((3-chloro-2-methylpyridin-4-yl)thio)pyrido[2,3-b]pyrazin-2-yl)-5-methoxy-1,3-dihydrospiro[indene-2,4'-piperidin]-1-amine (44 mg, 100% yield).

Step D: To a solution of (S)-1'-(6-((3-chloro-2-methylpyridin-4-yl)thio)pyrido[2,3-b]pyrazin-2-yl)-5-methoxy-1,3-dihydrospiro[indene-2,4'-piperidin]-1-amine (44 mg, 0.09 mmol) in DCM (200 µL) at 0° C. was added boron tribromide (170 µL, 0.17 mmol)(1.0M $CH_2Cl_2$) dropwise. The reaction was stirred for 2 hours at room temperature. The reaction was slowly added to 0° C. water followed by neutralization by slow addition of a saturated solution of sodium bicarbonate. The organic layer was washed with water and concentrated in vacuo. The concentrate was chromatographed (0-10% DCM/MeOH with 2% $NH_4OH$) to give (S)-1-amino-1'-(6-((3-chloro-2-methylpyridin-4-yl)thio)pyrido[2,3-b]pyrazin-2-yl)-1,3-dihydrospiro[indene-2,4'-piperidin]-5-ol (5 mg, 12% yield). $^1$H NMR (400 MHz, (DMSO) 9.11 (s, 1H), 9.03 (s, 1H), 8.25 (d, 1H, J=4.8 Hz), 8.03 (d, 1H, J=9.1 Hz), 7.71 (d, 1H, J=8.5 Hz), 7.16-7.04 (m, 2H), 6.61-6.54 (m, 2H), 4.45 (d, 2H, J=12.2 Hz), 3.75 (s, 1H), 3.42-3.33 (m, 2H), 2.99 (d, 1H, J=14.8 Hz), 2.61 (s, 3H), 2.57 (s, 1H), 1.82-1.63 (m, 3H), 1.54 (d, 1H, J=13.1 Hz), 1.22 (d, 2H, J=12.1 Hz); m/z (esi/APCI) M+1=505.2.

Example 157

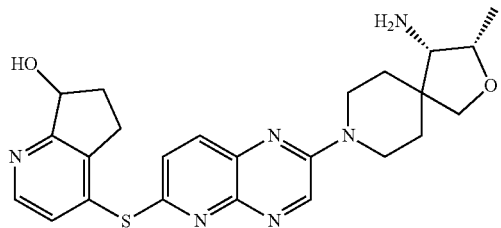 [SMILES: C[C@@H]1OCC2(CCN(c3cnc4nc(Sc5ccnc6c5CCC6O)ccc4n3)CC2)[C@@H]1N]

4-((2-((3S,4S)-4-amino-3-methyl-2-oxa-8-azaspiro[4.5]decan-8-yl)pyrido[2,3-b]pyrazin-6-yl)thio)-6,7-dihydro-5H-cyclopenta[b]pyridin-7-ol (3S,4S)-8-(6-chloropyrido[2,3-b]pyrazin-2-yl)-3-methyl-2-oxa-8-azaspiro[4.5]decan-4-amine (30 mg, 0.090 mmol) [Example 4, Step A] and methyl 3-((7-hydroxy-6,7-dihydro-5H-cyclopenta[b]pyridin-4-yl)thio)propanoate (45.5 mg, 0.18 mmol) were dissolved in DMF (1 mL) nitrogen bubbled through for 2 minutes. Potassium 2-methylpropan-2-olate (180 µL, 0.180 mmol) was added and heated to 100° C. overnight. The reaction was cooled, diluted with water (10 mL), and partitioned between brine and EtOAc. The aqueous layer was poured onto large SCX column, flushed with MeOH, then 1:1 MeOH:7N NEE in MeOH. The product containing fractions were concentrated and purified over silica gel (5-20% MeOH in DCM with NH₃) to afford 4-((2-((3S,4S)-4-amino-3-methyl-2-oxa-8-azaspiro[4.5]decan-8-yl)pyrido[2,3-b]pyrazin-6-yl)thio)-6,7-dihydro-5H-cyclopenta[b]pyridin-7-ol (11.0 mg, 0.024 mmol, 26% yield) as a yellow solid. $^1$H NMR (CDCl$_3$) δ 8.74 (s, 1H), 8.40 (d, J=5.1 Hz, 1H), 7.91 (d, J=8.8 Hz, 1H), 7.45 (d, J=8.8 Hz, 1H), 7.37 (d, J=5.3 Hz, 1H), 5.26 (t, J=6.6 Hz, 1H), 4.22 (m, 1H), 4.11 (m, 1H), 3.85 (d, J=8.8 Hz, 1H), 3.73 (d, H=8.8 Hz, 1H), 3.64 (m, 1H), 3.54 (m, 1H), 3.03 (d, J=4.6 Hz, 1H), 2.99 (ddd, 16.6, 9.0, 3.7 Hz, 1H), 2.75 (m, 1H), 2.56 (m, 1H), 2.04 (m, 1H), 1.95 (m, 1H), 1.85-1.71 (m, 3H), 1.27 (d, J=6.3 Hz, 3H). Mass spectrum: m/z=465.2 (M⁺H).

Example 158

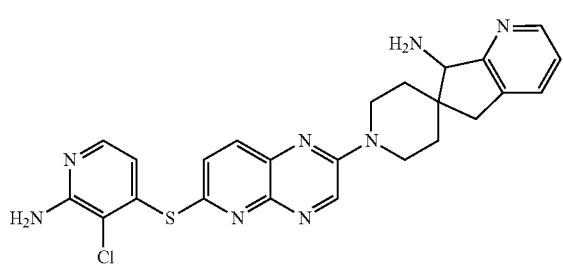 [SMILES: Nc1nccc(Sc2ccc3nc(N4CCC5(CC4)Cc4cccnc4C5N)cnc3n2)c1Cl]

1'-(6-((2-amino-3-chloropyridin-4-yl)thio)pyrido[2,3-b]pyrazin-2-yl)-5,7-dihydrospiro[cyclopenta[b]pyridine-6,4'-piperidin]-7-amine Step A: tert-butyl 7-oxo-5,7-dihydrospiro[cyclopenta[b]pyridine-6,4'-piperidine]-1'-carboxylate (500 mg, 1.65 mmol) was dissolved in MeOH (15 mL) and NaBH₄ (125 mg, 3.31 mmol) was added and stirred for 10 min. The reaction was quenched with aqueous NH₄Cl, extracted with EtOAc, dried over sodium sulfate, filtered and concentrated. The residue was purified over silica gel (20-100% EtOAc in hexanes) to afford tert-butyl 7-hydroxy-5,7-dihydrospiro[cyclopenta[b]pyridine-6,4'-piperidine]-1'-carboxylate (430 mg, 1.41 mmol, 85% yield) as a white solid.

Step B: tert-butyl 7-hydroxy-5,7-dihydrospiro[cyclopenta[b]pyridine-6,4'-piperidine]-1'-carboxylate (50 mg, 0.16 mmol) was dissolved in toluene (2 mL). Diphenyl phosphorazidate (70 µL, 0.33 mmol) was added, followed by dropwise addition of DBU (49 µL, 0.33 mmol). The reaction was heated to 100° C. overnight. The reaction was partitioned between saturated aqueous NaHCO₃ and EtOAc, dried over sodium sulfate, filtered and concentrated. The residue was purified over silica gel (20-100% EtOAc in hexanes) to afford tert-butyl 7-azido-5,7-dihydrospiro[cyclopenta[b]pyridine-6,4'-piperidine]-1'-carboxylate (46 mg, 0.14 mmol, 85% yield) as an oil.

Step C: tert-butyl 7-azido-5,7-dihydrospiro[cyclopenta[b]pyridine-6,4'-piperidine]-1'-carboxylate (46 mg, 0.14 mmol) was dissolved in DCM (1 mL) and TFA (0.5 mL) added. After 10 min, the reaction was concentrated to afford 7-azido-5,7-dihydrospiro[cyclopenta[b]pyridine-6,4'-piperidine] bis(2,2,2-trifluoroacetate) (64 mg, 0.140 mmol) as a crude material with was taken on to next reaction without further purification.

Step D: 6-chloropyrido[2,3-b]pyrazin-2-yl 4-nitrobenzenesulfonate (42.8 mg, 0.12 mmol) was dissolved in dioxane (1 mL) and 7-azido-5,7-dihydrospiro[cyclopenta[b]pyridine-6,4'-piperidine] bis(2,2,2-trifluoroacetate) (64 mg, 0.14 mmol) was added, followed by triethylamine (97.5 µL, 0.70 mmol). After stirring overnight, the resulting suspension was filtered through celite. The filtrate was purged with nitrogen and sodium 2-amino-3-chloropyridine-4-thiolate (42 mg, 0.23 mmol) was added and the reaction heated to 80° C. for 2 d. The reaction was concentrated and purified over silica gel (1-10% MeOH in DCM) to afford 4-((2-(7-azido-5,7-dihydrospiro[cyclopenta[b]pyridine-6,4'-piperidin]-1'-yl)pyrido[2,3-b]pyrazin-6-yl)thio)-3-chloropyridin-2-amine (26 mg, 0.05 mmol, 44% yield).

Step E: 4-((2-(7-azido-5,7-dihydrospiro[cyclopenta[b]pyridine-6,4'-piperidin]-1'-yl)pyrido[2,3-b]pyrazin-6-yl)thio)-3-chloropyridin-2-amine (26 mg, 0.05 mmol) was dissolved in MeOH/EtOAc (1:1, 3 mL). PPh₃ (excess) and water (0.3 mL) were added and stirred overnight. The reaction was filtered through celite, concentrated and purified over silica gel (2-20% MeOH in DCM with NH₃) to afford T-(6-((2-amino-3-chloropyridin-4-yl)thio)pyrido[2,3-b]pyrazin-2-yl)-5,7-dihydrospiro[cyclopenta[b]pyridine-6,4'-piperidin]-7-amine (4.0 mg, 0.0081 mmol, 16% yield) as a yellow solid. $^1$H NMR (CDCl$_3$) δ 8.76 (s, 1H), 8.43 (m, 1H), 7.91 (d, J=8.6 Hz, 1H), 7.84 (d, J=5.3 Hz, 1H), 7.54 (m, 1H), 7.50 (d, J=8.4 Hz, 1H), 7.13 (dd, J=7.6, 5.1 Hz, 1H), 6.69 (d, J=5.3 Hz, 1H), 4.93 (br s, 2H), 4.37 (m, 2H), 4.03 (s, 1H), 3.51-3.40 (m, 4H), 3.11 (d, J=15.8 Hz, 1H), 2.75 (d, J=15.8 Hz, 1H), 2.06 (m, 2H), 1.73 (m, 1H), 1.41 (m, 1H). Mass spectrum: m/z=491.1 (M⁺H).

Example 159

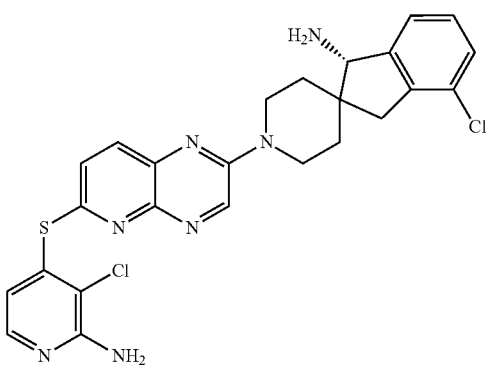 [SMILES: Nc1nccc(Sc2ccc3nc(N4CCC5(CC4)Cc4c(Cl)cccc4[C@H]5N)cnc3n2)c1Cl]

(S)-1'-(6-((2-amino-3-chloropyridin-4-yl)thio)pyrido[2,3-b]pyrazin-2-yl)-4-chloro-1,3-dihydrospiro[indene-2,4'-piperidin]-1-amine Step A: tert-butyl (S)-1-(((R)-tert-butylsulfinyl)amino)-4-chloro-1,3-dihydrospiro[indene-2,4'-piperidine]-1'-carboxylate (100 mg, 0.23 mmol) was dissolved in a few drops of DCM and then 4N HCl in dioxane (0.5 mL) was added and stirred for 30 min. The reaction was diluted with Et$_2$O (5 mL) and filtered. The tacky solid was dried in vacuum oven to afford (S)-4-chloro-1,3-dihydrospiro[indene-2,4'-piperidin]-1-amine dihydrochloride (70 mg, 99% yield).

Step B: (S)-4-chloro-1,3-dihydrospiro[indene-2,4'-piperidin]-1-amine dihydrochloride (35 mg, 0.113 mmol) was suspended in dioxane (1 mL) and 6-chloropyrido[2,3-b]pyrazin-2-yl trifluoromethanesulfonate (35.4 mg, 0.11 mmol) was added, followed by triethylamine (78.8 μL, 0.57 mmol). The reaction was heated to 50° C. for 20 min. Sodium 3-amino-2-chlorobenzenethiolate (24.6 mg, 0.136 mmol) was added and the reaction heated to 90° C. for 30 min. The reaction was cooled to RT, purged with nitrogen for 1 min, sodium 3-amino-2-chlorobenzenethiolate (24.6 mg, 0.14 mmol) was added and heated to 90° C. under nitrogen for 3 hr. The reaction was cooled and added directly to 12 g column (0-10% MeOH in EtOAc with 1% NH4OH) to afford (R)-1'-(6-((2-amino-3-chloropyridin-4-yl)thio)pyrido[2,3-b]pyrazin-2-yl)-4-chloro-1,3-dihydrospiro[indene-2,4'-piperidin]-1-amine (24.8 mg, 0.047 mmol, 42% yield) as a yellow solid. $^1$H NMR (CDCl$_3$) δ 8.76 (s, 1H), 7.92 (d, J=8.4 Hz, 1H), 7.83 (d, J=5.3 Hz, 1H), 7.50 (d, J=8.6 Hz, 1H), 7.25-7.17 (m, 3H), 6.69 (d, J=5.3 Hz, 1H), 4.97 (br s, 2H), 4.45 (m, 2H), 4.04 (s, 1H), 3.40 (m, 2H), 3.19 (d, J=16.2 Hz, 1H), 2.78 (d, J=16.2 Hz, 1H), 1.97-1.79 (m, 3H), 1.70 (m, 2H), 1.43 (m, 1H). Mass spectrum: m/z=524.1 (M$^+$H).

The following compounds in Table 5 were prepared according to the above procedures using appropriate starting materials and intermediates.

TABLE 5

| Ex. | Structure | Name | Prep | MS |
|---|---|---|---|---|
| 160 | 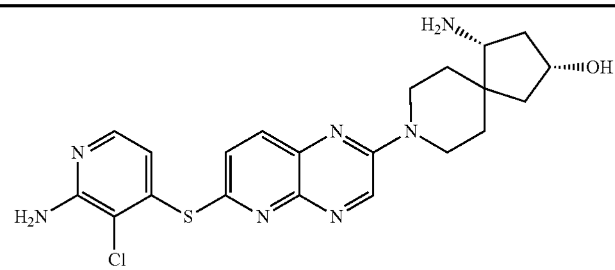 | (2R,4R)-4-amino-8-(6-((2-amino-3-chloropyridin-4-yl)thio)pyrido[2,3-b]pyrazin-2-yl)-8-azaspiro[4.5]decan-2-ol | Ex 76 | 458.2 |
| 161 | 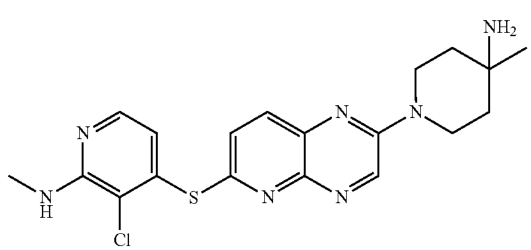 | 4-((2-(4-amino-4-methylpiperidin-1-yl)pyrido[2,3-b]pyrazin-6-yl)thio)-3-chloro-N-methylpyridin-2-amine | Ex 67 | 416.1 |
| 162 | 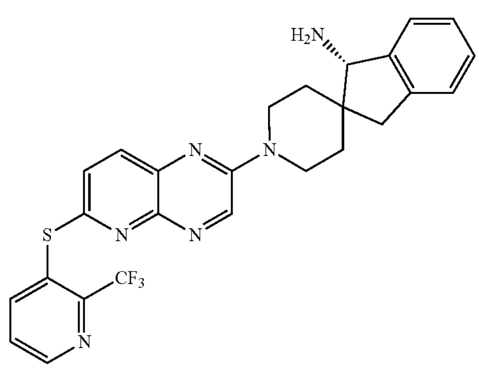 | (S)-1'-(6-((2-(trifluoromethyl)pyridin-3-yl)thio)pyrido[2,3-b]pyrazin-2-yl)-1,3-dihydrospiro[indene-2,4'-piperidin]-1-amine | Ex 13 | 509.2 |

TABLE 5-continued

| Ex. | Structure | Name | Prep | MS |
|---|---|---|---|---|
| 163 | 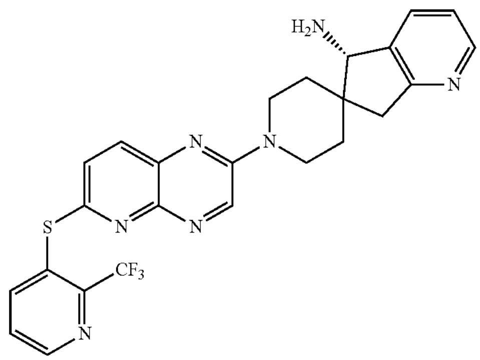 [SMILES: N[C@@H]1c2cccnc2CC12CCN(c1cnc3nc(Sc4cccnc4C(F)(F)F)ccc3n1)CC2] | (S)-1'-(6-((2-(trifluoromethyl)pyridin-3-yl)thio)pyrido[2,3-b]pyrazin-2-yl)-5,7-dihydrospiro[cyclopenta[b]pyridine-6,4'-piperidin]-5-amine | Ex 124 | 510.1 |
| 164 | 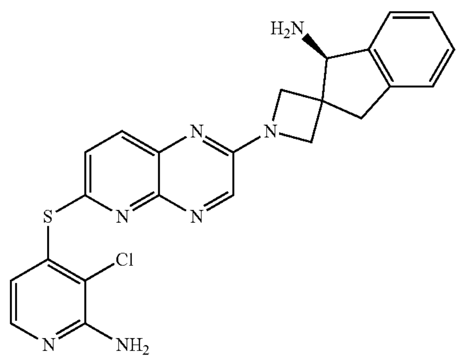 [SMILES: Nc1nccc(Sc2ccc3nc(N4CC5(Cc6ccccc6[C@@H]5N)C4)cnc3n2)c1Cl] | (S)-1-(6-((2-amino-3-chloropyridin-4-yl)thio)pyrido[2,3-b]pyrazin-2-yl)-1',3'-dihydrospiro[azetidine-3,2'-inden]-1'-amine | Ex 124 | 462.1 |
| 165 | 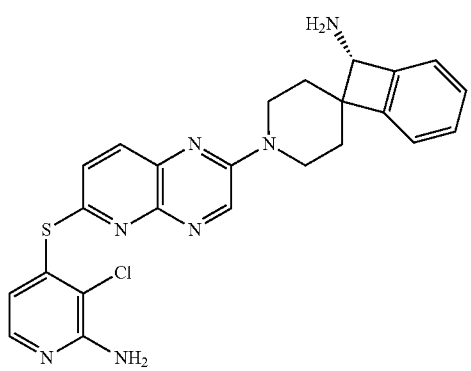 [SMILES: Nc1nccc(Sc2ccc3nc(N4CCC5(CC4)c4ccccc4[C@H]5N)cnc3n2)c1Cl] | (S)-1'-(6-((2-amino-3-chloropyridin-4-yl)thio)pyrido[2,3-b]pyrazin-2-yl)spiro[bicyclo[4.2.0]octane-7,4'-piperidine]-1(6),2,4-trien-8-amine | Ex 124 | 474.1 |
| 166 | 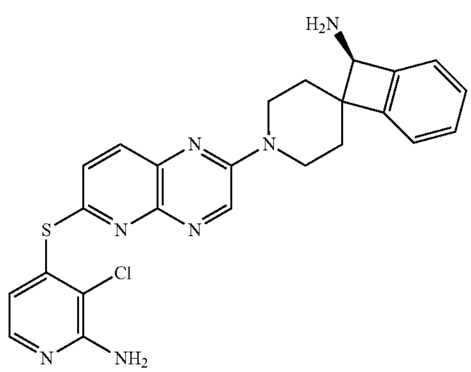 [SMILES: Nc1nccc(Sc2ccc3nc(N4CCC5(CC4)c4ccccc4[C@@H]5N)cnc3n2)c1Cl] | (R)-1'-(6-((2-amino-3-chloropyridin-4-yl)thio)pyrido[2,3-b]pyrazin-2-yl)spiro[bicyclo[4.2.0]octane-7,4'-piperidine]-1(6),2,4-trien-8-amine | Ex 124 | 474.1 |

TABLE 5-continued

| Ex. | Structure | Name | Prep | MS |
|---|---|---|---|---|
| 167 | 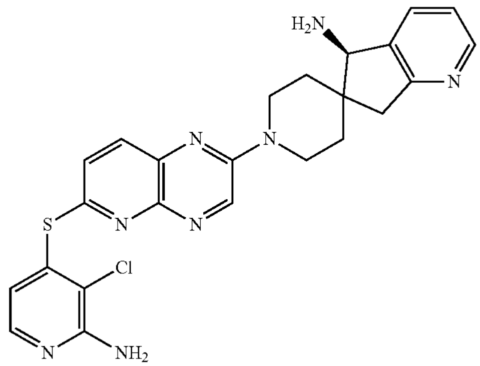 [SMILES: Nc1nccc(Sc2ccc3nc(N4CCC5(CC4)Cc4ncccc4[C@@H]5N)cnc3n2)c1Cl] | (R)-1'-(6-((2-amino-3-chloropyridin-4-yl)thio)pyrido[2,3-b]pyrazin-2-yl)-5,7-dihydrospiro[cyclopenta[b]pyridine-6,4'-piperidin]-5-amine | Ex 124 | 491.1 |
| 168 | 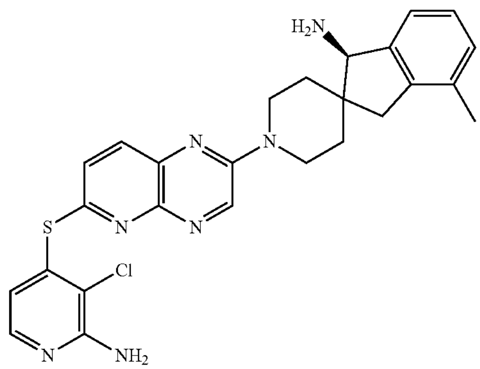 [SMILES: Cc1cccc2c1CC1(CCN(c3cnc4nc(Sc5ccnc(N)c5Cl)ccc4n3)CC1)[C@H]2N] | (R)-1'-(6-((2-amino-3-chloropyridin-4-yl)thio)pyrido[2,3-b]pyrazin-2-yl)-4-methyl-1,3-dihydrospiro[indene-2,4'-piperidin]-1-amine | Ex 126 | 504.1 |
| 169 | 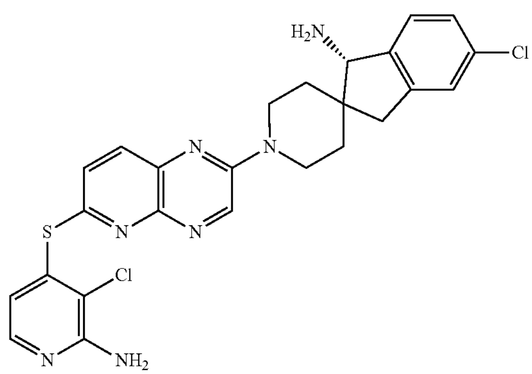 [SMILES: Nc1nccc(Sc2ccc3nc(N4CCC5(CC4)Cc4cc(Cl)ccc4[C@H]5N)cnc3n2)c1Cl] | (S)-1'-(6-((2-amino-3-chloropyridin-4-yl)thio)pyrido[2,3-b]pyrazin-2-yl)-5-chloro-1,3-dihydrospiro[indene-2,4'-piperidin]-1-amine | Ex 126 | 525.2 |
| 170 | 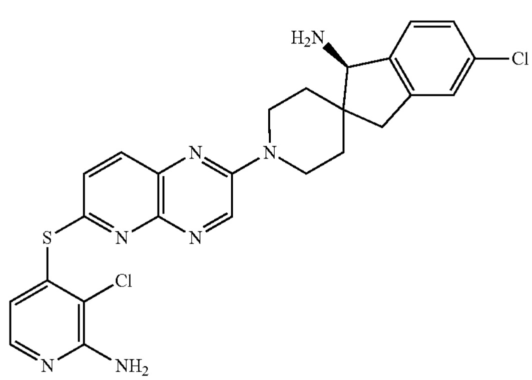 [SMILES: Nc1nccc(Sc2ccc3nc(N4CCC5(CC4)Cc4cc(Cl)ccc4[C@@H]5N)cnc3n2)c1Cl] | (R)-1'-(6-((2-amino-3-chloropyridin-4-yl)thio)pyrido[2,3-b]pyrazin-2-yl)-5-chloro-1,3-dihydrospiro[indene-2,4'-piperidin]-1-amine | Ex 126 | 525.2 |

TABLE 5-continued

| Ex. | Structure | Name | Prep | MS |
|---|---|---|---|---|
| 171 | 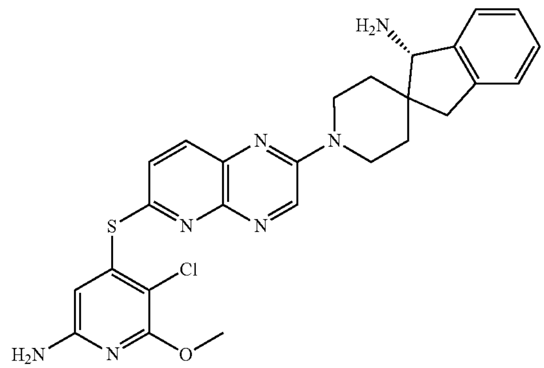 [SMILES: COc1nc(N)cc(Sc2ccc3nc(N4CCC5(CC4)Cc4ccccc4[C@H]5N)cnc3n2)c1Cl] | (S)-1'-(6-((6-amino-3-chloro-2-methoxypyridin-4-yl)thio)pyrido[2,3-b]pyrazin-2-yl)-1,3-dihydrospiro[indene-2,4'-piperidin]-1-amine | Ex 126 | 520.1 |
| 172 | 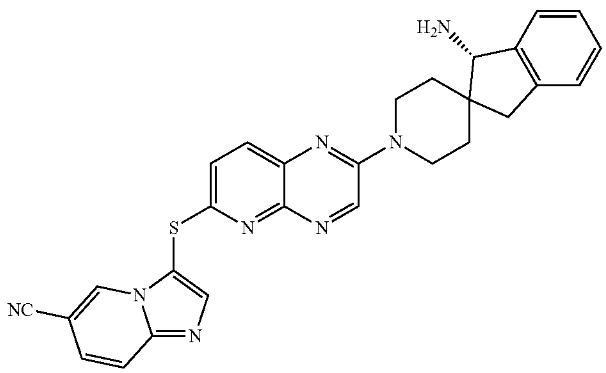 [SMILES: N#Cc1ccc2ncc(Sc3ccc4nc(N5CCC6(CC5)Cc5ccccc5[C@H]6N)cnc4n3)n2c1] | (S)-3-((2-(1-amino-1,3-dihydrospiro[indene-2,4'-piperidin]-1'-yl)pyrido[2,3-b]pyrazin-6-yl)thio)imidazo[1,2-a]pyridine-6-carbonitrile | Ex 127 | 505.2 |
| 173 | 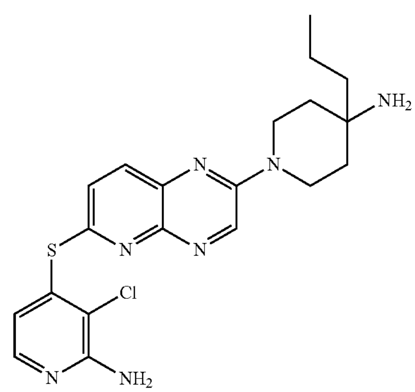 [SMILES: CCCC1(N)CCN(c2cnc3nc(Sc4ccnc(N)c4Cl)ccc3n2)CC1] | 4-((2-(4-amino-4-propylpiperidin-1-yl)pyrido[2,3-b]pyrazin-6-yl)thio)-3-chloropyridin-2-amine | Ex 130 | 430.1 |
| 174 | 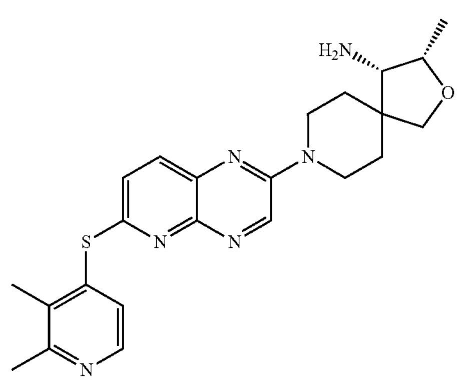 [SMILES: Cc1nccc(Sc2ccc3nc(N4CCC5(CC4)CO[C@@H](C)[C@H]5N)cnc3n2)c1C] | (3S,4S)-8-(6-((2,3-dimethylpyridin-4-yl)thio)pyrido[2,3-b]pyrazin-2-yl)-3-methyl-2-oxa-8-azaspiro[4.5]decan-4-amine | Ex 131 | 437.2 |

TABLE 5-continued

| Ex. | Structure | Name | Prep | MS |
|---|---|---|---|---|
| 175 | 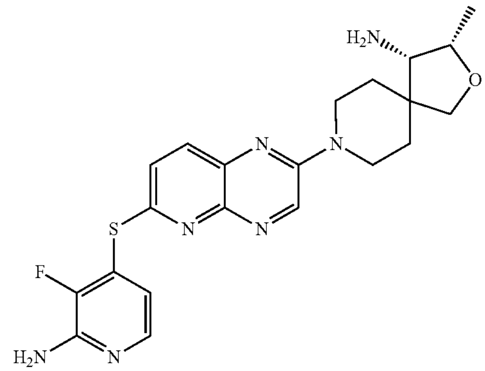 [SMILES: C[C@@H]1OCC2(CCN(c3cnc4nc(Sc5ccnc(N)c5F)ccc4n3)CC2)[C@@H]1N] | (3S,4S)-8-(6-((2-amino-3-fluoropyridin-4-yl)thio)pyrido[2,3-b]pyrazin-2-yl)-3-methyl-2-oxa-8-azaspiro[4.5]decan-4-amine | Ex 131 | 442.2 |
| 176 | 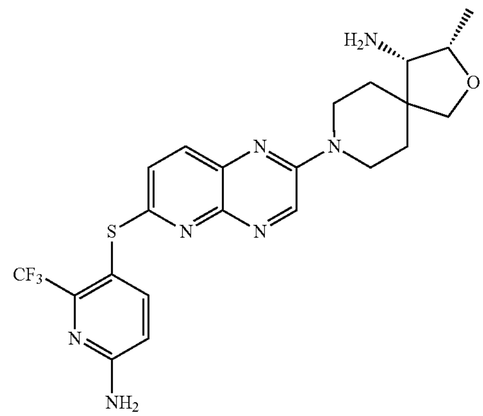 [SMILES: C[C@@H]1OCC2(CCN(c3cnc4nc(Sc5ccc(N)nc5C(F)(F)F)ccc4n3)CC2)[C@@H]1N] | (3S,4S)-8-(6-((6-amino-2-(trifluoromethyl)pyridin-3-yl)thio)pyrido[2,3-b]pyrazin-2-yl)-3-methyl-2-oxa-8-azaspiro[4.5]decan-4-amine | Ex 131 | 492.2 |
| 177 | 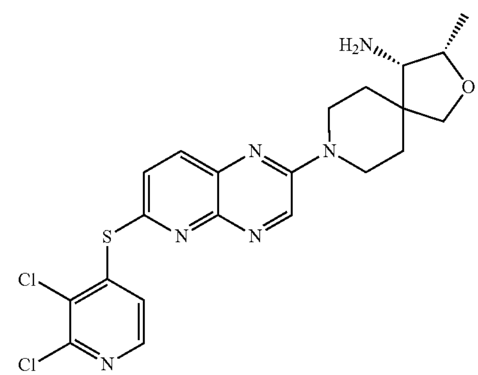 [SMILES: C[C@@H]1OCC2(CCN(c3cnc4nc(Sc5ccnc(Cl)c5Cl)ccc4n3)CC2)[C@@H]1N] | (3S,4S)-8-(6-((2,3-dichloropyridin-4-yl)thio)pyrido[2,3-b]pyrazin-2-yl)-3-methyl-2-oxa-8-azaspiro[4.5]decan-4-amine | Ex 131 | 477.1 |
| 178 | 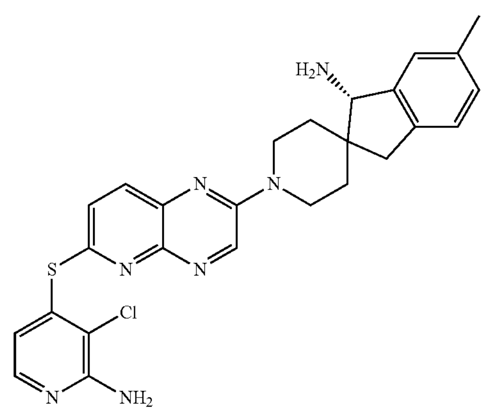 [SMILES: Cc1ccc2c(c1)[C@@H](N)C1(CCN(c3cnc4nc(Sc5ccnc(N)c5Cl)ccc4n3)CC1)C2] | (S)-1'-(6-((2-amino-3-chloropyridin-4-yl)thio)pyrido[2,3-b]pyrazin-2-yl)-6-methyl-1,3-dihydrospiro[indene-2,4'-piperidin]-1-amine | Ex 133 | 504.1 |

TABLE 5-continued

| Ex. | Structure | Name | Prep | MS |
|---|---|---|---|---|
| 179 | 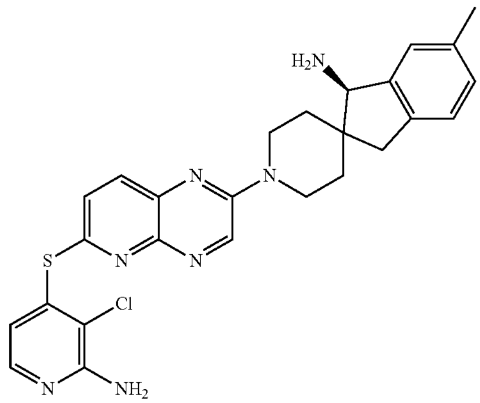 [SMILES: Cc1ccc2c(c1)[C@H](N)C1(CCN(c3cnc4nc(Sc5ccnc(N)c5Cl)ccc4n3)CC1)C2] | (R)-1'-(6-((2-amino-3-chloropyridin-4-yl)thio)pyrido[2,3-b]pyrazin-2-yl)-6-methyl-1,3-dihydrospiro[indene-2,4'-piperidin]-1-amine | Ex 133 | 504.1 |
| 180 | 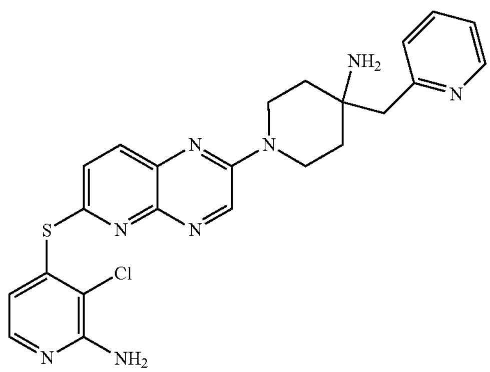 [SMILES: Nc1nccc(Sc2ccc3nc(N4CCC(N)(Cc5ccccn5)CC4)cnc3n2)c1Cl] | 4-((2-(4-amino-4-(pyridin-2-ylmethyl)piperidin-1-yl)pyrido[2,3-b]pyrazin-6-yl)thio)-3-chloropyridin-2-amine | Ex 121 | 479.2 |
| 181 | 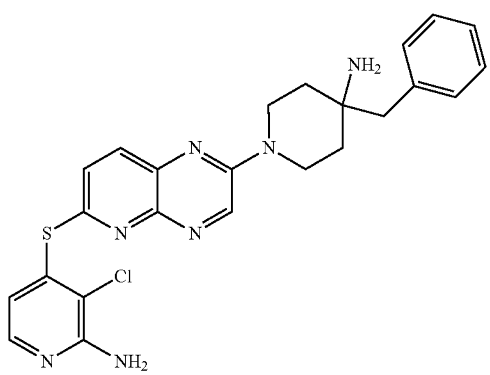 [SMILES: Nc1nccc(Sc2ccc3nc(N4CCC(N)(Cc5ccccc5)CC4)cnc3n2)c1Cl] | 4-((2-(4-amino-4-benzylpiperidin-1-yl)pyrido[2,3-b]pyrazin-6-yl)thio)-3-chloropyridin-2-amine | Ex 121 | 478.2 |
| 182 | 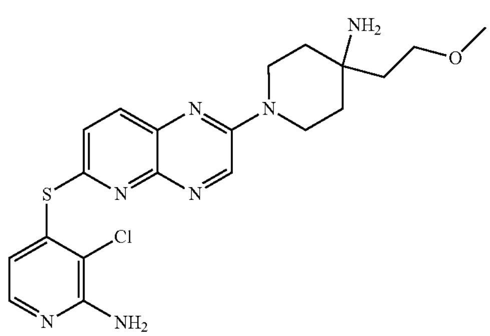 [SMILES: COCCC1(N)CCN(c2cnc3nc(Sc4ccnc(N)c4Cl)ccc3n2)CC1] | 4-((2-(4-amino-4-(2-methoxyethyl)piperidin-1-yl)pyrido[2,3-b]pyrazin-6-yl)thio)-3-chloropyridin-2-amine | Ex 121 | 446.2 |

TABLE 5-continued

| Ex. | Structure | Name | Prep | MS |
|---|---|---|---|---|
| 183 | 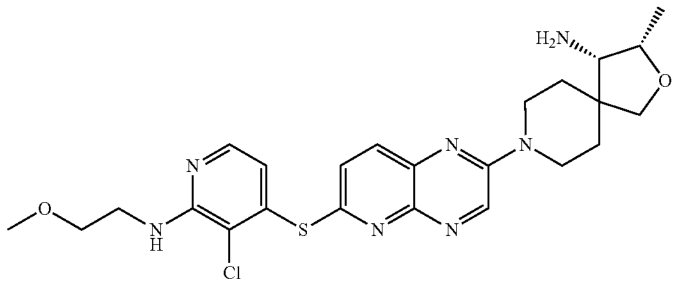 [SMILES: COCCNc1nccc(Sc2ccc3nc(N4CCC5(CC4)CO[C@@H](C)[C@H]5N)cnc3n2)c1Cl] | (3S,4S)-8-(6-((3-chloro-2-((2-methoxyethyl)amino)pyridin-4-yl)thio)pyrido[2,3-b]pyrazin-2-yl)-3-methyl-2-oxa-8-azaspiro[4.5]decan-4-amine | Ex 13 | 517.2 |
| 184 | 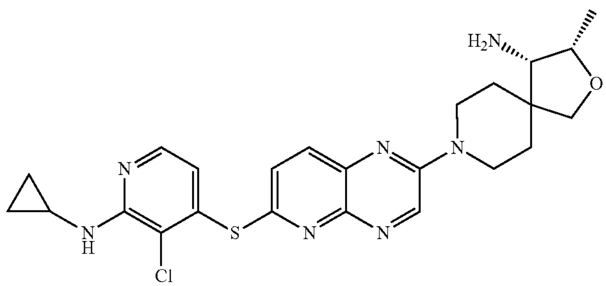 [SMILES: C[C@@H]1OCC2(CCN(c3cnc4nc(Sc5ccnc(NC6CC6)c5Cl)ccc4n3)CC2)[C@@H]1N] | (3S,4S)-8-(6-((3-chloro-2-(cyclopropylamino)pyridin-4-yl)thio)pyrido[2,3-b]pyrazin-2-yl)-3-methyl-2-oxa-8-azaspiro[4.5]decan-4-amine | Ex 13 | 498.2 |
| 185 | 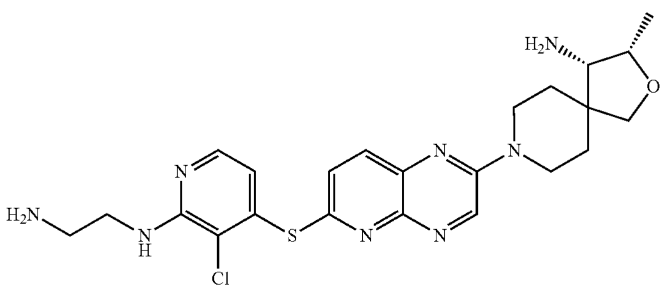 [SMILES: C[C@@H]1OCC2(CCN(c3cnc4nc(Sc5ccnc(NCCN)c5Cl)ccc4n3)CC2)[C@@H]1N] | 2-((4-((2-((3S,4S)-4-amino-3-methyl-2-oxa-8-azaspiro[4.5]decan-8-yl)pyrido[2,3-b]pyrazin-6-yl)thio)-3-chloropyridin-2-yl)amino)ethan-1-ol | Ex 13 | 502.2 |
| 186 | 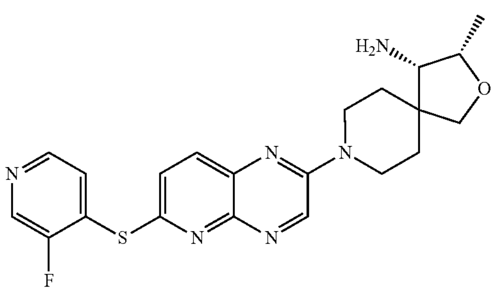 [SMILES: C[C@@H]1OCC2(CCN(c3cnc4nc(Sc5ccncc5F)ccc4n3)CC2)[C@@H]1N] | (3S,4S)-8-(6-((3-fluoropyridin-4-yl)thio)pyrido[2,3-b]pyrazin-2-yl)-3-methyl-2-oxa-8-azaspiro[4.5]decan-4-amine | Ex 13 | 427.2 |
| 187 | 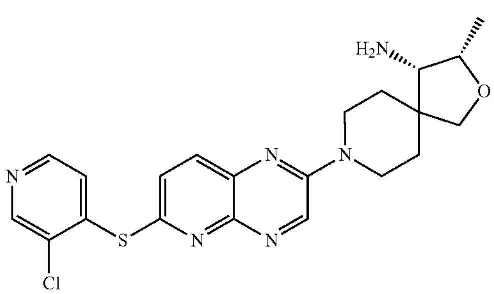 [SMILES: C[C@@H]1OCC2(CCN(c3cnc4nc(Sc5ccncc5Cl)ccc4n3)CC2)[C@@H]1N] | (3S,4S)-8-(6-((3-chloropyridin-4-yl)thio)pyrido[2,3-b]pyrazin-2-yl)-3-methyl-2-oxa-8-azaspiro[4.5]decan-4-amine | Ex 13 | 443.1 |

TABLE 5-continued

| Ex. | Structure | Name | Prep | MS |
|---|---|---|---|---|
| 188 | 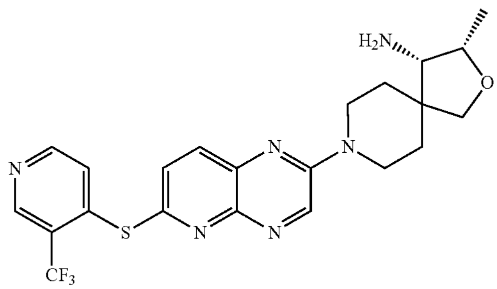 [SMILES: C[C@@H]1OCC2(CCN(c3cnc4nc(Sc5ccncc5C(F)(F)F)ccc4n3)CC2)[C@@H]1N] | (3S,4S)-3-methyl-8-(6-((3-(trifluoromethyl)pyridin-4-yl)thio)pyrido[2,3-b]pyrazin-2-yl)-2-oxa-8-azaspiro[4.5]decan-4-amine | Ex 13 | 477.2 |
| 189 | 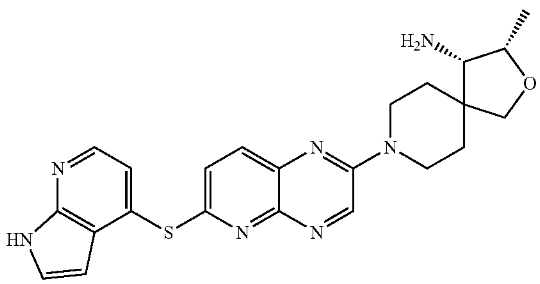 [SMILES: C[C@@H]1OCC2(CCN(c3cnc4nc(Sc5ccnc6[nH]ccc56)ccc4n3)CC2)[C@@H]1N] | (3S,4S)-8-(6-((1H-pyrrolo[2,3-b]pyridin-4-yl)thio)pyrido[2,3-b]pyrazin-2-yl)-3-methyl-2-oxa-8-azaspiro[4.5]decan-4-amine | Ex 13 | 448.2 |
| 190 | 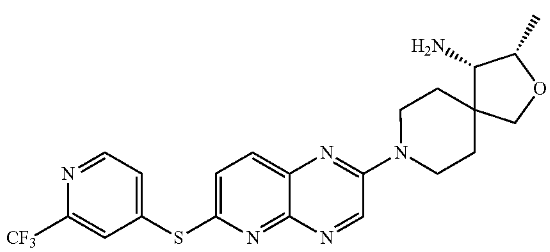 [SMILES: C[C@@H]1OCC2(CCN(c3cnc4nc(Sc5ccnc(C(F)(F)F)c5)ccc4n3)CC2)[C@@H]1N] | (3S,4S)-3-methyl-8-(6-((2-(trifluoromethyl)pyridin-4-yl)thio)pyrido[2,3-b]pyrazin-2-yl)-2-oxa-8-azaspiro[4.5]decan-4-amine | Ex 13 | 477.2 |
| 191 | 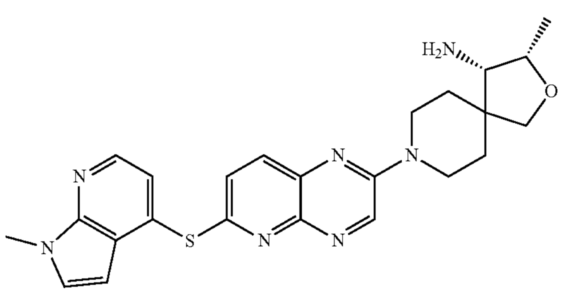 [SMILES: C[C@@H]1OCC2(CCN(c3cnc4nc(Sc5ccnc6c5ccn6C)ccc4n3)CC2)[C@@H]1N] | (3S,4S)-3-methyl-8-(6-((1-methyl-1H-pyrrolo[2,3-b]pyridin-4-yl)thio)pyrido[2,3-b]pyrazin-2-yl)-2-oxa-8-azaspiro[4.5]decan-4-amine | Ex 13 | 462.2 |
| 192 | 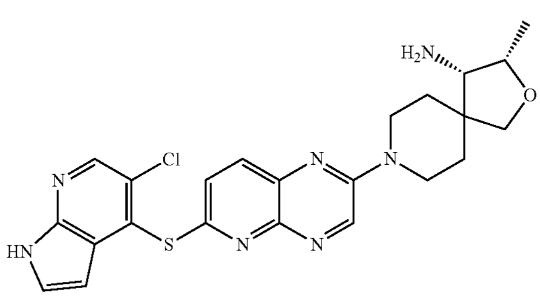 [SMILES: C[C@@H]1OCC2(CCN(c3cnc4nc(Sc5c(Cl)cnc6[nH]ccc56)ccc4n3)CC2)[C@@H]1N] | (3S,4S)-8-(6-((5-chloro-1H-pyrrolo[2,3-b]pyridin-4-yl)thio)pyrido[2,3-b]pyrazin-2-yl)-3-methyl-2-oxa-8-azaspiro[4.5]decan-4-amine | Ex 13 | 482.1 |

TABLE 5-continued

| Ex. | Structure | Name | Prep | MS |
|---|---|---|---|---|
| 193 | 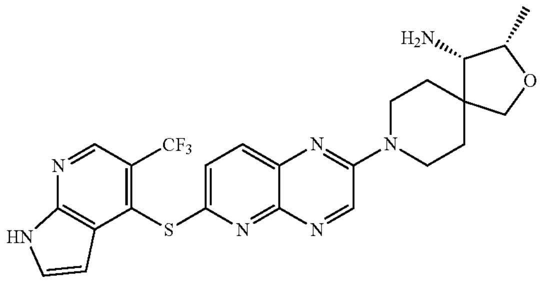 [SMILES: C[C@@H]1OCC2(CCN(c3cnc4nc(Sc5c(C(F)(F)F)cnc6[nH]ccc56)ccc4n3)CC2)[C@@H]1N] | (3S,4S)-3-methyl-8-(6-((5-(trifluoromethyl)-1H-pyrrolo[2,3-b]pyridin-4-yl)thio)pyrido[2,3-b]pyrazin-2-yl)-2-oxa-8-azaspiro[4.5]decan-4-amine | Ex 13 | 516.2 |
| 194 | 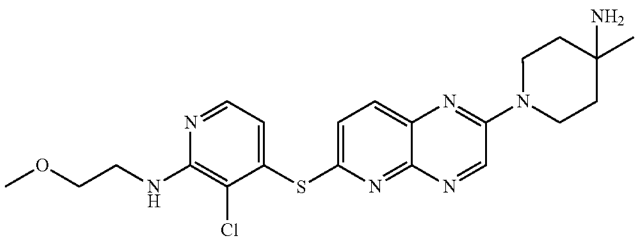 | 4-((2-(4-amino-4-methylpiperidin-1-yl)pyrido[2,3-b]pyrazin-6-yl)thio)-3-chloro-N-(2-methoxyethyl)pyridin-2-amine | Ex 134 | 460.2 |
| 195 | 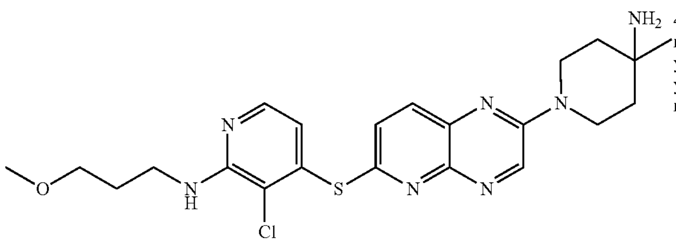 | 4-((2-(4-amino-4-methylpiperidin-1-yl)pyrido[2,3-b]pyrazin-6-yl)thio)-3-chloro-N-(3-methoxypropyl)pyridin-2-amine | Ex 134 | 474.2 |
| 196 | 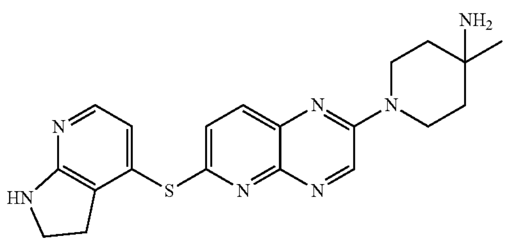 [SMILES: CC1(N)CCN(c2cnc3nc(Sc4ccnc5c4CCN5)ccc3n2)CC1] | 1-(6-((2,3-dihydro-1H-pyrrolo[2,3-b]pyridin-4-yl)thio)pyrido[2,3-b]pyrazin-2-yl)-4-methylpiperidin-4-amine | Ex 134 | 394.2 |
| 197 | 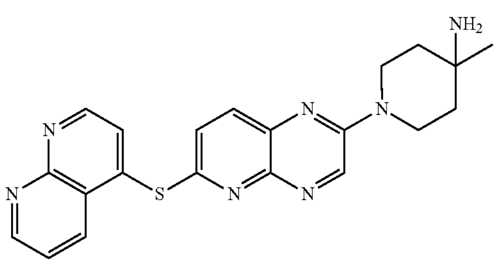 [SMILES: CC1(N)CCN(c2cnc3nc(Sc4ccnc5ncccc45)ccc3n2)CC1] | 1-(6-((1,8-naphthyridin-4-yl)thio)pyrido[2,3-b]pyrazin-2-yl)-4-methylpiperidin-4-amine | Ex 134 | 404.2 |
| 198 | 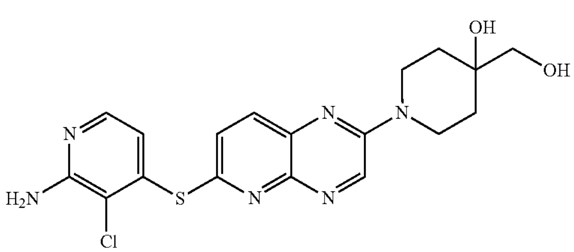 [SMILES: Nc1nccc(Sc2ccc3nc(N4CCC(O)(CO)CC4)cnc3n2)c1Cl] | 1-(6-((2-amino-3-chloropyridin-4-yl)thio)pyrido[2,3-b]pyrazin-2-yl)-4-(hydroxymethyl)piperidin-4-ol | Ex 137 | 419.1 |

TABLE 5-continued

| Ex. | Structure | Name | Prep | MS |
|---|---|---|---|---|
| 199 | 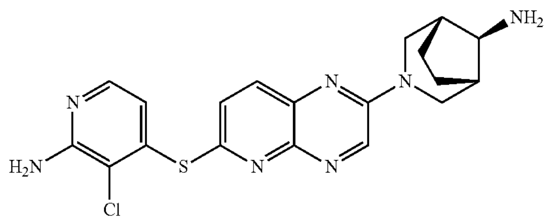 [SMILES: Nc1nccc(Sc2ccc3nc(N4C[C@H]5CC[C@@H](C4)[C@@H]5N)cnc3n2)c1Cl] | (1R,5S,8s)-3-(6-((2-amino-3-chloropyridin-4-yl)thio)pyrido[2,3-b]pyrazin-2-yl)-3-azabicyclo[3.2.1]octan-8-amine | Ex 137 | 414.1 |
| 200 | 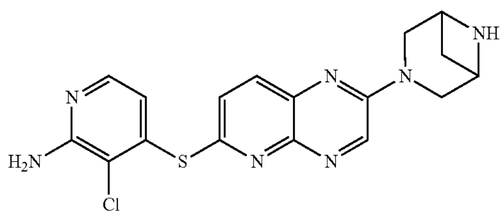 [SMILES: Nc1nccc(Sc2ccc3nc(N4CC5CC(C4)N5)cnc3n2)c1Cl] | 4-((2-(3,6-diazabicyclo[3.1.1]heptan-3-yl)pyrido[2,3-b]pyrazin-6-yl)thio)-3-chloropyridin-2-amine | Ex 137 | 386.1 |
| 201 | 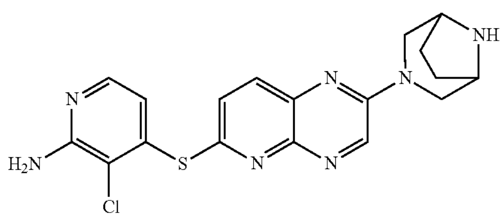 [SMILES: Nc1nccc(Sc2ccc3nc(N4CC5CCC(C4)N5)cnc3n2)c1Cl] | 4-((2-(3,8-diazabicyclo[3.2.1]octan-3-yl)pyrido[2,3-b]pyrazin-6-yl)thio)-3-chloropyridin-2-amine | Ex 137 | 400.1 |
| 202 | 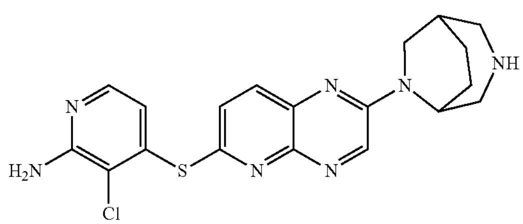 [SMILES: Nc1nccc(Sc2ccc3nc(N4CC5CCC4CNC5)cnc3n2)c1Cl] | 4-((2-(3,6-diazabicyclo[3.2.2]nonan-6-yl)pyrido[2,3-b]pyrazin-6-yl)thio)-3-chloropyridin-2-amine | Ex 137 | 414.2 |
| 203 | 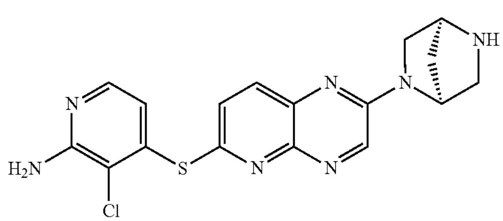 [SMILES: Nc1nccc(Sc2ccc3nc(N4C[C@@H]5C[C@H]4CN5)cnc3n2)c1Cl] | 4-((2-((1S,4S)-2,5-diazabicyclo[2.2.1]heptan-2-yl)pyrido[2,3-b]pyrazin-6-yl)thio)-3-chloropyridin-2-amine | Ex 137 | 386.1 |
| 204 | 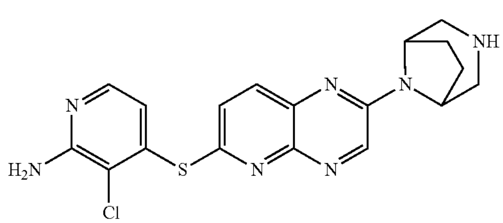 [SMILES: Nc1nccc(Sc2ccc3nc(N4C5CCC4CNC5)cnc3n2)c1Cl] | 4-((2-(3,8-diazabicyclo[3.2.1]octan-8-yl)pyrido[2,3-b]pyrazin-6-yl)thio)-3-chloropyridin-2-amine | Ex 137 | 400.2 |
| 205 | 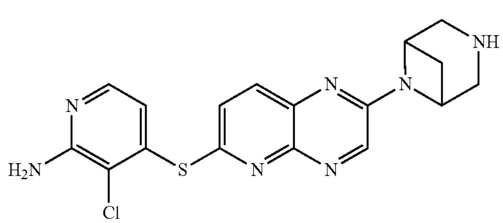 [SMILES: Nc1nccc(Sc2ccc3nc(N4C5CNCC4C5)cnc3n2)c1Cl] | 4-((2-(3,8-diazabicyclo[3.2.1]octan-8-yl)pyrido[2,3-b]pyrazin-6-yl)thio)-3-chloropyridin-2-amine | Ex 137 | 386.1 |

TABLE 5-continued

| Ex. | Structure | Name | Prep | MS |
|---|---|---|---|---|
| 206 | 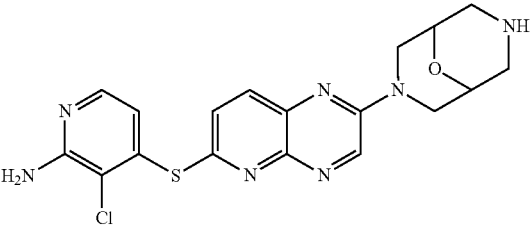 [SMILES: Nc1nccc(Sc2ccc3nc(N4CC5CNCC(C4)O5)cnc3n2)c1Cl] | 4-((2-(9-oxa-3,7-diazabicyclo[3.3.1]nonan-3-yl)pyrido[2,3-b]pyrazin-6-yl)thio)-3-chloropyridin-2-amine | Ex 137 | 416.1 |
| 207 | 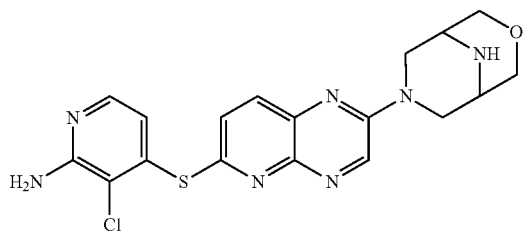 [SMILES: Nc1nccc(Sc2ccc3nc(N4CC5COCC(C4)N5)cnc3n2)c1Cl] | 4-((2-(3-oxa-7,9-diazabicyclo[3.3.1]nonan-7-yl)pyrido[2,3-b]pyrazin-6-yl)thio)-3-chloropyridin-2-amine | Ex 137 | 416.1 |
| 208 | 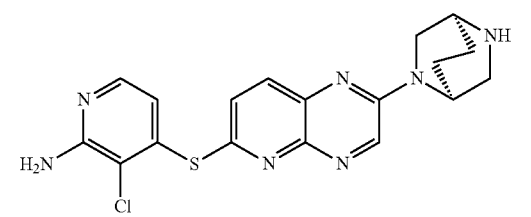 [SMILES: Nc1nccc(Sc2ccc3nc(N4C[C@@H]5CC[C@H]4CN5)cnc3n2)c1Cl] | 4-((2-((1S,4S)-2,5-diazabicyclo[2.2.2]octan-2-yl)pyrido[2,3-b]pyrazin-6-yl)thio)-3-chloropyridin-2-amine | Ex 137 | 400.1 |
| 209 | 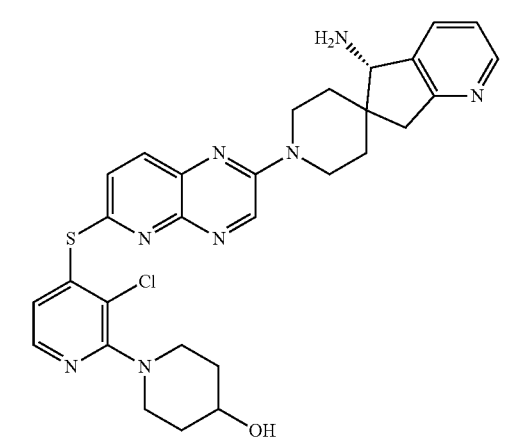 [SMILES: N[C@@H]1c2cccnc2CC12CCN(c1cnc3nc(Sc4ccnc(N5CCC(O)CC5)c4Cl)ccc3n1)CC2] | (S)-1-(4-((2-(5-amino-5,7-dihydrospiro[cyclopenta[b]pyridine-6,4'-piperidin]-1'-yl)pyrido[2,3-b]pyrazin-6-yl)thio)-3-chloropyridin-2-yl)piperidin-4-ol | | 575.2 |
| 210 | 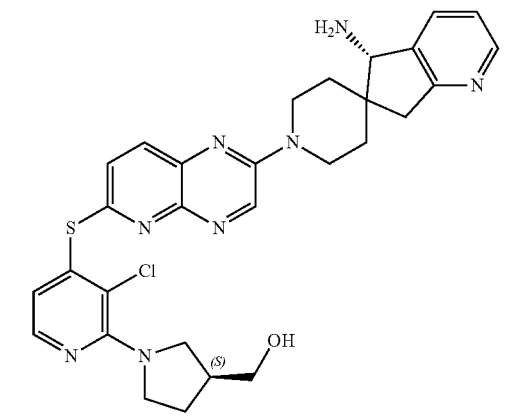 | ((S)-1-(4-((2-((S)-5-amino-5,7-dihydrospiro[cyclopenta[b]pyridine-6,4'-piperidin]-1'-yl)pyrido[2,3-b]pyrazin-6-yl)thio)-3-chloropyridin-2-yl)pyrrolidin-3-yl)methanol | | 575.2 |

TABLE 5-continued

| Ex. | Structure | Name | Prep | MS |
|---|---|---|---|---|
| 211 | 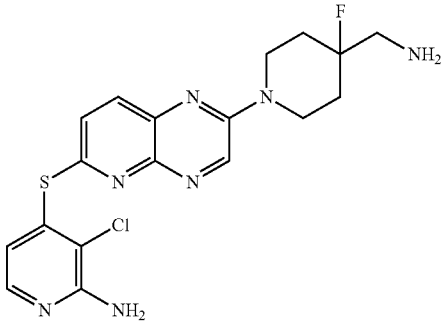 [SMILES: NCC1(F)CCN(c2cnc3nc(Sc4ccnc(N)c4Cl)ccc3n2)CC1] | 4-((2-(4-(aminomethyl)-4-fluoropiperidin-1-yl)pyrido[2,3-b]pyrazin-6-yl)thio)-3-chloropyridin-2-amine | Ex 12 | 420.1 |
| 212 | 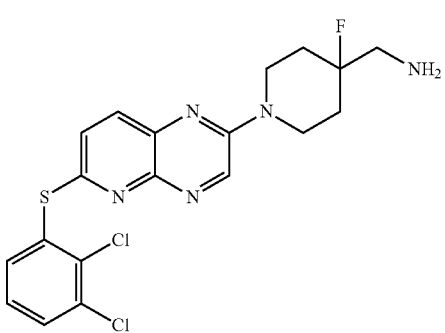 [SMILES: NCC1(F)CCN(c2cnc3nc(Sc4cccc(Cl)c4Cl)ccc3n2)CC1] | (1-(6-((2,3-dichlorophenyl)thio)pyrido[2,3-b]pyrazin-2-yl)-4-fluoropiperidin-4-yl)methanamine | Ex 12 | 438.1 |
| 213 | 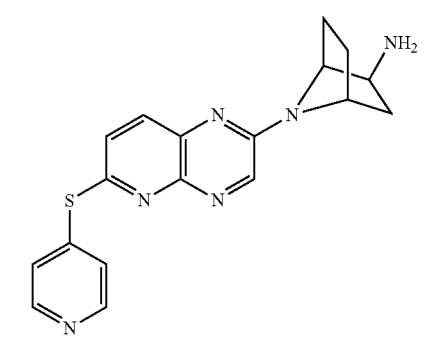 [SMILES: NC1CC2CCC1N2c1cnc2nc(Sc3ccncc3)ccc2n1] | (1S,2S,4R)-7-(6-((2-amino-3-chloropyridin-4-yl)thio)pyrido[2,3-b]pyrazin-2-yl)-7-azabicyclo[2.2.1]heptan-2-amine | Ex. '4346 | 400.1 |
| 214 | 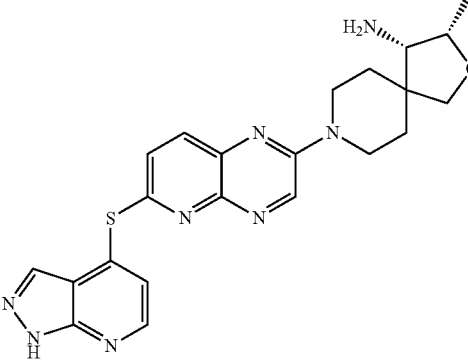 | (3S,4S)-8-(6-((1H-pyrazolo[3,4-b]pyridin-4-yl)thio)pyrido[2,3-b]pyrazin-2-yl)-3-methyl-2-oxa-8-azaspiro[4.5]decan-4-amine | Ex 153 | 449.2 |

TABLE 5-continued

| Ex. | Structure | Name | Prep | MS |
|---|---|---|---|---|
| 215 | 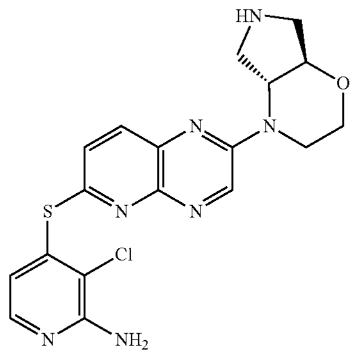 [SMILES: Nc1nccc(Sc2ccc3nc(N4CCO[C@@H]5CNC[C@H]54)cnc3n2)c1Cl] | 3-chloro-4-((2-((4aR,7aR)-hexahydropyrrolo[3,4-b][1,4]oxazin-4(4aH)-yl)pyrido[2,3-b]pyrazin-6-yl)thio)235yridine-2-amine | Ex 154 | 416.1 |
| 216 | 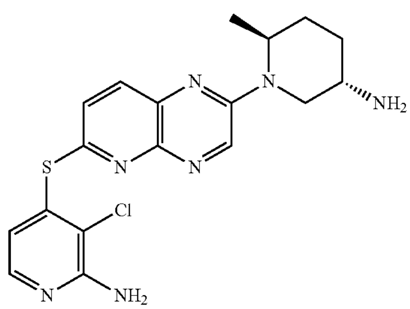 [SMILES: C[C@H]1CC[C@H](N)CN1c1cnc2nc(Sc3ccnc(N)c3Cl)ccc2n1] | 4-((2-((2S,5S)-5-amino-2-methylpiperidin-1-yl)pyrido[2,3-b]pyrazin-6-yl)thio)-3-chloropyridin-2-amine | Ex 154 | 402.2 |
| 217 | 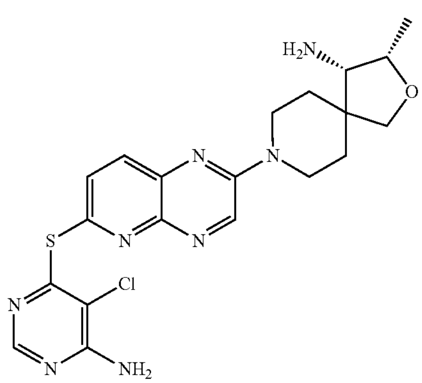 [SMILES: C[C@@H]1OCC2(CCN(c3cnc4nc(Sc5ncnc(N)c5Cl)ccc4n3)CC2)[C@@H]1N] | (3S,4S)-8-(6-((6-amino-5-chloropyrimidin-4-yl)thio)pyrido[2,3-b]pyrazin-2-yl)-3-methyl-2-oxa-8-azaspiro[4.5]decan-4-amine | Ex 90 | 459.2 |
| 218 | 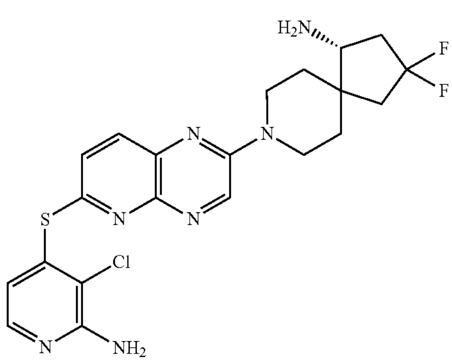 [SMILES: Nc1nccc(Sc2ccc3nc(N4CCC5(CC4)CC(F)(F)C[C@H]5N)cnc3n2)c1Cl] | 8-(6-((2-amino-3-chloropyridin-4-yl)thio)pyrido[2,3-b]pyrazin-2-yl)-3,3-difluoro-8-azaspiro[4.5]decan-1-amine | Ex 13 | 478.1 |

TABLE 5-continued

| Ex. | Structure | Name | Prep | MS |
|---|---|---|---|---|
| 219 | 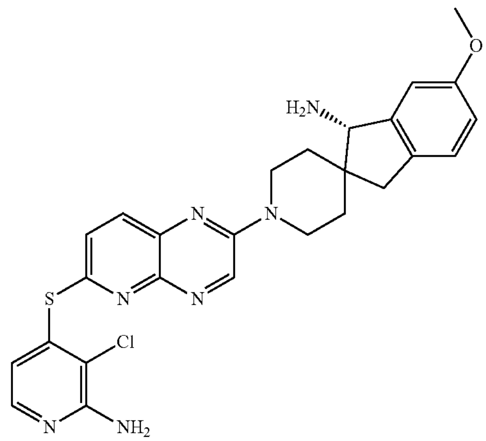 [SMILES: COc1ccc2c(c1)[C@@H](N)C1(CCN(c3cnc4nc(Sc5ccnc(N)c5Cl)ccc4n3)CC1)C2] | (S)-1'-(6-((2-amino-3-chloropyridin-4-yl)thio)pyrido[2,3-b]pyrazin-2-yl)-6-methoxy-1,3-dihydrospiro[indene-2,4'-piperidin]-1-amine | Ex. '4972 | 520.2 |
| 220 | 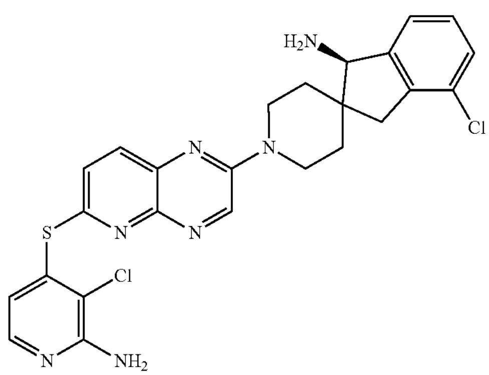 [SMILES: Nc1nccc(Sc2ccc3nc(N4CCC5(CC4)Cc4c(Cl)cccc4[C@@H]5N)cnc3n2)c1Cl] | (R)-1'-(6-((2-amino-3-chloropyridin-4-yl)thio)pyrido[2,3-b]pyrazin-2-yl)-4-chloro-1,3-dihydrospiro[indene-2,4'-piperidin]-1-amine | Ex 159 | 524.1 |
| 221 | 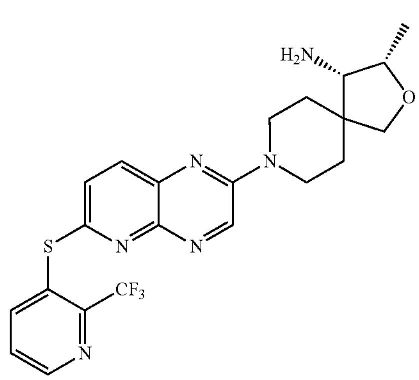 [SMILES: C[C@@H]1OCC2(CCN(c3cnc4nc(Sc5cccnc5C(F)(F)F)ccc4n3)CC2)[C@@H]1N] | (3S,4S)-3-methyl-8-(6-((2-(trifluoromethyl)pyridin-3-yl)thio)pyrido[2,3-b]pyrazin-2-yl)-2-oxa-8-azaspiro[4.5]decan-4-amine | Ex 13 | 477.2 |

It will be understood that the enumerated embodiments are not intended to limit the invention to those embodiments. On the contrary, the invention is intended to cover all alternatives, modifications and equivalents, which may be included within the scope of the present invention as defined by the claims. Thus, the foregoing description is considered as illustrative only of the principles of the invention.

What is claimed is:

1. A compound selected from Formula Ia:

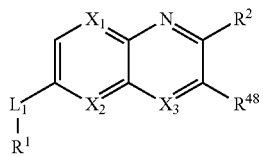

or a stereoisomer, tautomer, or pharmaceutically acceptable salt thereof, wherein:

$X_1$ is selected from CH and N;
$X_2$ is selected from CH and N;
$X_3$ is selected from CH and N;
$L_1$ is S;
$R^1$ is selected from phenyl, heteroaryl, bicyclic aryl, bicyclic heterocyclyl, and bicyclic heteroaryl,
wherein the phenyl, heteroaryl, bicyclic aryl, bicyclic heterocyclyl and bicyclic heteroaryl are optionally substituted with one or more groups selected from the group consisting of halogen, OH, oxo, cyano, alkyl optionally substituted with halogen, cyano or OH, —O(alkyl) optionally substituted with halogen, cyano or OH, $NHR^a$, and a heterocycle optionally substituted with halogen, cyano, OH or alkyl optionally substituted with OH or oxo;
$R^2$ is:

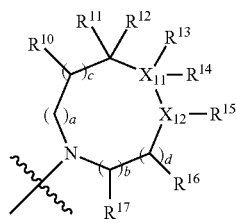

$X_{11}$ is selected from $CR^{13}R^{14}$, $SiR^{13}R^{14}$, NH and O;
$X_{12}$ is selected from $CHR^{15}$ and NH, wherein one or both of $X_{11}$ and $X_{12}$ must be carbon;
$R^{10}$ is selected from hydrogen and alkyl;
$R^{11}$ is selected from hydrogen, OH and $CH_2NH_2$;
$R^{12}$, $R^{16}$ and $R^{17}$ are hydrogen;
$R^{13}$ is selected from hydrogen, OH, and ($C_0$-$C_3$ alkyl) $NR^bR^c$;
$R^{14}$ is selected from hydrogen, OH, alkyl optionally substituted with halogen, OH, methyl, $OCH_3$ and a heteroaryl;
$R^{15}$ is selected from hydrogen or $NH_2$;
or one of the following groups may join together:
$R^{10}$ and $R^{11}$ may join together as $CH_2NHCH_2$ to form a fused bicyclic,
$R^{10}$ and $R^{15}$ may join together as alkyl to form a bridged bicyclic,
$R^{11}$ and $R^{12}$ may join together as alkyl substituted with $NH_2$ to form a spirocycle,
$R^{13}$ and $R^{14}$ may join together as a group selected from cycloalkyl, heterocycle, bicyclic carbocycle, and bicyclic heterocycle, wherein the cycloalkyl, heterocycle, carbocycle and heterocycle are optionally substituted with F, Cl, OH, $OCH_3$, CN, methyl or $NH_2$ to form a spirocycle, $R^{10}$ and $R^{16}$ may join together as alkyl, O or NH to form a bridged bicyclic,
$R^{11}$ and $R^{15}$ may join together as alkyl to form a bridged bicyclic,
$R^{11}$ and $R^{16}$ may join together as alkyl or O to form a bridged bicyclic,
$R^{11}$ and $R^{17}$ may join together as alkyl to form a bridged bicyclic, or
$R^{13}$ and $R^{15}$ may join together as $NHCH_2$, or cycloalkyl wherein the cycloalkyl is substituted with $NH_2$ to form a fused bicyclic;
$R^{48}$ is selected from hydrogen and methyl;
$R^a$ is hydrogen, alkyl optionally substituted with OH, methoxy, halogen or cyano, or cyclopropyl;
$R^b$ and $R^c$ are independently selected from hydrogen, alkyl and a Boc group; and
a, b, c and d are selected from 0 and 1.

2. The compound of claim 1, wherein only one or two of $X_1$, $X_2$ and $X_3$ may be N.

3. The compound of claim 1, wherein the compounds have the structure of Formula IIa:

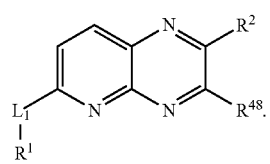

4. The compound of claim 1, wherein the compounds have the structure of Formula IIIa:

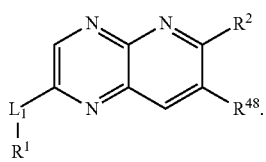

5. The compound of claim 1, wherein the compounds have the structure of Formula IVa:

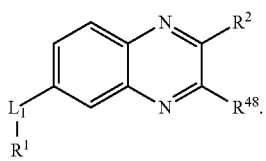

6. The compound of claim 1, wherein $R^1$ is selected from the group consisting of phenyl, 2,3-dichlorophenyl, 3-chlorophenyl, 4-fluorophenyl, 3-chloro-2-trifluoromethylphenyl, 2-chloro-3-methoxyphenyl, 3-chloro-2-fluorophenyl, 2-chloro-6-fluoro-3-methoxyphenyl, 2,3-dichloro-4-methoxyphenyl, 2-chloro-3-cyanophenyl, 2-chloro-3-fluorophenyl, 2-amino-3-chloropyridin-4-yl, 3-chloro-2-(pyrrolidine-1-yl)pyridine-4-yl, 3-chloro-2-methoxypyridin-4-yl, 3-chloro-2-(methylamino)pyridine-4-yl), 3-chloro-2-(3-hydroxypyrrolidin-1-yl)pyridine-4-yl, 3-chloro-2-((2-hydroxyethyl)amino)pyridin-4-yl, 3-chloro-2-methylpyridin-4-yl, 6-amino-2,3-dichloropyridin-4-yl, 3-chloro-2-(2-(hydroxymethyl)pyrrolidin-1-yl)pyridin-4-yl, 2-amino-3-methylpyridin-4-yl, 3-chloro-2-(1,1-dioxidothiomorpholino)pyridin-4-yl, 3-chloro-2-(4-hydroxypiperidin-1-yl)pyridin-4-yl, 3-chloro-2-morpholinopyridin-4-yl, 2-(4-acetylpiperazin-1-yl)-3-chloropyridin-4-yl, 3-chloro-2-((S)-3-(hydroxymethyl)pyrrolidin-1-yl)pyridin-4-yl, 3-chloro-2-((S)-3-hydroxypyrrolidin-1-yl)pyridin-4-yl, 3-chloro-2-(3-hydroxypyrrolidin-1-yl)pyridin-4-yl, 3-chloro-2-(hydroxymethyl)pyridin-4-yl, 3-chloro-2-methylpyridin-4-yl, 2-aminopyridin-3-yl, 6-chloro-2-methylpyridin-3-yl, 6-amino-2-chloropyridin-3-yl, 2-chloro-6-methylpyridin-3-yl, 3-chloro-2-((R)-3-(hydroxymethyl)pyrrolidin-1-yl)pyridin-4-yl, 2,3-dimethylpyridin-4-yl, 2-amino-3-fluoropyridin-4-yl, 6-amino-2-(trifluoromethyl)pyridin-3-yl, 2-amino-5-chloropyridin-4-yl, 6-amino-4,5-dichloropyridin-3-yl, 6-amino-3-chloro-2-methoxypyridin-4-yl, 2-amino-3-methoxypyridin-4-yl, 6-amino-5-chloropyrimidin-4-yl, 2-(trifluoromethyl)pyridin-3-yl, 3-chloro-2-((2-methoxyethyl)amino)pyridin-4-yl, 3-chloro-2-(cyclopropylamino)pyridin-4-yl, 3-fluoropyridin-4-yl, 3-chloropyridin-4-yl, 3-(trifluoromethyl)pyridin-4-yl, 3-chloro-2-((2-cyano-2-methylpropyl)amino)pyridin-4-yl, 3-chloro-2-((3-methoxypropyl)amino)pyridin-4-yl, 2-amino-3-(trifluoromethyl)pyridin-4-yl, 2-(trifluoromethyl)pyridin-4-yl, 3,4-dihydroquinolin-1(2H)-yl, 3,4-dihydroquinoxalin-1(2H)-yl, 2,3-dihydro-1H-pyrrolo[2,3-b]pyridin-4-yl, 3,4-dihydro-1,5-naphthyridin-1(2H)-yl, 3,3-difluoro-2-oxo-2,3-dihydro-1H-pyrrolo[2,3-b]pyridin-4-yl, 7-hydroxy-6,7-dihydro-5H-cyclopenta[b]pyridin-4-yl, naphthalen-1-yl, 1-methyl-1H-indazol-7-yl, pyrazolo[1,5-a]pyridine-4-yl, pyrazolo[1,5-a]pyrazin-4-yl, isoquinolin-8-yl, 3H-imidazo[4,5-b]pyridin-7-yl, 6-chloroimidazo[1,2-a]pyridin-3-yl, 6-cyanoimidazo[1,2-a]pyridin-3-yl, 1H-pyrazolo[3,4-b]pyridin-4-yl, 1,8-naphthyridin-4-yl, 1H-pyrrolo[2,3-b]pyridin-4-yl, 1-methyl-1H-pyrrolo[2,3-b]pyridin-4-yl, 5-chloro-1H-pyrrolo[2,3-b]pyridin-4-yl, 5-(trifluoromethyl)-1H-pyrrolo[2,3-b]pyridin-4-yl, 3-methyl-1H-pyrrolo[2,3-b]pyridin-4-yl, 6-amino-1H-pyrrolo[2,3-b]pyridin-4-yl and 5-fluoro-1H-pyrrolo[2,3-b]pyridin-4-yl.

7. The compound of claim 1, wherein R² is selected from the group consisting of:

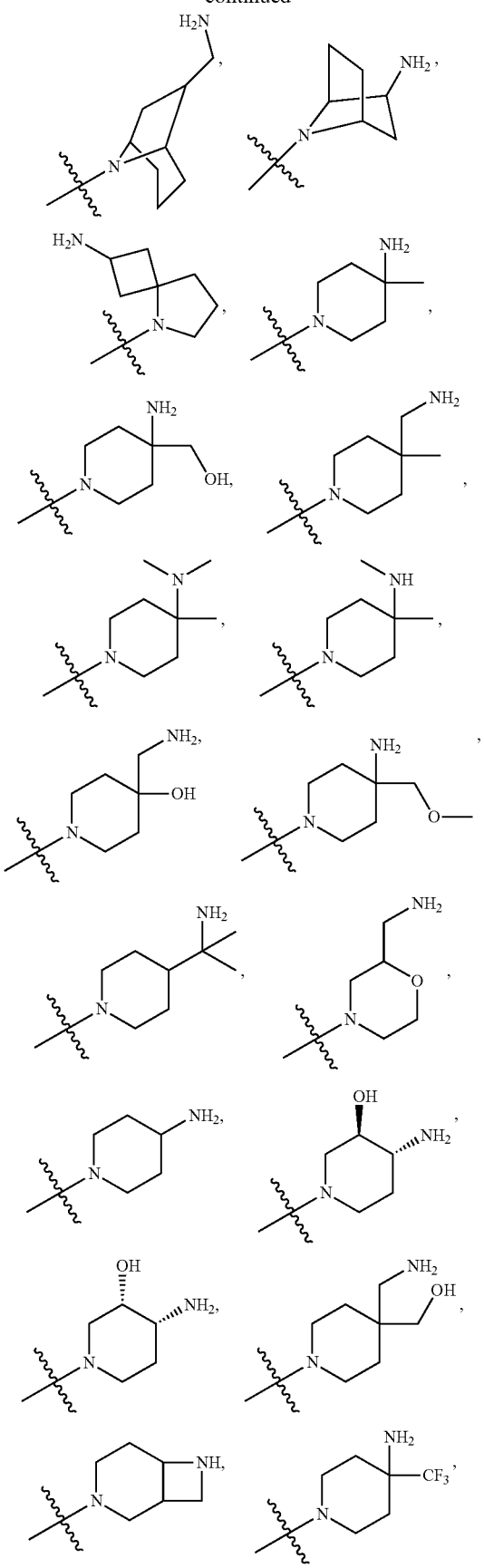

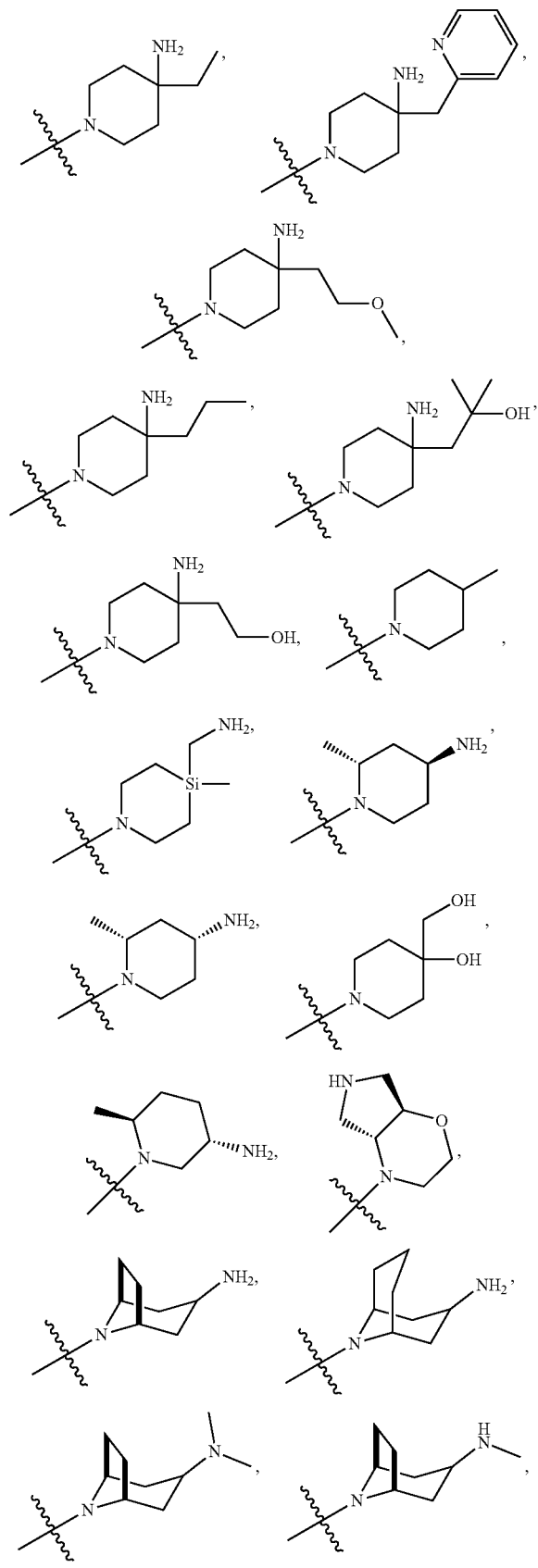
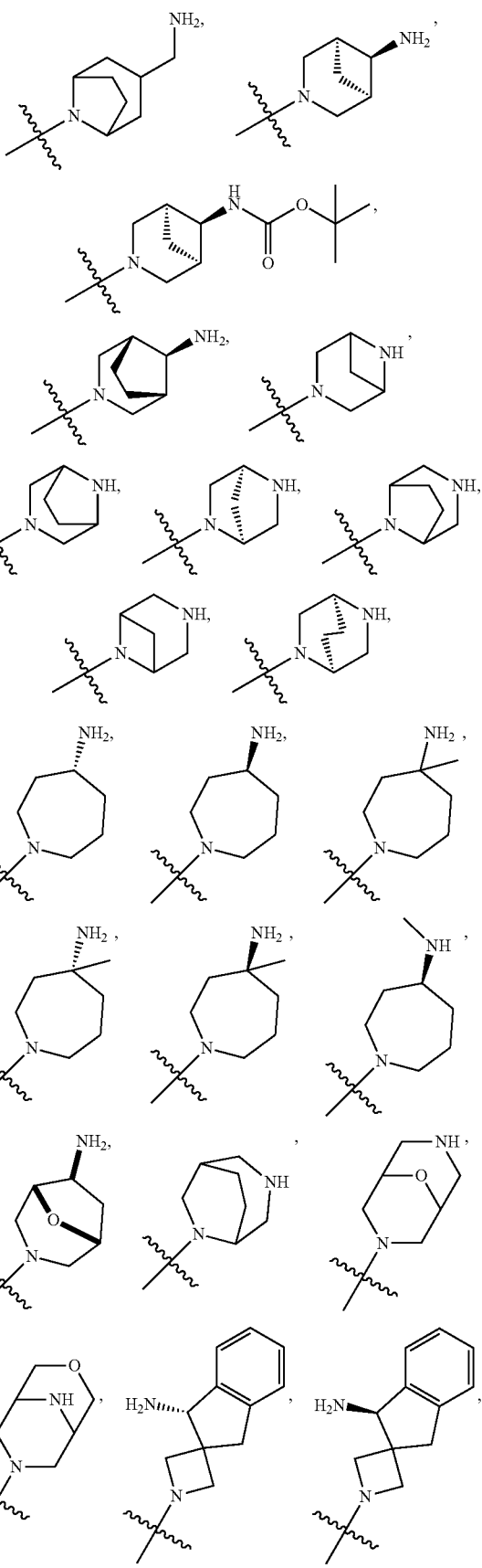

263
-continued
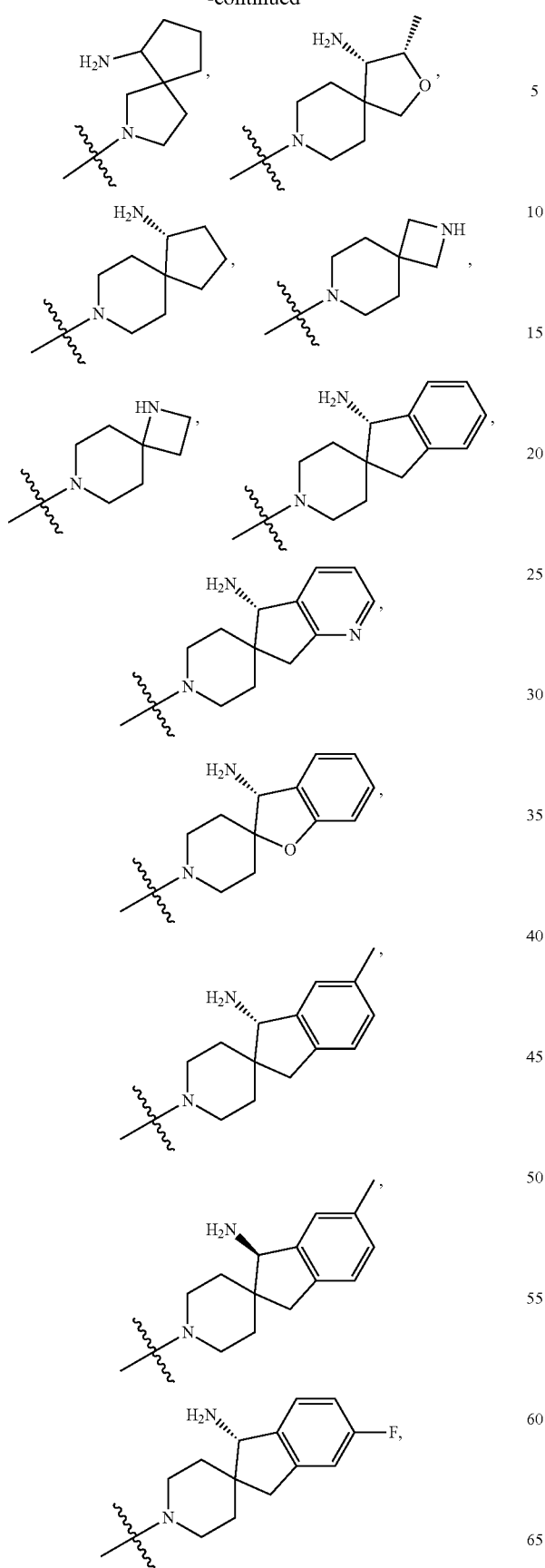
264
-continued
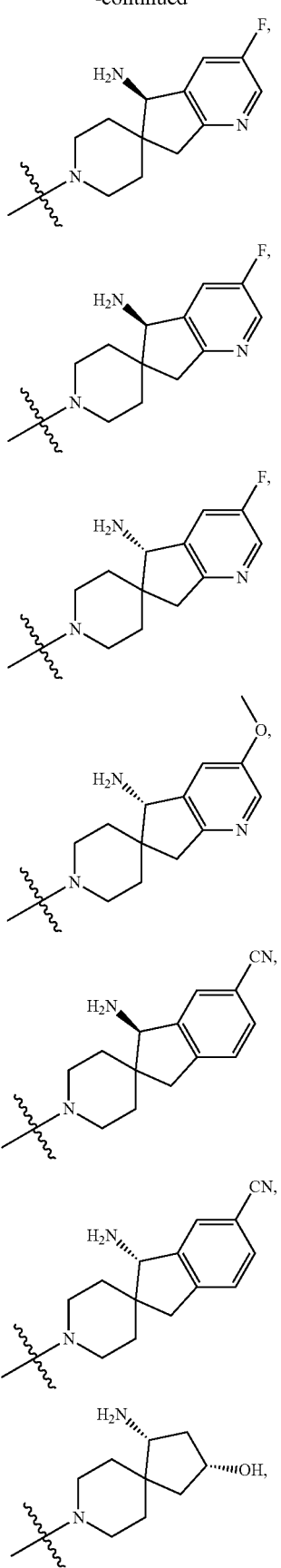

-continued
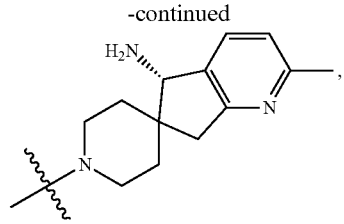
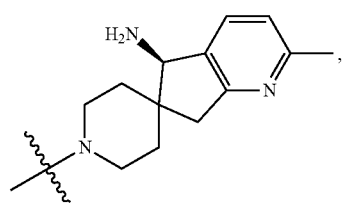
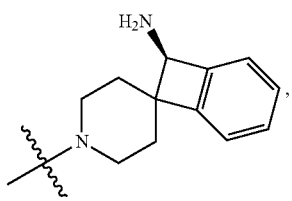
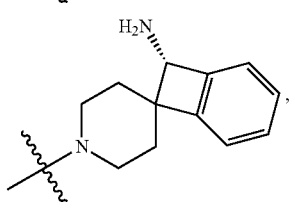
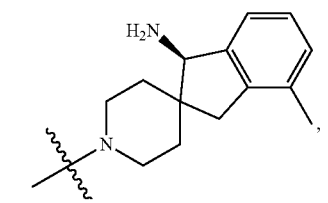
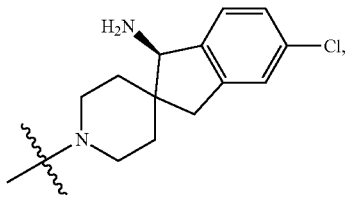
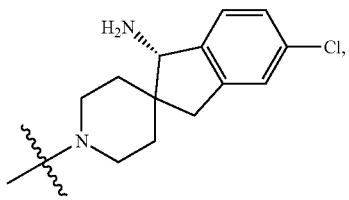
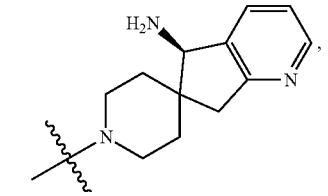
-continued
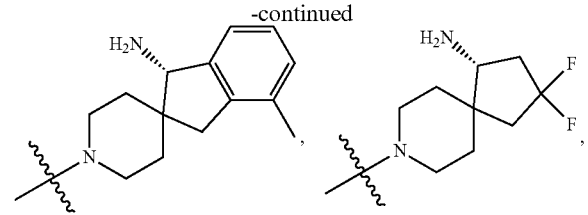
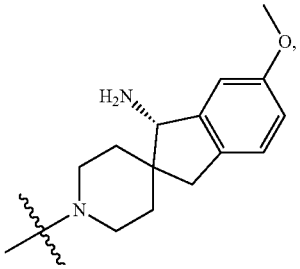
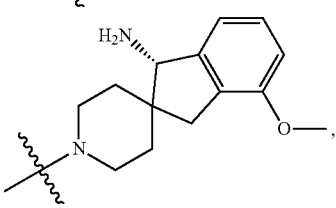
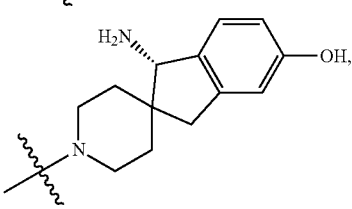
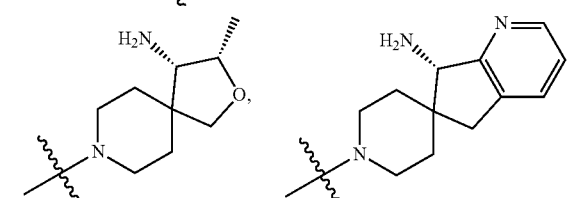
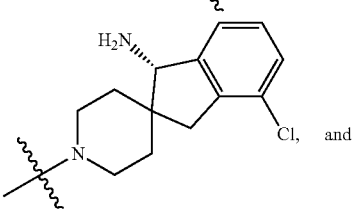
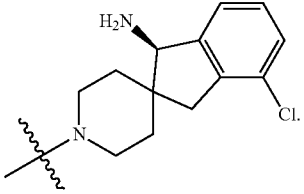 [SMILES: *N1CCC2(CC1)Cc1c(Cl)cccc1[C@@H]2N]
8. The compound of claim 1, wherein $R^{48}$ is hydrogen.
9. The compound of claim 1 wherein the compound is selected from the group consisting of:
4-((2-(4-amino-4-methylpiperidin-1-yl)pyrido[2,3-b]pyrazin-6-yl)thio)-3-chloropyridin-2-amine;
(3S,4S)-8-(6-((2,3-dichlorophenyl)thio)pyrido[2,3-b]pyrazin-2-yl)-3-methyl-2-oxa-8-azaspiro[4.5]decan-4-amine;

(3S,4S)-8-(2-((2,3-dichlorophenyl)thio)pyrido[2,3-b]pyrazin-6-yl)-3-methyl-2-oxa-8-azaspiro[4.5]decan-4-amine;
1-(6-((2,3-dichlorophenyl)thio)pyrido[2,3-b]pyrazin-2-yl)-4-methylpiperidin-4-amine;
1-(2-((2,3-dichlorophenyl)thio)pyrido[2,3-b]pyrazin-6-yl)-4-methylpiperidin-4-amine;
(R)-8-(6-((2,3-dichlorophenyl)thio)pyrido[2,3-b]pyrazin-2-yl)-8-azaspiro[4.5]decan-1-amine;
(4-amino-1-(6-((2,3-dichlorophenyl)thio)pyrido[2,3-b]pyrazin-2-yl)piperidin-4-yl)methanol;
4-((2-(4-(aminomethyl)-4-methylpiperidin-1-yl)pyrido[2,3-b]pyrazin-6-yl)thio)-3-chloropyridin-2-amine;
(3S,4S)-8-(6-((2-amino-3-chloropyridin-4-yl)thio)pyrido[2,3-b]pyrazin-2-yl)-3-methyl-2-oxa-8-azaspiro[4.5]decan-4-amine;
1-(6-((2-chloro-3-methoxyphenyl)thio)pyrido[2,3-b]pyrazin-2-yl)-4-methylpiperidin-4-amine;
1-(6-((3-chloro-2-methoxypyridin-4-yl)thio)pyrido[2,3-b]pyrazin-2-yl)-4-methylpiperidin-4-amine;
(R)-4-((2-(3-amino-3-methylpyrrolidin-1-yl)pyrido[2,3-b]pyrazin-6-yl)thio)-3-chloropyridin-2-amine;
(3S,4S)-8-(6-((3-chloro-2-(pyrrolidin-1-yl)pyridin-4-yl)thio)pyrido[2,3-b]pyrazin-2-yl)-3-methyl-2-oxa-8-azaspiro[4.5]decan-4-amine;
3-chloro-4-((2-(4-methyl-4-(methylamino)piperidin-1-yl)pyrido[2,3-b]pyrazin-6-yl)thio)pyridin-2-amine;
(3S,4S)-8-(6-((3-chloro-2-(methylamino)pyridin-4-yl)thio)pyrido[2,3-b]pyrazin-2-yl)-3-methyl-2-oxa-8-azaspiro[4.5]decan-4-amine;
4-methyl-1-(6-((1-methyl-1H-indazol-7-yl)thio)pyrido[2,3-b]pyrazin-2-yl)piperidin-4-amine;
3-((2-(4-amino-4-methylpiperidin-1-yl)pyrido[2,3-b]pyrazin-6-yl)thio)-2-chlorobenzonitrile;
4-methyl-1-(6-(pyrazolo[1,5-a]pyridin-4-ylthio)pyrido[2,3-b]pyrazin-2-yl)piperidin-4-amine;
4-methyl-1-(6-(pyrazolo[1,5-a]pyrazin-4-ylthio)pyrido[2,3-b]pyrazin-2-yl)piperidin-4-amine;
(R)-1-(6-((2-amino-3-chloropyridin-4-yl)thio)pyrido[2,3-b]pyrazin-2-yl)azepan-4-amine;
1-(6-((2-amino-3-chloropyridin-4-yl)thio)pyrido[2,3-b]pyrazin-2-yl)-4-(aminomethyl)piperidin-4-ol;
(4-amino-1-(6-((2-amino-3-chloropyridin-4-yl)thio)pyrido[2,3-b]pyrazin-2-yl)piperidin-4-yl)methanol;
(4-amino-1-(6-((3-chloro-2-methoxypyridin-4-yl)thio)pyrido[2,3-b]pyrazin-2-yl)piperidin-4-yl)methanol;
(4-amino-1-(6-((3-chloro-2-(pyrrolidin-1-yl)pyridin-4-yl)thio)pyrido[2,3-b]pyrazin-2-yl)piperidin-4-yl)methanol;
1-(6-(isoquinolin-8-ylthio)pyrido[2,3-b]pyrazin-2-yl)-4-methylpiperidin-4-amine;
1-(6-((3-chloro-2-(pyrrolidin-1-yl)pyridin-4-yl)thio)pyrido[2,3-b]pyrazin-2-yl)-4-methylpiperidin-4-amine;
(S)-1-(6-((2-amino-3-chloropyridin-4-yl)thio)pyrido[2,3-b]pyrazin-2-yl)azepan-4-amine;
(1R,3s,5S)-8-(6-((2-amino-3-chloropyridin-4-yl)thio)pyrido[2,3-b]pyrazin-2-yl)-8-azabicyclo[3.2.1]octan-3-amine;
4-((2-(4-amino-4-(methoxymethyl)piperidin-1-yl)pyrido[2,3-b]pyrazin-6-yl)thio)-3-chloropyridin-2-amine;
4-((2-(2,7-diazaspiro[3.5]nonan-7-yl)pyrido[2,3-b]pyrazin-6-yl)thio)-3-chloropyridin-2-amine;
4-((2-(1,7-diazaspiro[3.5]nonan-7-yl)pyrido[2,3-b]pyrazin-6-yl)thio)-3-chloropyridin-2-amine;
(1R,5S)-9-(6-((2-amino-3-chloropyridin-4-yl)thio)pyrido[2,3-b]pyrazin-2-yl)-9-azabicyclo[3.3.1]nonan-3-amine;
(4-amino-1-(6-((3-chloro-2-methylpyridin-4-yl)thio)pyrido[2,3-b]pyrazin-2-yl)piperidin-4-yl)methanol;
(1R,5R,6S)-3-(6-((2-amino-3-chloropyridin-4-yl)thio)pyrido[2,3-b]pyrazin-2-yl)-8-oxa-3-azabicyclo[3.2.1]octan-6-amine;
(1R,5R,6S)-3-(6-((2,3-dichlorophenyl)thio)pyrido[2,3-b]pyrazin-2-yl)-8-oxa-3-azabicyclo[3.2.1]octan-6-amine;
4-((2-(4-(2-aminopropan-2-yl)piperidin-1-yl)pyrido[2,3-b]pyrazin-6-yl)thio)-3-chloropyridin-2-amine;
2-(1-(6-((2,3-dichlorophenyl)thio)pyrido[2,3-b]pyrazin-2-yl)piperidin-4-yl)propan-2-amine;
4-((2-(2-(aminomethyl)morpholino)pyrido[2,3-b]pyrazin-6-yl)thio)-3-chloropyridin-2-amine;
(4-(6-((2,3-dichlorophenyl)thio)pyrido[2,3-b]pyrazin-2-yl)morpholin-2-yl)methanamine;
(1R,3s,5S)-8-(6-((3-chloro-2-methylpyridin-4-yl)thio)pyrido[2,3-b]pyrazin-2-yl)-8-azabicyclo[3.2.1]octan-3-amine dihydrochloride;
(3S,4S)-8-(6-((6-amino-2,3-dichloropyridin-4-yl)thio)pyrido[2,3-b]pyrazin-2-yl)-3-methyl-2-oxa-8-azaspiro[4.5]decan-4-amine;
((S)-1-(4-((2-((3S,4S)-4-amino-3-methyl-2-oxa-8-azaspiro[4.5]decan-8-yl)pyrido[2,3-b]pyrazin-6-yl)thio)-3-chloropyridin-2-yl)pyrrolidin-2-yl)methanol;
(3S,4S)-8-(6-((2-amino-3-methylpyridin-4-yl)thio)pyrido[2,3-b]pyrazin-2-yl)-3-methyl-2-oxa-8-azaspiro[4.5]decan-4-amine;
1-(6-((2-amino-3-chloropyridin-4-yl)thio)pyrido[2,3-b]pyrazin-2-yl)-4-methylazepan-4-amine;
(R)-1-(6-((2-amino-3-chloropyridin-4-yl)thio)pyrido[2,3-b]pyrazin-2-yl)-4-methylazepan-4-amine;
(S)-1-(6-((2-amino-3-chloropyridin-4-yl)thio)pyrido[2,3-b]pyrazin-2-yl)-4-methylazepan-4-amine;
(S)-1'-(6-((2-amino-3-chloropyridin-4-yl)thio)pyrido[2,3-b]pyrazin-2-yl)-1,3-dihydrospiro[indene-2,4'-piperidin]-1-amine;
4-(4-((2-((3S,4S)-4-amino-3-methyl-2-oxa-8-azaspiro[4.5]decan-8-yl)pyrido[2,3-b]pyrazin-6-yl)thio)-3-chloropyridin-2-yl)thiomorpholine 1,1-dioxide;
1-(4-((2-((3S,4S)-4-amino-3-methyl-2-oxa-8-azaspiro[4.5]decan-8-yl)pyrido[2,3-b]pyrazin-6-yl)thio)-3-chloropyridin-2-yl)piperidin-4-ol;
(3S,4S)-8-(6-((3-chloro-2-morpholinopyridin-4-yl)thio)pyrido[2,3-b]pyrazin-2-yl)-3-methyl-2-oxa-8-azaspiro[4.5]decan-4-amine;
1-(4-(4-((2-((3S,4S)-4-amino-3-methyl-2-oxa-8-azaspiro[4.5]decan-8-yl)pyrido[2,3-b]pyrazin-6-yl)thio)-3-chloropyridin-2-yl)piperazin-1-yl)ethan-1-one;
4-((2-(4-aminopiperidin-1-yl)pyrido[2,3-b]pyrazin-6-yl)thio)-3-chloropyridin-2-amine;
(3R,4R)-4-amino-1-(6-((2-amino-3-chloropyridin-4-yl)thio)pyrido[2,3-b]pyrazin-2-yl)piperidin-3-ol;
2-(6-((2-amino-3-chloropyridin-4-yl)thio)pyrido[2,3-b]pyrazin-2-yl)-2-azaspiro[4.4]nonan-6-amine;
(3S,4R)-4-amino-1-(6-((2-amino-3-chloropyridin-4-yl)thio)pyrido[2,3-b]pyrazin-2-yl)piperidin-3-ol;
4-((2-(3-(aminomethyl)azetidin-1-yl)pyrido[2,3-b]pyrazin-6-yl)thio)-3-chloropyridin-2-amine;
(1-(6-((2-amino-3-chloropyridin-4-yl)thio)pyrido[2,3-b]pyrazin-2-yl)-4-(aminomethyl)piperidin-4-yl)methanol;

((S)-1-(4-((2-((3S,4S)-4-amino-3-methyl-2-oxa-8-azaspiro[4.5]decan-8-yl)pyrido[2,3-b]pyrazin-6-yl)thio)-3-chloropyridin-2-yl)pyrrolidin-3-yl)methanol;

(S)-1-(4-((2-((3S,4S)-4-amino-3-methyl-2-oxa-8-azaspiro[4.5]decan-8-yl)pyrido[2,3-b]pyrazin-6-yl)thio)-3-chloropyridin-2-yl)pyrrolidin-3-ol;

1-(4-((2-((3S,4S)-4-amino-3-methyl-2-oxa-8-azaspiro[4.5]decan-8-yl)pyrido[2,3-b]pyrazin-6-yl)thio)-3-chloropyridin-2-yl)pyrrolidin-3-ol;

(4-((2-((3S,4S)-4-amino-3-methyl-2-oxa-8-azaspiro[4.5]decan-8-yl)pyrido[2,3-b]pyrazin-6-yl)thio)-3-chloropyridin-2-yl)methanol;

(S)-1-(6-((2-amino-3-chloropyridin-4-yl)thio)pyrido[2,3-b]pyrazin-2-yl)-N-methylazepan-4-amine;

(1R,3s,5S)-8-(6-((2-amino-3-chloropyridin-4-yl)thio)pyrido[2,3-b]pyrazin-2-yl)-N,N-dimethyl-8-azabicyclo[3.2.1]octan-3-amine;

(1R,3s,5S)-8-(6-((2-amino-3-chloropyridin-4-yl)thio)pyrido[2,3-b]pyrazin-2-yl)-N-methyl-8-azabicyclo[3.2.1]octan-3-amine;

1-(6-((3-chloro-2-methylpyridin-4-yl)thio)pyrido[2,3-b]pyrazin-2-yl)-4-methylpiperidin-4-amine;

3-((2-(4-amino-4-methylpiperidin-1-yl)pyrido[2,3-b]pyrazin-6-yl)thio)pyridin-2-amine;

1-(6-((6-chloro-2-methylpyridin-3-yl)thio)pyrido[2,3-b]pyrazin-2-yl)-4-methylpiperidin-4-amine;

5-((2-(4-amino-4-methylpiperidin-1-yl)pyrido[2,3-b]pyrazin-6-yl)thio)-6-chloropyridin-2-amine;

1-(6-((2-chloro-6-methylpyridin-3-yl)thio)pyrido[2,3-b]pyrazin-2-yl)-4-methylpiperidin-4-amine;

2-(6-((2-amino-3-chloropyridin-4-yl)thio)pyrido[2,3-b]pyrazin-2-yl)octahydro-1H-isoindol-4-amine;

2-(6-((2-amino-3-chloropyridin-4-yl)thio)pyrido[2,3-b]pyrazin-2-yl)octahydrocyclopenta[c]pyrrol-4-amine;

4-((2-(3-(aminomethyl)-9-azabicyclo[3.3.1]nonan-9-yl)pyrido[2,3-b]pyrazin-6-yl)thio)-3-chloropyridin-2-amine;

4-((2-(3-(aminomethyl)-8-azabicyclo[3.2.1]octan-8-yl)pyrido[2,3-b]pyrazin-6-yl)thio)-3-chloropyridin-2-amine;

4-((2-(3,7-diazabicyclo[4.2.0]octan-3-yl)pyrido[2,3-b]pyrazin-6-yl)thio)-3-chloropyridin-2-amine;

4-((2-(4-amino-4-(trifluoromethyl)piperidin-1-yl)pyrido[2,3-b]pyrazin-6-yl)thio)-3-chloropyridin-2-amine;

(3S,4S)-8-(6-((6-amino-2-chloropyridin-3-yl)thio)pyrido[2,3-b]pyrazin-2-yl)-3-methyl-2-oxa-8-azaspiro[4.5]decan-4-amine;

((R)-1-(4-((2-((3S,4S)-4-amino-3-methyl-2-oxa-8-azaspiro[4.5]decan-8-yl)pyrido[2,3-b]pyrazin-6-yl)thio)-3-chloropyridin-2-yl)pyrrolidin-3-yl)methanol;

(R)-1-(4-((2-((3S,4S)-4-amino-3-methyl-2-oxa-8-azaspiro[4.5]decan-8-yl)pyrido[2,3-b]pyrazin-6-yl)thio)-3-chloropyridin-2-yl)pyrrolidin-3-ol;

(S)-2-((4-((2-(5-amino-5,7-dihydrospiro[cyclopenta[b]pyridine-6,4'-piperidin]-1'-yl)pyrido[2,3-b]pyrazin-6-yl)thio)-3-chloropyridin-2-yl)amino)ethan-1-ol;

4-((2-(4-(Aminomethyl)-4-methyl-1,4-azasilinan-1-yl)pyrido[2,3-b]pyrazin-6-yl)thio)-3-chloropyridin-2-amine;

(S)-2-((4-((2-(1-amino-1,3-dihydrospiro[indene-2,4'-piperidin]-1'-yl)pyrido[2,3-b]pyrazin-6-yl)thio)-3-chloropyridin-2-yl)amino)ethan-1-ol;

(R)-1-amino-1'-(6-((2-amino-3-chloropyridin-4-yl)thio)pyrido[2,3-b]pyrazin-2-yl)-1,3-dihydrospiro[indene-2,4'-piperidine]-6-carbonitrile;

(S)-1-amino-1'-(6-((2-amino-3-chloropyridin-4-yl)thio)pyrido[2,3-b]pyrazin-2-yl)-1,3-dihydrospiro[indene-2,4'-piperidine]-6-carbonitrile;

(R)-1'-(6-((2-amino-3-chloropyridin-4-yl)thio)pyrido[2,3-b]pyrazin-2-yl)-2-methyl-5,7-dihydrospiro[cyclopenta[b]pyridine-6,4'-piperidin]-5-amine;

(S)-1'-(6-((2-amino-3-chloropyridin-4-yl)thio)pyrido[2,3-b]pyrazin-2-yl)-2-methyl-5,7-dihydrospiro[cyclopenta[b]pyridine-6,4'-piperidin]-5-amine;

(S)-1'-(6-((2-amino-3-chloropyridin-4-yl)thio)pyrido[2,3-b]pyrazin-2-yl)-3-methoxy-5,7-dihydrospiro[cyclopenta[b]pyridine-6,4'-piperidin]-5-amine;

(R)-1'-(6-((2-amino-3-chloropyridin-4-yl)thio)pyrido[2,3-b]pyrazin-2-yl)-2-methoxy-5,7-dihydrospiro[cyclopenta[b]pyridine-6,4'-piperidin]-5-amine;

(S)-1'-(6-((2-amino-3-chloropyridin-4-yl)thio)pyrido[2,3-b]pyrazin-2-yl)-3-fluoro-5,7-dihydrospiro[cyclopenta[b]pyridine-6,4'-piperidin]-5-amine;

(R)-1'-(6-((2-amino-3-chloropyridin-4-yl)thio)pyrido[2,3-b]pyrazin-2-yl)-3-fluoro-5,7-dihydrospiro[cyclopenta[b]pyridine-6,4'-piperidin]-5-amine;

(S)-1'-(6-((6-amino-4,5-dichloropyridin-3-yl)thio)pyrido[2,3-b]pyrazin-2-yl)-1,3-dihydrospiro[indene-2,4'-piperidin]-1-amine;

1-(6-((2,3-dichlorophenyl)thio)-3-methylpyrido[2,3-b]pyrazin-2-yl)-4-methylpiperidin-4-amine;

4-((2-((2R,4R)-4-amino-2-methylpiperidin-1-yl)pyrido[2,3-b]pyrazin-6-yl)thio)-3-chloropyridin-2-amine;

4-((2-((2R,4S)-4-amino-2-methylpiperidin-1-yl)pyrido[2,3-b]pyrazin-6-yl)thio)-3-chloropyridin-2-amine dihydrochloride;

(R)-1-(6-((2-amino-3-chloropyridin-4-yl)thio)pyrido[2,3-b]pyrazin-2-yl)-1',3'-dihydrospiro[azetidine-3,2'-inden]-1'-amine;

(S)-1'-(6-((2-amino-3-chloropyridin-4-yl)thio)pyrido[2,3-b]pyrazin-2-yl)-5,7-dihydrospiro[cyclopenta[b]pyridine-6,4'-piperidin]-5-amine;

(S)-1'-(6-((2-amino-3-chloropyridin-4-yl)thio)pyrido[2,3-b]pyrazin-2-yl)-4-methyl-1,3-dihydrospiro[indene-2,4'-piperidin]-1-amine;

(S)-1'-(6-((6-chloroimidazo[1,2-a]pyridin-3-yl)thio)pyrido[2,3-b]pyrazin-2-yl)-1,3-dihydrospiro[indene-2,4'-piperidin]-1-amine;

2-(4-amino-1-(6-((2-amino-3-chloropyridin-4-yl)thio)pyrido[2,3-b]pyrazin-2-yl)piperidin-4-yl)ethan-1-ol;

1-(4-amino-1-(6-((2-amino-3-chloropyridin-4-yl)thio)pyrido[2,3-b]pyrazin-2-yl)piperidin-4-yl)-2-methylpropan-2-ol;

4-((2-(4-amino-4-ethylpiperidin-1-yl)pyrido[2,3-b]pyrazin-6-yl)thio)-3-chloropyridin-2-amine;

(3S,4S)-8-(6-((3H-imidazo[4,5-b]pyridin-7-yl)thio)pyrido[2,3-b]pyrazin-2-yl)-3-methyl-2-oxa-8-azaspiro[4.5]decan-4-amine;

(R)-1'-(6-((2-amino-3-chloropyridin-4-yl)thio)pyrido[2,3-b]pyrazin-2-yl)-3H-spiro[benzofuran-2,4'-piperidin]-3-amine;

(S)-1'-(6-((2-amino-5-chloropyridin-4-yl)thio)pyrido[2,3-b]pyrazin-2-yl)-5,7-dihydrospiro[cyclopenta[b]pyridine-6,4'-piperidin]-5-amine;

3-((4-((2-(4-amino-4-methylpiperidin-1-yl)pyrido[2,3-b]pyrazin-6-yl)thio)-3-chloropyridin-2-yl)amino)-2,2-dimethylpropanenitrile;

(3S,4S)-8-(6-((2-amino-3-(trifluoromethyl)pyridin-4-yl)thio)pyrido[2,3-b]pyrazin-2-yl)-3-methyl-2-oxa-8-azaspiro[4.5]decan-4-amine;

((1R,5S,6r)-3-(6-((2-amino-3-chloropyridin-4-yl)thio)pyrido[2,3-b]pyrazin-2-yl)-3-azabicyclo[3.1.1]heptan-6-amine;

(tert-butyl ((1R,5S,6r)-3-(6-((2-amino-3-chloropyridin-4-yl)thio)pyrido[2,3-b]pyrazin-2-yl)-3-azabicyclo[3.1.1]heptan-6-yl)carbamate;

(3S,4S)-3-methyl-8-(6-((3-methyl-1H-pyrrolo[2,3-b]pyridin-4-yl)thio)pyrido[2,3-b]pyrazin-2-yl)-2-oxa-8-azaspiro[4.5]decan-4-amine;

(3S,4S)-8-(6-((6-amino-1H-pyrrolo[2,3-b]pyridin-4-yl)thio)pyrido[2,3-b]pyrazin-2-yl)-3-methyl-2-oxa-8-azaspiro[4.5]decan-4-amine;

(3S,4S)-8-(6-((5-fluoro-1H-pyrrolo[2,3-b]pyridin-4-yl)thio)pyrido[2,3-b]pyrazin-2-yl)-3-methyl-2-oxa-8-azaspiro[4.5]decan-4-amine;

(S)-4-((2-(1-amino-1,3-dihydrospiro[indene-2,4'-piperidin]-1'-yl)pyrido[2,3-b]pyrazin-6-yl)thio)-3,3-difluoro-1,3-dihydro-2H-pyrrolo[2,3-b]pyridin-2-one;

3-chloro-4-((2-(4-methylpiperidin-1-yl)pyrido[2,3-b]pyrazin-6-yl)thio)pyridin-2-amine;

(3S,4S)-8-(6-((2-amino-5-chloropyridin-4-yl)thio)pyrido[2,3-b]pyrazin-2-yl)-3-methyl-2-oxa-8-azaspiro[4.5]decan-4-amine;

(S)-1'-(6-((2-amino-3-chloropyridin-4-yl)thio)pyrido[2,3-b]pyrazin-2-yl)-5-fluoro-1,3-dihydrospiro[indene-2,4'-piperidin]-1-amine;

1-(6-((3-chloro-2-(methylamino)pyridin-4-yl)thio)pyrido[2,3-b]pyrazin-2-yl)-4-methylazepan-4-amine;

1-(6-((3-chloro-2-methylpyridin-4-yl)thio)pyrido[2,3-b]pyrazin-2-yl)-4-methylazepan-4-amine;

(R)-1-(6-((3-chloro-2-(methylamino)pyridin-4-yl)thio)pyrido[2,3-b]pyrazin-2-yl)-4-methylazepan-4-amine;

(S)-1-(6-((3-chloro-2-(methylamino)pyridin-4-yl)thio)pyrido[2,3-b]pyrazin-2-yl)-4-methylazepan-4-amine;

(R)-1-(6-((3-chloro-2-methylpyridin-4-yl)thio)pyrido[2,3-b]pyrazin-2-yl)-4-methylazepan-4-amine;

(S)-1-(6-((3-chloro-2-methylpyridin-4-yl)thio)pyrido[2,3-b]pyrazin-2-yl)-4-methylazepan-4-amine;

(3S,4S)-8-(6-((2-amino-3-methoxypyridin-4-yl) thio)pyrido[2,3-b]pyrazin-2-yl)-3-methyl-2-oxa-8-azaspiro[4.5] decan-4-amine;

5-(6-((2-amino-3-chloropyridin-4-yl)thio)pyrido[2,3-b]pyrazin-2-yl)-5-azaspiro[3.4]octan-2-amine;

6-((2-amino-3-chloropyridin-4-yl)thio)-N-(3-(aminomethyl)tetrahydrofuran-3-yl)pyrido[2,3-b]pyrazin-2-amine;

(S)-1-amino-1'-(6-((3-chloro-2-methylpyridin-4-yl)thio)pyrido[2,3-b]pyrazin-2-yl)-1,3-dihydrospiro[indene-2,4'-piperidin]-5-ol;

4-((2-((3S,4S)-4-amino-3-methyl-2-oxa-8-azaspiro[4.5]decan-8-yl)pyrido[2,3-b]pyrazin-6-yl)thio)-6,7-dihydro-5H-cyclopenta[b]pyridin-7-ol;

1'-(6-((2-amino-3-chloropyridin-4-yl)thio)pyrido[2,3-b]pyrazin-2-yl)-5,7-dihydrospiro[cyclopenta[b]pyridine-6,4'-piperidin]-7-amine;

(S)-1'-(6-((2-amino-3-chloropyridin-4-yl)thio)pyrido[2,3-b]pyrazin-2-yl)-4-chloro-1,3-dihydrospiro[indene-2,4'-piperidin]-1-amine;

(2R,4R)-4-amino-8-(6-((2-amino-3-chloropyridin-4-yl)thio)pyrido[2,3-b]pyrazin-2-yl)-8-azaspiro[4.5]decan-2-ol;

4-((2-(4-amino-4-methylpiperidin-1-yl)pyrido[2,3-b]pyrazin-6-yl)thio)-3-chloro-N-methylpyridin-2-amine;

(S)-1'-(6-((2-(trifluoromethyl)pyridin-3-yl)thio)pyrido[2,3-b]pyrazin-2-yl)-1,3-dihydrospiro[indene-2,4'-piperidin]-1-amine;

(S)-1'-(6-((2-(trifluoromethyl)pyridin-3-yl)thio)pyrido[2,3-b]pyrazin-2-yl)-5,7-dihydrospiro[cyclopenta[b]pyridine-6,4'-piperidin]-5-amine;

(S)-1-(6-((2-amino-3-chloropyridin-4-yl)thio)pyrido[2,3-b]pyrazin-2-yl)-1',3'-dihydrospiro[azetidine-3,2'-inden]-1'-amine;

(S)-1'-(6-((2-amino-3-chloropyridin-4-yl)thio)pyrido[2,3-b]pyrazin-2-yl)spiro[bicyclo[4.2.0]octane-7,4'-piperidine]-1(6),2,4-trien-8-amine;

(R)-1'-(6-((2-amino-3-chloropyridin-4-yl)thio)pyrido[2,3-b]pyrazin-2-yl)spiro[bicyclo[4.2.0]octane-7,4'-piperidine]-1(6),2,4-trien-8-amine;

(R)-1'-(6-((2-amino-3-chloropyridin-4-yl)thio)pyrido[2,3-b]pyrazin-2-yl)-5,7-dihydrospiro[cyclopenta[b]pyridine-6,4'-piperidin]-5-amine;

(R)-1'-(6-((2-amino-3-chloropyridin-4-yl)thio)pyrido[2,3-b]pyrazin-2-yl)-4-methyl-1,3-dihydrospiro[indene-2,4'-piperidin]-1-amine;

(S)-1'-(6-((2-amino-3-chloropyridin-4-yl)thio)pyrido[2,3-b]pyrazin-2-yl)-5-chloro-1,3-dihydrospiro[indene-2,4'-piperidin]-1-amine;

(R)-1'-(6-((2-amino-3-chloropyridin-4-yl)thio)pyrido[2,3-b]pyrazin-2-yl)-5-chloro-1,3-dihydrospiro[indene-2,4'-piperidin]-1-amine;

(S)-1'-(6-((6-amino-3-chloro-2-methoxypyridin-4-yl)thio)pyrido[2,3-b]pyrazin-2-yl)-1,3-dihydrospiro[indene-2,4'-piperidin]-1-amine;

(S)-3-((2-(1-amino-1,3-dihydrospiro[indene-2,4'-piperidin]-1'-yl)pyrido[2,3-b]pyrazin-6-yl)thio)imidazo[1,2-a]pyridine-6-carbonitrile;

4-((2-(4-amino-4-propylpiperidin-1-yl)pyrido[2,3-b]pyrazin-6-yl)thio)-3-chloropyridin-2-amine;

(3S,4S)-8-(6-((2,3-dimethylpyridin-4-yl)thio)pyrido[2,3-b]pyrazin-2-yl)-3-methyl-2-oxa-8-azaspiro[4.5]decan-4-amine;

(3S,4S)-8-(6-((2-amino-3-fluoropyridin-4-yl)thio)pyrido[2,3-b]pyrazin-2-yl)-3-methyl-2-oxa-8-azaspiro[4.5]decan-4-amine;

(3S,4S)-8-(6-((6-amino-2-(trifluoromethyl)pyridin-3-yl)thio)pyrido[2,3-b]pyrazin-2-yl)-3-methyl-2-oxa-8-azaspiro[4.5]decan-4-amine;

(3S,4S)-8-(6-((2,3-dichloropyridin-4-yl)thio)pyrido[2,3-b]pyrazin-2-yl)-3-methyl-2-oxa-8-azaspiro[4.5]decan-4-amine;

(S)-1'-(6-((2-amino-3-chloropyridin-4-yl)thio)pyrido[2,3-b]pyrazin-2-yl)-6-methyl-1,3-dihydrospiro[indene-2,4'-piperidin]-1-amine;

(R)-1'-(6-((2-amino-3-chloropyridin-4-yl)thio)pyrido[2,3-b]pyrazin-2-yl)-6-methyl-1,3-dihydrospiro[indene-2,4'-piperidin]-1-amine;

4-((2-(4-amino-4-(pyridin-2-ylmethyl)piperidin-1-yl)pyrido[2,3-b]pyrazin-6-yl)thio)-3-chloropyridin-2-amine;

4-((2-(4-amino-4-benzylpiperidin-1-yl)pyrido[2,3-b]pyrazin-6-yl)thio)-3-chloropyridin-2-amine;

4-((2-(4-amino-4-(2-methoxyethyl)piperidin-1-yl)pyrido[2,3-b]pyrazin-6-yl)thio)-3-chloropyridin-2-amine;

(3S,4S)-8-(6-((3-chloro-2-((2-methoxyethyl)amino)pyridin-4-yl)thio)pyrido[2,3-b]pyrazin-2-yl)-3-methyl-2-oxa-8-azaspiro[4.5]decan-4-amine;

(3S,4S)-8-(6-((3-chloro-2-(cyclopropylamino)pyridin-4-yl)thio)pyrido[2,3-b]pyrazin-2-yl)-3-methyl-2-oxa-8-azaspiro[4.5]decan-4-amine;

2-((4-((2-((3S,4S)-4-amino-3-methyl-2-oxa-8-azaspiro[4.5]decan-8-yl)pyrido[2,3-b]pyrazin-6-yl)thio)-3-chloropyridin-2-yl)amino)ethan-1-ol;

(3S,4S)-8-(6-((3-fluoropyridin-4-yl)thio)pyrido[2,3-b]
    pyrazin-2-yl)-3-methyl-2-oxa-8-azaspiro[4.5]decan-4-
    amine;
(3S,4S)-8-(6-((3-chloropyridin-4-yl)thio)pyrido[2,3-b]
    pyrazin-2-yl)-3-methyl-2-oxa-8-azaspiro[4.5]decan-4-
    amine;
(3S,4S)-3-methyl-8-(6-((3-(trifluoromethyl)pyridin-4-yl)
    thio)pyrido[2,3-b]pyrazin-2-yl)-2-oxa-8-azaspiro[4.5]
    decan-4-amine;
(3S,4S)-8-(6-((1H-pyrrolo[2,3-b]pyridin-4-yl)thio)pyrido
    [2,3-b]pyrazin-2-yl)-3-methyl-2-oxa-8-azaspiro[4.5]
    decan-4-amine;
(3S,4S)-3-methyl-8-(6-((2-(trifluoromethyl)pyridin-4-yl)
    thio)pyrido[2,3-b]pyrazin-2-yl)-2-oxa-8-azaspiro[4.5]
    decan-4-amine;
(3S,4S)-3-methyl-8-(6-((1-methyl-1H-pyrrolo[2,3-b]
    pyridin-4-yl)thio)pyrido[2,3-b]pyrazin-2-yl)-2-oxa-8-
    azaspiro[4.5]decan-4-amine;
(3S,4S)-8-(6-((5-chloro-1H-pyrrolo[2,3-b]pyridin-4-yl)
    thio)pyrido[2,3-b]pyrazin-2-yl)-3-methyl-2-oxa-8-
    azaspiro[4.5]decan-4-amine;
(3S,4S)-3-methyl-8-(6-((5-(trifluoromethyl)-1H-pyrrolo
    [2,3-b]pyridin-4-yl)thio)pyrido[2,3-b]pyrazin-2-yl)-2-
    oxa-8-azaspiro[4.5]decan-4-amine;
4-((2-(4-amino-4-methylpiperidin-1-yl)pyrido[2,3-b]
    pyrazin-6-yl)thio)-3-chloro-N-(2-methoxyethyl)pyri-
    din-2-amine;
4-((2-(4-amino-4-methylpiperidin-1-yl)pyrido[2,3-b]
    pyrazin-6-yl)thio)-3-chloro-N-(3-methoxypropyl)pyri-
    din-2-amine;
1-(6-((2,3-dihydro-1H-pyrrolo[2,3-b]pyridin-4-yl)thio)
    pyrido[2,3-b]pyrazin-2-yl)-4-methylpiperidin-4-
    amine;
1-(6-((1,8-naphthyridin-4-yl)thio)pyrido[2,3-b]pyrazin-
    2-yl)-4-methylpiperidin-4-amine;
1-(6-((2-amino-3-chloropyridin-4-yl)thio)pyrido[2,3-b]
    pyrazin-2-yl)-4-(hydroxymethyl)piperidin-4-ol;
(1R,5S,8s)-3-(6-((2-amino-3-chloropyridin-4-yl)thio)
    pyrido[2,3-b]pyrazin-2-yl)-3-azabicyclo[3.2.1]octan-
    8-amine;
4-((2-(3,6-diazabicyclo[3.1.1]heptan-3-yl)pyrido[2,3-b]
    pyrazin-6-yl)thio)-3-chloropyridin-2-amine;
4-((2-(3,8-diazabicyclo[3.2.1]octan-3-yl)pyrido[2,3-b]
    pyrazin-6-yl)thio)-3-chloropyridin-2-amine;
4-((2-(3,6-diazabicyclo[3.2.2]nonan-6-yl)pyrido[2,3-b]
    pyrazin-6-yl)thio)-3-chloropyridin-2-amine;
4-((2-((1 S,4S)-2,5-diazabicyclo[2.2.1]heptan-2-yl)
    pyrido[2,3-b]pyrazin-6-yl)thio)-3-chloropyridin-2-
    amine;
4-((2-(3,8-diazabicyclo[3.2.1]octan-8-yl)pyrido[2,3-b]
    pyrazin-6-yl)thio)-3-chloropyridin-2-amine;
4-((2-(3,8-diazabicyclo[3.2.1]octan-8-yl)pyrido[2,3-b]
    pyrazin-6-yl)thio)-3-chloropyridin-2-amine;
4-((2-(9-oxa-3,7-diazabicyclo[3.3.1]nonan-3-yl)pyrido[2,
    3-b]pyrazin-6-yl)thio)-3-chloropyridin-2-amine;
4-((2-(3-oxa-7,9-diazabicyclo[3.3.1]nonan-7-yl)pyrido[2,
    3-b]pyrazin-6-yl)thio)-3-chloropyridin-2-amine;
4-((2-((1 S,4S)-2,5-diazabicyclo[2.2.2]octan-2-yl)pyrido
    [2,3-b]pyrazin-6-yl)thio)-3-chloropyridin-2-amine;
(S)-1-(4-((2-(5-amino-5,7-dihydrospiro[cyclopenta[b]
    pyridine-6,4'-piperidin]-1'-yl)pyrido[2,3-b]pyrazin-6-
    yl)thio)-3-chloropyridin-2-yl)piperidin-4-ol;
((S)-1-(4-((2-((S)-5-amino-5,7-dihydrospiro[cyclopenta
    [b]pyridine-6,4'-piperidin]-1'-yl)pyrido[2,3-b]pyrazin-
    6-yl)thio)-3-chloropyridin-2-yl)pyrrolidin-3-yl)metha-
    nol;

4-((2-(4-(aminomethyl)-4-fluoropiperidin-1-yl)pyrido[2,
    3-b]pyrazin-6-yl)thio)-3-chloropyridin-2-amine;
(1-(6-((2,3-dichlorophenyl)thio)pyrido[2,3-b]pyrazin-2-
    yl)-4-fluoropiperidin-4-yl)methanamine;
(1 S,2S,4R)-7-(6-((2-amino-3-chloropyridin-4-yl)thio)
    pyrido[2,3-b]pyrazin-2-yl)-7-azabicyclo[2.2.1]heptan-
    2-amine;
(3S,4S)-8-(6-((1H-pyrazolo[3,4-b]pyridin-4-yl)thio)
    pyrido[2,3-b]pyrazin-2-yl)-3-methyl-2-oxa-8-azaspiro
    [4.5]decan-4-amine;
3-chloro-4-((2-((4aR,7aR)-hexahydropyrrolo[3,4-b][1,4]
    oxazin-4(4aH)-yl)pyrido[2,3-b]pyrazin-6-yl)thio)
    24pyridine-2-amine;
4-((2-((2S,5S)-5-amino-2-methylpiperidin-1-yl)pyrido[2,
    3-b]pyrazin-6-yl)thio)-3-chloropyridin-2-amine;
(3S,4S)-8-(6-((6-amino-5-chloropyrimidin-4-yl)thio)
    pyrido[2,3-b]pyrazin-2-yl)-3-methyl-2-oxa-8-azaspiro
    [4.5]decan-4-amine;
8-(6-((2-amino-3-chloropyridin-4-yl)thio)pyrido[2,3-b]
    pyrazin-2-yl)-3,3-difluoro-8-azaspiro[4.5]decan-1-
    amine;
(S)-1'-(6-((2-amino-3-chloropyridin-4-yl)thio)pyrido[2,
    3-b]pyrazin-2-yl)-6-methoxy-1,3-dihydrospiro[indene-
    2,4'-piperidin]-1-amine;
(R)-1'-(6-((2-amino-3-chloropyridin-4-yl)thio)pyrido[2,
    3-b]pyrazin-2-yl)-4-chloro-1,3-dihydrospiro[indene-2,
    4'-piperidin]-1-amine; and
(3S,4S)-3-methyl-8-(6-((2-(trifluoromethyl)pyridin-3-yl)
    thio)pyrido[2,3-b]pyrazin-2-yl)-2-oxa-8-azaspiro[4.5]
    decan-4-amine;
and pharmaceutically acceptable salts thereof.

10. A pharmaceutical composition comprising a compound of claim 1 or a pharmaceutically acceptable salt thereof.

11. A pharmaceutical composition comprising a compound of claim 9 or a pharmaceutically acceptable salt thereof.

12. A pharmaceutical composition comprising a compound of claim 1 for use in the treatment of a hyperproliferative disease.

13. A method of inhibiting SHP2 protein tyrosine phosphatase activity in a cell comprising treating the cell with a compound of claim 1.

14. A method of inhibiting SHP2 protein tyrosine phosphatase activity in a patient in need thereof comprising the step of administering to the patient a compound according to claim 1.

15. A method of treating or ameliorating the severity of a hyperproliferative disorder in a patient in need thereof comprising administering to the patient a compound according to claim 1.

16. The method of claim 15, wherein the hyperproliferative disease is selected from the group consisting of melanoma, juvenile myelomoncytic leukemias, neuroblastoma, Philadelphia chromosome positive chronic myeloid, Philadelphia chromosome positive acute lymphoblastic leukemias, acute myeloid leukemias, myeloproliferative neoplasms, breast cancer, lung cancer, liver cancer, colorectal cancer, esophageal cancer, gastric cancer, squamous-cell carcinoma of the head and neck, glioblastoma, anaplastic large-cell lymphoma, thyroid carcinoma, and spitzoid neoplasms.

17. The method of claim 15, wherein the hyperproliferative disease is selected from the group consisting of Neurofibramatosis and Noonan Syndrome.

18. The method of claim 14, wherein the compound is co-administered with at least one other chemotherapeutic agent used to treat or ameliorate a hyperproliferative disorder.

19. The compound:

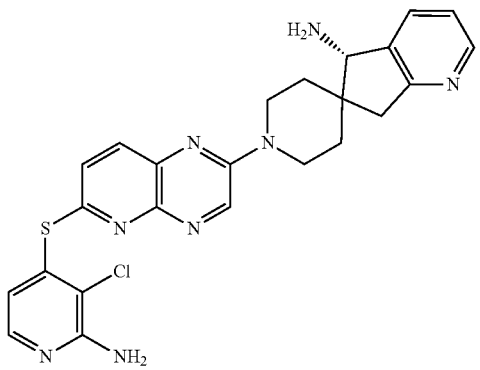 [SMILES: Nc1nccc(Sc2ccc3nc(N4CCC5(CC4)Cc4ncccc4[C@H]5N)cnc3n2)c1Cl]

and pharmaceutically acceptable salts thereof.

20. A pharmaceutical composition comprising a compound of claim 19 or a pharmaceutically acceptable salt thereof.

21. The compound:

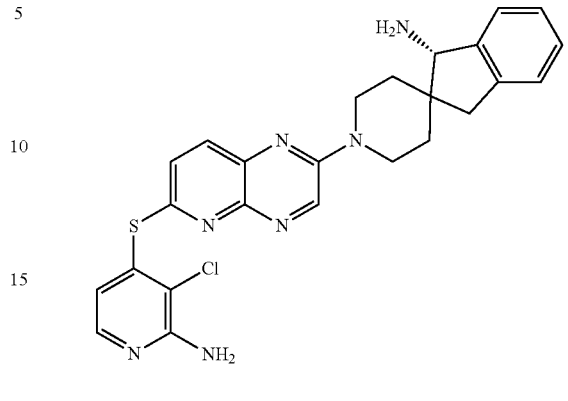

and pharmaceutically acceptable salts thereof.

22. A pharmaceutical composition comprising a compound of claim 21 or a pharmaceutically acceptable salt thereof.

* * * * *